US011274309B2

(12) United States Patent
Jarvis et al.

(10) Patent No.: US 11,274,309 B2
(45) Date of Patent: Mar. 15, 2022

(54) TWO-PART DEVICE FOR T-CELL RECEPTOR SYNTHESIS AND STABLE GENOMIC INTEGRATION TO TCR-PRESENTING CELLS

(71) Applicant: GENOVIE AB, Södertälje (SE)

(72) Inventors: Reagan Micheal Jarvis, Stockholm (SE); Ryan Edward Hill, Stockholm (SE); Luke Benjamin Pase, Stockholm (SE)

(73) Assignee: GENOVIE AB, Södertälje (SE)

( * ) Notice: Subject to any disclaimer, the term of this patent is extended or adjusted under 35 U.S.C. 154(b) by 0 days.

(21) Appl. No.: 16/347,723

(22) PCT Filed: Nov. 7, 2017

(86) PCT No.: PCT/EP2017/078378

§ 371 (c)(1),
(2) Date: May 6, 2019

(87) PCT Pub. No.: WO2018/083318

PCT Pub. Date: May 11, 2018

(65) Prior Publication Data

US 2019/0283017 A1 Sep. 19, 2019

(30) Foreign Application Priority Data

Nov. 7, 2016 (DK) .......................... PA 2016 70875
Jul. 18, 2017 (DK) .......................... PA 2017 70577
Jul. 18, 2017 (EP) .................................. 17181798

(51) Int. Cl.

*C12N 15/63* (2006.01)
*C12Q 1/6806* (2018.01)
*C12Q 1/686* (2018.01)
*C12N 15/10* (2006.01)
*C07K 14/725* (2006.01)

(52) U.S. Cl.

CPC .......... *C12N 15/63* (2013.01); *C07K 14/7051* (2013.01); *C12N 15/1006* (2013.01); *C12N 15/1093* (2013.01); *C12Q 1/686* (2013.01); *C12Q 1/6806* (2013.01)

(58) Field of Classification Search

None
See application file for complete search history.

(56) References Cited

U.S. PATENT DOCUMENTS

2015/0203886 A1 7/2015 Kishi et al.
2017/0290858 A1 10/2017 Zhao et al.
2018/0245242 A1 8/2018 Schendel et al.
2019/0359934 A1 11/2019 Jarvis et al.
2020/0095574 A1 3/2020 Jarvis et al.
2020/0115432 A1 4/2020 Jarvis et al.

FOREIGN PATENT DOCUMENTS

CN 105316362 A 2/2016
EP 2 899 269 A1 7/2015
JP 2013-535209 A 9/2013
WO WO-03/065977 A2 8/2003
WO WO-2008/095927 A1 8/2008
WO WO-2011/154147 A1 12/2011
WO WO-2012/017081 A1 2/2012
WO WO-2013/144257 A1 10/2013
WO WO-2014/153470 A2 9/2014
WO WO-2015/136072 A1 9/2015
WO WO-2016/069282 A1 5/2016
WO WO-2016/073755 A2 5/2016
WO WO-2016/146618 A1 9/2016
WO WO-2016/193299 A1 12/2016

OTHER PUBLICATIONS

Ziemann et al. Gene name errors are widespread in the scientific literature. 2016. Genome Biology. Vol. 17, No. 177, 3 pages. (Year: 2016).*

Guo et al., "Rapid cloning, expression, and functional characterization of paired αβ and γδ T-Cell receptor chains from single-cell analysis," Molecular Therapy—Methods and Clinical Development, vol. 3, No. 15054, 12 pages, (Jan. 2016).

Hamana et al., "A novel, rapid and efficient method of cloning functional antigen-specific T-cell receptors from single human and mouse T-cells," Biochemical and Biophysical Research Communication, vol. 474, No. 4, pp. 709-714 (May 2016).

Han et al., "Linking T-cell receptor sequence to function al phenotype at the single-cell level," Nature Biotechnology, vol. 32, No. 7, pp. 684-692 (Jun. 2014).

Kobayashi et al., "A new cloning and expression system yields and validates TCRs from blood lymphocytes of patients with cancer within 10 days," Nature Medicine, vol. 19, No. 11, pp. 1542-1546 (Oct. 2013).

Richman et al., "Display, engineering, and applications of antigen-specific T cell receptors," Biomolecular Engineering, vol. 24, No. 4, pp. 361-373 (Sep. 2007).

Zhang et al., "Transduction of Human T Cells with a Novel T-Cell Receptor Confers Anti-HCV Reactivity," PLoS Pathogens, vol. 6, No. 7, e1001018, 13 pages (Jul. 2010).

Karste et al., "Not Limited to *E. coli*: Versatile Expression Vectors for Mammalian Protein Expression," In: Burgess-Brown N. (eds) Heterologous Gene Expression in *E.coli*. Methods in Molecular Biology, vol. 1586, pp. 313-324 (2017) (Available online May 2017).

Office Action dated Jan. 12, 2021, in U.S. Appl. No. 16/347,691 (US 2020-0095574).

(Continued)

*Primary Examiner* — Channing S Mahatan
(74) *Attorney, Agent, or Firm* — Foley & Lardner LLP

(57) ABSTRACT

The present invention relates to a two-part device, wherein a first part is a multicomponent TCR ORF reconstitution and engineering system (TORES), and a second part is a multicomponent engineered TCR-presenting cell system (eTPCS).

32 Claims, 38 Drawing Sheets

Figure 1:
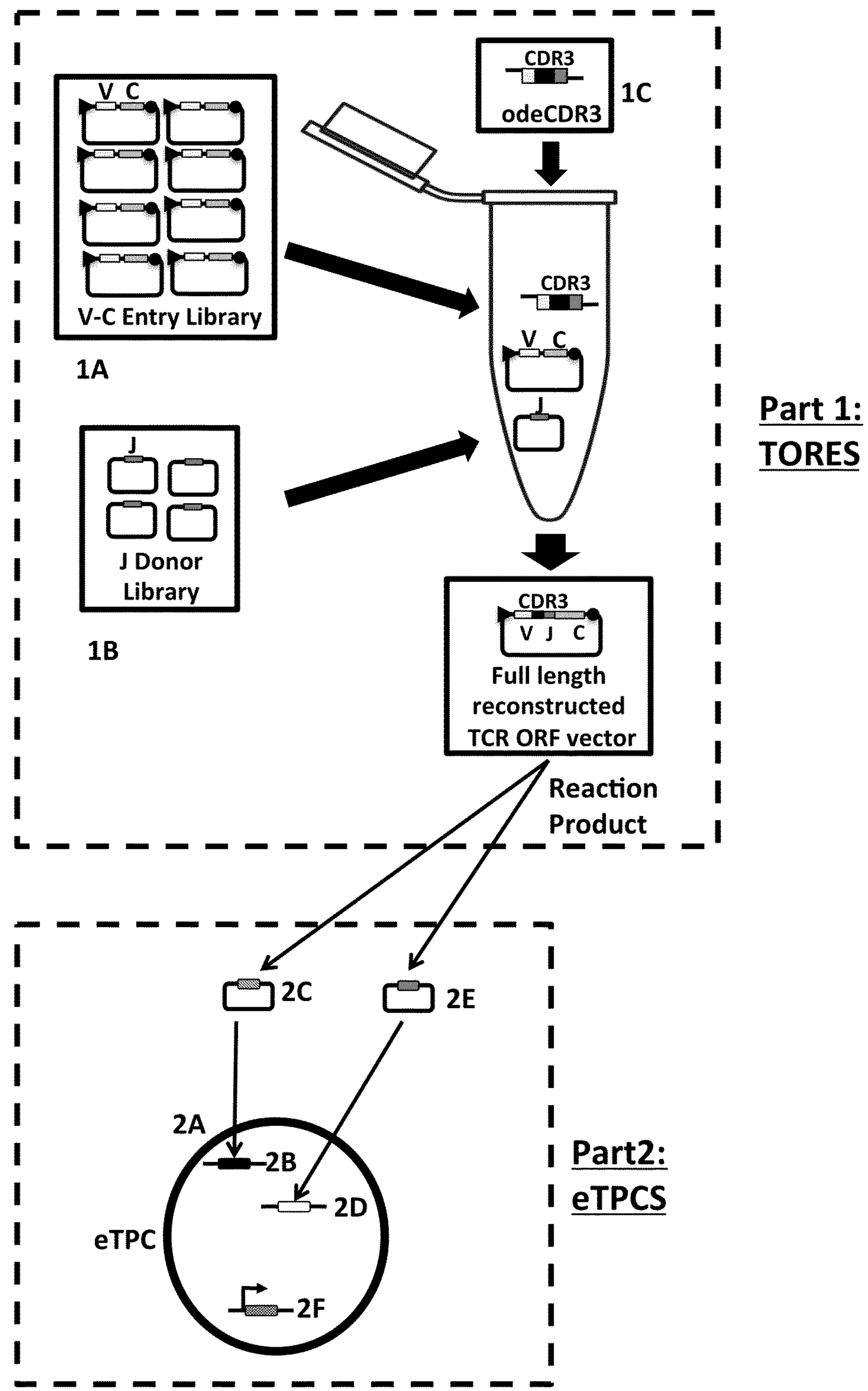

Specification includes a Sequence Listing.

(56) References Cited

OTHER PUBLICATIONS

Turan et al., "Recombinase-Mediated Cassette Exchange (RMCE): Traditional Concepts and Current Challenges," Journal of Microbiology, vol. 407, pp. 193-221 (2011) (Available online Jan. 2011).
Restriction Requirement dated Jun. 26, 2020, in U.S. Appl. No. 16/347,691 (US 2020-0095574).
U.S. Appl. No. 16/632,301, filed Jan. 17, 2020, Jarvis et al.
U.S. Appl. No. 16/863,119, filed Apr. 30, 2020, Jarvis et al.
Butler et al., "A panel of human cell-based artificial APC enables the expansion of long-lived antigen-specific CD4 T cells restricted by prevalent HLA-DR alleles," International Immunology, vol. 22, No. 11, pp. 863-873 (Nov. 2010).
Dupont et al., "Artificial antigen-presenting cells transduced with telomerase efficiently expand epitope-specific, human leukocyte antigen-restricted cytotoxic T cells," Cancer Research, American Association for Cancer Research, vol. 65, No. 12, pp. 5417-5427, (Jun. 2005).
Latouche et al., "Induction of human cytotoxic T lymphocytes by artificial antigen-presenting cells," Nature Biotechnology, vol. 18, No. 4 pp. 405-409 (Apr. 2000).
Turan et al., "Recombinase-mediated cassette exchange (RMCE)—A rapidly-expanding toolbox for targeted genomic modifications," Gene, vol. 515, No. 1, pp. 1-27, (Feb. 2013) (Available online Nov. 2012).
Bhatta et al., "Engagement of CD45 alters early signaling events in human T cells co-stimulated through TCR + CD28," Cellular Immunology 353 (2020) 104130, pp. 1-11 (Available online May 13, 2020).
CD3 (immunology)—Wikipedia; pp. 1-3, downloaded Apr. 19, 2021. Available online, URL: https://en.wikipedia.org/wiki/CD3_(immunology).
Office Action dated Apr. 22, 2021 in U.S. Appl. No. 16/347,691 (US 2020-0095574).
Baser et al. "A method for specifically targeting two independent genomic integration sites for co-expression of genes in CHO cells" Methods 95, pp. 3-12 (2016) (Available online Dec. 2015).

* cited by examiner

V cloning Fragment example

C cloning Fragment example

V-C entry vector backbone example

J receiving cassette fragment example

J Donor vector backbone example

J receiving cassette vector example

Figure 31

| Overhang *5’ | J segment part | A | Overhang *6’ |
|---|---|---|---|

J segment part example

TCRa expected size:566 bp

TCRb expected size:610 bp

TWO-PART DEVICE FOR T-CELL RECEPTOR SYNTHESIS AND STABLE GENOMIC INTEGRATION TO TCR-PRESENTING CELLS

CROSS-REFERENCE TO RELATED APPLICATIONS

The present application is the U.S. National Stage of International Application No. PCT/EP2017/078378, filed Nov. 7, 2017, and claims priority to Denmark Patent Application Nos. PA 2016 70875, filed Nov. 7, 2016 and PA 2017 70577, filed Jul. 18, 2017, and European Patent Application No. 17181798.4, filed Jul. 18, 2017.

SEQUENCE LISTING

The instant application contains a Sequence Listing, which has been filed electronically in ASCII format and is hereby incorporated by reference in its entirety. Said ASCII copy, created on Aug. 17, 2020, is named 114621-0109_SL.txt and is 434,176 bytes in size.

FIELD OF THE INVENTION

The present invention relates to the construction, assembly and use of a two-part device for rapid synthesis of native and sequence-diversified T-cell receptor (TCR) open reading frames (ORFs), and the integration of these TCR ORFs to the genome of TCR-presenting cells. Due to the large degree of diversity generated in the natural TCR genesis process by somatic recombination, it is challenging to provide TCR open reading frames (ORFs) within genetic constructs on a high-throughput and cost-effective basis for testing and manipulation of TCR function. The first part of the present invention provides a pre-assembled two-component vector library system consisting of Variable-Constant entry vectors (V-C entry) and Joining donor (J donor) vectors comprising portions of TCR gene segments. The two component system is designed in such a way that when a V-C entry vector selected from the V-C entry vector library is combined with a J donor vector selected from the J donor vector library, along with a synthetic DNA oligonucleotide duplex encoding TCR complementarity determining region 3 (odeCDR3) in a restriction enzyme digestion/ligase cycle reaction, a single vector is created reconstituting the full-length TCR ORF. Such a vector library system enables PCR-independent methods for rapid and cost effective generation of TCR ORFs in a selected vector context. In addition, this system permits novel workflows for generating synthetic TCR sequences for affinity and/or functional maturation workflows. This TCR ORF Reconstitution and Engineering System (TORES) is thus a strong tool for TCR functional analysis and engineering, when combined with the second part of the present invention, which represents an engineered TCR-presenting cell (eTPC). These eTPC cells contain a pair of synthetic genomic receiver sites that are paired with the TCR-encoding vector outputs from the TORES. Thus, TCR ORFs generated within the TORES are directly submitted to integration to the genome of an eTPC, such that the eTPC may be used for rapid, high-throughput generation of stable derivative cells that present TCR pairs (eTPC-t) for various analytical purposes. Importantly, the eTPC constitutively expresses all components of the CD3 complex, but lacks endogenous expression of TCR alpha, beta, gamma and delta chains. Overall, this two-part device may be used to rapidly generate eTPC-t as central components for analytical and clinical immunodiagnostic systems. Furthermore, the present invention relates to the use of the two-part device to identify, characterise and engineer TCRs for diagnostics, medicine, research and development.

INTRODUCTION TO THE INVENTION

Immune surveillance by T lymphocytes (T-cells) is a central function in the adaptive immunity of all jawed vertebrates. Immune surveillance by T-cells is achieved through a rich functional diversity across T-cell subtypes, which serve to eliminate pathogen-infected and neoplastic cells and orchestrate adaptive immune responses to invading pathogens, commensal microorganisms, commensal non-self factors such as molecular components of foodstuffs, and even maintain immune tolerance of self. In order to respond to various foreign and self factors, T-cells must be able to specifically detect molecular constituents of these foreign and self factors. Thus T-cells must be able to detect a large cross-section of the self and non-self molecules that an individual encounters, with sufficient specificity to mount efficient responses against pathogenic organisms and diseased self, while avoiding the mounting of such responses against healthy self. The highly complex nature of this task becomes clear when considering the practically unlimited diversity of both foreign and self molecules, and that pathogenic organisms are under evolutionary pressure to evade detection by T-cells.

The T-Cell Receptor (TCR)

T-cells are primarily defined by the expression of a T-cell receptor (TCR). The TCR is the component of the T-cell that is responsible for interacting with and sensing the targets of T-cell adaptive immunity. In general terms, the TCR is comprised of a heterodimeric protein complex presented on the cell surface. Each of the two TCR chains are composed of two extracellular domains, being the variable (V)-region and the constant (C)-region, both of the immunoglobulin superfamily (IgSF) domain, forming antiparallel β-sheets. These are anchored in the cell membrane by a type-I transmembrane domain, which adjoins a short cytoplasmic tail. The quality of the T-cells to adapt and detect diverse molecular constituents arises from variation in the TCR chains that is generated during T-cell genesis. This variation is generated by somatic recombination in a similar manner to antibody genesis in B-cells.

TCR Chain Diversity

The T-cell pool consists of several functionally and phenotypically heterogeneous subpopulations. However, T-cells may be broadly classified as αβ or γδ according to the somatically rearranged TCR isoform they express at their surface. There exist two TCR chain pair isoforms; TCR alpha (TRA) and TCR beta (TRB) pairs; and TCR gamma (TRG) and TCR delta (TRD) pairs. T-cells expressing TRA:TRB pairs are referred to as αβ T-cells, while T-cells expressing TRG:TRD pairs are often referred to as γδ T-cells.

TCRs of both αβ and γδ forms are responsible for recognition of diverse ligands, or 'antigens', and each T-cell generates αβ or γδ receptor chains de novo during T-cell maturation. These de novo TCR chain pairs achieve diversity of recognition through generation of receptor sequence diversity in a process called somatic V(D)J recombination after which each T-cell expresses copies of a single distinctly rearranged TCR. At the TRA and TRG loci, a number of discrete variable (V) and functional (J) gene segments are available for recombination and juxtaposed to a constant (C) gene segments, thus referred to as VJ recombination.

Recombination at the TRB and TRD loci additionally includes a diversity (D) gene segment, and is referred to as VDJ recombination.

Each recombined TCR possess potential for unique ligand specificity, determined by the structure of the ligand-binding site formed by the α and β chains in the case of αβ T-cells or γ and δ chains in the case of γδ T-cells. The structural diversity of TCRs is largely confined to three short hairpin loops on each chain, called complementarity-determining regions (CDR). Three CDRs are contributed from each chain of the receptor chain pair, and collectively these six CDR loops sit at the membrane-distal end of the TCR extracellular domain to form the antigen-binding site.

Sequence diversity in each TCR chain is achieved in two modes. First, the random selection of gene segments for recombination provides basal sequence diversity. For example, TRB recombination occurs between 47 unique V, 2 unique D and 13 unique J germline gene segments. In general, the V gene segment contributes both the CDR1 and CDR2 loops, and are thus germline encoded. The second mode to generate sequence diversity occurs within the hypervariable CDR3 loops, which are generated by random deletion of template nucleotides and addition of non-template nucleotides, at the junctions between recombining V, (D) and J gene segments.

TCR:CD3 Complex

Mature αβ and γδ TCR chain pairs are presented at the cell surface in a complex with a number of accessory CD3 subunits, denoted ε, γ, δ and ζ. These subunits associate with αβ or γδ TCRs as three dimers (εγ, εδ, ζζ). This TCR:CD3 complex forms the unit for initiation of cellular signalling responses upon engagement of a αβ or γδ TCR with cognate antigen. The CD3 accessories associated as a TCR:CD3 complex contribute signalling motifs called immunoreceptor tyrosine-based activation motifs (ITAMs). CD3ε, CD3γ and CD35δ each contribute a single ITAM while the CD3ζ homodimer contains 3 ITAMs. The three CD3 dimers (εγ, εδ, ζζ) that assemble with the TCR thus contribute 10 ITAMs. Upon TCR ligation with cognate antigen, phosphorylation of the tandem tyrosine residues creates paired docking sites for proteins that contain Src homology 2 (SH2) domains, such as the critical ζ-chain-associated protein of 70 kDa (ZAP-70). Recruitment of such proteins initiate the formation of TCR:CD3 signalling complexes that are ultimately responsible for T-cell activation and differentiation.

αβ T-cells

αβ T-cells are generally more abundant in humans than their γδ T-cell counterparts. A majority of αβ T-cells interact with peptide antigens that are presented by complexes on the cell surface. These complexes are referred to as Major Histocompatibility Complexes (MHC), encoded by Human Leucocyte Antigen (HLA) family of genes, for simplicity both the gene and MHC will collectively be referred to herein as HLA. Peptide-HLA (pHLA)-recognising T-cells were the first to be described and are by far the best characterised. More rare forms of αβ T-cells have also been described. Mucosal-associated invariant T (MAIT) cells appear to have a relatively limited a and p chain diversity, and recognise bacterial metabolites rather than protein fragments. The invariant natural killer T-cells (iNK T-cells) and germline-encoded mycolyl-reactive T-cells (GEM T-cells) are restricted to recognition of glycolipids that are cross-presented by non-HLA molecules. iNK T-cells are largely considered to interact with CD1d-presented glycolipids, whereas GEM T-cells interact with CD1b-presented glycolipids. Further forms of T-cells are thought to interact with glycolipids in the context of CD1a and CD1c, however, such cells are yet to be characterised in significant detail.

Conventional αβ T-Cells

The key feature of most αβ T-cells is the recognition of peptide antigens in the context of HLA molecules. These are often referred to as 'conventional' αβ T-cells. Within an individual, self-HLA molecules present peptides from self and foreign proteins to T-cells, providing the essential basis for adaptive immunity against malignancies and foreign pathogens, adaptive tolerance towards commensal organisms, foodstuffs and self. The HLA locus that encodes HLA proteins is the most gene-dense and polymorphic region of the human genome, and there are in excess of 12,000 alleles described in humans. The high degree of polymorphism in the HLA locus ensures a diversity of peptide antigen presentation between individuals, which is important for immunity at the population level.

HLA Class I and II

There are two forms of classical HLA complexes: HLA class I (HLAI) and HLA class II (HLAII). There are three classical HLAI genes: HLA-A, HLA-B, HLA-C. These genes encode a membrane-spanning α-chain, which associates with an invariant β2-microglobulin (β2M) chain. The HLAI α-chain is composed of three domains with an immunoglobulin fold: α1, α2 and α3. The α3 domain is membrane-proximal and largely invariant, while the α1 and α2 domains together form the polymorphic membrane-distal antigen-binding cleft. There are six classical HLAII genes: HLA-DPA1, HLA-DPB1, HLA-DQA1, HLA-DQB1, HLA-DRA, and HLA-DRB1. These genes encode paired DP, DQ and DR heterodimeric HLA complexes comprising a α-chain and a β-chain. Each chain has two major structural domains with an immunoglobulin fold, where the α2 and β2 domain comprise membrane-proximal and largely invariant modules similar to that of HLAI α3 domain. The HLAII α2 and β2 domains together form the membrane-distal antigen-binding cleft and are regions of high polymorphism.

The antigen-binding cleft of HLAI and HLAII comprises two anti-parallel α-helices on a platform of eight anti-parallel β-sheets. In this cleft the peptide antigen is bound and presented in an extended conformation. The peptide-contacting residues in HLAI and HLAII are the location of most of the sequence polymorphism, which constitutes the molecular basis of the diverse peptide repertoires presented by different HLA alleles. The peptide makes extensive contacts with the antigen-binding cleft and as a result each HLA allele imposes distinct sequence constraints and preferences on the presented peptides. A given peptide will thus only bind a limited number of HLAs, and reciprocally each allele only accommodates a particular fraction of the peptide collection from a given protein. The set of HLAI and HLAII alleles that is present in each individual is called the HLA haplotype. The polymorphism of HLAI and HLAII genes and the co-dominant expression of inherited alleles drives very large diversity of HLA haplotype across the human population, which when coupled to the enormous sequence diversity of αβ TCR, presents high obstacles to standardisation of analysis of these HLA-antigen-TCR interactions.

αβ TCR Engagement of HLAI and HLAII

The αβ TCR recognize peptides as part of a mixed pHLA binding interface formed by residues of both the HLA and the peptide antigen (altered self). HLAI complexes are presented on the surface of nearly all nucleated cells and are generally considered to present peptides derived from endogenous proteins. T-cells can thus interrogate the endogenous cellular proteome of an HLAI-presenting cell by sampling pHLAI complexes of an interacting cell. Engagement of HLAI requires the expression of the TCR co-receptor CD8 by the interacting T-cell, thus HLAI sampling is restricted to $CD8^+$ αβ T-cells. In contrast, the surface presentation of HLAII complexes is largely restricted to professional APC, and are generally considered to present peptides derived from proteins exogenous to the presenting cell. An interacting T-cell can therefore interrogate the proteome of the extracellular microenvironment in which the presenting cell resides. The engagement of HLAII requires the expression of the TCR co-receptor CD4 by the interacting T-cell, thus HLAII sampling is restricted to $CD4^+$ αβ T-cells.

Thymic Selection of αβ TCR

The role of αβ TCR as described above is the detection of pHLA complexes, such that the TCR-presenting T-cell can raise responses germane to the role of that T-cell in establishing immunity. It should be considered that the αβ TCR repertoire generated within an individual must account for the immense and unforeseen diversity of all foreign antigens likely to be encountered in the context of a specific haplotype and prior to their actual occurrence. This outcome is achieved on a background where extremely diverse and numerous αβ TCRs are generated in a quasi-randomised manner with the potential to recognise unspecified pHLA complexes while only being specifically instructed to avoid strong interactions with self pHLA. This is carefully orchestrated during T-cell maturation in a process call thymic selection.

During the first step of T-cell maturation in the thymus, T-cells bearing αβ TCRs that are incapable of interacting with self-pHLA complexes with sufficient affinity, are deprived of a survival signal and eliminated. This step called positive selection assures that the surviving T-cells carry a TCR repertoire that is at least potentially capable of recognizing foreign or altered peptides presented in the right HLA context. Subsequently, αβ TCR that strongly interact with self-pHLA and thus have the potential to drive autoimmunity are actively removed through a process of negative selection. This combination of positive and negative selection results in only T-cells bearing αβ TCRs with low affinity for self-pHLA populating the periphery. This establishes an αβ T-cell repertoire that is self-restricted but not self-reactive. This highly individualised nature of T-cell genesis against HLA haplotype underscores the challenges in standardised analysis αβ TCR-antigen-HLA interactions. Moreover, it forms the basis of both graft rejection and graft versus host disease and the general principle that αβ TCRs identified in one individual may have completely different effect in a second individual, which has clear implications for TCR-based and T-cell based therapeutic and diagnostic strategies emerging in clinical practice.

Unconventional αβ T-Cells

The non-HLA-restricted, or 'unconventional', forms of αβ T-cells have very different molecular antigen targets. These unconventional αβ T-cells do not engage classical HLA complexes, but rather engage conserved HLA-like proteins such as the CD1 family or MR1. The CD1 family comprises four forms involved in antigen cross-presentation (CD1a, b, c and d). These cell surface complexes have an α-chain resembling HLAI, which forms heterodimers with β2M. A small hydrophobic pocket presented at the membrane distal surface of the α-chain forms a binding site for pathogen-derived lipid-based antigens. Innate like NK T-cells (iNK T-cells) form the most well understood example of lipid/CD1 family recognition and GEM T-cells representing another prominent example. The 'Type I' iNK T-cells are known to interact strongly with the lipid α-GalCer in the context of CD1d. These iNK T-cells display very limited TCR diversity with a fixed TCR α-chain (Vα10/Jα18) and a limited number of β-chains (with restricted vβ usage) and they have been likened to innate pathogen-associated molecular patterns (PAMPS) recognition receptors such as Toll-like and Nod-like receptors. In contrast, 'Type II' NK T-cells present a more diverse TCR repertoire, and appear to have a more diverse mode of CD1d-lipid complex engagement. GEM T-cells recognize mycobacteria-derived glycolipids presented by CD1b, however, the molecular details of antigen presentation by CD1a, b and c as well as their T-cell recognition are only beginning to be understood.

MAIT cells largely express an invariant TCR α-chain (TRAV1-2 ligated to TRAJ33, TRAJ20, or TRAJ12), which is capable of pairing with an array of TCR β-chains. Instead of peptides or lipids MAIT TCRs can bind pathogen-derived folate- and riboflavinbased metabolites presented by the HLAI-like molecule, MR1. The limited but significant diversity in the TCRs observed on MAIT TCRs appear to enable the recognition of diverse but related metabolites in the context of the conserved MR1.

It is not well-understood how non-classical HLA-restricted αβ T-cell TCRs are selected in the thymus during maturation. However, it appears likely that the fundamental process of negative and positive selection outlined above still applies and some evidence suggests that this occurs in specialized niches within the thymus.

γδ T-Cells

In contrast to the detailed mechanistic understanding of αβ TCR genesis and pHLA engagement, relatively little is known about the antigen targets and context of their γδ T-cell counterparts. This is in part due to their relatively low abundance in the circulating T-cell compartment. However, it is broadly considered that γδ T-cells are not strictly HLA restricted and appear to recognize surface antigen more freely, similar to antibodies. More recently it has become appreciated that γδ T-cells can dominate the resident T-cell compartment of epithelial tissues, the main interaction site of the immune system with foreign antigen. In addition, various mechanisms for γδ T-cell tumour immunuosurveillance and surveillance of other forms of dysregulated-self are beginning to emerge in the literature. The specific antigen targets of both innate-like and adaptive γδ T-cells remain poorly defined but the tissue distribution and fast recognition of PAMPs suggests a fundamental role for γδ T-cells both early in responses to foreign antigens as well as early in life when the adaptive immune system is still maturing.

The diverse functions of γδ T-cells appear to be based on different Vγ Vδ gene segment usage and can be broadly understood in two main categories in which γδ T-cells with largely invariant TCRs mediate innate-like recognition of PAMPs very early during infection. Beyond PAMPs these type of γδ T-cells are furthermore believed to recognize self-molecules, including phosphoantigens that could provide very early signatures of cellular stress, infection and potentially neoplastic development. Recognition of PAMPs and such so-called danger associated molecular patterns (DAMPS) as well as the large numbers of tissue-restricted innate-like γδ T-cells strongly suggests that these cells are suited to respond rapidly to antigenic challenge without the need for prior activation, homing and clonal expansion.

A second form of γδ T-cells are considered to be more adaptive in nature, with a highly diverse γδ TCR repertoire and the ability to peripherally circulate and access lymphoid tissues directly. Such antigen-specific γδ T-cells have been described for common human pathogens such as CMV and they appear to form a memory response. However, it has also been observed that γδ T-cells show only relatively limited clonal proliferation after activation and little data is available on the extent of TCR diversity and specific responses of γδ T-cells in peripheral circulation, or in tissues. Furthermore, while it is generally considered that γδ TCRs do not interact with pHLA complexes and thus, do not engage with peptide antigens in this context, only a few antigen targets of γδ T-cells have been characterised and the underlying molecular framework is only poorly understood.

The low frequency of peripheral γδ T-cells and the difficulty to study tissue-resident T-cells in humans has limited our knowledge of how this important and diverse type of T-cells participate in adaptive immune responses. This emerging area of research would require more reliable technologies with which to capture and characterise rare γδ T-cells, isolate their TCR pairs, and to identify their cognate antigens.

Antigens and Antigen-Presenting Cells

In the context of T-cells and TCRs, antigens may be defined as any molecule that may be engaged by a TCR and resulting in a signal being transduced within the T-cell. The most well characterised T-cell antigens are peptides presented in an HLAI and HLAII complex, and which are engaged by conventional αβ T-cells. However, in recent years it has become apparent that non-conventional αβ T-cells and γδ T-cells are able to engage a wide range of biomolecules as antigens, including lipids, lipopeptides, glycopeptides, glycolipds and a range of metabolites and catabolites. In addition, it has emerged that γδ T-cells may be able to engage fully folded proteins directly in an antibody-like fashion. Therefore, the view of T-cell antigens being largely restricted to HLA-presented peptides has expanded over the past two decades to include almost any biomolecule. With this concept in mind, it is relevant to define what may be considered an antigen-presenting cell (APC).

As defined in the previous sections, HLAI and HLAII have a disparate expression profiles across cell types. It is widely accepted that nearly all nucleated cells present HLAI complexes on the cell surface, and are thus competent to present peptide antigens for T-cell sampling. In contrast, HLAII has a restricted expression profile, and at least in steady state conditions is only expressed on the surface of cells that have a specialist role in antigen presentation, including dendritic cells (DC), macrophage and B-cells. These specialist cell types are often referred to as professional APC. For the purposes of this document, the term APC is used to describe any nucleated cell that is capable of presenting an antigen for sampling by αβ or γδ T-cells. Such antigens are not restricted to those presented as 'cargo' in specific antigen-presenting complexes such as HLA and HLA-like molecules, but may also include any cell-surface presented moiety that is able to engage a αβ or γδ TCR-bearing cell.

Therapeutic Use of TCRs

Adoptive transfer of primary T-cells was first trialled in a clinical setting in the early 1990s, starting with ex vivo expanded T-cells polarised towards viral antigens to confer viral immunity in immunocompromised patients. Similar approaches using primary T-cells expanded ex vivo against specific cancer antigens were soon after trialled in treatment of malignancies. One limitation in these early approaches that continues to be a challenge today is a lack of understanding of the nature and diversity of T-cells clashing with the need to finely-optimize their composition in the therapeutic product. At present, the use of ex vivo expanded primary T-cells has largely been abandoned by the pharmaceutical industry with the exception of a handful of initiatives using primary T-cells with specificity for viral antigens.

In recent years the ability to reliably introduce genetic material into primary human cells has seen a variety of experimental genetically modified T-cell therapeutics arise. Such therapeutic cell products aim to harness the power of T-cell responses and redirect T-cell specificity towards a disease-associated antigen target, for example, an antigen uniquely expressed by malignant cells. These have largely relied on the transfer of a chimeric antigen receptor (CAR) into recipient T-cells, rather than actual TCR chain pairs. A CAR represents a targeting moiety (most often a single-chain antibody element targeting a surface expressed protein of malignant cells) grafted to signal receptor elements such as the ζ-chain of the CD3 complex, to produce a synthetic chimeric receptor that mimics CD3-TCR function. These so-called CAR T-cell (CAR-T) products have met mixed success in clinical trials to date and despite their potential are not easy to translate beyond tumours with inherent unique molecular targets such as B-cell malignancies. Alternatively, the transfer of full-length TCR chain pair ORFs into T-cells is of emerging interest. Such TCR-engineered T-cell therapeutics are at present limited by challenging manufacturing processes, and like the CAR-T products, a dearth of validated antigen targets and targeting constructs. To date this has been focused on the use of αβ TCRs for recognition of peptide antigens presented by HLAI on malignant cells and a fundamental challenge of this approach is the need for antigens that are specific to malignant cells.

It has been considered that since the TCR-pHLA interaction is of relatively low-affinity, native TCRs are likely to be suboptimal for TCR-engineered T-cell therapies. Several approaches have been devised to affinity-mature TCRs in vitro, in much the same manner as single-chain antibody affinity maturation. These TCR affinity maturation approaches generally also utilise a single-chain formats, wherein the V-region of one chain is fused to V-region of another chain to make a single polypeptide construct. Such single polypeptides may then be used in phage- or yeast-display systems adapted from antibody engineering workflows, and passed through rounds of selection based on target binding. Two inherent limitations exist in such a single-chain TCR approach in terms of yielding functional TCR chain pairs. Firstly, the selection is based on binding affinity to the target. However, it has been well documented that TCR affinity does not always correlate to the strength or competency of TCR signalling output. Secondly, the selection of single-chain constructs based on affinity does not always translate to equivalent affinities once they are reconstituted as full-length receptors.

In a therapeutic context, there exists an additional and crucial limitation in affinity-matured TCR pairs. That is, considering their sequences have been altered, the resulting constructs by definition have no longer been subject to thymic selection, wherein TCRs that react strongly to self-antigens are deleted from the repertoire. Therefore, these modified TCRs carry an inherent risk of being auto-reactive, which is very difficult to rule out in vitro using current methods. For the same reason, any selected or engineered TCR for therapeutic application needs to be individualised. If TCRs are artificially engineered or native TCRs applied across individuals, cross-reactivities have to be ruled out on the basis of the HLA haplotype and presented peptide repertoire of each specific individual in order to avoid potentially catastrophic autoimmunity. This is due to the fact that thymic selection is conducted on a background of all available HLA molecules specific only to that given individual. The likelihood of such cross-reactivity is unclear. However, the ability of our TCR repertoire to recognize pHLA complexes of other individuals of the same species as foreign is a fundamental property of adaptive immunity and underpins graft rejection and graft versus host disease. Recent clinical trials using a matured TCR chain pair against the cancer-specific melanoma associated antigen (MAGE) highlighted the potential problem of bypassing thymic selection. When autologous T-cells harbouring the matured TCRs were infused back to two cancer patients, these patients rapidly developed a fatal heart disease. Subsequent studies determined that the MAGE-specific matured TCRs were cross-reactive with an HLAI-presented peptide from the heart protein titin. This strongly suggests that cross-reactivity is a distinct possibility in therapeutic use of TCRs.

A distinct avenue of utilising TCRs for therapeutic purposes is in their use as affinity reagents in much the same manner as antibody therapeutic substances. Single-chain TCR molecules have been trialled for delivery of conjugated drug substances to specific HLA-antigen expressing cell populations. Such an approach is generally considered safer than CAR-T or TCR engineered T-cell therapeutics, as administration of the drug substance may simply be withdrawn. However, the potential for cross-reactivity and off target effects that are difficult to predict remains a potential limitation in this setting.

TCR Repertoire Detection in Clinical Diagnostics

In a related aspect, there is an emerging interest in using the detection of the abundance of specific TCR sequences for clinical diagnostic purposes. With the rise of deep-sequencing methods in particular, it is possible to capture the full TCR diversity within an individual globally and for matched as pairs in specific contexts. This potentially represents a means to diagnose specific conditions and disease states simply by detecting the abundance of expanded T-cell clones, as proxy readout for established immune response against a disease-associated antigen in the patient. However, such global approaches are currently limited to very strong immune responses with established clinical time-points and suffer from the underlying difficulty in identifying the specific antigen target of any particular TCR identified via sequencing.

Therapeutic and Diagnostic Use of T-Cell Antigens

The fundamental strength of harnessing adaptive immune responses translates into a central technical challenge in that the exquisite specificity of the TCR-antigen interaction requires detailed knowledge of the antigens specifically associated with each pathogen, cancer cell or autoimmune disease. Furthermore, each antigen may be presented by a specific antigen presenting complex, or allele thereof, such that antigen discovery must be performed for each relevant HLA gene and allele. For several infectious diseases like HIV, influenza and CMV that are associated with strong adaptive immune responses and generally display conserved epitope response hierarchies, the most important epitopes have been mapped in context of some common HLA. Similarly, the fields of cancer, allergy and autoimmunity have seen increased and systematic efforts to map the associated T-cell antigens. However, these are challenging procedures and the efforts to systematically describe T-cell antigens associated with different clinical contexts are hindered by the absence of efficient, robust, fast and scalable protocols.

Specifically, cancer cells represent a challenging and important aspect as most of the peptides presented on the surface of malignant cells are self antigens or very similar to self antigens. Therefore, thymic selection will have deleted TCRs that could strongly recognize these peptides, while at the same time the tumour has evolved to evade immune recognition. This means that potent immune responses against established tumours are relatively rare and targets difficult to predict or discover. However, these responses do exist and, importantly, are generally associated with better outcome. The target of such responses, tumour-associated-antigens (TAA), will in most cases have distinguishing characteristics from self and be derived from proteins that are overexpressed during cancer development, otherwise absent from the cell type at this stage of development or specifically altered through genetic mutation or post-translational modifications such as phosphorylation.

When available, the knowledge of such epitopes makes it possible to interrogate the associated T-cell response for fundamental discovery, diagnostic purposes and for example as a test of vaccine efficacy. Importantly, they also provide highly specific targets for T-cell tolerization in allergy and autoimmunity and, crucially, point towards valuable targets for specific immunotherapy and against malignant cells. Malignancies represent a particularly valuable target as the promise of cellular immunotherapies and the progress in the T-cell manipulations are slowed by a lack of validated target TAAs that go beyond the few cases where specific markers for the type of cancer happen to be available. In the light of the potential of cellular therapy and lack of validated targets the identification of promising TCR antigens remains one of the most pressing bottlenecks of TCR-based immunotherapy, particularly in the effort to treat cancer.

Technological Aspects of TCR and T-Cell Antigen Analyses

Overall, the development of TCR-based therapies is still in its early stages, and success has been limited. Diagnostic approaches, while of immense potential, have seldom been deployed into controlled clinical studies that aim to assess patient disease states or response to therapy. Underdeveloped techniques for the reliable capture of native TCR chain pairs, and standardised systematic analysis of TCR-antigen interactions at high-throughput and in a functional context of cell-cell communication, has been the main hurdle to the development of TCR-based therapies and diagnostics.

Deep sequencing approaches have led to an improved understanding of T-cell receptor diversity in heath and disease. However, these approaches have generally focused on short stretches spanning the CDR3 regions, mainly of the TCR β-chain. Most studies have ignored the contribution of the TCR α-chain, and few have sought to analyse paired as chains as well as the antigen specificity of TCRs determined to be of interest. Recent workflows using single cell encapsulation and genetic barcoding has enabled the pairing of native TCR αβ or γδ chain pairs and analysis of full-length sequences, however, such workflows remain experimental.

Isolated TCR chain pairs may be analysed in terms of antigen specificity in either biophysical or functional modes. Biophysical analysis requires the recombinant production of both the TCR as well as the analyte antigen in soluble form. In the case of HLA-restricted TCRs this would thus require the generation of all individual TCRs as well as the cognate pHLA complexes. This is technically highly challenging, slow and very low-throughput. Furthermore, such analysis would only provide interaction affinities, which are not well-correlated with functional characteristics in predictable ways.

Until recently, the detailed functional analysis of isolated TCR sequences in a cellular context has been limited to laborious protocols of transfection of analyte TCR chain pairs into primary T-cells or immortal T-cell lines, and detection of cellular responses by traditional flow cytometric analysis of cell activation, or detection of secreted factors from the transfected cells upon antigen challenge. In a recent publication by Guo et al, rapid cloning, expression, and functional characterization of paired TCR chains from single-cells was reported (Molecular Therapy—Methods and clinical development (2016) 3:15054). In this study, analyte human αβ TCR pairs were expressed in a reporter cell line that lacked αβ TCR expression, and which contained a green fluorescent protein (GFP) reporter system linked to the Nur77 promoter that is activated upon TCR stimulation. This system remains inefficient due to the lack of standardised TCR integration into the reporter cell line genome, and does not provide a systematic manner for cell-bound antigen challenge by an APC element.

Similar to workflows for identification of TCRs against known T-cell antigens, the de novo discovery of novel T-cell antigens in health and disease remains highly challenging. Most approaches remain biophysical in nature, and aim to produce candidate antigens that may be tested in immunisation protocols, or through identifying cognate TCRs as addressed above. Little or no standardisation exists in the field of T-cell antigen discovery, and the field is largely restricted to academic study.

With the accumulating interest in TCRs and their cognate antigen in both therapeutic and diagnostic use, and the emergence of means to capture significant numbers of native TCR as and γδ chain pairs, there remains a lack of reliable high-throughput and standardised technologies for the systematic analysis of TCR-antigen interactions. Importantly, there is a lack of standardised systems for functional analysis of TCR chain pairs in the native context of cell-cell communication wherein both the TCR and antigen are presented by a viable cell. Moreover, there is a lack of systems that may achieve TCR candidate selection, and/or affinity/functional maturation of TCR chain pairs, in the relevant context of cell-cell communication.

As described, there is currently a lack of standardised technologies for the high-throughput generation and expression of TCR chains, and their expression in a native cellular context. It is highly desirable to possess a system in which full-length TCRs may be generated rapidly, and inserted as single copies into the genome of a TCR-presenting cell such that said TCRs are presented in a native CD3 cell-surface complex for analysis. A CD3 complex-presented TCR pair assures that affinity analyses are reflective of the actual native TCR composition, which is not the case for single-chain TCR and other non-native TCR-display technology. Moreover, the presentation of TCR pairs in a CD3 complex is an absolute requirement for functional analysis of TCR pairs. Functional analysis, meaning analysis of TCR signalling output, is of critical importance in TCR engineering workflows where signal output is the parameter that is generally of greatest importance for therapeutic use, and is not well-correlated with the affinity of a TCR with cognate antigen/HLA.

DETAILED DESCRIPTION OF THE INVENTION

The present invention addresses the above-mentioned needs. The present invention provides a two-part device suited for the genetic reconstitution and/or sequence diversification of TCR ORFs, and then insertion of these ORFs into engineered TCR-presenting cells (eTPC) for functional analysis and/or selection. Such a device is suitable for obtaining native and/or sequence-diversified chain pairs that may be rapidly analysed and selected in the native cell surface context of a CD3 complex.

The first part of the two-part device contains of a two-component vector system comprising pre-assembled libraries of vectors harbouring variable (V), joining (J) and constant (C) sequences for TCR chains. The first component of the system comprises and V-C entry vector containing V and C sequences (component 1A). The second component of the system comprises a J donor vector containing J sequence (component 1B). The two-component vector system is pre-assembled into libraries of V-C entry vectors and J donor vectors with all desirable V-C sequence combinations and J sequences, respectively. The two-component vector system is designed in such a manner that a single V-C entry vector and a single J donor vector with desired sequences can be combined with a third component, a short DNA oligonucleotide duplex encoding CDR3 (odeCDR3) (component 1C) sequence to reconstitute a full-length TCR ORF in vitro, in a single-tube reaction, in a restriction enzyme and ligase dependent and PCR independent manner. This three component TCR ORF reconstitution and engineering system (TORES) is ideally suited to rapidly generate large libraries of native, sequence-diversified or synthetic TCR ORFs for affinity or functional maturation workflows.

The first part of the present invention, defined as TORES, is summarised in FIG. 1, Part 1. A selected V-C entry vector containing V and C TCR gene segments required for a target full-length TCR ORF is combined with a J donor vector that contains the required J TCR gene segment. The full-length TCR ORF is completed by the addition of an odeCDR3, which accounts for non-germline sequence generated during V(D)J recombination, and interposed by fixed germline encoded V and J sequence encoded by the V-C entry vector and J donor vector, respectively. The two-component vector system, and the third odeCDR3 component, is designed such that when combined into a restriction enzyme and ligase reaction, the desired full V-CDR3-J-C TCR ORF is reconstituted. Thus, this first part of the two-part device is used to assemble TCR ORFs into specific vector contexts, such that these TCR-encoding vectors represent integration vectors for operation of the second part of the two-part device.

The second part of the two-part device, comprises an engineered multicomponent cellular system, defined as engineered T-cell receptor presenting cell system (eTPCS). The second part. The multi-component system, comprised of at least three components summarised in FIG. 1, Part 2. Firstly, an engineered TCR presenting cell (eTPC) (component 2A). secondly containing a pair of engineered genomic receiver sites (component 2B and 2D). Thirdly TCR-encoding genetic integration vectors derived from the first, TORES part, of the two-part device, which match the genomic receiver sites contained within the eTPC (component 2C and 2E). The matched genomic receiver site and integration vector (termed an integration couple) is used for rapid, stable integration of genetic material encoding TCR pairs. The eTPC may also further include an optional fourth component, a TCR-stimulation response element (component 2F), for in vitro detection and characterisation of TCR signalling response.

The two-part device is thus used to obtain native or sequence-diversified TCR ORFs in a specific integration vector context, or libraries thereof, and by combining these integration vectors with a matched eTPC, obtain an analyte eTPC expressing a single TCR pair (eTPC-t), or library thereof.

Figure 24:
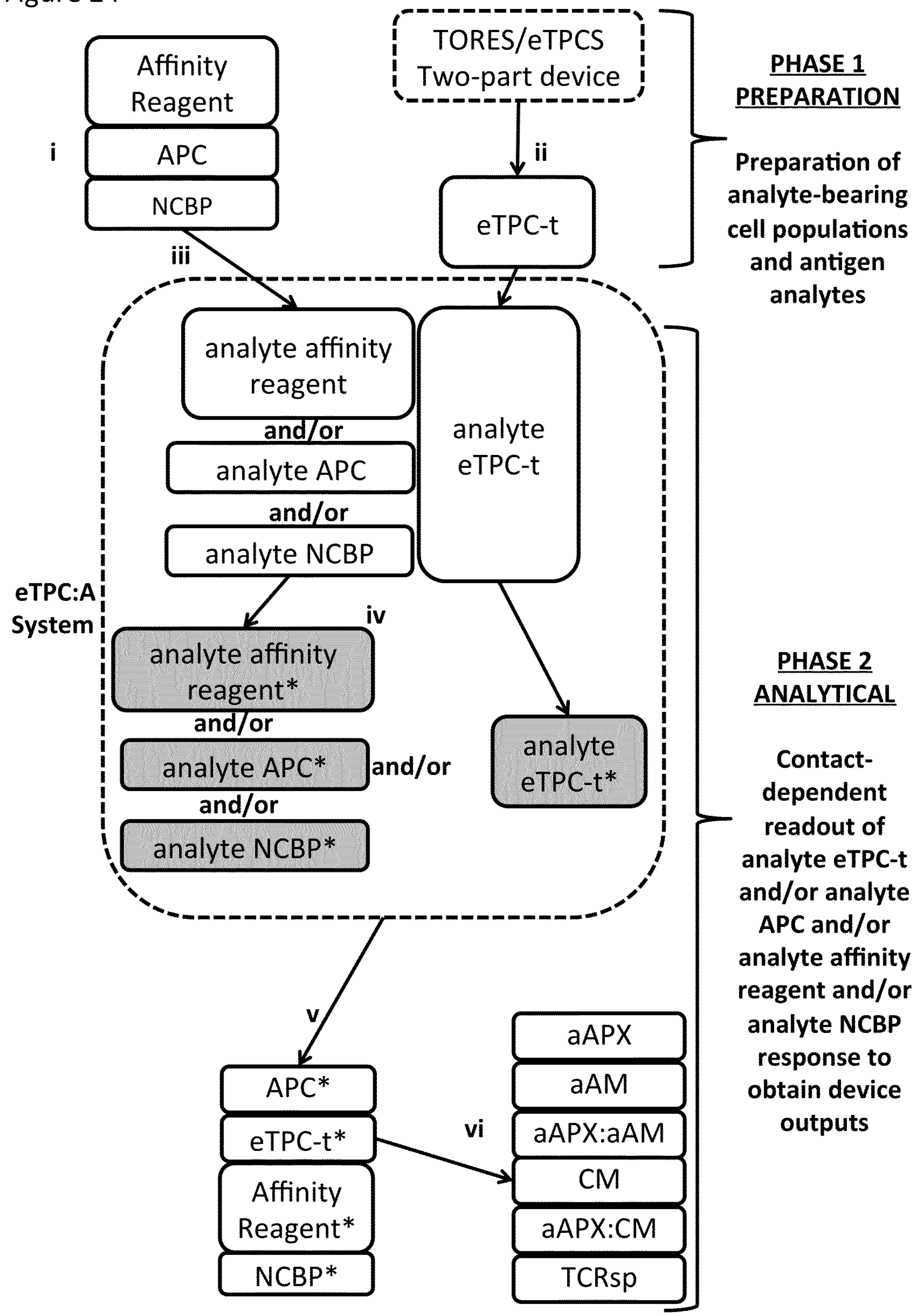

The present invention is used for rapid, high-throughput generation of stable derivative analyte cells that present full-length TCR pairs (eTPC-t). This two-part device is well suited for generating TCR-centric cell-based inputs to an analytical system that may be used directly in both research settings and clinical immunodiagnostic procedures. Thus, the two-part device is generally employed to derive TCR ORFs to subsequently prepare one or more analyte eTPC-t. These analyte eTPC-t are then combined with one or more analyte antigens (collectively the eTPC:Antigen system, eTPC:A) to obtain one or more outputs (FIG. 24). The analyte antigen is provided by analyte antigen-presenting cells (APC) and/or as soluble or immobilised analyte antigen and/or presented on non-cell based particles (NCBP).

The present invention provides a standardised, flexible and systemisable two-part device to generate TCR ORFs (TORES) and engineered cell lines stably expressing TCR pairs on the cell surface (eTPCS). Single TCR ORF pairs may be presented by the engineered cells within the two-part device for detailed analyses, as may libraries of TCR ORFs. The generation of libraries of native or sequence-diversified TCR-presenting cells may be used for analytical or screening purposes to identify or engineer novel TCR specificities, or identify a cognate antigen for particular TCR pairs. The standardisation that is central to the present invention is a significant improvement on existing methodologies in terms of increasing reproducibility, decreasing production cycle times and thus decreasing costs of generating such analyte material. This standardisation is achieved through the robust integration vector/genomic receiver site subsystems that permit reliable ORF integration in controlled copy number at controlled genomic location; a significant improvement over previous random integrative and viral approaches to achieve similar TCR-presenting cells.

TORES: First Part of the Two-Part Device

The first part of the two-part device is denoted a TORES, which comprises a two-component vector system assembled into a library containing all required V, C and J gene segments for reconstitution of target TCR ORFs (FIG. 1, Part 1). For instance, a library can be constructed to contain all gene segments encoding native protein sequences of the human TRA and TRB loci as described in Example 1.

It is sufficient to reconstitute a full-length TCR ORF using TORES, using sequence information that define the target TCR, V, J and C gene segment usage, along with non-germline CDR3 sequence. From this information, the V-C entry vector and J donor vector that correspond to the V/C and J usage of the target TCR ORF are first selected. An odeCDR3, representing a third component of the first part, corresponding the non-germline CDR3 sequence that is needed to complete the full-length TCR ORF is also generated. The three components are combined with a Type IIS restriction enzyme and DNA ligase enzyme in a reaction to generate the target full-length TCR ORF, and by-products, as described in FIG. 2. The resulting reconstituted full-length TCR is contained within the V-C entry vector backbone, thus contains all vector features contained within this parent construct.

Figure 2:
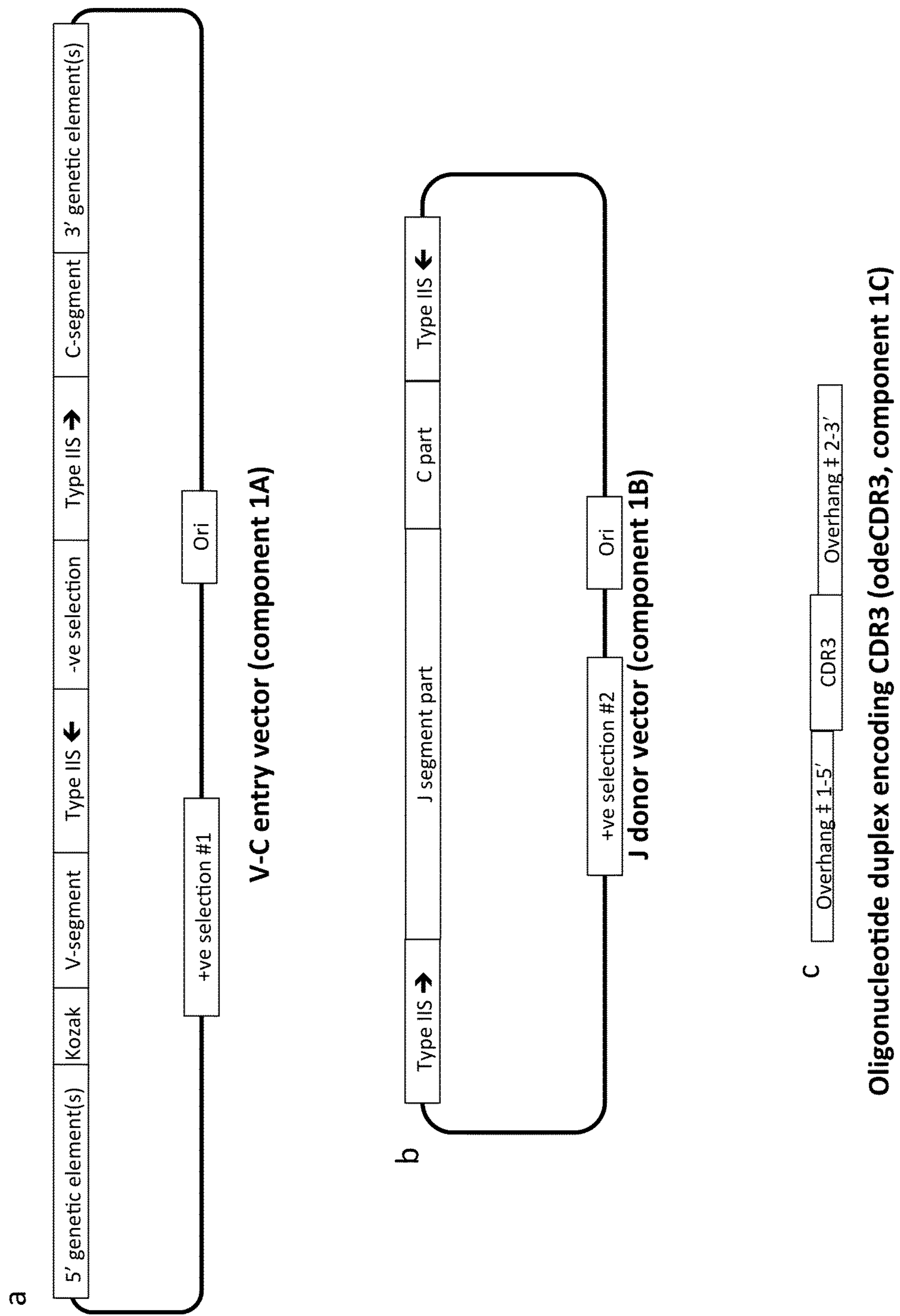
Figure 2:
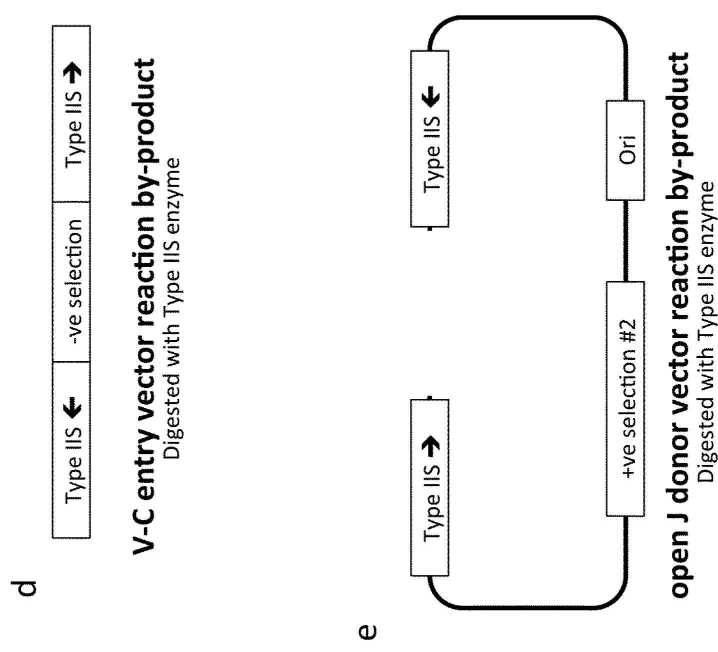
Figure 2:
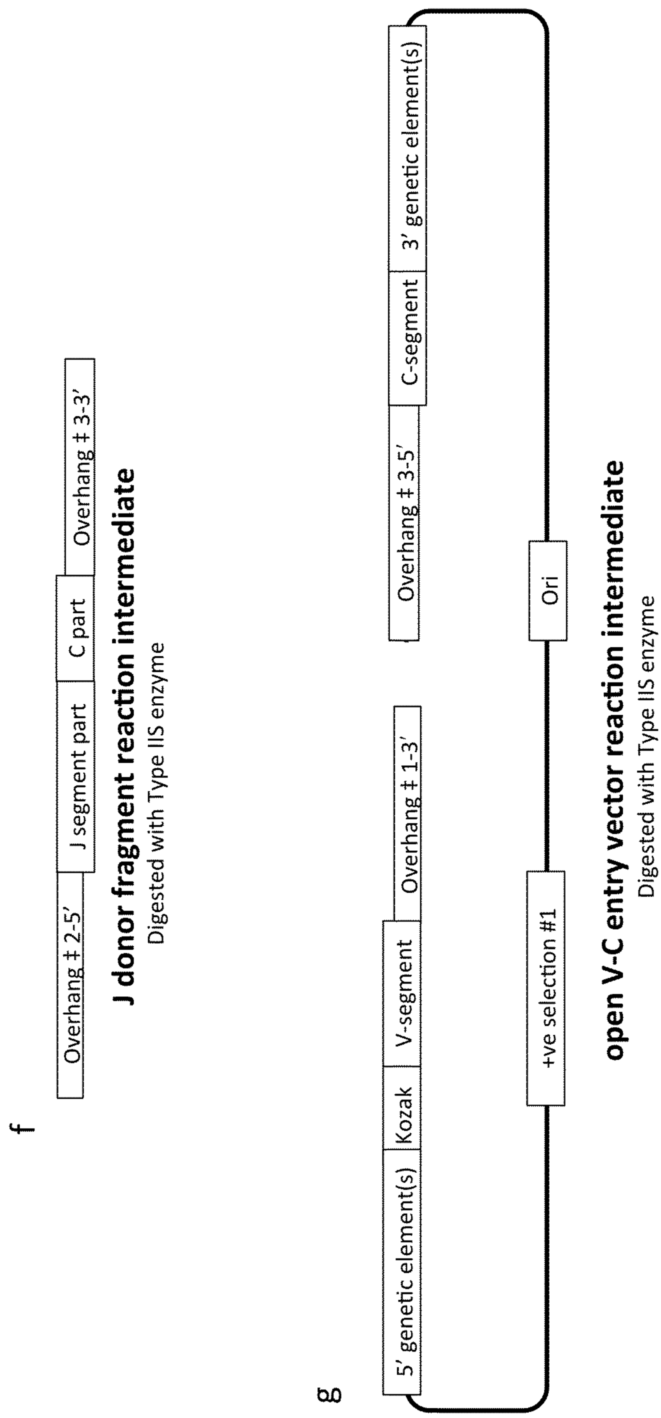
Figure 2:
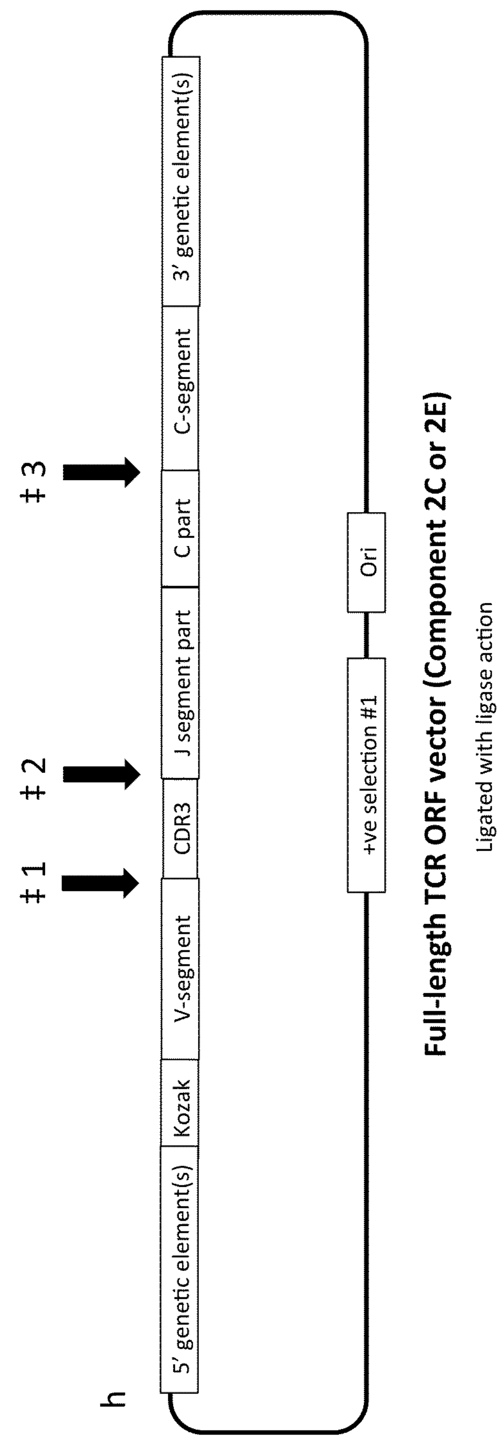

The action of the Type IIS restriction enzyme of the three combined components (FIG. 2,*b*,*c*) within a restriction enzyme/ligase reaction, results in two reaction by-products and two reaction intermediates. The V-C entry vector derived reaction by product is the excised native selection marker and Type IIS binding sites (FIG. 2*d*). The J donor vector backbone from which the J segment part has been excised represents a second reaction by product (FIG. 2*e*). The excised J segment part from the J donor vector represents a reaction intermediate, and contains both a J segment part, a small C part from the C segment, and single stranded overhangs required for ligation (FIG. 2*f*). The second reaction intermediate is the parental V-C entry backbone containing the V and C segments, and single stranded overhangs required for ligation (FIG. 2*g*). The final product of reaction represents a full-length TCR ORF reconstituted within the parental V-C entry vector backbone, comprised of ligation of the odeCDR3 (FIG. 2*c*), the excised J segment part (FIG. 2*f*) and the V-C entry backbone carrying the V and C gene segments (FIG. 2*g*).

The V-C Entry Vector and J Donor Vector Components of the First Part

The first part of the two-part device includes one or more V-C entry vector (component 1A) containing a. origin of replication,
b. a first positive selection marker,
c. 5' genetic element, or elements,
d. Kozak Sequence,
e. TCR variable gene segment,
f. a first Type IIS sequence, for site specific recognition and cleavage by a Type IIS restriction enzyme,
g. a negative selection marker,
h. a second Type IIS sequence
i. TCR constant gene segment, and
j. 3' genetic element, or elements wherein, a) and b) are used for propagation and selection of both parental V-C entry vector and the reconstituted TCR ORF-containing vector in a bacterial host; c) and j) are used to define the mode of integration to a matched genomic receiver site (component 2B or 2D) of the second part of the two part device, and any additional features required for downstream application; d) ensures efficient initiation of translation in eukaryotic cells; e) represents the variable (V) gene segment from the start codon to a motif at the 5' edge of the CDR3 region conserved across all V segments in a given two-component vector system; f) represents a Type IIS recognition sequence that directs a Type IIS restriction enzyme to cut in the 5' direction as to create a standardised single stranded overhang at the 3' end of the V gene segment; g) represents a negative selection marker to eliminate parental V-C entry vector during operation of the system to reconstitute a full-length TCR ORF; h) represents a Type IIS recognition sequence that directs a Type IIS restriction enzyme to cut in the 3' direction as to create a standardised single stranded overhang at the 5' end of the C gene segment; i) represents the C gene segment from a motif at the 5' end of the C gene segment conserved across all C segments, or part of the C gene segment lacking a proportion of the 5' end of the C gene segment, in a given two-component vector system, and which defines the boundary with the J segment (see FIG. 2*a*).

The first part of the two-part device comprises a component designated 1B, includes one or more J-donor vector containing a. origin of replication,
b. a second positive selection marker,
c. a third Type IIS sequence,
d. TCR Joining gene segment,
e. A C part, corresponding to a small 5' portion of a constant gene segment, and
f. a fourth Type IIS sequence.

wherein, a) and b) are used for propagation and selection of the J donor vector; c) represents a Type IIS recognition sequence that directs a Type IIS restriction enzyme to cut in the 3' direction as to create a standardised single stranded overhang at the 5' end of the J gene segment; d) represents the Joining (J) gene segment starting from a 5' motif defining the 3' edge of the CDR3 region conserved across all J segments in a given two-component vector system, to a 3' sequence that incorporates C part, representing a 5' portion of the C segment encoded by V-C entry vector(s) contained within the two-component system; f) represents a Type IIS recognition sequence that directs a Type IIS restriction enzyme to cut in the 5' direction as to create a standardised single stranded overhang at the 3' end of the J gene segment, and contained within the C part portion of the sequence (see FIG. 2*b*).

A J-donor vector does not strictly need to carry a C part sequence, encoding a small 5' portion of the C gene segment. This C part is used to optimise and standardise overhangs for the reconstitution reaction during operation of a TORES. This is because of the higher sequence variation found at the 3' end of J gene segments, such that inclusion of a C part thus allows standardisation by generation of overhangs within the less diverse C gene segment. In the instance of constructing a TORES for a TCR loci from other organism that does not have 3' J segment diversity, or using synthetic J gene segments, this C-part may be omitted in favour of standardisation of overhangs within said J segments. This would reduce the complexity of the J donor library construction.

Each of the first, second, third and fourth Type IIS sequences encoded in the V-C entry vector(s) and J donor vector(s), may be the same or different. Preferably, they are the same. This ensures that each of the restriction sites within the two-component vector system is compatible with the same Type IIS enzyme, and only a single enzyme is needed for the restriction enzyme/ligase reaction during reconstitution of full-length TCR ORF using TORES. Type IIS enzymes do not cut within their recognition sequence, and thus the single-stranded overhangs are generated extrinsic to the recognition sequence. Therefore, the nature of the overhang generated upon Type IIS restriction enzyme action is dependent on both the orientation of the recognition sequence, and indeed the adjacent sequence (see Example 1).

Alternatively, each of the Type IIS restriction sequences may be different from one another. However, with the addition of each unique recognition sequence, an additional Type IIS enzyme must be incorporated into the restriction enzyme/ligase reaction. This would increase the complexity and cost of a reconstitution reaction for assembling a full-length TCR ORF.

The first and second positive selection markers within the V-C entry vector and J donor vector, respectively, are preferably different. This is to ensure that the V-C entry vector, which provides the backbone of the final full-length TCR ORF product, can be selected for independently of the J donor vector, and thus eliminate transformants that carry undigested or re-circularised J donor vectors that would otherwise contribute background to the reconstitution reaction (see FIG. 2).

The positive selection markers can be selected from a. an antibiotic resistance gene, b. an auxotroph complementing gene, c. a reporter gene wherein the choice, formatting and application of such positive selection markers are well known to those skilled in the art.

The 5' genetic element incorporated into a V-C entry vector comprises one or more elements selected from a. gene cis/acting element, b. heterospecific recognition site for recombinase enzymes, c. a 5' homologous recombination arm for a genomic site of interest, d. a mRNA splice acceptor site, e. an internal ribosomal entry site, and f. epigenetic insulator sequence wherein, at least one of b) and c) are included, and are matched to the genomic receiver sites included for as component 2B and 2D of the two part device; a) drives expression of the transcript encoded by the full-length TCR ORF product reconstituted within the V-C entry vector backbone; b) represents a sequence that directs site-directed recombination in the presence of recombinase enzymes to insert the full-length TCR ORF product reconstituted within the V-C entry vector backbone into a specific genomic context of the eTPC of part 2 of the two part device; c) represents a sequence that directs site-directed homologous recombination to insert the full-length TCR ORF product reconstituted within the V-C entry vector backbone into a genomic context of the eTPC of part 2 of the two part device; d) permits engineered domain-fusion approaches to manipulate the form of the protein expressed from the full-length TCR ORF reconstituted in the V-C entry vector backbone e) permits cap-independent initiation of translation of the mRNA expressed from the full-length TCR ORF reconstituted in the V-C entry vector backbone f) permits insulation of transcriptional activity otherwise affected by enhancer elements in a genomic context of where the full-length TCR ORF reconstituted in the V-C entry vector backbone may be inserted.

A cis/acting element may be included to drive expression of TCRs reconstituted into a V-C entry vector backbone once inserted to the genomic receiver sites of the eTPC. However, this would permit transient expression of TCR chains on delivery of the generated integration vectors to the eTPC during integration. Therefore, it is preferential for cis/acting element(s) to be included within the genomic receiver site itself, such that TCR chains may only be expressed once integrated to the correct genomic context.

A V-C entry vector backbone may encode a heterospecific recognition site for recombinase enzymes permitting recombinase mediated cassette exchange (RMCE) of reconstituted full length TCR ORFs, Example 1, when said vector containing a reconstituted TCR ORF is transfected into mammalian cells in the presence of appropriate recombinase enzyme.

A first Type IIS recognition sequence that is included in the V-C entry vector is orientated to cleave 5' of said recognition sequence and within the TCR variable gene segment (FIG. 2*a*) to produce a single-stranded DNA overhang at the 3' end of the variable gene segment (FIG. 2*g*) that is complementary to that at the 5' end of the synthesised odeCDR3 (FIG. 2*c*) For details on how this first Type IIS recognition sequence is designed, see Examples 1 and 2.

A V-C entry vector contains a negative selection marker between the first Type IIS recognition sequence, and the second Type IIS recognition sequence (infra vide, FIG. 2*a*). This negative selection marker is selected from one or more a. a restriction enzyme recognition site not contained elsewhere in the first component or within the TCR joining gene segment, b. a gene encoding a bactericidal agent, c. a reporter element.

wherein, the negative selection marker is used to eliminate host cells transformed with parental V-C entry vector, and thus reduce the background of a reconstitution reaction when using the first positive selection marker to select for transformants containing the target TCR ORF within the V-C entry vector backbone (see Example 3).

With the exception of the negative selection marker itself, all other sequences in the two-part system must be devoid of said sequence as to not confer undue negative selection of the basis of the inclusion of this sequence elsewhere in the system.

In the present context, a second Type IIS recognition sequence that is included in the V-C entry vector is orientated to cleave 3' of said recognition sequence and within the TCR constant gene segment (FIG. 2*a*) to produce a single-stranded DNA overhang at the 5' end of the constant gene segment (FIG. 2*g*) that is complementary to that at the 3' end of the J donor fragment reaction intermediate (FIG. 2*f*) For details on how this second Type IIS recognition sequence is designed, see Examples 1 and 2.

The 3' genetic element incorporated into a V-C entry vector comprises one or more elements selected from a. a terminator element,
b. heterospecific recognition site for recombinase enzymes,
c. a 3' homologous recombination arm for a genomic site of interest,
d. a mRNA splice donor site,
e. an internal ribosomal entry site, and
f. epigenetic insulator sequence.

wherein, at least one of b) and c) are included, and are matched to the genomic receiver sites included for as component 2B and 2D of the two part device; a) represents a sequence that directs transcriptional termination for effective mRNA production of the TCR ORF in situ and may encode a poly-A signal; b) represents a sequence that directs site-directed recombination in the presence of recombinase enzymes to insert the full-length TCR ORF product reconstitute within the V-C entry vector backbone into a specific genomic context of the eTPC of part 2 of the two part device c) represents a sequence that directs site-directed homologous recombination to insert the full-length TCR ORF product reconstituted within the V-C entry vector backbone into a specific genomic context of the eTPC of part 2 of the two part device; d) permits the fusion of a TCR ORF to a transcriptional unit after integration into a genomic locus encoding a downstream mRNA splice acceptor site to manipulate the strength of TCR expression levels or form of the protein expressed from the full-length TCR ORF reconstituted in the V-C entry vector backbone e) permits cap-independent initiation of translation of the mRNA expressed from the full-length TCR ORF reconstituted in the V-C entry vector backbone f) Prevent inappropriate interaction between adjacent chromatin domains, thus insulating the full-length TCR ORF from adjacent transcriptional regulation or spread of heterochromatin in a genomic context of where the reconstituted TCR ORF in the V-C entry vector backbone may be inserted A terminator element may be included to ensure transcriptional termination during expression of TCRs reconstituted into a V-C entry vector backbone, and integrated into the genomic receiver sites of the eTPC. The terminator sequence may also be included within the genomic receiver site itself as outlined in Example 1.

A V-C entry vector backbone may encode a heterospecific recognition site for recombinase enzymes permitting recombinase mediated cassette exchange (RMCE) of reconstituted full length TCR ORFs, Examples 1, when said vector containing a reconstituted TCR ORF is a transfected into eTPC with matched genomic receiver sites in the presence of appropriate recombinase enzyme as outlined in Examples 3, 4 and 5.

A J donor vector contains a J gene segment with a C-part sequence, representing a 5' fragment of the C gene segment, to the 3' of the J gene segment (FIG. 2*b*).

The C-part sequence is designed to standardise the single stranded overhangs generated by Type IIS enzyme action within the at the 3' end of the J donor vector-derived J fragment reaction intermediate (FIG. 2*f*), and that at the 5' end of the C gene segment within the Type IIS digested open V-C entry vector reaction intermediate (FIG. 2*g*).

A third Type IIS recognition sequence that is included in the J donor vector is orientated to cleave 3' of said recognition sequence and within the TCR joining gene segment (FIG. 2*b*) to produce a single-stranded DNA overhang at the 5' end of the joining gene segment (FIG. 2*f*) that is complementary to that at the 5' end of the synthesised odeCDR3 (FIG. 2*c*) For details on how this third Type IIS recognition sequence is designed, see Examples 1 and 2

A fourth Type IIS recognition sequence that is included in the J donor vector is orientated to cleave 5' of said recognition sequence and within the TCR C-part (FIG. 2*b*) to produce a single-stranded DNA overhang at the 3' end of the C-part (FIG. 2*f*) that is complementary to that at the 5' Type IIS digested open V-C entry vector reaction intermediate (FIG. 2*g*). For details on how this third Type IIS recognition sequence is designed, see Examples 1 and 2.

Within the two-part vector system, all vectors sequences should not contain extra Type IIS recognition sequences for the Type IIS restriction enzyme used for TORES assembly reactions. Inclusion of such sequences would result in Type IIS restriction enzyme action within the encoded gene segments or parts, and result in disruption of the TCR reconstitution process. Similarly, the Type IIS recognition sequences should not be included in the odeCDR3 representing a third system component (infra vide).

A two-component vector system of the TORES may be constructed for any collection of TCR chains. In example 1 below, two-component vector systems are constructed for the human TRA and TRB loci, encoding the human TCR alpha and beta chains, respectively. The construction of such a TORES is equally applicable in the context of the TRD and TRG loci, encoding the TCR delta and gamma chain pair, respectively, or indeed for any TRA/TRB, TRD/TRG or variant TCR chain pair system found in jawed vertebrates. Such a TORES system may also incorporate synthetic TCR gene fragments to permit assembly of synthetic variant TCR OFRs for engineering of cell-expressed TCRs or recombinant TCR proteins.

The Third odeCDR3 Component of the First Part of the Two-Part System

To reconstitute a full-length TCR ORF using any given TORES, a small ORF fragment not encoded by the two-component V-C entry vector and J donor vector system is required as a third component. This third component takes the form of an oligonucleotide duplex encoding CDR3 (odeCDR3), designated component 1C.

Such a third component 1C, odeCDR3, comprises a. a first single strand overhang sequence complimentary to the overhang generated by the Type IIS restriction enzyme binding to the first Type IIS recognition site within the TCR variable gene segment of the V-C entry vector,
b. a double strand segment encoding a TCR CDR3 region and devoid of negative selection element, which negative selection element is as defined in claim 10, and also devoid of any Type IIS restriction sequences for the Type IIS restriction enzyme(s) added to the TORES reactions mix.

c. a second single strand overhang sequence complimentary to the overhang generated by the Type IIS restriction enzyme binding to the third Type IIS recognition site within the TCR joining gene segment of the J donor vector.

Alternatively, d. the odeCDR3 can be comprised of a dsDNA molecule encoding the CDR3 flanked by two Type IIS enzymes consistent with the first or second component, oriented such that when digested a product comprising of a, b and c described previously is generated, and two by-products encoding short dsDNA fragments the Type IIS sites. This alternative dsDNA odeCDR3 is compatible the restriction enzyme/ligase reaction, not requiring prior digestion.

Methods to Use a TORES to Reconstitute Full-Length TCR ORFs

A TORES, the first part of the two-part device, can be used to reconstitute a full-length TCR ORF in a genetic vector context, from sequence information, as is presented for a human TRA/TRB chain pair in Example 3.

To operate a TORES to reconstitute a full-length TCR ORF from sequence information, given the resource of a two-component vector system for a given TCR chain, the method comprises a. selecting a V-C entry vector,
b. selecting a J donor vector,
c. selecting an odeCDR3,
d. combining a, b and c to react with i) Type IIS restriction enzyme(s) to cleave all Type IIS restriction enzyme recognition and cleavage sites present in the V-C entry vector and in the J donor vector and ii) DNA ligase enzyme and iii) subjecting the combined mix to a temperature controlled reaction,
e. transforming the reaction product obtained from step d to a selectable host organism competent for DNA vector propagation, and
f. performing a selection of host organism to obtain full length reconstituted TCR open reading frame in the V-C entry vector backbone.

wherein, a) and b) are selected on the basis of the selected vector encoding the V, J and C gene segments in the target full-length TCR ORF; c) is selected on the basis of completing the full-length TCR ORF sequence not encoded by the V-C entry or J donor vectors selected in a) and b), and bounded by the Variable and Joining segments encoded therein; d) combining the three selected components into a reaction mixture along with a restriction enzyme that will cut the first, second, third and fourth Type IIS restriction enzyme recognition sequences within the V-C entry and J donor vectors; e) generally represents transformation-competent bacteria; f) selection of host is on the basis of the first positive selection marker provided by the V-C entry vector backbone.

Generally, a workflow to select and define the genetic elements of a full-length TCR ORF for reconstitution entails de novo sequencing of TCR chains from target organism tissues. A generalised workflow, would incorporate reverse transcription and PCR based amplification of TCR chain pairs from sorted single cells with subsequent Sanger sequencing. Alternative sequencing methods may be applied; the generally critical parameter is to maintain TCR ORF pairing. Moreover, There exists a requirement for high-quality sequence information spanning V, CDR3, J and C segments of the TCR ORF, which dictates the specific sequencing approach(es) taken.

A method for selecting and reconstituting a TCR open reading frame thus comprises a. Obtaining a TCR open reading frame sequence wherein said sequence information is sufficient to identify i) variable gene segment usage ii) constant gene segment usage iii) joining gene segment usage iv) a full CDR3 sequence spanning the variable gene segment border to the joining gene segment border, and
b. selecting a V-C entry vector corresponding to the variable and constant gene segments identified in step a. i) and a. ii), respectively, and
c. selecting a J donor vector corresponding to the joining gene segment identified in step a, iii), and
d. generating an odeCDR3 corresponding to CDR3 sequence identified in step a. iv), and
e. combining b, c and d to react with i) Type IIS restriction enzyme(s) to cleave all Type IIS restriction enzyme recognition and cleavage sites present in the V-C entry vector and in the J donor vector and ii) DNA ligase enzyme, iii) subjecting the combined mix to a temperature controlled reaction, and
f. transforming the reaction product obtained from step e. to a selectable host organism competent for plasmid replication, and
g. performing a selection of host organism to obtain full length reconstituted TCR ORF in the V-C entry vector backbone.

wherein, a) is conducted by sequencing methods well known to one skilled in the art, able to obtain sufficient sequence length and quality to identify all four required genetic elements; b) and c) are selected from a TORES library containing required vectors; d) is synthesised de novo, or selected from a odeCDR3 library; e) is conducted in a single reaction vessel.

In order to select the appropriate V-C entry vector, J donor vector and odeCDR3, target TCR sequences were aligned against a library of V, C and J gene segments for their corresponding TCR chains to determine the V, C and J segment usage of the target chain. This sequence alignment and analysis step must also permit the definition of the CDR3 coding sequence, and thus the definition of odeCDR3 sequence. Thus, overall such sequence analysis permits the selection of V-C entry vectors and J donor vectors for TCR chain reconstitution. The analysis also permits the synthesis of odeCDR3 for each chain reconstitution reaction.

It is desirable to conduct the Type IIS digestion and DNA ligase-dependent ligation (step e) in a single reaction. This minimises processing steps, and is made possible by the design of the system, with Type IIS restriction enzymes cutting outside their recognition sequences, such that a number of unique overhangs may be generated with a single enzyme, thus maintaining efficient directional cloning of the J donor vector reaction intermediate and odeCDR3 into the V-C entry vector backbone.

Alternatively, the Type IIS restriction digest and DNA ligation may be performed in sequential procedures.

One example of a common application of the TORES is exemplified in the context of single-cell fluorescence-activated cell sorting (FACS) of antigen-specific=T-cells from human tissues for reverse transcription and PCR based amplification of TRA/TRB TCR chain pairs, followed by Sanger sequencing. This is a generally applicable workflow, wherein any tissue may be the source of T-cells from any jawed vertebrate, and cells may be sorted based on any phenotypic characteristics. The single-sorted cells need not be stained for antigen specificity using pHLA-multimer reagents.

The TCR sequencing approach used is not restricted to any particular method or technology, provided sufficient high-quality sequence information is obtained such that the above-defined genetic characteristics of the TCR ORF(s) can be defined based on said sequence information.

The use of FACS for partitioning single cells such that native TCR chain pairs may be sequenced and identified is a powerful method due to the accurate and rich phenotypic information that may be collected with multi-specificity antibody panels. However, other methods exist to partition cells, including; emulsion PCR; digital PCR approaches using microfluidic cell encapsulation, droplet digital PCR using physical partitioning substrates.

It is generally desirable to obtain native TCR pairs from a source material, as both chains of a TCR pair contribute to HLA-antigen engagement and recognition. However, there are instances where recovery of just a single chain may be desirable, such as high-throughout screening of a single chain against a set specificity. In such a case, TCRs may be amplified and/or sequenced from non-partitioned cells.

Methods to Use a TORES to Generate Full-Length TCR ORFs with Diversified Sequence A TORES system is ideally suited to generate diversified full-length TCR ORFs in several systematic modes. Such systematic diversification may be applied to affinity and/or functional maturation workflows for TCR chains. Such diversification of target TCR chain sequences is well described in Example 5.

Such TCR ORF sequence diversification methods follow the same general scheme as for a reconstitution reaction. Diversification can be conducted in multiple parallel reconstitution reactions, whereby a single variant TCR ORF is generated per reaction. However, in most scenarios it is desirable to generate a pool of variant TCR ORFs in a single reaction. Each of these approaches is achieved by providing multiple variants of one or more of each genetic component (V-C entry vector, J donor vector, odeCDR3) to a reconstitution reaction.

Figure 3:
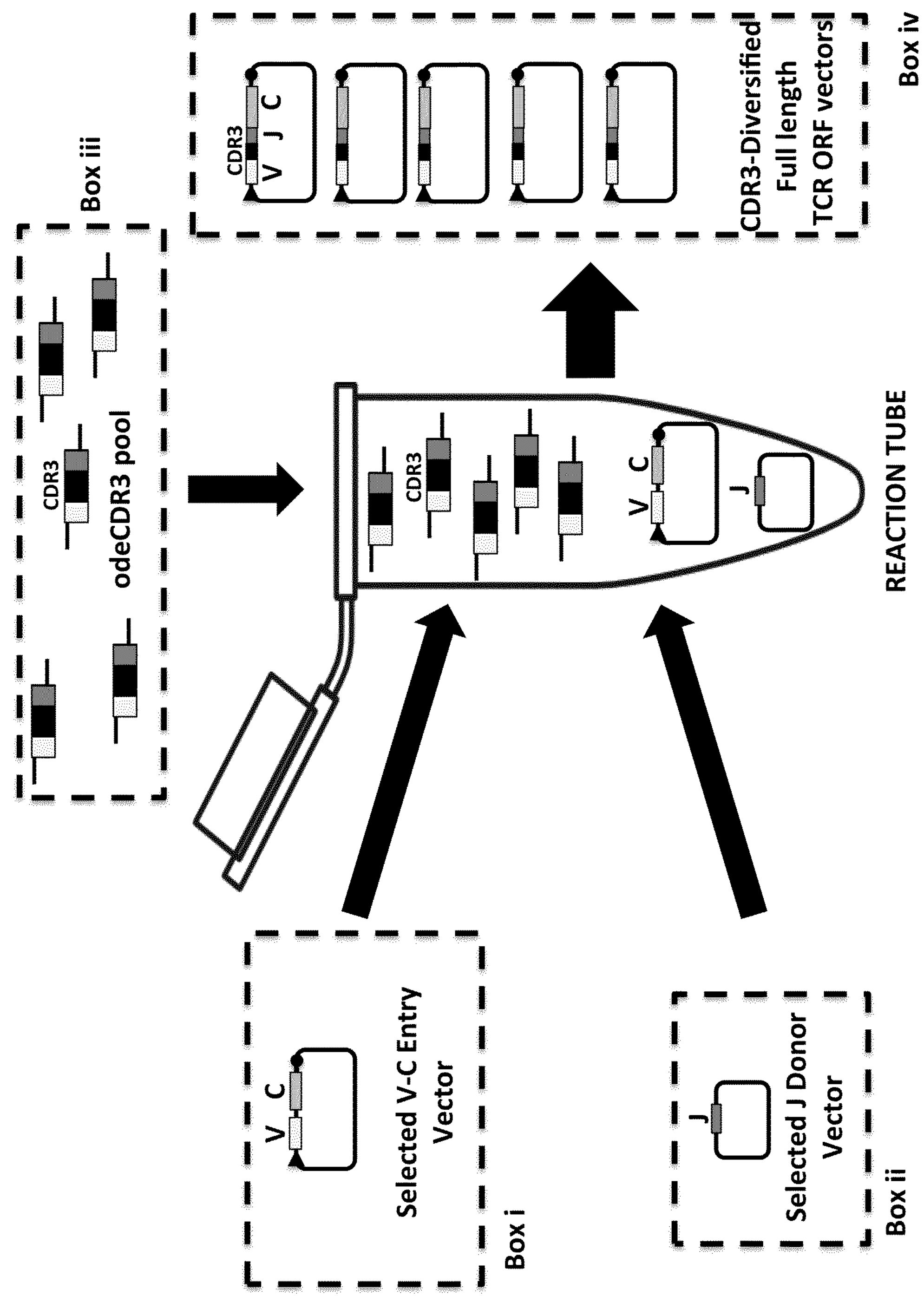

As described in Example 5, a TCR ORF can be systematically diversified at the CDR3 region by adding a pool of odeCDR3 with defined positional sequence diversity (FIG. 3).

A method for selecting and reconstituting a TCR open reading frame to achieve TCR ORF diversity in the CDR3 region, thus comprises a. Obtaining a TCR open reading frame sequence wherein said sequence information is sufficient to identify i) variable gene segment usage ii) constant gene segment usage iii) joining gene segment usage iv) a full CDR3 sequence spanning the variable gene segment border to the joining gene segment border, and
b. selecting a V-C entry vector corresponding to the variable and constant gene segments identified in step a. i) and a. ii), respectively, and
c. selecting a J donor vector corresponding to the joining gene segment identified in step a, iii), and
d. generating two or more odeCDR3 corresponding to CDR3 sequence identified in step a. iv), with variant sequence composition, and
e. combining b, c and d to react with i) Type IIS restriction enzyme(s) to cleave all Type IIS restriction enzyme recognition and cleavage sites present in the V-C entry vector and in the J donor vector and ii) DNA ligase enzyme, iii) subjecting the combined mix to a temperature controlled reaction, and
f. transforming the reaction product obtained from step e. to a selectable host organism competent for plasmid replication, and
g. performing a selection of host organism to obtain full length reconstituted TCR open reading frame in the V-C entry vector backbone.

wherein, a) is conducted by sequencing methods well known to one skilled in the art, able to obtain sufficient sequence length and quality to identify all four required genetic elements; b) and c) are selected from a TORES library containing required vectors; d) is synthesised de novo, or selected from a odeCDR3 library; e) is conducted in a single reaction vessel Such a method can be achieved by pooling all odeCDR3 variants to a single reaction to generate a pool of sequence-diversified, but may be equally achieved by providing each odeCDR3 variant to a parallel reaction.

Variant odeCDR3 can be generated via a variety of methods well known to those skilled in the art. The selection of position and extent of odeCDR3 degeneracy/diversity can range from a single residue change at a single position, to completely degenerate sequence to the length of the odeCDR3.

Figure 4:
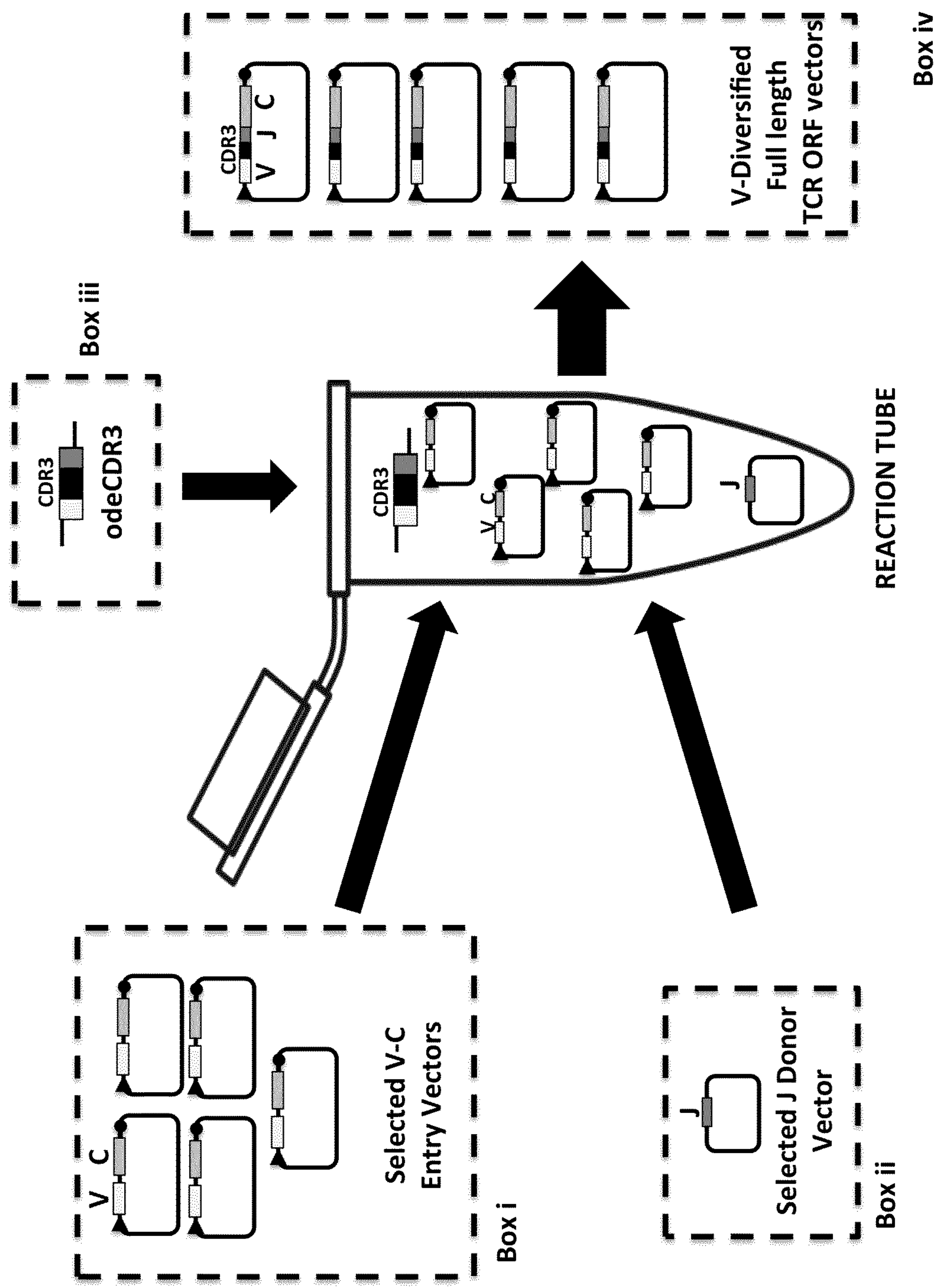
Figure 5:
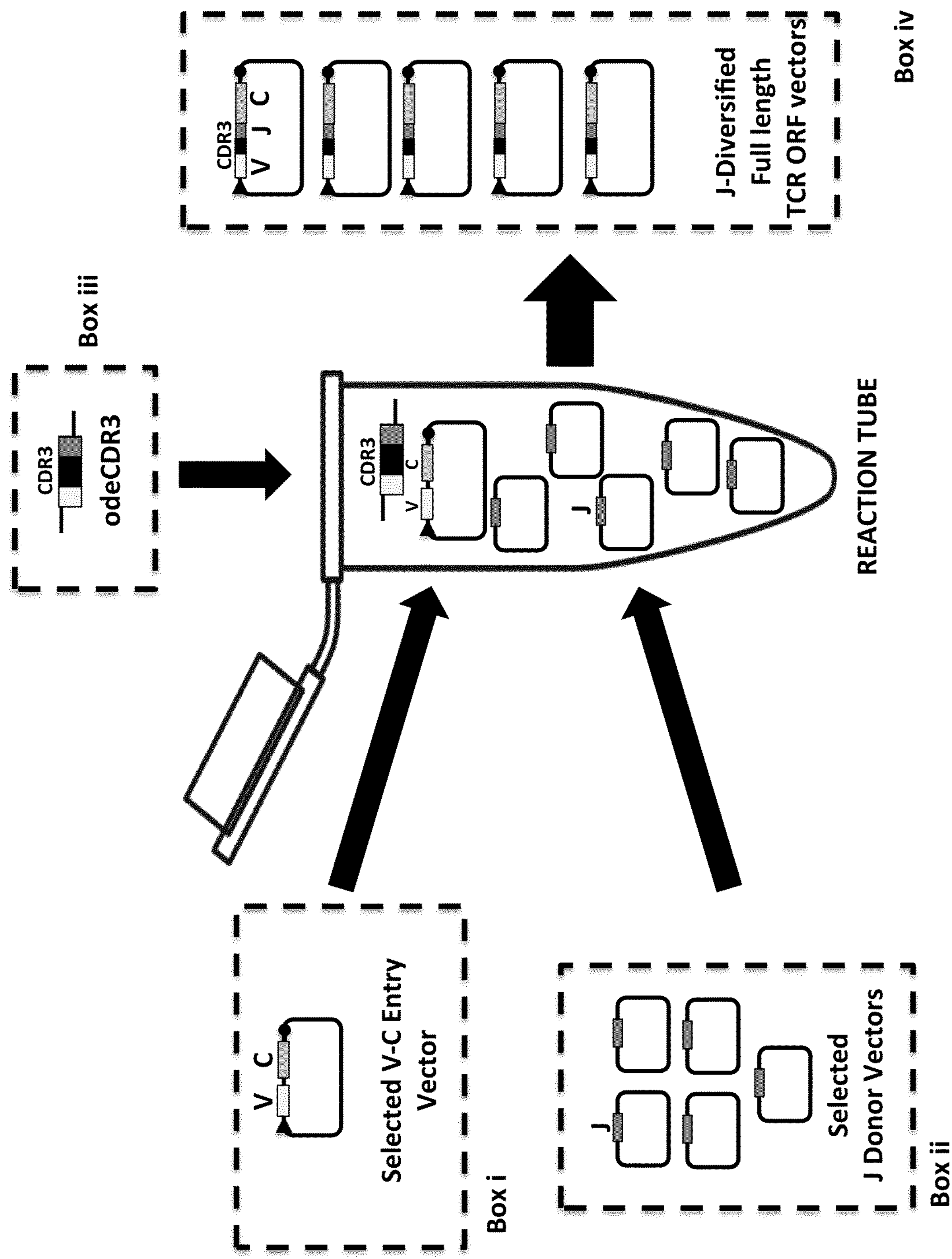
Figure 6:
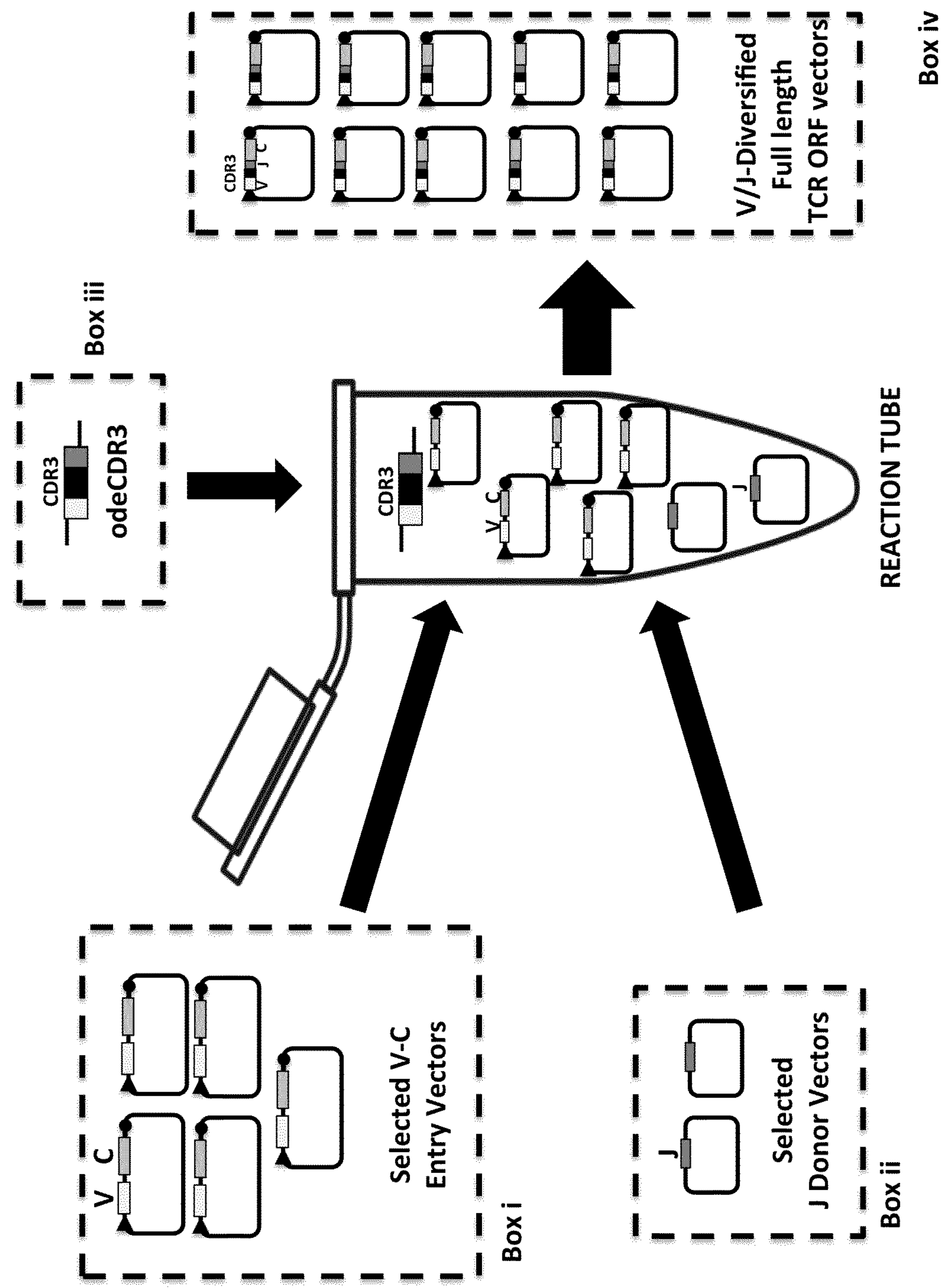

A TCR ORF can be systematically diversified by maintaining the CDR3 region via provision of a single odeCDR3, but diversifying V, C and J segment usage by providing two or more of the V-C entry vector and/or J donor vector to the reconstitution reaction (FIGS. 4, 5 and 6).

A method for selecting and reconstituting a TCR open reading frame with diversified V, C and/or J segment usage, thus comprises a. Obtaining a TCR open reading frame sequence wherein said sequence information is sufficient to identify i) variable gene segment usage ii) constant gene segment usage iii) joining gene segment usage iv) a full CDR3 sequence spanning the variable gene segment border to the joining gene segment border, and
b. selecting two or more V-C entry vectors not corresponding to the variable and constant gene segments identified in step a. i) and a. ii), respectively, and
c. selecting two or more J donor vectors not corresponding to the joining gene segment identified in step a, iii), and
d. generating an odeCDR3 corresponding to CDR3 sequence identified in step a. iv), and
e. combining b, c and d to react with i) Type IIS restriction enzyme(s) to cleave all Type IIS restriction enzyme recognition and cleavage sites present in the V-C entry vector and in the J donor vector and ii) DNA ligase enzyme, iii) subjecting the combined mix to a temperature controlled reaction, and
f. transforming the reaction product obtained from step e. to a selectable host organism competent for plasmid replication, and
g. performing a selection of host organism to obtain full length reconstituted TCR open reading frame in the V-C entry vector backbone.

wherein, a) is conducted by sequencing methods well known to one skilled in the art, able to obtain sufficient sequence length and quality to identify all four required genetic elements; b) and c) are selected from a TORES library containing required vectors; d) is synthesised de novo, or selected from a odeCDR3 library; e) is conducted in a single reaction vessel.

Such a method can be achieved by pooling all V-C entry vectors and/or J donor vector variants to a single reaction to generate a pool of sequence-diversified, but may be equally achieved by proving each vector variant to a parallel reaction.

Each V-C entry and J donor vector from a given library could be selected to provide full coverage of V, C and J gene segments.

Any combination of CDR3 and V, C and J diversification describe above could be used to generate pools or libraries of diversified TCR ORFs.

This system can be used to generate entirely synthetic libraries of TCRs ORFs with full coverage of native V, C and J gene segment usage, and defined CDR3 characteristics.

Features of a TORES with Regard to Reconstitution and Diversification Methods

As mentioned above, it is desirable to conduct the assembly reaction with a single Type IIS restriction enzyme. This economises the use of restriction enzyme, and is made possible by the nature of Type IIS action, and the design of unique single stranded overhangs in the two-component vector system and odeCDR3.

Alternatively, up to four Type IIS restriction enzyme recognition sequences across the four Type IIS recognition sites of the V-C entry vector and J donor vector.

For efficient cloning of TCR ORF products, at least one step of negative selection is performed during the assembly of a full-length TCR ORF using the TORES, selected from a. performing restriction enzyme digest of reaction product to eliminate parental V-C entry vector
b. performing a conditional bactericidal agent selection to eliminate competent hosts transformed with parental V-C entry vector, and/or
c. performing selection of host cells transformed with parental V-C entry vector by way of reporter identification.

wherein, the negative selection is used to eliminate parental V-C entry vector that have remained undigested by the Type IIS enzyme(s), or have re-ligated to the parental form after digestion.

Elimination of parental V-C entry vector is critical, considering that the V-C entry vector backbone, and thus the positive selection marker carried in this backbone, is used for positive selection of the vector containing the full-length TCR ORF reaction product.

In the present context, negative selection is performed using a restriction enzyme site has been designed within the reaction by-product excised from the V-C entry vector (FIG. 2*d*). This negative selection procedure is described in examples 3.

Any one, or a combination of the above-mentioned negative selection methods can be employed to eliminate parental V-C entry vector from the final cloned products. Such a negative selection procedure may be omitted if the cloning efficiency is deemed high enough for efficient recovery of cloned reaction products.

The selection of the cloned full-length TCR ORF containing vectors in transformed host organism is required to obtain the final cloned product. Such selections are well-known to those skilled in the art.

A host organism represents bacteria that are either induced or naturally transformation competent, and the selection of transformants containing the full-length TCR ORF contained in a V-C entry vector backbone comprises antibiotic selection. This entails adding antibiotic to the culture system in which the transformed cells are placed, and resistance to this antibiotic is encoded by the gene represented as the first positive selection marker in the V-C entry vector backbone.

Alternatively, removal of auxotrophic factors of the culture system in which transformants are placed can be a form of positive selection, wherein auxotrophic complementation is conferred by a gene product encoded in the V-C entry vector backbone. A combination of the above-described positive selections may be employed.

V-C Entry Vector and J Donor Vector Libraries

For the efficient operation of a TORES to perform reconstitution or diversification of selected TCR ORFs, the preconstruction of a V-C entry vector and J donor vector library is required. It is from this library, which is specific for each TCR chain form, that selections are made to fulfil the V/J/C usage of the target TCR ORF sequence, when complemented with the odeCDR3 sequence.

V-C entry and J donor vector libraries may be constructed to contain all germline TCR V/J/C gene segments of an organism having such TCRs. Such a library may also include all V-C combinations in the V-C entry vector, as for the TRB locus specific TORES presented in Example 1, wherein the library is replicated with both Constant gene segments against each Variable segment.

A library of V-C entry and J donor vectors may contain V/J/C gene segments, such that translated amino acid sequence of the encoded protein is unmodified in relation to the protein sequence encoded by the germline gene segments.

Such a library permits change in the underlying nucleic acid sequence as to generate a library otherwise devoid of unwanted Type IIS recognition sequences, or positive and negative selection elements. Changes in the underlying nucleic acid sequence can also be used for codon optimisation, for optimal expression of reconstituted TCR chains.

Alternatively, a library of V-C entry and J donor vectors may contain V/J/C gene segments, such that translated amino acid sequence of the encoded protein is modified in relation to the protein sequence encoded by the germline gene segments.

Such a library may be used to construct TCRs with characteristics that are optimised for different diagnostic or therapeutic uses. Changes in framework residues or regions within the V/J/C gene segments could be used to increase expression or stability in various scenarios, such as expression of TCRs as soluble reagents. Similarly, alterations in framework regions that are not involved in direct HLA-antigen contacts may be used to alter the signalling capacity of reconstituted TCRs produced by the TORES. Affinity tags or immunogenic sequences may also be encoded within framework regions as to aid in purification and/or detection of the reconstituted TCRs in downstream applications.

V-C entry and J donor vector libraries may be assembled into kit comprising a combination of a. one or more V-C entry vectors encoding combinations of Variable and Constant gene segments, and
b. one or more J donor vectors encoding J gene segments, and optionally
c. one or more odeCDR3, or one or more pooled libraries of odeCDR3, with single stranded overhangs, pre-exposed or flanked by Type IIS restriction sites for liberation during the restriction digestion/ligation reaction, matched to V-C entry vector and J donor vector single strand overhangs, and optionally
d. one or more standardised odeCDR3 with single stranded overhangs, pre-exposed or flanked by Type IIS restriction sites for liberation during the restriction digestion/ligation reaction, matched to V-C entry vector and J donor vector single strand overhangs as positive control odeCDR3, and optionally e. A pre-assembled full-length TCR ORF as a reference wherein, a) and b) cover the required genetic diversity of gene segments from a target organism, with unmodified or modified amino acid sequence relevant for the intended application; c) is used for reconstitution of TCR chains with defined or diversified CDR3; d) is used as a positive control in reconstitution reactions, e) is used as a positive control in downstream applications of full-length TCR ORFs reconstituted with the V-C entry vector and J donor vector libraries provided in said kit.

Definition of Part 1 Device Outputs as Part 2 Device Inputs

In operation of the overall two-part device, the first part (TORES) is used to generate one or more TCR chains within the defined integration vector context. TCR represent heterodimeric complexes, such that a TORES will generally comprise two parallel assembly subsystems for each chain of a TCR chain pair. Thus, a TORES, as the first part of the two-part device will generate two outputs comprising two integration vectors each encoding one chain of a TCR chain pair, or libraries thereof. Products components 2C and 2E of the TORES system this represent integration vectors that are presented in the V-C entry backbone of component 1A.

These outputs from part 1 of the two-part device are used as direct inputs to the second part of the two-part device (FIG. 1). These vector outputs from the first part and inputs to the second part are designated components 2C and 2E. Each of these inputs is paired with a genomic receiver site components 2B and 2D, respectively, encoded within the eTPC (component 2A), to form two independent integration couples.

The pair of integration couples are independently isolated from one another as to ensure that each integration event delivers only a single TCR ORF for each chain of a TCR pair, and thereby preferentially obtaining a standardised eTPC that presents a single species of TCR surface protein (TCRsp), designated eTPC-t.

eTPCS: Second Part of the Two-Part Device

Figure 8:
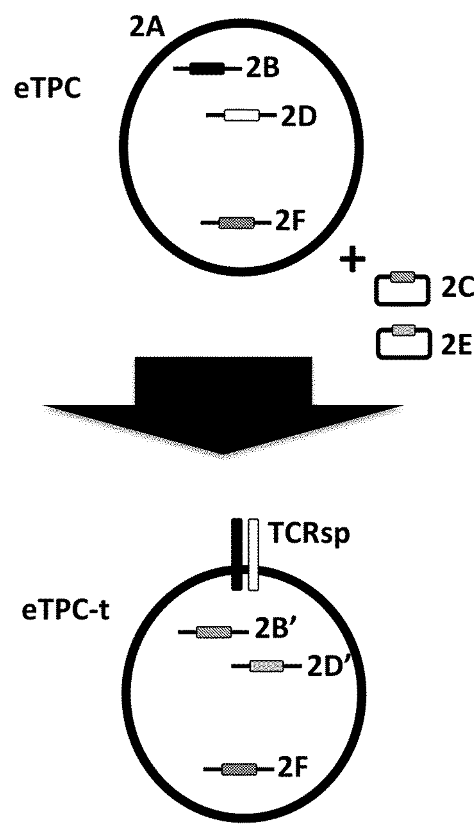

The multicomponent eTPC system (eTPCS) is depicted in FIG. 1, part 2. The multi-component eTPCS comprises a first component eTPC, designated component 2A, containing two genomic receiver sites, components 2B and 2D, which are paired with two TCR-encoding integration vectors obtained from the first part of the device, components 2C and 2E. Overall, the introduction of a complementary pair of TCR chains to the genomic receiver sites (components 2B and 2D) via integration vectors (components 2C and 2E), converts the eTPC (component 2A) into a variant eTPC that expresses TCR surface protein (TCRsp), designated eTPC-t (FIG. 8).

An eTPC, component 2A, represents the base component of the multicomponent system, to which all other components of the system relate. Therefore, the eTPC contains certain features, that are native or engineered, that make the eTPC suitable for use to create analyte eTPC-t populations, and their use.

The eTPC, component 2A, i. Lacks endogenous expression of TCR chains alpha, beta, delta and gamma, and
ii. Expresses CD3 proteins which are conditionally presented on the surface of the cell only when the cell expresses a complementary pair of TCR chains and
iii. Contains further modification, designated components 2B and 2D, as genomic receiver sites for integration of a single ORF encoding one analyte TCR chain of alpha, beta, delta or gamma at each site wherein i) may be obtained by selection of a naturally occurring cell population lacking said expression, or may be engineered to lack such expression; ii) may be obtained by selection of a naturally occurring cell population comprising said expression, or may be engineered to comprise such expression; iii) may be achieved by utilising sequences intrinsic to the genome of the eTPC, or introduced by means of genetic engineering.

The selection of an eTPC cell candidate that lacks TCR chains alpha, beta, delta and gamma from naturally occurring cell populations can be achieved by methods well known in the art. Staining of target cells with affinity reagents specifically for TCR chains alpha, beta, delta and gamma, and selection of cells TCR chains alpha, beta, delta and gamma may directly achieve this.

Engineering an eTPC to lack TCR chains alpha, beta, delta and gamma expression may be achieved by untargeted and targeted means. Untargeted mutagenesis of the cell can be achieved by providing a chemical, radiological or other mutagen to the cell, and then selecting cells lacking expression target TCR chains alpha, beta, delta and gamma expression. Targeted mutation of the genomic loci can be achieved via different means, including but not limited to site directed mutagenesis via i. zinc-finger nucleases
ii. CRISPR/Cas9 mediated targeting
iii. Synthetic transcription activator-like effector nucleases (TALEN)

wherein said site-directed nucleases induce site-specific double stranded DNA breaks increasing the chance of error prone DNA repair at the target loci, after which mutated cells are obtained by selecting cells lacking TCR alpha, beta, delta and gamma expression.

Options for integration of CD3 and the components 2B and/or 2D are well known to those skilled in the art but may include homology directed recombination (HDR) and/or random integration methods, wherein HDR may be promoted by targeted mutation of the genomic loci at which HDR is to occur, and can be achieved via different means, including but not limited to site directed mutagenesis via i. zinc-finger nucleases
ii. CRISPR/Cas9 mediated targeting
iii. Synthetic transcription activator-like effector nucleases (TALEN)

wherein said site-directed nucleases induce site-specific DNA-repair by HDR at target loci. After such events, a proportion of cells will have incorporated HDR vector, an can be selected and/or determined via any combination of the following, iv. Non-destructive phonotypical expression analysis
v. Destructive phonotypical expression analysis
vi. Genetic analysis Wherein iv and vi are the preferred methods for selection and determination of successful genomic integration events.

Alternatively, viral vectors could be used to deliver the required components in a site-directed or undirected manner.

Considering that the eTPC component 2A is designed to be used in conjunction with the analyte antigens within analytical workflows, in the preferred aspect the eTPC contains features that minimise the eTPC presenting factors that would interfere in such analyses.

The eTPC component 2A optionally lacks endogenous surface expression of at least one family of analyte antigen presenting complexes (aAPX) and/or analyte antigenic molecules (aAM), wherein the lack of surface expression is selected as to minimise interference in matched analyses of target analyte antigens.

The family of aAPX may be any of the following i. HLA class I ii. HLA class II iii. non-HLA antigen-presenting complex.

An aAM is selected from i. a polypeptide or complex of polypeptides translated from the analyte antigenic molecule ORF(s)

ii. a peptide derived from a polypeptide translated from the analyte antigenic molecule ORF(s)

iii. a peptide derived from altering the component A proteome iv. a polypeptide derived from altering the component A proteome v. a metabolite derived from altering the component A metabolome The component 2A eTPC may optionally additionally include T-cell co-receptors, wherein such features permit robust or varying forms of communication of the analyte eTPC to the analyte APC, wherein the tuneable communication is relevant to identification or characterisation of specific analyte TCRsp and/or analyte antigens.

In the present context, the eTPC component 2A may optionally express CD4 and/or CD8, wherein expression of CD4 or CD8 restrict eTPC to engaging aAPX of type HLAII and HLAI, respectively.

The eTPC component 2A may optionally expresses CD28 and/or CD45, wherein CD28 and CD45 contribute to signal sensitivity through positive feed forward effects on signalling, whereas they may also contribute to signal specificity through negative feedback effects on signalling, as it relates to signalling though an expressed analyte TCRsp.

The component 2A eTPC may optionally additionally include introduced cell surface adhesion molecule components, or ablation of endogenous cell surface adhesion molecules, to promote the eTPC engagement with analyte APC and formation of the immunological synapse, or to avoid tight binding and formation of deleterious cell clustering within analytical workflows involving APC, respectively.

Such adhesion molecules that may be introduced as additional ORFs to component 2A, or genetically ablated from component 2A, can be selected from the integrin family of adhesion proteins.

An eTPC is designed to assay binding of cognate analyte antigen, either through detectable engagement of analyte antigen reagents, or through a native or engineered eTPC-centric response to stimulation by cognate antigen, within analytical workflows using the eTPC:A system (infra vide). It is thus desirable to have a standardised reporter readout for signalling response from stimulation of the expressed TCRsp.

The eTPC component 2A, may further contain a component designated 2F, a synthetic genomic TCR-stimulation response element selected from i. A single component synthetic construct containing at least one native promoter and/or at least one synthetic promoter and at least one reporter ii. A multi-component synthetic construct designed with at least one native promoter and/or at least one synthetic promoter and at least one reporter wherein activation of i and/or ii is dependent on at least one signal transduction pathway selected from a synthetic pathway, a native pathway or a combination thereof.

The TCR-encoding integration vectors that form pairs with the genomic receiver site as part of the eTPC, are designated Components 2C and 2E.

Each of these components 2C and 2E encode a single TCR chain ORF, and are required to convert an eTPC into a TCRsp-expressing eTPC-t.

Each of the vectors, components 2C or 2E, carry 5' and 3' genetic elements flanking the encoded TCR ORF is designed to target either genomic receiver site 2B or 2D, respectively. These integration couples must be reasonably insulated from each other as to assure only one TCR ORF is inserted into each genomic receiver site as determined by the 2B-2C or 2D-2E integration coupling relationship.

As described above, Components 2C and 2E are derived from the TORES, representing the first part of the device. Thus, the features of the first part vector backbone architecture is matched to the genomic receiver sites, components 2B and 2D, of the component 2A eTPC.

The pair of integration couples contained within the eTPC as described above preferably have a feature(s) that permit re-use of the site to remove a single TCR chain from a genomic receiver site once integrated.

Such cycling between TCR ORF and a non-TCRsp expressing construct can permit interchange of a single TCR ORF expressed in an eTPC-t, as to generate and intermediate expressing a single chain of TCR, and thus no TCRsp expression. This intermediate is designated eTPC-x (See FIG. 7). Such recycling can be achieved with recombinase enzymes, as to execute RCME.

Genomic receiver site recycling may also be achieved by use of other recombinase-like enzymes, use of transposable elements, and/or the use of homologous directed recombination with or without the use of site-directed endonucleases.

The genomic receiver sites, components 2B and 2D, may be selected from the following i. A synthetic construct designed for recombinase mediated cassette exchange (RMCE)

ii. A synthetic construct designed for site directed homologous recombination wherein i) is the preferred form a genomic receiver site for RMCE. The RMCE method may employ selected heterospecific sites that are specific for individual recombinase enzymes, such that each component 2B and 2D possess insulated specificity.

The genomic receiver sites, component 2B and 2D comprises of at least one of the following genetic elements i. Heterospecific recombinase sites ii. Homologous arms iii. Eukaryotic promoter iv. Eukaryotic conditional regulatory element v. Eukaryotic terminator vi. Selection marker vii. Splice acceptor site viii. Splice donor site ix. Non-protein coding gene x. Insulator xi. Mobile genetic element xii. Meganuclease recognition site xiii. Internal ribosome entry site (IRES)

xiv. Viral self-cleaving peptide element xv. A kozak consensus sequence

Wherein, at least i) or ii) should be included.

A preferred genomic receiver site would comprise of two different arrangements using the following selected elements from the previously stated list of element.

The first arrangement is for receiving a single ORF encoding one TCR chains and a selection mark of integration, via RMCE integration wherein the arrangement is

5'-[A] [B] [C] [D] [E] [F]-3' wherein

A) is element iii) a constitutive or inducible Eukaryotic promoter
B) is element i) heterospecific recombinase site 1
C) is element xv) a Kozak consensus sequence
D) is element vi) a FACS and/or MACS compatible encoded protein marker
E) is element i) heterospecific recombinase site 2
F) is element v) Eukaryotic terminator The second arrangement is for receiving a two ORF encoding one or more TCR chains and/or a selection mark of integration, via RMCE integration wherein the arrangement is

5'-[A] [B] [C] [D] [E] [F] [G] [H] [I]-3' wherein

A) is element iii) a constitutive or inducible Eukaryotic promoter
B) is element i) heterospecific recombinase site 1
C) is element xv) a Kozak consensus sequence
D) is element vi) a FACS and/or MACS compatible encoded protein marker 1
E) is element v) a Eukaryotic bidirectional transcriptional terminator
F) is element vi) a FACS and/or MACS compatible encoded protein marker 2
G) is element xv) a Kozak consensus sequence
H) is element i) heterospecific recombinase site 2
I) is element iii) a constitutive or inducible Eukaryotic promoter furthermore, in this second arrangement the elements F, G, and I are encoded in the antisense direction.

Component 2C and 2E comprise of at least one of the following genetic elements i. Heterospecific recombinase sites
ii. Homologous arms
iii. Eukaryotic promoter
iv. Eukaryotic conditional regulatory element
v. Eukaryotic terminator
vi. Selection marker
vii. Splice acceptor site
viii. Splice donor site
ix. Non-protein coding gene
x. Insulator
xi. Mobile genetic element
xii. Meganuclease recognition site
xiii. Internal ribosome entry site (IRES)
xiv. Viral self-cleaving peptide element
xv. A kozak consensus sequence
xvi. Selection marker of integration
xvii. An antibiotic resistance cassette
xviii. A bacterial origin of replication
xix. A yeast origin of replication
xx. A cloning site A preferred genetic integration vector, component 2C and component 2E, would comprise of two different possible arrangements using the following selected elements from the previously stated list of elements.

The first arrangement is for delivery of a single ORF encoding one or more TCR chains and/or a selection marker of integration, via RMCE integration wherein the arrangement is

5'-[A] [B] [C] [D] [E]-3' wherein

A) is element i) heterospecific recombinase site 1
B) is element xv) a Kozak consensus sequence
C) is element xx) a cloning site of a single ORF encoding a TCR chain and/or element xvi) a selection marker of integration
D) is element i) heterospecific recombinase site 2
E) is element xvii) An antibiotic resistance cassette and element xviii) a bacterial origin of replication, in no specific orientation furthermore, the elements viii and/or xiv may be used to link multiple TCR chains and/or element xvi together.

The second arrangement is for delivery of one or more ORFs encoding one TCR chains and/or a selection mark of integration, via RMCE integration wherein the arrangement is

5'-[A] [B] [C] [D] [E] [F]-3' wherein

A) is element i) heterospecific recombinase site 1
B) is element xv) a Kozak consensus sequence
C) is element xx) a cloning site for introduction of two or more ORF, with eukaryotic terminators, encoding at least one TCR chain and/or element xvi) a selection marker of integration
D) is element xv) a Kozak consensus sequence (antisense direction)
E) is element i) heterospecific recombinase site 2
F) is element xvii) An antibiotic resistance cassette and element xviii) and/or a bacterial origin of replication, in no specific orientation furthermore, the elements viii and/or xiv may be used to link multiple TCR chains and/or element xvi together within each ORF.

A preferred genetic integration vector, component 2Y and component 2Z, for conversion of eTPC-t to eTPC-x (see FIGS. 7 and 10) would comprise the same integration vector requirements as 2C and 2E above, though not encoding any TCR chain ORF, and preferably encoding a marker of integration.

Use of Integration Couples to Compile eTPC-x and eTPC-t

The above described multicomponent system may be used in multiple ways to prepare distinct forms of analyte eTPC populations, or libraries thereof, that serve to present analyte TCRsp to analyte antigen within analytical or preparative workflows of the eTPC:A system.

Figure 7:
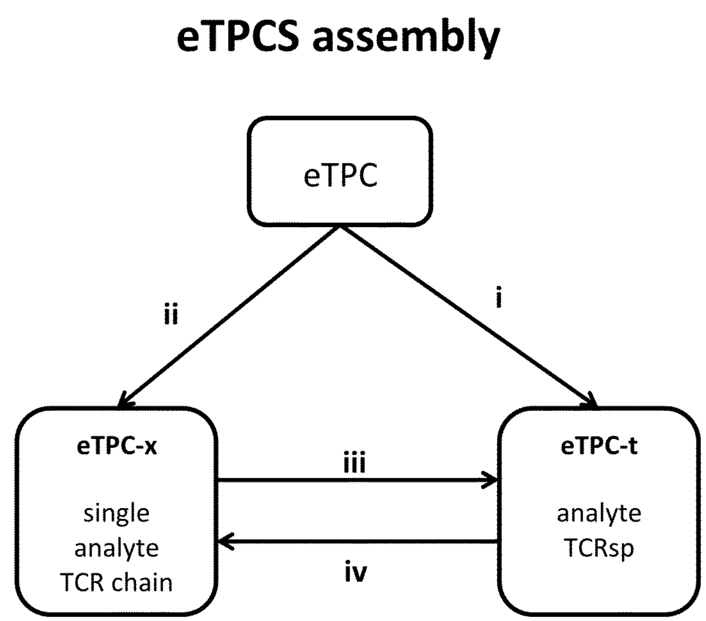

The efficient integration of a predictable copy number of one or more ORFs into the genomic receiver site is highly advantageous for operation of a standardised eTPCS, where analyte eTPC-t populations may be rapidly prepared and characterised. Thus, the genomic receiver site(s) and coupled integration vector(s) are critical to the function of the eTPCS. It is also desirable that the component 2B and component 2D are amenable to a method of preparation of an eTPC-t, as described above, wherein, the introduction of a single pair of complementary TCR chains is rapid, repeatable, with a high likelihood of correct integration and delivery of only a single pair. The combination of the genetic integration vectors with an eTPC to produce eTPC-x and/or eTPC-t can be achieved in several modes (FIG. 7). The eTPC-t populations that are created need to derive analyte TCR chains from certain sources with which to analyse candidate antigens.

The sources of analyte TCR chain sequences information to define the components used in the TORES reaction can be derived from i. Paired cloning of TCR chain ORF sequence(s) from primary T-cells
ii. Unpaired cloning of TCR chain ORF sequence(s) from primary T-cells
iii. Synthetic TCR chain ORF sequence(s)

wherein i) is preferable for discovery of native TCRsp that are not likely to be generally cross reactive against self aAPX and/or the aAPX cargo due to thymic selection; ii) may be used to identify candidate TCR affinity reagents; iii) may be used in affinity maturation of TCR affinity reagents or de novo creation of TCR chains.

Figure 9:
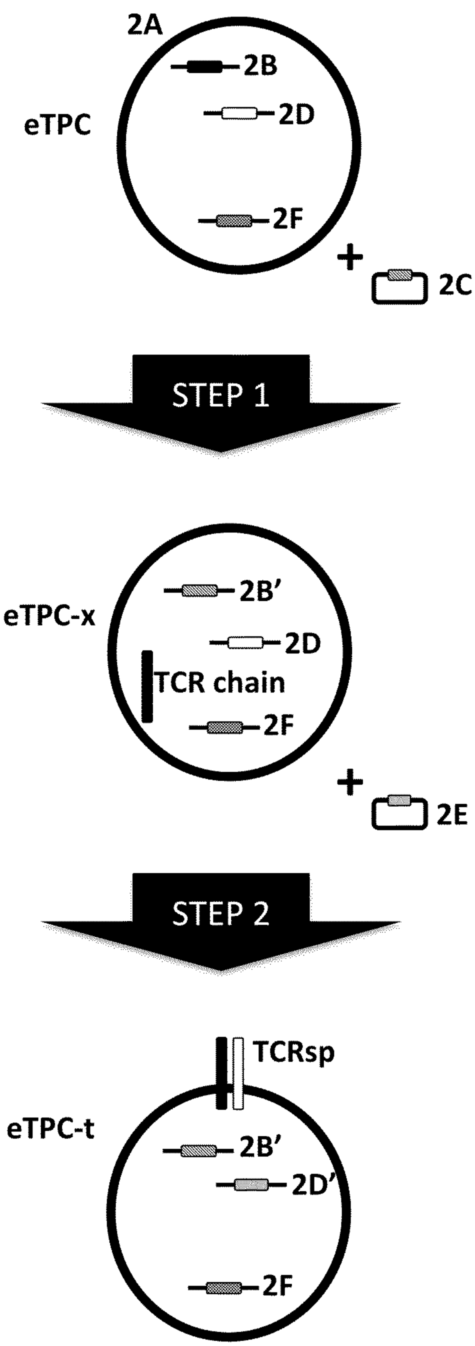

A multicomponent system comprising two integration couples may be used to prepare an eTPC-t from component 2A, by providing component 2C and 2E each combined with one ORF encoding one chain of a complementary TCR chain pair, such that both analyte TCR chains are integrated to genomic receiver site, component 2B or 2D, to create 2B' and 2D'. The resulting cell line expresses the provided TCR pair, and it is presented at the cell surface as a TCRsp. An eTPC-t may be prepared by simultaneous integration of two complementary TCR chains to form a TCRsp (FIG. 8). An eTPC-t may be prepared by stepwise integration of two complementary TCR chains to form a TCRsp, via an eTPC-x intermediate (FIG. 9).

Figure 10:
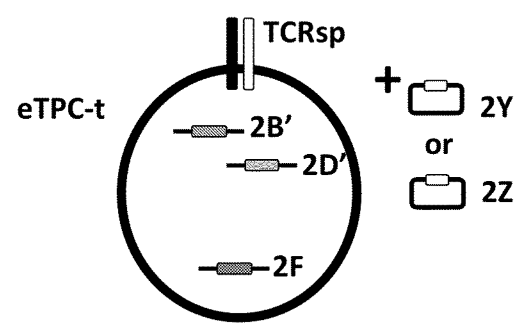
Figure 10:
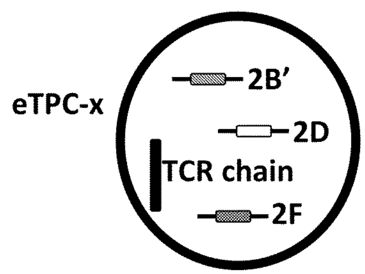

An eTPC-x may be prepared from an eTPC-t by providing either one of further integration vectors, components 2Y or 2Z, which encode markers of integration or no ORF (FIG. 10). Combination of component 2Y or 2Z to an eTPC-t would exchange either of the sites to obtain a single TCR chain expressing eTPC-x.

In the abovementioned examples of preparing analyte eTPC-x and/or eTPC-t populations from eTPC, the multicomponent system (eTPCS) is used to provide known analyte TCR chains in a defined manner to prepare discrete populations of analyte eTPC expressing defined TCRsp. Such a process may be repeated many times to build libraries of eTPC-x and/or eTPC-t as input to analytical or preparative workflows. An alternative approach is to take pooled libraries of analyte TCR chains combined with genetic integration vectors, and integrate these in a shotgun fashion to obtain pooled libraries of analyte eTPC-t wherein each eTPC-t express a single species of TCRsp, but collectively as a pool present multiple TCRsp species (see FIGS. 11 to 14). This is particularly useful when analysing large libraries of candidate TCRsp against analyte antigens.

Figure 11:
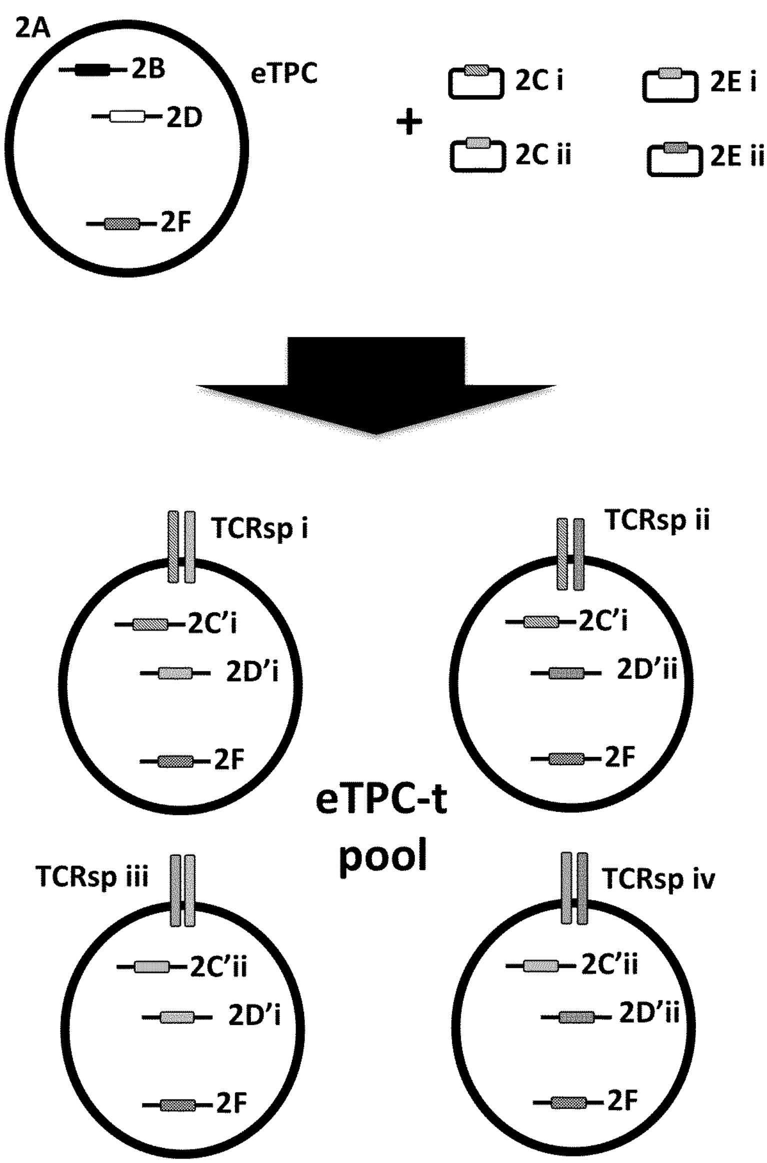

An eTPCS comprising two integration couples may be used to prepare an eTPC-t pool from component 2A in one step, by providing component 2C combined with a library of multiple ORF encoding a pool of single analyte TCR chains such that each pair is integrated to site 2B, to create 2B', within each cell. Simultaneously, providing component 2E combined with a library of multiple ORF encoding a pool of single analyte TCR chains complementary to first library provided in component 2C, such that each analyte complementary TCR chain is integrated to site 2D, to create 2D', within each cell. Each resulting cell in the eTPC-t pool has a randomised single selection of complementary analyte TCR chains, such that each cell in the pool expresses a unique randomised TCRsp. Such a pooled library would contain all possible combinations of provided complementary TCR chains from the sets proceed in C' and E' (FIG. 11).

Figure 12:
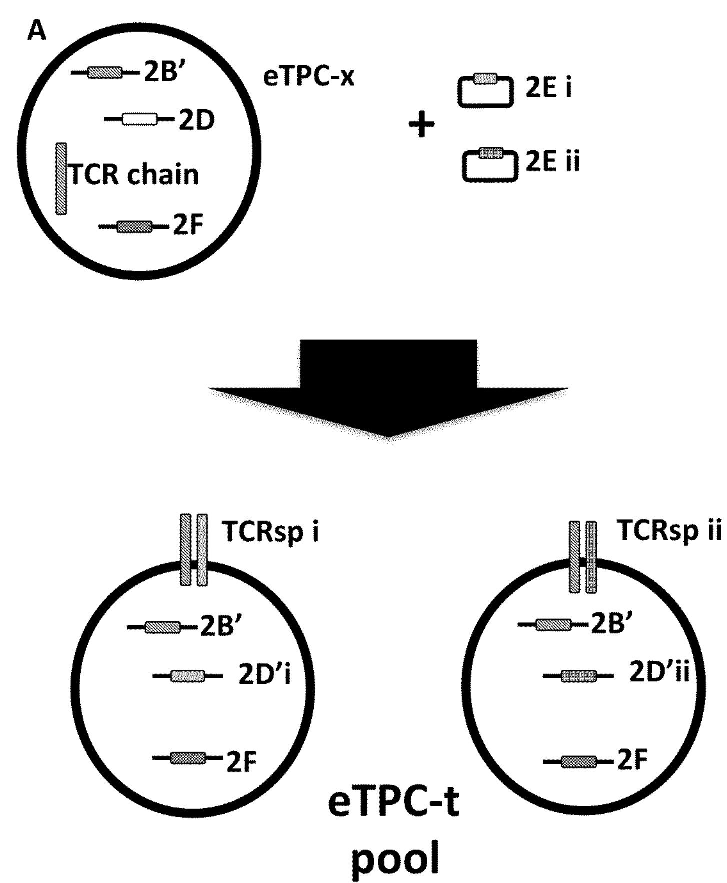

An eTPCS comprising two integration couples may be used to prepare an eTPC-t pool from a previously obtained e-TPC-x in one step, wherein the site 2B has been converted to 2B' and contains the single analyte TCR chain. An eTPC-t is prepared by providing component 2E combined with a library of multiple ORF encoding a pool of single analyte TCR chains complementary to the already integrated chain, such that each TCR chain of the provided component 2E library is singularly integrated to site 2D, to create 2D'. Each resulting cell in the eTPC-t pool has the analyte TCR chain provided by the starting eTPC-x, and a randomised single selection of the complementary analyte TCR chain, such that each cell in the pool expresses a unique TCRsp. Such an approach is used when analysing the effect of varying a single chain against a fixed chain in a complementary TCR chain pair (FIG. 12).

Figure 13:
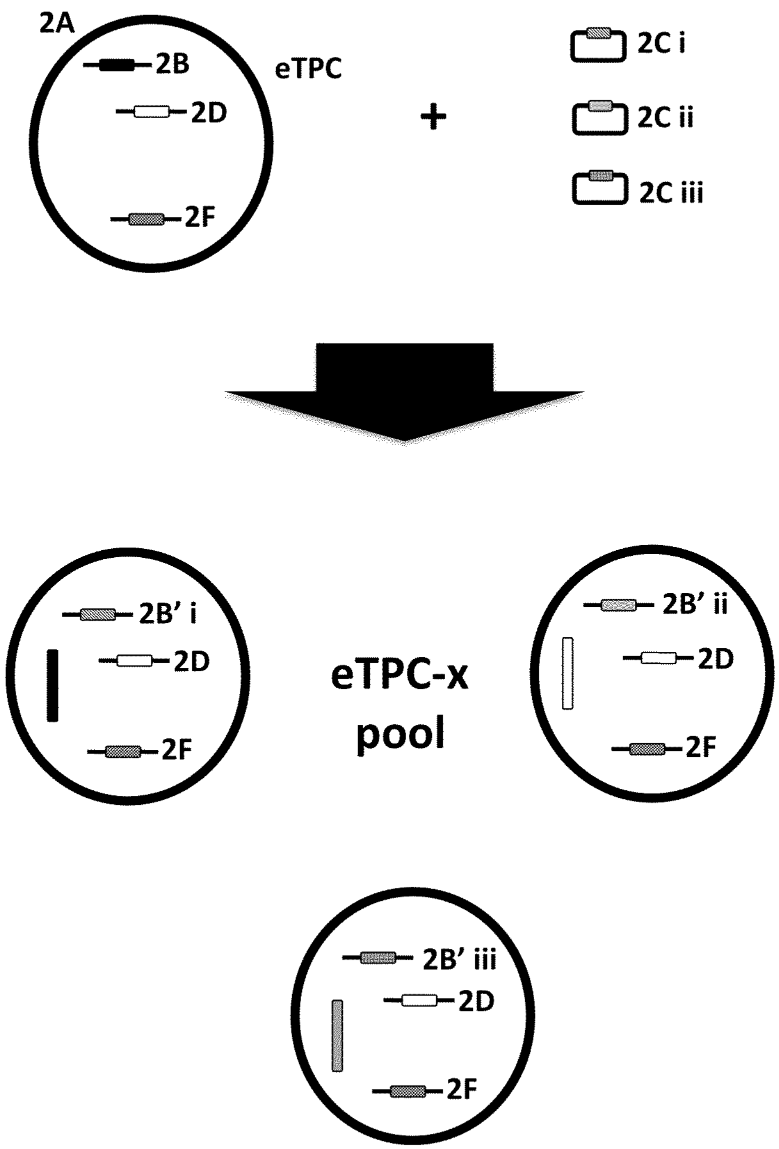
Figure 14:
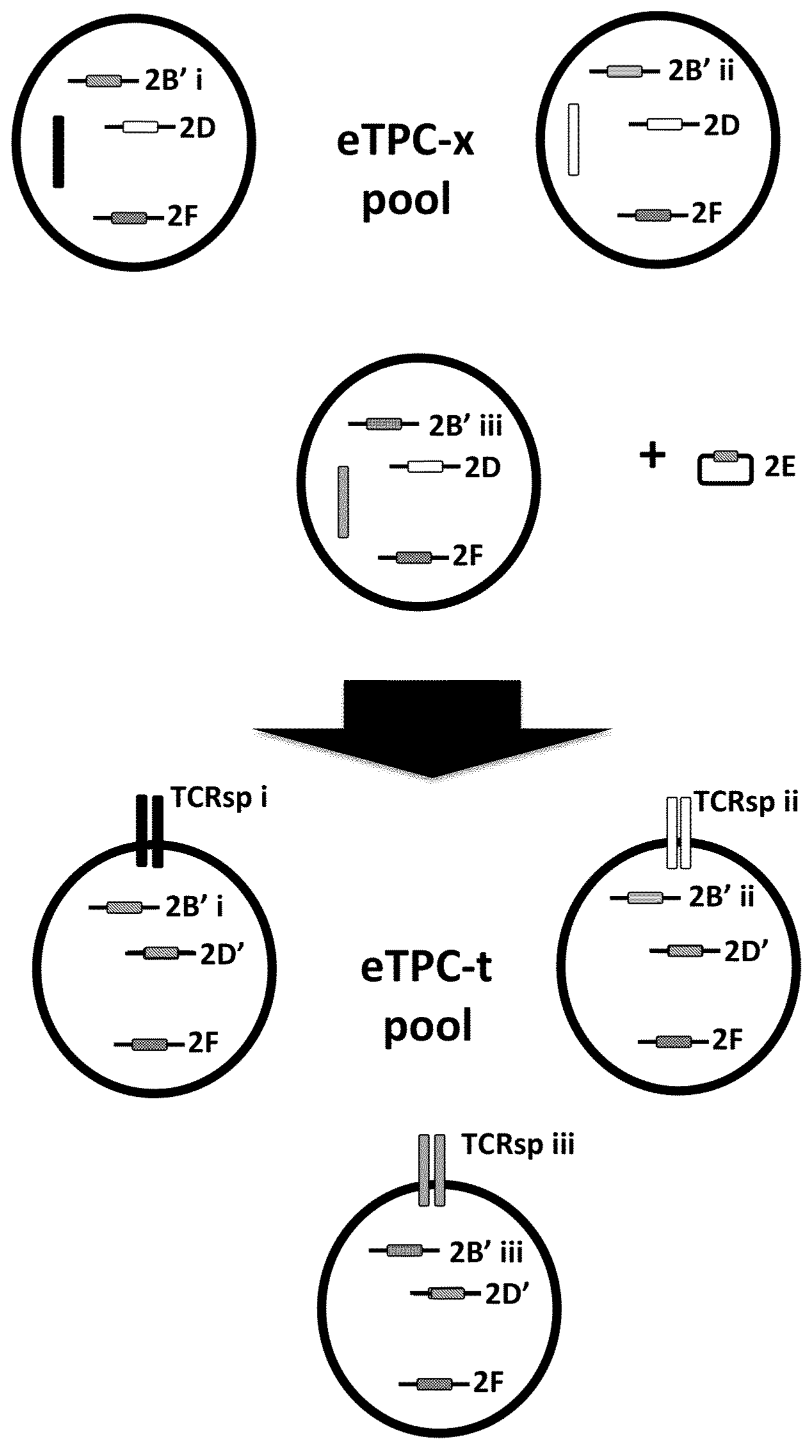

An eTPCS comprising two integration couples may be used to prepare an eTPC-x pool. An eTPC-x is prepared by providing component 2C combined with a library of multiple ORF encoding a pool of single analyte TCR chains, wherein the complementary chain is omitted, such that each TCR chain of the provided component 2C library is integrated to site 2B, to create 2B', within each cell. Each resulting cell in the in the eTPC-x, has a randomised single selection of complementary analyte TCR chain, such that each cell in the pool expresses a unique single TCR chain (FIG. 13). Such an approach is used when preparing an eTPC-x library to assay against single or multiple complementary TCR chains integrated via the second integration couple as in the previous example (FIG. 14).

An eTPC-x, or libraries thereof, can be used for transient transfection of a TCR chain ORF that is complementary to the integrated TCR ORF at 2B' in the eTPC-x, in order to rapidly screen TCRsp derivatives in a target assay.

Contacting Analyte eTPC-t with Analyte Antigen

The present invention relates to the provision of two multicomponent systems that form a two-part device for use in deriving analytical eTPC-t populations for compilation of analytical devices that are collectively termed eTPC:Antigen (eTPC:A) systems (FIG. 24). Within the two-part device, the first part is used to derive TCR ORFs in integration vector contexts, which are then inserted to a matched eTPC comprising the second part. Thus, the operation of the two-part device entails the use of one or more of each component 1A, 1B and 1C to derive one or more component 2C and 2E, which are used in conjunction with component 2A, containing at least components 2B and 2D, to compile one or more eTPC-t. These analyte eTPC-t are then combined with one or more analyte antigens within an analytical eTPC:A system to obtain one or more outputs. The analyte antigen is provided by analyte antigen-presenting cells (APC) and/or as soluble or immobilised affinity reagent and/or presented on non-cell based particles (NCBP).

An analyte antigen represents any entity that a TCR can putatively engage in the eTPC:A system, and may be represented by;

i. aAPX (analyte Antigen-presenting complex) and/or
ii. aAM (analyte antigenic molecule) and/or
iii. aAPX:aAM (analyte Antigen-presenting complex presenting an analyte antigenic molecule) and/or
iv. CM (a non-analyte cargo molecule) and/or
v. aAPX:CM (analyte Antigen-presenting complex presenting a cargo molecule)

wherein an aAPX represents a complex that is able to present an aAM; an aAM is any molecule that is directly recognised by a TCR or when loaded in an aAPX; an aAPX:aAM is an aAPX with a loaded aAM; a CM is a cargo molecule that may be loaded in the aAPX, but which is not an analyte, thus may be derived from an analyte antigen presenting cell (APC) or the assay system itself; aAPX:CM is an aAPX with a CM loaded.

These forms of analyte antigens may be presented to the eTPC in different modes within an eTPC:A system, represented as;

i. an analyte antigen presenting cell (APC) and/or
ii. a soluble or immobilised affinity reagent and/or
iii. a non-cell based particle (NCBP), wherein an analyte antigen presenting cell (APC) is considered any APC that is able to present an antigen to the eTPC-t; an affinity reagent is considered any reagent that is prepared as analyte to probe TCRsp binding and/or stimulation at the cell surface of the eTPC-t in an eTPC:A system. Such reagents will often represent analyte antigenic molecules (aAM), analyte antigen-presenting complexes (aAPX), or aAPX loaded with aAM (aAPX:aAM). A typical example of an aAPX:aAM is an pHLA-multimer reagent (e.g. 'tetramers') used to stain TCRs. Affinity reagents in this context could also represent antibodies or similar entities; a non-cell based particle (NCBP) acts in a similar manner to an affinity reagent, inasmuch that the particle presents an analyte antigen or other entity that is to be assessed for TCRsp engagement at the surface of a eTPC-t within and eTPC:A system. However, an NCBP is considered as a larger entity that can further carry genetic or other information that is to act as an identifier, either directly or by proxy, of the presented analyte antigen or other binding entity. A typical example of an NCBP would be a bacteriophage in a phage-display scenario, wherein phage may display antibody fragment antigen binding (FAB). Positively labelled eTPC-t may be recovered along with the phage, and sequenced to identify FABs specific for the TCRsp at the surface of a eTPC-t.

An analytical eTPC:A system is comprised of a selection of one or more of analyte antigen with one or more eTPC-t populations (FIG. 24). The analyte eTPC-t populations are prepared using the multicomponent system as described above (FIGS. 1 to 14). The eTPC:A system is provided in a format that permits physical contact between the analyte antigens and analyte eTPC-t populations, wherein such contact is permissive of complex formation between one or more analyte antigen and TCRsp of one or more analyte eTPC-t, wherein the analyte antigen is any of the following vi. aAPX (analyte Antigen-presenting complex) and/or
vii. aAM (analyte antigenic molecule) and/or
viii. aAPX:aAM (analyte Antigen-presenting complex presenting a analyte antigenic molecule) and/or
ix. CM (a non-analyte cargo molecule) and/or
x. aAPX:CM (analyte Antigen-presenting complex presenting a cargo molecule)

wherein the analyte antigen is either, presented by an analyte APC, or presented by a soluble and/or immobilised affinity reagent, or NCBP such that complex formation may lead to stabilisation of such a complex and wherein such complex formation leads to observable labelling of the eTPC-t and/or the induction of signalling within the analyte eTPC via component 2F, if included and/or an observable signal in the analyte APC, which may be measured.

In the present context, an eTPC:A system comprises of:

i. an input of a single analyte eTPC-t; or
ii. an input of a pooled library of analyte eTPC-t
and combined with one of the following:
iii. an input of a single analyte APC; or
iv. an input of a single analyte affinity reagent; or
v. an input of a single analyte NCBP; or
vi. an input of a pooled library of analyte APC; or
vii. an input of a pooled library of analyte affinity reagent; or
viii. an input of a pooled library of analyte NCBP Contacting in a Buffer System A contact between an analyte APC and analyte eTPC-t is performed in a permissive cell culture or buffer system, wherein said system comprises media that is permissive to the function of both analyte APC and analyte eTPC-t cells.

A contact between a soluble analyte affinity, immobilised affinity reagent and/or analyte NCBP and an analyte eTPC-t is performed in a permissive buffered system, wherein said system comprises a buffered medium that is permissive to function of both the analyte antigen and analyte eTPC-t cells.

Labelling eTPC-t with Affinity Reagents or NCBP

Figure 15:
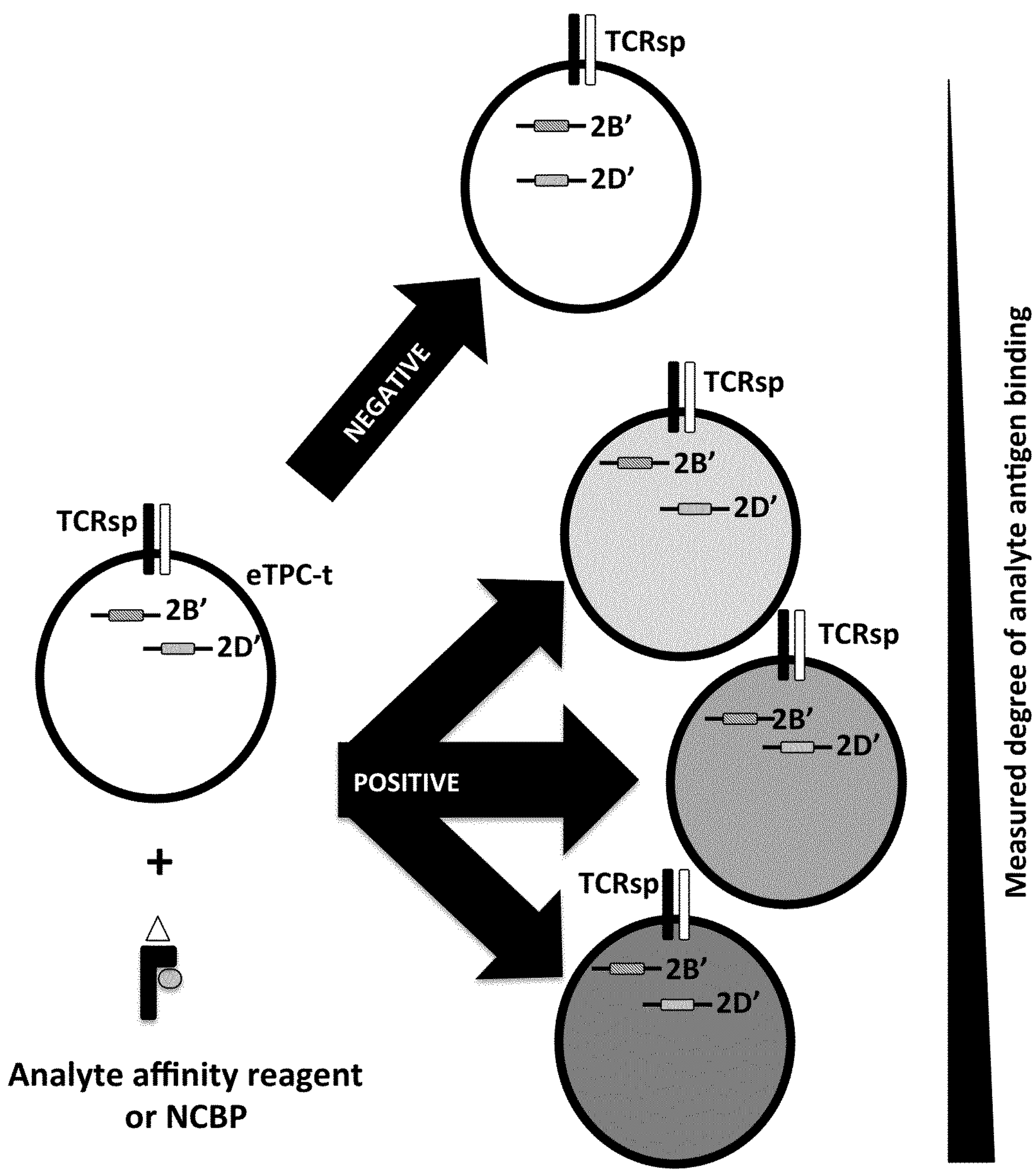

An analyte eTPC-t obtained from the two-part device may be used for characterisation of a TCRsp presented by the eTPC-t. Such characterisation may be conducted in a manner where the analyte eTPC-t is contacted with an immobilised or soluble affinity reagent or non-cell based particle (NCBP) in such a manner as to label the eTPC-t (FIG. 15).

Figure 16:
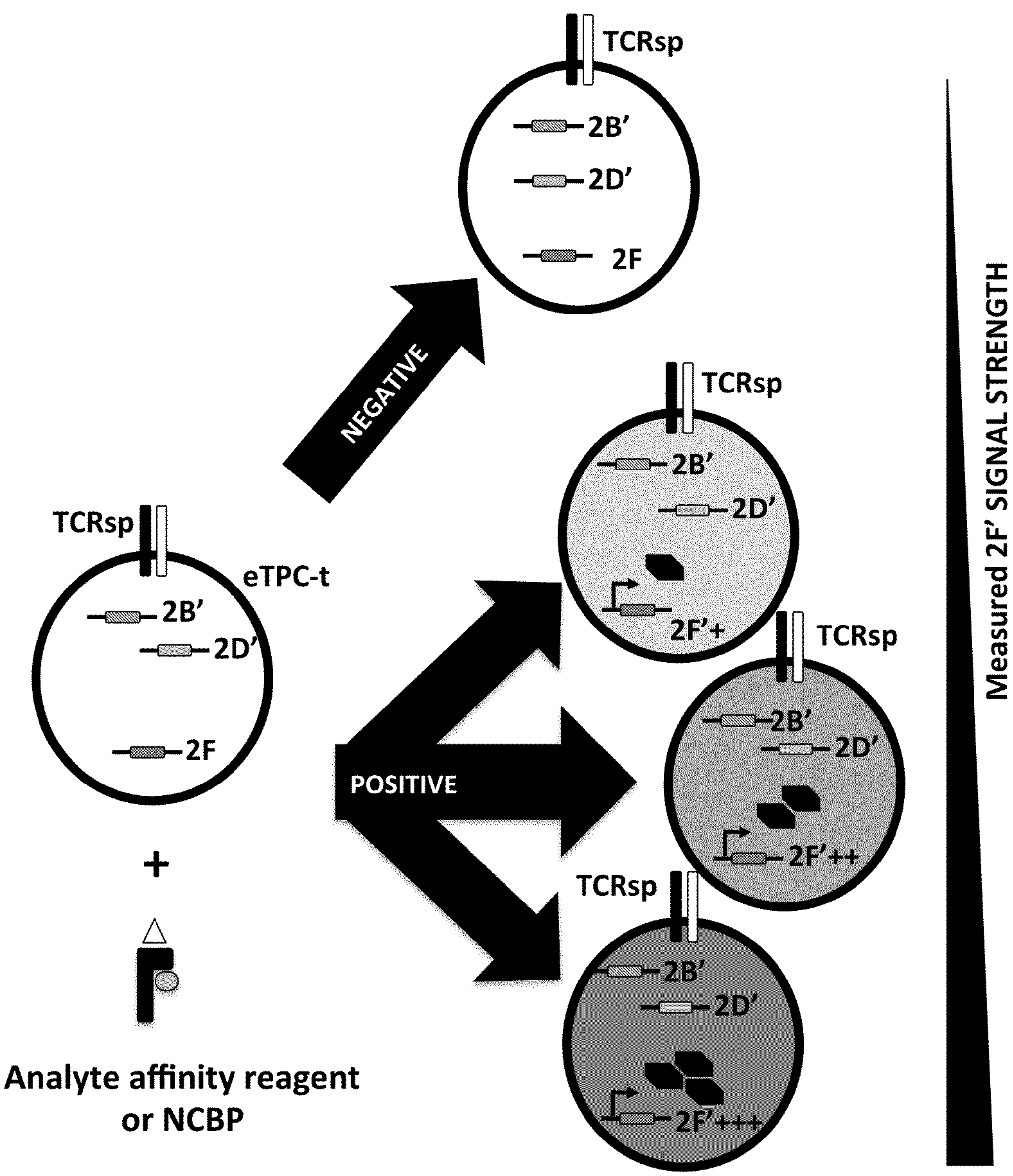

Labelling may be considered to be detected by direct observation of the label through such methods as flow cytometry, microscopy, spectrometry or luminometry or alternatively by means of capture with an immobilised affinity reagent or NCBP. In a similar manner, the affinity reagent or NCBP may stimulate the reporter element, component 2F, if included. Stimulation of component 2F would allow selection of eTPC-t and/or affinity reagent or NCBP for identification (FIG. 16).

Signal Responses Definition

Figure 17:
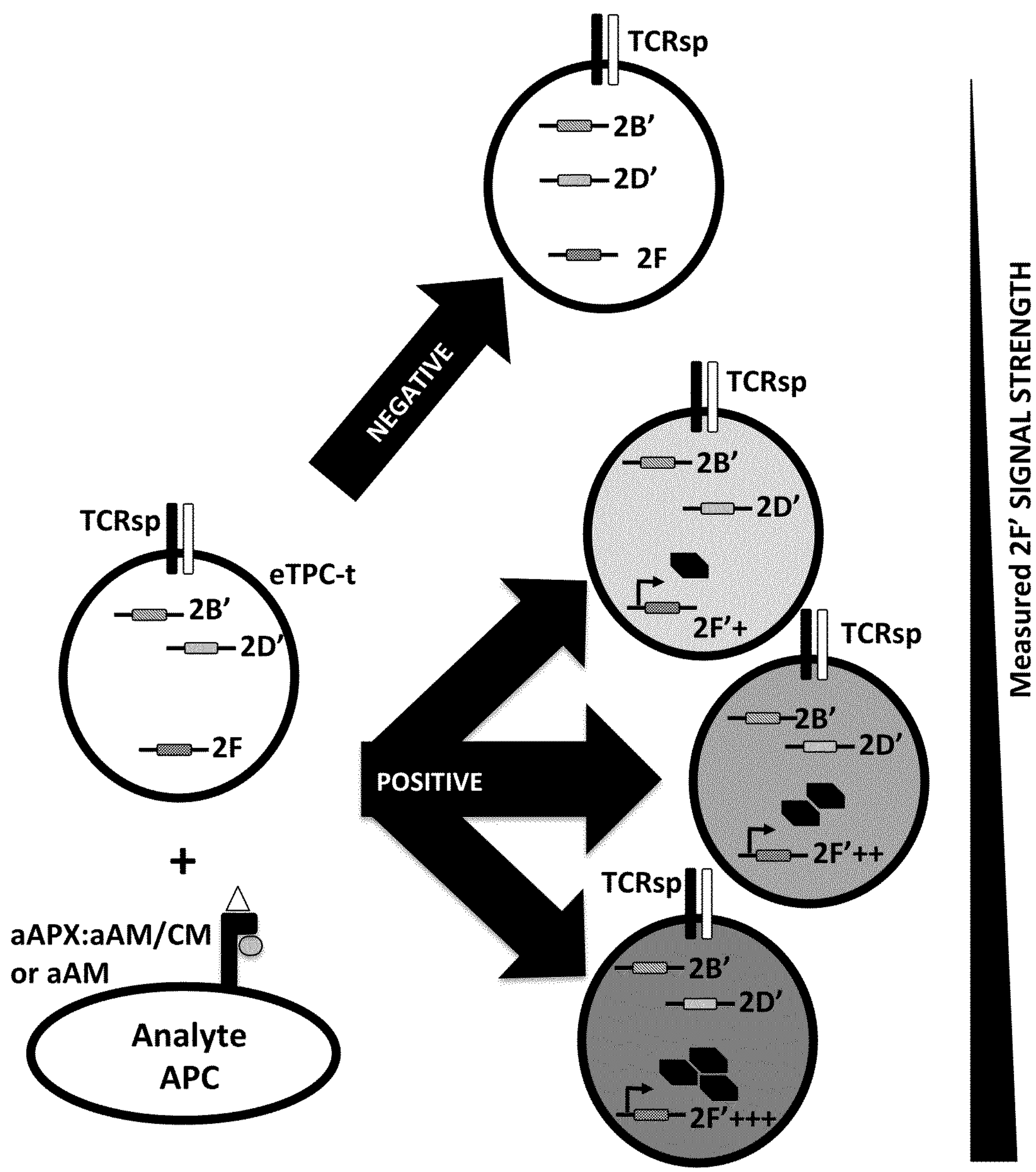
Figure 18:
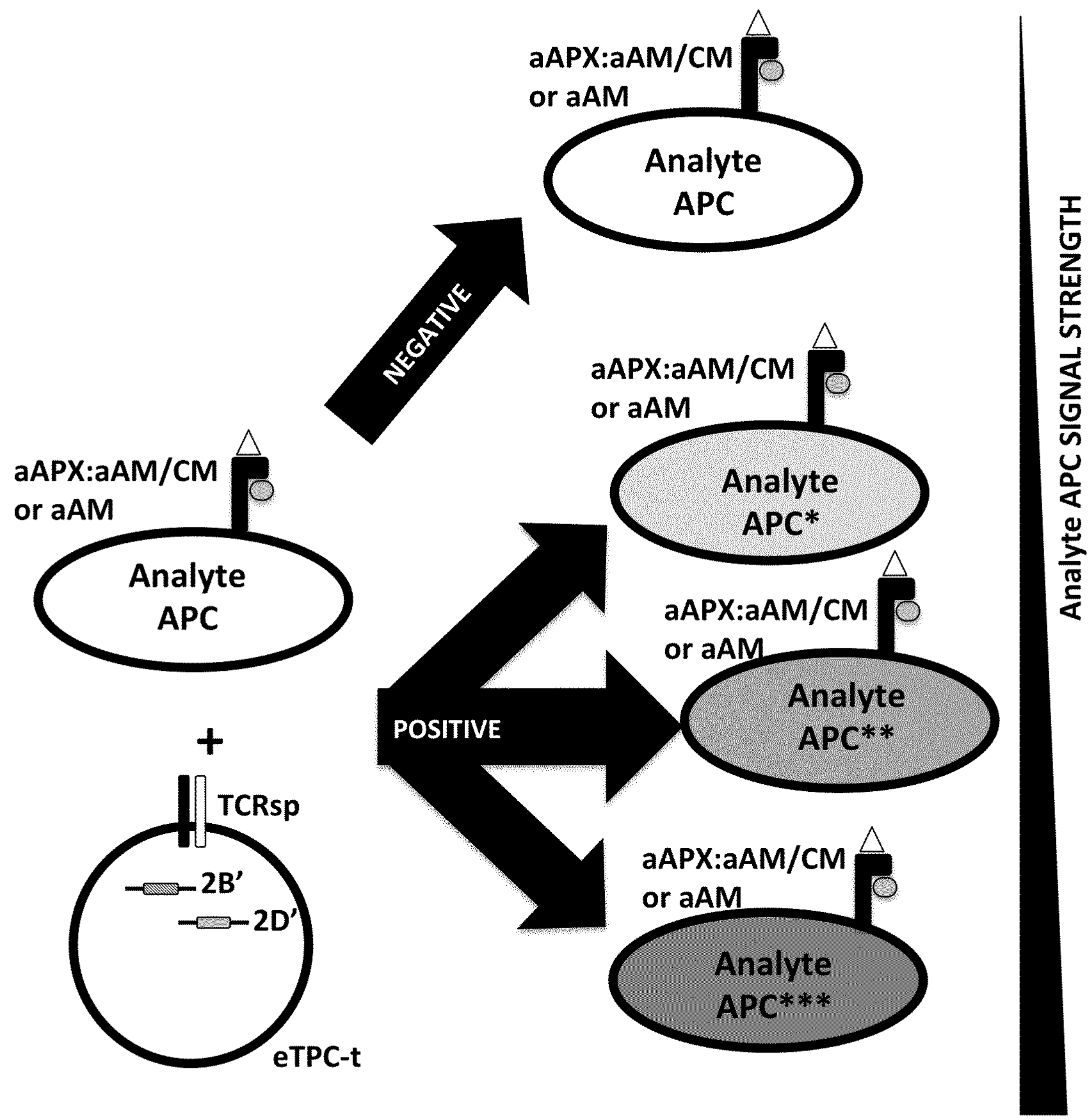

An analyte eTPC-t obtained from the two-part device is used for characterisation of a signal response of the analyte eTPC-t, expressing analyte TCRsp, to an analyte antigen, wherein such a signal response may be either binary or graduated, and may be measured as intrinsic to the eTPC-t (FIGS. 15, 16 and 17) and/or intrinsic to the APC, if included (FIG. 18). Such signals may be detected through methods such as flow cytometry, microscopy, spectrometry or luminometry or other methods known to those skilled in the art.

Contacting with an APC with Signal Responses

An analyte APC may also be contacted with the eTPC-t within an eTPC:A system. Generally, the response will be measured by reported signal within the eTPC-t (FIG. 17), but may also be measured by reported signal within the APC (FIG. 18).

General Method—Selecting an eTPC-t

The method for selecting one or more analyte eTPC-t from an input analyte eTPC-t or a library of analyte eTPC-t, from the combined eTPC:A system, to obtain one or more analyte eTPC-t wherein the expressed TCRsp binds to one or more analyte antigen comprises i. Combining one or more analyte eTPC-t with one or more analyte antigen resulting in a contact between an analyte TCRsp with an analyte antigen and at least one of
ii. Measuring a formation, if any, of a complex between one or more analyte TCRsp with one or more analyte antigen and/or
iii. Measuring a signal from a labelled analyte antigen and/or
iv. Measuring a signal response by the analyte eTPC-t, if any, induced by the formation of a complex between one or more analyte TCRsp with one or more analyte antigen and/or
v. Measuring a signal response by the analyte APC, if any, induced by the formation of a complex between one or more analyte TCRsp with one or more analyte antigen and
vi. Selecting one or more analyte eTPC-t based on step ii, iii, iv and/or v wherein the selection is made by a positive and/or negative measurement wherein i, iv and vi or i, v and vi comprise the preferred arrangements.

General Method—Selecting an Analyte Antigen

The method for selecting one or more analyte antigen from an input analyte antigen or a library of analyte antigen, to obtain one or more analyte antigen wherein the expressed analyte antigen binds to one or more analyte TCRsp presented by the analyte eTPC-t comprises i. Combining one or more analyte antigen with one or more analyte eTPC-t, resulting in a contact between an analyte antigen presented by the analyte antigen with analyte TCRsp of one or more analyte eTPC-t and
ii. Measuring a formation, if any, of a complex between one or more analyte antigen with one or more analyte TCRsp and/or
iii. Measuring a signal from a labelled analyte antigen and/or
iv. Measuring a signal response in the one or more analyte eTPC-t, if any, induced by the formation of a complex between the analyte TCRsp with the analyte antigen and/or
v. Measuring a signal response, if any, by the analyte APC induced by the formation of a complex between one or more analyte TCRsp with one or more analyte antigen and
vi. Selecting one or more analyte antigen from step ii, iii, iv and/or v wherein the selection is made by a positive and/or negative measurement wherein i, iv and vi or i, v and vi comprise the preferred arrangements.

General Method for Signal Response

A method for selecting analyte eTPC-t and/or analyte APC and/or affinity reagents and/or NCBP from the combined eTPC:A system on the basis of a reported signal response comprises i. Determining a native signalling response and/or
ii. Determining a synthetic signalling response, if the eTPC-t contains component 2F, and/or if the APC contains an equivalent synthetic reporter element.

An induced native or synthetic signal response that is intrinsic to APC and/or eTPC-t is measured by detecting an increase or decrease in one or more of the following i. a secreted biomolecule
ii. a secreted chemical
iii. an intracellular biomolecule
iv. an intracellular chemical
v. a surface expressed biomolecule
vi. a cytotoxic action of the analyte eTPC-t upon the analyte APC
vii. a paracrine action of the analyte eTPC-t upon the analyte APC such that a signal response is induced in the analyte APC and is determined by detecting an increase or decrease any of i to v
viii. a proliferation of the analyte eTPC-t
ix. an immunological synapse between the analyte eTPC-t and the analyte APC wherein said detected signal responses are compared to the non-induced signal response state intrinsic to analyte APC and/or analyte eTPC-t prior to assemble of the combined eTPC:A system and/or a parallel assembled combined system wherein analyte APC and/or analyte eTPC-t may present control analyte antigen and/or analyte TCR species and/or soluble analyte antigen that are known not to induce a signal response within the combined eTPC:A system in use.

Method of Selection by Labelling and/or Signal Response

A method for selecting analyte eTPC-t and/or analyte affinity reagents and/or analyte NCBP from the combined eTPC:A system on the basis of a measureable labelling of an eTPC-t by said affinity reagent or NCBP comprises;

i. Determining a labelling of the eTPC-t by an affinity reagent or NCBP and may also comprise
ii. Determining a native signalling response and/or
iii. Determining a synthetic signalling response, if the eTPC-t contains component 2F.

wherein selecting an eTPC-t and/or affinity reagent and/or NCBP by detecting labelling of the eTPC-t may comprise detection of the surface labelling of the eTPC-t by an affinity reagent and/or NCBP via including a detectable label on the affinity reagent and/or NCBP. Such detectable labels may be fluorescent, luminescent, spectrometric, chemical, radiochemical or affinity moieties. Thus, such selection of eTPC-t may be conducted on the basis of FACS, MACS or equivalent high-throughput screening and selection methodologies.

Summary

Within the combined eTPC:A system, measuring a signal response in the one or more analyte eTPC-t or in the one or more analyte APC, or the labelling of an eTPC-t, which may be mediated by the formation of a complex between the analyte TCRsp with the analyte antigen, is critical to selection of primary system outputs (FIG. 24 step v), wherein the primary system outputs are single cells or pools of cells, and/or or single affinity reagent or pools of affinity reagents and/or or single NCBP or pools of NCBP. The selection of cells or reagents may be made on the presence or absence of a reported signal response in either and/or both of the contacted analyte APC or analyte eTPC-t cells, or through the measurable labelling of eTPC-t with an affinity reagent or NCBP.

Obtaining Primary System Outputs from the eTPC:a System

The present invention relates to the provision of a two-part device from which analyte eTPC-t are derived. These analyte eTPC-t are then combined with one or more analyte antigens via the eTPC:A system as described previously to obtain one or more outputs. The analyte antigen is provided by analyte antigen-presenting cells (APC) and/or as soluble or immobilised analyte antigen and/or presented on non-cell based particles (NCBP). The system is comprised of a selection of one or more of analyte antigen with one or more eTPC-t populations (FIG. 24). The eTPC:A system is provided in a format that permits physical contact between the analyte antigens and analyte eTPC-t populations, wherein such contact is permissive of complex formation between one or more analyte antigen and TCRsp of one or more analyte eTPC-t, wherein the analyte antigen is any of the following i. aAPX and/or
ii. aAM and/or
iii. aAPX:aAM and/or
iv. CM and/or
v. aAPX:CM wherein the analyte antigen is either provided as, presented by an analyte APC, or presented by a soluble and/or immobilised analyte affinity reagent or analyte NCBP such that complex formation may lead to stabilisation of such a complex and wherein leads to labelling of the eTPC-t and/or the induction of signalling within the analyte eTPC, if included and/or the analyte APC, may be reported and measured.

The modes of induced signal response reporting, and/or eTPC-t labelling, are described above, and it is these reported responses and/or labelling that are required to be measured in obtaining the primary output of the two-part device compiled into an eTPC:A system.

Primary outputs from the eTPC:A system are selected cell populations and/or selected affinity reagents or selected NCBP, wherein the selection is made on the basis of;

i. a measurable labelling of eTPC-t by affinity reagent or NCBP and/or
ii. a detected signal response in an eTPC-t and/or
iii. lack of a detected signal response in an eTPC-t and/or
iv. a detected signal response in an analyte APC and/or
v. a lack of detected signal response in an analyte APC;

wherein a primary output may be represented as a single cell, or a pool of cells and/or one or more eTPC-t-associated affinity regent or NCBP.

A selection of analyte affinity reagent, NCBP or analyte APC and/or analyte eTPC-t from the combined eTPC:A system may be made on the basis of a response in the contacting cell. That is, an analyte APC may be selected on that basis of a reported response, or lack thereof, in the contacting analyte eTPC-t. Conversely, an analyte eTPC-t may be selected on that basis of a reported response, or lack thereof, in the contacting analyte antigen, or in the case wherein the analyte antigen is an analyte affinity reagent or NCBP, the analyte affinity reagent or NCBP can selected from the eTPC-t response.

Primary APC outputs from the system are selected cells, wherein selection is made based on the presence or absence of a reported signal response in either analyte APC or eTPC-t, and these cells may comprise one or more of APC and/or eTPC-t wherein the selected cells may comprise a single cell, a pool of cells of the same identity, a pool of cells of different identities (FIG. 24 step v).

Primary eTPC-t outputs from the system are selected cells, wherein selection is made based on the presence or absence of a reported signal response, and these cells comprise eTPC-t, wherein selected cells may comprise a single cell, a pool of cells of the same identity, a pool of cells of different identities (FIG. 24 step v).

Primary analyte affinity reagents or NCBP outputs from the system are selected cells with or without associated affinity reagent or NCBP, wherein selection is made based on the presence or absence of a labelling or reported signal response by the analyte eTPC-t, wherein selected affinity reagent or NCBP may comprise a single affinity reagent or NCBP, a pool of affinity reagent or NCBP of the same identity, a pool of affinity reagent or NCBP of different identities (FIG. 24 step v).

The reported signals in the analyte APC and/or analyte eTPC-t in a combined eTPC:A system may be used to select analyte cell populations or analyte affinity reagents or NCBP to provide the primary outputs.

A primary output of APC and/or eTPC-t types may be achieved in an instance wherein the combined eTPC:A system is of binary culture nature (e.g. FIGS. 15 to 18) by selecting the desired analyte APC and/or analyte eTPC-t population from the binary system.

A primary output of an eTPC-t may be achieved in an instance wherein the combined eTPC:A system is of binary composition of one or more analyte eTPC-t with a analyte antigen (e.g. FIGS. 19 to 21) by selecting the desired analyte eTPC-t population that is labelled with the analyte affinity reagent or NCBP, or activated by the analyte affinity reagent or NCBP or analyte APC within the eTPC:A system.

A primary output of an analyte affinity reagent or NCBP may be achieved in an instance wherein the combined eTPC:A system is of binary composition of one or more analyte eTPC-t with a analyte affinity reagent or NCBP (e.g. FIG. 21) by selecting the desired analyte eTPC-t population that is labelled with, and/or has a signal induced by, the analyte affinity regent or NCBP from the eTPC:A system.

A primary output of APC may be achieved from an instance wherein the combined eTPC:A system is of fixed analyte eTPC-t and pooled library analyte APC (e.g. FIG. 22) by selecting analyte APC based on a detection of a response, or lack thereof, within the analyte APC.

Modes of Obtaining Outputs from the eTPC:A System

There are several distinct modes in which the primary outputs may be obtained, wherein each mode entails a step of sorting. Sorting may be achieved through fluorescence-activated cell sorting (FACS) and/or magnetic-activated cell sorting (MACS) and/or distinct affinity-activated cell sorting methods.

Primary output APC and/or eTPC-t cells, and/or eTPC-associated affinity reagents or NCBP, may be obtained by single cell sorting to obtain a single cell and/or cell sorting to a pool to obtain a pool of cells.

Primary output APC and/or eTPC-t cells may be obtained by single cell sorting to obtain a single cell, and optionally subsequent outgrowth of the single cells to obtain monoclonal pool of selected APC or eTPC-t cells.

Primary output APC and/or eTPC-t cells may be obtained by cell sorting to a pool to obtain a pool of cells, and optionally subsequent outgrowth of the pool of cells to obtain a pool of selected APC and/or eTPC-t cells.

Obtaining Terminal System Outputs from the eTPC:A System

Subsequent to the above-described methods of obtaining primary outputs, wherein primary outputs are selected analyte APC and/or analyte eTPC-t that are selected on the basis of a measured signal response, or stable complex formation, such that the terminal outputs from the eTPC:A system may be obtained via further processing of the selected APC and/or eTPC primary outputs.

In the present context, terminal outputs from the multicomponent system are the identities of i. aAPX and/or
ii. aAM and/or
iii. aAPX:aAM and/or
iv. CM and/or
v. aAPX:CM and/or
vi. TCRsp presented by the analyte APC or analyte eTPC-t or an analyte affinity reagent or NCBP, and obtained as primary outputs from the multicomponent system by their selection from the combined eTPC:A system.

Within the eTPC:A system, it is often the case that analyte molecules that are presented by the analyte APC and analyte eTPC are genetically encoded. It may also be the case that an analyte NCBP has a genetically encoded identity, in the case of bacteriophage displayed NCBP, for example. Therefore, to identify the analyte molecules presented by the analyte APC or analyte eTPC-t, genetic sequencing of the prepared analyte APC, eTPC-t and analyte NCBP may be performed.

APC may be processed such that genetic sequence is obtained for the genome or transcriptome of the sorted and/or expanded APC cells to determine the identity of i. aAPX and/or
ii. aAM and/or
iii. aAPX:aAM
iv. CM and/or
v. aAPX:CM and/or wherein the obtained identities represent terminal outputs from the eTPC:A system. In the present context, analyte NCBP that possess a genetic component may be processed such that genetic sequence is obtained for the genome or transcriptome of the sorted and/or expanded analyte NCBP to determine the identity of analyte NCBP, wherein the obtained identities represent terminal outputs from the eTPC:A system.

An eTPC-t may be processed such that genetic sequence is obtained for component 2B' and/or component 2D' of the sorted and/or expanded eTPC-t cells to determine the identity of TCRsp, wherein the obtained identify of the TORES generated TCRsp represents a terminal output from the eTPC:A system.

eTPC may be processed such that genetic sequence is obtained for the genome or transcriptome of the sorted and/or expanded eTPC-t cells to determine the identity of TCRsp, wherein the obtained identify of TCRsp represents a terminal output from the eTPC:A system.

Genetic sequencing can be achieved by a range of modes, and from a range of genetic material sources, with and without specific processing.

In the present context, the sequencing step may be preceded by i. Extracting of genomic DNA and/or
ii. Extracting of components 2B' and/or 2D' RNA transcript and/or
iii. Amplifying by a PCR of the DNA encoding component 2B' and/or 2D'
iv. Amplifying by a RT-PCR of RNA transcript derived from component 2B' and/or 2D'.

The sequencing step may be destructive to the APC or eTPC-t or analyte NCBP, or pool thereof, obtained as primary outputs from the multicomponent system.

If it is desirable to obtain primary outputs from the eTPC:A system wherein the sequencing step has been destructive to the primary output eTPC-t, the sequence information obtained as terminal output of the two-part device may be used to prepare equivalent output eTPC-t as analyte eTPC-t.

In the above described scenarios of genetically encoded analyte molecules, the terminal outputs of the eTPC:A system may be obtained by obtaining sequence information from component 2B' and/or 2D', and/or from the cell genome and/or transcriptome. However, in some embodiments the antigen information will not be genetically encoded. Post-translationally modified antigens, antigens provided to the combined eTPC:A system through non-genetic means, antigens that are emergent from a induced or modified state of the analyte APC proteome or metabolite, CM intrinsic to the eTPC:A system, and affinity reagents or NCBP without a genetic element, may not reasonably be identified through genetic sequencing means.

In the important case of aAM that may be provided to the eTPC:A system by non-genetic means, there are two distinct modes through which an APC may present a provided aAM as an aAPX:aAM complex. In the first scenario the aAM is provided in a form that may directly bind to the aAPX and forms an aAPX:aAM complex at the cells surface. An example of such an aAM would be a peptide antigen for an HLA complex. In the second scenario, the aAM is provided is in a form that may be taken up by the analyte APC and processed such that it is loaded as cargo in the aAPX and forms an aAPX:aAM complex at the cells surface.

A method to select and identify an aAM cargo or a CM cargo, wherein the cargo is a metabolite and/or a peptide, that is loaded in an aAPX of an APC selected and obtained by as a primary output of the multicomponent system, comprises i. isolating an aAPX:aAM or an aAPX:CM or the cargo aM or the cargo CM and
ii. identifying the loaded cargo wherein the identified loaded cargo (CM or aAM) represent terminal outputs of the two-part device.

There are generally two modes through which a cargo molecule may be identified from a selected APC. First, a forced release of the cargo from the aAPX:aAM or aAPX:CM results in isolation of the aAM or CM that is available for subsequent identification. An example of this is acid-washing of the APC to liberate peptide aAM from HLA complexes. Secondly, the capture of the aAPX:aAM or aAPX:CM, for example, by liberation of the complex and immunoaffinity isolation methods, results in isolation of the aAPX:aAM or aAPX:CM complexes, such that aAM or CM can be identified.

Methods for identifying isolated aAM and/or CM directly, or from the isolated aAPX:aAM or an aAPX:CM complexes, can comprise i. Mass spectrometry analysis
ii. Peptide sequencing analysis wherein the contain aAM and/or CM identities are terminal outputs from the two-part device.

Determining the Affinity of the TCRsp for Analyte Antigen Using the Two-Part Device as an eTPC:A System Subsequent to the above-described methods of obtaining primary outputs, wherein primary outputs are selected analyte eTPC-t cells that are selected on the basis of a measured signal response, the eTPC-t primary outputs may be subjected to an affinity analysis to determine the affinity of the TCRsp to a cognate analyte antigen wherein the analyte antigen is any of the following i. aAPX and/or
ii. aAM and/or
iii. aAPX:aAM and/or
iv. CM and/or
v. aAPX:CM and wherein the analyte antigen is either provided as a soluble affinity reagent or presented by an analyte APC, or analyte NCBP such that the affinity of the analyte TCRsp is determined according to the following method i. Labelling the selected analyte eTPC-t with the analyte antigen at range of concentrations
ii. Conducting FACS analysis on the stained analyte eTPC-t of step a
iii. Determining the intensity of fluorescent labelling of the analyte eTPC-t over the range of concentrations of analyte antigen
iv. Calculating the affinity of the TCRsp to the analyte antigen The affinity of the analyte TCRsp may also be determined by the previously described method but wherein a labelled reference may also be included, such that the affinity is calculated using the ratio of the analyte antigen fluorescence intensity to the reference fluorescence intensity wherein the labelled reference is selected from i. The analyte eTPC-t labelled with an affinity reagent to one of the analyte TCR chains or to both analyte TCR chains
ii. The analyte eTPC-t labelled with an affinity reagent to one or more of the CD3 proteins
iii. a cell or particle presenting a labelled reference single TCR chain or labelled reference pair of TCR chains

LEGENDS TO FIGURES

FIG. 1. A two-part device comprising a TCR ORF reconstitution and engineering system (TORES) and engineered TCR-presenting cell system (eTPCS).

Part one of the two-part device represents a TCR ORF reconstitution and engineering system (TORES, upper panel). This system represents a library-based two-component vector system of fixed sequence, which when combined with a third component of unfixed sequence is used to reconstitute and diversify TCR ORFs. The function of the overall library feature of the TCR ORF reconstitution system is illustrated in the upper panel. A single V-C entry vector is selected from a library of V-C entry vectors with varying V-C combinations (Component 1A). This selection is based on the required V-C combination sequences for a selected TCR chain. A single J entry vector is selected from a library of J donor vectors with varying J gene segments encoded (Component 1B). This selection is based on the required J combination sequences for the same selected TCR chain as that of the V-C entry vector. Finally, an oligomeric duplex encoding CDR3 (odeCDR3) is selected as to complete the full-length ORF of the target TCR chain (Component 1C). These three components (1A, 1B and 1C) are combined into a single reaction along with appropriate restriction and ligase enzymes. The reaction cycle produces a reconstituted TCR ORF in a single step in the V-C entry vector backbone context (Reaction Product). This TCR ORFs represent integration vector components 2C and 2E of the second part of the two-part device.

Part two of the two-part device represents an engineered TCR presenting cell system (eTPCS), comprising five or six components. The first component 2A is the eTPC line itself with all required engineered features of that cell. The eTPC 2A contains three further components, two of which are 2B and 2D, which are genomic receiver sites for integration of an analyte TCR chain pair. A third optional component included in the eTPC, 2A, is a synthetic reporter construct that is induced upon TCR ligation, 2F. Two additional independent components, 2C and 2E, represent genetic integration vectors for site-directed integration of ORFs into sites 2B and 2D, respectively, where arrows indicate coupled specificity. Components 2C and 2E each represent a reaction product from the first part of the two-part device.

FIG. 2. Generic description of genetic input, byproducts, intermediates and product of the two-component vector system to assemble a TCR ORF using a TORES.

Depicted are the two components of the vector system (a and b), the oligonucleotide duplex (c), when these three components are combined into a single reaction with Type IIS restriction enzyme and ligase, two reaction byproducts (d and e), two reaction intermediates (f and g) and one reaction product (h) is generated. Input vectors and product of the two-component system are depicted as circularized plasmid schematics with genetic elements depicted as labeled boxes; open plasmid vectors that represent byproduct or intermediate are non-circularized plasmid schematics with genetic elements depicted as labeled boxes; and linear DNA are depicted as series of labeled boxes describing genetic elements.

a) Depicts is a circularized plasmid schematic of a V-C entry vector with minimally required genetic elements depicted as labelled boxes. Kozak, refers to consensus sequence that plays a role in the efficient initiation of translation. V-segment, refers to a selected sequence encoding a proportion of a TCR variable germline ORF, or mutant/synthetic ORF. Type IIS←, refers to a Type IIS restriction enzyme binding site orientated such the enzyme cleaves in the 5' direction. Type IIS→, refers to a Type IS restriction enzyme binding site orientated such the enzyme cleaves in the 3' direction. −ve selection, refers to a negative selection element designed to be detrimental to a plasmid harboring the sequence during the full-length TCR reconstruction reaction, or subsequent selection steps. C-segment, refers to a selected sequence encoding a proportion of a TCR constant germline ORF, or mutant/synthetic ORF. +ve selection #1, refers to the first positive selection marker of the TORES used to convey a selective advantage to the organism harboring the vector, and which is different to the positive selection marker of the second vector component (b). Ori, refers to an origin of replication used for the propagation of plasmid within a compatible host. 5' genetic element, refers to any desired genetic element that provides attributes required for downstream application of the reconstructed full-length TCR, and should be situated 5' of the reconstructed full-length TCR, at least including a sequence guiding directed integration to the genomic receiver sites contained within the eTPCS. 3' genetic element, refers to to any desired genetic element that provides attributes required for downstream application of the reconstructed full-length TCR, and should be situated 3' of the full-length TCR ORF, at least including a sequence guiding directed integration to the genomic receiver sites contained within the eTPCS.

b) Depicts a circularized plasmid schematic of a J donor vector with minimally required genetic features depicted as labeled boxes. J segment part, refers to a DNA sequence encoding a proportion of a TCR joining germline ORF, or mutant/synthetic J gene segment. C part, refers to a small 5' portion of the TCR Constant gene segment. Type IIS←, refers to a Type IIS restriction enzyme binding site orientated such the enzyme cleaves in the 5' direction. Type IIS→, refers to a Type IIS restriction enzyme binding site orientated such the enzyme cleaves in the 3' direction. +ve selection #2, refers to the second positive selection marker of the TORES used to convey a selective advantage to the organism harbouring the vector, and which is different to the first positive selection marker of the first vector component (a). Ori, refers to an origin of replication used for the propagation of plasmid within a compatible host.

c) Depicted is a third component that completes the target TCR ORF sequence as an oligonucleotide duplex encoding CDR3 region (odeCDR3). This DNA duplex containing CDR3 sequence flanked by two single stranded DNA overhangs, overhang ‡1-5' and overhang ‡1-3'. Overhang ‡1-5' is compatible with the overhang ‡1-3' in the open V-C entry vector intermediate (g). Overhang ‡2-3' is compatible with the overhang ‡2-5' in the donor fragment intermediate (f).

d) Digestion of the V-C entry vector (a) by the Type IIS restriction enzyme results in a linear DNA V-C entry vector reaction byproduct containing the −ve selection element and the Type IIS← and Type IIS→elements.

e) Digestion of the J donor vector (b) by the Type IIS restriction enzyme results in a linearised plasmid byproduct containing all genetic elements of the parental plasmid except those carried in the excised J donor fragment intermediate (f).

f) Digestion of the J donor vector (b) by the Type IIS restriction enzyme results in a linear DNA fragment containing the J segment part and C part flanked by single strand DNA overhangs, overhang ‡2-5' and overhang ‡3-3'. Overhang ‡2-5' is compatible with the overhang ‡2-3' in CDR3 DNA oligonucleotide duplex (c). Overhang ‡3-3' is compatible with the overhang ‡3-5' in the open V-C entry vector intermediate (g).

g) Digestion of the V-C entry vector (a) by the Type IIS restriction enzyme results in a non-circularized plasmid intermediate containing all genetic elements of the parental plasmid except those carried in the excised linear DNA V-C entry vector reaction by-product (d). Digestion additionally creates two single stranded DNA overhangs, overhang ‡1-3' and overhang ‡3-5'. Overhang ‡1-3' compatible with the overhang ‡1-5' in the CDR3 DNA oligonucleotide duplex (c). Overhang ‡3-5' is compatible with the overhang ‡3-3' in the J donor fragment intermediate (f).

h) Ligation of all three compatible single-stranded DNA overhangs results in the full-length TCR ORF vector as circularized plasmid (h). This plasmid contains all genetic elements of the parental V-C entry vector (a) with the exception of the excised V-C entry vector reaction by-product (d). In addition, the full-length TCR ORF vector incorporates the CDR3 sequence from the CDR3 DNA oligonucleotide duplex (c) and J segment part and C part from the J donor fragment reaction intermediate (f). Arrows indicate the approximate points of ligation between compatible single-stranded DNA overhangs ‡1, ‡2 and ‡3. Ligation point ‡1 is comprised of the ‡1-3' and ‡1-5' elements donated by the V-C entry vector reaction intermediate (g) and CDR3 DNA oligonucleotide duplex (c), respectively. Ligation point ‡2 is comprised ‡2-3' and ‡2-5' elements donated by the CDR3 DNA oligonucleotide duplex (c) and the J donor fragment reaction intermediate (f), respectively. Ligation point ‡3 is comprised ‡3-3' and ‡3-5' elements donated by the J donor fragment reaction intermediate (f) and the V-C entry vector reaction intermediate (g), respectively.

FIG. 3 Operation of the TORES to generate CDR3-diversified TCR chains

Depicted is a schematic representation of the TORES when used to generate full-length TCR chains with diversified CDR3 inserts. A parental TCR is defined with V-J-C usage, and defined CDR3 region sequence. The corresponding single V-C entry vector (box i) and single J donor vector (box ii) are placed in the reaction tube. A pool of odeCDR3 with defined positional nucleotide degeneracy and/or point mutagenesis that changes the coded amino acid sequence is synthesized (Box iii). Such a CDR3 pool could include completely randomized CDR3 sequences within the bounds of the defined odeCDR3 framework, as to create 'synthetic' CDR3 containing full-length TCR ORF with germline V-J-C usage. These three components (Box i, ii and iii) are combined into a single reaction along with appropriate restriction and ligase enzymes. The reaction cycle produces a number of variant reconstituted full-length TCR ORFs, proportional to the number of variant odeCDR3 included, in a single step in the V-C entry vector backbone context (Box iv).

FIG. 4 Operation of the TORES to generate V-segment diversified TCR chains

Depicted is a schematic representation of the TORES when used to generate full-length TCR chains with diversified V-segment usage. A parental TCR is defined with VJ-C usage, and defined CDR3 region sequence. The corresponding single J donor vector (box ii) is placed in the reaction tube, as is the single odeCDR3 synthesized to correspond with parental CDR3 region sequence (Box iii). A selection of V-C entry vectors is also added to the reaction tube, corresponding to the V- and C-segments desired in the product V-segment diversified full length TCR ORF product (Box i). These three components (Box i, ii and iii) are combined into a single reaction along with appropriate restriction and ligase enzymes. The reaction cycle produces a number of variant reconstituted full-length TCR ORFs, proportional to the number of variant V-C entry vectors included, in a single step in the V-C entry vector backbone context (Box iv).

FIG. 5 Operation of the TORES to generate J-segment diversified TCR chains

Depicted is a schematic representation of the TORES when used to generate full-length TCR chains with diversified J-segment usage. A parental TCR is defined with VJ-C usage, and defined CDR3 region sequence. The corresponding single V-C entry vector (box i) is placed in the reaction tube, as is the single odeCDR3 synthesized to correspond with parental CDR3 region sequence (Box iii). A selection of J donor is also added to the reaction tube, corresponding to the J segments desired in the product J-segment diversified full length TCR ORF product (Box ii). These three components (Box i, ii and iii) are combined into a single reaction along with appropriate restriction and ligase enzymes. The reaction cycle produces a number of variant reconstituted full-length TCR ORFs, proportional to the number of variant J donor vectors included, in a single step in the V-C entry vector backbone context (Box iv).

FIG. 6 Operation of the TORES to generate V/J-segment diversified TCR chains Depicted is a schematic representation of the TORES when used to generate full-length TCR chains with diversified V- and J-segment usage. A parental TCR is defined with V-J-C usage, and defined CDR3 region sequence. The corresponding single odeCDR3 synthesized to correspond with parental CDR3 region sequence (Box iii). A selection of V-C entry vectors and J donor vectors are added to the reaction tube, corresponding to the combination of V-(C-) and J-segments desired in the product V/J-segment diversified full length TCR ORF product (Box ii). These three components (Box i, ii and iii) are combined into a single reaction along with appropriate restriction and ligase enzymes. The reaction cycle produces a number of variant reconstituted full-length TCR ORFs, proportional to the number of V-C and J donor vector combinations possible from those included, in a single step in the V-C entry vector backbone context (Box iv).

FIG. 7 Compilation of intermediate eTPC-x and analyte eTPC-t populations from eTPC.

The operation of the two-part device entails the insertion of vectors prepared within the TORES into eTPCS to prepare analyte eTPC populations to create cells expressing analyte TCRsp, or an intermediate expressing single analyte TCR chains. An eTPC presenting TCRsp is termed eTPC-t, and may be created by introduction of two complimentary TCR chain encoding ORFs to the eTPC (step i). An eTPC expressing a single analyte TCR chain alone is termed an eTPC-x, and may be created by introduction of a single TCR chain encoding ORF(s) to the eTPC (step ii). A eTPC-t may alternatively be created from an eTPC-x, wherein a second complimentary TCR chain encoding ORF is introduced to an existing eTPC-x (step iii). In some instances, an eTPC-x may be created from an eTPC-t by removing a single analyte TCR chain (step iv).

FIG. 8 Compilation of an eTPC-t in one step.

The eTPC 2A contains distinct genomic receiver sites 2B and 2D. The eTPC 2A may further contain a TCR signal response element 2F. Distinct genetic integration vectors 2C and 2E generated within the TORES are independently coupled to 2B and 2D, respectively. Integration vector 2C encodes a single TCR chain, and integration vector 2E encodes a second complementary TCR chain. The eTPC 2A is combined with integration vectors 2C and 2E. The resulting cell has insert 2C exchanged to the 2B genomic receiver site to create site 2B' and deliver an ORF for a first TCR chain. In addition, the resulting cell line has insert 2E exchanged to the 2D genomic receiver site to create site 2D' and deliver an ORF for a second TCR chain. This cell is capable of presenting a TCRsp at the surface, and is thus designated a eTPC-t.

FIG. 9 Compilation of an eTPC-t in two steps via an eTPC-x intermediate.

The eTPC 2A contains distinct genomic receiver sites 2B and 2D. The eTPC 2A may further contain a TCR signal response element 2F. Distinct genetic integration vectors 2C and 2E generated within the TORES are independently coupled to 2B and 2D, respectively. Integrative vector 2C encodes a single TCR chain, and integration vector 2E encodes a second reciprocal TCR chain. In STEP 1 an eTPC 2A is combined with integrative vector 2C. The resulting cell has the TCR ORF of 2C exchanged to the 2B genomic receiver site to create site 2B' and deliver an ORF for a first TCR chain. This cell expresses only a single TCR chain and is thus designated a eTPC-x. Genomic receiver site 2D remains unused. In STEP 2, the eTPC-x is combined with integration vector 2E. The resulting cell has insert 2E exchanged to the 2D genomic receiver site to create site 2D' and deliver an ORF for a second complementary TCR chain. This cell is capable of presenting a TCRsp at the surface, and is thus designated a eTPC-t.

FIG. 10 Reversion of an eTPC-t to an eTPC-x

The cell depicted in the upper panel is capable of presenting a TCRsp at the surface, and is thus designated a eTPC-t. This eTPC-t has genomic receiver sites 2B and 2D occupied by TCR ORFs, rendering them in the 2B' and 2D' forms. Genetic integration vectors harbouring genomic receiver site marker(s), and coupled to sites 2B' or 2D', designated 2Y and 2Z. Addition of 2Y or 2Z to the eTPC-t will exchange the genomic receiver site marker for the TCR chain encoded by either 2B' or 2D'. The resulting cell expresses only a single TCR chain, and thus is designated eTPC-x.

FIG. 11 Shotgun compilation of an eTPC-t pool from an eTPC to express random combinations of TCRsp from a TCR chain library.

The eTPC 2A contains distinct genomic receiver sites 2B and 2D. Distinct genetic integration vectors 2C and 2E are independently coupled to 2B and 2D, respectively. Integration vectors 2C i and 2C ii each encode a single TCR chain, and integration vectors 2E i and 2E ii each encode a complementary single TCR chain. The eTPC 2A may further contain a TCR signal response element 2F. The eTPC 2A is combined with integration vectors 2C i, 2C ii, 2E i and 2E ii. The resulting cell pool has TCR ORF of 2C i or 2C ii exchanged to the 2B genomic receiver site, in multiple independent instances to create sites 2B' i and 2B' ii, each delivering a single ORF for a TCR chain. The resulting cell pool further has insert 2E i or 2E ii exchanged to the 2D genomic receiver site, in multiple independent instances to create sites 2D' i and 2D' ii, each delivering a single ORF for a TCR chain complementary to those at sites 2C'i and 2C'ii. The resulting eTPC-t cell pool comprises a mixed population of four distinct cell cohorts each expressing a discrete randomised TCRsp at the surface comprised of one of each complementary TCR chains contained in the initial vector library. This process can be scaled to different number of 2C and 2E variants to achieve cell libraries with randomized TCRsp presentation at various scales.

FIG. 12 Shotgun compilation of an eTPC-t pool from an eTPC-x with unpaired analyte TCR chains to express random combinations of paired TCR chain pairs from a TCR chain library.

A precompiled eTPC-x contains the exchanged genomic receiver site 2B' expressing a single TCR chains and the distinct genomic receiver site 2D. Distinct genetic integration vectors 2E i and 2E ii are coupled to 2D. Integration vectors 2E i and 2E ii each encode a single TCR chain. The eTPC-x may further contain a TCR signal response element 2F. The eTPC-x is combined with integration vectors 2E i and 2E ii. The resulting cell pool has insert 2E i or 2E ii exchanged to the 2D genomic receiver site, in multiple independent instances to create sites 2E i and 2E ii, each delivering a single ORF for a TCR chain. The resulting eTPC-t cell pool comprises a mixed population of distinct cell cohorts expressing a discrete TCRsp at the surface comprised of the TCR chain expressed from 2B' paired with a single randomised complementary TCR chain contained in the initial vector library.

FIG. 13 Shotgun compilation of an eTPC-x pool from an eTPC to express random members of a TCR chain library.

The eTPC 2A contains distinct genomic receiver sites 2B and 2D. Distinct genetic integration vectors 2C and 2E are independently coupled to 2B and 2D, respectively. Integration vectors 2C i, 2C ii and 2C ii each encode a single TCR chain. The eTPC 2A may further contain a TCR signal response element 2F. The eTPC 2A is combined with integration vectors 2C i, 2C ii, and 2C iii. The resulting cell pool has TCR OFF of 2C i, 2C ii or 2C iii exchanged to the 2B genomic receiver site, in multiple independent instances to create sites 2B' i, 2B' ii or 2B' iii each delivering a single ORF for a TCR chain. The resulting eTPC-x cell pool comprises a mixed population of distinct cell cohorts each expressing a discrete randomised TCR chain contained in the initial vector library. This process can be scaled to different number of 2C variants to achieve cell libraries with randomized TCR chain presentation at various scales.

FIG. 14 Shotgun compilation of an eTPC-t pool from a pool of eTPC-x with unpaired analyte TCR chains to express random combinations of paired TCRsp from a TCR chain library.

A pool of eTPC-x contains the exchanged genomic receiver site 2B' i, 2B' ii or 2B' iii, each expressing a single TCR chain, and the distinct genomic receiver site 2D. Distinct genetic integration vectors 2E is coupled to 2D. Integration vectors 2E encodes a single TCR chain. The eTPC-x may further contain a TCR signal response element 2F. The eTPC-x pool is combined with integration vectors 2E. The resulting cell pool has TCR ORF of 2E exchanged to the 2D genomic receiver site, in multiple independent instances to create site 2D', delivering a single ORF for a TCR chain. The resulting eTPC-t cell pool comprises a mixed population of distinct cell cohorts expressing a discrete TCRsp at the surface comprised of the TCR chain expressed from a combination of the 2B' encoded TCR chains, paired with TCR chain contained in 2D'. This process can be scaled to different number of 2E variants to achieve cell libraries with randomized TCRsp presentation at various scales.

FIG. 15 Operation of a combined analyte eTPC:A system showing possible analyte affinity reagent- or NCBP-bound eTPC-t output states.

The analyte eTPC-t contains sites 2B' and 2D' each integrated with one ORF encoding a reciprocal TCRsp at the surface. When analyte eTPC-t and analyte affinity reagent or NCBP are contacted, different eTPC-t labelling states can be achieved; in this example one negative and three positive. The negative state is the resting state of the input eTPC-t, with no detectable binding of the analyte affinity reagent or NCBP, denoting failure of the analyte affinity reagent or NCBP to form a stable complex with the eTPC-t-presented TCRsp. Three positive states show hypothetical range of the degree of binding of the analyte affinity reagent or NCBP, as denoted by darker shading of the cells. This indicates a graded binding of analyte affinity reagent or NCBP analyte to the TCRsp expressed by eTPC-t population.

FIG. 16 Operation of a combined analyte eTPC:A system showing possible signal-reported eTPC-t-output states in response to analyte affinity reagent or NCBP.

The analyte eTPC-t contains sites 2B' and 2D' each integrated with one ORF encoding a reciprocal TCRsp at the surface. The eTPC-t further contains a TCR signal response element 2F. When analyte eTPC-t and analyte affinity reagent or NCBP are contacted, different eTPC-t response states can be achieved, in this example one negative and three positive. The negative state is the resting state of the eTPC-t, with no signal strength at the 2F element, denoting failure of the analyte affinity reagent or NCBP to form a complex and stimulate the eTPC-t presented TCRsp. Three positive states show increasing signal strength from the 2F. States 2F'+, 2F'++ and 2F'+++ denote low, medium and high signal strength, respectively. The gene product of 2F denoted as hexagons accumulates to report signal strength of each cell state, as denoted by darker shading of the cells. This indicates a graded response of analyte TCRsp expressed by eTPC-t population towards analyte affinity reagent or NCBP resulting in signal transduction to the 2F element.

FIG. 17 Operation of a combined analyte eTPC:A system showing possible signal-reported eTPC-t-output states in response to analyte APC.

The analyte eTPC-t contains sites 2B' and 2D' each integrated with one ORF encoding a reciprocal TCRsp at the surface. The eTPC-t further contains a TCR signal response element 2F. When analyte eTPC-t and analyte APC populations are contacted, different eTPC-t response states can be achieved, in this example one negative and three positive. The negative state is the resting state of the eTPC-t, with no signal strength at the 2F element, denoting failure of the analyte APC-presented aAPX:aAM/CM or aAM to stimulate the eTPC-t presented TCRsp. Three positive states show increasing signal strength from the 2F. States 2F'+, 2F'++ and 2F'+++ denote low, medium and high signal strength, respectively. The gene product of 2F denoted as hexagons accumulates to report signal strength of each cell state, as denoted by darker shading of the cells. This indicates a graded response of analyte TCRsp expressed by eTPC-t population towards analyte aAPX:aAM/CM or aAM presented by the analyte APC.

FIG. 18 Operation of a combined analyte eTPC:A system showing possible analyte APC output states.

The analyte eTPC-t contains sites 2B' and 2D' each integrated with one ORF encoding a reciprocal TCRsp at the surface. The eTPC-t further contains a TCR signal response element 2F. When analyte eTPC-t and analyte APC populations are contacted, different APC response states can be achieved, in this example one negative and three positive. The negative state is the resting state of the analyte APC, denoting failure of the TCRsp chain pair to stimulate the aAPX:aAM/CM or aAM complex presented by the analyte APC. Three positive states show increasing signal strength from the contacted aAPX:aAM/CM or aAM. The reported signal strength of each cell state, is denoted by *, , *, and also denoted by darker shading of the cells. This indicates a graded response of analyte aAPX:aAM/CM or aAM towards the analyte TCRsp chain pair presented by the analyte eTPC-t.

Figure 19:
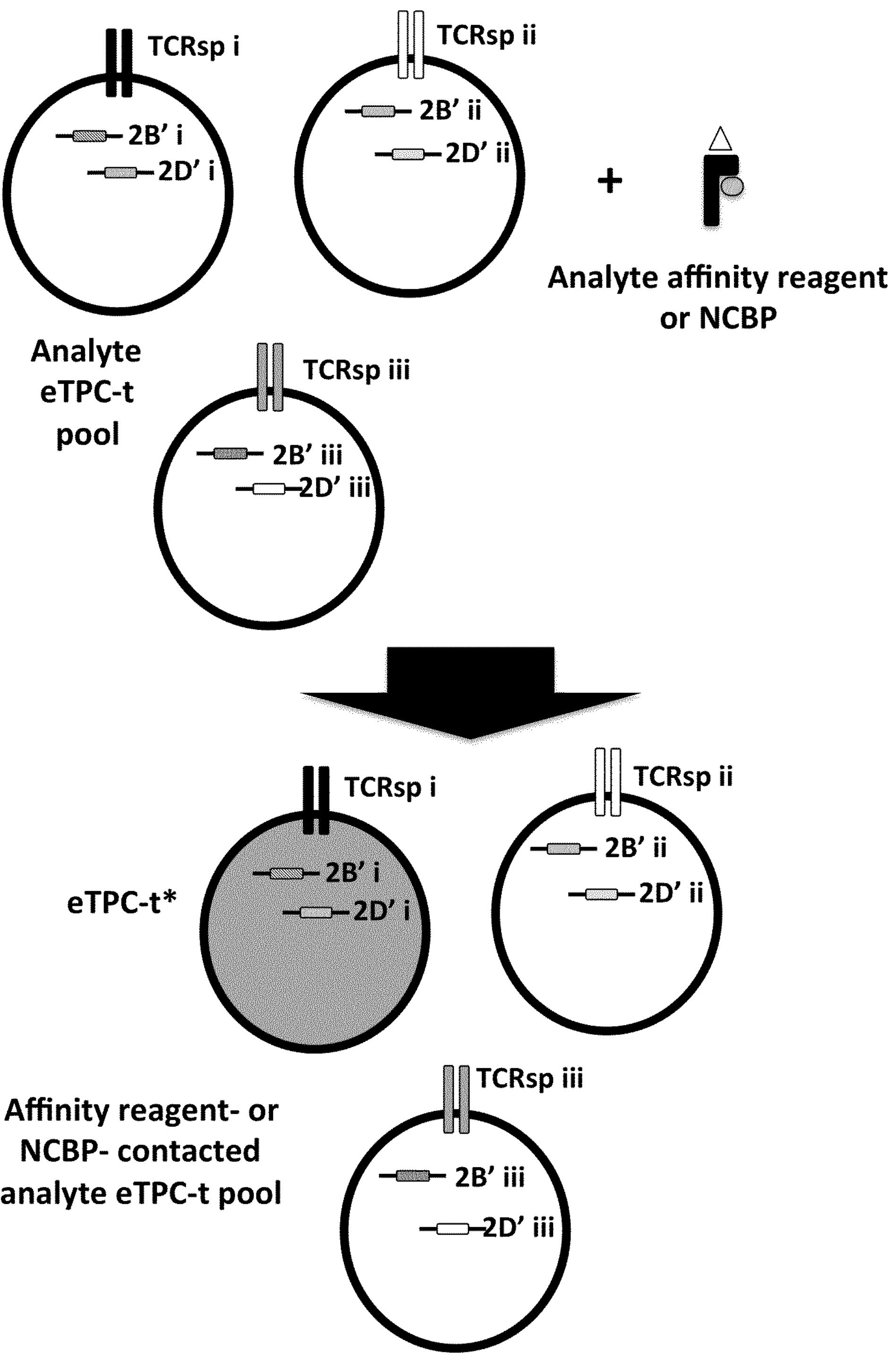

FIG. 19 Operation of a combined eTPC:A to identify TCRsp chain pairs binding with analyte affinity reagent or NCBP from a pool of eTPC-t.

The eTPC-t pool contains cells harbouring sites 2B' i, ii or iii and 2D' i, ii or iii, wherein each eTPC-t is integrated with a pair of ORFs encoding a pair of complementary TCR chains, and thus each cell cohort in the population expresses a discrete TCRsp at the surface. An analyte affinity reagent or NCBP is contacted with the analyte eTPC-t pool. In the present example, only the pair of TCR chains expressed from 2B' i/2D' i (TCRsp i) is specific for the analyte affinity reagent or NCBP such that, only the cell cohort of the eTPC-t that bears TCRsp i (etTPC-t*) is able to detectably bind the analyte antigen or NCBP (*). The eTPC-t* bound to analyte affinity reagent- or NCBP-may be selected from the pool on the basis of the affinity reagent- or NCBP-labelling. Subsequently the analyte TCRsp-encoding ORFs of the selected and isolated eTPC-t* can be identified by sequencing of 2B' and 2D' DNA directly or indirectly through reverse-transcriptase PCR of the expressed transcripts of 2B' and 2D'.

Figure 20:
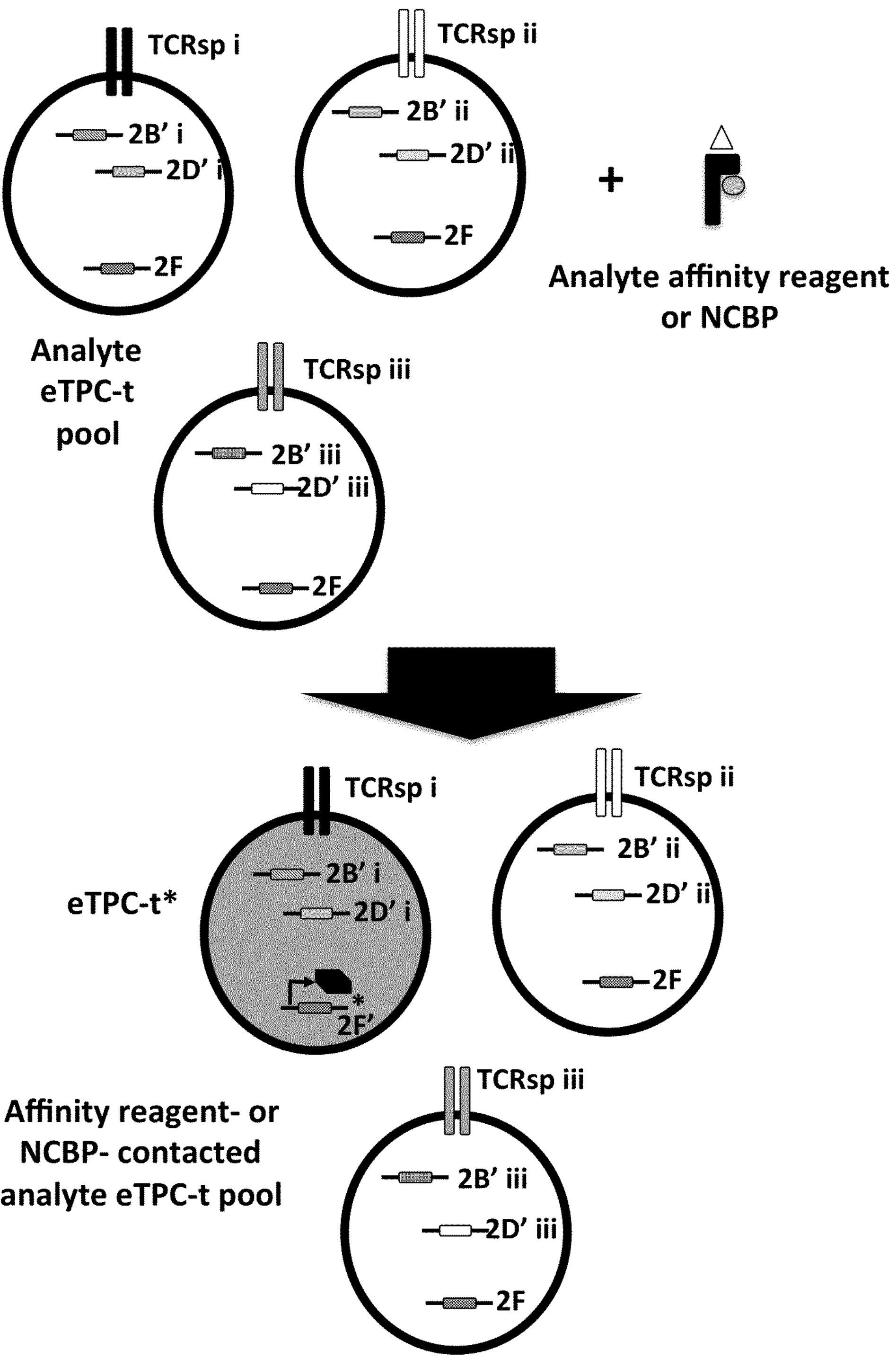

FIG. 20 Operation of a combined eTPC:A system to identify TCRsp chain pairs from a pool of eTPC-t via induction of a signal-report response through stimulation with analyte affinity reagent or NCBP.

The eTPC-t pool contains cells harbouring sites 2B' i, ii or iii and 2D' i, ii or iii, wherein each eTPC-t is integrated with a pair of ORFs encoding a complementary Pair of TCR chains, and thus each cell cohort in the population expresses a discrete TCRsp at the surface. The eTPC-t further contains a TCR signal response element 2F. An analyte antigen or NCBP is contacted with the analyte eTPC-t pool. In the present example, only the Pair of TCR chains expressed from 2B' i/2D' i (TCRsp i) is specific for the analyte affinity reagent or NCBP such that, only the cell cohort of the eTPC-t that bears TCRsp i (eTPC-t*) is able to induce a signal report response via element 2F (*). The eTPC-t* bound to analyte affinity reagent- or NCBP-may be selected from the pool of eTPC-t on the basis of the affinity reagent- or NCBP-labelling. Subsequently, the analyte TCRsp-encoding ORFs of the selected and isolated eTPC-t* can be identified by sequencing of 2B' and 2D' DNA directly or indirectly through reverse-transcriptase PCR of the expressed transcripts of 2B' and 2D'.

Figure 21:
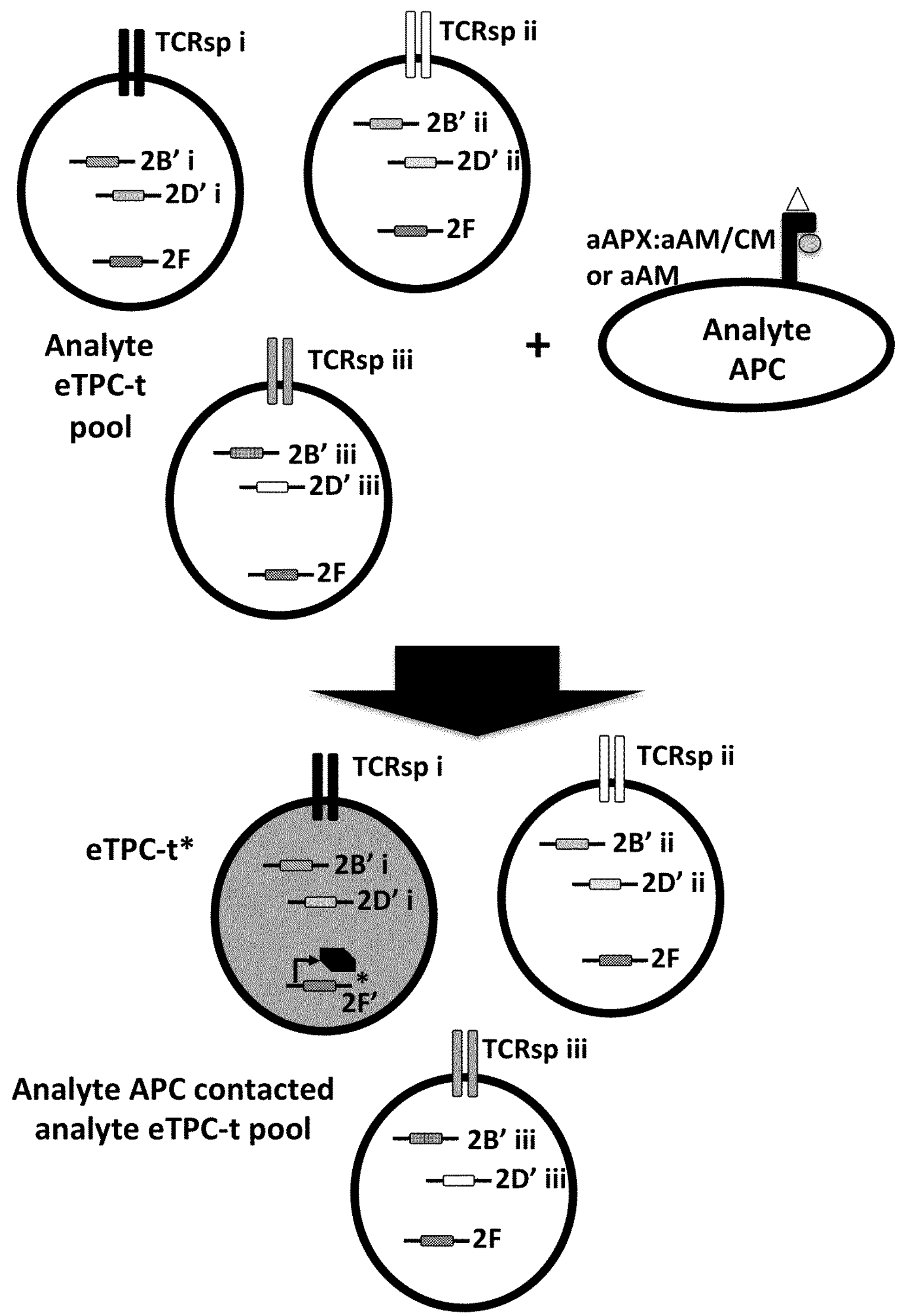

FIG. 21 Operation of a combined eTPC:A system to identify TCRsp chain pairs from an eTPC-t pool via induction of a signal-report response through stimulation with analyte APC The eTPC-t pool contains cells harboring sites 2B' i, ii or iii and 2D' i, ii or iii, wherein each eTPC-t is integrated with a pair of ORFs encoding a reciprocal TCR chain pair, and thus each cell cohort in the population expresses a discrete TCRsp at the surface. The eTPC-t further contains a TCR signal response element 2F. The analyte APC express on the surface an aAPX:aAM/CM or aAM. In the present example, only the TRC chain pair expressed from 2B' i/2D' i (TCRsp i) is specific for the aAPX:aAM/CM or aAM presented by the analyte APC, such that when eTPC-t pool and analyte APC population are contacted, only the cell cohort of the eTPC-t that bears TCRsp i (eTPC-t*) reports TCRsp engagement through state 2F'. The eTPC-t* stimulated by the analyte APC may be selected from the pool on the basis of signal-report response. Subsequently, the analyte TCRsp-encoding ORFs of the selected and isolated eTPC-t* can be identified by sequencing of 2B' and 2D' DNA directly or indirectly through reverse-transcriptase PCR of the expressed transcripts of 2B' and 2D'.

Figure 22:
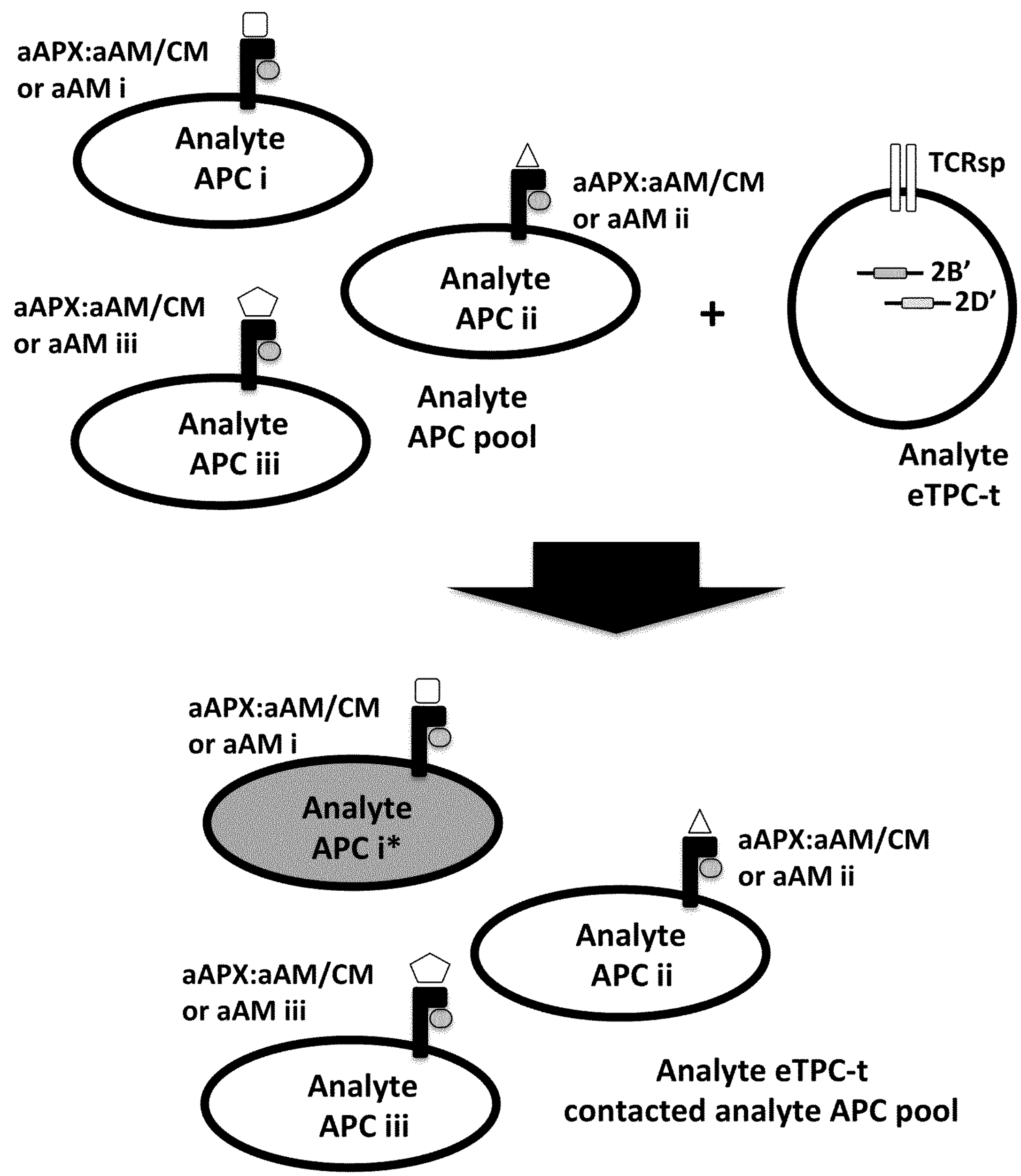

FIG. 22 Operation of a combined eTPC:A system to identify analyte antigens presented by analyte APC, via induction of an APC-centric signal-report response The analyte APC pool contains cells expressing varied aAPX:aAM/CM or aAM on their surface. The analyte eTPC-t contain the exchanged genomic receiver site 2B' and 2D' driving the expression of a TCRsp at the surface. In the present example, only the complex aAPX:aAM/CM or aAM i is specific for the TCRsp presented by the analyte eTPC-t, such that when analyte APC pool and analyte eTPC-t population are contacted, only the cell cohort expressing aAPX:aAM/CM i responds (*). This response may be an intrinsic signal response to eTPC-t engagement, such as a change in surface phenotype, transcript abundance or cell death. The responding analyte APC may be selected to determine aAPX:aAM/CM or aAM that has been contacted by the analyte TCRsp presented bet the analyte eTPC-t.

Figure 23:
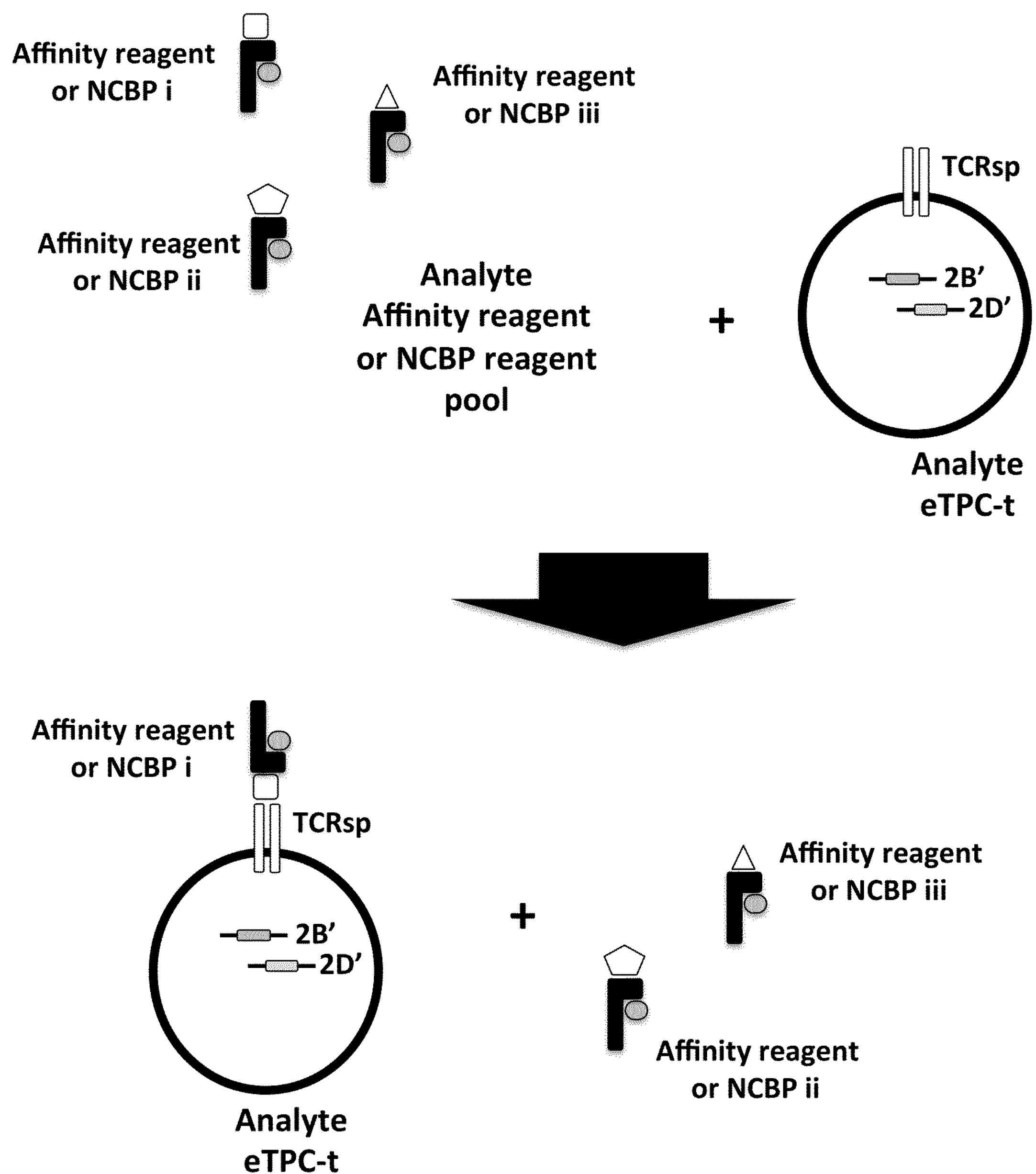

FIG. 23 Operation of a combined eTPC:A system to identify affinity reagent or NCBP from a pool of such entities via capture of the affinity reagent or NCBP reagent by an eTPC-t The analyte eTPC-t contain the exchanged genomic receiver site 2B' and 2D' driving the expression of a TCRsp at the surface. An affinity reagent or NCBP pool is contacted with analyte eTPC-t, which permits the binding of analyte affinity reagent or NCBP specific for TCRsp presented by the analyte eTPC-t. In the present depiction, the TCRsp specifically binds only affinity reagent or NCBP i, and thus the analyte eTPC-t is labelled with only affinity reagent or NCBP i. An affinity reagent or NCBP may thus be selected from the pool via association with the eTPC-t, to identify those affinity reagents or NCBP specific for the analyte TCRsp presented by the analyte eTPC-t.

FIG. 24 Operation of the two-part TORES/eTPCS device for preparing eTPC-t for assembly of a combined eTPC:A system The overall analytical system in which the two-part TORES/eTPCS device is used to prepare analyte engineered TCR-presenting cells (eTPC-t) with various analyte antigens or antigen-presenting cells or particles into combined eTPC:A system. It is from the combined eTPC:A system that primary outputs are derived, and from these primary outputs that terminal outputs are derived. Operation of the overall system comprises two phases, the preparation phase, and the analytical phase.

In one aspect of Phase 1, analyte antigens provided as analyte affinity reagents, APC and/or NCBP are prepared. Such analyte antigens express antigens in various forms of antigenic moiety; analyte antigen-presenting complexes (aAPX); analyte antigenic molecules (aAM); aAPX with loaded aAM cargo (aAPX:aAM); a cargo molecule (CM); an aAPX loaded with CM (aAPX:CM); wherein the analyte antigens represent those to be tested for affinity or signal induction against the analyte eTPC-t (step i). In another aspect of Phase 1, the two-part TORES/eTPCS device is used to prepare cells expressing analyte TCR chain pairs (TCRsp) at the cell surface (step ii). An eTPC presenting a TCRsp at the cell surface is termed an eTPC-t, wherein the eTPC-t present TCRsp to analyte antigens to test affinity or signal induction against the analyte antigens. The contact of eTPC-t and analyte antigens results from the assembly of a combined eTPC:A system (step iii).

Phase 2 of the overall system is the contacting of eTPC-t and analyte antigens prepared in Phase 1, resulting in the assembly of a combined eTPC:A system (step iii). Contacted analyte affinity reagent, APC and NCBP present analyte antigen moieties to the analyte eTPC-t and potentially bind eTPC-t based on complex formation with the presented TCRsp. Within the combined eTPC:A system, outputs of the analyte antigens, or analyte eTPC-t may change their signal state (denoted with *, and the darker shading) such that those responding species may be identified (step iv). Based on altered signal states within the eTPC:A system, specific analyte affinity reagent, APC and/or NCBP may be selected on their ability to induce a response in an eTPC-t, or the ability of an eTPC-t to induce a response in them. A response may be any detectable change in the state of any analyte, including an active signal-based reporting response from a cell-based analyte, or the binding of one analyte to another. Similarly, an analyte eTPC-t may be selected on the ability of to induce a response in the contacted analyte antigens, or for those analytes to induce a signal response in the eTPC-t. Selection based on this responsiveness yields the primary outputs of the combined eTPC:A system (step v). By obtaining the analyte cells, affinity reagents or NCBPs from step v, the presented analyte aAPX, aAM, aAPX:aAM, CM, aAPX:CM and/or TCRsp, may be identified as the terminal output of the device operation (step vi).

Figure 25:
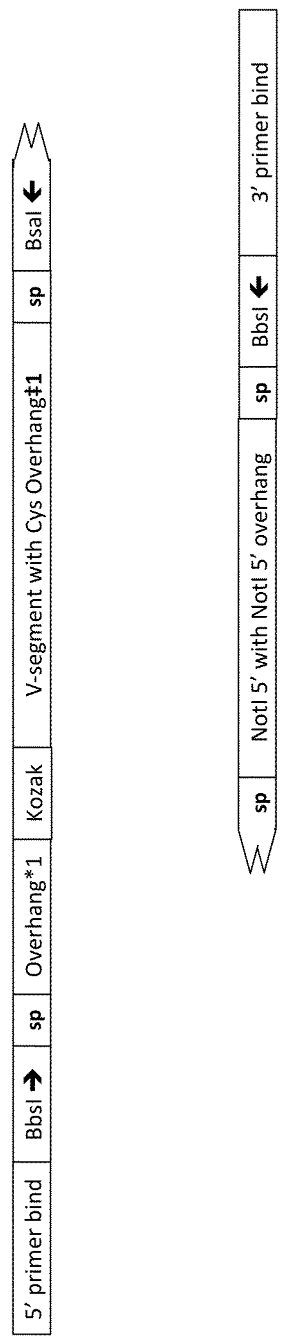

FIG. 25 Arrangement of V cloning fragments for the construction of V-C entry vectors Depicted is a representation of the V cloning fragments used to assemble V-C entry vectors of a TORES for human TRA and TRB TCR chains as described in Example 1.

The V cloning fragment is flanked by unique primer bind sequences at 5' and 3' end to facilitate PCR-mediated amplification of the cloning fragments. Bbsl sites represent a specific Type IIS restriction enzyme binding sites used in the assembly of the V-C entry vector, where→ indicates that the recognition site is orientated to cut in the 3' direction of the site, and ← indicates that the site is orientated to cut in the 5' direction. The Bbsl→ site cuts 5' of the encoded Kozak sequence to create overhang*1. The Bsal← site cuts to create the 5' Notl overhang within the Notl 5' fragment. Overhang*1 and the 5' Notl overhang ultimately ligate with overhang*1' of digested V-C entry vector backbone, and the 3' Notl overhang of the digested C cloning fragment, respectively, in assembly of the V-C entry vector. The Notl 5' fragment represents a 6 nucleotide 5' fragment of the Notl recognition sequence, wherein Notl acts as the negative selection marker to eliminate parental V-C entry vector in operation of the TORES. The complete Notl recognition site is reconstituted with the 3' Notl fragment, provided by the C cloning fragment. The V-segment represents the TCR V gene segment that is to be encoded by the final V-C entry vector, and encodes from the ATG start codon of the give V segment to the last Cys codon of the V segment that defines the border of the CDR3 region. The Bsal← site is the Type IIS restriction enzyme recognition sequence used during operation of the TORES system to reconstitute a full-length TCR ORF. Action of the Bsal enzyme, wherein the site is orientated to cut in the 5' direction, results in the creation of overhang ‡1 at the 3' end of the V segment that encompasses the three nucleotides of the last Cys codon of each V segment, and the third nucleotide of the codon preceding that Cys codon. This overhang is standardized among all V segments in a given TORES set. Ultimately, the overhang ‡1 at the 3' of the V segment ligates with overhang overhang ‡1 at the 5' odeCDR3 in operation of the TORES system to reconstitution of a full-length TCR ORF. All sp denote the addition of one or more nucleotides to create the correct spacing between the Type IIS recognition sequences and the target overhang sequences, or to space the Notl recognition and cut site for efficient action.

Figure 26:
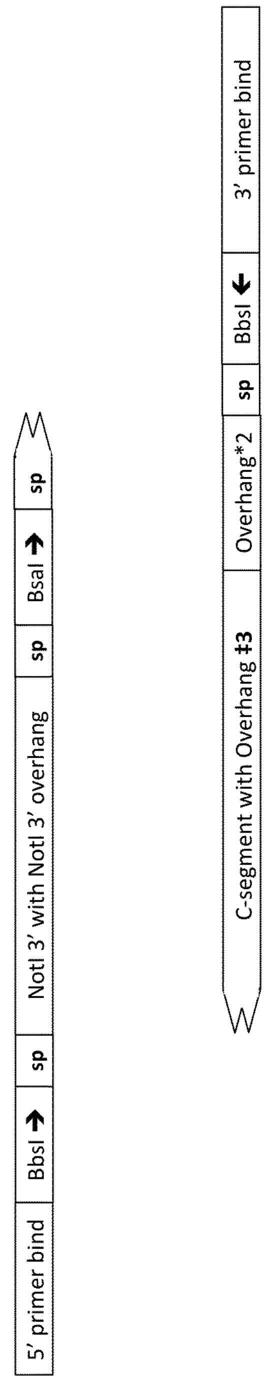

FIG. 26 Arrangement of C cloning fragments for the construction of V-C entry vectors Depicted is a representation of the C cloning fragments used to assemble V-C entry vectors of a TORES for human TRA and TRB TCR chains as described in Example 1.

The C cloning fragment is flanked by unique primer bind sequences at 5' and 3' end to facilitate PCR-mediated amplification of the cloning fragments. Bbsl sites represent a specific Type IIS restriction enzyme binding sites used in the assembly of the V-C entry vector, where→ indicates that the recognition site is orientated to cut in the 3' direction of the site, and ← indicates that the site is orientated to cut in the 5' direction. The Bbsl→ site cuts to create the 3' Notl overhang within the Notl 3' fragment. The Bsal← site cuts 3' of the stop codon of the C segment to create overhang*2 at the 3' end of the C segment. Overhang*2 and the 3' Notl overhang ultimately ligate with Overhang*2' of the digested V-C entry vector backbone, and the 5' Notl overhang of the digested V cloning fragment, respectively, in assembly of the V-C entry vector. The Notl 3' fragment represents a 6 nucleotide 3' fragment of the Notl recognition sequence, wherein Notl acts as the negative selection marker to eliminate parental V-C entry vector in operation of the TORES. The complete Notl recognition site is reconstituted with the 5' Notl fragment, provided by the V cloning fragment.

The C-segment represents the TCR C gene segment that is to be encoded by the final V-C entry vector, and encodes from the cytosine residue 5' of the first Glu codon of the C gene segment to the stop codon. The Bsal→ site is the TyeIIS restriction enzyme recognition sequence used during operation of the TORES system to reconstitute a full-length TCR ORF. Action of the Bsal enzyme, wherein the site is orientated to cut in the 3' direction, results in the creation of overhang ‡3 at the 5' end of the C segment.

This overhang is standardized among all C segments in a given TORES set. Ultimately, the overhang ‡3 at the 5' of the C segment ligates with overhang overhang ‡3 at the 3' C part of the J donor vector in operation of the TORES system to reconstitution of a full-length TCR ORF. All sp denote the addition of one or more nucleotides to create the correct spacing between the Type IIS recognition sequences and the target overhang sequences, or to space the Notl recognition and cut site for efficient action.

Figure 27:
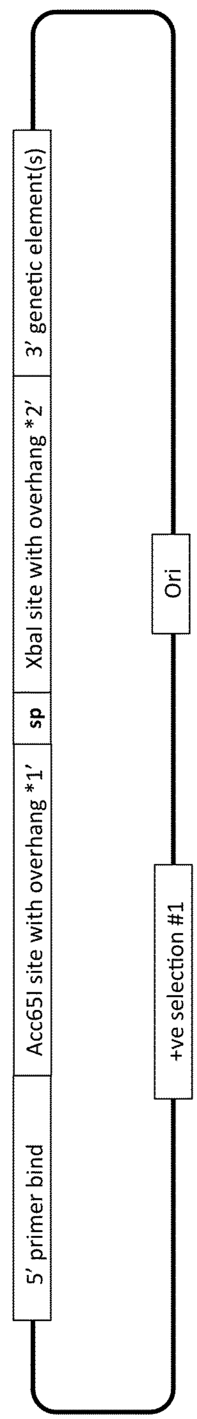

FIG. 27 Arrangement of V-C entry vector backbone for the construction of V-C entry vectors Depicted is a representation of the V-C entry vector backbone used to assemble V-C entry vectors of a TORES for human TRA and TRB TCR chains as described in Example 1.

The circular plasmid DNA contains an origin of replication (Ori) and a positive selection marker #1. This selection marker is used for selection of transformed hosts when isolating clones of V-C entry vector backbone and V-C entry vectors during the assembly, and also for the selection of vectors containing full-length TCR ORFs during operation of the TORES. 5' and 3' genetic elements encode the target elements that flank the final TCR ORF after generation of full-length TCR ORF after its generation by TORES operation. A 5' genetic element might represent a mammalian promoter element to drive the expression of TCR transcripts, and a 3' genetic element might represent a transcriptional terminator sequence. The ACC65I site represents a restriction enzyme recognition sequence, wherein action of the Acc65I enzyme results in the creation of Overhang*1'. This Overhang*1' ligates with Overhang*1 in the digested V cloning fragment during assembly of the V-C entry vector. The Xbal site represents a restriction enzyme recognition sequence, wherein action of the Xbal enzyme results in the creation of Overhang*2'. This Overhang*2' ligates with Overhang*2 in the digested C cloning fragment during assembly of the V-C entry vector. Sp denotes the addition of nucleotides to space the Acc65I and Xbal recognition sites for efficient action of both enzymes.

Figure 28:
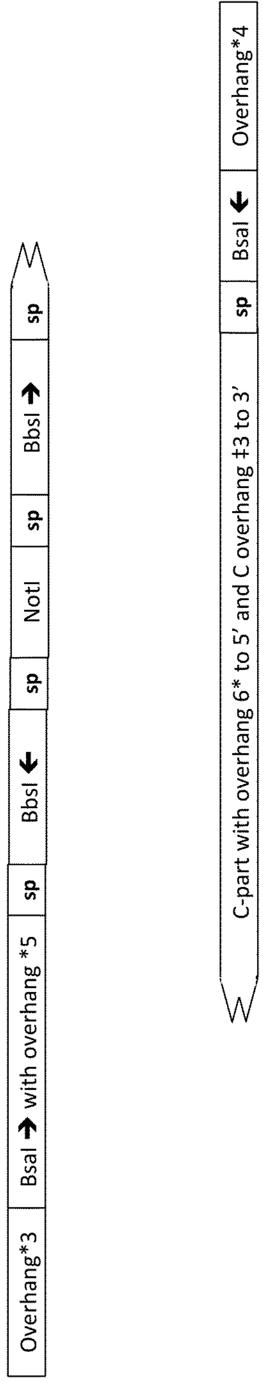

FIG. 28 Arrangement of the J receiving cassette fragment

Depicted is a representation of a J receiving cassette fragment used in the assembly of J donor vectors of a TORES for human TRA and TRB TCR chains as described in Example 1. A J receiving cassette fragment is inserted into a J donor backbone to generate a J receiving cassette vector.

A J receiving cassette fragment is generated by annealing two complimentary oligonucleotides to create a linear double stranded DNA construct with 4-nucleotide single stranded overhangs at the 5' and 3' ends that are used for insertion of the fragment to the J donor vector backbone. Overhang*3 at the 5' end of the J receiving cassette fragment ligates with Overhang*3' of the digested J donor vector backbone, whereas Overhang*4 at the 3' end ligates with Overhang*4' of the digested J donor vector backbone.

The Bsal sites represent the Type IIS restriction recognition sites used in the operation of the TORES to assemble a full-length TCR ORF. Bsal← site is orientated to cut in the 5' direction, and acts ipon the C part sequence to generate Overhang ‡3 at the 3' C part. Bsal→ site ultimate acts on the J segment part of the J donor vector to create Overhang ‡2 at the 5'end of the J segment part. Bsal→ element also contains Overhang*5, which is generated by action of the Bbsl on the Bbsl← site during assembly of the J donor vector.

The Bbsl sites represent the Type IIS restriction recognition sites used to assemble the J donor vector. The Bbsl← site cuts the Bsal→ element to generate Overhang*5, whereas the Bbsl→ site cuts the 5' end of the C part to generate Overhang*6. Overhang*5 and Overhang*6 ultimately ligate with Overhang*5' and Overhang*6' of the J segment part, respectively. The C part represents a small portion of the target C gene segment to permit standardized generation of non-palindromic overhangs during operation of the TORES. This C part is ultimately carried at the 3' end of the J segment part, and forms part of the sequence that ligates with the C segment carried by the digested V-C entry vector in operation of the TORES to generate a full-length TCR ORF. The Notl site represents a negative selection marker used to eliminate the parental J receiving cassette vector during generation of the J donor vector. All sp denote the addition of one or more nucleotides to create the correct spacing between the Type IS recognition sequences and the target overhang sequences, or to space the Notl recognition and cut site for efficient action.

Figure 29:
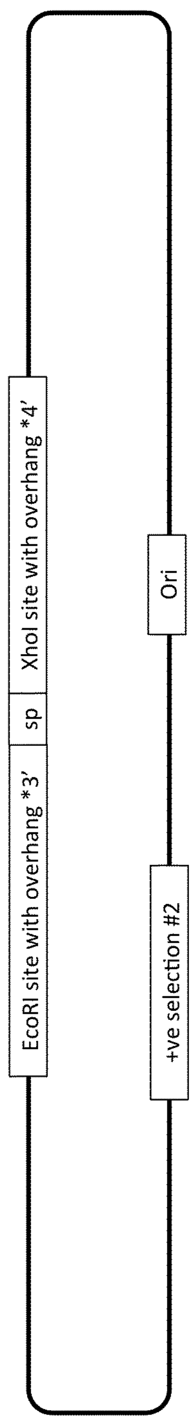

FIG. 29 Arrangement of the J donor backbone

Depicted is a representation of J a donor vector backbone used in the assembly of J donor vectors of a TORES for human TRA and TRB TCR chains as described in Example 1. A J receiving cassette fragment is inserted into a J donor backbone to generate a J receiving cassette vector.

The circular plasmid DNA contains an origin of replication (Ori) and a positive selection marker #2. This selection marker is used for selection of transformed hosts when isolating clones of J donor vector backbone and J donor vectors during the assembly. Importantly, this positive selection marker is distinct from positive selection marker #1 within the V-C entry vectors, such that parental J donor vectors are eliminated under positive selection on #1 during operation of the TORES to generate full-length TCR ORFs in the context of the V-C entry vector backbone.

The EcoRI site represents a restriction enzyme recognition sequence, wherein action of the EcoRI enzyme results in the creation of Overhang*3'. This Overhang*3' ligates with Overhang*3 in the annealed J receiving cassette fragment during assembly of the J receiving cassette vector. The Xbal site represents a restriction enzyme recognition sequence, wherein action of the Xbal enzyme results in the creation of Overhang*4'. This Overhang*4' ligates with Overhang*4 in the annealed J receiving cassette fragment during assembly of the J receiving cassette vector. Sp denotes the addition of nucleotides to space the Acc65I and Xbal recognition sites for efficient action of both enzymes.

Figure 30:
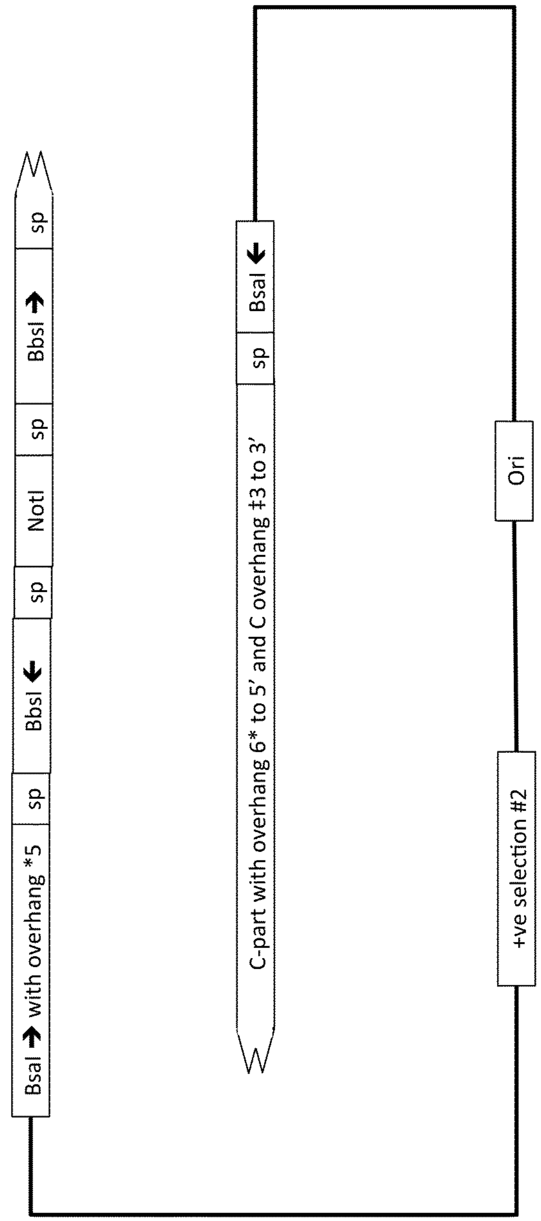

FIG. 30 Arrangement of the J receiving cassette vector

Depicted is a representation of a J donor vector backbone used in the assembly of J donor vectors of a TORES for human TRA and TRB TCR chains as described in Example 1. A J receiving cassette vector is created by insertion of a J receiving cassette fragment into a J donor backbone.

The circular plasmid DNA contains an origin of replication (Ori) and a positive selection marker #2. This selection marker is used for selection of transformed hosts when isolating clones of J donor vector backbone and J donor vectors during the assembly. Importantly, this positive selection marker is distinct from positive selection marker #1 within the V-C entry vectors, such that parental J donor vectors are eliminated under positive selection on #1 during operation of the TORES to generate full-length TCR ORFs in the context of the V-C entry vector backbone.

The Bsal sites represent the Type IIS restriction recognition sites used in the operation of the TORES to assemble a full-length TCR ORF. Bsal← site is orientated to cut in the 5' direction, and acts ipon the C part sequence to generate Overhang ‡3 at the 3' C part. Bsal→ site ultimate acts on the J segment part of the J donor vector to create Overhang ‡2 at the 5'end of the J segment part. Bsal→ element also contains Overhang*5, which is generated by action of the Bbsl on the Bbsl← site during assembly of the J donor vector.

The Bbsl sites represent the Type IIS restriction recognition sites used to assemble the J donor vector. The Bbsl← site cuts the Bsal→ element to generate Overhang*5, whereas the Bbsl→ site cuts the 5' end of the C part to generate Overhang*6. Overhang*5 and Overhang*6 ultimately ligate with Overhang*5' and Overhang*6' of the J segment part, respectively.

The C part represents a small portion of the target C gene segment to permit standardized generation of non-palindromic overhangs during operation of the TORES. This C part is ultimate carried at the 3' end of the J segment part, and forms part of the sequence that ligates with the C segment carried by the digested V-C entry vector in operation of the TORES to generate a full-length TCR ORF. The Notl site represents a negative selection marker used to eliminate the parental J receiving cassette vector during generation of the J donor vector.

All sp denote the addition of one or more nucleotides to create the correct spacing between the Type IIS recognition sequences and the target overhang sequences, or to space the Notl recognition and cut site for efficient action.

Figure 31:
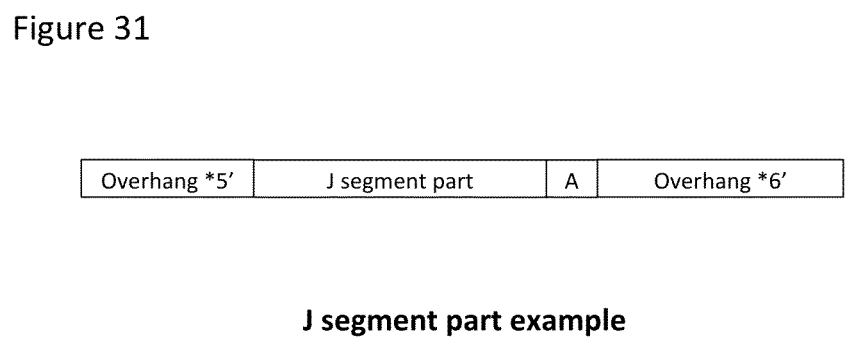

FIG. 31 Arrangement of a J segment part Depicted is a representation of a J segment part that is used in the assembly of J donor vectors of a TORES for human TRA and TRB TCR chains as described in Example 1. A J segment part is inserted into a J receiving cassette vector to create a J donor vector.

Annealing complimentary single stranded oligonucleotides to form a linear double stranded DNA construct with single stranded overhangs at either terminus generates a J segment part. Overhang*5' at the 5' terminus anneals with Overhang*5 generated within the J receiving cassette vector digested with Bbsl. Overhang*6' at the 3' terminus anneals with Overhang*6 generated within the J receiving cassette vector digested with Bbsl.

The J segment part represents the target J gene segment sequence. Depending on the style of the J donor vector being constructed (i.e. short or long) the 5' border of the J segment part is defined differently. For short J donor vectors, the 5' border of the J segment part is defined as the Phe-Ala/Gly or Trp-Gly motifs that are used to define the canonical border between the J and CDR3 portions of a full-length TCR ORF. For long J donor vectors, the 5' border of the J segment part is extended ten to twelve nucleotides 5' of the Phe-Ala/Gly or Trp-Gly motif. This extends the portion of the overall TCR ORF encoded by the J donor vector, and conversely shortens the length of the odeCDR3 required to construct a full-length TCR ORF in operation of the TORES. At the 3' end of the J segment part is encoded a single Adenine residue (A), which represent the first nucleotide of the C fragment. This adenine is excluded from the J receiving cassette vector.

Figure 32:
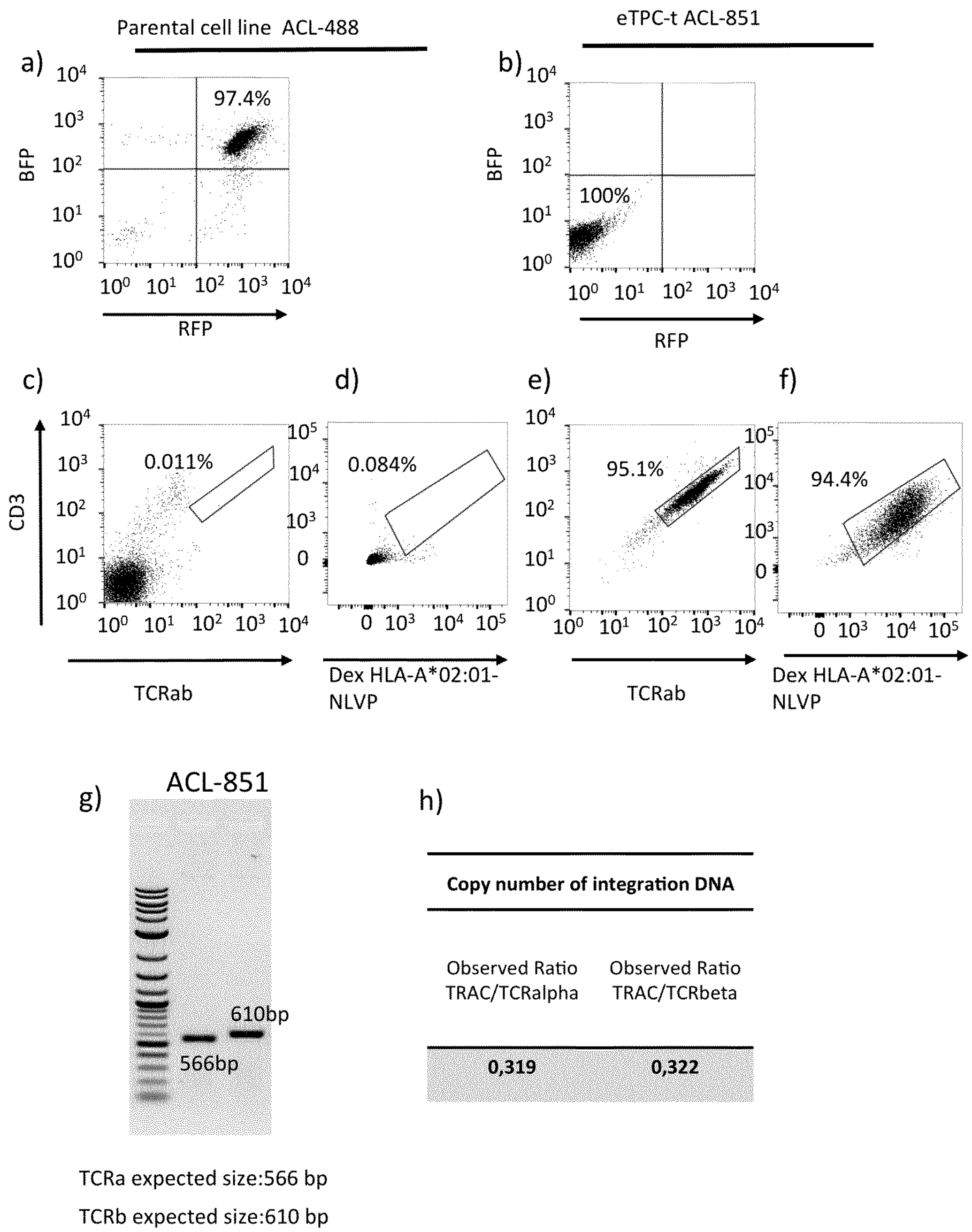

FIG. 32 Validation of reconstituted TORES TRA and TRB vectors by integration to eTPC The TORES system was used to generate a model TCR alpha/beta pair (JG9-TCR), which has a known specificity for a HCMV antigen presented in HLA-A*02:01. The TORES produced each chain in either a Component 2C or 2E context (see example 3). An eTPC-t was created through RMCE by transfection of component 2C and 2E plasmids and a construct encoding flp recombinase into the eTPC line ACL-488, which harbours two genomic integration sites, 2B and 2D, encoding reporters BFP and RFP, respectively. 10 days after transfection, individual cells diminished for the BFP and RFP signals, encoded by Components 2B and 2D selection markers, were sorted as single cells. Resulting monoclonal eTPC-t ACL-851 were analysed in parallel with the parental eTPC, and a single example presented. a) and b) Parental eTPC cell line ACL-488 and an example monoclonal was analysed by flow cytometry for BFP and RFP signals. The plot displays live single cells as BFP versus RFP, showing the eTPC cell line is positive for selection markers present in component 2B and 2D (a), and resulting monoclone has lost these markers as expected for integration couple events between 2B/2C and 2D/2E (b). Percentage values represent the percentage of double positive cells in a) and double negative cells in b). c) to f) eTPC ACL-488 and monoclone eTPC-t ACL-851 were stained with antibodies for CD3 and TCR alpha/beta (TCRab) and HLA multimer reagent specific for the JG9-TCR (Dex HLA-A*02:01-NLVP) and analysed by flow cytometry and gated for live single cells. The parental eTPC line showed no positive staining for CD3 or TCR on the cell surface (c), and was also negative for staining with HLA multimer reagent (d). In contrast, the resulting monoclone showed positive staining for both CD3 and TCR on the cell surface (e) and showed positive staining with the multimer reagent specific for the expressed JG9-TCR. Percentage values represent the percentage of CD3/TCRab double positive cells in c) and e), and CD3/HLA-multimer double positive cells in d) and f. g) Genomic DNA was prepared from monoclonal eTPC-t ACL-851 and subjected to PCR with primers specific for the JG9-TCR-alpha chain encoded by component 2D', or the JG9-TCR-beta chain encoded by component 2B'. PCR products were resolved by agarose gel and observed as expected band size. h) Genomic DNA was prepared from monoclonal eTPC-t ACL-851 and subjected to digital drop PCR with primers and probes specific for the JG9-TCR-alpha chain encoded by component 2D', or the JG9-TCR-beta chain encoded by component 2B'. A reference amplicon primer/probe pair for an intron of the TCR alpha constant (TRAC) was included. The table presents ratios of reference to TCR alpha and TCR beta. A ratio of close to 0.33 indicates that a single copy of each TCR alpha and beta chain is present in the eTPC-t line ACL-851, which is a triploid line.

Figure 33:
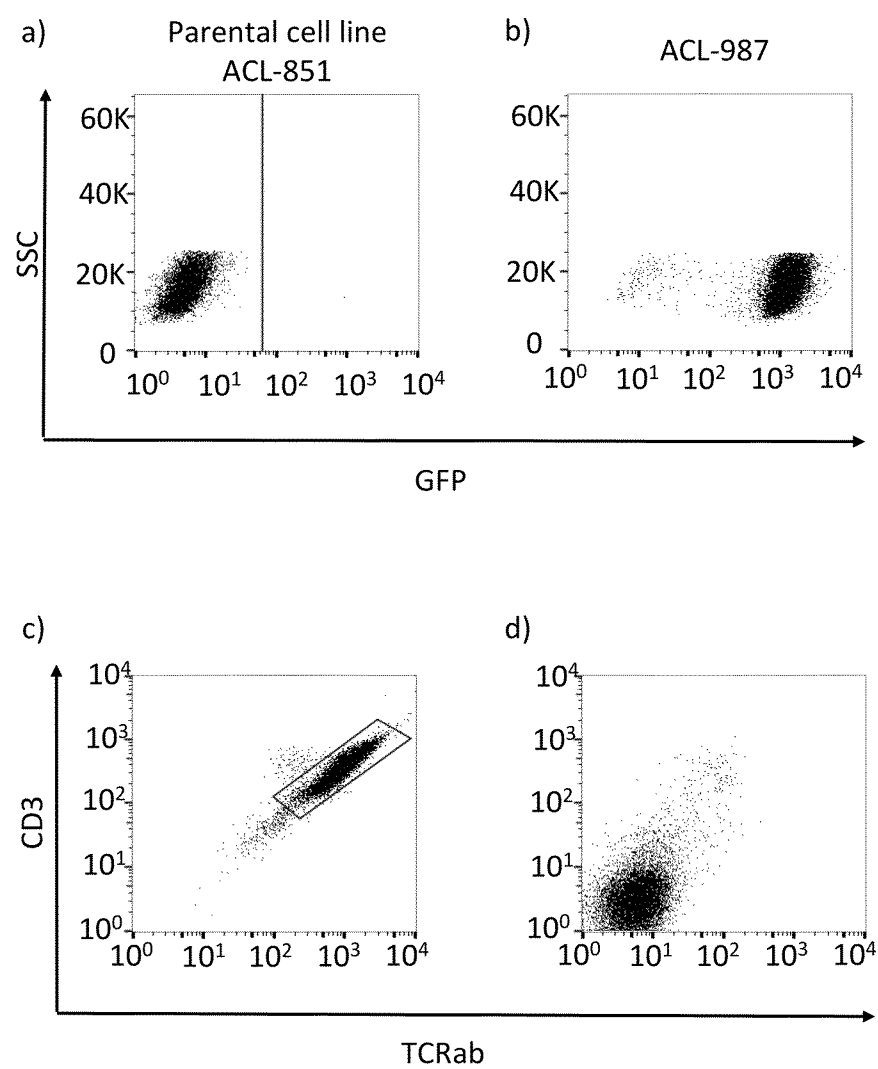

FIG. 33: Demonstration of eTPC-x reversion from eTPC-t

A parental eTPC-t cell line ACL-851, expressing a TCR alpha and beta chain at site D' and B', respectively was reverted to a eTPC-x line by exchanging component D' with a donor vector encoding GFP (Component Z). Component Z contained recombinase heterospecific F14/F15 sites flanking the GFP ORF, and was thus compatible with Component D'. eTPC-t line ACL-851 was transfected with Component Z along with a construct encoding flp recombinase. 7 days after transfection, individual cells positive for GFP signals were sorted and grown as monoclones. Resulting monoclonal eTPC-x lines were analysed by flow cytometry in parallel with the parental eTPC-t, and a single example presented. a) and b) The monolcone eTPC-x ACL-987 derived from parental eTPC-t ACL-851 was analysed by flow cytometry for GFP expression along with the parental line. Plots display SSC versus GFP parameters of gated live single cells. The parental cell line has no GFP expression (a), while the monoclone ACL-987 has gained GFP as expected (b), indicating exchange of the TCR alpha ORF for a GPF ORF. c) and d) The monolcone eTPC-x ACL-987 derived from parental ACL-851 along with the parental eTPC-t ACL-851 were stained with antibodies for CD3 and TCRab and analysed by flow cytometry. Plots display CD3 versus TCRab parameters gated on live single cells. The parental cell showed positive staining for both CD3 and TCRab (c), while the derived monoclone showed negative staining for both (d); confirming loss of TCR alpha ORF in the derived eTPC-x line.

Figure 34:
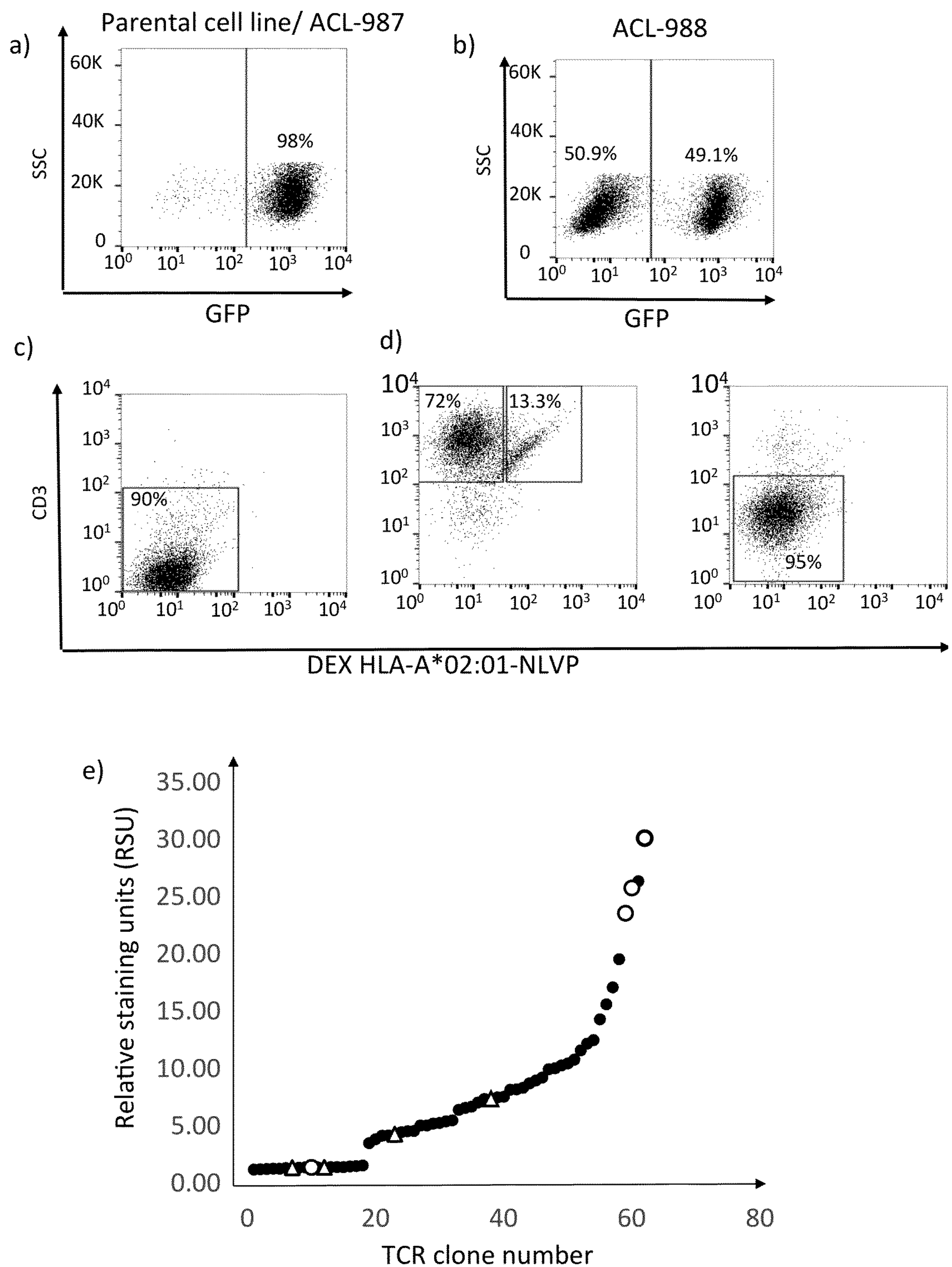

FIG. 34: Demonstration of shotgun integration into eTPC-x to create pool of eTPC-t An eTPC-t pool was created from an eTPC-x parental line expressing a single TCR beta chain in Component B'. The eTPC-x line expressed GFP as the reporter at available site 2D. A pool of 64 variant TCR alpha chains, including the parental chain, were constructed with the TORES system to represent a pool of Component 2E (see Example 5). The parental TCR chain pair represents the JG9-TCR with known specificity for a HCMV antigen presented in HLA-A*02:01. The Component 2E pool was transfected into the parental eTPC-x ACL-987 along with a construct encoding flp recombinase. A polyclonal line was selected by sorting for GFP positive cells 10 days after transfection. The resulting ACL-988 polyclonal eTPC-t was subsequently sorted on the basis of negative staining for GFP and positive or negative staining for HLA multimer reagent (DEX HLA-A*02:01-NLVP). Recovered single cells were sequenced to identify the encoded TCR-alpha chains and compared to a parallel analysis of each of the TCR-alpha chain variants paired with the native TCR-beta chain in terms of staining with an HLA multimer reagent specific for the parental TCR chain pair. a) and b) Parental eTPC-x ACL-987 line and resulting polyclone eTPC-t ACL-988 line were analysed by flow cytometry for GFP expression. Plots display SSC versus GFP parameters of live single cells. Parental cell line shows positive signal for GFP, indicating intact component 2D (a). Derived polyclonal line shows half positive and half negative for GFP (b), indicating that half of the cells in the polyclonal population have potentially exchanged the GFP ORF at 2D for TCR alpha ORF to form component 2D'. c) and d) Parental eTPC-x ACL-987 line and resulting polyclone eTPC-t ACL-988 line were stained with and CD3 antibody and HLA multimer with specificity for the parental JG9-TCR (DEX HLA-A*02:01-NLVP), and analysed by flow cytometry. Plots display CD3 versus HLA multimer parameters of live single cells. The parental cell line is negative for both CD3 and HLA multimer staining (c). The left hand panel of d) displays gated GFP-negative events, and the right hand GFP-positive events. Only GFP-negative events, where the component 2D is converted to 2D', shows CD3 positive staining, of which a subset shows positive staining for HLA multimer. Single cells from the gated HLA multimer negative and positive gate were sorted and the integrated ORF at component 2D' sequenced to determine identity of TCR alpha ORF.

e) All 64 JG9-TCR-alpha variants were cloned into an expression construct that permitted each to be independently transfected to parental eTPC-x (ACL-987). Relative staining units (RSU) against the HLA-A*02:01-NLVP tetramer reagent was determined for each. RSU is calculated as the ratio of the mean fluorescence intensity (MFI) of HLAA*02:01-NLVP tetramer signal for the CD3 positive population over the CD3 negative population, and is indicative of the binding strength of each TCR chain pair variant to the HLA multimer reagent. Each point plotted in Figure e) represents the observed RSU for each 64 variants. Open circles correlate to the sequenced cells recovered from the GFP-negative/HLA multimer-positive gate. Open triangles correlate to the sequenced cells recovered from the GFP-negative/HLA multimer-negative gate.

Figure 35:
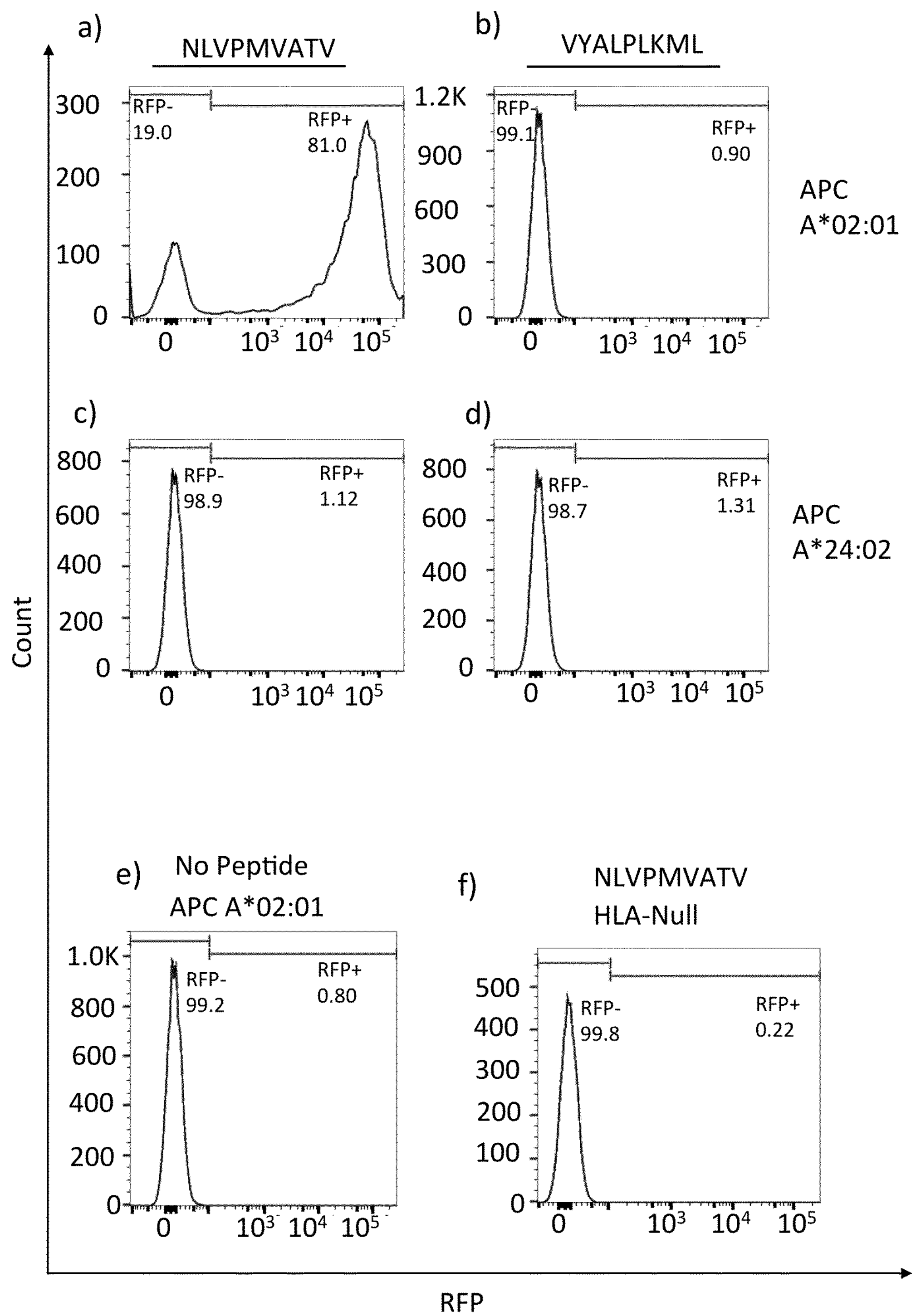

FIG. 35: Functional demonstration of component 2F

The eTPC-t cell line carrying a component 2F (ACL-1277), wherein the TCR chains at Component 2B' and 2D' encode a TCR pair that is specific for HMCV antigenic peptide NLVPMVATV presented in HLA-A*02:01. The component 2F reporter was RFP. This eTPC-t was contacted for 24 hours with various APC lines of differing HLA characteristics in the presence and absence of model peptide antigens, and the contact cultures analysed by flow cytometry. Flow cytometry histogram plots show event counts against RFP signal of viable single T-cells identified by antibody staining for a specific surface marker that was not presented by the APCs. a) and b) APC cells expressing only HLAA*02:01 (ACL-209) were pulsed with NLVPMVATV (a) or VYALPLKML (b) peptides and subsequently co-cultured with eTPC-t for 24 hrs. c) and d) APC cells expressing only HLA-A*24:02 (ACL-963) were pulsed with NLVPMVATV (c) or VYALPLKML (d) peptides and subsequently co-cultured with eTPC-t for 24 hrs. e) APC cells expressing only HLA-A*02:01 (ACL-209) were left without peptide pulsing and subsequently co-cultured with eTPC-t for 24 hrs. f) APC cells that express no HLA on the cell surface (ACL-128) were pulsed with NLVPMVATV and subsequently co-cultured with eTPC-t for 24 hrs. RFP signal was significantly increased in the eTPC-t ACL-1277 only in the presence of HLA-A*02:01 expressing cells pulsed with NLVPMVATV, representing the known target of the expressed TCR. Histogram gates and values reflect percentage of events in the RFP positive and RFP negative gates. This indicates the specific response of Component 2F to engagement of eTPC-t expressed TCRsp with cognate HLA/antigen (aAPX:aAM).

MATERIALS AND METHODS

DNA Sequencing

All sequencing referred to within the presented examples was conducted by the Sanger method, and conducted by GATC Biotec AB, Sweden.

DNA Synthesis

All DNA synthesis referred to within the presented examples was conducted by Integrated DNA technologies BVBA, Belgium.

DNA Fragments >125 bp were synthesised as linear double stranded DNA molecules as a 'gBlock Gene Fragments' product.

DNA Fragments 15-60 nt were synthesised as single stranded DNA molecules as a 'Custom Oligonucleotide Fragment' product.

DNA Fragments 61-124 nt were synthesised as single stranded DNA molecules as a 'Ultramer DNA oligonucleotide Fragment' product.

Vector Library Assembly and Cloning

The construction of vectors described in the examples comprises a variety of methods well known to those skilled in the art, and specific reaction compositions are outlined in detail in Examples 1 to 3. The following key materials were used in the described procedures:

TABLE 1

Vector library assembly and cloning reagents

| Product | Supplier | Supplier Number |
|---|---|---|
| Acc651 | New England BioLabs | R0599L |
| BbsI HF | New England BioLabs | R3539L |
| DH5alpha competent cells | Thermo Fisher Scientific | 18265017 |
| DNA clean and concentrator kit | Zymo Research | D4030 |
| EcoR1 | New England BioLabs | R3101S |
| NotI | New England BioLabs | R3189L |
| QIAamp DNA Mini kit | Qiagen | 51306 |
| QIAquick Gel Extraction kit | Qiagen | 28704 |
| Qiagen Plasmid Plus Midi kit | Qiagen | 12945 |
| T4 ligase | New England BioLabs | M0202L |
| T4 ligase buffer 10x | New England BioLabs | B0202S |
| XbaI | New England BioLabs | R0145S |
| XhoI | New England BioLabs | R0146S |

Oligonucleotide Duplex Encoding CDR3 (odeCDR3) Assembly odeCDR3 were routinely assembled by annealing partially complementary single stranded oligonucleotides. A detailed description of reaction composition and conditions is provided in Example 2. The following key materials were used in the described procedures:

TABLE 2

Oligonucleotide duplex assembly reagents

| Product | Supplier | Supplier Number |
|---|---|---|
| T4 ligase buffer 10 x | New England BioLabs | B0202S |
| T4 PNK | New England BioLabs | M0201L |

TCR Reconstitution

A detailed description of reaction composition and conditions is provided in Example 3. The following key materials were used in the described procedures.

TABLE 3

TCR reconstitution reagents

| Product | Supplier | Supplier Number |
|---|---|---|
| BsaI-HF | New England BioLabs | R3535L |
| CutSmart buffer 10 x | New England BioLabs | B7204S |
| DH5alpha competent cells | Thermo Fisher Scientific | 18265017 |
| NotI-HF | New England BioLabs | R3189L |
| QIAamp DNA Mini kit | Qiagen | 51306 |
| T4 Ligase | New England BioLabs | M0202L |
| T4 Ligase buffer 10 x | New England BioLabs | B0202S |

Transfection of Cells

All cells used in this application were derived from HEK293 cells. One day prior to transfection, cells were seeded at a density of 1.2-1.4×$10^6$ cells/60 mm dish in 90% DMEM+2 mML-glutamine+10% HI-FBS (Life Technologies).

The following day, cells with 65% confluency were transfected with a total amount of 5 ug DNA and jetPEI® (Polyplus transfection reagent, Life Technologies) at a N/P ratio of 6. Stock solutions of DNA and jetPEI® were diluted in sterile 1M NaCl and 150 mM NaCl respectively. The final volume of each solution was equivalent to 50% of the total mix volume. The PEI solution was then added to the diluted DNA and the mixture was incubated at room temperature for 15 min. Finally, the DNA/PEI mixtures were added to the 60-mm dishes, being careful not to disrupt the cell film. The cells were incubated for 48 hours at (37° C., 5% CO2, 95% relative humidity) prior to DNA delivery marker expression analysis. The medium was replaced before transfection.

RMCE Between a Paired Integration Couple

For RMCE integration, cells were transfected with 0.6 μg of DNA vectors encoding FLP, (V4.1.8), 2 μg of Component 2C/2Y, 2 μg of Component 2E/2Z, 0.4 μg of DNA encoding a marker to track DNA delivery. 2 days after transfection cell positive for the DNA delivery marker, either GFP or RFP positive, were sorted by FACS. 4-10 days after transfection, individual cells displaying diminished fluorescent protein signal, encoded by Components 2D and 2B selection markers were sorted by FACS. The exception being for generating ACL-987 where individual cells displaying GFP positivity were sorted by FACS.

Transient Expression of TCR Chain Pairs to Characterization of their RSU

For transient expression, cells were transfected with DNA vectors encoding FLP, (V4.1.8), JG9-TCR-alpha variant (VP.7751.RC1.A1 to VP.7751.RC1.H8), JG9-TCR-beta WT chain (V3.C.5), and DNA vector vehicle (V1.C.2). 2 days after transfection, all cells were stained with HLA-A*02:01-NLVP tetramer and anti-CD3 antibodies. RSU were calculated as the ratio of the mean fluorescence intensity (MFI) of HLA-A*02:01-NLVP tetramer signal for the CD3 positive population over the CD3 negative population, and was indicative of the binding strength of each TCR chain pair variant.

Fluorescence Activated Cell Sorting (FACS)

Single cell sorting or polyclone sorting was achieved through standard cell sorting methodologies using a BDInflux instrument. Briefly, ACL cells were harvested with TrypLE™ Express Trypsin (ThermoFisher Scientific) and resuspended in a suitable volume of DPBS 1× (Life Technologies) prior to cell sorting, in DMEM 1× medium containing 20% HI-FBS and Anti-Anti 100× (Life Technologies).

Cells were stained with HLA-multimer reagent on ice for 10 mins, then with CD3 and/or TCRab antibodies. Detection of specific cell fluorescent properties by the BDInflux instrument are defined in table 4.

Sorting of single cells for monoclonal generation, the cells displaying the phenotype interest were deposited into 96-well plates, containing 200 ul of growth medium. One to two plates was sorted per sample. Polyclonal cell sorts were directed into FACS tubes, containing media, using the Two-way sorting setting in the cell sorter Influx™ (BD Biosciences).

Single cells sorts for molecular characterization of their JG9-TCR-alpha variant were sorted to PCR plate pre-loaded with 5 μL of nuclease-free water. Specimens were snap-frozen until subsequent processing.

TABLE 4

Vectors

| ID | Name |
|---|---|
| V1.A.4 | pcDNA3.1_GFP |
| V1.A.6 | pcDNA3.1_RFP |
| V1.C.2 | pMA-SV40pA |
| V3.C.5 | pMA-CS-JG9-TCRbeta |
| V4.H.9 | pMA-F14-GFP-F15 |
| V7.A.3 | pMA-F14-TCR-JG9-alpha-F15 |
| V7.A.4 | pMA-FRT-TCR-JG9-beta-F3 |
| V8.F.8 | F14-TCRaF15 CDR3degen.64mix |
| V4.I.8 | CMVpro-Flp-sv40pA-V2 |
| VP.7751.RC 1-A1 to H8 | 64 individual vectors, each encode a different member of JG9-TRA CDR3 64 variants set |

TABLE 5

BD Influx filters

| Protein | Fluorochrome | Filter |
|---|---|---|
| Cas9/GFP | GFP | 488-530/40 |
| HLA-A, B, C | PE-Cy5 | 561-670/30 |
| BFP | BFP | 405-460/50 |
| RFP | RFP | 561-585/29 |
| TCRab (R63) | APC | 640-670/30 |
| CD3 (R78) | APC-H7 | 640-750LP |
| CD3 (R71) | APC | 640-760/30 |
| DEX HLA-A*02:01-NLVP | PE | 561-585/29 |

Genomic DNA Extraction for Genetic Chararterization

DNA was extracted from $5\times10^6$ cells using the QIAamp DNA Minikit (Qiagen). DNA was stored in 1×TE (10 mM Tris pH8.0 and 0.1 mM EDTA)

PCR Reactions to Assess the RMCE-Integration of the TRA-ORF and TRB-ORF into Component 2B or 2D Primers used to assess integration of the TRA-ORF, annealed to the TRA-C segment (forward primer 1.F.7) and the sv40 pA terminator (Reverse primer 15.H.2) that is a preexisting part of the genomic receiving sites. Expected size 566 bp Primers used to assess integration of the TRB-ORF, annealed to the TRB-C segment (forward primer 1.F.9) and the sv40 pA terminator (Reverse primer 15.H.2) that is a preexisting part of the genomic receiving sites. Expected size 610 bp.

TABLE 6

PCR reagents for assess integration of the TRA-ORF or TRB-ORF

| | volumes/reaction |
|---|---|
| PCR TRA specific primers | |
| 5xPhusion buffer | 4 ul |
| DNTPs | 0.2 ul |
| Phusion DNA polymerase | 0.15 ul |
| 1.F.7 TRAC-GT-F1 | 0.5 ul |
| 15.H.2 sv40pA-GT-R1 | 0.5 ul |
| H20 | up to 20 ul |
| DNA (100 ng) | 1 ul (100 ng/ul) |
| PCR TRB specific primers | |
| 5xPhusion buffer | 4 ul |
| DNTPs | 0.2 ul |
| Phusion DNA polymerase | 0.15 ul |
| 1.F.9 TRBC2-GT-F1 | 0.5 ul |
| 15.H.2 sv40pA-GT-R1 | 0.5 ul |
| H20 | up to 20 ul |
| DNA (100 ng) | 1 ul (100 ng/ul) |

TABLE 7

PCR cycle conditions

| Step | Temperature | Time |
|---|---|---|
| Initial Denaturation | 98° C. | 30 sec |
| 30 cycles | 98° C. | 10 sec |
| | 60° C. | 10 sec |
| | 72° C. | 15 sec |
| Final extenstion | 72° C. | 10 min |

PCR products were run on a 1% Agarose gel in 1×TAE buffer, using the PowerPac Basic (Bio-Rad), stained with 10,000 dilution of sybersafe and analyzed with Fusion SL (Vilber Lourmat).

ddPCR Reactions to Assess the Copy Number of TRA-ORF and TRB-ORF in the Genome after DNA Delivery.

DNA of selected ACL-851 monoclones was analysed by using specific primers and probed targeting the TCR_ORF C segment of interest Primers and probe used to assess TRA-ORF copy number, annealed to the TRA-C segment (forward primer 1.F.7, Reverse primer 1.F.8 and probe 1.G.1)

Primers and probe used to assess TRB-ORF copy number, annealed to the TRB-C segment (forward primer 1.F.9, Reverse primer 1.F.10 and probe 1.G.2)

In all cases, a reference gene (TRAC) was simultaneously screened to chromosome determine copy numbers, using primers 10.A.9 and 10.A.10 together with the fluorescent probe 10.B.6 conjugated with HEX. Integration copy number considered that HEK293 cells are triploid for reference gene (TRAC).

Prior to Droplet Digital PCR, DNA was digested with Mfel (NEB) to separate tandem integrations. The reaction setup and cycling conditions were followed according to the protocol for ddPCR™ Supermix for Probes (No dUTP) (Bio-Rad), using the QX200™ Droplet Reader and Droplet Generator and the C1000 Touch™ deep-well Thermal cycler (Bio-Rad).

TABLE 8

| ddPCR conditions | | | | | |
|---|---|---|---|---|---|
| Step 1 | Step 2 | Step 3 | Step 4 | Step 5 | Step 6 |
| 95° C. | 94° C. | 60° C. | Goto 2 × 39 | 98° C. | 8° C. |
| 10:00 | 0:30 | 1:00 | | 10:00 | ∞ |

Data was acquired using the QuantaSoft™ Software, using Ch1 to detect FAM and Ch2 for HEX.

TABLE 9

| ddPCR Primers and probes | | |
|---|---|---|
| ID | Name | Sequence |
| 1.F.7 | TRAC-GT-F1 | ATGTGCAAACGCCTTCAAC |
| 1.F.8 | TRAC-GT-R1 | TTCGGAACCCAATCACTGAC |
| 1.G.1 | TRAC-probe-FAM | TTTCTCGACCAGCTTGACATCACAGG |
| 1.F.9 | TRBC2-GT-F1 | GCTGTCAAGTCCAGTTCTACG |
| 1.F.10 | TRBC2-GT-R1 | CTTGCTGGTAAGACTCGGAG |
| 1.G.2 | TRBC2-probe-FAM | CAAACCCGTCACCCAGATCGTCA |
| 10.A.9 | TRAC-TCRA-ex1-F1 | CTGATCCTCTTGTCCCACAGATA |
| 10.A.10 | TRAC-TCRA-ex1-F1 | GACTTGTCACTGGATTTAGAGTCTCT |
| 10.B.6 | TRAC-probe(HEX) | ATCCAGAACCCTGACCCTGCCG |

TABLE 10

| ACL cell lines | | |
|---|---|---|
| ID | Components | Comments |
| ACL-488 | 2B, 2D | 2B encodes BFP, 2D encodes RFP |
| ACL-851 | 2B', 2D' | eTPC-t, 2B' encodes wtJG9-TCRb, 2D' encodes wtJG9-TCRa |
| ACL-987 | 2B', 2D | eTPC-x, 2B' encodes wtJG9-TCRb, 2D' encodes GFP |
| ACL-988 | 2B', 2D' | Polyclone eTPC-t, 2B' encodes wtJG9-TCRb, 2D' encodes a JG9-TCRa 64x variant |
| ACL-1063 | 2B, 2D, 2F | eTPC with responder element, 2B and 2D encodes selection markers |
| ACL-1277 | 2B', 2D', 2F | eTPC-t with responder element, 2B' and 2D' encodes TCR chain pairs |
| ACL-209 | | eAPC-p, expressing HLA-A*02:01 |
| ACL-963 | | eAPC-p, expressing HLA-A*24:02 |
| ACL-128 | | eAPC, HLA-ABC null |

Sequencing of TCR Alpha and Beta Chains from Single T-Cells

Individual FACS-sorted eTPC-t-cells were subjected to a two-step amplification process that entails a V-region specific primer collection for each TRA and TRB, followed by paired nested PCR reactions that create TRA and TRB amplicons for sequence analysis. This procedure is described previously (Han et. al. Nat Biotechnol. 2014 32(7): 684-692). The following materials were used in the described procedures:

TABLE 11

| Single cell RT-PCR and nested PCR reagents | | |
|---|---|---|
| Product | Supplier | Supplier Number |
| 2x Reaction Mix | Thermo Scientific | 12574035 |
| 5X Phusion HF Buffer | Thermo Fisher Scientific | F-549S |
| dNTPs | Thermo Fisher Scientific | 10297018 |
| Nuclease free water | Qiagen | 129114 |
| Phusion Hot Start II DNA Polymerase | Thermo Fisher Scientific | F-549S |
| SuperScript ® III One- Step RT-PCR System with Platinum ® Taq High Fidelity DNA Polymerase | Thermo Scientific | 12574035 |

Demonstration of Functional Component 2F eTPC-t and APC cells were routinely cultured in RPMI+ 10% heat-inactivated Fetal Calf Serum (complete media) between 0.2×10ˆ6-1.5×10ˆ6 cells/ml, at 37° C., 90% relative humidity and 5% C02. Peptides NLVPMVATV and VYALPLKML were synthetized by Genescript, and received lyophilized. Peptide primary stocks were suspended in 10% DMSO and sorted at −80'C. Working stocks were prepared at the time of administration, at 50 μM in complete media (50× concentrated). The following APCs presenting HLA-A*02:01 (ACL-209) or HLA-A*24:02 (ACL-963) or HLA-null (ACL-128) were used. The eTPC-t cell line (ACL-1277, Component 2A) was engineered with two unique genomic receiver sites (Components 2B, 2D), engineered to be HLA Null, utilizing native CD3 expression, and harboring a two-component, synthetic response element (Component 2F). In addition, ACL-1277 had Components B, D converted to B'/D' with the integration of TCR alpha/beta ORF encoding a TCRsp specific for pHLA: HLA-A*02:01-NLVPMVATV (See Example 8).

Antigen Pulsing Procedure

Actively growing cultures of APC cells (0.5-1.0×10ˆ6 cells/ml) were suspended, sample taken and counted to determine cell concentration. Subsequently, 1 million cells were harvested, washed once with Dulbecco's phosphate buffered saline (DPBS, Gibco) followed by suspension in complete media with 1 μM of peptide or no peptide at a cell concentration between 1 to 2×10ˆ6 cells/ml. Cells were incubated for 2 h in standard culturing conditions, in a 24-well culture plate. After 2 h the cells were harvested, pelleted by centrifugation (400 rcf, 3 min), followed by 3×10 ml washes with DPBS. Cells were subsequently suspended at 0.2×10ˆ6 cells/ml in complete media.

eTPC-t Havesting

Actively growing cultures of eTPC-t cells (0.5-1.0×10ˆ6 cells/ml) were suspended, sample taken and counted to determine cell concentration. Cells were harvested, washed once with PBS and then suspended at a concentration of 0.6×10ˆ6 cells/ml in complete media.

Contacting eTPC-t and APC in an eTPC:A System

To each well of a 96-well round-bottom plate, 50 μl of complete media, 50 μl of APC, followed by 50 μl of eTPC-t were added. This equated to approximately 10,000 APC and 30,000 eTPC-t for a ratio of 1:3, at a total cell concentration of approximately 0.27×10ˆ6 cells/ml. The cell mixture was then incubated for approximately 24 hours at standard culturing conditions.

Staining and Analysis

After 24 hours incubation, the cells were harvested, and transplanted into 0.75 ml V-bottom Micronic tubes, washed once with 500 μl DPBS and subsequently stained with Dead Cell Marker (DCM-APC-H7) as follows; to each well 25 μl of staining solution was added, cells suspended by mixing and then incubated for 15-20 min. The staining solution comprised of 0.5 μl DCM-APC-H7 per 100 μl staining solution. After incubation, cells were washed twice with 500 μl DPBS+2% FCS (Wash Buffer). Cells were then stained for surface markers unique to the eTPC-t; to each well 30 μl of staining solution was added, cells suspended by mixing and then incubated for 30-45 min. The staining solution comprised of 2.5 μl anti-myc-AF647 per 100 μl staining solution (clone 9E10, Santa Cruz Biotech). After incubation, cells were washed twice with 500 μl Wash buffer, then suspended in 200 μl of Wash buffer and then analysed by FACS on a LSR-Fortessa (BD Biosciences).

EXAMPLES

Example 1 Design and Assembly of a TORES System for Human TRA and TRB

A TORES consists of a V-C entry vector library and J donor vector library for a given TCR chain. When combined with a target odeCDR3 sequence to be inserted into a selected V-J-C context, a full-length TCR ORF can be reconstituted. Through varying odeCDR3 sequence features and/or V/J/C selection, this reconstitution step may also represent a sequence diversification step in TCR ORF engineering workflows. In the present example, the design and assembly of a complete TORES system for human TRA and TRB chains is described.

Design and Assembly of TRA V-C Entry Vector Library for Native Human TRA Repertoire In the present example, the design and assembly of a TRA V-C entry vector library that contains the native human TRA V-C sequence repertoire is described. A modular assembly method is used, such that the construction of V-C entry vector libraries may be rapidly cycled for other TCR chains from humans, other organisms, or for synthetic TCR chains.

The DNA components required for a TRA V-C vector library are:

I. A TRA V cloning fragment for each functional TRA V gene segment encoded in the human genome II. Single TRA C cloning fragment Ill. A V-C entry vector backbone In the present example, the TRA V and TRA C cloning fragments were synthesized and used to assemble into a target V-C entry vector backbone in a single restriction enzyme and ligase reaction.

In the present example, a pair of heterospecific FRT V-C entry vector backbones are used to assemble TRA and TRB V-C entry vector libraries. Each TRA and TRB V-C entry vector libraries are constructed with vector backbones containing distinct flippase recognition target (FRT) sequences, representing the 5' and 3' genetic elements included in the V-C entry system, component 2C and 2E. Thus, the product TRA/TRB pairs generated in operation of this TORES may be submitted to rapid genomic integration into the eTPC cells containing genomic receiver sites (components 2B and 2D) that include compatible FRT sites within their 5' and 3' genetic elements.

In the present example, TRA V-C entry vector contains F14 and F15 FRT sequences as the 5' and 3' genetic elements, respectively. This F14/F15 V-C entry vector backbone sequence is presented as SEQ0688.

In the present example, the TRA V-C entry vector library is constructed using Type IS restriction enzyme Bbsl. The Type IIS restriction enzyme used in functioning of the complete TORES to reconstitute full-length TRA ORFs is Bsal.

Design of Synthetic TRA V Cloning Fragments

The arrangement of genetic elements of the TRA V cloning fragments in the present example is depicted in FIG. 25.

Each end of the TRA V cloning fragment encodes a standardized 5' and 3' primer bind DNA sequence of 20 nucleotides for propagation of the overall fragment by PCR.

Proximal to the 5' primer bind a Bbsl Type IIS restriction enzyme binding site is encoded, wherein the direction of the Bbsl binding site guides the Bbsl enzyme to cut the DNA 3' to its recognition sequence. Overhangs generated by Bbsl enzymatic activity are encoded by Overhang *1. This overhang is designed to permit directed ligase-dependent cloning with an arm of the V-C entry vector backbone.

A consensus kozak sequence is encoded 5' of the ATG start codon within the TRA V gene segment for efficient initiation of translation of the final reconstituted and expressed TRA mRNA. In the present example, each TRA V segment encodes all amino acids from the start methionine residue until its last cysteine (Cys) of the TRA V segment. This Cys residue is generally recognised as a border of the TRA variable gene segments, the deletion of which is rare in naturally occurring recombined and functional TRA chains. Where necessary, native human TRA V consensus sequences have been edited to remove recognition sequences for any restriction enzymes used within assembly or reconstitution operations with the TORES, and also any enzymes used in downstream applications.

To the 3' end of the TRA V segment a Bsal Type IIS restriction enzyme binding site is encoded, Bsal←. The direction of the Bsal binding site guides the Bsal enzyme to cut the DNA 5' to its recognition sequence. The resulting overhang sequence is designed to encompass the last cysteine codon of the V segment element and the 3$^{rd}$ nucleotide for amino acid codon preceding the cysteine. Thus the action of Bsal on the designed sequence creates a TRA V Cys-overhang ‡1 at the 3' end of the TRA V segment. In the present example, this Cys-overhang ‡1 is standardized among all included TRA V segments to simplify and unify the cloning strategy. Where necessary the nucleotides encoding the TRA V genetic element were changed to encode this standardised overhang but not change the translated amino acid sequence. This Bsal← site is utilized during the full length TRA reconstitution reaction.

In this present example, the V-C entry vector negative selection marker is a Notl restriction enzyme binding site. To construct a Notl binding site, two halves of the site are combined when the TRA V cloning fragment and TRA C cloning fragment are ligated together. The TRA V cloning fragment encodes the Notl 5' segment of six nucleotides.

To the 5' end of the 3' primer bind sequence encodes a second Bbsl restriction site, that directs Bbsl enzyme to cut the DNA 5' to its recognition sequence, Bbsl←. The action of Bbsl on the designed sequence thus creates an overhang of 4 nucleotides, Notl 5' overhang, which is designed to be complementary to the overhang generated on the TRA C DNA fragment and reconstitute a Notl binding site upon ligation.

Sp denote nucleotide additions to specific points of the TRA V cloning fragment to achieve the correct spacing of Type IIS restriction enzyme binding site and the cut site, when adjacent to such sites. Sp blocks flanking the Notl restriction enzyme binding site sequence have been used to space the Notl binding and cut site appropriately for efficient action. The selection of nucleotides considered the potential impact of DAM methylation of the Bsal binding site.

Full DNA sequences for the TRA V cloning fragments in the present example of native human TRA chains are provided as SEQ0001 to SEQ0046. These sequences includes the 5' primer bind and 3' primer bind sequences.

Design of Synthetic TRA C Cloning Fragment

The arrangement of genetic elements of the TRA C cloning fragments in the present example is depicted in FIG. 26.

Each end of the TRA C cloning fragment encodes a standardized 5' and 3' primer bind DNA sequence of 20 nucleotides for propagation of the overall fragment by PCR.

Proximal to the 5' primer bind sequence a Bbsl restriction enzyme recognition site is encoded, such that Bbsl enzyme will cut the DNA 3' to its recognition sequence, Bbsl→.

The TRA C cloning fragment encodes the Notl 3' segment of six nucleotides, which completes a Notl recognition site that will make up the V-C entry vector negative selection marker. The adjacent Bbsl→ restriction site acts upon the Notl 3' element to create the Notl 3' overhang of four nucleotides. This overhang is designed to be complementary to the Notl 5' overhang generated on the TRA V DNA fragment and reconstitute a full Notl binding site upon assembly of V-C entry vectors.

To the 3' end of the Notl 3' element, the TRA C cloning fragment encodes a Bsal restriction enzyme binding site, Bsal→. The direction of the Bsal binding site guides the Bsal enzyme to cut the DNA 5' to its recognition sequence. The resulting overhang sequence is designed to start from the first cytosine of the TRA C genetic fragment, TRA C overhang ‡3. This Bsal→ site is utilized during the full length TRA reconstitution reaction. The Bsal→ enzyme acts upon the TRA C segment encoded in the V-C entry vector to create the necessary TRA C overhang ‡3 during reconstitution reactions. A consensus TRA C sequence from the cytosine residue 5' of the first glutamine codon until the stop codon is included in the TRA C cloning fragment in the present example To the 5' of the 3' primer bind encodes a Bbsl restriction enzyme recognition sequence, Bbsl←. The direction of the Bbsl binding site guides the Bbsl enzyme to cut the DNA 5' to its recognition sequence. Overhangs generated by Bbsl enzymatic activity are encoded by Overhang *2. The design of this overhang permits directed ligase-dependent cloning with an arm of the V-C entry vector backbone during assembly.

Sp denote nucleotide additions to specific points of the TRA C cloning fragment to achieve the correct spacing of Type IIS restriction enzyme binding site and the cut site, when adjacent to such sites. Sp blocks flanking the Notl restriction enzyme binding site sequence have been used to space the Notl binding and cut site appropriately for efficient action. The selection of nucleotides considered the potential impact of DAM methylation of the Bsal binding site The full DNA sequence for the TRA C cloning fragment in the present example of native human TRA chains are presented as, SEQ0047. This sequence includes the 5' primer bind and 3' primer bind sequences.

Design of V-C Entry Vector Backbone for Transient Expression of Reconstituted TRA ORF in Mammalian Cells In the present example, the V-C entry vector backbone is derived from the pMA plasmid. It encodes a Col E1 origin of replication, ori, along with antibiotic resistance beta-lactamase gene, positive selection #1. Beta-lactamase confers resistance to the penicillin group of beta-lactam antibiotics such as ampicillin and carbenicillin.

The vector backbone, as depicted in FIG. 27, encodes the required genetic elements that confer the appropriate functionality for downstream applications of the fully reconstituted TRA ORF. In this present example, the 5' genetic element encodes the CMV constitutive mammalian promoter and the 3' genetic element encodes the SV40 pA polyadenylation signal to permit transient expression of the fully reconstituted TRA ORF in a mammalian cell.

In the present example, the vector backbone encodes Acc65I and Xbal restriction enzyme binding sites that generate overhang *1' and overhang *2', respectively. Overhang *1' is complementary to overhang *1 within the TRA V cloning fragment (FIG. 25). Overhang *2' is complementary to overhang *2 within the TRA C cloning fragment (FIG. 26). These complementary overhangs permit directed cloning of the TRA V and TRA C cloning fragments into the V-C entry vector backbone.

Sp feature denotes nucleotides added between the Acc65I and Xbal restriction enzyme recognition sites required for distancing the two sites for efficient action.

The sequence of the vector backbone from the 5' genetic element encoding the FRT F14 site, to the 3' genetic element encoding the FRT F15 is presented as SEQ0688.

Method to Assemble TRA V-C Entry Vector Library

This method utilizes standard molecular biology techniques to assemble selected TRA V cloning fragment (FIG. 25) and TRA C cloning fragment (FIG. 26) into a given V-C entry vector backbone (FIG. 2) to create a TRA V-C entry vector (Component 1A, FIG. 2*a*). In this present example, the method performs the restriction enzyme digestion and ligation reaction in a single reaction.

RE Digestion and Ligation Reaction 100 ng of linear vector backbone (linearised by ACC65I and Xbal digestion)
10 ng of TRA V genetic fragment
20 ng of TRA C genetic fragment
2 μl 10×NEB ligase buffer
0.5 μl of Bbsl
1 μl of T4 DNA ligase
Up to 20 μl of $H_2O$ Reaction Conditions Step 1; 2 min at 37° C.
Step 2; 3 min at 16° C.
Repeat step 1 and 2, 20 times
5 min at 50° C.
5 min at 80° C.
Return to room temperature Resulting product is transformed into competent *E. coli* cells that are selected for carbenicillin-resistant colonies. Plasmids isolated from selected colonies are sequenced to determine correctly assembled constructs. The procedure is repeated for each independent V segment cloning fragment. The resulting constructs make up the TRA V-C entry vector library for use in reconstitution of full-length TRA ORFs for later use in transient expression of said reconstituted TRA in mammalian cells. The sequence of the cloned V-C fragments that make up the TRA V-C entry vector library is presented as SEQ0049 to SEQ0094. The presented sequences include all the Kozac sequence preceding the start codon of the variable segment, to the stop codon of the C segment.

Design and Assembly of TRA J Donor Vector Library for Native Human TRA Repertoire In the present example, a TRA J receiving cassette fragments are constructed and inserted to a J donor vector backbone to create a J receiving cassette vector. Subsequently, a synthetic TRA J segment parts may be assembled into a TRA J receiving cassette vector to create the J Donor vector library. This flexible multistep assembly method allows rapid and cost effective engineering of J donor segment features, such as variations in J segment length.

The DNA components required for a TRA J donor vector library are:

I. TRA J receiving cassette fragment

II. J donor vector backbone

III. TRA J receiving cassette vector

IV. TRA J segment part

Design of Synthetic TRA J Receiving Cassette Fragment

The annealing of two single stranded DNA oligonucleotides is used to generate the receiving site cassette fragment that by design contains 4-nucleotide single-strand overhangs at each end of the DNA fragment; Overhang *3 and Overhang *4. The 4-nucleotide overhangs to permit directed ligase-dependent cloning into a J donor vector backbone to create the TRA J receiving cassette vector, depicted in FIG. 28.

The pair of Type IIS restriction sites, Bsal 4 and Bsal 4 are positioned at the 5' and 3' end of the receiving site cassette DNA fragment. The direction of the Bsal recognition site is to guide Bsal enzyme to cut the DNA towards the centre of the construct. These sites are used during TRA ORF reconstitution protocol by generating overhang ‡2-5' and overhang ‡3-3'. Overhang ‡3 is a component of the TRA C part encoded in the receiving cassette fragment, while overhang ‡2 is defined after the TRA J segment part is cloned (infra vide).

The Bbsl pair of Type IIS recognition sites Bbsl← and Bbsl→ are encoded near the middle of the cassette and used for assembly of the TRA J donor vector, in creating complementary overhangs included in synthesized TRA J segment parts (infra vide). The 5' Bbsl site, Bbsl←, cuts into the Bsal site to create overhang *5 at the 3' end of this feature. The 3 Bbsl site, Bbsl→, cuts into the TRA C part element, to create overhang *6 at the 5' end of this element. These overhangs are encoded within the Bsal and TRA C part features of this construct as to avoid addition of non-native nucleotides that would be incorporated into the final reconstituted TRA ORF.

The region between Bbsl→ enzyme generated overhang and the Bsal← enzyme generated overhang encodes a proportion of the TRA C region starting from the second nucleotide of the TRA C genetic fragment, TRA C part. The motivation for starting from the second nucleotide of the TRA C genetic fragment is because in the present example of a human TRA locus TORES, the resulting overhang is TATC and not a palindromic overhang, which would be the case if the beginning of the TRA C genetic fragment were including (resulting overhang ATAT). A palindromic overhang should be avoided, as it would permit two vector ends joining without the required TRA J segment part insert. The orientation of the Bbsl→ site permits the in-frame ligase dependent cloning of all TRA J fragments 3' end to the 5' beginning of the TRA C region in the receiving site cassette. The orientation of the Bsal← site permits the in-frame ligase-dependent cloning of the beginning of the TRA C region with the remaining TRA C fragments in the final step of the TRA full length ORF reconstitution protocol using a complete TORES.

Between the two Bbsl binding sites is an 8 nucleotide recognition sequence for the enzyme Notl. This restriction site is utilized as a negative selection marker to reduce the background of the parental plasmid colonies. This is achieved when Notl enzyme is added after the TRA J gene fragment insertion has been performed. Therefore plasmids correctly cloning a TRA J gene fragment would remain circular in the presence of Notl enzyme but parental plasmids that did not exchange its Notl site for a TRA J gene fragment will be linearized, in turn biasing the bacterial transformation to propagate a complete circular TRA J fragment-containing plasmid.

Sp denote nucleotide additions to specific points of the TRA J receiving cassette fragment to achieve the correct spacing of Type IIS restriction enzyme binding site and the cut site, when adjacent to such sites. Sp blocks flanking the Notl restriction enzyme binding site sequence have been used to space the Notl binding and cut site appropriately for efficient action. Additional nucleotides have been included to maintain correct reading frame within the final reconstituted full-length TRA. The selection of nucleotides considered the potential impact of DAM methylation of the Bsal binding site.

The full DNA sequence for the TRA J receiving cassette fragment oligonucleotides in the present example of native human TRA chains are presented as, SEQ0095 and SEQ0096. Both forward (F1) and reverse (R1) oligonucleotide sequences are listed.

Design of the J Donor Vector Backbone

The J donor vector backbone is used to insert the TRA J receiving cassette fragment to create the TRA J receiving cassette vector. The backbone is thus carried through to the J Donor vector library. In the final reaction to create TRA full-length ORFs, this backbone is a reaction byproduct (FIG. 2*e*), and thus carries minimal features as depicted in FIG. 29.

In the present example, the J donor vector backbone encodes a Col E1 origin of replication, ori. The antibiotic resistance is the aminoglycoside 3'-phosphotransferase gene, positive selection selection #2. Aminoglycoside 3'-phosphotransferase confers resistance to antibiotic substrates such as kanamycin, streptomycin, neomycin, and gentamicin. This alternate positive selection is used to ensure J donor vectors are not selected for after full-length TCR ORF reconstitution, which are selected on positive selection #1.

In the present example the vector EcoRI and Xhol restriction enzyme binding sites that generates complementary overhang, overhang *3' and overhang *4', respectively. Overhang *3' is complementary with Overhang *3 contained within the TRA J receiving cassette fragment. Overhang *4' is complementary with Overhang *4 contained within the TRA J receiving cassette fragment. These overhangs permits directed cloning of the TRA J receiving cassette fragment.

Sp block denotes nucleotides added between the EcoRI and Xhol restriction enzyme binding sites for distancing the two sites to ensure efficient action.

In the present example, the J donor backbone is presented as SEQ0097.

Method to Assemble the TRA J Receiving Cassette Vector

This method utilizes standard molecular biology techniques to assemble the given TRA J receiving cassette fragments (FIG. 28) into a given J donor vector backbone (FIG. 29) to create a TRA J receiving cassette vector (FIG. 30). The resulting TRA J receiving cassette vector is used to insert TRA J segment parts (FIG. 31) to construct TRA J Donor vectors (Component 1B, FIG. 2*b*).

First, the two oligonucleotides to form the TRA J receiving cassette DNA fragment must be phosphorylated and annealed.

Reaction Mix

| | |
|---|---|
| Oligonucleotide (sense strand) (100 μM) | 1 μl |
| Oligonucleotide (anti-sense strand) (100 μM) | 1 μl |
| T4 ligase buffer 10x | 1 μl |
| T4 PNK | 1 μl |
| $H_2O$ | 6 μl |

Reaction Conditions

Incubate for 37° C. for 1 hour

Denature at 95° C. for 5 min

Anneal sense and anti-sense oligonucleotides by slowly cooling the reaction down to 25° C. at 3° C. per min Assembly ligation of TRA J receiving cassette fragments and J donor vector backbone.

Reaction Mix

| | |
|---|---|
| Linear vector backbone | 100 ng |
| Receiving site cassette DNA fragment (0.5 μM) | 2 μl |
| T4 ligase buffer 10x | 2 μl |
| T4 ligase | 0.5 μl |
| $H_2O$ | up to 20 μl |

Reaction Conditions

Incubate for 1 hour at 25° C.

Heat inactivate at 65° C. for 10 min

Resulting product is transformed into competent *E. coli* cells and selected for Kanamycin resistant colonies. Resistant colonies are selected to determine correctly assembled constructs. The resulting plasmid is the TRA J receiving cassette vector. In the present example, the TRA J receiving cassette vector is presented as SEQ0098 and depicted in FIG. 30.

Design of Synthetic TRA J Segment Parts

Having generated the TRA J receiving cassette vector synthetic TRA J segment parts must be generated to insert into this vector. Each TRA J sequence is inserted into an independent TRA J receiving cassette vector context to generate the TRA J donor vector library as part of the human TRA TORES.

The TRA J donor vector library comes in two different forms, comprised of a long or short J segment part. The short TRA J segment part encodes all amino acids from the start of the CDR3 border codon. However, considering that the majority of TRA J segments are trimmed back by less than 10 nucleotides during TCR rearrangement, a TRA J donor library containing a longer TRA J germline segment is designed, long TRA J segment part. The motivation for a longer TRA J gene fragment library is that a shorter oligonucleotide duplex encoding CDR3 (odeCDR3) would be required for the full length TRA reconstitution, than if the short TRA J fragment would be used. Since highly variable sequences are provided as short oligonucleotide duplexes, odeCDR3, a shorter CDR3 oligonucleotide synthesis is less likely to contain truncated or mutated oligonucleotide contaminants and therefore reduce the likelihood of oligonucleotide duplex with sequence errors being cloned during full length TRA reconstruction. Furthermore, shorter odeCDR3 syntheses are cost-saving.

The TRA J segment parts are constructed by annealing two single-stranded DNA oligonucleotides designed to contain 4-nucleotide single-strand overhangs at each end of the DNA fragment. The resulting TRA J segment part is depicted in FIG. 31.

The 5' overhang designated Overhang *5' is complementary to the Overhang *5 generated within J donor receiving cassette vector by Bbsl action. The 3' overhang designated Overhang *6' is complementary to the Overhang *6 generated within J donor receiving cassette vector by Bbsl action. This pair of complementary overhangs permits directional cloning of the TRA J segment parts into the TRA J receiving cassette vector.

The Short TRA J segment part encodes all amino acids from the start of the CDR3-J border Phe codon. The CDR3 is defined as the sequence flanked by the C-terminal-conserved Cys of the V region, and Phe of the J region which is part of the Phe-Gly/Ala conserved motif. This conserved Phe-Gly/Ala motif is utilized to standardize the 5' overhangs of the TRA J fragments to TTTG for downstream TRA reconstitution. The exceptions to this standardization in the present example are human TRAJ33 and TRAJ38 that border the CDR3 region with Trp and Gly. The 5' overhangs are TGGG for both TRAJ33 and TRAJ38 in the present example.

The long TRA J segment part is designed to encode more amino acids N-terminal of the CDR3 border amino acids. The start point of each long gene fragment is at the first nucleotide of an amino acid codon positioned 10-12 nt from the 5' end of the germline encoded TCR joining element. The 5' end of each long TRA J segment part remains identical to that of the short TRA J segment part.

To both short and long TRA J segment parts an adenine, represented as the A block in FIG. 11, is added to the 3' end of each TRA J segment part. This adenine represents the first nucleotide of the TRA C fragment that is excluded from the TRA J receiving cassette.

The sequences of the short TRA J segment parts of the present example of native human J segments are presented as SEQ0099 to SEQ0210 and the long TRA J segment parts SEQ0211 to SEQ0322. In both cases, both forward (F1) and reverse (R1) oligonucleotide sequences are listed.

Method to Assemble the Short or Long J-Donor Vector Library

This method utilizes standard molecular biology techniques to clone the Short TRA J segment or Long TRA J segment part part (FIG. 31) into the TRA J receiving cassette vector (FIG. 30) to create TRA J donor vectors (Component 1B, FIG. 2*b*) containing the short or long TRA J segments. In this present example, the method performs the restriction enzyme digestion and ligation reaction in a single reaction.

The DNA components required for a J donor vector library is as follows:

I. Short TRA J segment part or Long TRA J segment part

II. J donor receiving cassette vector

Phosphorylation and Annealing Two Oligonucleotides to Form the TRA J Segment Part DNA Fragment Reaction Mix

| | |
|---|---|
| Oligonucleotide (sense strand) (100 μM) | 1 μl |
| Oligonucleotide (anti-sense strand) (100 μM) | 1 μl |
| T4 ligase buffer 10x | 1 μl |
| T4 PNK | 1 μl |
| $H_2O$ | 6 μl |

Reaction Conditions

Incubate for 37° C. for 1 hour

Denature at 95° C. for 5 min

Anneal sense and anti-sense oligonucleotides by slowly cooling the reaction down to 25° C. at 3° C. per min RE Digestion and Ligation Reaction

| | |
|---|---|
| TRA J receiving cassette backbone | 100 ng |
| TRA J DNA fragment (0.5 μM) | 2 μl |
| 10x NEB T4 ligase buffer | 2 μl |
| BbsI | 0.5 μl |
| T4 DNA ligase | 0.5 μl |
| $H_2O$ | up to 20 μl |

Reaction Conditions

Step 1; 2 min at 37° C.

Step 2; 3 min at 16° C.

Repeat step 1 and 2, 20 times 5 min at 50° C.

5 min at 80° C.

Return to room temperature

Add 0.5 μl of NotI enzyme and incubate for 30 min at 37° C. to linearize parental vector.

Reaction product is transformed into competent *E. coli* cells and selected for Kanamycin resistance. Selected resistant colonies are sequenced to determine correctly assembled constructs. The resulting constructs make up the TRA J donor vector library, encoding either a long or a short TRA J gene fragment.

The sequence of the resulting libraries, excluding backbone sequence outside of the Bsal recognition sites, are presented as SEQ0323 to SEQ0378 for the TRA short J donor library and SEQ0379 to SEQ0434 for the TRA long J donor library.

Design and Assembly of TRB V-C Entry Vector and TRB J Donor Vector Libraries for Native Human TRB Repertoire In the above sections, the design and assembly of V-C entry vector and J donor vector libraries for the native human TRA repertoire was described in detail. The overall design and assembly of such vector libraries encoding sequences of the TRB repertoire is essentially the same. In the present example, the design and assembly of the TRB V-C entry vector and TRB J Donor vector libraries will be briefly outlined in order to construct a TORES or the native human TRB TCR locus.

It is important to note that the V-C entry vector backbones for the TRA and TRB chains contain differing FRT sites, as to pair the resultant vector products from operation of the system (Components 2C and 2E), with the genomic receiver sites of the eTPC-t (Components 2B and 2D). This means that only a single TRA or TRB chain will be integrated into each eTPC cell via the paired integration couple. In the present example, whereas the TRA chains have been placed in a V-C entry vevtor context bouded by FRT F14 and F15 sites, the TRB chains have been bounded by FRT FRT and F3 sites.

Design and Assembly of TRB V-C Entry Vector Library for Native Human TRB Repertoire In the present example, the design and assembly of a TRB V-C entry vector library that contains the native human TRB V-C sequence repertoire.

The DNA components required for a TRB V-C vector library are:

I. A TRB V cloning fragment for each functional TRB V gene segment encoded in the human genome II. TRB C1 or TRB C2 cloning fragment III. A V-C entry vector backbone In contrast to the human TRA locus, the human TRB locus encodes two distinct constant segments, TRB C1 and C2. Thus, to capture both constant regions, two V-C entry vector sets are constructed to pair each of the V segments with each C1 and C2 segments.

In the present example, the TRB V and TRB C cloning fragments were synthesized and used to assemble into a target V-C entry vector backbone in a single restriction enzyme and ligase reaction. In the present example, the target V-C entry backbone was designed to permit transient expression of reconstituted TRB ORFs within mammalian cells.

In the present example, the TRB V-C entry vector library is constructed using Type IS restriction enzyme Bbsl. The Type IIS restriction enzyme used in functioning of the library to reconstitute full-length TRB ORFs is Bsal.

Design of Synthetic TRB V Cloning Fragments

The arrangement of genetic elements of the TRB V cloning fragments is identical to those of the TRA V cloning fragments described above 1, as depicted in FIG. 25.

Full DNA sequences for the TRB V cloning fragments in the present example of native human TRB chains are presented as SEQ0435 to SEQ481.

Design of Synthetic TRB C Cloning Fragment

The arrangement of genetic elements of the TRB C cloning fragments is identical to those of the TRA C cloning fragments described above, as depicted in FIG. 26.

The TRB locus encodes two distinct C segments, and both are included in the design of the TRB V-C entry vector library.

The full DNA sequence for the TRB C cloning fragments in the present example of native human TRB chains are presented as SEQ0482 and SEQ0483.

Method to Assemble TRB V-C Entry Vector Library

The method to assemble the given TRB V and TRB C cloning fragments into a given V-C entry vector backbone to create a TRB V-C entry vector is identical to that described above for the TRA system. The V-C entry vector backbone used for the TRB V-C entry vector in the present example contains FRT and F3 FRT sequences as the 5' and 3' genetic elements, respectively. This FRT/F3 V-C entry vector backbone sequence is presented as SEQ0689. The differing FRT site context between TRA and TRB TORES systems insulates the integration vectors from one another, and pairs them with the gemoic receiver sites of the eTPC as a pair of integration couples.

The sequence of the cloned V-C fragments that make up the TRA V-C entry vector library is presented as SEQ0484 to SEQ0577.

Design and Assembly of TRB J Donor Vector Library for Native Human TRB Repertoire In the present example, the design and assembly of a TRB J Donor vector library that contains the native human TRB J sequence repertoire.

In the present example, a TRB J receiving cassette fragments are constructed and inserted to a J donor vector backbone to create a TRB J receiving cassette vector. Subsequently, a synthetic TRB J segment part may be assembled into a TRB J receiving cassette vector to create the TRB J Donor vector library. This flexible multistep assembly method allows rapid and cost effective engineering of J donor segment features, such as variations in J segment length.

This procedure follows the same pattern as the TRA J donor vector assembly described in Example 2. However, it should be noted that since the J receiving cassette fragments contain parts of the C segment, the TRA J and TRB J receiving cassette fragments differ with regard to the C part sequence, that must correspond to the respective C gene segments. Moreover, in contrast to TRA J scenario that only requires a single J receiving cassette fragments, the TRB J requires two distinct J receiving cassette fragments to account for the use of alternate C1 and C2 segments.

The DNA components required for a TRB J donor vector library are:

I. TRB J C1 or TRB J C2 receiving cassette fragment

II. J donor vector backbone

III. TRB J C1 or TRB J C2 receiving cassette vector

IV. TRB J segment part

Design of Synthetic TRA J Receiving Cassette Fragment

The annealing of two single stranded DNA oligonucleotides is used to generate the receiving cassette fragments, which contain 4-nucleotide single-strand overhangs at each end of the DNA fragment, depicted in FIG. 28. The 4-nucleotide overhangs permit directed ligase-dependent cloning into a J donor vector backbone to create the TRB J receiving cassette vector, The two receiving cassette fragments required for alternate use of C1 and C2 segments are presented as SEQ0578 and SEQ0581. For each fragment, the forward (F1) and reverse (R1) oligonucleotide sequences are provided.

Method to Assemble the TRB J Receiving Cassette Vectors

The method for assembly of the TRB J receiving cassette vectors is identical to that of the method for assembly of TRA J receiving cassette vectors described in Example 2. The same J donor vector backbone (SEQ0097) is used to generate two TRB J receiving cassette vectors, each containing one C1 or C2 part corresponding to the alternate C segments for the TRB locus.

The resulting two TRB J receiving cassette vector is used to insert TRB J segment parts to construct TRB J Donor vectors.

The resulting TRB J receiving cassette vectors are presented as SEQ0582 and SEQ0583.

Design of Synthetic TRB J Segment Parts

The TRB J segment parts are constructed by annealing two single-stranded DNA oligonucleotides designed to contains 4-nucleotide single-strand overhangs at each end of the DNA fragment. The arrangement of this part and method of assembly are identical to that of the TRA J segment parts, and depicted in FIG. 31.

In the case of the Short TRB J segment part encodes all amino acids from the start of the CDR3-J border Phe codon. The CDR3 is defined as the sequence flanked by the C-terminal-conserved Cys of the V region, and Phe of the J region, which is part of the Phe-Gly motif conserved across all human TRB J segments. This conserved Phe-Gly motif is utilized to standardize the 5' overhangs of the TRA J fragments to TTTG for downstream TRB reconstitution. Unlike the TRA J segments, there are no exceptions to this standardized overhang in the TRA J segment parts in the present example.

To both short and long TRB J segment parts an adenine, represented as the A block in FIG. 11, is added to the 3' end of each TRB J segment part. This adenine represents the first nucleotide of the TRB C fragment that is excluded from the TRB J receiving cassettes.

The sequences of the short TRB J segment parts of the present example of native human J segments are presented as SEQ0584 to SEQ0609, and the long TRB J segment parts SEQ0610 to SEQ0635. In both cases, both forward (F1) and reverse (R1) oligonucleotide sequences are listed.

Method to Assemble TRB Short or Long J Donor Vector Library

The procedure to assemble the TRB J donor libraries is identical to that of the TRA libraries described above. However, in the case of the TRB libraries, there are four libraries to generate, in contrast to the short and long libraries for the TRA locus segments.

In the case of TRB libraries, each short and long libraries can be constructed to carry each of the alternate C1 and C2 C segments, resulting in four subsets within the TRB J donor library.

The DNA components required for a J donor vector library is as follows:

I. Short TRB J segment part or Long TRB J segment part

II. TRB J C1 or TRB J C2 receiving cassette vector

Following the same procedure as described above, the four resulting subsets within the TRB J donor library are generated. The sequence of the resulting libraries, excluding backbone sequence outside of the BsaI recognition sites is presented.

TRB C1 short J donor library presented as SEQ0636 to SEQ0648

TRB C2 short J donor library presented as SEQ0649 to SEQ0661

TRB C1 long J donor library presented as SEQ0662 to SEQ0674

TRB C2 long J donor library presented as SEQ0675 to SEQ0687

Example 2 Design and Generation of Oligonucleotide Duplex Encoding CDR3 (odeCDR3)

In the above example, the design and construction of the TORES as V-C entry vector and J donor vector libraries human TRA and TRB chains is described to output full-length human TCR chains as components 2C and 2E of the overall two-part device.

The utilization of these V-C entry vector and J donor vector libraries for one-step reconstitution of full-length TCR open reading frames requires an oligonucleotide duplex encoding CDR3 (odeCDR3) construct to be provided in order to complete the target full-length TCR chain sequence (FIG. 2*c*). Once V-C entry vector and J donor vector libraries are generated, these vectors represent stock items that may be drawn upon indefinitely to select desired V-J-C combinations of target full-length TCR chains sequences. In contrast, the odeCDR3 represents a short unique sequence specific to the target full-length TCR ORF.

The present example describes the design and generation of odeCDR3 for use in the native human TRA and TRB vector platforms.

Design of the TRA odeCDR3

The annealing of two single stranded DNA oligonucleotides generates an odeCDR3 that contains 4-nucleotide single-strand overhangs at each end of the DNA fragment, as depicted in FIG. 2*c*. The 4-nucleotide overhangs are designed to permit directed ligase dependent cloning to the 3' end of the TRA V segment encoded in the entry vector, (Overhang ‡1-5') and the 5' end of the TRA J fragment during TRA reconstitution (Overhang ‡2-3'). Overhang ‡1-5' is standardised to CTGC, complementary to the standardized Overhang ‡1-5 encoded in the V segment of the TRA V-C entry vector. In the case of Overhang ‡2-3', there are two sequence forms that this can take, which is determined by sequence divergence among J segments from the human TRA locus. For native human TRA J segments TRAJ33 and TRAJ38, the Overhang ‡2-3' is standardized to TGGG, complementary to the Overhang ‡2-3 encoded in the J donor vector of these two J segments. For all other human TRA J segments Overhang ‡2-3' is standardized to TTTG, complementary to the Overhang ‡2-3 encoded in the J donor vector of these J segments (see Example 1).

Design of the TRB odeCDR3

As for the TRB odeCDR3, the annealing of two single stranded DNA oligonucleotides generates an odeCDR3 that contains 4-nucleotide single-strand overhangs at each end of the DNA fragment, as depicted in FIG. 4*c*. The 4-nucleotide overhangs are designed to permit directed ligase dependent cloning to the 3' end of the TRB V segment encoded in the entry vector, Overhang ‡1-5', and the 5' end of the TRB J fragment during TRB reconstitution, Overhang ‡2-3'. The Overhang ‡1-5' is standardised to TTGC, complementary to the standardized Overhang ‡1-5 encoded in the V segment of the TRB V-C entry vectors. In contrast to the TRA odeCDR3 where two alternative Overhang ‡2-3 forms are required, for the TRB odeCDR3 Overhang ‡2-3 is standardized to TTTG, complementary to the Overhang ‡2-3 encoded in the J donor vector of all TRB J segments (see Example 1).

General odeCDR3 Design

In general, an odeCDR3 design must be matched to the overhangs the 4-nucleotide overhangs are designed to permit directed ligase dependent cloning to the 3' end of the V segment encoded in the entry vector (Overhang ‡1-5') and the 5' end of the J fragment during reconstitution, (Overhang ‡2-3').

Method to Generate Phosphorylated CDR3 DNA Oligonucleotide Duplex

Phosphorylation and Annealing Two Oligonucleotides to Form the odeCDR3

Reaction Mix

| | |
|---|---|
| Oligonucleotide (sense strand) (100 μM) | 1 μl |
| Oligonucleotide (anti-sense strand) (100 μM) | 1 μl |
| T4 ligase buffer 10x | 1 μl |
| T4 PNK | 1 μl |
| $H_2O$ | 6 μl |

Reaction Conditions

Incubate for 37° C. for 1 hour

Denature at 95° C. for 5 min

Anneal sense and anti-sense oligonucleotides by slowly cooling the reaction down to 25° C. at 3° C. per min Example 3 Demonstration of the Two-Part Device Comprising of TORES and eTPCS to Generate a eTPC-t This example describes the steps used for defining the vector library components and odeCDR3 required to reconstitute TRA and TRB full length TCR ORFs given sequence information of the target TCRs. The present example demonstrates the TORES process to assemble a full-length model TRA and TRB TCR chain pair. The present example also demonstrates eTPCS by integration of the said vectors into an eTPC via RMCE tp generate a eTPC-t and subsequently confirm its TCR pair specificity by staining of surface-presented TCR with specific HLA-multimer reagent.

Selection of V-C Entry Vector, J Donor Vector and odeCDR3

The sequences of all possible germline fragments that are represented in the cloning library are aligned to a TRA or TRB sequences of interest. The genetic fragments with the highest identity to the TRA or TRB sequence determines which V, J and C genetic element will constitute the desired TRA or TRB clonotype sequences. For TRA, the appropriate V-C entry vector is selected based on the determination of the V usage of the desired TRA. For TRB, when sequence coverage is sufficient to determine the V and C usage, the appropriate V-C entry vector will be selected that corresponds to the V usage of the desired TRB clonotype, in addition to whether said clonotype uses TRBC1 or TRBC2.

In the case when both the short and long version of the specific TRAJ or TRB J genetic element align to the TRA and TRB sequence, respectively, the corresponding plasmids encoding the longer genetic elements will be used for the TRA reconstruction.

The odeCDR3 sequence required for the TRA to be synthesised is determined as the region between the 3' end of the TRA V aligned genetic fragment and the 5' end of the aligned TRAJ genetic fragment. The oligonucleotide sense strand requires the additional 5' 4-nucleotide overhang, Overhang ‡1-5', CTGC that is universal to the overhang generated on the TRA V entry vector when digested with Bsal, Overhang ‡1-3'. The complementary oligonucleotide anti-senses strand requires the additional 5' 4-nucleotide overhang, Overhang ‡2-3', that is unique to the overhang specifically for the TRAJ vector added to the TRA reconstruction reaction, Overhang ‡2-5'.

The CDR3 sequence required for the TRB to be synthesised is determined as the region between the 3' end of the TRB V aligned genetic fragment and the 5' end of the aligned TRB J genetic fragment. The oligonucleotide sense strand requires the additional 5' 4-nucleotide overhang, Overhang ‡1-5', TTGC that is universal to the overhang generated on the TRB V entry vector when digested with Bsal, Overhang ‡1-3'. The complementary oligonucleotide anti-senses strand requires the additional 5' 4-nucleotide overhang, Overhang ‡2-3', that is unique to the overhang specifically for the TRB J vector added to the TCR reconstruction reaction Overhang ‡2-5'.

In the present example, a model TCR TRA/TRB pair (JG9-TCR) is used with a known specificity for a Human cytomegalovirus (HCMV) antigen presented in HLA-A*02:01. This antigenic peptide is derived from the HCMV pp65 protein, and the full amino acid sequence of the peptide antigen that is presented in HLA-A*02:01 is NLVPMVATV. The sequences of the TRA (JG9-TCR-alpha) and TRB (JG9-TCR-beta) chains are presented as SEQ701 and SEQ702, respectively.

Based on this full-length sequence it was straightforward to select the appropriate V-C entry and J donor vectors from the TRA and TRB libraries.

In the present example the TRA V-C entry vector SEQ0088 (from list 0049 to 0094), in the SEQ0698 backbone, and J donor vector SEQ0371 (from list 0323 to 0378) were selected.

In the present example the TRB V-C entry vector SEQ0563 (from list 0484 to 0577), in the SEQ0688 backbone, and J donor vector SEQ0637 (from list 0636 to 0687) were selected.

The odeCDR3 synthesised for the TRA chain is presented in SEQ703 and SEQ704 as sense and antisense, respectively.

The odeCDR3 synthesised for the TRB chain is presented in SEQ705 and SEQ706 as sense and antisense, respectively.

Method for Full-Length Reconstitution

For each of the TRA and TRB components selected above, restriction enzyme/ligase cycle reactions were performed as described below.

RE Digestion and Ligation Reaction

| | |
|---|---|
| V-C entry vector | 100 ng |
| J donor vector | 60 ng |

-continued

| | |
|---|---|
| odeCDR3 oligonucleotide duplex (0.5 μM) | 2 μl |
| 10x T4 ligase buffer | 2 μl |
| BsaI | 0.5 μl |
| T4 DNA ligase | 0.5 μl |
| $H_2O$ | up to 20 μl |

Reaction Conditions
Step 1; 2 min at 37° C.
Step 2; 3 min at 16° C.
Repeat step 1 and 2, 20 times
5 min at 50° C.
5 min at 80° C.
Return to room temperature
Add 0.5 μl of NotI enzyme and incubate for 30 min at 37° C.

The resulting reaction product was transformed into competent *E. coli* cells and plated on carbenicillin containing plates.

Screening and sequencing carbenicillin resistant colonies was conducted to determine correctly assembled constructs. Screening of colonies was performed by restriction enzyme diagnostic digest of isolated plasmid DNA, and the expected DNA fragment sizes were observed by DNA electrophoresis. The resulting constructs encode the full length TCR alpha and beta clone sequences.

Validation of Reconstituted TRA Ad TRB Vectors

To verify the specificity of the reconstituted TCR TRA/TRB pair above, an eTPC-t in was generated with said pair, wherein the parental eTPC contains distinct synthetic genomic receiver sites Component 2B and 2D. The sites Component 2B and 2D designed to match the RMCE sites in the generated integration vectors Component 2C and 2E, each of which encodes a single chain of a TCR pair (JG9-TCR)

This example uses a parental eTPC cell line ACL-488, which is TCR null, HLA null, CD4 null and CD8 null, and further containing Component 2B and 2D. Component 2B comprises two unique heterospecific recombinase sites, FRT and F3 that flank a Kozak sequence and ORF encoding the selection marker, blue fluorescent protein (BFP). Encoded 5' of the FRT site, is an EF1a promoter and 3' of the F3 site is a SV40 polyadenylation signal terminator. Component 2D comprises two unique heterospecific recombinase sites, F14 and F15, which were different to Component 2B. These sites flank a Kozak sequence and ORF that encodes the selection marker, the red fluorescent protein, (RFP). Encoded 5' of the F14 site is an EF1a promoter, and 3' of the F15 site is a SV40 polyadenylation signal terminator.

The above-described components 2C and 2E generated with the TORES comprise two heterospecific recombinase sites, FRT/F3 (2C) and F14/F15 (2E), thus being matched to Component 2B and 2D, respectively. Component 2C further comprises, between the FRT/F3 sites, of a Kozak sequence, start codon and TCR ORF encoding JG9-TCR-beta chain. Component 2E further comprises, between the F14/F15 sites, of a Kozak sequence, start codon and TCR ORF encoding JG9-TCR-alpha chain.

An eTPC-t was created through RMCE by electroporation ACL-488 (eTPC). Four to ten days after electroporation, individual cells displaying diminished fluorescent protein signal, BFP and RFP, encoded by Components 2D and 2B selection markers, were sorted by FACS. Individual monoclones were outgrown and then phenotypically assessed. The resulting monoclone, ACL-851, was BFP and RFP negative (FIG. 32 *a* and *b*). ACL-851 also showed TCR and CD3 surface expression while the parental cell line did not (FIG. 32 *c* and *e*). Furthermore, the introduced JG9-TCR showed specific staining with the HLA-A*02:01-NLVP tetramer, indicating that it is a functional TCRsp on the surface of the eTPC-t (FIG. 32 *d* to *f*). ACL-851 was confirmed by PCR to contain the TCRsp encoded by Component 2B' and Component 2D' integrated into the genome (FIG. 32 *g* and *h*).

In summary, an eTPC was converted to an eTPC-t, by use of an RMCE based integration method to integrate TCR ORF delivered in Component 2C and 2E, generated in the TORES, such that Components 2B and 2D were converted into Component 2B' and 2D', and where by this eTPC-t expressed a functional TCRsp on the surface of the cell. Furthermore, this example demonstrates operation of a simple eTPC:A system, where a binary composition of an eTPC-t and analyte antigen were combined and the eTPC-t selected based on a complex formation between the soluble analyte antigen (HLA multimer: HLA-A*02:01-NLVPMVATV).

Example 4: Demonstration of eTPC-x Reversion from eTPC-t

The present example describes conversion of an eTPC-t to an eTPC-x, wherein the eTPC-x has component 2B' encoding a TCR chain ORF and Component 2D is available for integration of complementary TCR chain ORF. Conversion of Component 2D' of the eTPC-t to Component D of the eTPC-x is achieved by use of a genetic donor vector (Component 2Z) matched to Component 2D'.

In this example, the parental eTPC-t cell line ACL-851 generated in example 3 was used. Component 2Z is a plasmid vector comprised of two heterospecific recombinase sites, F14/F15 matched to Component 2D', a Kozak sequence, start codon and an ORF encoding a green fluorescent protein (GFP) as a selection marker of integration. The eTPC-t was combined with Component 2Z and a vector encoding RMCE recombinase enzyme by electroporation, whereupon the cells were subsequently selected for loss of CD3 presentation and gain of the GFP selection marker of integration. The monolcone ACL-987 was phenotypically characterised by FACS, and it was observed that the ACL-987 has gained GFP and lost CD3 and TCRab (FIG. 33 *b, d*), indicating successful exchange of JG9-TCR-alpha with the GFP ORF and conversion of Component D' to Component D, and thus generation of an eTPC-x. In comparison the parental eTPC-t, ACL-851, is lacking GFP expression and has CD3 and TCRab surface expression (FIG. 33 *a* to *c*).

In summary, this example demonstrates conversion of an eTPC-t to an eTPC-x, with removal of the JG9-TCR-alpha TCR ORF at Component 2D' in exchange for the GFP selection marker of integration thereby creating Component 2D, for further integration coupling events of alternative complementary TCR chain ORF. This conversion was conducted using the RMCE method for genomic integration.

Example 5: Demonstration of Generation of Sequence-Diversified Pool of TCR Variants in One Step Via TORES, and Shotgun Integration into eTPC-x to Create Pool of eTPC-t The present example describes how a pool of vectors encoding 64 single JG9-TCR-alpha variants (as Component 2E) were generated and integrated into a parental eTPC-x cell line containing a single JG9-TCR-beta (described in example 4) to create a pooled eTPC-t library where each individual cell integrated a single TRA chain to present a library of eTPC-t where each cell expresses a single discrete TCRsp on the surface. Such a method is referred to as 'shotgun' integration. The 64 JG9-TCRα variants have been created by modifying the CDR3 sequence that falls at the junction of the V and J fragments by way of a method described in FIG. 3. This single-reaction diversification is shown to produce a TCR set with a wide range of affinities to a specific HLA-multimer reagent when presented on the surface of mammalian cells with its natural TRB chain pair. This approach is ideally suited for rapid TCR-engineering using full-length TCR ORFs that may be presented and selected in a functional context of viable mammalian cells.

Rapid TCR Chain Diversification Via odeCDR3 Degeneracy

The diversification and selection of TCR ORFs is desirable to engineer TCRs chain pairs with altered specificities, affinities and/or signalling capacity. The TORES system is suited to the rapid generation of collections of TCR chains that are systematically altered from the original target sequence. In the present example, an approach of diversifying a model TCR chain pair by including an odeCDR3 to a reconstitution reaction with a defined and limited nucleotide degeneracy at selected codon positions is presented. This approach was used to diversify the JG9-TCR-alpha chain of the model JG9-TCR pair presented in Example 3.

Generation of Diverse TRA Chain Collection

FIG. 3 presents the overall strategy for generating a sequence-diversified collection of TCR chains in a single reaction by use of an odeCDR3 pool. A single C-V entry vector and J donor vector are selected to represent the target V, J and C gene segments in the final full-length TCR product (FIG. 3, box i and box ii). An odeCDR3 pool is generated with selected diversity, such that there are a number of different CDR3 sequences represented in the odeCDR3 pool (FIG. 3, Box iii). When all components are combined into a restriction enzyme/ligase cycle reaction, the resulting product are a collection of constructs containing full-length TCR chains of defined V, J C gene segment usage, and a defined diversity in the CDR3 region (FIG. 3, Box iv). The number of diversified full-length TCR chains in the final product is directly proportional to the number of odeCDR3 variants in the initial odeCDR3 pool added to the reaction.

In the present example, the JG9-TRA-alpha chain was the target of sequence diversification, and this was achieved through synthesis of odeCDR3 sense and antisense oligos with nucleotide degeneracy at 3 distinct positions, each altering a separate codon to result in the possibility of 4 different amino acids at each of the three codons. The codons were selected for degeneracy were spaced across the CDR3 loop. The odeCDR3 oligos are presented as SEQ0743 and SEQ0744, wherein degenerate codons are denoted N.

The odeCDR3 oligos were annealed by the method outlined in Example 2, with the 4-fold amino acid degeneracy at 3 separate codon positions resulting in an odeCDR3 product pool with 64 unique sequences, including the original coding sequence (i.e. SEQ0701).

The odeCDR3 was used to assemble the full-length TRA ORFs by the method outlined in Example 3 to create 64 unique TRA ORFs with 4-fold amino acid degeneracy at 3 distinct codon positions. In the present example, the odeCDR3 was synthesised with degenerated nucleotide usage at the indicated positions, and thus reconstitution was performed in a single tube to generate all 64 chain variants.

In parallel, each variant JG9-TCR-alpha chain, and the JG9-TCR-beta chain, was also cloned into a separate V-C entry backbone (SEQ0048), which permits transient transfection for parallel characterisation. All of the expected clones were prepared as isolated vectors and sequence confirmed.

Characterisation of Diversified JG9-TCR-Alpha Chains with TRB Chain Pair

In this example, the parental eTPC-x cell line ACL-987, expressing JG9-TCR-beta (in Component 2B') and CD3 chains (the construction of the cell line is described in example 4), was used. Component 2D encodes the selection marker GFP and is described in example 6. In this example, the 64 JG9-TCR-alpha variants were generated, creating a pool of Component 2E, flanked by F14/F15 sites.

An eTPC-t pool was created through RMCE by electroporation of the 64 Components 2E into ACL-987. Polyclones were selected on the basis of GFP expression. The resulting polyclone, ACL-988, comprised of both GFP positive and GFP negative cell populations, unlike the parental line which comprised of only GFP positive cells (FIGS. 34*a* and *b*). However, only GFP negative population showed consistently strong CD3 expression, indicating successful conversion of Component 2D into Component 2D' and therefore eTPC-x has been converted into eTPC-t (FIGS. 34*c* and *d*). Furthermore, ACL-988 GFP negative populations showed two distinct intensities when stained with the JG9-TCR specific tetramer reagent (HLA-A*02:01-NLVP), suggesting that this population is comprised of cells that express TCR variants with varying binding efficiency. In parallel, characterization of all 64 JG9-TCR-alpha variants together with WT JG9-TCR-beta were transiently expressed in a parental eTPC (ACL-987). Using this transient assay, relative staining units (RSU) against the HLA-A*02:01-NLVP tetramer reagent to a reference for each TCR pair presented in the above-described pooled eTPC-t expressing variant JG9-TCR were determined. RSU were calculated as the ratio of the mean fluorescence intensity (MFI) of HLA-A*02:01-NLVP tetramer signal for the CD3 positive population over the CD3 negative population, and was indicative of the binding strength of each TCR chain pair variant. After the independent transfection of the parental ACL-987 line with each JG9-TCR-alpha variant, the cells were stained with antibodies against CD3 and with a HLA-A*02:01-NLVP tetramer reagent and analysed by flow cytometry. Each point plotted in FIG. 34*e* represents the observed RSU for each 64 variants.

To confirm ACL-988 cells that were HLA-A*02:01 NLVP positive encode high RSU TRA variants and those HLA-A*02:01 NLVP negative encode low RSU TRA variants, individual cells for each population and their TRA were sequenced and are plotted in FIG. 34*e*. Indeed, individual ACL-988 cells that were HLA-A*02:01 NLVP positive encoded TRA variants that predominantly showed high RSU results in the individually tested variants (FIG. 34*e*, open circles). Moreover, individual ACL-988 cells that were HLA-A*02:01 NLVP negative encoded TRA variants that predominantly showed low RSU results (FIG. 34*e* open triangles).

In summary, the present example generates the generation of a pooled library of CDR3-diversified TCR ORF encoding vectors in a single reaction. This pooled library is encoded in a vector context that is matched with an eTPC genomic receiver site. A pooled eTPC-t library containing multiple TCRs was successfully generated in a single step using shotgun integration into an eTPC-x encoding a native reciprocal TCR ORF. The genetically modified polyclonal cell line ACL-988 that was generated presented a library of TCRsp that could be functionally selected for a range of staining intensities against an HLA tetramer reagent specific for the native pair. This represents a powerful and rapid approach for selective engineering of TCR pairs that are selected in the native context of a CD3 complex presented on the surface of a human cell.

Example 6: Functional Demonstration of Component 2F

Herein describes an eTPC cell line (ACL-1063, Component 2A) engineered with two unique genomic receiver sites (Components 2B and 2D), engineered to be null for HLA expression, utilizing native CD3 expression, and harbouring a two-component, synthetic response element (Component 2F).

The response elements comprised of a Driver-Activator component and an Amplifier-Report component, wherein both units utilized synthetic enhancers. The Driver is a synthetic enhancers that is responsive to the native TCR signalling pathways, encoding three sets of tandem transcription factor binding sites for NFAT-AP1-NFkB (3×NF-AP-NB). Upon transcriptional activation, the Driver induces expression of the activator protein, a synthetic designed transcription factor derived by fusion of the Herpes VP16 activation domain, the GAL4 DNA binding domain and two nuclear localization signals at the N- and C-terminals (NV16G4N), to which the cognate DNA recognition sequence is present 6 times in tandem in the Amplifier enhancers region. Both the Driver and Amplifier enhancers utilized the core promoter sequence (B recognition element (BRE), TATA Box, Initiator (INR) and transcriptional start site (TSS) from CMV IE1 promoter, immediately 3' of the respective transcription factor binding sites. The Amplifier upon transcriptional activation drives expression of the reporter, RFP.

In this experiment, the eTPC cell line was converted to an eTPC-t cell line (ACL-1277) as described previously in example 3, wherein the TCR chains at Component 2B' and 2D' encode a TCR pair that is specific for HCMV HLA-A*02:01-NLVPMVATV.

The eTPC-t cell line was then challenged against APCs presenting HLA-A*02:01 (ACL-209) or HLA-A*24:02 (ACL-963) or was HLA-null (ACL-128). Wherein the APCs were pulsed with either peptide NLVPMVATV or VYALPLKML or no peptide. Subsequently, 30,000 eTPC-t were co-cultured with 10,000 APCs for 24h. After 24h the cells were harvested, washed, stained with markers specific for the eTPC and APC in order to distinguish the populations, and analysed by flow cytometry. Strong activation of the eTPC-t, Component 2F (RFP+ expression >80%) was only observed in eTPC-t challenged with the known cognate target antigen, i.e. the APC with A*02:01-NLVPMATV (FIG. 35).

In conclusion, an eTPC cell line containing a functional component 2F was engineered, and subsequently used to create an eTPC-t. Upon interaction of the eTPC-t with APC presenting its cognate target T-cell antigen, a response was measurable as an increase in RFP expression. Conversely, when contacted with APC presenting a non-cognate T-cell antigen and HLA, or no HLA allele, no measurable increase in RFP expression above background was exhibited by the eTPC-t. The eTPC-t with a functional component 2F can therefore be used for the identification and characterization of the functional interaction between T cell receptors and cognate T-cell antigens presented by APC.

Sequences

In the following is given a table showing the sequences mentioned herein.

| SEQ number | Name | Reference example | Description |
|---|---|---|---|
| 0001-0046 | TRA V cloning fragments | Example 1 | Full DNA sequences of the TRA V fragment |
| 0047 | TRA C constant cloning fragment | Example 1 | Full DNA sequence of the TRA C fragment |
| 0048 | V-C entry vector backbone transient | Example 5 | DNA sequence of the vector backbone from the 5' genetic element encoding the CMV constitutive promoter to the 3' genetic element encoding the SV40pA polyadenylation signal |
| 0049-0094 | TRA V-C entry vector library sequence | Example 1 | DNA sequences of the cloned V-C fragments that make up the TRA V-C entry vector library |
| 0095-0096 | TRA J receiving cassette fragments | Example 1 | Full DNA sequence of the TRA J receiving cassette fragment oligonucleotides |
| 0097 | J donor backbone | Example 1 | J donor vector backbone is used to insert the TRA J receiving cassette fragment to create the TRA J receiving cassette vector |
| 0098 | TRA J receiving cassette vector | Example 1 | See above |
| 0099-0210 | TRA J Short segment part | Example 1 | Encodes all amino acids from the start of the CDR3-J border Phe codon |
| 0211-0322 | TRA J Long segment part | Example 1 | Encodes more amino acids N-terminal of the CDR3 border amino acids |
| 0323-0378 | TRA J Short donor vector | Example 1 | TRA short J donor library |
| 0379-0434 | TRA J Long donor vector | Example 1 | TRA long J donor library |
| 0435-0481 | TRB V cloning fragment | Example 1 | Full DNA sequences for the TRB V cloning fragments |
| 0482-0483 | TRB C constant cloning fragments | Example 1 | Full DNA sequences of the TRB C cloning fragments |
| 0484-0577 | TRB V-C entry vector library sequence | Example 1 | Sequences of the cloned V-C fragments that make up the TRA V-C entry vector library |
| 0578-0581 | TRB J receiving cassette fragments | Example 1 | TRB J receiving cassette fragments are constructed and inserted into a J donor vector backbone to create a TRB J receiving cassette vector |
| 0582-0583 | TRB J receiving cassette vectors | Example 1 | See above |
| 0584-0609 | TRB J Short segment part | Example 1 | DNA sequences of the short TRB J segment parts |
| 0610-0635 | TRB J Long segment part | Example 1 | DNA sequences of the long TRB J segment parts |
| 0636-0648 | TRB C1 J Short donor vector | Example 1 | TRB C1 short J donor library |
| 0649-0661 | TRB C2 J Short donor vector | Example 1 | TRB C2 short J donor library |
| 0662-0674 | TRB C1 J Long donor vector | Example 1 | TRB C1 long J donor library |

-continued

| SEQ number | Name | Reference example | Description |
|---|---|---|---|
| 0675-0687 | TRB C2 J Long donor vector | Example 1 | TRB C2 long J donor library |
| 0688 | V-C entry vector backbone F14-F15 | Example 1 | F14/F15 V-C entry vector backbone sequence used to construct TRA V-C entry library |
| 0689 | V-C entry vector backbone FRT-F3 | Example 1 | FRT/F3 V-C entry vector backbone sequence used to construct TRB V-C entry library |
| 0701-0702 | JG9 TRA and TRB full sequences copy | Example 3 | DNA sequences of the TRA and TRB chains |
| 0703-0706 | JG9 odeCDR3 sequences | Example 3 | odeCDR3 synthesised for the TRA and TRB chains |
| 0743-0744 | degenerate TRA odeCDR3s Example 9 | Example 5 | odeCDR3 oligos |

<210>745<223>pcDNA3.1_GFP vector V1.A.4
<210>746<223>pcDNA3.1_RFP vector V1.A.6
<210>747<223>pMA-SV40 pA vector V1.C.2
<210>748<223>pMA-CS-JG9-TCRbeta vector V3.C.5
<210>749<223>pMA-F14-GFP-F15 vector V4.H9
<210>750<223>pMA-F14-TCR-JG9-alpha-F15 vector V7.A.3
<210>751<223>pMA-FRT-TCR-JG9-beta-F3 vector V7.A.4
<210>752<223>F14-TCRaF15 CDR3degen.64mix vector V8.F.8
<210>753<223>CMVpro-Flp-sv40 pA-V2 vector V4.1.8
<210>754<223>JG9-TRA CDR3 64 variants vectors backbone VP.7751.RC1-A1 to H8
<210>755<223>CDR3 sequence of a JG9-TRA 64 variant VP.7751.RC1_A1
<210>756<223>CDR3 sequence of a JG9-TRA 64 variant VP.7751.RC1_A2
<210>757<223>CDR3 sequence of a JG9-TRA 64 variant VP.7751.RC1_A3
<210>758<223>CDR3 sequence of a JG9-TRA 64 variant VP.7751.RC1_A4
<210>759<223>CDR3 sequence of a JG9-TRA 64 variant VP.7751.RC1_A5
<210>760<223>CDR3 sequence of a JG9-TRA 64 variant VP.7751.RC1_A6
<210>761<223>CDR3 sequence of a JG9-TRA 64 variant VP.7751.RC1_A7
<210>762<223>CDR3 sequence of a JG9-TRA 64 variant VP.7751.RC1_A8
<210>763<223>CDR3 sequence of a JG9-TRA 64 variant VP.7751.RC1_B1
<210>764<223>CDR3 sequence of a JG9-TRA 64 variant VP.7751.RC1_B2
<210>765<223>CDR3 sequence of a JG9-TRA 64 variant VP.7751.RC1_B3
<210>766<223>CDR3 sequence of a JG9-TRA 64 variant VP.7751.RC1_B4
<210>767<223>CDR3 sequence of a JG9-TRA 64 variant VP.7751.RC1_B5
<210>768<223>CDR3 sequence of a JG9-TRA 64 variant VP.7751.RC1_B6
<210>769<223>CDR3 sequence of a JG9-TRA 64 variant VP.7751.RC1_B7
<210>770<223>CDR3 sequence of a JG9-TRA 64 variant VP.7751.RC1_B8
<210>771<223>CDR3 sequence of a JG9-TRA 64 variant VP.7751.RC1_C1
<210>772<223>CDR3 sequence of a JG9-TRA 64 variant VP.7751.RC1_C2
<210>773<223>CDR3 sequence of a JG9-TRA 64 variant VP.7751.RC1_C3
<210>774<223>CDR3 sequence of a JG9-TRA 64 variant VP.7751.RC1_C4
<210>775<223>CDR3 sequence of a JG9-TRA 64 variant VP.7751.RC1_C5
<210>776<223>CDR3 sequence of a JG9-TRA 64 variant VP.7751.RC1_C6
<210>777<223>CDR3 sequence of a JG9-TRA 64 variant VP.7751.RC1_C7
<210>778<223>CDR3 sequence of a JG9-TRA 64 variant VP.7751.RC1_D1
<210>779<223>CDR3 sequence of a JG9-TRA 64 variant VP.7751.RC1_D2
<210>780<223>CDR3 sequence of a JG9-TRA 64 variant VP.7751.RC1_D3
<210>781<223>CDR3 sequence of a JG9-TRA 64 variant VP.7751.RC1_D4
<210>782<223>CDR3 sequence of a JG9-TRA 64 variant VP.7751.RC1_D5
<210>783<223>CDR3 sequence of a JG9-TRA 64 variant VP.7751.RC1_D6
<210>784<223>CDR3 sequence of a JG9-TRA 64 variant VP.7751.RC1_D7
<210>785<223>CDR3 sequence of a JG9-TRA 64 variant VP.7751.RC1_D8
<210>786<223>CDR3 sequence of a JG9-TRA 64 variant VP.7751.RC1_E1
<210>787<223>CDR3 sequence of a JG9-TRA 64 variant VP.7751.RC1_E2
<210>788<223>CDR3 sequence of a JG9-TRA 64 variant VP.7751.RC1_E3
<210>789<223>CDR3 sequence of a JG9-TRA 64 variant VP.7751.RC1_E4
<210>790<223>CDR3 sequence of a JG9-TRA 64 variant VP.7751.RC1_E5
<210>791<223>CDR3 sequence of a JG9-TRA 64 variant VP.7751.RC1_E6
<210>792<223>CDR3 sequence of a JG9-TRA 64 variant VP.7751.RC1_E7
<210>793<223>CDR3 sequence of a JG9-TRA 64 variant VP.7751.RC1_E8
<210>794<223>CDR3 sequence of a JG9-TRA 64 variant VP.7751.RC1_F1
<210>795<223>CDR3 sequence of a JG9-TRA 64 variant VP.7751.RC1_F2
<210>796<223>CDR3 sequence of a JG9-TRA 64 variant VP.7751.RC1_F3
<210>797<223>CDR3 sequence of a JG9-TRA 64 variant VP.7751.RC1_F4
<210>798<223>CDR3 sequence of a JG9-TRA 64 variant VP.7751.RC1_F5
<210>799<223>CDR3 sequence of a JG9-TRA 64 variant VP.7751.RC1_F6
<210>800<223>CDR3 sequence of a JG9-TRA 64 variant VP.7751.RC1_F7
<210>801<223>CDR3 sequence of a JG9-TRA 64 variant VP.7751.RC1_F8
<210>802<223>CDR3 sequence of a JG9-TRA 64 variant VP.7751.RC1_G1

<210>803<223>CDR3 sequence of a JG9-TRA 64 variant VP.7751.RC1_G2

<210>804<223>CDR3 sequence of a JG9-TRA 64 variant VP.7751.RC1_G3

<210>805<223>CDR3 sequence of a JG9-TRA 64 variant VP.7751.RC1_G4

<210>806<223>CDR3 sequence of a JG9-TRA 64 variant VP.7751.RC1_G5

<210>807<223>CDR3 sequence of a JG9-TRA 64 variant VP.7751.RC1_G6

<210>808<223>CDR3 sequence of a JG9-TRA 64 variant VP.7751.RC1_G7

<210>809<223>CDR3 sequence of a JG9-TRA 64 variant VP.7751.RC1_G8

<210>810<223>CDR3 sequence of a JG9-TRA 64 variant VP.7751.RC1_H1

<210>811<223>CDR3 sequence of a JG9-TRA 64 variant VP.7751.RC1_H2

<210>812<223>CDR3 sequence of a JG9-TRA 64 variant VP.7751.RC1_H3

<210>813<223>CDR3 sequence of a JG9-TRA 64 variant VP.7751.RC1_H4

<210>814<223>CDR3 sequence of a JG9-TRA 64 variant VP.7751.RC1_H5

<210>815<223>CDR3 sequence of a JG9-TRA 64 variant VP.7751.RC1_H6

<210>816<223>CDR3 sequence of a JG9-TRA 64 variant VP.7751.RC1_H7

<210>817<223>CDR3 sequence of a JG9-TRA 64 variant VP.7751.RC1_H8

ABBREVIATIONS aAM Analyte antigenic molecule
aAPX Analyte antigen-presenting complex
α-GalCer Alpha-Galactosylceramide
aT Analyte TCR
APC Antigen-presenting cell
APX Antigen-presenting complex
B-cell B lymphocytes
β2M Beta 2 Microglobulin
BFP Blue fluorescent protein
C (-region) Constant region
CAR Chimeric antigen receptor
CAR-T CAR T-cell
CD1b Cluster of differentiation 1b
CD1d Cluster of differentiation 1d
CD3 Cluster of differentiation 3
CDR Complementarity-determining regions
CM Cargo molecules
CMV Cytomegalovirus
C-region Constant region
CRISPR Clustered Regularly Interspaced Short Palindromic Repeats
D (-region) Diversity region
DAMPS Danger associated molecular patterns
DC Dendritic cells
DNA Deoxyribonucleic acid
dsDNA Double stranded DNA
eAPC Engineered antigen-presenting cell
eAPC-a Engineered antigen-presenting cell expressing an analyte antigenic molecule
eAPC-p Engineered antigen-presenting cell that present an analyte antigen-presenting complex
Engineered antigen-presenting cell that presents an analyte antigen-presenting
eAPC-pa complex and analyte antigenic molecule
eAPCS Engineered antigen-presenting cell system
eTPC Engineered TCR-presenting cell
eTPC-t Engineered TCR-presenting cell that present full-length TCR pairs
eTPCS Engineered TCR-presenting cell system
FAB Antibody fragment antigen binding
FACS Fluorescence-activated cell sorting
FRT Flippase recognition target
GEM T-cells Germ line-encoded mycolyl-reactive T-cells
GFP Green fluorescent protein
gRNA Cas9 guide RNA
HCMV Human Cytomegalovirus
HDR Homology directed recombination
HIV Human immunodeficiency virus
HLA Human leukocyte antigen
HLAI HLA class I
HLAII HLA class II
IgSF Immunoglobulin superfamily
iNK T-cells Invariant natural killer T-cells
IRES Internal ribosome entry site
ITAM Immunoreceptor tyrosine-based activation motif
J-donor Joining donor
J-region Joining region
MACS Magnetic-activated cell sorting
MAGE Melanoma associated antigen
MAIT Mucosal-associated invariant T
MHC Major Histocompatability Complex
MR1 Major histocompatibility complex class I-related gene protein
mRNA Messenger ribonucleic acid
NCBP Non-cell based particles
NK T-cells Natural killer T cells
odeCDR3 Oligonucleotide duplex encoding CDR3
ORF Open reading frame
PAMPS Pathogen-associated molecular patterns
PCR Polymerase chain reaction
pHLA Peptide HLA
RFP Red fluorescent protein
RMCE Recombinase mediated cassette exchange
RNA Ribonucleic acid
RT Reverse Transcription
SH2 Src homology 2
T-cells T lymphocytes
TAA Tumour-associated-antigens
TALEN Transcription activator-like effector nucleases
TCR T-cell Receptor
TCRsp TCR surface proteins in complex with CD3
TORES TCR ORF Reconstitution and Engineering System
TRA TCR alpha
TRB TCR beta
TRD TCR delta
TRG TCR gamma
V-C entry vector Variable-Constant entry vector
V (-region) Variable region
ZAP-70 ζ-chain-associated protein of 70 kDa

DEFINITIONS

Adaptive immunity: A subsystem of the overall immune system that is composed of highly specialized, systemic cells and processes that eliminate pathogens or prevent their growth.

A pair of complementary TCR chains: Two TCR chains wherein the translated proteins are capable of forming a TCRsp on the surface of a TCR presenting cell Affinity: Kinetic or equilibrium parameter of an interaction between two or more molecules or proteins Affinity Reagent: Any reagent that is prepared as analyte to probe TCRsp binding and/or stimulation at the cell surface of the eTPC-t in an eTPC:A system Allele: Variant form of a given gene aAM: Analyte antigenic molecule. Generally, a protein but could also be a metabolite that is expressed by a cell from their genomic DNA and/or a specific introduced genetic sequence. The AM is expressed in the cell and a fragment can then be presented on the cell surface by an APX as cargo or on its own. Either as cargo or not, the AM can then be the target of T-cell receptor bearing cells or related affinity reagents.

Amplicon: a piece of DNA or RNA that is the source and/or product of artificial amplification using various methods including PCR.

Analyte: an entity that is of interest to be identified and/or measured and/or queried in the combined system Antibody: Affinity molecule that is expressed by specialized cells of the immune system called B-cells and that contains of two chains.

Antigen: any molecule that may be engaged by a TCR and results in a signal being transduced within the T-cell Analyte antigen: collectively the eTPC:Antigen system (eTPC:A) representing any entity presenting an antigen for analytical determination Antigen-binding cleft: long cleft or groove that is the site at which peptide antigens bind to the MHC-1 molecule.

APC: Antigen-presenting cell. A cell capable of presenting antigen on its cell surface, generally in the context of an HLA.

aAPX: Analyte antigen-presenting complex. A protein that is expressed and presented on the cell surface by nucleated cells from genes/ORF encoding genomic DNA and/or a specific introduced genetic sequence. The APX presents a cargo, being either a peptide or other metabolite molecules.

Autoimmunity: is the system of immune responses of an organism against its own healthy cells and tissues.

C (-region): Constant gene segment. One of the gene segments that is used to assemble the T-cell receptor. The c-region is a distinct segment that rather than driving diversity of the TCR, defines its general function in the immune system.

C cloning fragment: Constant Cloning fragment. Also referred to as a C gene segment cloning fragment. A construct carrying a portion of a C gene segment used to construct a V-C entry vector.

Cargo-loading machinery: Cellular set of proteins that generate and load cargo molecules on APX from proteins or other presented molecules found in the cell.

Cis-acting element: regions of non-coding DNA that regulate the transcription of nearby ORFs.

C-part: Constant part. A small portion of Constant gene segment sequence carried by a J receiving cassette fragment, J receiving cassette and J donor vector to standardise overhang sequences for operation of the TORES to reconstitute TCR ORFs.

CDR: complementarity-determining regions. Short sequences on the antigen-facing end of TCRs and antibodies that perform most of the target binding function. Each antibody and TCR contains six CDRs and they are generally the most variable part of the molecules allowing detection of a large number of diverse target molecules.

CM: Cargo molecules. Peptide or metabolite that is presented by an antigen-presenting complex for example a HLA I or HLA II. The CM can be expressed by the cell intrinsically from the genomic DNA, introduced into the culture medium or expressed from a specifically introduced genetic sequence.

Cognate Antigen: An antigen, often presented by an HLA, that is recognised in a particular TCR. TCR and antigen are cognate objects.

Copy-number: The whole number occurrence of a defined sequence encoded within the genome of a cell.

Cytogenetic: The study of inheritance in relation to the structure and function of chromosomes, i.e. determine the karyotype of a cell Cytotoxic/Cytotoxicity: Process in which a T-cells releases factors that directly and specifically damage a target cell.

D (-region): Diversity gene segment. One of the gene segments that is used to assemble the T-cell receptor. Each individual has a large number of different variations of these regions making it possible for each individual to arm T-cells with a very large variety of different TCR.

Dimer: is an oligomer consisting of two structurally similar monomers joined by bonds that can be either strong or weak, covalent or intermolecular.

DNA: Desoxyribonucleic acid. Chemical name of the molecule that forms genetic material encoding genes and proteins.

Endogenous: Substance that originated from within a cell eTPC:A system: eTPC:Antigen system. The system in which a eTPC-t is contacted with analyte antigen Eukaryotic conditional regulatory element: A DNA sequence that can influence the activity of a promoter, which may be induced or repressed under defined conditions Eukaryotic Promoter: A DNA sequence that encodes a RNA polymerase binding site and response elements. The sequence of the promoter region controls the binding of the RNA polymerase and transcription factors, therefore promoters play a large role in determining where and when your gene of interest will be expressed.

Eukaryotic terminator/Signal terminator: A DNA sequence that are recognized by protein factors that are associated with the RNA polymerase and which trigger the termination process of transcription. It also encodes the poly-A signal Engineered Cell: A cell whereby the genome has been engineered through genetic modification modified.

Epitope: An epitope, also known as antigenic determinant, is the part of an antigen that is recognized by the immune system, specifically by antibodies, B cells, or T cells. For example, the epitope is the specific piece of the antigen to which an antibody binds.

Epigenetic insulator sequence: DNA element that disrupts the communication between a regulatory sequence, such as an enhancer or a silencer, and a promoter.

eTPC system: eTPCS, the system by which eTPC-t cells, or libraries thereof, are prepared for combination in the eAPC:eTPC system FACS/Flow Cytometry: Fluorescence-activated cell sorting. Flow cytometry is a technique by which individual cells can be analyzed en masse for the expression of specific cell surface and intracellular markers. A variation of that technique, cell sorting, allows cells that carry a defined set of markers to be retrieved for further analysis.

Family of APX: A set of several similar genes that encode functionally related proteins, which constitute an antigen pressing complex FIp Recombinase: A recombinase (Flippase, Flp) derived from the 2 μm plasmid of baker's yeast *Saccharomyces cerevisiae.*

Fluorescent (protein) marker: Molecule that has specific extinction and emission characteristics and can be detected by Microscopy, FACS and related techniques.

Germline gene segments: (TCR) Gene segments that are naturally occurring in humans.

Gene cis acting elements: are present on the same molecule of DNA as the gene they regulate whereas trans-regulatory elements can regulate genes distant from the gene from which they were transcribed. Cis-regulatory elements are often binding sites for one or more trans-acting factors.

Genetic barcoding: DNA barcoding is a taxonomic method that uses a short genetic marker in an organism's DNA to identify it as belonging to a particular species.

Genomic Receiver Site: A site within the genome for targeted integration of donor genetic material encoded within a Genetic Donor Vector.

Genomic Receiver Site Recycling: The reversion of an occupied genomic receiver site back to the conformation wherein a new analyte (TCR) ORF can be integrated Haplotype: a set of genetic determinants located on a single chromosome.

HLA haplotype: a set of HLAI and HLA II alleles that are present in each individual.

Heterospecific recombinase sites: A DNA sequence that is recognized by a recombinase enzyme to promote the cross-over of two DNA molecules.

HLA I: Human Leukocyte Antigen class 1. A gene that is expressed in humans in all nucleated cells and exported to the cell surface where it presents as cargo short fragments, peptides, of internal proteins to T-cell receptors. As such it presents fragments of potential ongoing infections along with intrinsic proteins. The HLA I can additionally present as cargo peptides that are added to the culture medium, generated from proteins expressed form introduced genetic elements or generated from proteins that are taken up by the cell. HLA class I genes are polymorphic meaning that different individuals are likely to have variation in the same gene leading to a variation in presentation. Related to HLA class II.

HLA II: Human Leukocyte Antigen Class II. A gene that is expressed in humans in specific cells that are coordinating and helping the adaptive immune response for example dendritic cells. Related to HLA class I. HLA class II proteins are exported to the cell surface where they present as cargo short fragments, peptides, of external proteins to T-cell receptors. As such it presents fragments of potential ongoing infections along with intrinsic proteins. The HLA II can additionally present as cargo peptides that are added to the culture medium, generated from proteins expressed form introduced genetic elements or generated from proteins that are taken up by the cell. HLA class II genes are polymorphic meaning that different individuals are likely to have variation in the same gene leading to a variation in presentation.

Homologous arms: A stretch of DNA that has near identical sequence identity to a complement homologous arm and therefore promote the exchange of two DNA molecules by the cellular process, homology directed repair.

Immune surveillance: Process in which the immune system detects and becomes activated by infections, malignancies or other potentially pathogenic alterations.

Immunotherapy: a type of treatment that boosts the body's natural defenses to fight a disease. It uses substances made by the body or in a laboratory to improve or restore immune system function.

Insulator: A DNA sequence that prevents a gene from being influenced by the activation or repression of nearby genes. Insulators also prevent the spread of heterochromatin from a silenced gene to an actively transcribed gene.

Integration: The physical ligation of a DNA sequence into a chromosome of a cell Integration vector: The product of TORES containing TCR ORFs, and matched to genomic receiver sites, containing genetic elements at the 5' and 3' ends to enable integration.

Integration couple: matched integration vector and genomic receiver site

Internal ribosome entry site (IRES): A DNA sequence that once transcribed encodes a RNA element that allows the initiation of translation in a cap-independent manner Isoform: any of two or more functionally similar proteins that have a similar but not identical amino acid sequence and are either encoded by different genes or by RNA transcripts from the same gene which have had different exons removed.

J (-region): Joining segment. One of the gene segments that is used to assemble the T-cell receptor. Each individual has a large number of different variations of these regions making it possible for each individual to arm T-cells with a very large variety of different TCR.

J donor backbone: Joining donor backbone. The vector backbone into which a J receiving cassette fragment is inserted to create a J receiving cassette vector.

J donor vector: The vector of the two-component vector system that carries the J TCR segment, and donates this segment to the V-C entry vector during reconstitution of a full-length TCR ORF.

J receiving cassette fragment: Joining receiving cassette fragment. A cloning fragment that carries a C-part used to construct a J receiving cassette vector.

J receiving cassette vector: Joining receiving cassette vector. The vector, carrying a C-part, into which a J segment part is inserted to create a J donor vector.

J segment part: Joining segment part. A DNA construct carring a portion of a J gene segment that is inserted into a J receiving cassette vector to generate a J donor vector.

Kozak Sequence: Short sequence required for the efficient initiation of translation Major HLA class I: a Family of APX that comprise of the genes HLA-A, HLA-B and HLA-C Matched: When two components encode genetic elements that direct and restrict the interaction between the complemented components Meganuclease recognition site: A DNA sequence that is recognized by a endodeoxyribonuclease, commonly referred to as a meganuclease Metabolite: A molecule created or altered through metabolic pathways of the cell Mobile genetic element: A DNA sequence that can permit the integration of DNA with the activity of transposases enzymes Monoclone cell line: A defined group of cells produced from a single ancestral cell by repeated cellular replication mRNA splice acceptor site: At the 5 end the DNA nucleotides are GT [GU in the pre-messenger RNA (pre-mRNA)]; at the 3' end they are AG. These nucleotides are part of the splicing sites. DONOR-SPLICE: splicing site at the beginning of an intron, intron 5' left end. ACCEPTOR-SPLICE: splicing site at the end of an intron, intron 3' right end.

Multimer: A protein complex consisting of multiple identical monomers. Often used in context of HLA multimer reagent.

Native: an entity that is naturally occurring in the cell

Negative Selection Marker: A selectable marker that confers negative selection of a vector and/or of host organism carrying said marker-bearing vector Non-cell-based Particle: (NCBP) acts in a similar manner to an affinity reagent, inasmuch that the particle presents an analyte antigen or other entity that is to be assessed for TCRsp engagement at the surface of a eTPC-t within and eTPC:A system. However, an NCBP is considered as a larger entity that can further carry genetic or other information that is to act as an identifier, either directly or by proxy, of the presented analyte antigen or other binding entity. A typical example of an NCBP would be a bacteriophage in a phage-display scenario Non-coding gene: A non protein coding DNA sequence that is transcribed into functional non-coding RNA molecules odeCDR3: oligonulcotide duplex encoding complementarity-determining regions. A synthetic construct carrying CDR3 genetic sequence with terminal overhangs, used in conjunction with the two-component vector system to reconstitute a full-length TCR ORF.

Origin of replication: a particular sequence in a vector, plasmid or genome at which replication is initiated.

ORF: Open reading frame. Stretch of genetic material that encodes a translation frame for synthesis of a protein (polypeptide) by the ribosome Overhang: A single stranded sequence at the terminus of a double stranded nucleic acid molecule. Often referred to as sticky or cohesive ends.

PCR: Polymerase chain reaction in which a specific target DNA molecule is exponentially amplified Peptide: short string of amino acids between 6-30 amino acids in length Phenotypic analysis: Analysis of the observable characteristics of a cell.

Plasmid: A genetic construct can replicate independently of the chromosomes, typically a small circular DNA strand in the cytoplasm of a bacterium or protozoan.

Polymorphic: Present in different forms in individuals of the same species through the presence of different alleles of the same gene.

Polypeptide: Protein consisting of a stretch of peptides, forming a three-dimensional structure.

Positive Selection Marker: A selectable marker that confers positive selection of a vector and/or host organism carrying said marker-bearing vector Primer: Short DNA sequence that allows specific recognition of a target DNA sequence for example during a PCR.

Professional APC: any nucleated cell capable of presenting an antigen for sampling by alpha beta and gamma delta T-cells.

Promoter: Regulatory DNA element for the controlled initiation of gene expression.

Recombinase: Enzymes that mediate genetic recombination.

Reporter Element: A genetic element that mediates a reported signal in the organism or vector bearing said element. May be used as a positive or negative selection maker.

Restriction Enzyme Cleavage Sequence: The genetic sequence cleaved by a restriction enzyme, which can be extrinsic or intrinsic to the recognition sequence of said restriction enzyme.

Restriction Enzyme Recognition Sequence: The genetic sequence recognised and engaged by a restriction enzyme.

Selectable marker: A DNA sequence that confers a trait suitable for artificial selection methods Splice acceptor site: A DNA sequence at the 3' end of the intron AM, APX CM or affinity reagent for interaction with cells with TCRsp on the surface, or TCRsp based reagents Splice donor site: A DNA sequence at the 5' end of the intron Somatic V(D)J recombination: process after which each T-cell expresses copies of a single distinctly rearranged TCR. Refers to recombination at the TRB and TRD loci and additionally include a diversity (D) gene segment.

Suicide gene: A gene that will mediate cell death within the host organism carrying said gene. May be used as a positive or negative selection marker.

Synthetic: an entity that is artificially generated.

T-cell: T lymphocyte. White blood cell that expresses a T-cell receptor on its surface.

Selected by the immune system to not react with the own body but have the potential to recognize infections and malignancies as well as reject grafts from most members of the same species.

T-cell maturation: process that allows T-cells to distinguish cells that belong to the body and are healthy from those that aren't healthy or don't belong to the body at all. Takes place in the thymus T-cell repertoire: distinct set of T-cell receptors TCR: T-cell Receptor. Affinity molecule expressed by a subgroup of lymphocytes called T-lymphocytes. In humans the TCR recognizes cargo presented by APX CM or APX AM, including fragments from virus or bacterial infections or cancerous cells. Therefore, the TCR recognition is an integral part of the adaptive immune system. The TCR consists of two chains that are paired on the cell surface. The TCR expressed on the surface of each cells is assembled at random from a large pool of varied genes (the v,d,j and c segments) and thus each individual has a pool of T-cells expressing a very large and diverse repertoire of different TCRs.

Terminator element: is a section of nucleic acid sequence that marks the end of a gene or operon in genomic DNA during transcription. This sequence mediates transcriptional termination by providing signals in the newly synthesized mRNA that trigger processes which release the mRNA from the transcriptional complex. These processes include the direct interaction of the mRNA secondary structure with the complex and/or the indirect activities of recruited termination factors. Release of the transcriptional complex frees RNA polymerase and related transcriptional machinery to begin transcription of new mRNAs. The termination element is in the template strand of DNA and consists of two inverted repeats separated by half a dozen bases and followed by a run of adenines (A's).

Thymic selection: Immature thymocytes undergo a process of selection, based on the specificity of their T-cell receptors. This involves selection of T cells that are functional (positive selection), and elimination of T cells that are autoreactive (negative selection). The medulla of the thymus is the site of T Cell maturation.

Tumour associated antigens: Tumor antigen is an antigenic substance produced in tumor cells, i.e., it triggers an immune response in the host. Tumor antigens are useful tumor markers in identifying tumor cells with diagnostic tests and are potential candidates for use in cancer therapy.

TRA: TCR alpha encoding locus. One of the four different locus encoding genes that can form a VDJ recombined TCR chain. Translated TCR alpha chain proteins typically pair with translated TCR beta chain proteins to form alpha/beta TCRsp.

TRB: TCR beta encoding locus. One of the four different locus encoding genes that can form a VDJ recombined TCR chain. Translated TCR beta chain proteins typically pair with TCR alpha chain proteins to form alpha/beta TCRsp.

TRD: TCR delta encoding locus. One of the four different locus encoding genes that can form a VDJ recombined TCR chain. Translated TCR delta chain proteins typically pair with translated TCR gamma chain proteins to form gamma/delta TCRsp.

TRG: TCR gamma encoding locus. One of the four different locus encoding genes that can form a VDJ recombined TCR chain. Translated TCR gamma chain proteins typically pair with translate TCR delta chain proteins to form gamma/delta TCRsp.

Two-component vector system: a single V-C entry vector and a single J donor vector with desired sequences can be combined with a short DNA oligonucleotide duplex encoding CDR3 (odeCDR3) sequence to reconstitute a full length TCR ORF in vitro in a single-tube reaction, in a restriction enzyme and ligase dependent and PCR independent manner.

Type I transmembrane domain: single-pass molecules anchored to the lipid membrane with a stop-transfer anchor sequence and their N-terminal domain targeted to the endoplasmic reticulum lumen during synthesis (and the extracellular space, if mature forms are located on Plasmalemma).

Type IIS Restriction Enzyme: restriction enzymes that recognize asymmetric DNA sequences and cleave outside of their recognition sequence.

V (-region): Variable region. One of the gene segments that is used to assemble the T-cell receptor. Each individual has a large number of different variations of these regions making it possible for each individual to arm T-cells with a very large variety of different TCR.

V-C entry vector: The vector of the two-component vector system that carries the V and C TCR segments, and which receives sequences from the J donor vectors and odeCDR3 during reconstitution of a full-length TCR ORF.

V cloning fragment: Variable Cloning fragment. Also referred to as a V gene segment cloning fragment. A construct carrying a portion of a V gene segment used to construct a V-C entry vector.

Vector: A vector is a genetic construct that carries genetic information. In the present context vector usually describes plasmidic DNA vectors. A vector can represent any such construct that can be propagated and selected in a host organism.

SEQUENCE LISTING

```
<160> NUMBER OF SEQ ID NOS: 826

<210> SEQ ID NO 1
<211> LENGTH: 396
<212> TYPE: DNA
<213> ORGANISM: Homo sapiens
<220> FEATURE:
<223> OTHER INFORMATION: TRAV1-1_BB_1

<400> SEQUENCE: 1

gtcagatact ccatgagcac gaagacttgt acgccaccat gtggggagct ttccttctct     60

atgtttccat gaagatggga ggcactgcag gacaaagcct tgagcagccc tctgaagtga    120

cagctgtgga aggagccatt gtccagataa actgcacgta ccagacatct gggttttatg    180

ggctgtcctg gtaccagcaa catgatggcg gagcacccac atttctttct tacaatgctc    240

tggatggttt ggaggagaca ggtcgttttt cttcattcct tagtcgctct gatagttatg    300

gttacctcct tctacaggag ctccagatga aagactctgc ctcttacttc tgcagagacc    360

ttgcggccgt gtcttcgact agtagctcac ctacga                              396


<210> SEQ ID NO 2
<211> LENGTH: 396
<212> TYPE: DNA
<213> ORGANISM: Homo sapiens
<220> FEATURE:
<223> OTHER INFORMATION: TRAV1-2_BB_1

<400> SEQUENCE: 2

gtcagatact ccatgagcac gaagacttgt acgccaccat gtggggagtt ttccttcttt     60

atgtttccat gaagatggga ggcactacag gacaaaacat tgaccagccc actgagatga    120

cagctacgga aggtgccatt gtccagatca actgcacgta ccagacatct gggttcaacg    180

ggctgttctg gtaccagcaa catgctggcg aagcacccac atttctgtct tacaatgttc    240

tggatggttt ggaggagaaa ggtcgttttt cttcattcct tagtcggtct aaagggtaca    300

gttacctcct tttgaaggag ctccagatga aagactctgc ctcttacctc tgcagagacc    360
```

```
ttgcggccgt gtcttcgact agtagctcac ctacga                          396


<210> SEQ ID NO 3
<211> LENGTH: 408
<212> TYPE: DNA
<213> ORGANISM: Homo sapiens
<220> FEATURE:
<223> OTHER INFORMATION: TRAV2_BB_1

<400> SEQUENCE: 3

gtcagatact ccatgagcac gaagacttgt acgccaccat ggctttgcag agcactctgg     60

gggcggtgtg gctagggctt ctcctcaact ctctctggaa ggttgcagaa agcaaggacc    120

aagtgtttca gccttccaca gtggcatctt cagagggagc tgtggtggaa atcttctgta    180

atcactctgt gtccaatgct tacaacttct tctggtacct tcacttcccg ggatgtgcac    240

caagactcct tgttaaaggc tcaaagcctt ctcagcaggg acgatacaac atgacctatg    300

aacggttctc ttcatcgctg ctcatcctcc aggtgcggga ggcagatgct gctgtttact    360

actgcagaga ccttgcggcc gtgtcttcga ctagtagctc acctacga                 408


<210> SEQ ID NO 4
<211> LENGTH: 411
<212> TYPE: DNA
<213> ORGANISM: Homo sapiens
<220> FEATURE:
<223> OTHER INFORMATION: TRAV3_BB_1

<400> SEQUENCE: 4

gtcagatact ccatgagcac gaagacttgt acgccaccat ggcctctgca cccatctcga     60

tgcttgcgat gctcttcaca ttgagtgggc tgagagctca gtcagtggct cagccggaag    120

atcaggtcaa cgttgctgaa gggaatcctc tgactgtgaa atgcacctat tcagtctctg    180

gaaaccctta tctttttgg tatgttcaat accccaaccg aggcctccag ttccttctga    240

aatacatcac aggggataac ctggttaaag gcagctatgg ctttgaagct gaatttaaca    300

agagccaaac ctccttccac ctgaagaaac catctgccct tgtgagcgac tccgctttgt    360

acttctgcag agaccttgcg gccgtgtctt cgactagtag ctcacctacg a             411


<210> SEQ ID NO 5
<211> LENGTH: 396
<212> TYPE: DNA
<213> ORGANISM: Homo sapiens
<220> FEATURE:
<223> OTHER INFORMATION: TRAV4_BB_1

<400> SEQUENCE: 5

gtcagatact ccatgagcac gaagacttgt acgccaccat gaggcaagtg gcgagagtga     60

tcgtgttcct gaccctgagt actttgagcc ttgctaagac cacccagccc atctccatgg    120

actcatatga aggacaagaa gtgaacataa cctgtagcca caacaacatt gctacaaatg    180

attatatcac gtggtaccaa cagtttccca gccaaggacc acgatttatt attcaaggat    240

acaagacaaa agttacaaac gaagtggcct ccctgtttat ccctgccgac agaaagtcca    300

gcactctgag cctgccccgg gtttccctga gcgacactgc tgtgtactac tgcagagacc    360

ttgcggccgt gtcttcgact agtagctcac ctacga                          396


<210> SEQ ID NO 6
<211> LENGTH: 411
<212> TYPE: DNA
```

<213> ORGANISM: Homo sapiens
<220> FEATURE:
<223> OTHER INFORMATION: TRAV5_BB_1

<400> SEQUENCE: 6

```
gtcagatact ccatgagcac gaagacttgt acgccaccat gaaaacattt gctggatttt     60

cgttcctgtt tttgtggctg cagctggact gtatgagtag aggagaggat gtggagcaga    120

gtcttttcct gagtgtccga gagggagaca gctccgttat aaactgcact tacacagaca    180

gctcctccac ctacttatac tggtataagc aagaacctgg agcaggtcta cagttgctga    240

cgtatatttt ttcaaatatg gacatgaaac aagaccaaag actcactgtt ctattgaata    300

aaaaggataa acatctgtct ctgcgcattg cagacaccca gactggggac tcagctatct    360

acttctgcag agaccttgcg gccgtgtctt cgactagtag ctcacctacg a             411
```

<210> SEQ ID NO 7
<211> LENGTH: 411
<212> TYPE: DNA
<213> ORGANISM: Homo sapiens
<220> FEATURE:
<223> OTHER INFORMATION: TRAV6_BB_1

<400> SEQUENCE: 7

```
gtcagatact ccatgagcac gaagacttgt acgccaccat ggagtcattc ctgggaggtg     60

ttttgctgat tttgtggctt caagtggact gggtgaagag ccaaaagata gaacagaatt    120

ccgaggccct gaacattcag gagggtaaaa cggccaccct gacctgcaac tatacaaact    180

attccccagc atacttacag tggtaccgac aagatccagg aagaggccct gttttcttgc    240

tactcatacg tgaaaatgag aaagaaaaaa ggaaagaaag actgaaggtc acctttgata    300

ccacccttaa acagagtttg tttcatatca cagcctccca gcctgcagac tcagctacct    360

acctctgcag agaccttgcg gccgtgtctt cgactagtag ctcacctacg a             411
```

<210> SEQ ID NO 8
<211> LENGTH: 408
<212> TYPE: DNA
<213> ORGANISM: Homo sapiens
<220> FEATURE:
<223> OTHER INFORMATION: TRAV7_BB_1

<400> SEQUENCE: 8

```
gtcagatact ccatgagcac gaagacttgt acgccaccat ggagaagatg cgtagacctg     60

tcctaattat attttgtcta tgtcttggct gggcaaatgg agaaaaccag gtggagcaca    120

gccctcattt tctgggaccc cagcagggag acgttgcctc catgagctgc acgtactctg    180

tcagtcgttt taacaatttg cagtggtaca ggcaaaatac agggatgggt cccaaacacc    240

tattatccat gtattcagct ggatatgaga agcagaaagg aaggctaaat gctacattac    300

tgaagaatgg aagcagcttg tacattacag ccgtgcagcc tgaagattca gccacctatt    360

tctgcagaga ccttgcggcc gtgtcttcga ctagtagctc acctacga                 408
```

<210> SEQ ID NO 9
<211> LENGTH: 411
<212> TYPE: DNA
<213> ORGANISM: Homo sapiens
<220> FEATURE:
<223> OTHER INFORMATION: TRAV8-1_BB_1

<400> SEQUENCE: 9

```
gtcagatact ccatgagcac gaagacttgt acgccaccat gctcctgttg ctcataccag     60
```

```
tgctggggat gatttttgcc ctgagagatg ccagagccca gtctgtgagc cagcataacc    120

accacgtaat tctctctgaa gcagcctcac tggagttggg atgcaactat tcctatggtg    180

gaactgttaa tctcttctgg tatgtccagt accctggtca acaccttcag cttctcctca    240

agtacttttc aggggatcca ctggttaaag gcatcaaggg ctttgaggct gaatttataa    300

agagtaaatt ctcctttaat ctgaggaaac cctctgtgca gtggagtgac acagctgagt    360

acttctgcag agaccttgcg gccgtgtctt cgactagtag ctcacctacg a             411
```

<210> SEQ ID NO 10
<211> LENGTH: 411
<212> TYPE: DNA
<213> ORGANISM: Homo sapiens
<220> FEATURE:
<223> OTHER INFORMATION: TRAV8-2_BB_1

<400> SEQUENCE: 10

```
gtcagatact ccatgagcac gaagacttgt acgccaccat gctcctgctg ctcgtcccag     60

tgctcgaggt gatttttact ctgggaggaa ccagagccca gtcggtgacc cagcttgaca    120

gccacgtctc tgtctctgaa ggaaccccgg tgctgctgag gtgcaactac tcatcttctt    180

attcaccatc tctcttctgg tatgtgcaac accccaacaa aggactccag cttctcctga    240

agtacacatc agcggccacc ctggttaaag gcatcaacgg ttttgaggct gaatttaaga    300

agagtgaaac ctccttccac ctgacgaaac cctcagccca tatgagcgac gcggctgagt    360

acttctgcag agaccttgcg gccgtgtctt cgactagtag ctcacctacg a             411
```

<210> SEQ ID NO 11
<211> LENGTH: 411
<212> TYPE: DNA
<213> ORGANISM: Homo sapiens
<220> FEATURE:
<223> OTHER INFORMATION: TRAV8-3_BB_1

<400> SEQUENCE: 11

```
gtcagatact ccatgagcac gaagacttgt acgccaccat gctcctggag cttatcccac     60

tgctggggat acattttgtc ctgagaactg ccagagccca gtcagtgacc cagcctgaca    120

tccacatcac tgtctctgaa ggagcctcac tggagttgag atgtaactat tcctatgggg    180

caacacctta tctcttctgg tatgtccagt cccccggcca aggcctccag ctgctcctga    240

agtacttttc aggagacact ctggttcaag gcattaaagg ctttgaggct gaatttaaga    300

ggagtcaatc ttccttcaat ctgaggaaac cctctgtgca ttggagtgat gctgctgagt    360

acttctgcag agaccttgcg gccgtgtctt cgactagtag ctcacctacg a             411
```

<210> SEQ ID NO 12
<211> LENGTH: 411
<212> TYPE: DNA
<213> ORGANISM: Homo sapiens
<220> FEATURE:
<223> OTHER INFORMATION: TRAV8-4_BB_1

<400> SEQUENCE: 12

```
gtcagatact ccatgagcac gaagacttgt acgccaccat gctcctgctg ctcgtcccag     60

tgctcgaggt gatttttacc ctgggaggaa ccagagccca gtcggtgacc cagcttggca    120

gccacgtctc tgtctctgaa ggagccctgg ttctgctgag gtgcaactac tcatcgtctg    180

ttccaccata tctcttctgg tatgtgcaat accccaacca aggactccag cttctcctga    240
```

agtacacatc agcggccacc ctggttaaag gcatcaacgg ttttgaggct gaatttaaga 300
agagtgaaac ctccttccac ctgacgaaac cctcagccca tatgagcgac gcggctgagt 360
acttctgcag agaccttgcg gccgtgtctt cgactagtag ctcacctacg a 411

<210> SEQ ID NO 13
<211> LENGTH: 411
<212> TYPE: DNA
<213> ORGANISM: Homo sapiens
<220> FEATURE:
<223> OTHER INFORMATION: TRAV8-6_BB_1

<400> SEQUENCE: 13
gtcagatact ccatgagcac gaagacttgt acgccaccat gctcctgctg ctcgtcccag 60
cgttccaggt gatttttacc ctgggaggaa ccagagccca gtctgtgacc cagcttgaca 120
gccaagtccc tgtctttgaa gaagcccctg tggagctgag gtgcaactac tcatcgtctg 180
tttcagtgta tctcttctgg tatgtgcaat accccaacca aggactccag cttctcctga 240
agtatttatc aggatccacc ctggttaaag gcatcaacgg ttttgaggct gaatttaaca 300
agagtcaaac ttccttccac ttgaggaaac cctcagtcca tataagcgac acggctgagt 360
acttctgcag agaccttgcg gccgtgtctt cgactagtag ctcacctacg a 411

<210> SEQ ID NO 14
<211> LENGTH: 408
<212> TYPE: DNA
<213> ORGANISM: Homo sapiens
<220> FEATURE:
<223> OTHER INFORMATION: TRAV8-7_BB_1

<400> SEQUENCE: 14
gtcagatact ccatgagcac gaagacttgt acgccaccat gctcttagtg gtcattctgc 60
tgcttggaat gttcttcaca ctgagaacca gaacccagtc ggtgacccag cttgatggcc 120
acatcactgt ctctgaagaa gcccctctgg aactgaagtg caactattcc tatagtggag 180
ttccttctct cttctggtat gtccaatact ctagccaaag cctccagctt ctcctcaaag 240
acctaacaga ggccacccag gttaaaggca tcagaggttt tgaggctgaa tttaagaaga 300
gcgaaacctc cttctacctg aggaaaccat caacccatgt gagtgatgct gctgagtact 360
tctgcagaga ccttgcggcc gtgtcttcga ctagtagctc acctacga 408

<210> SEQ ID NO 15
<211> LENGTH: 408
<212> TYPE: DNA
<213> ORGANISM: Homo sapiens
<220> FEATURE:
<223> OTHER INFORMATION: TRAV9-1_BB_1

<400> SEQUENCE: 15
gtcagatact ccatgagcac gaagacttgt acgccaccat gaattcttct ccaggaccag 60
cgattgcact attcttaatg tttgggggaa tcaatggaga ttcagtggtc cagacagaag 120
gccaagtgct cccctctgaa ggggattccc tgattgtgaa ctgctcctat gaaaccacac 180
agtacccttc cctttttgg tatgtccaat atcctggaga aggtccacag ctccacctga 240
aagccatgaa ggccaatgac aagggaagga acaaaggttt tgaagccatg taccgtaaag 300
aaaccacttc tttccacttg gagaaagact cagttcaaga gtcagactcc gctgtgtact 360
tctgcagaga ccttgcggcc gtgtcttcga ctagtagctc acctacga 408

<210> SEQ ID NO 16
<211> LENGTH: 408
<212> TYPE: DNA
<213> ORGANISM: Homo sapiens
<220> FEATURE:
<223> OTHER INFORMATION: TRAV9-2_BB_1

<400> SEQUENCE: 16

```
gtcagatact ccatgagcac gaagacttgt acgccaccat gaactattct ccaggcttag     60

tatctctgat actcttactg cttggaagaa cccgtggaaa ttcagtgacc cagatggaag    120

ggccagtgac tctctcagaa gaggccttcc tgactataaa ctgcacgtac acagccacag    180

gataccettc ccttttctgg tatgtccaat atcctggaga aggtctacag ctcctcctga    240

aagccacgaa ggctgatgac aagggaagca acaaaggttt tgaagccaca taccgtaaag    300

aaaccacttc tttccacttg gagaaaggct cagttcaagt gtcagactca gcggtgtact    360

tctgcagaga ccttgcggcc gtgtcttcga ctagtagctc acctacga                 408
```

<210> SEQ ID NO 17
<211> LENGTH: 414
<212> TYPE: DNA
<213> ORGANISM: Homo sapiens
<220> FEATURE:
<223> OTHER INFORMATION: TRAV10_BB_1

<400> SEQUENCE: 17

```
gtcagatact ccatgagcac gaagacttgt acgccaccat gaaaaagcat ctgacgacct     60

tcttggtgat tttgtggctt tatttttata gggggaatgg caaaaaccaa gtggagcaga    120

gtcctcagtc cctgatcatc ctggagggaa agaactgcac tcttcaatgc aattatacag    180

tgagcccctt cagcaactta aggtggtata agcaagatac tgggagaggt cctgtttccc    240

tgacaatcat gactttcagt gagaacacaa agtcgaacgg aagatataca gcaactctgg    300

atgcagacac aaagcaaagc tctctgcaca tcacagcctc ccagctcagc gattcagcct    360

cctacatctg cagagacctt gcggccgtgt cttcgactag tagctcacct acga           414
```

<210> SEQ ID NO 18
<211> LENGTH: 408
<212> TYPE: DNA
<213> ORGANISM: Homo sapiens
<220> FEATURE:
<223> OTHER INFORMATION: TRAV12-1_BB_1

<400> SEQUENCE: 18

```
gtcagatact ccatgagcac gaagacttgt acgccaccat gatatccttg agagttttac     60

tggtgatcct gtggcttcag ttaagctggg tttggagcca acggaaggag gtggagcagg    120

atcctggacc cttcaatgtt ccagagggag ccactgtcgc tttcaactgt acttacagca    180

acagtgcttc tcagtctttc ttctggtaca gacaggattg caggaaagaa cctaagttgc    240

tgatgtccgt atactccagt ggtaatgaag atggaaggtt tacagcacag ctcaatagag    300

ccagccagta tatttccctg ctcatcagag actccaagct cagtgattca gccacctacc    360

tctgcagaga ccttgcggcc gtgtcttcga ctagtagctc acctacga                 408
```

<210> SEQ ID NO 19
<211> LENGTH: 414
<212> TYPE: DNA
<213> ORGANISM: Homo sapiens
<220> FEATURE:
<223> OTHER INFORMATION: TRAV12-2_BB_1

<400> SEQUENCE: 19
gtcagatact ccatgagcac gaagacttgt acgccaccat gatgaaatcc ttgagagttt 60
tactagtgat cctgtggctt cagttgagct gggtttggag ccaacagaag gaggtggagc 120
agaattctgg accoctcagt gttccagagg gagccattgc ctctctcaac tgcacttaca 180
gtgaccgagg ttcccagtcc ttcttctggt acagacaata ttctgggaaa agccctgagt 240
tgataatgtt catatactcc aatggtgaca aagaagatgg aaggtttaca gcacagctca 300
ataaagccag ccagtatgtt tctctgctca tcagagactc ccagcccagt gattcagcca 360
cctacctctg cagagacctt gcggccgtgt cttcgactag tagctcacct acga 414

<210> SEQ ID NO 20
<211> LENGTH: 414
<212> TYPE: DNA
<213> ORGANISM: Homo sapiens
<220> FEATURE:
<223> OTHER INFORMATION: TRAV12-3_BB_1

<400> SEQUENCE: 20
gtcagatact ccatgagcac gaagacttgt acgccaccat gatgaaatcc ttgagagttt 60
tactggtgat cctgtggctt cagttaagct gggtttggag ccaacagaag gaggtggagc 120
aggatcctgg accactcagt gttccagagg gagccattgt ttctctcaac tgcacttaca 180
gcaacagtgc ttttcaatac ttcatgtggt acagacagta ttccagaaaa ggccctgagt 240
tgctgatgta cacatactcc agtggtaaca aagaagatgg aaggtttaca gcacaggtcg 300
ataaatccag caagtatatc tccttgttca tcagagactc acagcccagt gattcagcca 360
cctacctctg cagagacctt gcggccgtgt cttcgactag tagctcacct acga 414

<210> SEQ ID NO 21
<211> LENGTH: 408
<212> TYPE: DNA
<213> ORGANISM: Homo sapiens
<220> FEATURE:
<223> OTHER INFORMATION: TRAV13-1_BB_1

<400> SEQUENCE: 21
gtcagatact ccatgagcac gaagacttgt acgccaccat gacatccatt cgagctgtat 60
ttatattcct gtggctgcag ctggacttgg tgaatggaga gaatgtggag cagcatcctt 120
caaccctgag tgtccaggag ggagacagcg ctgttatcaa gtgtacttat tcagacagtg 180
cctcaaacta cttcccttgg tataagcaag aacttggaaa aggacctcag cttattatag 240
acattcgttc aaatgtgggc gaaaagaaag accaacgaat tgctgttaca ttgaacaaga 300
cagccaaaca tttctccctg cacatcacag aaacccaacc tgaggactcg gctgtctact 360
tctgcagaga ccttgcggcc gtgtcttcga ctagtagctc acctacga 408

<210> SEQ ID NO 22
<211> LENGTH: 411
<212> TYPE: DNA
<213> ORGANISM: Homo sapiens
<220> FEATURE:
<223> OTHER INFORMATION: TRAV13-2_BB_1

<400> SEQUENCE: 22
gtcagatact ccatgagcac gaagacttgt acgccaccat ggcaggcatt cgagctttat 60
ttatgtactt gtggctgcag ctggactggg tgagcagagg agagagtgtg gggctgcatc 120
ttcctaccct gagtgtccag gagggtgaca actctattat caactgtgct tattcaaaca 180

```
gcgcctcaga ctacttcatt tggtacaagc aagaatctgg aaaaggtcct caattcatta    240

tagacattcg ttcaaatatg gacaaaaggc aaggccaaag agtcaccgtt ttattgaata    300

agacagtgaa acatctctct ctgcaaattg cagctactca acctggagac tcagctgtct    360

acttctgcag agaccttgcg gccgtgtctt cgactagtag ctcacctacg a             411
```

<210> SEQ ID NO 23
<211> LENGTH: 417
<212> TYPE: DNA
<213> ORGANISM: Homo sapiens
<220> FEATURE:
<223> OTHER INFORMATION: TRAV14DV4_BB_1

<400> SEQUENCE: 23

```
gtcagatact ccatgagcac gaagacttgt acgccaccat gtcactttct agcctgctga     60

aggtggtcac agcttcactg tggctaggac ctggcattgc ccagaagata actcaaaccc    120

aaccaggaat gttcgtgcag gaaaaggagg ctgtgactct ggactgcaca tatgacacca    180

gtgatcaaag ttatggtcta ttctggtaca agcagcccag cagtggggaa atgatttttc    240

ttatttatca ggggtcttat gacgagcaaa atgcaacaga aggtcgctac tcattgaatt    300

tccagaaggc aagaaaatcc gccaaccttg tcatctccgc ttcacaactg gggactcag     360

caatgtattt ctgcagagac cttgcggccg tgtcttcgac tagtagctca cctacga       417
```

<210> SEQ ID NO 24
<211> LENGTH: 399
<212> TYPE: DNA
<213> ORGANISM: Homo sapiens
<220> FEATURE:
<223> OTHER INFORMATION: TRAV16_BB_1

<400> SEQUENCE: 24

```
gtcagatact ccatgagcac gaagacttgt acgccaccat gaagcccacc ctcatctcag     60

tgcttgtgat aatatttata ctcagaggaa caagagccca gagagtgact cagcccgaga    120

agctcctctc tgtctttaaa ggggccccag tggagctgaa gtgcaactat tcctattctg    180

ggagtcctga actcttctgg tatgtccagt actccagaca acgcctccag ttactcttga    240

gacacatctc tagagagagc atcaaaggct tcactgctga ccttaacaaa ggcgagacat    300

ctttccacct gaagaaacca tttgctcaag aggaagattc agccatgtat tactgcagag    360

accttgcggc cgtgtcttcg actagtagct cacctacga                           399
```

<210> SEQ ID NO 25
<211> LENGTH: 408
<212> TYPE: DNA
<213> ORGANISM: Homo sapiens
<220> FEATURE:
<223> OTHER INFORMATION: TRAV17_BB_1

<400> SEQUENCE: 25

```
gtcagatact ccatgagcac gaagacttgt acgccaccat ggaaactctc ctgggagtgt     60

ctttggtgat tctatggctt caactggcta gggtgaacag tcaacaggga gaagaggatc    120

ctcaggcctt gagcatccag gagggtgaaa atgccaccat gaactgcagt tacaaaacta    180

gtataaacaa tttacagtgg tatagacaaa attcaggtag aggccttgtc cacctaattt    240

taatacgttc aaatgaaaga gagaaacaca gtggaagatt aagagtcacg cttgacactt    300

ccaagaaaag cagttccttg ttgatcacgg cttcccgggc agcagacact gcttcttact    360
```

tctgcagaga ccttgcggcc gtgtcttcga ctagtagctc acctacga 408

<210> SEQ ID NO 26
<211> LENGTH: 405
<212> TYPE: DNA
<213> ORGANISM: Homo sapiens
<220> FEATURE:
<223> OTHER INFORMATION: TRAV18_BB_1

<400> SEQUENCE: 26
gtcagatact ccatgagcac gaagacttgt acgccaccat gctgtctgct tcctgctcag 60
gacttgtgat cttgttgata ttcagaagga ccagtggaga ctcggttacc cagacagaag 120
gcccagttac cctccctgag agggcagctc tgacattaaa ctgcacttat cagtccagct 180
attcaacttt tctattctgg tatgtccagt atctaaacaa agagcctgag ctcctcctga 240
aaagttcaga aaaccaggag acggacagca gaggttttca ggccagtcct atcaagagtg 300
acagttcctt ccacctggag aagccctcgg tgcagctgtc ggactctgcc gtgtactact 360
gcagagacct tgcggccgtg tcttcgacta gtagctcacc tacga 405

<210> SEQ ID NO 27
<211> LENGTH: 417
<212> TYPE: DNA
<213> ORGANISM: Homo sapiens
<220> FEATURE:
<223> OTHER INFORMATION: TRAV19_BB_1

<400> SEQUENCE: 27
gtcagatact ccatgagcac gaagacttgt acgccaccat gctgactgcc agcctgttga 60
gggcagtcat agcctccatc tgtgttgtat ccagcatggc tcagaaggta actcaagcgc 120
agactgaaat ttctgtggtg gagaaggagg atgtgacctt ggactgtgtg tatgaaaccc 180
gtgatactac ttattactta ttctggtaca agcaaccacc aagtggagaa ttggttttcc 240
ttattcgtcg gaactctttt gatgagcaaa atgaaataag tggtcggtat tcttggaact 300
tccagaaatc caccagttcc ttcaacttca ccatcacagc ctcacaagtc gtggactcag 360
cagtatactt ctgcagagac cttgcggccg tgtcttcgac tagtagctca cctacga 417

<210> SEQ ID NO 28
<211> LENGTH: 408
<212> TYPE: DNA
<213> ORGANISM: Homo sapiens
<220> FEATURE:
<223> OTHER INFORMATION: TRAV20_BB_1

<400> SEQUENCE: 28
gtcagatact ccatgagcac gaagacttgt acgccaccat ggagaaaatg ttggagtgtg 60
cattcatagt cttgtggctt cagcttggct ggttgagtgg agaggaccag gtgacgcaga 120
gtcccgaggc cctgagactc caggagggag agagtagcag tcttaactgc agttacacag 180
tcagcggttt aagagggctg ttctggtata ggcaagatcc tgggaaaggc cctgaattcc 240
tcttcaccct gtattcagct ggggaagaaa aggagaaaga aaggctaaaa gccacattaa 300
caaagaagga aagctttctg cacatcacag cccctaaacc tgaggactca gccacttatc 360
tctgcagaga ccttgcggcc gtgtcttcga ctagtagctc acctacga 408

<210> SEQ ID NO 29
<211> LENGTH: 408
<212> TYPE: DNA
<213> ORGANISM: Homo sapiens

<220> FEATURE:
<223> OTHER INFORMATION: TRAV21_BB_1

<400> SEQUENCE: 29

```
gtcagatact ccatgagcac gaagacttgt acgccaccat ggagaccctc ttgggcctgc     60
ttatcctttg gctgcagctg caatgggtga gcagcaaaca ggaggtgacg cagattcctg    120
cagctctgag tgtcccagaa ggagaaaact tggttctcaa ctgcagtttc actgatagcg    180
ctatttacaa cctccagtgg tttaggcagg accctgggaa aggactcaca tctctgttgc    240
ttattcagtc aagtcagaga gagcaaacaa gtggacgcct taatgcctcg ctggataaat    300
catcaggacg tagtacttta tacattgcag cttctcagcc tggtgactca gccacctacc    360
tctgcagaga ccttgcggcc gtgtcttcga ctagtagctc acctacga                 408
```

<210> SEQ ID NO 30
<211> LENGTH: 402
<212> TYPE: DNA
<213> ORGANISM: Homo sapiens
<220> FEATURE:
<223> OTHER INFORMATION: TRAV22_BB_1

<400> SEQUENCE: 30

```
gtcagatact ccatgagcac gaagacttgt acgccaccat gaagaggata ttgggagctc     60
tgctggggct cttgagtgcc caggtttgct gtgtgagagg aatacaagtg gagcagagtc    120
ctccagacct gattctccag gagggagcca attccacgct gcggtgcaat tttctgact     180
ctgtgaacaa tttgcagtgg tttcatcaaa acccttgggg acagctcatc aacctgtttt    240
acattccctc agggacaaaa cagaatggaa gattaagcgc cacgactgtc gctacggaac    300
gctacagctt attgtacatt tcctcttccc agaccacaga ctcaggcgtt tatttctgca    360
gagaccttgc ggccgtgtct tcgactagta gctcacctac ga                       402
```

<210> SEQ ID NO 31
<211> LENGTH: 435
<212> TYPE: DNA
<213> ORGANISM: Homo sapiens
<220> FEATURE:
<223> OTHER INFORMATION: TRAV23DV6_BB_1

<400> SEQUENCE: 31

```
gtcagatact ccatgagcac gaagacttgt acgccaccat ggacaagatc ttaggagcat     60
catttttagt tctgtggctt caactatgct gggtgagtgg ccaacagaag gagaaaagtg    120
accagcagca ggtgaaacaa agtcctcaat ctttgatagt ccagaaagga gggatttcaa    180
ttataaactg tgcttatgag aacactgcgt ttgactactt tccatggtac caacaattcc    240
ctgggaaagg ccctgcatta ttgatagcca tacgtccaga tgtgagtgaa aagaaagaag    300
gaagattcac aatctccttc aataaaagtg ccaagcagtt ctcattgcat atcatggatt    360
cccagcctgg agactcagcc acctacttct gcagagacct tgcggccgtg tcttcgacta    420
gtagctcacc tacga                                                     435
```

<210> SEQ ID NO 32
<211> LENGTH: 417
<212> TYPE: DNA
<213> ORGANISM: Homo sapiens
<220> FEATURE:
<223> OTHER INFORMATION: TRAV24_BB_1

<400> SEQUENCE: 32

```
gtcagatact ccatgagcac gaagacttgt acgccaccat ggagaagaat cctttggcag    60

ccccattact aatcctctgg tttcatcttg actgcgtgag cagcatactg aacgtggaac   120

aaagtcctca gtcactgcat gttcaggagg gagacagcac caatttcacc tgcagcttcc   180

cttccagcaa tttttatgcc ttacactggt acagatggga aactgcaaaa agccccgagg   240

ccttgtttgt aatgacttta aatggggatg aaaagaagaa aggacgaata agtgccactc   300

ttaataccaa ggagggttac agctatttgt acatcaaagg atcccagcct gaagattcag   360

ccacatacct ctgcagagac cttgcggccg tgtcttcgac tagtagctca cctacga      417
```

<210> SEQ ID NO 33
<211> LENGTH: 402
<212> TYPE: DNA
<213> ORGANISM: Homo sapiens
<220> FEATURE:
<223> OTHER INFORMATION: TRAV25_BB_1

<400> SEQUENCE: 33

```
gtcagatact ccatgagcac gaagacttgt acgccaccat gctactcatc acatcaatgt    60

tggtcttatg gatgcaattg tcacaggtga atggacaaca ggtaatgcaa attcctcagt   120

accagcatgt acaagaagga gaggacttca ccacgtactg caattcctca actactttaa   180

gcaatataca gtggtataag caaaggcctg gtggacatcc cgtattcttg atacagttag   240

tgaagagtgg agaagtgaag aagcagaaaa gactgacatt tcagtttgga gaagcaaaaa   300

agaacagctc cctgcacatc acagccaccc agactacaga tgtaggaacc tacttctgca   360

gagaccttgc ggccgtgtct tcgactagta gctcacctac ga                      402
```

<210> SEQ ID NO 34
<211> LENGTH: 396
<212> TYPE: DNA
<213> ORGANISM: Homo sapiens
<220> FEATURE:
<223> OTHER INFORMATION: TRAV26-1_BB_1

<400> SEQUENCE: 34

```
gtcagatact ccatgagcac gaagacttgt acgccaccat gaggctggtg gcaagagtaa    60

ctgtgtttct gacctttgga actataattg atgctaagac cacccagccc ccctccatgg   120

attgcgctga aggaagagct gcaaacctgc cttgtaatca ctctaccatc agtggaaatg   180

agtatgtgta ttggtatcga cagattcact cccaggggcc acagtatatc attcatggtc   240

taaaaaacaa tgaaaccaat gaaatggcct ctctgatcat cacagaagat agaaagtcca   300

gcaccttgat cctgccccac gctacgctga gagacactgc tgtgtactac tgcagagacc   360

ttgcggccgt gtcttcgact agtagctcac ctacga                             396
```

<210> SEQ ID NO 35
<211> LENGTH: 396
<212> TYPE: DNA
<213> ORGANISM: Homo sapiens
<220> FEATURE:
<223> OTHER INFORMATION: TRAV26-2_BB_1

<400> SEQUENCE: 35

```
gtcagatact ccatgagcac gaagacttgt acgccaccat gaagttggtg acaagcatta    60

ctgtactcct atctttgggt attatgggtg atgctaagac cacacagcca aattcaatgg   120

agagtaacga agaagagcct gttcacttgc cttgtaacca ctccacaatc agtggaactg   180

attacataca ttggtatcga cagcttccct cccagggtcc agagtacgtg attcatggtc   240
```

```
ttacaagcaa tgtgaacaac agaatggcct ctctggcaat cgctgaggac agaaagtcca    300

gtaccttgat cctgcaccgt gctaccttga gagatgctgc tgtgtactac tgcagagacc    360

ttgcggccgt gtcttcgact agtagctcac ctacga                              396


<210> SEQ ID NO 36
<211> LENGTH: 402
<212> TYPE: DNA
<213> ORGANISM: Homo sapiens
<220> FEATURE:
<223> OTHER INFORMATION: TRAV27_BB_1

<400> SEQUENCE: 36

gtcagatact ccatgagcac gaagacttgt acgccaccat ggtcctgaaa ttctccgtgt     60

ccattctttg gattcagttg gcatgggtga gcacccagct gctggagcag agccctcagt    120

ttctaagcat ccaagaggga gaaaatctca ctgtgtactg caactcctca agtgtttttt    180

ccagcttaca atggtacaga caggagcctg ggaaggtcc tgtcctcctg gtgacagtag     240

ttacgggtgg agaagtgaag aagctgaaga gactaacctt tcagtttggt gatgcaagaa    300

aggacagttc tctccacatc actgcagccc agcctggtga tacaggcctc tacctctgca    360

gagaccttgc ggccgtgtct tcgactagta gctcacctac ga                       402


<210> SEQ ID NO 37
<211> LENGTH: 429
<212> TYPE: DNA
<213> ORGANISM: Homo sapiens
<220> FEATURE:
<223> OTHER INFORMATION: TRAV29DV5_BB_1

<400> SEQUENCE: 37

gtcagatact ccatgagcac gaagacttgt acgccaccat ggccatgctc ctgggggcat     60

cagtgctgat tctgtggctt cagccagact gggtaaacag tcaacagaag aatgatgacc    120

agcaagttaa gcaaaattca ccatccctga gcgtccagga aggaagaatt tctattctga    180

actgtgacta tactaacagc atgtttgatt atttcctatg gtacaaaaaa taccctgctg    240

aaggtcctac attcctgata tctataagtt ccattaagga taaaaatgaa gatggaagat    300

tcactgtttt cttaaacaaa agtgccaagc acctctctct gcacattgtg ccctcccagc    360

ctggagactc tgcagtgtac ttctgcagag accttgcggc cgtgtcttcg actagtagct    420

cacctacga                                                            429


<210> SEQ ID NO 38
<211> LENGTH: 408
<212> TYPE: DNA
<213> ORGANISM: Homo sapiens
<220> FEATURE:
<223> OTHER INFORMATION: TRAV30_BB_1

<400> SEQUENCE: 38

gtcagatact ccatgagcac gaagacttgt acgccaccat ggagactctc ctgaaagtgc     60

tttcaggcac cttgttgtgg cagttgacct gggtgagaag ccaacaacca gtgcagagtc    120

ctcaagccgt gatcctccga gaaggggaag atgctgtcat caactgcagt tcctccaagg    180

ctttatattc tgtacactgg tacaggcaga agcatggtga agcacccgtt ttcctgatga    240

tattactgaa gggtggagaa cagaagggtc atgaaaaaat atctgcttca tttaatgaaa    300

aaaagcagca aagctccctg taccttacgg cctcccagct cagttactca ggaacctact    360
```

```
tctgcagaga ccttgcggcc gtgtcttcga ctagtagctc acctacga              408


<210> SEQ ID NO 39
<211> LENGTH: 408
<212> TYPE: DNA
<213> ORGANISM: Homo sapiens
<220> FEATURE:
<223> OTHER INFORMATION: TRAV34_BB_1

<400> SEQUENCE: 39

gtcagatact ccatgagcac gaagacttgt acgccaccat ggagactgtt ctgcaagtac    60

tcctagggat attggggttc caagcagcct gggtcagtag ccaagaactg gagcagagtc   120

ctcagtcctt gatcgtccaa gagggaaaga atctcaccat aaactgcacg tcatcaaaga   180

cgttatatgg cttatactgg tataagcaaa agtatggtga aggtcttatc ttcttgatga   240

tgctacagaa aggtggggaa gagaaaagtc atgaaaagat aactgccaag ttggatgaga   300

aaaagcagca aagttccctg catatcacag cctcccagcc cagccatgca ggcatctacc   360

tctgcagaga ccttgcggcc gtgtcttcga ctagtagctc acctacga              408


<210> SEQ ID NO 40
<211> LENGTH: 402
<212> TYPE: DNA
<213> ORGANISM: Homo sapiens
<220> FEATURE:
<223> OTHER INFORMATION: TRAV35_BB_1

<400> SEQUENCE: 40

gtcagatact ccatgagcac gaagacttgt acgccaccat gctccttgaa catttattaa    60

taatcttgtg gatgcagctg acatgggtca gtggtcaaca gctgaatcag agtcctcaat   120

ctatgtttat ccaggaagga gaagatgtct ccatgaactg cacttcttca agcatattta   180

acacctggct atggtacaag caggaacctg gggaaggtcc tgtcctcttg atagccttat   240

ataaggctgg tgaattgacc tcaaatggaa ggctgactgc tcagtttggt ataaccagaa   300

aggacagctt cctgaatatc tcagcatcca tacctagtga tgtaggcatc tacttctgca   360

gagaccttgc ggccgtgtct tcgactagta gctcacctac ga                    402


<210> SEQ ID NO 41
<211> LENGTH: 411
<212> TYPE: DNA
<213> ORGANISM: Homo sapiens
<220> FEATURE:
<223> OTHER INFORMATION: TRAV36DV7_BB_1

<400> SEQUENCE: 41

gtcagatact ccatgagcac gaagacttgt acgccaccat gatgaagtgt ccacaggctt    60

tactagctat cttttggctt ctactgagct gggtgagcag tgaagataag gtggtacaaa   120

gccctctatc tctggttgtc cacgagggag acaccgtaac tctcaattgc agttatgaag   180

tgactaactt tcgaagccta ctatggtaca agcaggaaaa gaaagctccc acatttctat   240

ttatgctaac ttcaagtgga attgaaaaga agtcaggtag actaagtagc atattagata   300

agaaagaact ttccagcatc ctgaacatca cagccaccca gaccggagac tcggccatct   360

acctctgcag agaccttgcg gccgtgtctt cgactagtag ctcacctacg a          411


<210> SEQ ID NO 42
<211> LENGTH: 417
<212> TYPE: DNA
<213> ORGANISM: Homo sapiens
```

<220> FEATURE:
<223> OTHER INFORMATION: TRAV38-1_BB_1

<400> SEQUENCE: 42
gtcagatact ccatgagcac gaagacttgt acgccaccat gacacgagtt agcttgctgt 60
gggcagtcgt ggtcagtacc tgtcttgaat ccggcatggc ccagacagtc actcagtctc 120
aaccagagat gtctgtgcag gaggcagaga ctgtgaccct gagttgcaca tatgacacca 180
gtgagaataa ttattatttg ttctggtaca agcagcctcc cagcaggcag atgattctcg 240
ttattcgcca agaagcttat aagcaacaga atgcaacgga gaatcgtttc tctgtgaact 300
tccagaaagc agccaaatcc ttcagtctca agatctcaga ctcacagctg ggggacactg 360
cgatgtattt ctgcagagac cttgcggccg tgtcttcgac tagtagctca cctacga 417

<210> SEQ ID NO 43
<211> LENGTH: 417
<212> TYPE: DNA
<213> ORGANISM: Homo sapiens
<220> FEATURE:
<223> OTHER INFORMATION: TRAV38-2DV8_BB_1

<400> SEQUENCE: 43
gtcagatact ccatgagcac gaagacttgt acgccaccat ggcatgccct ggcttcctgt 60
gggcacttgt gatctccacc tgtcttgaat ttagcatggc tcagacagtc actcagtctc 120
aaccagagat gtctgtgcag gaggcagaga cggtgaccct gagctgcaca tatgacacca 180
gtgagagtga ttattattta ttctggtaca agcagcctcc cagcaggcag atgattctcg 240
ttattcgcca agaagcttat aagcaacaga atgcaacaga gaatcgtttc tctgtgaact 300
tccagaaagc agccaaatcc ttcagtctca agatctcaga ctcacagctg gggggatgccg 360 cgatgtattt ctgcagagac cttgcggccg tgtcttcgac tagtagctca cctacga 417

<210> SEQ ID NO 44
<211> LENGTH: 402
<212> TYPE: DNA
<213> ORGANISM: Homo sapiens
<220> FEATURE:
<223> OTHER INFORMATION: TRAV39_BB_1

<400> SEQUENCE: 44
gtcagatact ccatgagcac gaagacttgt acgccaccat gaagaagcta ctagcaatga 60
ttctgtggct tcaactagac cggttaagtg gagagctgaa agtggaacaa aaccctctgt 120
tcctgagcat gcaggaggga aaaaactata ccatctactg caattattca accacttcag 180
acagactgta ttggtacagg caggatcctg ggaaaagtct ggaatctctg tttgtgttgc 240
tatcaaatgg agcagtgaag caggagggac gattaatggc ctcacttgat accaaagccc 300
gtctcagcac cctccacatc acagctgccg tgcatgacct ctctgccacc tacttctgca 360
gagaccttgc ggccgtgtct tcgactagta gctcacctac ga 402

<210> SEQ ID NO 45
<211> LENGTH: 387
<212> TYPE: DNA
<213> ORGANISM: Homo sapiens
<220> FEATURE:
<223> OTHER INFORMATION: TRAV40_BB_1

<400> SEQUENCE: 45
gtcagatact ccatgagcac gaagacttgt acgccaccat gaactcctct ctggactttc 60

```
taattctgat cttaatgttt ggaggaacca gcagcaattc agtcaagcag acgggccaaa    120

taaccgtctc ggagggagca tctgtgacta tgaactgcac atacacatcc acggggtacc    180

ctaccctttt ctggtatgtg gaatacccca gcaaacctct gcagcttctt cagagagaga    240

caatggaaaa cagcaaaaac ttcggaggcg gaaatattaa agacaaaaac tcccccattg    300

tgaaatattc agtccaggta tcagactcag ccgtgtacta ctgcagagac cttgcggccg    360

tgtcttcgac tagtagctca cctacga                                        387
```

<210> SEQ ID NO 46
<211> LENGTH: 408
<212> TYPE: DNA
<213> ORGANISM: Homo sapiens
<220> FEATURE:
<223> OTHER INFORMATION: TRAV41_BB_1

<400> SEQUENCE: 46

```
gtcagatact ccatgagcac gaagacttgt acgccaccat ggtgaagatc cggcaatttt     60

tgttggctat tttgtggctt cagctaagct gtgtaagtgc cgccaaaaat gaagtggagc    120

agagtcctca gaacctgact gcccaggaag gagaatttat cacaatcaac tgcagttact    180

cggtaggaat aagtgcctta cactggctgc aacagcatcc aggaggaggc attgtttcct    240

tgtttatgct gagctcaggg aagaagaagc atggaagatt aattgccaca ataaacatac    300

aggaaaagca cagctccctg cacatcacag cctcccatcc cagagactct gccgtctaca    360

tctgcagaga ccttgcggcc gtgtcttcga ctagtagctc acctacga                 408
```

<210> SEQ ID NO 47
<211> LENGTH: 497
<212> TYPE: DNA
<213> ORGANISM: Homo sapiens
<220> FEATURE:
<223> OTHER INFORMATION: TRAC1 cloning fragment

<400> SEQUENCE: 47

```
gtgcactcct atgactaacg gaagactagg ccgcataggt ctcaccagaa ccctgaccct     60

gccgtgtacc agctgagaga ctctaaatcc agtgacaagt ctgtctgcct attcaccgat    120

tttgattctc aaacaaatgt gtcacaaagt aaggattctg atgtgtatat cacagacaaa    180

actgtgctag acatgaggtc tatggacttc aagagcaaca gtgctgtggc ctggagcaac    240

aaatctgact ttgcatgtgc aaacgccttc aacaacagca ttattccaga ggacaccttc    300

ttccccagcc cagaaagttc ctgtgatgtc aagctggtcg agaaaagctt tgaaacagat    360

acgaacctaa actttcaaaa cctgtcagtg attgggttcc gaatcctcct cctgaaagtg    420

gccgggttta atctgctcat gacgctgcgg ctgtggtcca gctgactagg tgtcttccct    480

atgctgaatc gatggtc                                                   497
```

<210> SEQ ID NO 48
<211> LENGTH: 3210
<212> TYPE: DNA
<213> ORGANISM: Artificial Sequence
<220> FEATURE:
<223> OTHER INFORMATION: V-C entry backbone transient

<400> SEQUENCE: 48

```
tctagacctg atcataatca agccatatca catctgtaga ggtttacttg ctttaaaaaa     60

cctccacacc tcccctgaa cctgaaacat aaaatgaatg caattgttgt tgttaacttg    120

tttattgcag cttataatgg ttacaaataa agcaatagca tcacaaattt cacaaataaa    180
```

```
gcattttttt cactgcattc tagttgtggt ttgtccaaac tcatcaatgt atcttatcat    240
gtctggatct gcggatccaa tctcgagctg ggcctcatgg gccttccgct cactgcccgc    300
tttccagtcg ggaaacctgt cgtgccagct gcattaacat ggtcatagct gtttccttgc    360
gtattgggcg ctctccgctt cctcgctcac tgactcgctg cgctcggtcg ttcgggtaaa    420
gcctggggtg cctaatgagc aaaaggccag caaaaggcca ggaaccgtaa aaaggccgcg    480
ttgctggcgt ttttccatag gctccgcccc cctgacgagc atcacaaaaa tcgacgctca    540
agtcagaggt ggcgaaaccc gacaggacta taaagatacc aggcgtttcc ccctggaagc    600
tccctcgtgc gctctcctgt tccgaccctg ccgcttaccg gatacctgtc cgcctttctc    660
ccttcgggaa gcgtggcgct ttctcatagc tcacgctgta ggtatctcag ttcggtgtag    720
gtcgttcgct ccaagctggg ctgtgtgcac gaaccccccg ttcagcccga ccgctgcgcc    780
ttatccggta actatcgtct tgagtccaac ccggtaagac acgacttatc gccactggca    840
gcagccactg gtaacaggat tagcagagcg aggtatgtag gcggtgctac agagttcttg    900
aagtggtggc ctaactacgg ctacactaga agaacagtat ttggtatctg cgctctgctg    960
aagccagtta ccttcggaaa aagagttggt agctcttgat ccggcaaaca aaccaccgct   1020
ggtagcggtg gtttttttgt ttgcaagcag cagattacgc gcagaaaaaa aggatctcaa   1080
gaagatcctt tgatcttttc tacggggtct gacgctcagt ggaacgaaaa ctcacgttaa   1140
gggattttgg tcatgagatt atcaaaaagg atcttcacct agatcctttt aaattaaaaa   1200
tgaagtttta aatcaatcta aagtatatat gagtaaactt ggtctgacag ttaccaatgc   1260
ttaatcagtg aggcacctat ctcagcgatc tgtctatttc gttcatccat agttgcctga   1320
ctccccgtcg tgtagataac tacgatacgg gagggcttac catctggccc cagtgctgca   1380
atgataccgc gagaaccacg ctcaccggct ccagatttat cagcaataaa ccagccagcc   1440
ggaagggccg agcgcagaag tggtcctgca actttatccg cctccatcca gtctattaat   1500
tgttgccggg aagctagagt aagtagttcg ccagttaata gtttgcgcaa cgttgttgcc   1560
attgctacag gcatcgtggt gtcacgctcg tcgtttggta tggcttcatt cagctccggt   1620
tcccaacgat caaggcgagt tacatgatcc cccatgttgt gcaaaaaagc ggttagctcc   1680
ttcggtcctc cgatcgttgt cagaagtaag ttggccgcag tgttatcact catggttatg   1740
gcagcactgc ataattctct tactgtcatg ccatccgtaa gatgcttttc tgtgactggt   1800
gagtactcaa ccaagtcatt ctgagaatag tgtatgcggc gaccgagttg ctcttgcccg   1860
gcgtcaatac gggataatac cgcgccacat agcagaactt taaaagtgct catcattgga   1920
aaacgttctt cggggcgaaa actctcaagg atcttaccgc tgttgagatc cagttcgatg   1980
taacccactc gtgcacccaa ctgatcttca gcatctttta ctttcaccag cgtttctggg   2040
tgagcaaaaa caggaaggca aaatgccgca aaaaagggaa taagggcgac acggaaatgt   2100
tgaatactca tactcttcct ttttcaatat tattgaagca tttatcaggg ttattgtctc   2160
atgagcggat acatatttga atgtatttag aaaaataaac aaataggggt tccgcgcaca   2220
tttccccgaa aagtgccacc taaattgtaa gcgttaatat tttgttaaaa ttcgcgttaa   2280
atttttgtta aatcagctca ttttttaacc aataggccga aatcggcaaa atcccttata   2340
aatcaaaaga atagaccgag atagggttga gtggccgcta cagggcgctc ccattcgcca   2400
ttcaggctgc gcaactgttg ggaagggcgt ttcggtgcgg gcctcttcgc tattacgcca   2460
gctggcgaaa gggggatgtg ctgcaaggcg attaagttgg gtaacgccag ggttttccca   2520
```

```
gtcacgacgt tgtaaaacga cggccagtga gcgcgacgta atacgactca ctatagggcg   2580

aattggcgga aggccgtcaa ggccgcatga attcgctacc ggtatagtaa tcaattacgg   2640

ggtcattagt tcatagccca tatatggagt tccgcgttac ataacttacg gtaaatggcc   2700

cgcctggctg accgcccaac gacccccgcc cattgacgtc aataatgacg tatgttccca   2760

tagtaacgcc aatagggact ttccattgac gtcaatgggt ggagtattta cggtaaactg   2820

cccacttggc agtacatcaa gtgtatcata tgccaagtac gccccctatt gacgtcaatg   2880

acggtaaatg gcccgcctgg cattatgccc agtacatgac cttatgggac tttcctactt   2940

ggcagtacat ctacgtatta gtcatcgcta ttaccatggt gatgcggttt tggcagtaca   3000

tcaatgggcg tggatagcgg tttgactcac ggggatttcc aagtctccac cccattgacg   3060

tcaatgggag tttgttttgg caccaaaatc aacgggactt tccaaaatgt cgtaacaact   3120

ccgccccatt gacgcaaatg ggcggtaggc gtgtacggtg ggaggtctat ataagcagag   3180

ctggtttagt gaaccgtcag atcaggtacc                                    3210
```

<210> SEQ ID NO 49
<211> LENGTH: 769
<212> TYPE: DNA
<213> ORGANISM: Homo sapiens
<220> FEATURE:
<223> OTHER INFORMATION: V-C entry TRAV1-1_TRAC

<400> SEQUENCE: 49

```
gccaccatgt ggggagcttt ccttctctat gtttccatga agatgggagg cactgcagga     60

caaagccttg agcagccctc tgaagtgaca gctgtggaag gagccattgt ccagataaac    120

tgcacgtacc agacatctgg gttttatggg ctgtcctggt accagcaaca tgatggcgga    180

gcacccacat ttctttctta caatgctctg gatggtttgg aggagacagg tcgttttttct   240

tcattcctta gtcgctctga tagttatggt tacctccttc tacaggagct ccagatgaaa    300

gactctgcct cttacttctg cagagacctt gcggccgcat aggtctcacc agaaccctga    360

ccctgccgtg taccagctga gagactctaa atccagtgac aagtctgtct gcctattcac    420

cgattttgat tctcaaacaa atgtgtcaca aagtaaggat tctgatgtgt atatcacaga    480

caaaactgtg ctagacatga ggtctatgga cttcaagagc aacagtgctg tggcctggag    540

caacaaatct gactttgcat gtgcaaacgc cttcaacaac agcattattc cagaggacac    600

cttcttcccc agcccagaaa gttcctgtga tgtcaagctg gtcgagaaaa gctttgaaac    660

agatacgaac ctaaactttc aaaacctgtc agtgattggg ttccgaatcc tcctcctgaa    720

agtggccggg tttaatctgc tcatgacgct gcggctgtgg tccagctga                769
```

<210> SEQ ID NO 50
<211> LENGTH: 769
<212> TYPE: DNA
<213> ORGANISM: Homo sapiens
<220> FEATURE:
<223> OTHER INFORMATION: V-C entry TRAV1-2_TRAC

<400> SEQUENCE: 50

```
gccaccatgt ggggagtttt ccttctttat gtttccatga agatgggagg cactacagga     60

caaaacattg accagcccac tgagatgaca gctacggaag gtgccattgt ccagatcaac    120

tgcacgtacc agacatctgg gttcaacggg ctgttctggt accagcaaca tgctggcgaa    180

gcacccacat ttctgtctta caatgttctg gatggtttgg aggagaaagg tcgtttttct    240

tcattcctta gtcggtctaa agggtacagt tacctccttt tgaaggagct ccagatgaaa    300
```

```
gactctgcct cttacctctg cagagacctt gcggccgcat aggtctcacc agaaccctga    360

ccctgccgtg taccagctga gagactctaa atccagtgac aagtctgtct gcctattcac    420

cgattttgat tctcaaacaa atgtgtcaca aagtaaggat tctgatgtgt atatcacaga    480

caaaactgtg ctagacatga ggtctatgga cttcaagagc aacagtgctg tggcctggag    540

caacaaatct gactttgcat gtgcaaacgc cttcaacaac agcattattc cagaggacac    600

cttcttcccc agcccagaaa gttcctgtga tgtcaagctg gtcgagaaaa gctttgaaac    660

agatacgaac ctaaactttc aaaacctgtc agtgattggg ttccgaatcc tcctcctgaa    720

agtggccggg tttaatctgc tcatgacgct gcggctgtgg tccagctga                769
```

<210> SEQ ID NO 51
<211> LENGTH: 781
<212> TYPE: DNA
<213> ORGANISM: Homo sapiens
<220> FEATURE:
<223> OTHER INFORMATION: V-C entry TRAV2_TRAC

<400> SEQUENCE: 51

```
gccaccatgg ctttgcagag cactctgggg gcggtgtggc tagggcttct cctcaactct     60

ctctggaagg ttgcagaaag caaggaccaa gtgtttcagc cttccacagt ggcatcttca    120

gagggagctg tggtggaaat cttctgtaat cactctgtgt ccaatgctta caacttcttc    180

tggtaccttc acttcccggg atgtgcacca agactccttg ttaaaggctc aaagccttct    240

cagcagggac gatacaacat gacctatgaa cggttctctt catcgctgct catcctccag    300

gtgcgggagg cagatgctgc tgtttactac tgcagagacc ttgcggccgc ataggtctca    360

ccagaaccct gaccctgccg tgtaccagct gagagactct aaatccagtg acaagtctgt    420

ctgcctattc accgattttg attctcaaac aaatgtgtca caaagtaagg attctgatgt    480

gtatatcaca gacaaaactg tgctagacat gaggtctatg gacttcaaga gcaacagtgc    540

tgtggcctgg agcaacaaat ctgactttgc atgtgcaaac gccttcaaca acagcattat    600

tccagaggac accttcttcc ccagcccaga aagttcctgt gatgtcaagc tggtcgagaa    660

aagctttgaa acagatacga acctaaactt tcaaaacctg tcagtgattg ggttccgaat    720

cctcctcctg aaagtggccg ggtttaatct gctcatgacg ctgcggctgt ggtccagctg    780

a                                                                    781
```

<210> SEQ ID NO 52
<211> LENGTH: 784
<212> TYPE: DNA
<213> ORGANISM: Homo sapiens
<220> FEATURE:
<223> OTHER INFORMATION: V-C entry TRAV3_TRAC

<400> SEQUENCE: 52

```
gccaccatgg cctctgcacc catctcgatg cttgcgatgc tcttcacatt gagtgggctg     60

agagctcagt cagtggctca gccggaagat caggtcaacg ttgctgaagg gaatcctctg    120

actgtgaaat gcacctattc agtctctgga aacccttatc ttttttggta tgttcaatac    180

cccaaccgag gcctccagtt ccttctgaaa tacatcacag ggataacct ggttaaaggc     240

agctatggct ttgaagctga atttaacaag agccaaacct ccttccacct gaagaaacca    300

tctgcccttg tgagcgactc cgctttgtac ttctgcagag accttgcggc cgcataggtc    360

tcaccagaac cctgaccctg ccgtgtacca gctgagagac tctaaatcca gtgacaagtc    420
```

```
tgtctgccta ttcaccgatt ttgattctca aacaaatgtg tcacaaagta aggattctga    480

tgtgtatatc acagacaaaa ctgtgctaga catgaggtct atggacttca agagcaacag    540

tgctgtggcc tggagcaaca aatctgactt tgcatgtgca aacgccttca acaacagcat    600

tattccagag gacaccttct tccccagccc agaaagttcc tgtgatgtca agctggtcga    660

gaaaagcttt gaaacagata cgaacctaaa ctttcaaaac ctgtcagtga ttgggttccg    720

aatcctcctc ctgaaagtgg ccgggtttaa tctgctcatg acgctgcggc tgtggtccag    780

ctga                                                                 784
```

<210> SEQ ID NO 53
<211> LENGTH: 769
<212> TYPE: DNA
<213> ORGANISM: Homo sapiens
<220> FEATURE:
<223> OTHER INFORMATION: V-C entry TRAV4_TRAC

<400> SEQUENCE: 53

```
gccaccatga ggcaagtggc gagagtgatc gtgttcctga ccctgagtac tttgagcctt     60

gctaagacca cccagcccat ctccatggac tcatatgaag gacaagaagt gaacataacc    120

tgtagccaca acaacattgc tacaaatgat tatatcacgt ggtaccaaca gtttcccagc    180

caaggaccac gatttattat tcaaggatac aagacaaaag ttacaaacga agtggcctcc    240

ctgtttatcc ctgccgacag aaagtccagc actctgagcc tgccccgggt ttccctgagc    300

gacactgctg tgtactactg cagagacctt gcggccgcat aggtctcacc agaaccctga    360

ccctgccgtg taccagctga gagactctaa atccagtgac aagtctgtct gcctattcac    420

cgattttgat tctcaaacaa atgtgtcaca aagtaaggat tctgatgtgt atatcacaga    480

caaaactgtg ctagacatga ggtctatgga cttcaagagc aacagtgctg tggcctggag    540

caacaaatct gactttgcat gtgcaaacgc cttcaacaac agcattattc cagaggacac    600

cttcttcccc agcccagaaa gttcctgtga tgtcaagctg gtcgagaaaa gctttgaaac    660

agatacgaac ctaaactttc aaaacctgtc agtgattggg ttccgaatcc tcctcctgaa    720

agtggccggg tttaatctgc tcatgacgct gcggctgtgg tccagctga                769
```

<210> SEQ ID NO 54
<211> LENGTH: 784
<212> TYPE: DNA
<213> ORGANISM: Homo sapiens
<220> FEATURE:
<223> OTHER INFORMATION: V-C entry TRAV5_TRAC

<400> SEQUENCE: 54

```
gccaccatga aaacatttgc tggattttcg ttcctgtttt tgtggctgca gctggactgt     60

atgagtagag gagaggatgt ggagcagagt cttttcctga gtgtccgaga gggagacagc    120

tccgttataa actgcactta cacagacagc tcctccacct acttatactg gtataagcaa    180

gaacctggag caggtctaca gttgctgacg tatatttttt caaatatgga catgaaacaa    240

gaccaaagac tcactgttct attgaataaa aaggataaac atctgtctct gcgcattgca    300

gacacccaga ctggggactc agctatctac ttctgcagag accttgcggc cgcataggtc    360

tcaccagaac cctgaccctg ccgtgtacca gctgagagac tctaaatcca gtgacaagtc    420

tgtctgccta ttcaccgatt ttgattctca aacaaatgtg tcacaaagta aggattctga    480

tgtgtatatc acagacaaaa ctgtgctaga catgaggtct atggacttca agagcaacag    540

tgctgtggcc tggagcaaca aatctgactt tgcatgtgca aacgccttca acaacagcat    600
```

tattccagag gacaccttct tccccagccc agaaagttcc tgtgatgtca agctggtcga 660
gaaaagcttt gaaacagata cgaacctaaa ctttcaaaac ctgtcagtga ttgggttccg 720
aatcctcctc ctgaaagtgg ccgggtttaa tctgctcatg acgctgcggc tgtggtccag 780
ctga 784

<210> SEQ ID NO 55
<211> LENGTH: 784
<212> TYPE: DNA
<213> ORGANISM: Homo sapiens
<220> FEATURE:
<223> OTHER INFORMATION: V-C entry TRAV6_TRAC

<400> SEQUENCE: 55
gccaccatgg agtcattcct gggaggtgtt ttgctgattt tgtggcttca agtggactgg 60
gtgaagagcc aaaagataga acagaattcc gaggccctga acattcagga gggtaaaacg 120
gccaccctga cctgcaacta tacaaactat tccccagcat acttacagtg gtaccgacaa 180
gatccaggaa gaggccctgt tttcttgcta ctcatacgtg aaaatgagaa agaaaaaagg 240
aaagaaagac tgaaggtcac ctttgatacc acccttaaac agagtttgtt tcatatcaca 300
gcctcccagc ctgcagactc agctacctac ctctgcagag accttgcggc cgcataggtc 360
tcaccagaac cctgaccctg ccgtgtacca gctgagagac tctaaatcca gtgacaagtc 420
tgtctgccta ttcaccgatt ttgattctca aacaaatgtg tcacaaagta aggattctga 480
tgtgtatatc acagacaaaa ctgtgctaga catgaggtct atggacttca agagcaacag 540
tgctgtggcc tggagcaaca aatctgactt tgcatgtgca aacgccttca acaacagcat 600
tattccagag gacaccttct tccccagccc agaaagttcc tgtgatgtca agctggtcga 660
gaaaagcttt gaaacagata cgaacctaaa ctttcaaaac ctgtcagtga ttgggttccg 720
aatcctcctc ctgaaagtgg ccgggtttaa tctgctcatg acgctgcggc tgtggtccag 780
ctga 784

<210> SEQ ID NO 56
<211> LENGTH: 781
<212> TYPE: DNA
<213> ORGANISM: Homo sapiens
<220> FEATURE:
<223> OTHER INFORMATION: V-C entry TRAV7_TRAC

<400> SEQUENCE: 56
gccaccatgg agaagatgcg tagacctgtc ctaattatat tttgtctatg tcttggctgg 60
gcaaatggag aaaaccaggt ggagcacagc cctcattttc tgggacccca gcagggagac 120
gttgcctcca tgagctgcac gtactctgtc agtcgtttta acaatttgca gtggtacagg 180
caaaatacag ggatgggtcc caaacaccta ttatccatgt attcagctgg atatgagaag 240
cagaaaggaa ggctaaatgc tacattactg aagaatggaa gcagcttgta cattacagcc 300
gtgcagcctg aagattcagc cacctatttc tgcagagacc ttgcggccgc ataggtctca 360
ccagaaccct gaccctgccg tgtaccagct gagagactct aaatccagtg acaagtctgt 420
ctgcctattc accgattttg attctcaaac aaatgtgtca caaagtaagg attctgatgt 480
gtatatcaca gacaaaactg tgctagacat gaggtctatg gacttcaaga gcaacagtgc 540
tgtggcctgg agcaacaaat ctgactttgc atgtgcaaac gccttcaaca acagcattat 600
tccagaggac accttcttcc ccagcccaga aagttcctgt gatgtcaagc tggtcgagaa 660

```
aagctttgaa acagatacga acctaaactt tcaaaacctg tcagtgattg ggttccgaat    720

cctcctcctg aaagtggccg ggtttaatct gctcatgacg ctgcggctgt ggtccagctg    780

a                                                                    781
```

<210> SEQ ID NO 57
<211> LENGTH: 784
<212> TYPE: DNA
<213> ORGANISM: Homo sapiens
<220> FEATURE:
<223> OTHER INFORMATION: V-C entry TRAV8-1_TRAC

<400> SEQUENCE: 57

```
gccaccatgc tcctgttgct cataccagtg ctggggatga tttttgccct gagagatgcc     60

agagcccagt ctgtgagcca gcataaccac cacgtaattc tctctgaagc agcctcactg    120

gagttgggat gcaactattc ctatggtgga actgttaatc tcttctggta tgtccagtac    180

cctggtcaac accttcagct tctcctcaag tacttttcag ggatccact ggttaaaggc     240

atcaagggct ttgaggctga atttataaag agtaaattct cctttaatct gaggaaaccc    300

tctgtgcagt ggagtgacac agctgagtac ttctgcagag accttgcggc cgcataggtc    360

tcaccagaac cctgaccctg ccgtgtacca gctgagagac tctaaatcca gtgacaagtc    420

tgtctgccta ttcaccgatt ttgattctca aacaaatgtg tcacaaagta aggattctga    480

tgtgtatatc acagacaaaa ctgtgctaga catgaggtct atggacttca agagcaacag    540

tgctgtggcc tggagcaaca aatctgactt tgcatgtgca aacgccttca acaacagcat    600

tattccagag gacaccttct tccccagccc agaaagttcc tgtgatgtca agctggtcga    660

gaaaagcttt gaaacagata cgaacctaaa ctttcaaaac ctgtcagtga ttgggttccg    720

aatcctcctc ctgaaagtgg ccgggtttaa tctgctcatg acgctgcggc tgtggtccag    780

ctga                                                                 784
```

<210> SEQ ID NO 58
<211> LENGTH: 784
<212> TYPE: DNA
<213> ORGANISM: Homo sapiens
<220> FEATURE:
<223> OTHER INFORMATION: V-C entry TRAV8-2_TRAC

<400> SEQUENCE: 58

```
gccaccatgc tcctgctgct cgtcccagtg ctcgaggtga tttttactct gggaggaacc     60

agagcccagt cggtgaccca gcttgacagc cacgtctctg tctctgaagg aaccccggtg    120

ctgctgaggt gcaactactc atcttcttat tcaccatctc tcttctggta tgtgcaacac    180

cccaacaaag gactccagct tctcctgaag tacacatcag cggccaccct ggttaaaggc    240

atcaacggtt ttgaggctga atttaagaag agtgaaacct ccttccacct gacgaaaccc    300

tcagcccata tgagcgacgc ggctgagtac ttctgcagag accttgcggc cgcataggtc    360

tcaccagaac cctgaccctg ccgtgtacca gctgagagac tctaaatcca gtgacaagtc    420

tgtctgccta ttcaccgatt ttgattctca aacaaatgtg tcacaaagta aggattctga    480

tgtgtatatc acagacaaaa ctgtgctaga catgaggtct atggacttca agagcaacag    540

tgctgtggcc tggagcaaca aatctgactt tgcatgtgca aacgccttca acaacagcat    600

tattccagag gacaccttct tccccagccc agaaagttcc tgtgatgtca agctggtcga    660

gaaaagcttt gaaacagata cgaacctaaa ctttcaaaac ctgtcagtga ttgggttccg    720

aatcctcctc ctgaaagtgg ccgggtttaa tctgctcatg acgctgcggc tgtggtccag    780
```

ctga 784

<210> SEQ ID NO 59
<211> LENGTH: 784
<212> TYPE: DNA
<213> ORGANISM: Homo sapiens
<220> FEATURE:
<223> OTHER INFORMATION: V-C entry TRAV8-3_TRAC

<400> SEQUENCE: 59
gccaccatgc tcctggagct tatcccactg ctggggatac attttgtcct gagaactgcc 60
agagcccagt cagtgaccca gcctgacatc cacatcactg tctctgaagg agcctcactg 120
gagttgagat gtaactattc ctatggggca acaccttatc tcttctggta tgtccagtcc 180
cccggccaag gcctccagct gctcctgaag tacttttcag gagacactct ggttcaaggc 240
attaaaggct ttgaggctga atttaagagg agtcaatctt ccttcaatct gaggaaaccc 300
tctgtgcatt ggagtgatgc tgctgagtac ttctgcagag accttgcggc cgcataggtc 360
tcaccagaac cctgaccctg ccgtgtacca gctgagagac tctaaatcca gtgacaagtc 420
tgtctgccta ttcaccgatt ttgattctca aacaaatgtg tcacaaagta aggattctga 480
tgtgtatatc acagacaaaa ctgtgctaga catgaggtct atggacttca agagcaacag 540
tgctgtggcc tggagcaaca aatctgactt tgcatgtgca aacgccttca acaacagcat 600
tattccagag gacaccttct tccccagccc agaaagttcc tgtgatgtca agctggtcga 660
gaaaagcttt gaaacagata cgaacctaaa ctttcaaaac ctgtcagtga ttgggttccg 720
aatcctcctc ctgaaagtgg ccgggtttaa tctgctcatg acgctgcggc tgtggtccag 780
ctga 784

<210> SEQ ID NO 60
<211> LENGTH: 784
<212> TYPE: DNA
<213> ORGANISM: Homo sapiens
<220> FEATURE:
<223> OTHER INFORMATION: V-C entry TRAV8-4_TRAC

<400> SEQUENCE: 60
gccaccatgc tcctgctgct cgtcccagtg ctcgaggtga tttttaccct gggaggaacc 60
agagcccagt cggtgaccca gcttggcagc cacgtctctg tctctgaagg agccctggtt 120
ctgctgaggt gcaactactc atcgtctgtt ccaccatatc tcttctggta tgtgcaatac 180
cccaaccaag gactccagct tctcctgaag tacacatcag cggccaccct ggttaaaggc 240
atcaacggtt ttgaggctga atttaagaag agtgaaacct ccttccacct gacgaaaccc 300
tcagcccata tgagcgacgc ggctgagtac ttctgcagag accttgcggc cgcataggtc 360
tcaccagaac cctgaccctg ccgtgtacca gctgagagac tctaaatcca gtgacaagtc 420
tgtctgccta ttcaccgatt ttgattctca aacaaatgtg tcacaaagta aggattctga 480
tgtgtatatc acagacaaaa ctgtgctaga catgaggtct atggacttca agagcaacag 540
tgctgtggcc tggagcaaca aatctgactt tgcatgtgca aacgccttca acaacagcat 600
tattccagag gacaccttct tccccagccc agaaagttcc tgtgatgtca agctggtcga 660
gaaaagcttt gaaacagata cgaacctaaa ctttcaaaac ctgtcagtga ttgggttccg 720
aatcctcctc ctgaaagtgg ccgggtttaa tctgctcatg acgctgcggc tgtggtccag 780
ctga 784

<210> SEQ ID NO 61
<211> LENGTH: 784
<212> TYPE: DNA
<213> ORGANISM: Homo sapiens
<220> FEATURE:
<223> OTHER INFORMATION: V-C entry TRAV8-6_TRAC

<400> SEQUENCE: 61
gccaccatgc tcctgctgct cgtcccagcg ttccaggtga tttttaccct gggaggaacc 60
agagcccagt ctgtgaccca gcttgacagc caagtccctg tctttgaaga agcccctgtg 120
gagctgaggt gcaactactc atcgtctgtt tcagtgtatc tcttctggta tgtgcaatac 180
cccaaccaag gactccagct tctcctgaag tatttatcag gatccaccct ggttaaaggc 240
atcaacggtt ttgaggctga atttaacaag agtcaaactt ccttccactt gaggaaaccc 300
tcagtccata taagcgacac ggctgagtac ttctgcagag accttgcggc cgcataggtc 360
tcaccagaac cctgaccctg ccgtgtacca gctgagagac tctaaatcca gtgacaagtc 420
tgtctgccta ttcaccgatt ttgattctca aacaaatgtg tcacaaagta aggattctga 480
tgtgtatatc acagacaaaa ctgtgctaga catgaggtct atggacttca agagcaacag 540
tgctgtggcc tggagcaaca aatctgactt tgcatgtgca aacgccttca acaacagcat 600
tattccagag gacaccttct tccccagccc agaaagttcc tgtgatgtca agctggtcga 660
gaaaagcttt gaaacagata cgaacctaaa ctttcaaaac ctgtcagtga ttgggttccg 720
aatcctcctc ctgaaagtgg ccgggtttaa tctgctcatg acgctgcggc tgtggtccag 780
ctga 784

<210> SEQ ID NO 62
<211> LENGTH: 781
<212> TYPE: DNA
<213> ORGANISM: Homo sapiens
<220> FEATURE:
<223> OTHER INFORMATION: V-C entry TRAV8-7_TRAC

<400> SEQUENCE: 62
gccaccatgc tcttagtggt cattctgctg cttggaatgt tcttcacact gagaaccaga 60
acccagtcgg tgacccagct tgatggccac atcactgtct ctgaagaagc ccctctggaa 120
ctgaagtgca actattccta tagtggagtt ccttctctct tctggtatgt ccaatactct 180
agccaaagcc tccagcttct cctcaaagac ctaacagagg ccacccaggt taaaggcatc 240
agaggttttg aggctgaatt taagaagagc gaaacctcct tctacctgag gaaaccatca 300
acccatgtga gtgatgctgc tgagtacttc tgcagagacc ttgcggccgc ataggtctca 360
ccagaaccct gaccctgccg tgtaccagct gagagactct aaatccagtg acaagtctgt 420
ctgcctattc accgattttg attctcaaac aaatgtgtca caaagtaagg attctgatgt 480
gtatatcaca gacaaaactg tgctagacat gaggtctatg gacttcaaga gcaacagtgc 540
tgtggcctgg agcaacaaat ctgactttgc atgtgcaaac gccttcaaca acagcattat 600
tccagaggac accttcttcc ccagcccaga aagttcctgt gatgtcaagc tggtcgagaa 660
aagctttgaa acagatacga acctaaactt tcaaaacctg tcagtgattg ggttccgaat 720
cctcctcctg aaagtggccg ggtttaatct gctcatgacg ctgcggctgt ggtccagctg 780
a 781

<210> SEQ ID NO 63
<211> LENGTH: 781

<212> TYPE: DNA
<213> ORGANISM: Homo sapiens
<220> FEATURE:
<223> OTHER INFORMATION: V-C entry TRAV9-1_TRAC

<400> SEQUENCE: 63
gccaccatga attcttctcc aggaccagcg attgcactat tcttaatgtt tgggggaatc 60
aatggagatt cagtggtcca gacagaaggc caagtgctcc cctctgaagg ggattccctg 120
attgtgaact gctcctatga aaccacacag tacccttccc tttttggta tgtccaatat 180 cctggagaag gtccacagct ccacctgaaa gccatgaagg ccaatgacaa gggaaggaac 240
aaaggttttg aagccatgta ccgtaaagaa accacttctt tccacttgga gaaagactca 300
gttcaagagt cagactccgc tgtgtacttc tgcagagacc ttgcggccgc ataggtctca 360
ccagaaccct gaccctgccg tgtaccagct gagagactct aaatccagtg acaagtctgt 420
ctgcctattc accgattttg attctcaaac aaatgtgtca caaagtaagg attctgatgt 480
gtatatcaca gacaaaactg tgctagacat gaggtctatg gacttcaaga gcaacagtgc 540
tgtggcctgg agcaacaaat ctgactttgc atgtgcaaac gccttcaaca acagcattat 600
tccagaggac accttcttcc ccagcccaga aagttcctgt gatgtcaagc tggtcgagaa 660
aagctttgaa acagatacga acctaaactt tcaaaacctg tcagtgattg ggttccgaat 720
cctcctcctg aaagtggccg ggtttaatct gctcatgacg ctgcggctgt ggtccagctg 780
a 781

<210> SEQ ID NO 64
<211> LENGTH: 781
<212> TYPE: DNA
<213> ORGANISM: Homo sapiens
<220> FEATURE:
<223> OTHER INFORMATION: V-C entry TRAV9-2_TRAC

<400> SEQUENCE: 64
gccaccatga actattctcc aggcttagta tctctgatac tcttactgct tggaagaacc 60
cgtggaaatt cagtgaccca gatggaaggg ccagtgactc tctcagaaga ggccttcctg 120
actataaact gcacgtacac agccacagga tacccttccc ttttctggta tgtccaatat 180
cctggagaag gtctacagct cctcctgaaa gccacgaagg ctgatgacaa gggaagcaac 240
aaaggttttg aagccacata ccgtaaagaa accacttctt tccacttgga gaaaggctca 300
gttcaagtgt cagactcagc ggtgtacttc tgcagagacc ttgcggccgc ataggtctca 360
ccagaaccct gaccctgccg tgtaccagct gagagactct aaatccagtg acaagtctgt 420
ctgcctattc accgattttg attctcaaac aaatgtgtca caaagtaagg attctgatgt 480
gtatatcaca gacaaaactg tgctagacat gaggtctatg gacttcaaga gcaacagtgc 540
tgtggcctgg agcaacaaat ctgactttgc atgtgcaaac gccttcaaca acagcattat 600
tccagaggac accttcttcc ccagcccaga aagttcctgt gatgtcaagc tggtcgagaa 660
aagctttgaa acagatacga acctaaactt tcaaaacctg tcagtgattg ggttccgaat 720
cctcctcctg aaagtggccg ggtttaatct gctcatgacg ctgcggctgt ggtccagctg 780
a 781

<210> SEQ ID NO 65
<211> LENGTH: 787
<212> TYPE: DNA
<213> ORGANISM: Homo sapiens
<220> FEATURE:

<223> OTHER INFORMATION: V-C entry TRAV10_TRAC

<400> SEQUENCE: 65

```
gccaccatga aaaagcatct gacgaccttc ttggtgattt tgtggcttta tttttatagg     60
gggaatggca aaaaccaagt ggagcagagt cctcagtccc tgatcatcct ggagggaaag    120
aactgcactc ttcaatgcaa ttatacagtg agccccttca gcaacttaag gtggtataag    180
caagatactg ggagaggtcc tgtttccctg acaatcatga ctttcagtga gaacacaaag    240
tcgaacggaa gatatacagc aactctggat gcagacacaa agcaaagctc tctgcacatc    300
acagcctccc agctcagcga ttcagcctcc tacatctgca gagaccttgc ggccgcatag    360
gtctcaccag aaccctgacc ctgccgtgta ccagctgaga gactctaaat ccagtgacaa    420
gtctgtctgc ctattcaccg attttgattc tcaaacaaat gtgtcacaaa gtaaggattc    480
tgatgtgtat atcacagaca aaactgtgct agacatgagg tctatggact tcaagagcaa    540
cagtgctgtg gcctggagca acaaatctga ctttgcatgt gcaaacgcct tcaacaacag    600
cattattcca gaggacacct tcttccccag cccagaaagt tcctgtgatg tcaagctggt    660
cgagaaaagc tttgaaacag atacgaacct aaactttcaa aacctgtcag tgattgggtt    720
ccgaatcctc ctcctgaaag tggccgggtt taatctgctc atgacgctgc ggctgtggtc    780
cagctga                                                              787
```

<210> SEQ ID NO 66
<211> LENGTH: 781
<212> TYPE: DNA
<213> ORGANISM: Homo sapiens
<220> FEATURE:
<223> OTHER INFORMATION: V-C entry TRAV12-1_TRAC

<400> SEQUENCE: 66

```
gccaccatga tatccttgag agttttactg gtgatcctgt ggcttcagtt aagctgggtt     60
tggagccaac ggaaggaggt ggagcaggat cctggaccct tcaatgttcc agagggagcc    120
actgtcgctt tcaactgtac ttacagcaac agtgcttctc agtctttctt ctggtacaga    180
caggattgca ggaaagaacc taagttgctg atgtccgtat actccagtgg taatgaagat    240
ggaaggttta cagcacagct caatagagcc agccagtata tttccctgct catcagagac    300
tccaagctca gtgattcagc cacctacctc tgcagagacc ttgcggccgc ataggtctca    360
ccagaaccct gaccctgccg tgtaccagct gagagactct aaatccagtg acaagtctgt    420
ctgcctattc accgattttg attctcaaac aaatgtgtca caaagtaagg attctgatgt    480
gtatatcaca gacaaaactg tgctagacat gaggtctatg gacttcaaga gcaacagtgc    540
tgtggcctgg agcaacaaat ctgactttgc atgtgcaaac gccttcaaca acagcattat    600
tccagaggac accttcttcc ccagcccaga aagttcctgt gatgtcaagc tggtcgagaa    660
aagctttgaa acagatacga acctaaactt tcaaaacctg tcagtgattg ggttccgaat    720
cctcctcctg aaagtggccg ggtttaatct gctcatgacg ctgcggctgt ggtccagctg    780
a                                                                    781
```

<210> SEQ ID NO 67
<211> LENGTH: 787
<212> TYPE: DNA
<213> ORGANISM: Homo sapiens
<220> FEATURE:
<223> OTHER INFORMATION: V-C entry TRAV12-2_TRAC

<400> SEQUENCE: 67

```
gccaccatga tgaaatcctt gagagtttta ctagtgatcc tgtggcttca gttgagctgg     60

gtttggagcc aacagaagga ggtggagcag aattctggac ccctcagtgt tccagaggga    120

gccattgcct ctctcaactg cacttacagt gaccgaggtt cccagtcctt cttctggtac    180

agacaatatt ctgggaaaag ccctgagttg ataatgttca tatactccaa tggtgacaaa    240

gaagatggaa ggtttacagc acagctcaat aaagccagcc agtatgtttc tctgctcatc    300

agagactccc agcccagtga ttcagccacc tacctctgca gagaccttgc ggccgcatag    360

gtctcaccag aaccctgacc ctgccgtgta ccagctgaga gactctaaat ccagtgacaa    420

gtctgtctgc ctattcaccg attttgattc tcaaacaaat gtgtcacaaa gtaaggattc    480

tgatgtgtat atcacagaca aaactgtgct agacatgagg tctatggact tcaagagcaa    540

cagtgctgtg gcctggagca acaaatctga ctttgcatgt gcaaacgcct tcaacaacag    600

cattattcca gaggacacct tcttccccag cccagaaagt tcctgtgatg tcaagctggt    660

cgagaaaagc tttgaaacag atacgaacct aaactttcaa aacctgtcag tgattgggtt    720

ccgaatcctc ctcctgaaag tggccgggtt taatctgctc atgacgctgc ggctgtggtc    780

cagctga                                                              787
```

<210> SEQ ID NO 68
<211> LENGTH: 787
<212> TYPE: DNA
<213> ORGANISM: Homo sapiens
<220> FEATURE:
<223> OTHER INFORMATION: V-C entry TRAV12-3_TRAC

<400> SEQUENCE: 68

```
gccaccatga tgaaatcctt gagagtttta ctggtgatcc tgtggcttca gttaagctgg     60

gtttggagcc aacagaagga ggtggagcag gatcctggac cactcagtgt tccagaggga    120

gccattgttt ctctcaactg cacttacagc aacagtgctt ttcaatactt catgtggtac    180

agacagtatt ccagaaaagg ccctgagttg ctgatgtaca catactccag tggtaacaaa    240

gaagatggaa ggtttacagc acaggtcgat aaatccagca agtatatctc cttgttcatc    300

agagactcac agcccagtga ttcagccacc tacctctgca gagaccttgc ggccgcatag    360

gtctcaccag aaccctgacc ctgccgtgta ccagctgaga gactctaaat ccagtgacaa    420

gtctgtctgc ctattcaccg attttgattc tcaaacaaat gtgtcacaaa gtaaggattc    480

tgatgtgtat atcacagaca aaactgtgct agacatgagg tctatggact tcaagagcaa    540

cagtgctgtg gcctggagca acaaatctga ctttgcatgt gcaaacgcct tcaacaacag    600

cattattcca gaggacacct tcttccccag cccagaaagt tcctgtgatg tcaagctggt    660

cgagaaaagc tttgaaacag atacgaacct aaactttcaa aacctgtcag tgattgggtt    720

ccgaatcctc ctcctgaaag tggccgggtt taatctgctc atgacgctgc ggctgtggtc    780

cagctga                                                              787
```

<210> SEQ ID NO 69
<211> LENGTH: 781
<212> TYPE: DNA
<213> ORGANISM: Homo sapiens
<220> FEATURE:
<223> OTHER INFORMATION: V-C entry TRAV13-1_TRAC

<400> SEQUENCE: 69

```
gccaccatga catccattcg agctgtattt atattcctgt ggctgcagct ggacttggtg     60
```

```
aatggagaga atgtggagca gcatccttca accctgagtg tccaggaggg agacagcgct    120

gttatcaagt gtacttattc agacagtgcc tcaaactact tcccttggta taagcaagaa    180

cttggaaaag gacctcagct tattatagac attcgttcaa atgtgggcga aaagaaagac    240

caacgaattg ctgttacatt gaacaagaca gccaaacatt tctccctgca catcacagaa    300

acccaacctg aggactcggc tgtctacttc tgcagagacc ttgcggccgc ataggtctca    360

ccagaaccct gaccctgccg tgtaccagct gagagactct aaatccagtg acaagtctgt    420

ctgcctattc accgattttg attctcaaac aaatgtgtca caaagtaagg attctgatgt    480

gtatatcaca gacaaaactg tgctagacat gaggtctatg gacttcaaga gcaacagtgc    540

tgtggcctgg agcaacaaat ctgactttgc atgtgcaaac gccttcaaca acagcattat    600

tccagaggac accttcttcc ccagcccaga aagttcctgt gatgtcaagc tggtcgagaa    660

aagctttgaa acagatacga acctaaactt tcaaaacctg tcagtgattg ggttccgaat    720

cctcctcctg aaagtggccg ggtttaatct gctcatgacg ctgcggctgt ggtccagctg    780

a                                                                    781
```

<210> SEQ ID NO 70
<211> LENGTH: 784
<212> TYPE: DNA
<213> ORGANISM: Homo sapiens
<220> FEATURE:
<223> OTHER INFORMATION: V-C entry TRAV13-2_TRAC

<400> SEQUENCE: 70

```
gccaccatgg caggcattcg agctttattt atgtacttgt ggctgcagct ggactgggtg     60

agcagaggag agagtgtggg gctgcatctt cctaccctga gtgtccagga gggtgacaac    120

tctattatca actgtgctta ttcaaacagc gcctcagact acttcatttg gtacaagcaa    180

gaatctggaa aaggtcctca attcattata gacattcgtt caaatatgga caaaaggcaa    240

ggccaaagag tcaccgtttt attgaataag acagtgaaac atctctctct gcaaattgca    300

gctactcaac ctggagactc agctgtctac ttctgcagag accttgcggc cgcataggtc    360

tcaccagaac cctgaccctg ccgtgtacca gctgagagac tctaaatcca gtgacaagtc    420

tgtctgccta ttcaccgatt ttgattctca aacaaatgtg tcacaaagta aggattctga    480

tgtgtatatc acagacaaaa ctgtgctaga catgaggtct atggacttca agagcaacag    540

tgctgtggcc tggagcaaca aatctgactt tgcatgtgca aacgccttca acaacagcat    600

tattccagag gacaccttct tccccagccc agaaagttcc tgtgatgtca agctggtcga    660

gaaaagcttt gaaacagata cgaacctaaa ctttcaaaac ctgtcagtga ttgggttccg    720

aatcctcctc ctgaaagtgg ccgggtttaa tctgctcatg acgctgcggc tgtggtccag    780

ctga                                                                 784
```

<210> SEQ ID NO 71
<211> LENGTH: 790
<212> TYPE: DNA
<213> ORGANISM: Homo sapiens
<220> FEATURE:
<223> OTHER INFORMATION: V-C entry TRAV14DV4_TRAC

<400> SEQUENCE: 71

```
gccaccatgt cactttctag cctgctgaag gtggtcacag cttcactgtg gctaggacct     60

ggcattgccc agaagataac tcaaacccaa ccaggaatgt tcgtgcagga aaaggaggct    120

gtgactctgg actgcacata tgacaccagt gatcaaagtt atggtctatt ctggtacaag    180
```

```
cagcccagca gtggggaaat gatttttctt atttatcagg ggtcttatga cgagcaaaat    240

gcaacagaag gtcgctactc attgaatttc cagaaggcaa gaaaatccgc caaccttgtc    300

atctccgctt cacaactggg ggactcagca atgtatttct gcagagacct tgcggccgca    360

taggtctcac cagaaccctg accctgccgt gtaccagctg agagactcta aatccagtga    420

caagtctgtc tgcctattca ccgattttga ttctcaaaca aatgtgtcac aaagtaagga    480

ttctgatgtg tatatcacag acaaaactgt gctagacatg aggtctatgg acttcaagag    540

caacagtgct gtggcctgga gcaacaaatc tgactttgca tgtgcaaacg ccttcaacaa    600

cagcattatt ccagaggaca ccttcttccc cagcccagaa agttcctgtg atgtcaagct    660

ggtcgagaaa agctttgaaa cagatacgaa cctaaacttt caaaacctgt cagtgattgg    720

gttccgaatc ctcctcctga aagtggccgg gtttaatctg ctcatgacgc tgcggctgtg    780

gtccagctga                                                            790
```

<210> SEQ ID NO 72
<211> LENGTH: 772
<212> TYPE: DNA
<213> ORGANISM: Homo sapiens
<220> FEATURE:
<223> OTHER INFORMATION: V-C entry TRAV16_TRAC

<400> SEQUENCE: 72

```
gccaccatga agcccaccct catctcagtg cttgtgataa tatttatact cagaggaaca     60

agagcccaga gagtgactca gcccgagaag ctcctctctg tctttaaagg ggccccagtg    120

gagctgaagt gcaactattc ctattctggg agtcctgaac tcttctggta tgtccagtac    180

tccagacaac gcctccagtt actcttgaga cacatctcta gagagagcat caaaggcttc    240

actgctgacc ttaacaaagg cgagacatct ttccacctga agaaaccatt tgctcaagag    300

gaagattcag ccatgtatta ctgcagagac cttgcggccg cataggtctc accagaaccc    360

tgaccctgcc gtgtaccagc tgagagactc taaatccagt gacaagtctg tctgcctatt    420

caccgatttt gattctcaaa caaatgtgtc acaaagtaag gattctgatg tgtatatcac    480

agacaaaact gtgctagaca tgaggtctat ggacttcaag agcaacagtg ctgtggcctg    540

gagcaacaaa tctgactttg catgtgcaaa cgccttcaac aacagcatta ttccagagga    600

caccttcttc cccagcccag aaagttcctg tgatgtcaag ctggtcgaga aaagctttga    660

aacagatacg aacctaaact ttcaaaacct gtcagtgatt gggttccgaa tcctcctcct    720

gaaagtggcc gggtttaatc tgctcatgac gctgcggctg tggtccagct ga            772
```

<210> SEQ ID NO 73
<211> LENGTH: 781
<212> TYPE: DNA
<213> ORGANISM: Homo sapiens
<220> FEATURE:
<223> OTHER INFORMATION: V-C entry TRAV17_TRAC

<400> SEQUENCE: 73

```
gccaccatgg aaactctcct gggagtgtct ttggtgattc tatggcttca actggctagg     60

gtgaacagtc aacagggaga agaggatcct caggccttga gcatccagga gggtgaaaat    120

gccaccatga actgcagtta caaaactagt ataaacaatt tacagtggta tagacaaaat    180

tcaggtagag gccttgtcca cctaatttta atacgttcaa atgaaagaga gaaacacagt    240

ggaagattaa gagtcacgct tgacacttcc aagaaaagca gttccttgtt gatcacggct    300
```

```
tcccgggcag cagacactgc ttcttacttc tgcagagacc ttgcggccgc ataggtctca    360

ccagaaccct gaccctgccg tgtaccagct gagagactct aaatccagtg acaagtctgt    420

ctgcctattc accgattttg attctcaaac aaatgtgtca caaagtaagg attctgatgt    480

gtatatcaca gacaaaactg tgctagacat gaggtctatg gacttcaaga gcaacagtgc    540

tgtggcctgg agcaacaaat ctgactttgc atgtgcaaac gccttcaaca acagcattat    600

tccagaggac accttcttcc ccagcccaga aagttcctgt gatgtcaagc tggtcgagaa    660

aagctttgaa acagatacga acctaaactt tcaaaacctg tcagtgattg ggttccgaat    720

cctcctcctg aaagtggccg ggtttaatct gctcatgacg ctgcggctgt ggtccagctg    780

a                                                                    781
```

<210> SEQ ID NO 74
<211> LENGTH: 778
<212> TYPE: DNA
<213> ORGANISM: Homo sapiens
<220> FEATURE:
<223> OTHER INFORMATION: V-C entry TRAV18_TRAC

<400> SEQUENCE: 74

```
gccaccatgc tgtctgcttc ctgctcagga cttgtgatct tgttgatatt cagaaggacc     60

agtggagact cggttaccca gacagaaggc ccagttaccc tccctgagag ggcagctctg    120

acattaaact gcacttatca gtccagctat tcaacttttc tattctggta tgtccagtat    180

ctaaacaaag agcctgagct cctcctgaaa agttcagaaa accaggagac ggacagcaga    240

ggttttcagg ccagtcctat caagagtgac agttccttcc acctggagaa gccctcggtg    300

cagctgtcgg actctgccgt gtactactgc agagaccttg cggccgcata ggtctcacca    360

gaaccctgac cctgccgtgt accagctgag agactctaaa tccagtgaca agtctgtctg    420

cctattcacc gattttgatt ctcaaacaaa tgtgtcacaa agtaaggatt ctgatgtgta    480

tatcacagac aaaactgtgc tagacatgag gtctatggac ttcaagagca acagtgctgt    540

ggcctggagc aacaaatctg actttgcatg tgcaaacgcc ttcaacaaca gcattattcc    600

agaggacacc ttcttcccca gcccagaaag ttcctgtgat gtcaagctgg tcgagaaaag    660

ctttgaaaca gatacgaacc taaactttca aaacctgtca gtgattgggt tccgaatcct    720

cctcctgaaa gtggccgggt ttaatctgct catgacgctg cggctgtggt ccagctga      778
```

<210> SEQ ID NO 75
<211> LENGTH: 790
<212> TYPE: DNA
<213> ORGANISM: Homo sapiens
<220> FEATURE:
<223> OTHER INFORMATION: V-C entry TRAV19_TRAC

<400> SEQUENCE: 75

```
gccaccatgc tgactgccag cctgttgagg gcagtcatag cctccatctg tgttgtatcc     60

agcatggctc agaaggtaac tcaagcgcag actgaaattt ctgtggtgga gaaggaggat    120

gtgaccttgg actgtgtgta tgaaacccgt gatactactt attacttatt ctggtacaag    180

caaccaccaa gtggagaatt ggttttcctt attcgtcgga actcttttga tgagcaaaat    240

gaaataagtg gtcggtattc ttggaacttc cagaaatcca ccagttcctt caacttcacc    300

atcacagcct cacaagtcgt ggactcagca gtatacttct gcagagacct tgcggccgca    360

taggtctcac cagaaccctg accctgccgt gtaccagctg agagactcta aatccagtga    420

caagtctgtc tgcctattca ccgattttga ttctcaaaca aatgtgtcac aaagtaagga    480
```

```
ttctgatgtg tatatcacag acaaaactgt gctagacatg aggtctatgg acttcaagag    540

caacagtgct gtggcctgga gcaacaaatc tgactttgca tgtgcaaacg ccttcaacaa    600

cagcattatt ccagaggaca ccttcttccc cagcccagaa agttcctgtg atgtcaagct    660

ggtcgagaaa agctttgaaa cagatacgaa cctaaacttt caaaacctgt cagtgattgg    720

gttccgaatc ctcctcctga aagtggccgg gtttaatctg ctcatgacgc tgcggctgtg    780

gtccagctga                                                           790
```

```
<210> SEQ ID NO 76
<211> LENGTH: 781
<212> TYPE: DNA
<213> ORGANISM: Homo sapiens
<220> FEATURE:
<223> OTHER INFORMATION: V-C entry TRAV20_TRAC

<400> SEQUENCE: 76

gccaccatgg agaaaatgtt ggagtgtgca ttcatagtct tgtggcttca gcttggctgg     60

ttgagtggag aggaccaggt gacgcagagt cccgaggccc tgagactcca ggagggagag    120

agtagcagtc ttaactgcag ttacacagtc agcggtttaa gagggctgtt ctggtatagg    180

caagatcctg ggaaaggccc tgaattcctc ttcaccctgt attcagctgg ggaagaaaag    240

gagaaagaaa ggctaaaagc cacattaaca aagaaggaaa gctttctgca catcacagcc    300

cctaaacctg aggactcagc cacttatctc tgcagagacc ttgcggccgc ataggtctca    360

ccagaaccct gaccctgccg tgtaccagct gagagactct aaatccagtg acaagtctgt    420

ctgcctattc accgattttg attctcaaac aaatgtgtca caaagtaagg attctgatgt    480

gtatatcaca gacaaaactg tgctagacat gaggtctatg gacttcaaga gcaacagtgc    540

tgtggcctgg agcaacaaat ctgactttgc atgtgcaaac gccttcaaca acagcattat    600

tccagaggac accttcttcc ccagcccaga aagttcctgt gatgtcaagc tggtcgagaa    660

aagctttgaa acagatacga acctaaactt tcaaaacctg tcagtgattg ggttccgaat    720

cctcctcctg aaagtggccg ggtttaatct gctcatgacg ctgcggctgt ggtccagctg    780

a                                                                    781
```

```
<210> SEQ ID NO 77
<211> LENGTH: 781
<212> TYPE: DNA
<213> ORGANISM: Homo sapiens
<220> FEATURE:
<223> OTHER INFORMATION: V-C entry TRAV21_TRAC

<400> SEQUENCE: 77

gccaccatgg agaccctctt gggcctgctt atcctttggc tgcagctgca atgggtgagc     60

agcaaacagg aggtgacgca gattcctgca gctctgagtg tcccagaagg agaaaacttg    120

gttctcaact gcagtttcac tgatagcgct atttacaacc tccagtggtt taggcaggac    180

cctgggaaag gactcacatc tctgttgctt attcagtcaa gtcagagaga gcaaacaagt    240

ggacgcctta atgcctcgct ggataaatca tcaggacgta gtactttata cattgcagct    300

tctcagcctg gtgactcagc cacctacctc tgcagagacc ttgcggccgc ataggtctca    360

ccagaaccct gaccctgccg tgtaccagct gagagactct aaatccagtg acaagtctgt    420

ctgcctattc accgattttg attctcaaac aaatgtgtca caaagtaagg attctgatgt    480

gtatatcaca gacaaaactg tgctagacat gaggtctatg gacttcaaga gcaacagtgc    540
```

```
tgtggcctgg agcaacaaat ctgactttgc atgtgcaaac gccttcaaca acagcattat    600

tccagaggac accttcttcc ccagcccaga aagttcctgt gatgtcaagc tggtcgagaa    660

aagctttgaa acagatacga acctaaactt tcaaaacctg tcagtgattg ggttccgaat    720

cctcctcctg aaagtggccg ggtttaatct gctcatgacg ctgcggctgt ggtccagctg    780

a                                                                    781
```

<210> SEQ ID NO 78
<211> LENGTH: 775
<212> TYPE: DNA
<213> ORGANISM: Homo sapiens
<220> FEATURE:
<223> OTHER INFORMATION: V-C entry TRAV22_TRAC

<400> SEQUENCE: 78

```
gccaccatga agaggatatt gggagctctg ctggggctct tgagtgccca ggtttgctgt     60

gtgagaggaa tacaagtgga gcagagtcct ccagacctga ttctccagga gggagccaat    120

tccacgctgc ggtgcaattt ttctgactct gtgaacaatt tgcagtggtt tcatcaaaac    180

ccttggggac agctcatcaa cctgttttac attccctcag ggacaaaaca gaatggaaga    240

ttaagcgcca cgactgtcgc tacggaacgc tacagcttat tgtacatttc ctcttcccag    300

accacagact caggcgttta tttctgcaga gaccttgcgg ccgcataggt ctcaccagaa    360

ccctgaccct gccgtgtacc agctgagaga ctctaaatcc agtgacaagt ctgtctgcct    420

attcaccgat tttgattctc aaacaaatgt gtcacaaagt aaggattctg atgtgtatat    480

cacagacaaa actgtgctag acatgaggtc tatggacttc aagagcaaca gtgctgtggc    540

ctggagcaac aaatctgact ttgcatgtgc aaacgccttc aacaacagca ttattccaga    600

ggacaccttc ttccccagcc cagaaagttc ctgtgatgtc aagctggtcg agaaaagctt    660

tgaaacagat acgaacctaa actttcaaaa cctgtcagtg attgggttcc gaatcctcct    720

cctgaaagtg gccgggttta atctgctcat gacgctgcgg ctgtggtcca gctga         775
```

<210> SEQ ID NO 79
<211> LENGTH: 808
<212> TYPE: DNA
<213> ORGANISM: Homo sapiens
<220> FEATURE:
<223> OTHER INFORMATION: V-C entry TRAV23DV6_TRAC

<400> SEQUENCE: 79

```
gccaccatgg acaagatctt aggagcatca tttttagttc tgtggcttca actatgctgg     60

gtgagtggcc aacagaagga gaaaagtgac cagcagcagg tgaaacaaag tcctcaatct    120

ttgatagtcc agaaaggagg gatttcaatt ataaactgtg cttatgagaa cactgcgttt    180

gactactttc catggtacca acaattccct gggaaaggcc ctgcattatt gatagccata    240

cgtccagatg tgagtgaaaa gaaagaagga agattcacaa tctccttcaa taaaagtgcc    300

aagcagttct cattgcatat catggattcc cagcctggag actcagccac ctacttctgc    360

agagaccttg cggccgcata ggtctcacca gaaccctgac cctgccgtgt accagctgag    420

agactctaaa tccagtgaca agtctgtctg cctattcacc gattttgatt ctcaaacaaa    480

tgtgtcacaa agtaaggatt ctgatgtgta tatcacagac aaaactgtgc tagacatgag    540

gtctatggac ttcaagagca acagtgctgt ggcctggagc aacaaatctg actttgcatg    600

tgcaaacgcc ttcaacaaca gcattattcc agaggacacc ttcttcccca gcccagaaag    660

ttcctgtgat gtcaagctgg tcgagaaaag ctttgaaaca gatacgaacc taaactttca    720
```

aaacctgtca gtgattgggt tccgaatcct cctcctgaaa gtggccgggt ttaatctgct 780
catgacgctg cggctgtggt ccagctga 808

<210> SEQ ID NO 80
<211> LENGTH: 790
<212> TYPE: DNA
<213> ORGANISM: Homo sapiens
<220> FEATURE:
<223> OTHER INFORMATION: V-C entry TRAV24_TRAC

<400> SEQUENCE: 80
gccaccatgg agaagaatcc tttggcagcc ccattactaa tcctctggtt tcatcttgac 60
tgcgtgagca gcatactgaa cgtggaacaa agtcctcagt cactgcatgt tcaggaggga 120
gacagcacca atttcacctg cagcttccct tccagcaatt tttatgcctt acactggtac 180
agatgggaaa ctgcaaaaag ccccgaggcc ttgtttgtaa tgactttaaa tggggatgaa 240
aagaagaaag gacgaataag tgccactctt aataccaagg agggttacag ctatttgtac 300
atcaaaggat cccagcctga agattcagcc acatacctct gcagagacct tgcggccgca 360
taggtctcac cagaaccctg accctgccgt gtaccagctg agagactcta aatccagtga 420
caagtctgtc tgcctattca ccgattttga ttctcaaaca aatgtgtcac aaagtaagga 480
ttctgatgtg tatatcacag acaaaactgt gctagacatg aggtctatgg acttcaagag 540
caacagtgct gtggcctgga gcaacaaatc tgactttgca tgtgcaaacg ccttcaacaa 600
cagcattatt ccagaggaca ccttcttccc cagcccagaa agttcctgtg atgtcaagct 660
ggtcgagaaa agctttgaaa cagatacgaa cctaaacttt caaaacctgt cagtgattgg 720
gttccgaatc ctcctcctga aagtggccgg gtttaatctg ctcatgacgc tgcggctgtg 780
gtccagctga 790

<210> SEQ ID NO 81
<211> LENGTH: 775
<212> TYPE: DNA
<213> ORGANISM: Homo sapiens
<220> FEATURE:
<223> OTHER INFORMATION: V-C entry TRAV25_TRAC

<400> SEQUENCE: 81
gccaccatgc tactcatcac atcaatgttg gtcttatgga tgcaattgtc acaggtgaat 60
ggacaacagg taatgcaaat tcctcagtac cagcatgtac aagaaggaga ggacttcacc 120
acgtactgca attcctcaac tactttaagc aatatacagt ggtataagca aaggcctggt 180
ggacatcccg tattcttgat acagttagtg aagagtggag aagtgaagaa gcagaaaaga 240
ctgacatttc agtttggaga agcaaaaaag aacagctccc tgcacatcac agccacccag 300
actacagatg taggaaccta cttctgcaga gaccttgcgg ccgcataggt ctcaccagaa 360
ccctgaccct gccgtgtacc agctgagaga ctctaaatcc agtgacaagt ctgtctgcct 420
attcaccgat tttgattctc aaacaaatgt gtcacaaagt aaggattctg atgtgtatat 480
cacagacaaa actgtgctag acatgaggtc tatggacttc aagagcaaca gtgctgtggc 540
ctggagcaac aaatctgact ttgcatgtgc aaacgccttc aacaacagca ttattccaga 600
ggacaccttc ttccccagcc cagaaagttc ctgtgatgtc aagctggtcg agaaaagctt 660
tgaaacagat acgaacctaa actttcaaaa cctgtcagtg attgggttcc gaatcctcct 720
cctgaaagtg gccgggttta atctgctcat gacgctgcgg ctgtggtcca gctga 775

<210> SEQ ID NO 82
<211> LENGTH: 769
<212> TYPE: DNA
<213> ORGANISM: Homo sapiens
<220> FEATURE:
<223> OTHER INFORMATION: V-C entry TRAV26-1_TRAC

<400> SEQUENCE: 82

```
gccaccatga ggctggtggc aagagtaact gtgtttctga cctttggaac tataattgat     60
gctaagacca cccagccccc ctccatggat tgcgctgaag gaagagctgc aaacctgcct    120
tgtaatcact ctaccatcag tggaaatgag tatgtgtatt ggtatcgaca gattcactcc    180
caggggccac agtatatcat tcatggtcta aaaaacaatg aaaccaatga aatggcctct    240
ctgatcatca cagaagatag aaagtccagc accttgatcc tgccccacgc tacgctgaga    300
gacactgctg tgtactactg cagagacctt gcggccgcat aggtctcacc agaaccctga    360
ccctgccgtg taccagctga gagactctaa atccagtgac aagtctgtct gcctattcac    420
cgattttgat tctcaaacaa atgtgtcaca aagtaaggat tctgatgtgt atatcacaga    480
caaaactgtg ctagacatga ggtctatgga cttcaagagc aacagtgctg tggcctggag    540
caacaaatct gactttgcat gtgcaaacgc cttcaacaac agcattattc cagaggacac    600
cttcttcccc agcccagaaa gttcctgtga tgtcaagctg gtcgagaaaa gctttgaaac    660
agatacgaac ctaaactttc aaaacctgtc agtgattggg ttccgaatcc tcctcctgaa    720
agtggccggg tttaatctgc tcatgacgct gcggctgtgg tccagctga                769
```

<210> SEQ ID NO 83
<211> LENGTH: 769
<212> TYPE: DNA
<213> ORGANISM: Homo sapiens
<220> FEATURE:
<223> OTHER INFORMATION: V-C entry TRAV26-2_TRAC

<400> SEQUENCE: 83

```
gccaccatga agttggtgac aagcattact gtactcctat ctttgggtat tatgggtgat     60
gctaagacca cacagccaaa ttcaatggag agtaacgaag aagagcctgt tcacttgcct    120
tgtaaccact ccacaatcag tggaactgat tacatacatt ggtatcgaca gcttccctcc    180
cagggtccag agtacgtgat tcatggtctt acaagcaatg tgaacaacag aatggcctct    240
ctggcaatcg ctgaggacag aaagtccagt accttgatcc tgcaccgtgc taccttgaga    300
gatgctgctg tgtactactg cagagacctt gcggccgcat aggtctcacc agaaccctga    360
ccctgccgtg taccagctga gagactctaa atccagtgac aagtctgtct gcctattcac    420
cgattttgat tctcaaacaa atgtgtcaca aagtaaggat tctgatgtgt atatcacaga    480
caaaactgtg ctagacatga ggtctatgga cttcaagagc aacagtgctg tggcctggag    540
caacaaatct gactttgcat gtgcaaacgc cttcaacaac agcattattc cagaggacac    600
cttcttcccc agcccagaaa gttcctgtga tgtcaagctg gtcgagaaaa gctttgaaac    660
agatacgaac ctaaactttc aaaacctgtc agtgattggg ttccgaatcc tcctcctgaa    720
agtggccggg tttaatctgc tcatgacgct gcggctgtgg tccagctga                769
```

<210> SEQ ID NO 84
<211> LENGTH: 775
<212> TYPE: DNA
<213> ORGANISM: Homo sapiens
<220> FEATURE:
<223> OTHER INFORMATION: V-C entry TRAV27_TRAC

<400> SEQUENCE: 84

```
gccaccatgg tcctgaaatt ctccgtgtcc attctttgga ttcagttggc atgggtgagc     60
acccagctgc tggagcagag ccctcagttt ctaagcatcc aagagggaga aaatctcact    120
gtgtactgca actcctcaag tgtttttttcc agcttacaat ggtacagaca ggagcctggg    180
gaaggtcctg tcctcctggt gacagtagtt acgggtggag aagtgaagaa gctgaagaga    240
ctaacctttc agtttggtga tgcaagaaag gacagttctc tccacatcac tgcagcccag    300
cctggtgata caggcctcta cctctgcaga gaccttgcgg ccgcataggt ctcaccagaa    360
ccctgaccct gccgtgtacc agctgagaga ctctaaatcc agtgacaagt ctgtctgcct    420
attcaccgat tttgattctc aaacaaatgt gtcacaaagt aaggattctg atgtgtatat    480
cacagacaaa actgtgctag acatgaggtc tatggacttc aagagcaaca gtgctgtggc    540
ctggagcaac aaatctgact ttgcatgtgc aaacgccttc aacaacagca ttattccaga    600
ggacaccttc ttccccagcc cagaaagttc ctgtgatgtc aagctggtcg agaaaagctt    660
tgaaacagat acgaacctaa actttcaaaa cctgtcagtg attgggttcc gaatcctcct    720
cctgaaagtg gccgggttta atctgctcat gacgctgcgg ctgtggtcca gctga          775
```

<210> SEQ ID NO 85
<211> LENGTH: 802
<212> TYPE: DNA
<213> ORGANISM: Homo sapiens
<220> FEATURE:
<223> OTHER INFORMATION: V-C entry TRAV29DV5_TRAC

<400> SEQUENCE: 85

```
gccaccatgg ccatgctcct gggggcatca gtgctgattc tgtggcttca gccagactgg     60
gtaaacagtc aacagaagaa tgatgaccag caagttaagc aaaattcacc atccctgagc    120
gtccaggaag gaagaatttc tattctgaac tgtgactata ctaacagcat gtttgattat    180
ttcctatggt acaaaaaata ccctgctgaa ggtcctacat tcctgatatc tataagttcc    240
attaaggata aaaatgaaga tggaagattc actgttttct taaacaaaag tgccaagcac    300
ctctctctgc acattgtgcc ctcccagcct ggagactctg cagtgtactt ctgcagagac    360
cttgcggccg cataggtctc accagaaccc tgaccctgcc gtgtaccagc tgagagactc    420
taaatccagt gacaagtctg tctgcctatt caccgatttt gattctcaaa caaatgtgtc    480
acaaagtaag gattctgatg tgtatatcac agacaaaact gtgctagaca tgaggtctat    540
ggacttcaag agcaacagtg ctgtggcctg gagcaacaaa tctgactttg catgtgcaaa    600
cgccttcaac aacagcatta ttccagagga caccttcttc cccagcccag aaagttcctg    660
tgatgtcaag ctggtcgaga aaagctttga aacagatacg aacctaaact ttcaaaacct    720
gtcagtgatt gggttccgaa tcctcctcct gaaagtggcc gggtttaatc tgctcatgac    780
gctgcggctg tggtccagct ga                                             802
```

<210> SEQ ID NO 86
<211> LENGTH: 781
<212> TYPE: DNA
<213> ORGANISM: Homo sapiens
<220> FEATURE:
<223> OTHER INFORMATION: V-C entry TRAV30_TRAC

<400> SEQUENCE: 86

```
gccaccatgg agactctcct gaaagtgctt tcaggcacct tgttgtggca gttgacctgg     60
```

```
gtgagaagcc aacaaccagt gcagagtcct caagccgtga tcctccgaga aggggaagat    120

gctgtcatca actgcagttc ctccaaggct ttatattctg tacactggta caggcagaag    180

catggtgaag cacccgtttt cctgatgata ttactgaagg gtggagaaca gaagggtcat    240

gaaaaaatat ctgcttcatt taatgaaaaa aagcagcaaa gctccctgta ccttacggcc    300

tcccagctca gttactcagg aacctacttc tgcagagacc ttgcggccgc ataggtctca    360

ccagaaccct gaccctgccg tgtaccagct gagagactct aaatccagtg acaagtctgt    420

ctgcctattc accgattttg attctcaaac aaatgtgtca caaagtaagg attctgatgt    480

gtatatcaca gacaaaactg tgctagacat gaggtctatg gacttcaaga gcaacagtgc    540

tgtggcctgg agcaacaaat ctgactttgc atgtgcaaac gccttcaaca acagcattat    600

tccagaggac accttcttcc ccagcccaga aagttcctgt gatgtcaagc tggtcgagaa    660

aagctttgaa acagatacga acctaaactt tcaaaacctg tcagtgattg ggttccgaat    720

cctcctcctg aaagtggccg ggtttaatct gctcatgacg ctgcggctgt ggtccagctg    780

a                                                                    781
```

<210> SEQ ID NO 87
<211> LENGTH: 781
<212> TYPE: DNA
<213> ORGANISM: Homo sapiens
<220> FEATURE:
<223> OTHER INFORMATION: V-C entry TRAV34_TRAC

<400> SEQUENCE: 87

```
gccaccatgg agactgttct gcaagtactc ctagggatat tggggttcca agcagcctgg     60

gtcagtagcc aagaactgga gcagagtcct cagtccttga tcgtccaaga gggaaagaat    120

ctcaccataa actgcacgtc atcaaagacg ttatatggct tatactggta taagcaaaag    180

tatggtgaag gtcttatctt cttgatgatg ctacagaaag gtggggaaga gaaaagtcat    240

gaaaagataa ctgccaagtt ggatgagaaa aagcagcaaa gttccctgca tatcacagcc    300

tcccagccca gccatgcagg catctacctc tgcagagacc ttgcggccgc ataggtctca    360

ccagaaccct gaccctgccg tgtaccagct gagagactct aaatccagtg acaagtctgt    420

ctgcctattc accgattttg attctcaaac aaatgtgtca caaagtaagg attctgatgt    480

gtatatcaca gacaaaactg tgctagacat gaggtctatg gacttcaaga gcaacagtgc    540

tgtggcctgg agcaacaaat ctgactttgc atgtgcaaac gccttcaaca acagcattat    600

tccagaggac accttcttcc ccagcccaga aagttcctgt gatgtcaagc tggtcgagaa    660

aagctttgaa acagatacga acctaaactt tcaaaacctg tcagtgattg ggttccgaat    720

cctcctcctg aaagtggccg ggtttaatct gctcatgacg ctgcggctgt ggtccagctg    780

a                                                                    781
```

<210> SEQ ID NO 88
<211> LENGTH: 775
<212> TYPE: DNA
<213> ORGANISM: Homo sapiens
<220> FEATURE:
<223> OTHER INFORMATION: V-C entry TRAV35_TRAC

<400> SEQUENCE: 88

```
gccaccatgc tccttgaaca tttattaata atcttgtgga tgcagctgac atgggtcagt     60

ggtcaacagc tgaatcagag tcctcaatct atgtttatcc aggaaggaga agatgtctcc    120

atgaactgca cttcttcaag catatttaac acctggctat ggtacaagca ggaacctggg    180
```

```
gaaggtcctg tcctcttgat agccttatat aaggctggtg aattgacctc aaatggaagg    240
ctgactgctc agtttggtat aaccagaaag gacagcttcc tgaatatctc agcatccata    300
cctagtgatg taggcatcta cttctgcaga gaccttgcgg ccgcataggt ctcaccagaa    360
ccctgaccct gccgtgtacc agctgagaga ctctaaatcc agtgacaagt ctgtctgcct    420
attcaccgat tttgattctc aaacaaatgt gtcacaaagt aaggattctg atgtgtatat    480
cacagacaaa actgtgctag acatgaggtc tatggacttc aagagcaaca gtgctgtggc    540
ctggagcaac aaatctgact ttgcatgtgc aaacgccttc aacaacagca ttattccaga    600
ggacaccttc ttccccagcc cagaaagttc ctgtgatgtc aagctggtcg agaaaagctt    660
tgaaacagat acgaacctaa actttcaaaa cctgtcagtg attgggttcc gaatcctcct    720
cctgaaagtg gccgggttta atctgctcat gacgctgcgg ctgtggtcca gctga         775
```

<210> SEQ ID NO 89
<211> LENGTH: 784
<212> TYPE: DNA
<213> ORGANISM: Homo sapiens
<220> FEATURE:
<223> OTHER INFORMATION: V-C entry TRAV36DV7_TRAC

<400> SEQUENCE: 89

```
gccaccatga tgaagtgtcc acaggcttta ctagctatct tttggcttct actgagctgg     60
gtgagcagtg aagataaggt ggtacaaagc cctctatctc tggttgtcca cgagggagac    120
accgtaactc tcaattgcag ttatgaagtg actaactttc gaagcctact atggtacaag    180
caggaaaaga aagctcccac atttctattt atgctaactt caagtggaat tgaaaagaag    240
tcaggtagac taagtagcat attagataag aaagaacttt ccagcatcct gaacatcaca    300
gccacccaga ccggagactc ggccatctac ctctgcagag accttgcggc cgcataggtc    360
tcaccagaac cctgaccctg ccgtgtacca gctgagagac tctaaatcca gtgacaagtc    420
tgtctgccta ttcaccgatt ttgattctca aacaaatgtg tcacaaagta aggattctga    480
tgtgtatatc acagacaaaa ctgtgctaga catgaggtct atggacttca agagcaacag    540
tgctgtggcc tggagcaaca aatctgactt tgcatgtgca aacgccttca acaacagcat    600
tattccagag gacaccttct tccccagccc agaaagttcc tgtgatgtca agctggtcga    660
gaaaagcttt gaaacagata cgaacctaaa ctttcaaaac ctgtcagtga ttgggttccg    720
aatcctcctc ctgaaagtgg ccgggtttaa tctgctcatg acgctgcggc tgtggtccag    780
ctga                                                                 784
```

<210> SEQ ID NO 90
<211> LENGTH: 790
<212> TYPE: DNA
<213> ORGANISM: Homo sapiens
<220> FEATURE:
<223> OTHER INFORMATION: V-C entry TRAV38-1_TRAC

<400> SEQUENCE: 90

```
gccaccatga cacgagttag cttgctgtgg gcagtcgtgg tcagtacctg tcttgaatcc     60
ggcatggccc agacagtcac tcagtctcaa ccagagatgt ctgtgcagga ggcagagact    120
gtgaccctga gttgcacata tgacaccagt gagaataatt attatttgtt ctggtacaag    180
cagcctccca gcaggcagat gattctcgtt attcgccaag aagcttataa gcaacagaat    240
gcaacggaga atcgtttctc tgtgaacttc cagaaagcag ccaaatcctt cagtctcaag    300
```

```
atctcagact cacagctggg ggacactgcg atgtatttct gcagagacct tgcggccgca    360

taggtctcac cagaaccctg accctgccgt gtaccagctg agagactcta aatccagtga    420

caagtctgtc tgcctattca ccgattttga ttctcaaaca aatgtgtcac aaagtaagga    480

ttctgatgtg tatatcacag acaaaactgt gctagacatg aggtctatgg acttcaagag    540

caacagtgct gtggcctgga gcaacaaatc tgactttgca tgtgcaaacg ccttcaacaa    600

cagcattatt ccagaggaca ccttcttccc cagcccagaa agttcctgtg atgtcaagct    660

ggtcgagaaa agctttgaaa cagatacgaa cctaaacttt caaaacctgt cagtgattgg    720

gttccgaatc ctcctcctga aagtggccgg gtttaatctg ctcatgacgc tgcggctgtg    780

gtccagctga                                                           790


<210> SEQ ID NO 91
<211> LENGTH: 790
<212> TYPE: DNA
<213> ORGANISM: Homo sapiens
<220> FEATURE:
<223> OTHER INFORMATION: V-C entry TRAV38-2DV8_TRAC

<400> SEQUENCE: 91

gccaccatgg catgccctgg cttcctgtgg gcacttgtga tctccacctg tcttgaattt     60

agcatggctc agacagtcac tcagtctcaa ccagagatgt ctgtgcagga ggcagagacg    120

gtgaccctga gctgcacata tgacaccagt gagagtgatt attatttatt ctggtacaag    180

cagcctccca gcaggcagat gattctcgtt attcgccaag aagcttataa gcaacagaat    240

gcaacagaga atcgtttctc tgtgaacttc cagaaagcag ccaaatcctt cagtctcaag    300

atctcagact cacagctggg ggatgccgcg atgtatttct gcagagacct tgcggccgca    360

taggtctcac cagaaccctg accctgccgt gtaccagctg agagactcta aatccagtga    420

caagtctgtc tgcctattca ccgattttga ttctcaaaca aatgtgtcac aaagtaagga    480

ttctgatgtg tatatcacag acaaaactgt gctagacatg aggtctatgg acttcaagag    540

caacagtgct gtggcctgga gcaacaaatc tgactttgca tgtgcaaacg ccttcaacaa    600

cagcattatt ccagaggaca ccttcttccc cagcccagaa agttcctgtg atgtcaagct    660

ggtcgagaaa agctttgaaa cagatacgaa cctaaacttt caaaacctgt cagtgattgg    720

gttccgaatc ctcctcctga aagtggccgg gtttaatctg ctcatgacgc tgcggctgtg    780

gtccagctga                                                           790


<210> SEQ ID NO 92
<211> LENGTH: 775
<212> TYPE: DNA
<213> ORGANISM: Homo sapiens
<220> FEATURE:
<223> OTHER INFORMATION: V-C entry TRAV39_TRAC

<400> SEQUENCE: 92

gccaccatga agaagctact agcaatgatt ctgtggcttc aactagaccg gttaagtgga     60

gagctgaaag tggaacaaaa ccctctgttc ctgagcatgc aggagggaaa aaactatacc    120

atctactgca attattcaac cacttcagac agactgtatt ggtacaggca ggatcctggg    180

aaaagtctgg aatctctgtt tgtgttgcta tcaaatggag cagtgaagca ggagggacga    240

ttaatggcct cacttgatac caaagcccgt ctcagcaccc tccacatcac agctgccgtg    300

catgacctct ctgccaccta cttctgcaga gaccttgcgg ccgcataggt ctcaccagaa    360

ccctgaccct gccgtgtacc agctgagaga ctctaaatcc agtgacaagt ctgtctgcct    420
```

```
attcaccgat tttgattctc aaacaaatgt gtcacaaagt aaggattctg atgtgtatat    480

cacagacaaa actgtgctag acatgaggtc tatggacttc aagagcaaca gtgctgtggc    540

ctggagcaac aaatctgact ttgcatgtgc aaacgccttc aacaacagca ttattccaga    600

ggacaccttc ttccccagcc cagaaagttc ctgtgatgtc aagctggtcg agaaaagctt    660

tgaaacagat acgaacctaa actttcaaaa cctgtcagtg attgggttcc gaatcctcct    720

cctgaaagtg gccgggttta atctgctcat gacgctgcgg ctgtggtcca gctga         775
```

<210> SEQ ID NO 93
<211> LENGTH: 760
<212> TYPE: DNA
<213> ORGANISM: Homo sapiens
<220> FEATURE:
<223> OTHER INFORMATION: V-C entry TRAV40_TRAC

<400> SEQUENCE: 93

```
gccaccatga actcctctct ggactttcta attctgatct taatgtttgg aggaaccagc     60

agcaattcag tcaagcagac gggccaaata accgtctcgg agggagcatc tgtgactatg    120

aactgcacat acacatccac ggggtaccct accctttttct ggtatgtgga ataccccagc   180

aaacctctgc agcttcttca gagagagaca atggaaaaca gcaaaaactt cggaggcgga    240

aatattaaag acaaaaactc cccattgtg aaatattcag tccaggtatc agactcagcc     300

gtgtactact gcagagacct tgcggccgca taggtctcac cagaaccctg accctgccgt    360

gtaccagctg agagactcta aatccagtga caagtctgtc tgcctattca ccgattttga    420

ttctcaaaca aatgtgtcac aaagtaagga ttctgatgtg tatatcacag acaaaactgt    480

gctagacatg aggtctatgg acttcaagag caacagtgct gtggcctgga gcaacaaatc    540

tgactttgca tgtgcaaacg ccttcaacaa cagcattatt ccagaggaca ccttcttccc    600

cagcccagaa agttcctgtg atgtcaagct ggtcgagaaa agctttgaaa cagatacgaa    660

cctaaacttt caaaacctgt cagtgattgg gttccgaatc ctcctcctga aagtggccgg    720

gtttaatctg ctcatgacgc tgcggctgtg gtccagctga                          760
```

<210> SEQ ID NO 94
<211> LENGTH: 781
<212> TYPE: DNA
<213> ORGANISM: Homo sapiens
<220> FEATURE:
<223> OTHER INFORMATION: V-C entry TRAV41_TRAC

<400> SEQUENCE: 94

```
gccaccatgg tgaagatccg gcaatttttg ttggctattt tgtggcttca gctaagctgt     60

gtaagtgccg ccaaaaatga agtggagcag agtcctcaga acctgactgc ccaggaagga    120

gaatttatca caatcaactg cagttactcg gtaggaataa gtgccttaca ctggctgcaa    180

cagcatccag gaggaggcat tgtttccttg tttatgctga gctcagggaa gaagaagcat    240

ggaagattaa ttgccacaat aaacatacag gaaaagcaca gctccctgca catcacagcc    300

tcccatccca gagactctgc cgtctacatc tgcagagacc ttgcggccgc ataggtctca    360

ccagaaccct gaccctgccg tgtaccagct gagagactct aaatccagtg acaagtctgt    420

ctgcctattc accgattttg attctcaaac aaatgtgtca caaagtaagg attctgatgt    480

gtatatcaca gacaaaactg tgctagacat gaggtctatg gacttcaaga gcaacagtgc    540

tgtggcctgg agcaacaaat ctgactttgc atgtgcaaac gccttcaaca acagcattat    600
```

tccagaggac accttcttcc ccagcccaga aagttcctgt gatgtcaagc tggtcgagaa 660
aagctttgaa acagatacga acctaaactt tcaaaacctg tcagtgattg ggttccgaat 720
cctcctcctg aaagtggccg ggtttaatct gctcatgacg ctgcggctgt ggtccagctg 780
a 781

<210> SEQ ID NO 95
<211> LENGTH: 53
<212> TYPE: DNA
<213> ORGANISM: Artificial Sequence
<220> FEATURE:
<223> OTHER INFORMATION: TRAJ_receiving_F1

<400> SEQUENCE: 95
aattcggtct cgaagtcttc tgcggccgct gaagacacta tccagtgaga ccc 53

<210> SEQ ID NO 96
<211> LENGTH: 53
<212> TYPE: DNA
<213> ORGANISM: Artificial Sequence
<220> FEATURE:
<223> OTHER INFORMATION: TRAJ_receiving_R1

<400> SEQUENCE: 96
tcgagggtct cactggatag tgtcttcagc ggccgcagaa gacttcgaga ccg 53

<210> SEQ ID NO 97
<211> LENGTH: 2308
<212> TYPE: DNA
<213> ORGANISM: Artificial Sequence
<220> FEATURE:
<223> OTHER INFORMATION: J donor backbone

<400> SEQUENCE: 97
ctcgagctgg gcctcatggg ccttccgctc actgcccgct ttccagtcgg gaaacctgtc 60
gtgccagctg cattaacatg gtcatagctg tttccttgcg tattgggcgc tctccgcttc 120
ctcgctcact gactcgctgc gctcggtcgt tcgggtaaag cctggggtgc ctaatgagca 180
aaaggccagc aaaaggccag gaaccgtaaa aaggccgcgt tgctggcgtt tttccatagg 240
ctccgccccc ctgacgagca tcacaaaaat cgacgctcaa gtcagaggtg gcgaaacccg 300
acaggactat aaagatacca ggcgtttccc cctggaagct ccctcgtgcg ctctcctgtt 360
ccgaccctgc cgcttaccgg atacctgtcc gcctttctcc cttcgggaag cgtggcgctt 420
tctcatagct cacgctgtag gtatctcagt tcggtgtagg tcgttcgctc caagctgggc 480
tgtgtgcacg aaccccccgt tcagcccgac cgctgcgcct tatccggtaa ctatcgtctt 540
gagtccaacc cggtaagaca cgacttatcg ccactggcag cagccactgg taacaggatt 600
agcagagcga ggtatgtagg cggtgctaca gagttcttga agtggtggcc taactacggc 660
tacactagaa gaacagtatt tggtatctgc gctctgctga agccagttac cttcggaaaa 720
agagttggta gctcttgatc cggcaaacaa accaccgctg gtagcggtgg tttttttgtt 780
tgcaagcagc agattacgcg cagaaaaaaa ggatctcaag aagatccttt gatcttttct 840
acggggtctg acgctcagtg gaacgaaaac tcacgttaag ggattttggt catgagatta 900
tcaaaaagga tcttcaccta gatcctttta aattaaaaat gaagttttaa atcaatctaa 960
agtatatatg agtaaacttg gtctgacagt tagaaaaatt cgtccagcat cagatgaaat 1020
tgcagtttgt tcatgtccgg gttatcaata ccatatttct ggaacagacg tttctgcagg 1080
ctcgggctaa attcacccag acaattccac agaattgcca gatcctgata acgatctgca 1140

```
ataccaacac gaccaacatc aatgcagcca atcagtttac cctcatcaaa aatcaggtta   1200

tccaggctaa aatcaccatg ggtaacaacg ctatccggac taaacggcag cagtttatgc   1260

atttctttcc aaacctgttc aacaggccaa ccattacgtt catcatcaaa atcgcttgca   1320

tcaaccagac cattattcat acggctctgt gcctgtgcca gacgaaaaac acgatcgcta   1380

ttaaacggac aattacaaac cggaatgcta tgcagacgac gcagaaaaac tgccagtgca   1440

tcaacaatat tttcgcctga atccggatat tcttccagaa cctgaaatgc ggttttaccc   1500

ggaattgcgg tggtcagcag ccatgcatca tccggtgtac gaataaaatg tttaatggtc   1560

ggcagcggca taaattcggt cagccaattc agacgaacca tttcatcggt cacatcattt   1620

gcaacgctac ctttaccatg tttcagaaac agttccggtg catccggttt accatacaga   1680

cgataaatgg ttgcaccgct ctgaccaaca ttatcacgtg cccatttata gccatacaga   1740

tctgcatcca tattgctatt cagacgcgga cggctacagc tggtttcacg ctgaatatgg   1800

ctcatactct tcctttttca atattattga agcatttatc agggttattg tctcatgagc   1860

ggatacatat ttgaatgtat ttagaaaaat aaacaaatag gggttccgcg cacatttccc   1920

cgaaaagtgc cacctaaatt gtaagcgtta atattttgtt aaaattcgcg ttaaattttt   1980

gttaaatcag ctcatttttt aaccaatagg ccgaaatcgg caaaatccct tataaatcaa   2040

aagaatagac cgagataggg ttgagtggcc gctacagggc gctcccattc gccattcagg   2100

ctgcgcaact gttgggaagg gcgtttcggt gcgggcctct tcgctattac gccagctggc   2160

gaaaggggga tgtgctgcaa ggcgattaag ttgggtaacg ccagggtttt cccagtcacg   2220

acgttgtaaa acgacggcca gtgagcgcga cgtaatacga ctcactatag ggcgaattgg   2280

cggaaggccg tcaaggccgc atgaattc                                      2308
```

```
<210> SEQ ID NO 98
<211> LENGTH: 2355
<212> TYPE: DNA
<213> ORGANISM: Artificial Sequence
<220> FEATURE:
<223> OTHER INFORMATION: TRA J receiving cassette vector

<400> SEQUENCE: 98

cgctattacg ccagctggcg aaagggggat gtgctgcaag gcgattaagt tgggtaacgc     60

cagggttttc ccagtcacga cgttgtaaaa cgacggccag tgagcgcgac gtaatacgac    120

tcactatagg gcgaattggc ggaaggccgt caaggccgca tgaattcggt ctcgaagtct    180

tctgcggccg ctgaagacac tatccagtga gaccctcgag ctgggcctca tgggccttcc    240

gctcactgcc cgctttccag tcgggaaacc tgtcgtgcca gctgcattaa catggtcata    300

gctgtttcct tgcgtattgg gcgctctccg cttcctcgct cactgactcg ctgcgctcgg    360

tcgttcgggt aaagcctggg gtgcctaatg agcaaaaggc cagcaaaagg ccaggaaccg    420

taaaaaggcc gcgttgctgg cgtttttcca taggctccgc ccccctgacg agcatcacaa    480

aaatcgacgc tcaagtcaga ggtggcgaaa cccgacagga ctataaagat accaggcgtt    540

tccccctgga agctccctcg tgcgctctcc tgttccgacc ctgccgctta ccggatacct    600

gtccgccttt ctcccttcgg gaagcgtggc gctttctcat agctcacgct gtaggtatct    660

cagttcggtg taggtcgttc gctccaagct gggctgtgtg cacgaacccc ccgttcagcc    720

cgaccgctgc gccttatccg gtaactatcg tcttgagtcc aacccggtaa gacacgactt    780

atcgccactg gcagcagcca ctggtaacag gattagcaga gcgaggtatg taggcggtgc    840
```

```
tacagagttc ttgaagtggt ggcctaacta cggctacact agaagaacag tatttggtat    900
ctgcgctctg ctgaagccag ttaccttcgg aaaaagagtt ggtagctctt gatccggcaa    960
acaaaccacc gctggtagcg gtggtttttt tgtttgcaag cagcagatta cgcgcagaaa   1020
aaaaggatct caagaagatc ctttgatctt ttctacgggg tctgacgctc agtggaacga   1080
aaactcacgt taagggattt tggtcatgag attatcaaaa aggatcttca cctagatcct   1140
tttaaattaa aaatgaagtt ttaaatcaat ctaaagtata tatgagtaaa cttggtctga   1200
cagttagaaa aattcgtcca gcatcagatg aaattgcagt ttgttcatgt ccgggttatc   1260
aataccatat ttctggaaca gacgtttctg caggctcggg ctaaattcac ccagacaatt   1320
ccacagaatt gccagatcct gataacgatc tgcaatacca acacgaccaa catcaatgca   1380
gccaatcagt ttaccctcat caaaaatcag gttatccagg ctaaaatcac catgggtaac   1440
aacgctatcc ggactaaacg gcagcagttt atgcatttct ttccaaacct gttcaacagg   1500
ccaaccatta cgttcatcat caaaatcgct tgcatcaacc agaccattat tcatacggct   1560
ctgtgcctgt gccagacgaa aaacacgatc gctattaaac ggacaattac aaaccggaat   1620
gctatgcaga cgacgcagaa aaactgccag tgcatcaaca atattttcgc ctgaatccgg   1680
atattcttcc agaacctgaa atgcggtttt acccggaatt gcggtggtca gcagccatgc   1740
atcatccggt gtacgaataa aatgtttaat ggtcggcagc ggcataaatt cggtcagcca   1800
attcagacga accatttcat cggtcacatc atttgcaacg ctacctttac catgtttcag   1860
aaacagttcc ggtgcatccg gtttaccata cagacgataa atggttgcac cgctctgacc   1920
aacattatca cgtgcccatt tatagccata cagatctgca tccatattgc tattcagacg   1980
cggacggcta cagctggttt cacgctgaat atggctcata ctcttccttt ttcaatatta   2040
ttgaagcatt tatcagggtt attgtctcat gagcggatac atatttgaat gtatttagaa   2100
aaataaacaa ataggggttc cgcgcacatt tccccgaaaa gtgccaccta aattgtaagc   2160
gttaatattt tgttaaaatt cgcgttaaat ttttgttaaa tcagctcatt ttttaaccaa   2220
taggccgaaa tcggcaaaat cccttataaa tcaaaagaat agaccgagat agggttgagt   2280
ggccgctaca gggcgctccc attcgccatt caggctgcgc aactgttggg aagggcgttt   2340
cggtgcgggc ctctt                                                    2355
```

```
<210> SEQ ID NO 99
<211> LENGTH: 39
<212> TYPE: DNA
<213> ORGANISM: Homo sapiens
<220> FEATURE:
<223> OTHER INFORMATION: TRAJ1*01_BB-S_F1

<400> SEQUENCE: 99

ctcgtttggc aaaggaacca gagtttccac ttctcccca                             39


<210> SEQ ID NO 100
<211> LENGTH: 39
<212> TYPE: DNA
<213> ORGANISM: Homo sapiens
<220> FEATURE:
<223> OTHER INFORMATION: TRAJ2*01_BB-S_F1

<400> SEQUENCE: 100

ctcgtttggg aaagggaccc atgtattcat tatatctga                             39


<210> SEQ ID NO 101
<211> LENGTH: 39
```

<212> TYPE: DNA
<213> ORGANISM: Homo sapiens
<220> FEATURE:
<223> OTHER INFORMATION: TRAJ3*01_BB-S_F1

<400> SEQUENCE: 101
ctcgtttgga tcagggacca gactcagcat ccggccaaa 39

<210> SEQ ID NO 102
<211> LENGTH: 39
<212> TYPE: DNA
<213> ORGANISM: Homo sapiens
<220> FEATURE:
<223> OTHER INFORMATION: TRAJ4*01_BB-S_F1

<400> SEQUENCE: 102
ctcgtttgga gcagggacca ggctggctgt acacccata 39

<210> SEQ ID NO 103
<211> LENGTH: 39
<212> TYPE: DNA
<213> ORGANISM: Homo sapiens
<220> FEATURE:
<223> OTHER INFORMATION: TRAJ5*01_BB-S_F1

<400> SEQUENCE: 103
ctcgtttggg agtggaacaa gactccaagt gcaaccaaa 39

<210> SEQ ID NO 104
<211> LENGTH: 39
<212> TYPE: DNA
<213> ORGANISM: Homo sapiens
<220> FEATURE:
<223> OTHER INFORMATION: TRAJ6*01_BB-S_F1

<400> SEQUENCE: 104
ctcgtttgga agaggaacca gccttattgt tcatccgta 39

<210> SEQ ID NO 105
<211> LENGTH: 39
<212> TYPE: DNA
<213> ORGANISM: Homo sapiens
<220> FEATURE:
<223> OTHER INFORMATION: TRAJ7*01_BB-S_F1

<400> SEQUENCE: 105
ctcgtttggg aaggggaacc aagtggtggt cataccaaa 39

<210> SEQ ID NO 106
<211> LENGTH: 39
<212> TYPE: DNA
<213> ORGANISM: Homo sapiens
<220> FEATURE:
<223> OTHER INFORMATION: TRAJ8*01_BB-S_F1

<400> SEQUENCE: 106
ctcgtttgga actggcaccc gacttctggt cagtccaaa 39

<210> SEQ ID NO 107
<211> LENGTH: 39
<212> TYPE: DNA
<213> ORGANISM: Homo sapiens
<220> FEATURE:
<223> OTHER INFORMATION: TRAJ9*01_BB-S_F1

<400> SEQUENCE: 107
ctcgtttgga gcaggaacaa gactatttgt taaagcaaa 39

<210> SEQ ID NO 108
<211> LENGTH: 39
<212> TYPE: DNA
<213> ORGANISM: Homo sapiens
<220> FEATURE:
<223> OTHER INFORMATION: TRAJ10*01_BB-S_F1

<400> SEQUENCE: 108
ctcgtttggg acaggcactc agctaaaagt ggaactcaa 39

<210> SEQ ID NO 109
<211> LENGTH: 39
<212> TYPE: DNA
<213> ORGANISM: Homo sapiens
<220> FEATURE:
<223> OTHER INFORMATION: TRAJ11*01_BB-S_F1

<400> SEQUENCE: 109
ctcgtttggg aaggggacta tgcttctagt ctctccaga 39

<210> SEQ ID NO 110
<211> LENGTH: 39
<212> TYPE: DNA
<213> ORGANISM: Homo sapiens
<220> FEATURE:
<223> OTHER INFORMATION: TRAJ12*01_BB-S_F1

<400> SEQUENCE: 110
ctcgtttggg agtgggacca gactgctggt caggcctga 39

<210> SEQ ID NO 111
<211> LENGTH: 39
<212> TYPE: DNA
<213> ORGANISM: Homo sapiens
<220> FEATURE:
<223> OTHER INFORMATION: TRAJ13*01_BB-S_F1

<400> SEQUENCE: 111
ctcgtttgga attggaacaa agctccaagt catcccaaa 39

<210> SEQ ID NO 112
<211> LENGTH: 39
<212> TYPE: DNA
<213> ORGANISM: Homo sapiens
<220> FEATURE:
<223> OTHER INFORMATION: TRAJ14*01_BB-S_F1

<400> SEQUENCE: 112
ctcgtttggg agtgggacaa gattatcagt aaaacctga 39

<210> SEQ ID NO 113
<211> LENGTH: 39
<212> TYPE: DNA
<213> ORGANISM: Homo sapiens
<220> FEATURE:
<223> OTHER INFORMATION: TRAJ15*01_BB-S_F1

<400> SEQUENCE: 113
ctcgtttggg aagggaaccc acctatcagt gagttccaa 39

<210> SEQ ID NO 114
<211> LENGTH: 39
<212> TYPE: DNA
<213> ORGANISM: Homo sapiens

<220> FEATURE:
<223> OTHER INFORMATION: TRAJ16*01_BB-S_F1

<400> SEQUENCE: 114
ctcgtttgca aggggaacca tgttaaaggt ggatcttaa 39

<210> SEQ ID NO 115
<211> LENGTH: 39
<212> TYPE: DNA
<213> ORGANISM: Homo sapiens
<220> FEATURE:
<223> OTHER INFORMATION: TRAJ17*01_BB-S_F1

<400> SEQUENCE: 115
ctcgtttgga ggaggaacca gggtgctagt taaaccaaa 39

<210> SEQ ID NO 116
<211> LENGTH: 39
<212> TYPE: DNA
<213> ORGANISM: Homo sapiens
<220> FEATURE:
<223> OTHER INFORMATION: TRAJ18*01_BB-S_F1

<400> SEQUENCE: 116
ctcgtttgga agaggaactc agttgactgt ctggcctga 39

<210> SEQ ID NO 117
<211> LENGTH: 39
<212> TYPE: DNA
<213> ORGANISM: Homo sapiens
<220> FEATURE:
<223> OTHER INFORMATION: TRAJ19*01_BB-S_F1

<400> SEQUENCE: 117
ctcgtttgga aagggatcca aacataatgt cactccaaa 39

<210> SEQ ID NO 118
<211> LENGTH: 39
<212> TYPE: DNA
<213> ORGANISM: Homo sapiens
<220> FEATURE:
<223> OTHER INFORMATION: TRAJ20*01_BB-S_F1

<400> SEQUENCE: 118
ctcgtttgga gccggaacca cagtaactgt aagagcaaa 39

<210> SEQ ID NO 119
<211> LENGTH: 39
<212> TYPE: DNA
<213> ORGANISM: Homo sapiens
<220> FEATURE:
<223> OTHER INFORMATION: TRAJ21*01_BB-S_F1

<400> SEQUENCE: 119
ctcgtttgga tctgggacca aactcaatgt aaaaccaaa 39

<210> SEQ ID NO 120
<211> LENGTH: 39
<212> TYPE: DNA
<213> ORGANISM: Homo sapiens
<220> FEATURE:
<223> OTHER INFORMATION: TRAJ22*01_BB-S_F1

<400> SEQUENCE: 120
ctcgtttgga tctgggacac aattgactgt tttacctga 39

<210> SEQ ID NO 121
<211> LENGTH: 39
<212> TYPE: DNA
<213> ORGANISM: Homo sapiens
<220> FEATURE:
<223> OTHER INFORMATION: TRAJ23*01_BB-S_F1

<400> SEQUENCE: 121
ctcgtttgga cagggaacgg agttatctgt gaaacccaa 39

<210> SEQ ID NO 122
<211> LENGTH: 39
<212> TYPE: DNA
<213> ORGANISM: Homo sapiens
<220> FEATURE:
<223> OTHER INFORMATION: TRAJ24*01_BB-S_F1

<400> SEQUENCE: 122
ctcgtttgga gcagggaccc aggttgtggt caccccaga 39

<210> SEQ ID NO 123
<211> LENGTH: 39
<212> TYPE: DNA
<213> ORGANISM: Homo sapiens
<220> FEATURE:
<223> OTHER INFORMATION: TRAJ25*01_BB-S_F1

<400> SEQUENCE: 123
ctcgtttggg aaggggacaa ggctgcttgt caagccaaa 39

<210> SEQ ID NO 124
<211> LENGTH: 39
<212> TYPE: DNA
<213> ORGANISM: Homo sapiens
<220> FEATURE:
<223> OTHER INFORMATION: TRAJ26*01_BB-S_F1

<400> SEQUENCE: 124
ctcgtttggt cccggaacca gattgtccgt gctgcccta 39

<210> SEQ ID NO 125
<211> LENGTH: 39
<212> TYPE: DNA
<213> ORGANISM: Homo sapiens
<220> FEATURE:
<223> OTHER INFORMATION: TRAJ27*01_BB-S_F1

<400> SEQUENCE: 125
ctcgtttggg gatgggacta cgctcactgt gaagccaaa 39

<210> SEQ ID NO 126
<211> LENGTH: 39
<212> TYPE: DNA
<213> ORGANISM: Homo sapiens
<220> FEATURE:
<223> OTHER INFORMATION: TRAJ28*01_BB-S_F1

<400> SEQUENCE: 126
ctcgtttggg aaggggacca aactctcggt cataccaaa 39

<210> SEQ ID NO 127
<211> LENGTH: 39
<212> TYPE: DNA
<213> ORGANISM: Homo sapiens
<220> FEATURE:
<223> OTHER INFORMATION: TRAJ29*01_BB-S_F1

<400> SEQUENCE: 127
ctcgtttgga aagggcacaa gactttctgt gattgcaaa 39

<210> SEQ ID NO 128
<211> LENGTH: 39
<212> TYPE: DNA
<213> ORGANISM: Homo sapiens
<220> FEATURE:
<223> OTHER INFORMATION: TRAJ30*01_BB-S_F1

<400> SEQUENCE: 128
ctcgtttgga aaagggacac gacttcatat tctccccaa 39

<210> SEQ ID NO 129
<211> LENGTH: 39
<212> TYPE: DNA
<213> ORGANISM: Homo sapiens
<220> FEATURE:
<223> OTHER INFORMATION: TRAJ31*01_BB-S_F1

<400> SEQUENCE: 129
ctcgtttgga gatggaactc agctggtggt gaagcccaa 39

<210> SEQ ID NO 130
<211> LENGTH: 39
<212> TYPE: DNA
<213> ORGANISM: Homo sapiens
<220> FEATURE:
<223> OTHER INFORMATION: TRAJ32*01_BB-S_F1

<400> SEQUENCE: 130
ctcgtttgga actggcactc tgcttgctgt ccagccaaa 39

<210> SEQ ID NO 131
<211> LENGTH: 39
<212> TYPE: DNA
<213> ORGANISM: Homo sapiens
<220> FEATURE:
<223> OTHER INFORMATION: TRAJ33*01_BB-S_F1

<400> SEQUENCE: 131
ctcgtggggc gctgggacca agctaattat aaagccaga 39

<210> SEQ ID NO 132
<211> LENGTH: 38
<212> TYPE: DNA
<213> ORGANISM: Homo sapiens
<220> FEATURE:
<223> OTHER INFORMATION: TRAJ34*01_BB-S_F1

<400> SEQUENCE: 132
ctcgtttggg actgggacca gattacaagt ctttccaa 38

<210> SEQ ID NO 133
<211> LENGTH: 39
<212> TYPE: DNA
<213> ORGANISM: Homo sapiens
<220> FEATURE:
<223> OTHER INFORMATION: TRAJ36*01_BB-S_F1

<400> SEQUENCE: 133
ctcgtttggg actggaacga gactcaccgt tattcccta 39

<210> SEQ ID NO 134

<211> LENGTH: 39
<212> TYPE: DNA
<213> ORGANISM: Homo sapiens
<220> FEATURE:
<223> OTHER INFORMATION: TRAJ37*01_BB-S_F1

<400> SEQUENCE: 134
ctcgtttggg caagggacaa ctttacaagt aaaaccaga 39

<210> SEQ ID NO 135
<211> LENGTH: 39
<212> TYPE: DNA
<213> ORGANISM: Homo sapiens
<220> FEATURE:
<223> OTHER INFORMATION: TRAJ38*01_BB-S_F1

<400> SEQUENCE: 135
ctcgtgggga ttgggaacaa gcctggcagt aaatccgaa 39

<210> SEQ ID NO 136
<211> LENGTH: 39
<212> TYPE: DNA
<213> ORGANISM: Homo sapiens
<220> FEATURE:
<223> OTHER INFORMATION: TRAJ39*01_BB-S_F1

<400> SEQUENCE: 136
ctcgtttgga ggaggaacaa ggttaatggt caaacccca 39

<210> SEQ ID NO 137
<211> LENGTH: 39
<212> TYPE: DNA
<213> ORGANISM: Homo sapiens
<220> FEATURE:
<223> OTHER INFORMATION: TRAJ40*01_BB-S_F1

<400> SEQUENCE: 137
ctcgtttgga acaggcacca ggctgaaggt tttagcaaa 39

<210> SEQ ID NO 138
<211> LENGTH: 39
<212> TYPE: DNA
<213> ORGANISM: Homo sapiens
<220> FEATURE:
<223> OTHER INFORMATION: TRAJ41*01_BB-S_F1

<400> SEQUENCE: 138
ctcgtttggc aaaggcacct cgctgttggt cacaccccca 39

<210> SEQ ID NO 139
<211> LENGTH: 39
<212> TYPE: DNA
<213> ORGANISM: Homo sapiens
<220> FEATURE:
<223> OTHER INFORMATION: TRAJ42*01_BB-S_F1

<400> SEQUENCE: 139
ctcgtttgga aaaggcacta aactctctgt taaaccaaa 39

<210> SEQ ID NO 140
<211> LENGTH: 39
<212> TYPE: DNA
<213> ORGANISM: Homo sapiens
<220> FEATURE:
<223> OTHER INFORMATION: TRAJ43*01_BB-S_F1

<400> SEQUENCE: 140
ctcgtttgga gcagggacca gactgacagt aaaaccaaa 39

<210> SEQ ID NO 141
<211> LENGTH: 39
<212> TYPE: DNA
<213> ORGANISM: Homo sapiens
<220> FEATURE:
<223> OTHER INFORMATION: TRAJ44*01_BB-S_F1

<400> SEQUENCE: 141
ctcgtttggg actggaacaa gacttcaggt cacgctcga 39

<210> SEQ ID NO 142
<211> LENGTH: 39
<212> TYPE: DNA
<213> ORGANISM: Homo sapiens
<220> FEATURE:
<223> OTHER INFORMATION: TRAJ45*01_BB-S_F1

<400> SEQUENCE: 142
ctcgtttggc aaagggactc atctaatcat ccagcccta 39

<210> SEQ ID NO 143
<211> LENGTH: 39
<212> TYPE: DNA
<213> ORGANISM: Homo sapiens
<220> FEATURE:
<223> OTHER INFORMATION: TRAJ46*01_BB-S_F1

<400> SEQUENCE: 143
ctcgtttggg accgggactc gtttagcagt taggcccaa 39

<210> SEQ ID NO 144
<211> LENGTH: 39
<212> TYPE: DNA
<213> ORGANISM: Homo sapiens
<220> FEATURE:
<223> OTHER INFORMATION: TRAJ47*01_BB-S_F1

<400> SEQUENCE: 144
ctcgtttggc gcaggaacca ttctgagagt caagtccta 39

<210> SEQ ID NO 145
<211> LENGTH: 39
<212> TYPE: DNA
<213> ORGANISM: Homo sapiens
<220> FEATURE:
<223> OTHER INFORMATION: TRAJ48*01_BB-S_F1

<400> SEQUENCE: 145
ctcgtttggg actggaacaa gactcaccat catacccaa 39

<210> SEQ ID NO 146
<211> LENGTH: 39
<212> TYPE: DNA
<213> ORGANISM: Homo sapiens
<220> FEATURE:
<223> OTHER INFORMATION: TRAJ49*01_BB-S_F1

<400> SEQUENCE: 146
ctcgtttggg acagggacaa gtttgacggt cattccaaa 39

<210> SEQ ID NO 147
<211> LENGTH: 39
<212> TYPE: DNA

<213> ORGANISM: Homo sapiens
<220> FEATURE:
<223> OTHER INFORMATION: TRAJ50*01_BB-S_F1

<400> SEQUENCE: 147
ctcgtttggg ccagggacaa gcttatcagt cattccaaa 39

<210> SEQ ID NO 148
<211> LENGTH: 39
<212> TYPE: DNA
<213> ORGANISM: Homo sapiens
<220> FEATURE:
<223> OTHER INFORMATION: TRAJ52*01_BB-S_F1

<400> SEQUENCE: 148
ctcgtttgga caagggacca tcttgactgt ccatccaaa 39

<210> SEQ ID NO 149
<211> LENGTH: 39
<212> TYPE: DNA
<213> ORGANISM: Homo sapiens
<220> FEATURE:
<223> OTHER INFORMATION: TRAJ53*01_BB-S_F1

<400> SEQUENCE: 149
ctcgtttgga aaaggaactc tcttaaccgt gaatccaaa 39

<210> SEQ ID NO 150
<211> LENGTH: 39
<212> TYPE: DNA
<213> ORGANISM: Homo sapiens
<220> FEATURE:
<223> OTHER INFORMATION: TRAJ54*01_BB-S_F1

<400> SEQUENCE: 150
ctcgtttggc caaggaacca ggctgactat caacccaaa 39

<210> SEQ ID NO 151
<211> LENGTH: 39
<212> TYPE: DNA
<213> ORGANISM: Homo sapiens
<220> FEATURE:
<223> OTHER INFORMATION: TRAJ56*01_BB-S_F1

<400> SEQUENCE: 151
ctcgtttgga aaaggaataa ctctgagtgt tagaccaga 39

<210> SEQ ID NO 152
<211> LENGTH: 39
<212> TYPE: DNA
<213> ORGANISM: Homo sapiens
<220> FEATURE:
<223> OTHER INFORMATION: TRAJ57*01_BB-S_F1

<400> SEQUENCE: 152
ctcgtttgga aagggaacga aactgacagt aaacccata 39

<210> SEQ ID NO 153
<211> LENGTH: 33
<212> TYPE: DNA
<213> ORGANISM: Homo sapiens
<220> FEATURE:
<223> OTHER INFORMATION: TRAJ59*01_BB-S_F1

<400> SEQUENCE: 153
ctcgtttgga atggggacgc aagtgagagt gaa 33

<210> SEQ ID NO 154
<211> LENGTH: 39
<212> TYPE: DNA
<213> ORGANISM: Homo sapiens
<220> FEATURE:
<223> OTHER INFORMATION: TRAJ61*01_BB-S_F1

<400> SEQUENCE: 154
ctcgtttgga gccaacacta gaggaatcat gaaactcaa 39

<210> SEQ ID NO 155
<211> LENGTH: 39
<212> TYPE: DNA
<213> ORGANISM: Homo sapiens
<220> FEATURE:
<223> OTHER INFORMATION: TRAJ1*01_BB-S_R1

<400> SEQUENCE: 155
gatatgggga gaagtggaaa ctctggttcc tttgccaaa 39

<210> SEQ ID NO 156
<211> LENGTH: 39
<212> TYPE: DNA
<213> ORGANISM: Homo sapiens
<220> FEATURE:
<223> OTHER INFORMATION: TRAJ2*01_BB-S_R1

<400> SEQUENCE: 156
gatatcagat ataatgaata catgggtccc tttcccaaa 39

<210> SEQ ID NO 157
<211> LENGTH: 39
<212> TYPE: DNA
<213> ORGANISM: Homo sapiens
<220> FEATURE:
<223> OTHER INFORMATION: TRAJ3*01_BB-S_R1

<400> SEQUENCE: 157
gatatttggc cggatgctga gtctggtccc tgatccaaa 39

<210> SEQ ID NO 158
<211> LENGTH: 39
<212> TYPE: DNA
<213> ORGANISM: Homo sapiens
<220> FEATURE:
<223> OTHER INFORMATION: TRAJ4*01_BB-S_R1

<400> SEQUENCE: 158
gatatatggg tgtacagcca gcctggtccc tgctccaaa 39

<210> SEQ ID NO 159
<211> LENGTH: 39
<212> TYPE: DNA
<213> ORGANISM: Homo sapiens
<220> FEATURE:
<223> OTHER INFORMATION: TRAJ5*01_BB-S_R1

<400> SEQUENCE: 159
gatatttggt tgcacttgga gtcttgttcc actcccaaa 39

<210> SEQ ID NO 160
<211> LENGTH: 39
<212> TYPE: DNA
<213> ORGANISM: Homo sapiens
<220> FEATURE:

<223> OTHER INFORMATION: TRAJ6*01_BB-S_R1

<400> SEQUENCE: 160
gatatacgga tgaacaataa ggctggttcc tcttccaaa 39

<210> SEQ ID NO 161
<211> LENGTH: 39
<212> TYPE: DNA
<213> ORGANISM: Homo sapiens
<220> FEATURE:
<223> OTHER INFORMATION: TRAJ7*01_BB-S_R1

<400> SEQUENCE: 161
gatatttggt atgaccacca cttggttccc cttcccaaa 39

<210> SEQ ID NO 162
<211> LENGTH: 39
<212> TYPE: DNA
<213> ORGANISM: Homo sapiens
<220> FEATURE:
<223> OTHER INFORMATION: TRAJ8*01_BB-S_R1

<400> SEQUENCE: 162
gatatttgga ctgaccagaa gtcgggtgcc agttccaaa 39

<210> SEQ ID NO 163
<211> LENGTH: 39
<212> TYPE: DNA
<213> ORGANISM: Homo sapiens
<220> FEATURE:
<223> OTHER INFORMATION: TRAJ9*01_BB-S_R1

<400> SEQUENCE: 163
gatatttgct ttaacaaata gtcttgttcc tgctccaaa 39

<210> SEQ ID NO 164
<211> LENGTH: 39
<212> TYPE: DNA
<213> ORGANISM: Homo sapiens
<220> FEATURE:
<223> OTHER INFORMATION: TRAJ10*01_BB-S_R1

<400> SEQUENCE: 164
gatattgagt tccactttta gctgagtgcc tgtcccaaa 39

<210> SEQ ID NO 165
<211> LENGTH: 39
<212> TYPE: DNA
<213> ORGANISM: Homo sapiens
<220> FEATURE:
<223> OTHER INFORMATION: TRAJ11*01_BB-S_R1

<400> SEQUENCE: 165
gatatctgga gagactagaa gcatagtccc cttcccaaa 39

<210> SEQ ID NO 166
<211> LENGTH: 39
<212> TYPE: DNA
<213> ORGANISM: Homo sapiens
<220> FEATURE:
<223> OTHER INFORMATION: TRAJ12*01_BB-S_R1

<400> SEQUENCE: 166
gatatcaggc ctgaccagca gtctggtccc actcccaaa 39

<210> SEQ ID NO 167
<211> LENGTH: 39
<212> TYPE: DNA
<213> ORGANISM: Homo sapiens
<220> FEATURE:
<223> OTHER INFORMATION: TRAJ13*01_BB-S_R1

<400> SEQUENCE: 167
gatatttggg atgacttgga gctttgttcc aattccaaa 39

<210> SEQ ID NO 168
<211> LENGTH: 39
<212> TYPE: DNA
<213> ORGANISM: Homo sapiens
<220> FEATURE:
<223> OTHER INFORMATION: TRAJ14*01_BB-S_R1

<400> SEQUENCE: 168
gatatcaggt tttactgata atcttgtccc actcccaaa 39

<210> SEQ ID NO 169
<211> LENGTH: 39
<212> TYPE: DNA
<213> ORGANISM: Homo sapiens
<220> FEATURE:
<223> OTHER INFORMATION: TRAJ15*01_BB-S_R1

<400> SEQUENCE: 169
gatattggaa ctcactgata ggtgggttcc cttcccaaa 39

<210> SEQ ID NO 170
<211> LENGTH: 39
<212> TYPE: DNA
<213> ORGANISM: Homo sapiens
<220> FEATURE:
<223> OTHER INFORMATION: TRAJ16*01_BB-S_R1

<400> SEQUENCE: 170
gatattaaga tccaccttta acatggttcc ccttgcaaa 39

<210> SEQ ID NO 171
<211> LENGTH: 39
<212> TYPE: DNA
<213> ORGANISM: Homo sapiens
<220> FEATURE:
<223> OTHER INFORMATION: TRAJ17*01_BB-S_R1

<400> SEQUENCE: 171
gatatttggt ttaactagca ccctggttcc tcctccaaa 39

<210> SEQ ID NO 172
<211> LENGTH: 39
<212> TYPE: DNA
<213> ORGANISM: Homo sapiens
<220> FEATURE:
<223> OTHER INFORMATION: TRAJ18*01_BB-S_R1

<400> SEQUENCE: 172
gatatcaggc cagacagtca actgagttcc tcttccaaa 39

<210> SEQ ID NO 173
<211> LENGTH: 39
<212> TYPE: DNA
<213> ORGANISM: Homo sapiens
<220> FEATURE:
<223> OTHER INFORMATION: TRAJ19*01_BB-S_R1

<400> SEQUENCE: 173
gatatttgga gtgacattat gtttggatcc ctttccaaa 39

<210> SEQ ID NO 174
<211> LENGTH: 39
<212> TYPE: DNA
<213> ORGANISM: Homo sapiens
<220> FEATURE:
<223> OTHER INFORMATION: TRAJ20*01_BB-S_R1

<400> SEQUENCE: 174
gatatttgct cttacagtta ctgtggttcc ggctccaaa 39

<210> SEQ ID NO 175
<211> LENGTH: 39
<212> TYPE: DNA
<213> ORGANISM: Homo sapiens
<220> FEATURE:
<223> OTHER INFORMATION: TRAJ21*01_BB-S_R1

<400> SEQUENCE: 175
gatatttggt tttacattga gtttggtccc agatccaaa 39

<210> SEQ ID NO 176
<211> LENGTH: 39
<212> TYPE: DNA
<213> ORGANISM: Homo sapiens
<220> FEATURE:
<223> OTHER INFORMATION: TRAJ22*01_BB-S_R1

<400> SEQUENCE: 176
gatatcaggt aaaacagtca attgtgtccc agatccaaa 39

<210> SEQ ID NO 177
<211> LENGTH: 39
<212> TYPE: DNA
<213> ORGANISM: Homo sapiens
<220> FEATURE:
<223> OTHER INFORMATION: TRAJ23*01_BB-S_R1

<400> SEQUENCE: 177
gatattgggt ttcacagata actccgttcc ctgtccaaa 39

<210> SEQ ID NO 178
<211> LENGTH: 39
<212> TYPE: DNA
<213> ORGANISM: Homo sapiens
<220> FEATURE:
<223> OTHER INFORMATION: TRAJ24*01_BB-S_R1

<400> SEQUENCE: 178
gatatctggg gtgaccacaa cctgggtccc tgctccaaa 39

<210> SEQ ID NO 179
<211> LENGTH: 39
<212> TYPE: DNA
<213> ORGANISM: Homo sapiens
<220> FEATURE:
<223> OTHER INFORMATION: TRAJ25*01_BB-S_R1

<400> SEQUENCE: 179
gatatttggc ttgacaagca gccttgtccc cttcccaaa 39

<210> SEQ ID NO 180
<211> LENGTH: 39

<212> TYPE: DNA
<213> ORGANISM: Homo sapiens
<220> FEATURE:
<223> OTHER INFORMATION: TRAJ26*01_BB-S_R1

<400> SEQUENCE: 180
gatatagggc agcacggaca atctggttcc gggaccaaa 39

<210> SEQ ID NO 181
<211> LENGTH: 39
<212> TYPE: DNA
<213> ORGANISM: Homo sapiens
<220> FEATURE:
<223> OTHER INFORMATION: TRAJ27*01_BB-S_R1

<400> SEQUENCE: 181
gatatttggc ttcacagtga gcgtagtccc atccccaaa 39

<210> SEQ ID NO 182
<211> LENGTH: 39
<212> TYPE: DNA
<213> ORGANISM: Homo sapiens
<220> FEATURE:
<223> OTHER INFORMATION: TRAJ28*01_BB-S_R1

<400> SEQUENCE: 182
gatatttggt atgaccgaga gtttggtccc cttcccaaa 39

<210> SEQ ID NO 183
<211> LENGTH: 39
<212> TYPE: DNA
<213> ORGANISM: Homo sapiens
<220> FEATURE:
<223> OTHER INFORMATION: TRAJ29*01_BB-S_R1

<400> SEQUENCE: 183
gatatttgca atcacagaaa gtcttgtgcc ctttccaaa 39

<210> SEQ ID NO 184
<211> LENGTH: 39
<212> TYPE: DNA
<213> ORGANISM: Homo sapiens
<220> FEATURE:
<223> OTHER INFORMATION: TRAJ30*01_BB-S_R1

<400> SEQUENCE: 184
gatattgggg agaatatgaa gtcgtgtccc ttttccaaa 39

<210> SEQ ID NO 185
<211> LENGTH: 39
<212> TYPE: DNA
<213> ORGANISM: Homo sapiens
<220> FEATURE:
<223> OTHER INFORMATION: TRAJ31*01_BB-S_R1

<400> SEQUENCE: 185
gatattgggc ttcaccacca gctgagttcc atctccaaa 39

<210> SEQ ID NO 186
<211> LENGTH: 39
<212> TYPE: DNA
<213> ORGANISM: Homo sapiens
<220> FEATURE:
<223> OTHER INFORMATION: TRAJ32*01_BB-S_R1

<400> SEQUENCE: 186
gatatttggc tggacagcaa gcagagtgcc agttccaaa 39

<210> SEQ ID NO 187
<211> LENGTH: 39
<212> TYPE: DNA
<213> ORGANISM: Homo sapiens
<220> FEATURE:
<223> OTHER INFORMATION: TRAJ33*01_BB-S_R1

<400> SEQUENCE: 187
gatatctggc tttataatta gcttggtccc agcgcccca 39

<210> SEQ ID NO 188
<211> LENGTH: 39
<212> TYPE: DNA
<213> ORGANISM: Homo sapiens
<220> FEATURE:
<223> OTHER INFORMATION: TRAJ34*01_BB-S_R1

<400> SEQUENCE: 188
gatatttgga aagacttgta atctggtccc agtcccaaa 39

<210> SEQ ID NO 189
<211> LENGTH: 39
<212> TYPE: DNA
<213> ORGANISM: Homo sapiens
<220> FEATURE:
<223> OTHER INFORMATION: TRAJ36*01_BB-S_R1

<400> SEQUENCE: 189
gatataggga ataacggtga gtctcgttcc agtcccaaa 39

<210> SEQ ID NO 190
<211> LENGTH: 39
<212> TYPE: DNA
<213> ORGANISM: Homo sapiens
<220> FEATURE:
<223> OTHER INFORMATION: TRAJ37*01_BB-S_R1

<400> SEQUENCE: 190
gatatctggt tttacttgta aagttgtccc ttgcccaaa 39

<210> SEQ ID NO 191
<211> LENGTH: 39
<212> TYPE: DNA
<213> ORGANISM: Homo sapiens
<220> FEATURE:
<223> OTHER INFORMATION: TRAJ38*01_BB-S_R1

<400> SEQUENCE: 191
gatattcgga tttactgcca ggcttgttcc caatcccca 39

<210> SEQ ID NO 192
<211> LENGTH: 39
<212> TYPE: DNA
<213> ORGANISM: Homo sapiens
<220> FEATURE:
<223> OTHER INFORMATION: TRAJ39*01_BB-S_R1

<400> SEQUENCE: 192
gatatggggt ttgaccatta accttgttcc tcctccaaa 39

<210> SEQ ID NO 193
<211> LENGTH: 39
<212> TYPE: DNA
<213> ORGANISM: Homo sapiens

<220> FEATURE:
<223> OTHER INFORMATION: TRAJ40*01_BB-S_R1

<400> SEQUENCE: 193
gatatttgct aaaaccttca gcctggtgcc tgttccaaa 39

<210> SEQ ID NO 194
<211> LENGTH: 39
<212> TYPE: DNA
<213> ORGANISM: Homo sapiens
<220> FEATURE:
<223> OTHER INFORMATION: TRAJ41*01_BB-S_R1

<400> SEQUENCE: 194
gatatggggt gtgaccaaca gcgaggtgcc tttgccaaa 39

<210> SEQ ID NO 195
<211> LENGTH: 39
<212> TYPE: DNA
<213> ORGANISM: Homo sapiens
<220> FEATURE:
<223> OTHER INFORMATION: TRAJ42*01_BB-S_R1

<400> SEQUENCE: 195
gatatttggt ttaacagaga gtttagtgcc ttttccaaa 39

<210> SEQ ID NO 196
<211> LENGTH: 39
<212> TYPE: DNA
<213> ORGANISM: Homo sapiens
<220> FEATURE:
<223> OTHER INFORMATION: TRAJ43*01_BB-S_R1

<400> SEQUENCE: 196
gatatttggt tttactgtca gtctggtccc tgctccaaa 39

<210> SEQ ID NO 197
<211> LENGTH: 39
<212> TYPE: DNA
<213> ORGANISM: Homo sapiens
<220> FEATURE:
<223> OTHER INFORMATION: TRAJ44*01_BB-S_R1

<400> SEQUENCE: 197
gatatcgagc gtgacctgaa gtcttgttcc agtcccaaa 39

<210> SEQ ID NO 198
<211> LENGTH: 39
<212> TYPE: DNA
<213> ORGANISM: Homo sapiens
<220> FEATURE:
<223> OTHER INFORMATION: TRAJ45*01_BB-S_R1

<400> SEQUENCE: 198
gatatagggc tggatgatta gatgagtccc tttgccaaa 39

<210> SEQ ID NO 199
<211> LENGTH: 39
<212> TYPE: DNA
<213> ORGANISM: Homo sapiens
<220> FEATURE:
<223> OTHER INFORMATION: TRAJ46*01_BB-S_R1

<400> SEQUENCE: 199
gatattgggc ctaactgcta aacgagtccc ggtcccaaa 39

<210> SEQ ID NO 200
<211> LENGTH: 39
<212> TYPE: DNA
<213> ORGANISM: Homo sapiens
<220> FEATURE:
<223> OTHER INFORMATION: TRAJ47*01_BB-S_R1

<400> SEQUENCE: 200
gatataggac ttgactctca gaatggttcc tgcgccaaa 39

<210> SEQ ID NO 201
<211> LENGTH: 39
<212> TYPE: DNA
<213> ORGANISM: Homo sapiens
<220> FEATURE:
<223> OTHER INFORMATION: TRAJ48*01_BB-S_R1

<400> SEQUENCE: 201
gatattgggt atgatggtga gtcttgttcc agtcccaaa 39

<210> SEQ ID NO 202
<211> LENGTH: 39
<212> TYPE: DNA
<213> ORGANISM: Homo sapiens
<220> FEATURE:
<223> OTHER INFORMATION: TRAJ49*01_BB-S_R1

<400> SEQUENCE: 202
gatatttgga atgaccgtca aacttgtccc tgtcccaaa 39

<210> SEQ ID NO 203
<211> LENGTH: 39
<212> TYPE: DNA
<213> ORGANISM: Homo sapiens
<220> FEATURE:
<223> OTHER INFORMATION: TRAJ50*01_BB-S_R1

<400> SEQUENCE: 203
gatatttgga atgactgata agcttgtccc tggcccaaa 39

<210> SEQ ID NO 204
<211> LENGTH: 39
<212> TYPE: DNA
<213> ORGANISM: Homo sapiens
<220> FEATURE:
<223> OTHER INFORMATION: TRAJ52*01_BB-S_R1

<400> SEQUENCE: 204
gatatttgga tggacagtca agatggtccc ttgtccaaa 39

<210> SEQ ID NO 205
<211> LENGTH: 39
<212> TYPE: DNA
<213> ORGANISM: Homo sapiens
<220> FEATURE:
<223> OTHER INFORMATION: TRAJ53*01_BB-S_R1

<400> SEQUENCE: 205
gatatttgga ttcacggtta agagagttcc ttttccaaa 39

<210> SEQ ID NO 206
<211> LENGTH: 39
<212> TYPE: DNA
<213> ORGANISM: Homo sapiens
<220> FEATURE:
<223> OTHER INFORMATION: TRAJ54*01_BB-S_R1

<400> SEQUENCE: 206
gatatttggg ttgatagtca gcctggttcc ttggccaaa 39

<210> SEQ ID NO 207
<211> LENGTH: 39
<212> TYPE: DNA
<213> ORGANISM: Homo sapiens
<220> FEATURE:
<223> OTHER INFORMATION: TRAJ56*01_BB-S_R1

<400> SEQUENCE: 207
gatatctggt ctaacactca gagttattcc ttttccaaa 39

<210> SEQ ID NO 208
<211> LENGTH: 39
<212> TYPE: DNA
<213> ORGANISM: Homo sapiens
<220> FEATURE:
<223> OTHER INFORMATION: TRAJ57*01_BB-S_R1

<400> SEQUENCE: 208
gatatatggg tttactgtca gtttcgttcc ctttccaaa 39

<210> SEQ ID NO 209
<211> LENGTH: 33
<212> TYPE: DNA
<213> ORGANISM: Homo sapiens
<220> FEATURE:
<223> OTHER INFORMATION: TRAJ59*01_BB-S_R1

<400> SEQUENCE: 209
gatattcact ctcacttgcg tccccattcc aaa 33

<210> SEQ ID NO 210
<211> LENGTH: 39
<212> TYPE: DNA
<213> ORGANISM: Homo sapiens
<220> FEATURE:
<223> OTHER INFORMATION: TRAJ61*01_BB-S_R1

<400> SEQUENCE: 210
gatattgagt ttcatgattc ctctagtgtt ggctccaaa 39

<210> SEQ ID NO 211
<211> LENGTH: 57
<212> TYPE: DNA
<213> ORGANISM: Homo sapiens
<220> FEATURE:
<223> OTHER INFORMATION: TRAJ1*01_BB-L_F1

<400> SEQUENCE: 211
ctcgattacc tcccagttgc aatttggcaa aggaaccaga gtttccactt ctcccca 57

<210> SEQ ID NO 212
<211> LENGTH: 60
<212> TYPE: DNA
<213> ORGANISM: Homo sapiens
<220> FEATURE:
<223> OTHER INFORMATION: TRAJ2*01_BB-L_F1

<400> SEQUENCE: 212
ctcgggaaca attgataaac tcacatttgg gaaagggacc catgtattca ttatatctga 60

<210> SEQ ID NO 213

<211> LENGTH: 57
<212> TYPE: DNA
<213> ORGANISM: Homo sapiens
<220> FEATURE:
<223> OTHER INFORMATION: TRAJ3*01_BB-L_F1

<400> SEQUENCE: 213
ctcgagtgct tccaagataa tctttggatc agggaccaga ctcagcatcc ggccaaa 57

<210> SEQ ID NO 214
<211> LENGTH: 57
<212> TYPE: DNA
<213> ORGANISM: Homo sapiens
<220> FEATURE:
<223> OTHER INFORMATION: TRAJ4*01_BB-L_F1

<400> SEQUENCE: 214
ctcgggctac aataagctga tctttggagc agggaccagg ctggctgtac acccata 57

<210> SEQ ID NO 215
<211> LENGTH: 54
<212> TYPE: DNA
<213> ORGANISM: Homo sapiens
<220> FEATURE:
<223> OTHER INFORMATION: TRAJ5*01_BB-L_F1

<400> SEQUENCE: 215
ctcgaggaga gcacttactt ttgggagtgg aacaagactc caagtgcaac caaa 54

<210> SEQ ID NO 216
<211> LENGTH: 57
<212> TYPE: DNA
<213> ORGANISM: Homo sapiens
<220> FEATURE:
<223> OTHER INFORMATION: TRAJ6*01_BB-L_F1

<400> SEQUENCE: 216
ctcgggaagc tacataccta catttggaag aggaaccagc cttattgttc atccgta 57

<210> SEQ ID NO 217
<211> LENGTH: 54
<212> TYPE: DNA
<213> ORGANISM: Homo sapiens
<220> FEATURE:
<223> OTHER INFORMATION: TRAJ7*01_BB-L_F1

<400> SEQUENCE: 217
ctcgaacaac agactcgctt ttgggaaggg gaaccaagtg gtggtcatac caaa 54

<210> SEQ ID NO 218
<211> LENGTH: 54
<212> TYPE: DNA
<213> ORGANISM: Homo sapiens
<220> FEATURE:
<223> OTHER INFORMATION: TRAJ8*01_BB-L_F1

<400> SEQUENCE: 218
ctcgtttcag aaacttgtat ttggaactgg cacccgactt ctggtcagtc caaa 54

<210> SEQ ID NO 219
<211> LENGTH: 54
<212> TYPE: DNA
<213> ORGANISM: Homo sapiens
<220> FEATURE:
<223> OTHER INFORMATION: TRAJ9*01_BB-L_F1

<400> SEQUENCE: 219
ctcgggcttc aaaactatct ttggagcagg aacaagacta tttgttaaag caaa 54

<210> SEQ ID NO 220
<211> LENGTH: 57
<212> TYPE: DNA
<213> ORGANISM: Homo sapiens
<220> FEATURE:
<223> OTHER INFORMATION: TRAJ10*01_BB-L_F1

<400> SEQUENCE: 220
ctcgggagga aacaaactca cctttgggac aggcactcag ctaaaagtgg aactcaa 57

<210> SEQ ID NO 221
<211> LENGTH: 54
<212> TYPE: DNA
<213> ORGANISM: Homo sapiens
<220> FEATURE:
<223> OTHER INFORMATION: TRAJ11*01_BB-L_F1

<400> SEQUENCE: 221
ctcgtacagc accctcacct ttgggaaggg gactatgctt ctagtctctc caga 54

<210> SEQ ID NO 222
<211> LENGTH: 54
<212> TYPE: DNA
<213> ORGANISM: Homo sapiens
<220> FEATURE:
<223> OTHER INFORMATION: TRAJ12*01_BB-L_F1

<400> SEQUENCE: 222
ctcgagttat aaattgatct ttgggagtgg gaccagactg ctggtcaggc ctga 54

<210> SEQ ID NO 223
<211> LENGTH: 57
<212> TYPE: DNA
<213> ORGANISM: Homo sapiens
<220> FEATURE:
<223> OTHER INFORMATION: TRAJ13*01_BB-L_F1

<400> SEQUENCE: 223
ctcgggttac cagaaagtta cctttggaat tggaacaaag ctccaagtca tcccaaa 57

<210> SEQ ID NO 224
<211> LENGTH: 45
<212> TYPE: DNA
<213> ORGANISM: Homo sapiens
<220> FEATURE:
<223> OTHER INFORMATION: TRAJ14*01_BB-L_F1

<400> SEQUENCE: 224
ctcgttcatc tttgggagtg ggacaagatt atcagtaaaa cctga 45

<210> SEQ ID NO 225
<211> LENGTH: 54
<212> TYPE: DNA
<213> ORGANISM: Homo sapiens
<220> FEATURE:
<223> OTHER INFORMATION: TRAJ15*01_BB-L_F1

<400> SEQUENCE: 225
ctcgggaact gctctgatct ttgggaaggg aacccaccta tcagtgagtt ccaa 54

<210> SEQ ID NO 226
<211> LENGTH: 54
<212> TYPE: DNA

<213> ORGANISM: Homo sapiens
<220> FEATURE:
<223> OTHER INFORMATION: TRAJ16*01_BB-L_F1

<400> SEQUENCE: 226
ctcgggacag aagctgctct ttgcaagggg aaccatgtta aaggtggatc ttaa 54

<210> SEQ ID NO 227
<211> LENGTH: 57
<212> TYPE: DNA
<213> ORGANISM: Homo sapiens
<220> FEATURE:
<223> OTHER INFORMATION: TRAJ17*01_BB-L_F1

<400> SEQUENCE: 227
ctcggcaggc aacaagctaa cttttggagg aggaaccagg gtgctagtta aaccaaa 57

<210> SEQ ID NO 228
<211> LENGTH: 60
<212> TYPE: DNA
<213> ORGANISM: Homo sapiens
<220> FEATURE:
<223> OTHER INFORMATION: TRAJ18*01_BB-L_F1

<400> SEQUENCE: 228
ctcgtcaacc ctggggaggc tatactttgg aagaggaact cagttgactg tctggcctga 60

<210> SEQ ID NO 229
<211> LENGTH: 54
<212> TYPE: DNA
<213> ORGANISM: Homo sapiens
<220> FEATURE:
<223> OTHER INFORMATION: TRAJ19*01_BB-L_F1

<400> SEQUENCE: 229
ctcgttctac aatttcacct ttggaaaggg atccaaacat aatgtcactc caaa 54

<210> SEQ ID NO 230
<211> LENGTH: 51
<212> TYPE: DNA
<213> ORGANISM: Homo sapiens
<220> FEATURE:
<223> OTHER INFORMATION: TRAJ20*01_BB-L_F1

<400> SEQUENCE: 230
ctcgtacaag ctcagctttg gagccggaac cacagtaact gtaagagcaa a 51

<210> SEQ ID NO 231
<211> LENGTH: 48
<212> TYPE: DNA
<213> ORGANISM: Homo sapiens
<220> FEATURE:
<223> OTHER INFORMATION: TRAJ21*01_BB-L_F1

<400> SEQUENCE: 231
ctcgaaattt tactttggat ctgggaccaa actcaatgta aaaccaaa 48

<210> SEQ ID NO 232
<211> LENGTH: 57
<212> TYPE: DNA
<213> ORGANISM: Homo sapiens
<220> FEATURE:
<223> OTHER INFORMATION: TRAJ22*01_BB-L_F1

<400> SEQUENCE: 232
ctcgtctgca aggcaactga cctttggatc tgggacacaa ttgactgttt tacctga 57

<210> SEQ ID NO 233
<211> LENGTH: 57
<212> TYPE: DNA
<213> ORGANISM: Homo sapiens
<220> FEATURE:
<223> OTHER INFORMATION: TRAJ23*01_BB-L_F1

<400> SEQUENCE: 233
ctcgcaggga ggaaagctta tctttggaca gggaacggag ttatctgtga aacccaa 57

<210> SEQ ID NO 234
<211> LENGTH: 57
<212> TYPE: DNA
<213> ORGANISM: Homo sapiens
<220> FEATURE:
<223> OTHER INFORMATION: TRAJ24*01_BB-L_F1

<400> SEQUENCE: 234
ctcgagttgg ggtaaattgc agtttggagc agggacccag gttgtggtca ccccaga 57

<210> SEQ ID NO 235
<211> LENGTH: 54
<212> TYPE: DNA
<213> ORGANISM: Homo sapiens
<220> FEATURE:
<223> OTHER INFORMATION: TRAJ25*01_BB-L_F1

<400> SEQUENCE: 235
ctcgggcttc tcctttatct ttgggaaggg gacaaggctg cttgtcaagc caaa 54

<210> SEQ ID NO 236
<211> LENGTH: 54
<212> TYPE: DNA
<213> ORGANISM: Homo sapiens
<220> FEATURE:
<223> OTHER INFORMATION: TRAJ26*01_BB-L_F1

<400> SEQUENCE: 236
ctcgggtcag aattttgtct ttggtcccgg aaccagattg tccgtgctgc ccta 54

<210> SEQ ID NO 237
<211> LENGTH: 54
<212> TYPE: DNA
<213> ORGANISM: Homo sapiens
<220> FEATURE:
<223> OTHER INFORMATION: TRAJ27*01_BB-L_F1

<400> SEQUENCE: 237
ctcggcaggc aaatcaacct ttggggatgg gactacgctc actgtgaagc caaa 54

<210> SEQ ID NO 238
<211> LENGTH: 60
<212> TYPE: DNA
<213> ORGANISM: Homo sapiens
<220> FEATURE:
<223> OTHER INFORMATION: TRAJ28*01_BB-L_F1

<400> SEQUENCE: 238
ctcggctggg agttaccaac tcacttttgg gaaggggacc aaactctcgg tcataccaaa 60

<210> SEQ ID NO 239
<211> LENGTH: 54
<212> TYPE: DNA
<213> ORGANISM: Homo sapiens
<220> FEATURE:

<223> OTHER INFORMATION: TRAJ29*01_BB-L_F1

<400> SEQUENCE: 239
ctcgaacaca cctcttgtct ttggaaaggg cacaagactt tctgtgattg caaa 54

<210> SEQ ID NO 240
<211> LENGTH: 51
<212> TYPE: DNA
<213> ORGANISM: Homo sapiens
<220> FEATURE:
<223> OTHER INFORMATION: TRAJ30*01_BB-L_F1

<400> SEQUENCE: 240
ctcggacaag atcatctttg gaaaagggac acgacttcat attctcccca a 51

<210> SEQ ID NO 241
<211> LENGTH: 51
<212> TYPE: DNA
<213> ORGANISM: Homo sapiens
<220> FEATURE:
<223> OTHER INFORMATION: TRAJ31*01_BB-L_F1

<400> SEQUENCE: 241
ctcggccaga ctcatgtttg gagatggaac tcagctggtg gtgaagccca a 51

<210> SEQ ID NO 242
<211> LENGTH: 60
<212> TYPE: DNA
<213> ORGANISM: Homo sapiens
<220> FEATURE:
<223> OTHER INFORMATION: TRAJ32*01_BB-L_F1

<400> SEQUENCE: 242
ctcgggtgct acaaacaagc tcatctttgg aactggcact ctgcttgctg tccagccaaa 60

<210> SEQ ID NO 243
<211> LENGTH: 51
<212> TYPE: DNA
<213> ORGANISM: Homo sapiens
<220> FEATURE:
<223> OTHER INFORMATION: TRAJ33*01_BB-L_F1

<400> SEQUENCE: 243
ctcgtatcag ttaatctggg gcgctgggac caagctaatt ataaagccag a 51

<210> SEQ ID NO 244
<211> LENGTH: 51
<212> TYPE: DNA
<213> ORGANISM: Homo sapiens
<220> FEATURE:
<223> OTHER INFORMATION: TRAJ34*01_BB-L_F1

<400> SEQUENCE: 244
ctcggacaag ctcatctttg ggactgggac cagattacaa gtctttccaa a 51

<210> SEQ ID NO 245
<211> LENGTH: 54
<212> TYPE: DNA
<213> ORGANISM: Homo sapiens
<220> FEATURE:
<223> OTHER INFORMATION: TRAJ36*01_BB-L_F1

<400> SEQUENCE: 245
ctcggcaaac aacctcttct ttgggactgg aacgagactc accgttattc ccta 54

<210> SEQ ID NO 246
<211> LENGTH: 57
<212> TYPE: DNA
<213> ORGANISM: Homo sapiens
<220> FEATURE:
<223> OTHER INFORMATION: TRAJ37*01_BB-L_F1

<400> SEQUENCE: 246
ctcgaacaca ggcaaactaa tctttgggca agggacaact ttacaagtaa aaccaga 57

<210> SEQ ID NO 247
<211> LENGTH: 57
<212> TYPE: DNA
<213> ORGANISM: Homo sapiens
<220> FEATURE:
<223> OTHER INFORMATION: TRAJ38*01_BB-L_F1

<400> SEQUENCE: 247
ctcgaacaac cgtaagctga tttggggatt gggaacaagc ctggcagtaa atccgaa 57

<210> SEQ ID NO 248
<211> LENGTH: 57
<212> TYPE: DNA
<213> ORGANISM: Homo sapiens
<220> FEATURE:
<223> OTHER INFORMATION: TRAJ39*01_BB-L_F1

<400> SEQUENCE: 248
ctcggcaggc aacatgctca cctttggagg aggaacaagg ttaatggtca aacccca 57

<210> SEQ ID NO 249
<211> LENGTH: 54
<212> TYPE: DNA
<213> ORGANISM: Homo sapiens
<220> FEATURE:
<223> OTHER INFORMATION: TRAJ40*01_BB-L_F1

<400> SEQUENCE: 249
ctcgacctac aaatacatct ttggaacagg caccaggctg aaggttttag caaa 54

<210> SEQ ID NO 250
<211> LENGTH: 57
<212> TYPE: DNA
<213> ORGANISM: Homo sapiens
<220> FEATURE:
<223> OTHER INFORMATION: TRAJ41*01_BB-L_F1

<400> SEQUENCE: 250
ctcgtccggg tatgcactca actttggcaa aggcacctcg ctgttggtca caccccca 57

<210> SEQ ID NO 251
<211> LENGTH: 60
<212> TYPE: DNA
<213> ORGANISM: Homo sapiens
<220> FEATURE:
<223> OTHER INFORMATION: TRAJ42*01_BB-L_F1

<400> SEQUENCE: 251
ctcgggaagc caaggaaatc tcatctttgg aaaaggcact aaactctctg ttaaaccaaa 60

<210> SEQ ID NO 252
<211> LENGTH: 48
<212> TYPE: DNA
<213> ORGANISM: Homo sapiens
<220> FEATURE:
<223> OTHER INFORMATION: TRAJ43*01_BB-L_F1

<400> SEQUENCE: 252
ctcggacatg cgctttggag cagggaccag actgacagta aaaccaaa 48

<210> SEQ ID NO 253
<211> LENGTH: 57
<212> TYPE: DNA
<213> ORGANISM: Homo sapiens
<220> FEATURE:
<223> OTHER INFORMATION: TRAJ44*01_BB-L_F1

<400> SEQUENCE: 253
ctcgactgcc agtaaactca cctttgggac tggaacaaga cttcaggtca cgctcga 57

<210> SEQ ID NO 254
<211> LENGTH: 60
<212> TYPE: DNA
<213> ORGANISM: Homo sapiens
<220> FEATURE:
<223> OTHER INFORMATION: TRAJ45*01_BB-L_F1

<400> SEQUENCE: 254
ctcgggaggt gctgacggac tcacctttgg caaagggact catctaatca tccagcccta 60

<210> SEQ ID NO 255
<211> LENGTH: 57
<212> TYPE: DNA
<213> ORGANISM: Homo sapiens
<220> FEATURE:
<223> OTHER INFORMATION: TRAJ46*01_BB-L_F1

<400> SEQUENCE: 255
ctcgagcgga gacaagctga cttttgggac cgggactcgt ttagcagtta ggcccaa 57

<210> SEQ ID NO 256
<211> LENGTH: 51
<212> TYPE: DNA
<213> ORGANISM: Homo sapiens
<220> FEATURE:
<223> OTHER INFORMATION: TRAJ47*01_BB-L_F1

<400> SEQUENCE: 256
ctcgaacaaa ctggtctttg gcgcaggaac cattctgaga gtcaagtcct a 51

<210> SEQ ID NO 257
<211> LENGTH: 57
<212> TYPE: DNA
<213> ORGANISM: Homo sapiens
<220> FEATURE:
<223> OTHER INFORMATION: TRAJ48*01_BB-L_F1

<400> SEQUENCE: 257
ctcgggaaat gagaaattaa cctttgggac tggaacaaga ctcaccatca tacccaa 57

<210> SEQ ID NO 258
<211> LENGTH: 51
<212> TYPE: DNA
<213> ORGANISM: Homo sapiens
<220> FEATURE:
<223> OTHER INFORMATION: TRAJ49*01_BB-L_F1

<400> SEQUENCE: 258
ctcgaaccag ttctattttg ggacagggac aagtttgacg gtcattccaa a 51

<210> SEQ ID NO 259
<211> LENGTH: 54

<212> TYPE: DNA
<213> ORGANISM: Homo sapiens
<220> FEATURE:
<223> OTHER INFORMATION: TRAJ50*01_BB-L_F1

<400> SEQUENCE: 259
ctcgtacgac aaggtgatat ttgggccagg gacaagctta tcagtcattc caaa 54

<210> SEQ ID NO 260
<211> LENGTH: 63
<212> TYPE: DNA
<213> ORGANISM: Homo sapiens
<220> FEATURE:
<223> OTHER INFORMATION: TRAJ52*01_BB-L_F1

<400> SEQUENCE: 260
ctcgggtact agctatggaa agctgacatt tggacaaggg accatcttga ctgtccatcc 60
aaa 63

<210> SEQ ID NO 261
<211> LENGTH: 60
<212> TYPE: DNA
<213> ORGANISM: Homo sapiens
<220> FEATURE:
<223> OTHER INFORMATION: TRAJ53*01_BB-L_F1

<400> SEQUENCE: 261
ctcgggtagc aactataaac tgacatttgg aaaaggaact ctcttaaccg tgaatccaaa 60

<210> SEQ ID NO 262
<211> LENGTH: 54
<212> TYPE: DNA
<213> ORGANISM: Homo sapiens
<220> FEATURE:
<223> OTHER INFORMATION: TRAJ54*01_BB-L_F1

<400> SEQUENCE: 262
ctcggcccag aagctggtat ttggccaagg aaccaggctg actatcaacc caaa 54

<210> SEQ ID NO 263
<211> LENGTH: 57
<212> TYPE: DNA
<213> ORGANISM: Homo sapiens
<220> FEATURE:
<223> OTHER INFORMATION: TRAJ56*01_BB-L_F1

<400> SEQUENCE: 263
ctcggccaat agtaagctga catttggaaa aggaataact ctgagtgtta gaccaga 57

<210> SEQ ID NO 264
<211> LENGTH: 57
<212> TYPE: DNA
<213> ORGANISM: Homo sapiens
<220> FEATURE:
<223> OTHER INFORMATION: TRAJ57*01_BB-L_F1

<400> SEQUENCE: 264
ctcgggatct gaaaagctgg tctttggaaa gggaacgaaa ctgacagtaa acccata 57

<210> SEQ ID NO 265
<211> LENGTH: 48
<212> TYPE: DNA
<213> ORGANISM: Homo sapiens
<220> FEATURE:
<223> OTHER INFORMATION: TRAJ59*01_BB-L_F1

<400> SEQUENCE: 265
ctcgaacagg aaatttacat ttggaatggg gacgcaagtg agagtgaa 48

<210> SEQ ID NO 266
<211> LENGTH: 54
<212> TYPE: DNA
<213> ORGANISM: Homo sapiens
<220> FEATURE:
<223> OTHER INFORMATION: TRAJ61*01_BB-L_F1

<400> SEQUENCE: 266
ctcgaatagg aaactgacat ttggagccaa cactagagga atcatgaaac tcaa 54

<210> SEQ ID NO 267
<211> LENGTH: 57
<212> TYPE: DNA
<213> ORGANISM: Homo sapiens
<220> FEATURE:
<223> OTHER INFORMATION: TRAJ1*01_BB-L_R1

<400> SEQUENCE: 267
gatatgggga gaagtggaaa ctctggttcc tttgccaaat tgcaactggg aggtaat 57

<210> SEQ ID NO 268
<211> LENGTH: 60
<212> TYPE: DNA
<213> ORGANISM: Homo sapiens
<220> FEATURE:
<223> OTHER INFORMATION: TRAJ2*01_BB-L_R1

<400> SEQUENCE: 268
gatatcagat ataatgaata catgggtccc tttcccaaat gtgagtttat caattgttcc 60

<210> SEQ ID NO 269
<211> LENGTH: 57
<212> TYPE: DNA
<213> ORGANISM: Homo sapiens
<220> FEATURE:
<223> OTHER INFORMATION: TRAJ3*01_BB-L_R1

<400> SEQUENCE: 269
gatatttggc cggatgctga gtctggtccc tgatccaaag attatcttgg aagcact 57

<210> SEQ ID NO 270
<211> LENGTH: 57
<212> TYPE: DNA
<213> ORGANISM: Homo sapiens
<220> FEATURE:
<223> OTHER INFORMATION: TRAJ4*01_BB-L_R1

<400> SEQUENCE: 270
gatatatggg tgtacagcca gcctggtccc tgctccaaaa atcagcttat tgtagcc 57

<210> SEQ ID NO 271
<211> LENGTH: 54
<212> TYPE: DNA
<213> ORGANISM: Homo sapiens
<220> FEATURE:
<223> OTHER INFORMATION: TRAJ5*01_BB-L_R1

<400> SEQUENCE: 271
gatatttggt tgcacttgga gtcttgttcc actcccaaaa gtaagtgctc tcct 54

<210> SEQ ID NO 272
<211> LENGTH: 57

<212> TYPE: DNA
<213> ORGANISM: Homo sapiens
<220> FEATURE:
<223> OTHER INFORMATION: TRAJ6*01_BB-L_R1

<400> SEQUENCE: 272
gatatacgga tgaacaataa ggctggttcc tcttccaaat gtaggtatgt agcttcc 57

<210> SEQ ID NO 273
<211> LENGTH: 54
<212> TYPE: DNA
<213> ORGANISM: Homo sapiens
<220> FEATURE:
<223> OTHER INFORMATION: TRAJ7*01_BB-L_R1

<400> SEQUENCE: 273
gatatttggt atgaccacca cttggttccc cttcccaaaa gcgagtctgt tgtt 54

<210> SEQ ID NO 274
<211> LENGTH: 54
<212> TYPE: DNA
<213> ORGANISM: Homo sapiens
<220> FEATURE:
<223> OTHER INFORMATION: TRAJ8*01_BB-L_R1

<400> SEQUENCE: 274
gatatttgga ctgaccagaa gtcgggtgcc agttccaaat acaagtttct gaaa 54

<210> SEQ ID NO 275
<211> LENGTH: 54
<212> TYPE: DNA
<213> ORGANISM: Homo sapiens
<220> FEATURE:
<223> OTHER INFORMATION: TRAJ9*01_BB-L_R1

<400> SEQUENCE: 275
gatatttgct ttaacaaata gtcttgttcc tgctccaaag atagttttga agcc 54

<210> SEQ ID NO 276
<211> LENGTH: 57
<212> TYPE: DNA
<213> ORGANISM: Homo sapiens
<220> FEATURE:
<223> OTHER INFORMATION: TRAJ10*01_BB-L_R1

<400> SEQUENCE: 276
gatattgagt tccactttta gctgagtgcc tgtcccaaag gtgagtttgt ttcctcc 57

<210> SEQ ID NO 277
<211> LENGTH: 54
<212> TYPE: DNA
<213> ORGANISM: Homo sapiens
<220> FEATURE:
<223> OTHER INFORMATION: TRAJ11*01_BB-L_R1

<400> SEQUENCE: 277
gatatctgga gagactagaa gcatagtccc cttcccaaag gtgagggtgc tgta 54

<210> SEQ ID NO 278
<211> LENGTH: 54
<212> TYPE: DNA
<213> ORGANISM: Homo sapiens
<220> FEATURE:
<223> OTHER INFORMATION: TRAJ12*01_BB-L_R1

<400> SEQUENCE: 278
gatatcaggc ctgaccagca gtctggtccc actcccaaag atcaatttat aact 54

<210> SEQ ID NO 279
<211> LENGTH: 57
<212> TYPE: DNA
<213> ORGANISM: Homo sapiens
<220> FEATURE:
<223> OTHER INFORMATION: TRAJ13*01_BB-L_R1

<400> SEQUENCE: 279
gatatttggg atgacttgga gctttgttcc aattccaaag gtaactttct ggtaacc 57

<210> SEQ ID NO 280
<211> LENGTH: 45
<212> TYPE: DNA
<213> ORGANISM: Homo sapiens
<220> FEATURE:
<223> OTHER INFORMATION: TRAJ14*01_BB-L_R1

<400> SEQUENCE: 280
gatatcaggt tttactgata atcttgtccc actcccaaag atgaa 45

<210> SEQ ID NO 281
<211> LENGTH: 54
<212> TYPE: DNA
<213> ORGANISM: Homo sapiens
<220> FEATURE:
<223> OTHER INFORMATION: TRAJ15*01_BB-L_R1

<400> SEQUENCE: 281
gatattggaa ctcactgata ggtgggttcc cttcccaaag atcagagcag ttcc 54

<210> SEQ ID NO 282
<211> LENGTH: 54
<212> TYPE: DNA
<213> ORGANISM: Homo sapiens
<220> FEATURE:
<223> OTHER INFORMATION: TRAJ16*01_BB-L_R1

<400> SEQUENCE: 282
gatattaaga tccacctta acatggttcc ccttgcaaag agcagcttct gtcc 54

<210> SEQ ID NO 283
<211> LENGTH: 57
<212> TYPE: DNA
<213> ORGANISM: Homo sapiens
<220> FEATURE:
<223> OTHER INFORMATION: TRAJ17*01_BB-L_R1

<400> SEQUENCE: 283
gatatttggt ttaactagca ccctggttcc tcctccaaaa gttagcttgt tgcctgc 57

<210> SEQ ID NO 284
<211> LENGTH: 60
<212> TYPE: DNA
<213> ORGANISM: Homo sapiens
<220> FEATURE:
<223> OTHER INFORMATION: TRAJ18*01_BB-L_R1

<400> SEQUENCE: 284
gatatcaggc cagacagtca actgagttcc tcttccaaag tatagcctcc ccagggttga 60

<210> SEQ ID NO 285
<211> LENGTH: 54
<212> TYPE: DNA
<213> ORGANISM: Homo sapiens

<220> FEATURE:
<223> OTHER INFORMATION: TRAJ19*01_BB-L_R1

<400> SEQUENCE: 285
gatatttgga gtgacattat gtttggatcc ctttccaaag gtgaaattgt agaa 54

<210> SEQ ID NO 286
<211> LENGTH: 51
<212> TYPE: DNA
<213> ORGANISM: Homo sapiens
<220> FEATURE:
<223> OTHER INFORMATION: TRAJ20*01_BB-L_R1

<400> SEQUENCE: 286
gatatttgct cttacagtta ctgtggttcc ggctccaaag ctgagcttgt a 51

<210> SEQ ID NO 287
<211> LENGTH: 48
<212> TYPE: DNA
<213> ORGANISM: Homo sapiens
<220> FEATURE:
<223> OTHER INFORMATION: TRAJ21*01_BB-L_R1

<400> SEQUENCE: 287
gatatttggt tttacattga gtttggtccc agatccaaag taaaattt 48

<210> SEQ ID NO 288
<211> LENGTH: 57
<212> TYPE: DNA
<213> ORGANISM: Homo sapiens
<220> FEATURE:
<223> OTHER INFORMATION: TRAJ22*01_BB-L_R1

<400> SEQUENCE: 288
gatatcaggt aaaacagtca attgtgtccc agatccaaag gtcagttgcc ttgcaga 57

<210> SEQ ID NO 289
<211> LENGTH: 57
<212> TYPE: DNA
<213> ORGANISM: Homo sapiens
<220> FEATURE:
<223> OTHER INFORMATION: TRAJ23*01_BB-L_R1

<400> SEQUENCE: 289
gatattgggt ttcacagata actccgttcc ctgtccaaag ataagctttc ctccctg 57

<210> SEQ ID NO 290
<211> LENGTH: 57
<212> TYPE: DNA
<213> ORGANISM: Homo sapiens
<220> FEATURE:
<223> OTHER INFORMATION: TRAJ24*01_BB-L_R1

<400> SEQUENCE: 290
gatatctggg gtgaccacaa cctgggtccc tgctccaaac tgcaatttac cccaact 57

<210> SEQ ID NO 291
<211> LENGTH: 54
<212> TYPE: DNA
<213> ORGANISM: Homo sapiens
<220> FEATURE:
<223> OTHER INFORMATION: TRAJ25*01_BB-L_R1

<400> SEQUENCE: 291
gatatttggc ttgacaagca gccttgtccc cttcccaaag ataaaggaga agcc 54

<210> SEQ ID NO 292
<211> LENGTH: 54
<212> TYPE: DNA
<213> ORGANISM: Homo sapiens
<220> FEATURE:
<223> OTHER INFORMATION: TRAJ26*01_BB-L_R1

<400> SEQUENCE: 292
gatatagggc agcacggaca atctggttcc gggaccaaag acaaaattct gacc 54

<210> SEQ ID NO 293
<211> LENGTH: 54
<212> TYPE: DNA
<213> ORGANISM: Homo sapiens
<220> FEATURE:
<223> OTHER INFORMATION: TRAJ27*01_BB-L_R1

<400> SEQUENCE: 293
gatatttggc ttcacagtga gcgtagtccc atccccaaag gttgatttgc ctgc 54

<210> SEQ ID NO 294
<211> LENGTH: 60
<212> TYPE: DNA
<213> ORGANISM: Homo sapiens
<220> FEATURE:
<223> OTHER INFORMATION: TRAJ28*01_BB-L_R1

<400> SEQUENCE: 294
gatatttggt atgaccgaga gtttggtccc cttcccaaaa gtgagttggt aactcccagc 60

<210> SEQ ID NO 295
<211> LENGTH: 54
<212> TYPE: DNA
<213> ORGANISM: Homo sapiens
<220> FEATURE:
<223> OTHER INFORMATION: TRAJ29*01_BB-L_R1

<400> SEQUENCE: 295
gatatttgca atcacagaaa gtcttgtgcc ctttccaaag acaagaggtg tgtt 54

<210> SEQ ID NO 296
<211> LENGTH: 51
<212> TYPE: DNA
<213> ORGANISM: Homo sapiens
<220> FEATURE:
<223> OTHER INFORMATION: TRAJ30*01_BB-L_R1

<400> SEQUENCE: 296
gatattgggg agaatatgaa gtcgtgtccc ttttccaaag atgatcttgt c 51

<210> SEQ ID NO 297
<211> LENGTH: 51
<212> TYPE: DNA
<213> ORGANISM: Homo sapiens
<220> FEATURE:
<223> OTHER INFORMATION: TRAJ31*01_BB-L_R1

<400> SEQUENCE: 297
gatattgggc ttcaccacca gctgagttcc atctccaaac atgagtctgg c 51

<210> SEQ ID NO 298
<211> LENGTH: 60
<212> TYPE: DNA
<213> ORGANISM: Homo sapiens
<220> FEATURE:
<223> OTHER INFORMATION: TRAJ32*01_BB-L_R1

<400> SEQUENCE: 298
gatatttggc tggacagcaa gcagagtgcc agttccaaag atgagcttgt ttgtagcacc 60

<210> SEQ ID NO 299
<211> LENGTH: 51
<212> TYPE: DNA
<213> ORGANISM: Homo sapiens
<220> FEATURE:
<223> OTHER INFORMATION: TRAJ33*01_BB-L_R1

<400> SEQUENCE: 299
gatatctggc tttataatta gcttggtccc agcgccccag attaactgat a 51

<210> SEQ ID NO 300
<211> LENGTH: 51
<212> TYPE: DNA
<213> ORGANISM: Homo sapiens
<220> FEATURE:
<223> OTHER INFORMATION: TRAJ34*01_BB-L_R1

<400> SEQUENCE: 300
gatatttgga aagacttgta atctggtccc agtcccaaag atgagcttgt c 51

<210> SEQ ID NO 301
<211> LENGTH: 54
<212> TYPE: DNA
<213> ORGANISM: Homo sapiens
<220> FEATURE:
<223> OTHER INFORMATION: TRAJ36*01_BB-L_R1

<400> SEQUENCE: 301
gatataggga ataacggtga gtctcgttcc agtcccaaag aagaggttgt ttgc 54

<210> SEQ ID NO 302
<211> LENGTH: 57
<212> TYPE: DNA
<213> ORGANISM: Homo sapiens
<220> FEATURE:
<223> OTHER INFORMATION: TRAJ37*01_BB-L_R1

<400> SEQUENCE: 302
gatatctggt tttacttgta aagttgtccc ttgcccaaag attagtttgc ctgtgtt 57

<210> SEQ ID NO 303
<211> LENGTH: 57
<212> TYPE: DNA
<213> ORGANISM: Homo sapiens
<220> FEATURE:
<223> OTHER INFORMATION: TRAJ38*01_BB-L_R1

<400> SEQUENCE: 303
gatattcgga tttactgcca ggcttgttcc caatccccaa atcagcttac ggttgtt 57

<210> SEQ ID NO 304
<211> LENGTH: 57
<212> TYPE: DNA
<213> ORGANISM: Homo sapiens
<220> FEATURE:
<223> OTHER INFORMATION: TRAJ39*01_BB-L_R1

<400> SEQUENCE: 304
gatatggggt ttgaccatta accttgttcc tcctccaaag gtgagcatgt tgcctgc 57

<210> SEQ ID NO 305

<211> LENGTH: 54
<212> TYPE: DNA
<213> ORGANISM: Homo sapiens
<220> FEATURE:
<223> OTHER INFORMATION: TRAJ40*01_BB-L_R1

<400> SEQUENCE: 305
gatatttgct aaaaccttca gcctggtgcc tgttccaaag atgtatttgt aggt 54

<210> SEQ ID NO 306
<211> LENGTH: 57
<212> TYPE: DNA
<213> ORGANISM: Homo sapiens
<220> FEATURE:
<223> OTHER INFORMATION: TRAJ41*01_BB-L_R1

<400> SEQUENCE: 306
gatatggggt gtgaccaaca gcgaggtgcc tttgccaaag ttgagtgcat acccgga 57

<210> SEQ ID NO 307
<211> LENGTH: 60
<212> TYPE: DNA
<213> ORGANISM: Homo sapiens
<220> FEATURE:
<223> OTHER INFORMATION: TRAJ42*01_BB-L_R1

<400> SEQUENCE: 307
gatatttggt ttaacagaga gtttagtgcc ttttccaaag atgagatttc cttggcttcc 60

<210> SEQ ID NO 308
<211> LENGTH: 48
<212> TYPE: DNA
<213> ORGANISM: Homo sapiens
<220> FEATURE:
<223> OTHER INFORMATION: TRAJ43*01_BB-L_R1

<400> SEQUENCE: 308
gatatttggt tttactgtca gtctggtccc tgctccaaag cgcatgtc 48

<210> SEQ ID NO 309
<211> LENGTH: 57
<212> TYPE: DNA
<213> ORGANISM: Homo sapiens
<220> FEATURE:
<223> OTHER INFORMATION: TRAJ44*01_BB-L_R1

<400> SEQUENCE: 309
gatatcgagc gtgacctgaa gtcttgttcc agtcccaaag gtgagtttac tggcagt 57

<210> SEQ ID NO 310
<211> LENGTH: 60
<212> TYPE: DNA
<213> ORGANISM: Homo sapiens
<220> FEATURE:
<223> OTHER INFORMATION: TRAJ45*01_BB-L_R1

<400> SEQUENCE: 310
gatatagggc tggatgatta gatgagtccc tttgccaaag gtgagtccgt cagcacctcc 60

<210> SEQ ID NO 311
<211> LENGTH: 57
<212> TYPE: DNA
<213> ORGANISM: Homo sapiens
<220> FEATURE:
<223> OTHER INFORMATION: TRAJ46*01_BB-L_R1

<400> SEQUENCE: 311
gatattgggc ctaactgcta aacgagtccc ggtcccaaaa gtcagcttgt ctccgct 57

<210> SEQ ID NO 312
<211> LENGTH: 51
<212> TYPE: DNA
<213> ORGANISM: Homo sapiens
<220> FEATURE:
<223> OTHER INFORMATION: TRAJ47*01_BB-L_R1

<400> SEQUENCE: 312
gatataggac ttgactctca gaatggttcc tgcgccaaag accagtttgt t 51

<210> SEQ ID NO 313
<211> LENGTH: 57
<212> TYPE: DNA
<213> ORGANISM: Homo sapiens
<220> FEATURE:
<223> OTHER INFORMATION: TRAJ48*01_BB-L_R1

<400> SEQUENCE: 313
gatattgggt atgatggtga gtcttgttcc agtcccaaag gttaatttct catttcc 57

<210> SEQ ID NO 314
<211> LENGTH: 51
<212> TYPE: DNA
<213> ORGANISM: Homo sapiens
<220> FEATURE:
<223> OTHER INFORMATION: TRAJ49*01_BB-L_R1

<400> SEQUENCE: 314
gatatttgga atgaccgtca aacttgtccc tgtcccaaaa tagaactggt t 51

<210> SEQ ID NO 315
<211> LENGTH: 54
<212> TYPE: DNA
<213> ORGANISM: Homo sapiens
<220> FEATURE:
<223> OTHER INFORMATION: TRAJ50*01_BB-L_R1

<400> SEQUENCE: 315
gatatttgga atgactgata agcttgtccc tggcccaaat atcaccttgt cgta 54

<210> SEQ ID NO 316
<211> LENGTH: 63
<212> TYPE: DNA
<213> ORGANISM: Homo sapiens
<220> FEATURE:
<223> OTHER INFORMATION: TRAJ52*01_BB-L_R1

<400> SEQUENCE: 316
gatatttgga tggacagtca agatggtccc ttgtccaaat gtcagctttc catagctagt 60
acc 63

<210> SEQ ID NO 317
<211> LENGTH: 60
<212> TYPE: DNA
<213> ORGANISM: Homo sapiens
<220> FEATURE:
<223> OTHER INFORMATION: TRAJ53*01_BB-L_R1

<400> SEQUENCE: 317
gatatttgga ttcacggtta agagagttcc ttttccaaat gtcagtttat agttgctacc 60

<210> SEQ ID NO 318

<211> LENGTH: 51
<212> TYPE: DNA
<213> ORGANISM: Homo sapiens
<220> FEATURE:
<223> OTHER INFORMATION: TRAJ54*01_BB-L_R1

<400> SEQUENCE: 318
gatatttggg ttgatagtca gcctggttcc ttggccaaat accagcttct g 51

<210> SEQ ID NO 319
<211> LENGTH: 57
<212> TYPE: DNA
<213> ORGANISM: Homo sapiens
<220> FEATURE:
<223> OTHER INFORMATION: TRAJ56*01_BB-L_R1

<400> SEQUENCE: 319
gatatctggt ctaacactca gagttattcc ttttccaaat gtcagcttac tattggc 57

<210> SEQ ID NO 320
<211> LENGTH: 57
<212> TYPE: DNA
<213> ORGANISM: Homo sapiens
<220> FEATURE:
<223> OTHER INFORMATION: TRAJ57*01_BB-L_R1

<400> SEQUENCE: 320
gatatatggg tttactgtca gtttcgttcc ctttccaaag accagctttt cagatcc 57

<210> SEQ ID NO 321
<211> LENGTH: 48
<212> TYPE: DNA
<213> ORGANISM: Homo sapiens
<220> FEATURE:
<223> OTHER INFORMATION: TRAJ59*01_BB-L_R1

<400> SEQUENCE: 321
gatattcact ctcacttgcg tccccattcc aaatgtaaat ttcctgtt 48

<210> SEQ ID NO 322
<211> LENGTH: 54
<212> TYPE: DNA
<213> ORGANISM: Homo sapiens
<220> FEATURE:
<223> OTHER INFORMATION: TRAJ61*01_BB-L_R1

<400> SEQUENCE: 322
gatattgagt ttcatgattc ctctagtgtt ggctccaaat gtcagtttcc tatt 54

<210> SEQ ID NO 323
<211> LENGTH: 56
<212> TYPE: DNA
<213> ORGANISM: Homo sapiens
<220> FEATURE:
<223> OTHER INFORMATION: J Donor_Short_TRAJ1

<400> SEQUENCE: 323
ggtctcgttt ggcaaaggaa ccagagtttc cacttctccc catatccagt gagacc 56

<210> SEQ ID NO 324
<211> LENGTH: 56
<212> TYPE: DNA
<213> ORGANISM: Homo sapiens
<220> FEATURE:
<223> OTHER INFORMATION: J Donor_Short_TRAJ2

<400> SEQUENCE: 324
ggtctcgttt gggaaaggga cccatgtatt cattatatct gatatccagt gagacc 56

<210> SEQ ID NO 325
<211> LENGTH: 56
<212> TYPE: DNA
<213> ORGANISM: Homo sapiens
<220> FEATURE:
<223> OTHER INFORMATION: J Donor_Short_TRAJ3

<400> SEQUENCE: 325
ggtctcgttt ggatcaggga ccagactcag catccggcca aatatccagt gagacc 56

<210> SEQ ID NO 326
<211> LENGTH: 56
<212> TYPE: DNA
<213> ORGANISM: Homo sapiens
<220> FEATURE:
<223> OTHER INFORMATION: J Donor_Short_TRAJ4

<400> SEQUENCE: 326
ggtctcgttt ggagcaggga ccaggctggc tgtacaccca tatatccagt gagacc 56

<210> SEQ ID NO 327
<211> LENGTH: 56
<212> TYPE: DNA
<213> ORGANISM: Homo sapiens
<220> FEATURE:
<223> OTHER INFORMATION: J Donor_Short_TRAJ5

<400> SEQUENCE: 327
ggtctcgttt gggagtggaa caagactcca agtgcaacca aatatccagt gagacc 56

<210> SEQ ID NO 328
<211> LENGTH: 56
<212> TYPE: DNA
<213> ORGANISM: Homo sapiens
<220> FEATURE:
<223> OTHER INFORMATION: J Donor_Short_TRAJ6

<400> SEQUENCE: 328
ggtctcgttt ggaagaggaa ccagccttat tgttcatccg tatatccagt gagacc 56

<210> SEQ ID NO 329
<211> LENGTH: 56
<212> TYPE: DNA
<213> ORGANISM: Homo sapiens
<220> FEATURE:
<223> OTHER INFORMATION: J Donor_Short_TRAJ7

<400> SEQUENCE: 329
ggtctcgttt gggaagggga accaagtggt ggtcatacca aatatccagt gagacc 56

<210> SEQ ID NO 330
<211> LENGTH: 56
<212> TYPE: DNA
<213> ORGANISM: Homo sapiens
<220> FEATURE:
<223> OTHER INFORMATION: J Donor_Short_TRAJ8

<400> SEQUENCE: 330
ggtctcgttt ggaactggca cccgacttct ggtcagtcca aatatccagt gagacc 56

<210> SEQ ID NO 331
<211> LENGTH: 56
<212> TYPE: DNA

<213> ORGANISM: Homo sapiens
<220> FEATURE:
<223> OTHER INFORMATION: J Donor_Short_TRAJ9

<400> SEQUENCE: 331
ggtctcgttt ggagcaggaa caagactatt tgttaaagca aatatccagt gagacc 56

<210> SEQ ID NO 332
<211> LENGTH: 56
<212> TYPE: DNA
<213> ORGANISM: Homo sapiens
<220> FEATURE:
<223> OTHER INFORMATION: J Donor_Short_TRAJ10

<400> SEQUENCE: 332
ggtctcgttt gggacaggca ctcagctaaa agtggaactc aatatccagt gagacc 56

<210> SEQ ID NO 333
<211> LENGTH: 56
<212> TYPE: DNA
<213> ORGANISM: Homo sapiens
<220> FEATURE:
<223> OTHER INFORMATION: J Donor_Short_TRAJ11

<400> SEQUENCE: 333
ggtctcgttt gggaagggga ctatgcttct agtctctcca gatatccagt gagacc 56

<210> SEQ ID NO 334
<211> LENGTH: 56
<212> TYPE: DNA
<213> ORGANISM: Homo sapiens
<220> FEATURE:
<223> OTHER INFORMATION: J Donor_Short_TRAJ12

<400> SEQUENCE: 334
ggtctcgttt gggagtggga ccagactgct ggtcaggcct gatatccagt gagacc 56

<210> SEQ ID NO 335
<211> LENGTH: 56
<212> TYPE: DNA
<213> ORGANISM: Homo sapiens
<220> FEATURE:
<223> OTHER INFORMATION: J Donor_Short_TRAJ13

<400> SEQUENCE: 335
ggtctcgttt ggaattggaa caaagctcca agtcatccca aatatccagt gagacc 56

<210> SEQ ID NO 336
<211> LENGTH: 56
<212> TYPE: DNA
<213> ORGANISM: Homo sapiens
<220> FEATURE:
<223> OTHER INFORMATION: J Donor_Short_TRAJ14

<400> SEQUENCE: 336
ggtctcgttt gggagtggga caagattatc agtaaaacct gatatccagt gagacc 56

<210> SEQ ID NO 337
<211> LENGTH: 56
<212> TYPE: DNA
<213> ORGANISM: Homo sapiens
<220> FEATURE:
<223> OTHER INFORMATION: J Donor_Short_TRAJ15

<400> SEQUENCE: 337
ggtctcgttt gggaagggaa cccacctatc agtgagttcc aatatccagt gagacc 56

<210> SEQ ID NO 338
<211> LENGTH: 56
<212> TYPE: DNA
<213> ORGANISM: Homo sapiens
<220> FEATURE:
<223> OTHER INFORMATION: J Donor_Short_TRAJ16

<400> SEQUENCE: 338
ggtctcgttt gcaaggggaa ccatgttaaa ggtggatctt aatatccagt gagacc 56

<210> SEQ ID NO 339
<211> LENGTH: 56
<212> TYPE: DNA
<213> ORGANISM: Homo sapiens
<220> FEATURE:
<223> OTHER INFORMATION: J Donor_Short_TRAJ17

<400> SEQUENCE: 339
ggtctcgttt ggaggaggaa ccagggtgct agttaaacca aatatccagt gagacc 56

<210> SEQ ID NO 340
<211> LENGTH: 56
<212> TYPE: DNA
<213> ORGANISM: Homo sapiens
<220> FEATURE:
<223> OTHER INFORMATION: J Donor_Short_TRAJ18

<400> SEQUENCE: 340
ggtctcgttt ggaagaggaa ctcagttgac tgtctggcct gatatccagt gagacc 56

<210> SEQ ID NO 341
<211> LENGTH: 56
<212> TYPE: DNA
<213> ORGANISM: Homo sapiens
<220> FEATURE:
<223> OTHER INFORMATION: J Donor_Short_TRAJ19

<400> SEQUENCE: 341
ggtctcgttt ggaaagggat ccaaacataa tgtcactcca aatatccagt gagacc 56

<210> SEQ ID NO 342
<211> LENGTH: 56
<212> TYPE: DNA
<213> ORGANISM: Homo sapiens
<220> FEATURE:
<223> OTHER INFORMATION: J Donor_Short_TRAJ20

<400> SEQUENCE: 342
ggtctcgttt ggagccggaa ccacagtaac tgtaagagca aatatccagt gagacc 56

<210> SEQ ID NO 343
<211> LENGTH: 56
<212> TYPE: DNA
<213> ORGANISM: Homo sapiens
<220> FEATURE:
<223> OTHER INFORMATION: J Donor_Short_TRAJ21

<400> SEQUENCE: 343
ggtctcgttt ggatctggga ccaaactcaa tgtaaaacca aatatccagt gagacc 56

<210> SEQ ID NO 344
<211> LENGTH: 56
<212> TYPE: DNA
<213> ORGANISM: Homo sapiens
<220> FEATURE:

<223> OTHER INFORMATION: J Donor_Short_TRAJ22

<400> SEQUENCE: 344
ggtctcgttt ggatctggga cacaattgac tgttttacct gatatccagt gagacc 56

<210> SEQ ID NO 345
<211> LENGTH: 56
<212> TYPE: DNA
<213> ORGANISM: Homo sapiens
<220> FEATURE:
<223> OTHER INFORMATION: J Donor_Short_TRAJ23

<400> SEQUENCE: 345
ggtctcgttt ggacagggaa cggagttatc tgtgaaaccc aatatccagt gagacc 56

<210> SEQ ID NO 346
<211> LENGTH: 56
<212> TYPE: DNA
<213> ORGANISM: Homo sapiens
<220> FEATURE:
<223> OTHER INFORMATION: J Donor_Short_TRAJ24

<400> SEQUENCE: 346
ggtctcgttt ggagcaggga cccaggttgt ggtcaccccca gatatccagt gagacc 56

<210> SEQ ID NO 347
<211> LENGTH: 56
<212> TYPE: DNA
<213> ORGANISM: Homo sapiens
<220> FEATURE:
<223> OTHER INFORMATION: J Donor_Short_TRAJ25

<400> SEQUENCE: 347
ggtctcgttt gggaagggga caaggctgct tgtcaagcca aatatccagt gagacc 56

<210> SEQ ID NO 348
<211> LENGTH: 56
<212> TYPE: DNA
<213> ORGANISM: Homo sapiens
<220> FEATURE:
<223> OTHER INFORMATION: J Donor_Short_TRAJ26

<400> SEQUENCE: 348
ggtctcgttt ggtcccggaa ccagattgtc cgtgctgccc tatatccagt gagacc 56

<210> SEQ ID NO 349
<211> LENGTH: 56
<212> TYPE: DNA
<213> ORGANISM: Homo sapiens
<220> FEATURE:
<223> OTHER INFORMATION: J Donor_Short_TRAJ27

<400> SEQUENCE: 349
ggtctcgttt ggggatggga ctacgctcac tgtgaagcca aatatccagt gagacc 56

<210> SEQ ID NO 350
<211> LENGTH: 56
<212> TYPE: DNA
<213> ORGANISM: Homo sapiens
<220> FEATURE:
<223> OTHER INFORMATION: J Donor_Short_TRAJ28

<400> SEQUENCE: 350
ggtctcgttt gggaagggga ccaaactctc ggtcatacca aatatccagt gagacc 56

<210> SEQ ID NO 351
<211> LENGTH: 56
<212> TYPE: DNA
<213> ORGANISM: Homo sapiens
<220> FEATURE:
<223> OTHER INFORMATION: J Donor_Short_TRAJ29

<400> SEQUENCE: 351
ggtctcgttt ggaaagggca caagactttc tgtgattgca aatatccagt gagacc 56

<210> SEQ ID NO 352
<211> LENGTH: 56
<212> TYPE: DNA
<213> ORGANISM: Homo sapiens
<220> FEATURE:
<223> OTHER INFORMATION: J Donor_Short_TRAJ30

<400> SEQUENCE: 352
ggtctcgttt ggaaaaggga cacgacttca tattctcccc aatatccagt gagacc 56

<210> SEQ ID NO 353
<211> LENGTH: 56
<212> TYPE: DNA
<213> ORGANISM: Homo sapiens
<220> FEATURE:
<223> OTHER INFORMATION: J Donor_Short_TRAJ31

<400> SEQUENCE: 353
ggtctcgttt ggagatggaa ctcagctggt ggtgaagccc aatatccagt gagacc 56

<210> SEQ ID NO 354
<211> LENGTH: 56
<212> TYPE: DNA
<213> ORGANISM: Homo sapiens
<220> FEATURE:
<223> OTHER INFORMATION: J Donor_Short_TRAJ32

<400> SEQUENCE: 354
ggtctcgttt ggaactggca ctctgcttgc tgtccagcca aatatccagt gagacc 56

<210> SEQ ID NO 355
<211> LENGTH: 56
<212> TYPE: DNA
<213> ORGANISM: Homo sapiens
<220> FEATURE:
<223> OTHER INFORMATION: J Donor_Short_TRAJ33

<400> SEQUENCE: 355
ggtctcgtgg ggcgctggga ccaagctaat tataaagcca gatatccagt gagacc 56

<210> SEQ ID NO 356
<211> LENGTH: 56
<212> TYPE: DNA
<213> ORGANISM: Homo sapiens
<220> FEATURE:
<223> OTHER INFORMATION: J Donor_Short_TRAJ34

<400> SEQUENCE: 356
ggtctcgttt gggactggga ccagattaca agtctttcca aatatccagt gagacc 56

<210> SEQ ID NO 357
<211> LENGTH: 56
<212> TYPE: DNA
<213> ORGANISM: Homo sapiens
<220> FEATURE:
<223> OTHER INFORMATION: J Donor_Short_TRAJ36

<400> SEQUENCE: 357
ggtctcgttt gggactggaa cgagactcac cgttattccc tatatccagt gagacc 56

<210> SEQ ID NO 358
<211> LENGTH: 56
<212> TYPE: DNA
<213> ORGANISM: Homo sapiens
<220> FEATURE:
<223> OTHER INFORMATION: J Donor_Short_TRAJ37

<400> SEQUENCE: 358
ggtctcgttt gggcaaggga caactttaca agtaaaacca gatatccagt gagacc 56

<210> SEQ ID NO 359
<211> LENGTH: 56
<212> TYPE: DNA
<213> ORGANISM: Homo sapiens
<220> FEATURE:
<223> OTHER INFORMATION: J Donor_Short_TRAJ38

<400> SEQUENCE: 359
ggtctcgtgg ggattgggaa caagcctggc agtaaatccg aatatccagt gagacc 56

<210> SEQ ID NO 360
<211> LENGTH: 56
<212> TYPE: DNA
<213> ORGANISM: Homo sapiens
<220> FEATURE:
<223> OTHER INFORMATION: J Donor_Short_TRAJ39

<400> SEQUENCE: 360
ggtctcgttt ggaggaggaa caaggttaat ggtcaaaccc catatccagt gagacc 56

<210> SEQ ID NO 361
<211> LENGTH: 56
<212> TYPE: DNA
<213> ORGANISM: Homo sapiens
<220> FEATURE:
<223> OTHER INFORMATION: J Donor_Short_TRAJ40

<400> SEQUENCE: 361
ggtctcgttt ggaacaggca ccaggctgaa ggttttagca aatatccagt gagacc 56

<210> SEQ ID NO 362
<211> LENGTH: 56
<212> TYPE: DNA
<213> ORGANISM: Homo sapiens
<220> FEATURE:
<223> OTHER INFORMATION: J Donor_Short_TRAJ41

<400> SEQUENCE: 362
ggtctcgttt ggcaaaggca cctcgctgtt ggtcacaccc catatccagt gagacc 56

<210> SEQ ID NO 363
<211> LENGTH: 56
<212> TYPE: DNA
<213> ORGANISM: Homo sapiens
<220> FEATURE:
<223> OTHER INFORMATION: J Donor_Short_TRAJ42

<400> SEQUENCE: 363
ggtctcgttt ggaaaaggca ctaaactctc tgttaaacca aatatccagt gagacc 56

<210> SEQ ID NO 364
<211> LENGTH: 56

<212> TYPE: DNA
<213> ORGANISM: Homo sapiens
<220> FEATURE:
<223> OTHER INFORMATION: J Donor_Short_TRAJ43

<400> SEQUENCE: 364
ggtctcgttt ggagcaggga ccagactgac agtaaaacca aatatccagt gagacc 56

<210> SEQ ID NO 365
<211> LENGTH: 56
<212> TYPE: DNA
<213> ORGANISM: Homo sapiens
<220> FEATURE:
<223> OTHER INFORMATION: J Donor_Short_TRAJ44

<400> SEQUENCE: 365
ggtctcgttt gggactggaa caagacttca ggtcacgctc gatatccagt gagacc 56

<210> SEQ ID NO 366
<211> LENGTH: 56
<212> TYPE: DNA
<213> ORGANISM: Homo sapiens
<220> FEATURE:
<223> OTHER INFORMATION: J Donor_Short_TRAJ45

<400> SEQUENCE: 366
ggtctcgttt ggcaaaggga ctcatctaat catccagccc tatatccagt gagacc 56

<210> SEQ ID NO 367
<211> LENGTH: 56
<212> TYPE: DNA
<213> ORGANISM: Homo sapiens
<220> FEATURE:
<223> OTHER INFORMATION: J Donor_Short_TRAJ46

<400> SEQUENCE: 367
ggtctcgttt gggaccggga ctcgtttagc agttaggccc aatatccagt gagacc 56

<210> SEQ ID NO 368
<211> LENGTH: 56
<212> TYPE: DNA
<213> ORGANISM: Homo sapiens
<220> FEATURE:
<223> OTHER INFORMATION: J Donor_Short_TRAJ47

<400> SEQUENCE: 368
ggtctcgttt ggcgcaggaa ccattctgag agtcaagtcc tatatccagt gagacc 56

<210> SEQ ID NO 369
<211> LENGTH: 56
<212> TYPE: DNA
<213> ORGANISM: Homo sapiens
<220> FEATURE:
<223> OTHER INFORMATION: J Donor_Short_TRAJ48

<400> SEQUENCE: 369
ggtctcgttt gggactggaa caagactcac catcataccc aatatccagt gagacc 56

<210> SEQ ID NO 370
<211> LENGTH: 56
<212> TYPE: DNA
<213> ORGANISM: Homo sapiens
<220> FEATURE:
<223> OTHER INFORMATION: J Donor_Short_TRAJ49

<400> SEQUENCE: 370
ggtctcgttt gggacaggga caagtttgac ggtcattcca aatatccagt gagacc 56

<210> SEQ ID NO 371
<211> LENGTH: 56
<212> TYPE: DNA
<213> ORGANISM: Homo sapiens
<220> FEATURE:
<223> OTHER INFORMATION: J Donor_Short_TRAJ50

<400> SEQUENCE: 371
ggtctcgttt gggccaggga caagcttatc agtcattcca aatatccagt gagacc 56

<210> SEQ ID NO 372
<211> LENGTH: 56
<212> TYPE: DNA
<213> ORGANISM: Homo sapiens
<220> FEATURE:
<223> OTHER INFORMATION: J Donor_Short_TRAJ52

<400> SEQUENCE: 372
ggtctcgttt ggacaaggga ccatcttgac tgtccatcca aatatccagt gagacc 56

<210> SEQ ID NO 373
<211> LENGTH: 56
<212> TYPE: DNA
<213> ORGANISM: Homo sapiens
<220> FEATURE:
<223> OTHER INFORMATION: J Donor_Short_TRAJ53

<400> SEQUENCE: 373
ggtctcgttt ggaaaaggaa ctctcttaac cgtgaatcca aatatccagt gagacc 56

<210> SEQ ID NO 374
<211> LENGTH: 56
<212> TYPE: DNA
<213> ORGANISM: Homo sapiens
<220> FEATURE:
<223> OTHER INFORMATION: J Donor_Short_TRAJ54

<400> SEQUENCE: 374
ggtctcgttt ggccaaggaa ccaggctgac tatcaaccca aatatccagt gagacc 56

<210> SEQ ID NO 375
<211> LENGTH: 56
<212> TYPE: DNA
<213> ORGANISM: Homo sapiens
<220> FEATURE:
<223> OTHER INFORMATION: J Donor_Short_TRAJ56

<400> SEQUENCE: 375
ggtctcgttt ggaaaaggaa taactctgag tgttagacca gatatccagt gagacc 56

<210> SEQ ID NO 376
<211> LENGTH: 56
<212> TYPE: DNA
<213> ORGANISM: Homo sapiens
<220> FEATURE:
<223> OTHER INFORMATION: J Donor_Short_TRAJ57

<400> SEQUENCE: 376
ggtctcgttt ggaaagggaa cgaaactgac agtaaaccca tatatccagt gagacc 56

<210> SEQ ID NO 377
<211> LENGTH: 50
<212> TYPE: DNA
<213> ORGANISM: Homo sapiens
<220> FEATURE:
<223> OTHER INFORMATION: J Donor_Short_TRAJ59

<400> SEQUENCE: 377
ggtctcgttt ggaatgggga cgcaagtgag agtgaatatc cagtgagacc 50

<210> SEQ ID NO 378
<211> LENGTH: 56
<212> TYPE: DNA
<213> ORGANISM: Homo sapiens
<220> FEATURE:
<223> OTHER INFORMATION: J Donor_Short_TRAJ61

<400> SEQUENCE: 378
ggtctcgttt ggagccaaca ctagaggaat catgaaactc aatatccagt gagacc 56

<210> SEQ ID NO 379
<211> LENGTH: 74
<212> TYPE: DNA
<213> ORGANISM: Homo sapiens
<220> FEATURE:
<223> OTHER INFORMATION: J Donor_Long_TRAJ1

<400> SEQUENCE: 379
ggtctcgatt acctcccagt tgcaatttgg caaaggaacc agagtttcca cttctcccca 60
tatccagtga gacc 74

<210> SEQ ID NO 380
<211> LENGTH: 77
<212> TYPE: DNA
<213> ORGANISM: Homo sapiens
<220> FEATURE:
<223> OTHER INFORMATION: J Donor_Long_TRAJ2

<400> SEQUENCE: 380
ggtctcggga acaattgata aactcacatt tgggaaaggg acccatgtat tcattatatc 60
tgatatccag tgagacc 77

<210> SEQ ID NO 381
<211> LENGTH: 74
<212> TYPE: DNA
<213> ORGANISM: Homo sapiens
<220> FEATURE:
<223> OTHER INFORMATION: J Donor_Long_TRAJ3

<400> SEQUENCE: 381
ggtctcgagt gcttccaaga taatctttgg atcagggacc agactcagca tccggccaaa 60
tatccagtga gacc 74

<210> SEQ ID NO 382
<211> LENGTH: 74
<212> TYPE: DNA
<213> ORGANISM: Homo sapiens
<220> FEATURE:
<223> OTHER INFORMATION: J Donor_Long_TRAJ4

<400> SEQUENCE: 382
ggtctcgggc tacaataagc tgatctttgg agcagggacc aggctggctg tacacccata 60
tatccagtga gacc 74

<210> SEQ ID NO 383
<211> LENGTH: 71
<212> TYPE: DNA

<213> ORGANISM: Homo sapiens
<220> FEATURE:
<223> OTHER INFORMATION: J Donor_Long_TRAJ5

<400> SEQUENCE: 383
ggtctcgagg agagcactta cttttgggag tggaacaaga ctccaagtgc aaccaaatat 60
ccagtgagac c 71

<210> SEQ ID NO 384
<211> LENGTH: 74
<212> TYPE: DNA
<213> ORGANISM: Homo sapiens
<220> FEATURE:
<223> OTHER INFORMATION: J Donor_Long_TRAJ6

<400> SEQUENCE: 384
ggtctcggga agctacatac ctacatttgg aagaggaacc agccttattg ttcatccgta 60
tatccagtga gacc 74

<210> SEQ ID NO 385
<211> LENGTH: 71
<212> TYPE: DNA
<213> ORGANISM: Homo sapiens
<220> FEATURE:
<223> OTHER INFORMATION: J Donor_Long_TRAJ7

<400> SEQUENCE: 385
ggtctcgaac aacagactcg cttttgggaa ggggaaccaa gtggtggtca taccaaatat 60
ccagtgagac c 71

<210> SEQ ID NO 386
<211> LENGTH: 71
<212> TYPE: DNA
<213> ORGANISM: Homo sapiens
<220> FEATURE:
<223> OTHER INFORMATION: J Donor_Long_TRAJ8

<400> SEQUENCE: 386
ggtctcgttt cagaaacttg tatttggaac tggcacccga cttctggtca gtccaaatat 60
ccagtgagac c 71

<210> SEQ ID NO 387
<211> LENGTH: 71
<212> TYPE: DNA
<213> ORGANISM: Homo sapiens
<220> FEATURE:
<223> OTHER INFORMATION: J Donor_Long_TRAJ9

<400> SEQUENCE: 387
ggtctcgggc ttcaaaacta tctttggagc aggaacaaga ctatttgtta aagcaaatat 60
ccagtgagac c 71

<210> SEQ ID NO 388
<211> LENGTH: 74
<212> TYPE: DNA
<213> ORGANISM: Homo sapiens
<220> FEATURE:
<223> OTHER INFORMATION: J Donor_Long_TRAJ10

<400> SEQUENCE: 388
ggtctcggga ggaaacaaac tcacctttgg gacaggcact cagctaaaag tggaactcaa 60
tatccagtga gacc 74

<210> SEQ ID NO 389
<211> LENGTH: 71
<212> TYPE: DNA
<213> ORGANISM: Homo sapiens
<220> FEATURE:
<223> OTHER INFORMATION: J Donor_Long_TRAJ11

<400> SEQUENCE: 389
ggtctcgtac agcaccctca cctttgggaa ggggactatg cttctagtct ctccagatat 60
ccagtgagac c 71

<210> SEQ ID NO 390
<211> LENGTH: 71
<212> TYPE: DNA
<213> ORGANISM: Homo sapiens
<220> FEATURE:
<223> OTHER INFORMATION: J Donor_Long_TRAJ12

<400> SEQUENCE: 390
ggtctcgagt tataaattga tctttgggag tgggaccaga ctgctggtca ggcctgatat 60
ccagtgagac c 71

<210> SEQ ID NO 391
<211> LENGTH: 74
<212> TYPE: DNA
<213> ORGANISM: Homo sapiens
<220> FEATURE:
<223> OTHER INFORMATION: J Donor_Long_TRAJ13

<400> SEQUENCE: 391
ggtctcgggt taccagaaag ttacctttgg aattggaaca aagctccaag tcatcccaaa 60
tatccagtga gacc 74

<210> SEQ ID NO 392
<211> LENGTH: 62
<212> TYPE: DNA
<213> ORGANISM: Homo sapiens
<220> FEATURE:
<223> OTHER INFORMATION: J Donor_Long_TRAJ14

<400> SEQUENCE: 392
ggtctcgttc atctttggga gtgggacaag attatcagta aaacctgata tccagtgaga 60
cc 62

<210> SEQ ID NO 393
<211> LENGTH: 71
<212> TYPE: DNA
<213> ORGANISM: Homo sapiens
<220> FEATURE:
<223> OTHER INFORMATION: J Donor_Long_TRAJ15

<400> SEQUENCE: 393
ggtctcggga actgctctga tctttgggaa gggaacccac ctatcagtga gttccaatat 60
ccagtgagac c 71

<210> SEQ ID NO 394
<211> LENGTH: 71
<212> TYPE: DNA
<213> ORGANISM: Homo sapiens
<220> FEATURE:
<223> OTHER INFORMATION: J Donor_Long_TRAJ16

<400> SEQUENCE: 394
ggtctcggga cagaagctgc tctttgcaag gggaaccatg ttaaaggtgg atcttaatat 60
ccagtgagac c 71

<210> SEQ ID NO 395
<211> LENGTH: 74
<212> TYPE: DNA
<213> ORGANISM: Homo sapiens
<220> FEATURE:
<223> OTHER INFORMATION: J Donor_Long_TRAJ17

<400> SEQUENCE: 395
ggtctcggca ggcaacaagc taacttttgg aggaggaacc agggtgctag ttaaaccaaa 60
tatccagtga gacc 74

<210> SEQ ID NO 396
<211> LENGTH: 77
<212> TYPE: DNA
<213> ORGANISM: Homo sapiens
<220> FEATURE:
<223> OTHER INFORMATION: J Donor_Long_TRAJ18

<400> SEQUENCE: 396
ggtctcgtca accctgggga ggctatactt tggaagagga actcagttga ctgtctggcc 60
tgatatccag tgagacc 77

<210> SEQ ID NO 397
<211> LENGTH: 71
<212> TYPE: DNA
<213> ORGANISM: Homo sapiens
<220> FEATURE:
<223> OTHER INFORMATION: J Donor_Long_TRAJ19

<400> SEQUENCE: 397
ggtctcgttc tacaatttca cctttggaaa gggatccaaa cataatgtca ctccaaatat 60
ccagtgagac c 71

<210> SEQ ID NO 398
<211> LENGTH: 68
<212> TYPE: DNA
<213> ORGANISM: Homo sapiens
<220> FEATURE:
<223> OTHER INFORMATION: J Donor_Long_TRAJ20

<400> SEQUENCE: 398
ggtctcgtac aagctcagct ttggagccgg aaccacagta actgtaagag caaatatcca 60
gtgagacc 68

<210> SEQ ID NO 399
<211> LENGTH: 65
<212> TYPE: DNA
<213> ORGANISM: Homo sapiens
<220> FEATURE:
<223> OTHER INFORMATION: J Donor_Long_TRAJ21

<400> SEQUENCE: 399
ggtctcgaaa ttttactttg gatctgggac caaactcaat gtaaaaccaa atatccagtg 60
agacc 65

<210> SEQ ID NO 400
<211> LENGTH: 74

```
<212> TYPE: DNA
<213> ORGANISM: Homo sapiens
<220> FEATURE:
<223> OTHER INFORMATION: J Donor_Long_TRAJ22

<400> SEQUENCE: 400

ggtctcgtct gcaaggcaac tgacctttgg atctgggaca caattgactg ttttacctga     60

tatccagtga gacc                                                       74


<210> SEQ ID NO 401
<211> LENGTH: 74
<212> TYPE: DNA
<213> ORGANISM: Homo sapiens
<220> FEATURE:
<223> OTHER INFORMATION: J Donor_Long_TRAJ23

<400> SEQUENCE: 401

ggtctcgcag ggaggaaagc ttatctttgg acagggaacg gagttatctg tgaaacccaa     60

tatccagtga gacc                                                       74


<210> SEQ ID NO 402
<211> LENGTH: 74
<212> TYPE: DNA
<213> ORGANISM: Homo sapiens
<220> FEATURE:
<223> OTHER INFORMATION: J Donor_Long_TRAJ24

<400> SEQUENCE: 402

ggtctcgagt tggggtaaat tgcagtttgg agcagggacc caggttgtgg tcaccccaga     60

tatccagtga gacc                                                       74


<210> SEQ ID NO 403
<211> LENGTH: 71
<212> TYPE: DNA
<213> ORGANISM: Homo sapiens
<220> FEATURE:
<223> OTHER INFORMATION: J Donor_Long_TRAJ25

<400> SEQUENCE: 403

ggtctcgggc ttctccttta tctttgggaa ggggacaagg ctgcttgtca agccaaatat     60

ccagtgagac c                                                          71


<210> SEQ ID NO 404
<211> LENGTH: 71
<212> TYPE: DNA
<213> ORGANISM: Homo sapiens
<220> FEATURE:
<223> OTHER INFORMATION: J Donor_Long_TRAJ26

<400> SEQUENCE: 404

ggtctcgggt cagaattttg tctttggtcc cggaaccaga ttgtccgtgc tgccctatat     60

ccagtgagac c                                                          71


<210> SEQ ID NO 405
<211> LENGTH: 71
<212> TYPE: DNA
<213> ORGANISM: Homo sapiens
<220> FEATURE:
<223> OTHER INFORMATION: J Donor_Long_TRAJ27

<400> SEQUENCE: 405

ggtctcggca ggcaaatcaa cctttgggga tgggactacg ctcactgtga agccaaatat     60
```

ccagtgagac c 71

<210> SEQ ID NO 406
<211> LENGTH: 77
<212> TYPE: DNA
<213> ORGANISM: Homo sapiens
<220> FEATURE:
<223> OTHER INFORMATION: J Donor_Long_TRAJ28

<400> SEQUENCE: 406
ggtctcggct gggagttacc aactcacttt tgggaagggg accaaactct cggtcatacc 60
aaatatccag tgagacc 77

<210> SEQ ID NO 407
<211> LENGTH: 71
<212> TYPE: DNA
<213> ORGANISM: Homo sapiens
<220> FEATURE:
<223> OTHER INFORMATION: J Donor_Long_TRAJ29

<400> SEQUENCE: 407
ggtctcgaac acacctcttg tctttggaaa gggcacaaga ctttctgtga ttgcaaatat 60
ccagtgagac c 71

<210> SEQ ID NO 408
<211> LENGTH: 68
<212> TYPE: DNA
<213> ORGANISM: Homo sapiens
<220> FEATURE:
<223> OTHER INFORMATION: J Donor_Long_TRAJ30

<400> SEQUENCE: 408
ggtctcggac aagatcatct ttggaaaagg gacacgactt catattctcc ccaatatcca 60
gtgagacc 68

<210> SEQ ID NO 409
<211> LENGTH: 68
<212> TYPE: DNA
<213> ORGANISM: Homo sapiens
<220> FEATURE:
<223> OTHER INFORMATION: J Donor_Long_TRAJ31

<400> SEQUENCE: 409
ggtctcggcc agactcatgt ttggagatgg aactcagctg gtggtgaagc ccaatatcca 60
gtgagacc 68

<210> SEQ ID NO 410
<211> LENGTH: 77
<212> TYPE: DNA
<213> ORGANISM: Homo sapiens
<220> FEATURE:
<223> OTHER INFORMATION: J Donor_Long_TRAJ32

<400> SEQUENCE: 410
ggtctcgggt gctacaaaca agctcatctt tggaactggc actctgcttg ctgtccagcc 60
aaatatccag tgagacc 77

<210> SEQ ID NO 411
<211> LENGTH: 68
<212> TYPE: DNA
<213> ORGANISM: Homo sapiens
<220> FEATURE:
<223> OTHER INFORMATION: J Donor_Long_TRAJ33

<400> SEQUENCE: 411
ggtctcgtat cagttaatct ggggcgctgg gaccaagcta attataaagc cagatatcca 60
gtgagacc 68

<210> SEQ ID NO 412
<211> LENGTH: 68
<212> TYPE: DNA
<213> ORGANISM: Homo sapiens
<220> FEATURE:
<223> OTHER INFORMATION: J Donor_Long_TRAJ34

<400> SEQUENCE: 412
ggtctcggac aagctcatct ttgggactgg gaccagatta caagtctttc caaatatcca 60
gtgagacc 68

<210> SEQ ID NO 413
<211> LENGTH: 71
<212> TYPE: DNA
<213> ORGANISM: Homo sapiens
<220> FEATURE:
<223> OTHER INFORMATION: J Donor_Long_TRAJ36

<400> SEQUENCE: 413
ggtctcggca aacaacctct tctttgggac tggaacgaga ctcaccgtta ttccctatat 60
ccagtgagac c 71

<210> SEQ ID NO 414
<211> LENGTH: 74
<212> TYPE: DNA
<213> ORGANISM: Homo sapiens
<220> FEATURE:
<223> OTHER INFORMATION: J Donor_Long_TRAJ37

<400> SEQUENCE: 414
ggtctcgaac acaggcaaac taatctttgg gcaagggaca actttacaag taaaaccaga 60
tatccagtga gacc 74

<210> SEQ ID NO 415
<211> LENGTH: 74
<212> TYPE: DNA
<213> ORGANISM: Homo sapiens
<220> FEATURE:
<223> OTHER INFORMATION: J Donor_Long_TRAJ38

<400> SEQUENCE: 415
ggtctcgaac aaccgtaagc tgatttgggg attgggaaca agcctggcag taaatccgaa 60
tatccagtga gacc 74

<210> SEQ ID NO 416
<211> LENGTH: 74
<212> TYPE: DNA
<213> ORGANISM: Homo sapiens
<220> FEATURE:
<223> OTHER INFORMATION: J Donor_Long_TRAJ39

<400> SEQUENCE: 416
ggtctcggca ggcaacatgc tcacctttgg aggaggaaca aggttaatgg tcaaacccca 60
tatccagtga gacc 74

<210> SEQ ID NO 417

<211> LENGTH: 71
<212> TYPE: DNA
<213> ORGANISM: Homo sapiens
<220> FEATURE:
<223> OTHER INFORMATION: J Donor_Long_TRAJ40

<400> SEQUENCE: 417
ggtctcgacc tacaaataca tctttggaac aggcaccagg ctgaaggttt tagcaaatat 60
ccagtgagac c 71

<210> SEQ ID NO 418
<211> LENGTH: 74
<212> TYPE: DNA
<213> ORGANISM: Homo sapiens
<220> FEATURE:
<223> OTHER INFORMATION: J Donor_Long_TRAJ41

<400> SEQUENCE: 418
ggtctcgtcc gggtatgcac tcaactttgg caaaggcacc tcgctgttgg tcacacccca 60
tatccagtga gacc 74

<210> SEQ ID NO 419
<211> LENGTH: 77
<212> TYPE: DNA
<213> ORGANISM: Homo sapiens
<220> FEATURE:
<223> OTHER INFORMATION: J Donor_Long_TRAJ42

<400> SEQUENCE: 419
ggtctcggga agccaaggaa atctcatctt tggaaaaggc actaaactct ctgttaaacc 60
aaatatccag tgagacc 77

<210> SEQ ID NO 420
<211> LENGTH: 65
<212> TYPE: DNA
<213> ORGANISM: Homo sapiens
<220> FEATURE:
<223> OTHER INFORMATION: J Donor_Long_TRAJ43

<400> SEQUENCE: 420
ggtctcggac atgcgctttg gagcagggac cagactgaca gtaaaaccaa atatccagtg 60
agacc 65

<210> SEQ ID NO 421
<211> LENGTH: 74
<212> TYPE: DNA
<213> ORGANISM: Homo sapiens
<220> FEATURE:
<223> OTHER INFORMATION: J Donor_Long_TRAJ44

<400> SEQUENCE: 421
ggtctcgact gccagtaaac tcacctttgg gactggaaca agacttcagg tcacgctcga 60
tatccagtga gacc 74

<210> SEQ ID NO 422
<211> LENGTH: 77
<212> TYPE: DNA
<213> ORGANISM: Homo sapiens
<220> FEATURE:
<223> OTHER INFORMATION: J Donor_Long_TRAJ45

<400> SEQUENCE: 422
ggtctcggga ggtgctgacg gactcacctt tggcaaaggg actcatctaa tcatccagcc 60
ctatatccag tgagacc 77

<210> SEQ ID NO 423
<211> LENGTH: 74
<212> TYPE: DNA
<213> ORGANISM: Homo sapiens
<220> FEATURE:
<223> OTHER INFORMATION: J Donor_Long_TRAJ46

<400> SEQUENCE: 423
ggtctcgagc ggagacaagc tgacttttgg gaccgggact cgtttagcag ttaggcccaa 60
tatccagtga gacc 74

<210> SEQ ID NO 424
<211> LENGTH: 68
<212> TYPE: DNA
<213> ORGANISM: Homo sapiens
<220> FEATURE:
<223> OTHER INFORMATION: J Donor_Long_TRAJ47

<400> SEQUENCE: 424
ggtctcgaac aaactggtct ttggcgcagg aaccattctg agagtcaagt cctatatcca 60
gtgagacc 68

<210> SEQ ID NO 425
<211> LENGTH: 74
<212> TYPE: DNA
<213> ORGANISM: Homo sapiens
<220> FEATURE:
<223> OTHER INFORMATION: J Donor_Long_TRAJ48

<400> SEQUENCE: 425
ggtctcggga aatgagaaat taacctttgg gactggaaca agactcacca tcatacccaa 60
tatccagtga gacc 74

<210> SEQ ID NO 426
<211> LENGTH: 68
<212> TYPE: DNA
<213> ORGANISM: Homo sapiens
<220> FEATURE:
<223> OTHER INFORMATION: J Donor_Long_TRAJ49

<400> SEQUENCE: 426
ggtctcgaac cagttctatt ttgggacagg gacaagtttg acggtcattc caaatatcca 60
gtgagacc 68

<210> SEQ ID NO 427
<211> LENGTH: 71
<212> TYPE: DNA
<213> ORGANISM: Homo sapiens
<220> FEATURE:
<223> OTHER INFORMATION: J Donor_Long_TRAJ50

<400> SEQUENCE: 427
ggtctcgtac gacaaggtga tatttgggcc agggacaagc ttatcagtca ttccaaatat 60
ccagtgagac c 71

<210> SEQ ID NO 428
<211> LENGTH: 80
<212> TYPE: DNA
<213> ORGANISM: Homo sapiens
<220> FEATURE:

<223> OTHER INFORMATION: J Donor_Long_TRAJ52

<400> SEQUENCE: 428
ggtctcgggt actagctatg gaaagctgac atttggacaa gggaccatct tgactgtcca 60
tccaaatatc cagtgagacc 80

<210> SEQ ID NO 429
<211> LENGTH: 77
<212> TYPE: DNA
<213> ORGANISM: Homo sapiens
<220> FEATURE:
<223> OTHER INFORMATION: J Donor_Long_TRAJ53

<400> SEQUENCE: 429
ggtctcgggt agcaactata aactgacatt tggaaaagga actctcttaa ccgtgaatcc 60
aaatatccag tgagacc 77

<210> SEQ ID NO 430
<211> LENGTH: 71
<212> TYPE: DNA
<213> ORGANISM: Homo sapiens
<220> FEATURE:
<223> OTHER INFORMATION: J Donor_Long_TRAJ54

<400> SEQUENCE: 430
ggtctcggcc cagaagctgg tatttggcca aggaaccagg ctgactatca acccaaatat 60
ccagtgagac c 71

<210> SEQ ID NO 431
<211> LENGTH: 74
<212> TYPE: DNA
<213> ORGANISM: Homo sapiens
<220> FEATURE:
<223> OTHER INFORMATION: J Donor_Long_TRAJ56

<400> SEQUENCE: 431
ggtctcggcc aatagtaagc tgacatttgg aaaaggaata actctgagtg ttagaccaga 60
tatccagtga gacc 74

<210> SEQ ID NO 432
<211> LENGTH: 74
<212> TYPE: DNA
<213> ORGANISM: Homo sapiens
<220> FEATURE:
<223> OTHER INFORMATION: J Donor_Long_TRAJ57

<400> SEQUENCE: 432
ggtctcggga tctgaaaagc tggtctttgg aaagggaacg aaactgacag taaacccata 60
tatccagtga gacc 74

<210> SEQ ID NO 433
<211> LENGTH: 65
<212> TYPE: DNA
<213> ORGANISM: Homo sapiens
<220> FEATURE:
<223> OTHER INFORMATION: J Donor_Long_TRAJ59

<400> SEQUENCE: 433
ggtctcgaac aggaaattta catttggaat ggggacgcaa gtgagagtga atatccagtg 60
agacc 65

<210> SEQ ID NO 434
<211> LENGTH: 71
<212> TYPE: DNA
<213> ORGANISM: Homo sapiens
<220> FEATURE:
<223> OTHER INFORMATION: J Donor_Long_TRAJ61

<400> SEQUENCE: 434
ggtctcgaat aggaaactga catttggagc caacactaga ggaatcatga aactcaatat 60
ccagtgagac c 71

<210> SEQ ID NO 435
<211> LENGTH: 414
<212> TYPE: DNA
<213> ORGANISM: Homo sapiens
<220> FEATURE:
<223> OTHER INFORMATION: TRBV2_BB_1

<400> SEQUENCE: 435
gttcgaagct ggcatgacac gaagacttgt acgccaccat ggatacctgg ctcgtatgct 60
gggcaatttt tagtctcttg aaagcaggac tcacagaacc tgaagtcacc cagactccca 120
gccatcaggt cacacagatg ggacaggaag tgatcttgcg ctgtgtcccc atctctaatc 180
acttatactt ctattggtac agacaaatct tggggcagaa agtcgagttt ctggtttcct 240
tttataataa tgaaatctca gagaagtctg aaatattcga tgatcaattc tcagttgaaa 300
ggcctgatgg atcaaatttc actctgaaga tccggtccac aaagctggag gactcagcca 360
tgtacttttg cagagacctt gcggccgtgt cttccgacgc tgacagtgta gata 414

<210> SEQ ID NO 436
<211> LENGTH: 411
<212> TYPE: DNA
<213> ORGANISM: Homo sapiens
<220> FEATURE:
<223> OTHER INFORMATION: TRBV3-1_BB_1

<400> SEQUENCE: 436
gttcgaagct ggcatgacac gaagacttgt acgccaccat gggctgcagg ctcctctgct 60
gtgtggtctt ttgcctcctc caagcaggtc ccttggacac agctgtttcc cagactccaa 120
aatacctggt cacacagatg ggaaacgaca agtccattaa atgtgaacaa aatctgggcc 180
atgatactat gtattggtat aaacaggact ctaagaaatt tctgaagata atgtttagct 240
acaataataa ggagctcatt ataaatgaaa cagttccaaa tcgcttctca cctaaatctc 300
cagacaaagc tcacttaaat cttcacatca attccctgga gcttggtgac tctgctgtgt 360
atttttgcag agaccttgcg gccgtgtctt ccgacgctga cagtgtagat a 411

<210> SEQ ID NO 437
<211> LENGTH: 411
<212> TYPE: DNA
<213> ORGANISM: Homo sapiens
<220> FEATURE:
<223> OTHER INFORMATION: TRBV4-1_BB_1

<400> SEQUENCE: 437
gttcgaagct ggcatgacac gaagacttgt acgccaccat gggctgcagg ctgctctgct 60
gtgcggttct ctgtctcctg ggagcagttc ccatagacac tgaagttacc cagacaccaa 120
aacacctggt catgggaatg acaaataaga agtctttgaa atgtgaacaa catatggggc 180
acagggctat gtattggtac aagcagaaag ctaagaagcc accggagctc atgtttgtct 240
acagctatga gaaactctct ataaatgaaa gtgtgccaag tcgcttctca cctgaatgcc 300
ccaacagctc tctcttaaac cttcacctac acgccctgca gccagaagat tcagccctgt 360
atctttgcag agaccttgcg gccgtgtctt ccgacgctga cagtgtagat a 411

<210> SEQ ID NO 438
<211> LENGTH: 411
<212> TYPE: DNA
<213> ORGANISM: Homo sapiens
<220> FEATURE:
<223> OTHER INFORMATION: TRBV4-2_BB_1

<400> SEQUENCE: 438
gttcgaagct ggcatgacac gaagacttgt acgccaccat gggctgcagg ctgctctgct 60
gtgcggttct ctgtctcctg ggagcggtcc ccatggaaac gggagttacg cagacaccaa 120
gacacctggt catgggaatg acaaataaga agtctttgaa atgtgaacaa catctggggc 180
ataacgctat gtattggtac aagcaaagtg ctaagaagcc actggagctc atgtttgtct 240
acaactttaa agaacagact gaaaacaaca gtgtgccaag tcgcttctca cctgaatgcc 300
ccaacagctc tcacttattc cttcacctac acaccctgca gccagaagat tcggccctgt 360
atctttgcag agaccttgcg gccgtgtctt ccgacgctga cagtgtagat a 411

<210> SEQ ID NO 439
<211> LENGTH: 411
<212> TYPE: DNA
<213> ORGANISM: Homo sapiens
<220> FEATURE:
<223> OTHER INFORMATION: TRBV4-3_BB_1

<400> SEQUENCE: 439
gttcgaagct ggcatgacac gaagacttgt acgccaccat gggctgcagg ctgctctgct 60
gtgcggttct ctgtctcctg ggagcggtcc ccatggaaac gggagttacg cagacaccaa 120
gacacctggt catgggaatg acaaataaga agtctttgaa atgtgaacaa catctgggtc 180
ataacgctat gtattggtac aagcaaagtg ctaagaagcc actggagctc atgtttgtct 240
acagtcttga agaacgggtt gaaaacaaca gtgtgccaag tcgcttctca cctgaatgcc 300
ccaacagctc tcacttattc cttcacctac acaccctgca gccagaagat tcggccctgt 360
atctttgcag agaccttgcg gccgtgtctt ccgacgctga cagtgtagat a 411

<210> SEQ ID NO 440
<211> LENGTH: 411
<212> TYPE: DNA
<213> ORGANISM: Homo sapiens
<220> FEATURE:
<223> OTHER INFORMATION: TRBV5-1_BB_1

<400> SEQUENCE: 440
gttcgaagct ggcatgacac gaagacttgt acgccaccat gggctccagg ctgctctgtt 60
gggtgctgct ttgtctcctg ggagcaggcc cagtaaaggc tggagtcact caaactccaa 120
gatatctgat caaaacgaga ggacagcaag tgacactgag ctgctcccct atctctgggc 180
ataggagtgt atcctggtac caacagaccc caggacaggg ccttcagttc ctctttgaat 240
acttcagtga gacacagaga aacaaaggaa acttccctgg tcgattctca gggcgccagt 300
tctctaactc tcgctctgag atgaatgtga gcaccttgga gctgggggac tcggcccttt 360
atctttgcag agaccttgcg gccgtgtctt ccgacgctga cagtgtagat a 411

<210> SEQ ID NO 441
<211> LENGTH: 411
<212> TYPE: DNA
<213> ORGANISM: Homo sapiens
<220> FEATURE:
<223> OTHER INFORMATION: TRBV5-4_BB_1

<400> SEQUENCE: 441
gttcgaagct ggcatgacac gaagacttgt acgccaccat gggccctggg ctcctctgct 60
gggtgctgct ttgtctcctg ggagcaggct cagtggagac tggagtcacc caaagtccca 120
cacacctgat caaaacgaga ggacagcaag tgactctgag atgctcttct cagtctgggc 180
acaacactgt gtcctggtac caacaggccc tgggtcaggg gccccagttt atctttcagt 240
attataggga ggaagagaat ggcagaggaa acttccctcc tagattctca ggactccagt 300
tccctaatta tagctctgag ctgaatgtga acgccttgga gctggacgac tcggccctgt 360
atctttgcag agaccttgcg gccgtgtctt ccgacgctga cagtgtagat a 411

<210> SEQ ID NO 442
<211> LENGTH: 411
<212> TYPE: DNA
<213> ORGANISM: Homo sapiens
<220> FEATURE:
<223> OTHER INFORMATION: TRBV5-5_BB_1

<400> SEQUENCE: 442
gttcgaagct ggcatgacac gaagacttgt acgccaccat gggccctggg ctcctctgct 60
gggtgctgct ttgtctcctg ggagcaggcc cagtggacgc tggagtcacc caaagtccca 120
cacacctgat caaaacgaga ggacagcaag tgactctgag atgctctcct atctctgggc 180
acaagagtgt gtcctggtac caacaggtcc tgggtcaggg gccccagttt atctttcagt 240
attatgagaa agaagagaga ggaagaggaa acttccctga tcgattctca gctcgccagt 300
tccctaacta tagctctgag ctgaatgtga acgccttgtt gctgggggac tcggccctgt 360
atctttgcag agaccttgcg gccgtgtctt ccgacgctga cagtgtagat a 411

<210> SEQ ID NO 443
<211> LENGTH: 411
<212> TYPE: DNA
<213> ORGANISM: Homo sapiens
<220> FEATURE:
<223> OTHER INFORMATION: TRBV5-6_BB_1

<400> SEQUENCE: 443
gttcgaagct ggcatgacac gaagacttgt acgccaccat gggccccggg ctcctctgct 60
gggcactgct ttgtctcctg ggagcaggct tagtggacgc tggagtcacc caaagtccca 120
cacacctgat caaaacgaga ggacagcaag tgactctgag atgctctcct aagtctgggc 180
atgacactgt gtcctggtac caacaggccc tgggtcaggg gccccagttt atctttcagt 240
attatgagga ggaagagaga cagagaggca acttccctga tcgattctca ggtcaccagt 300
tccctaacta tagctctgag ctgaatgtga acgccttgtt gctgggggac tcggccctct 360
atctttgcag agaccttgcg gccgtgtctt ccgacgctga cagtgtagat a 411

<210> SEQ ID NO 444
<211> LENGTH: 411
<212> TYPE: DNA
<213> ORGANISM: Homo sapiens
<220> FEATURE:
<223> OTHER INFORMATION: TRBV5-7_BB_1

<400> SEQUENCE: 444
gttcgaagct ggcatgacac gaagacttgt acgccaccat gggccccggg ctcctctgct 60
gggtgctgct ttgtccccta ggagaaggcc cagtggacgc tggagtcacc caaagtccca 120
cacacctgat caaaacgaga ggacagcacg tgactctgag atgctctcct atctctgggc 180
acaccagtgt gtcctcgtac caacaggccc tgggtcaggg gccccagttt atctttcagt 240
attatgagaa agaagagaga ggaagaggaa acttccctga tcaattctca ggtcaccagt 300
tccctaacta tagctctgag ctgaatgtga acgccttgtt gctaggggac tcggccctct 360
atctttgcag agaccttgcg gccgtgtctt ccgacgctga cagtgtagat a 411

<210> SEQ ID NO 445
<211> LENGTH: 411
<212> TYPE: DNA
<213> ORGANISM: Homo sapiens
<220> FEATURE:
<223> OTHER INFORMATION: TRBV5-8_BB_1

<400> SEQUENCE: 445
gttcgaagct ggcatgacac gaagacttgt acgccaccat gggacccagg ctcctcttct 60
gggcactgct ttgtctcctc ggaacaggcc cagtggaggc tggagtcaca caaagtccca 120
cacacctgat caaaacgaga ggacagcaag cgactctgag atgctctcct atctctgggc 180
acaccagtgt gtactggtac caacaggccc tgggtctggg cctccagttc ctcctttggt 240
atgacgaggg tgaagagaga aacagaggaa acttccctcc tagattttca ggtcgccagt 300
tccctaatta tagctctgag ctgaatgtga acgccttgga gctggaggac tcggccctgt 360
atctttgcag agaccttgcg gccgtgtctt ccgacgctga cagtgtagat a 411

<210> SEQ ID NO 446
<211> LENGTH: 411
<212> TYPE: DNA
<213> ORGANISM: Homo sapiens
<220> FEATURE:
<223> OTHER INFORMATION: TRBV6-1_BB_1

<400> SEQUENCE: 446
gttcgaagct ggcatgacac gaagacttgt acgccaccat gagcatcggg ctcctgtgct 60
gtgtggcctt ttctctcctg tgggcaagtc cagtgaatgc tggtgtcact cagaccccaa 120
aattccaggt cctgaaaaca ggacagagca tgacactgca gtgtgcccag gatatgaacc 180
ataactccat gtactggtat cgacaagacc caggcatggg actgaggctg atttattact 240
cagcttctga gggtaccact gacaaaggag aagtccccaa tggctacaat gtctccagat 300
taaacaaacg ggagttctcg ctcaggctgg agtcggctgc tccctcccag acatctgtgt 360
acttttgcag agaccttgcg gccgtgtctt ccgacgctga cagtgtagat a 411

<210> SEQ ID NO 447
<211> LENGTH: 411
<212> TYPE: DNA
<213> ORGANISM: Homo sapiens
<220> FEATURE:
<223> OTHER INFORMATION: TRBV6-3_BB_1

<400> SEQUENCE: 447
gttcgaagct ggcatgacac gaagacttgt acgccaccat gagcctcggg ctcctgtgct 60
gtggggtctt ttctctcctg tgggcaggtc cagtgaatgc tggtgtcact cagaccccaa 120
aattccgggt cctgaaaaca ggacagagca tgacactgct gtgtgcccag gatatgaacc 180

```
atgaatacat gtactggtat cgacaagacc caggcatggg gctgaggctg attcattact    240

cagttggtga gggtacaact gccaaaggag aggtccctga tggctacaat gtctccagat    300

taaaaaaaca gaatttcctg ctggggttgg agtcggctgc tccctcccaa acatctgtgt    360

acttttgcag agaccttgcg gccgtgtctt ccgacgctga cagtgtagat a             411
```

<210> SEQ ID NO 448
<211> LENGTH: 411
<212> TYPE: DNA
<213> ORGANISM: Homo sapiens
<220> FEATURE:
<223> OTHER INFORMATION: TRBV6-4_BB_1

<400> SEQUENCE: 448

```
gttcgaagct ggcatgacac gaagacttgt acgccaccat gagaatcagg ctcctgtgct     60

gtgtggcctt ttctctcctg tgggcaggtc cagtgattgc tgggatcacc caggcaccaa    120

catctcagat cctggcagca ggacggcgca tgacactgag atgtacccag gatatgagac    180

ataatgccat gtactggtat agacaagatc taggactggg gctaaggctc atccattatt    240

caaatactgc aggtaccact ggcaaaggag aagtccctga tggttatagt gtctccagag    300

caaacacaga tgatttcccc ctcacgttgg cgtctgctgt accctctcag acatctgtgt    360

acttttgcag agaccttgcg gccgtgtctt ccgacgctga cagtgtagat a             411
```

<210> SEQ ID NO 449
<211> LENGTH: 411
<212> TYPE: DNA
<213> ORGANISM: Homo sapiens
<220> FEATURE:
<223> OTHER INFORMATION: TRBV6-5_BB_1

<400> SEQUENCE: 449

```
gttcgaagct ggcatgacac gaagacttgt acgccaccat gagcatcggc ctcctgtgct     60

gtgcagcctt gtctctcctg tgggcaggtc cagtgaatgc tggtgtcact cagaccccaa    120

aattccaggt cctgaaaaca ggacagagca tgacactgca gtgtgcccag gatatgaacc    180

atgaatacat gtcctggtat cgacaagacc caggcatggg gctgaggctg attcattact    240

cagttggtgc tggtatcact gaccaaggag aagtccccaa tggctacaat gtctccagat    300

caaccacaga ggatttcccg ctcaggctgc tgtcggctgc tccctcccag acatctgtgt    360

acttttgcag agaccttgcg gccgtgtctt ccgacgctga cagtgtagat a             411
```

<210> SEQ ID NO 450
<211> LENGTH: 411
<212> TYPE: DNA
<213> ORGANISM: Homo sapiens
<220> FEATURE:
<223> OTHER INFORMATION: TRBV6-6_BB_1

<400> SEQUENCE: 450

```
gttcgaagct ggcatgacac gaagacttgt acgccaccat gagcatcagc ctcctgtgct     60

gtgcagcctt tcctctcctg tgggcaggtc cagtgaatgc tggtgtcact cagaccccaa    120

aattccgcat cctgaagata ggacagagca tgacactgca gtgtacccag gatatgaacc    180

ataactacat gtactggtat cgacaagacc caggcatggg gctgaagctg atttattatt    240

cagttggtgc tggtatcact gataaaggag aagtcccgaa tggctacaac gtctccagat    300

caaccacaga ggatttcccg ctcaggctgg agttggctgc tccctcccag acatctgtgt    360
```

acttttgcag agaccttgcg gccgtgtctt ccgacgctga cagtgtagat a 411

<210> SEQ ID NO 451
<211> LENGTH: 408
<212> TYPE: DNA
<213> ORGANISM: Homo sapiens
<220> FEATURE:
<223> OTHER INFORMATION: TRBV6-8_BB_1

<400> SEQUENCE: 451
gttcgaagct ggcatgacac gaagacttgt acgccaccat gagcctcggg ctcctgtgct 60
gtgcggcctt ttctctcctg tgggcaggtc ccgtgaatgc tggtgtcact cagaccccaa 120
aattccacat cctgaaaaca ggacagagca tgacactgca gtgtgcccag gatatgaacc 180
atggatacat gtcctggtat cgacaagacc caggcatggg gctgagactg atttactact 240
cagctgctgc tggtactact gacaaagaag tccccaatgg ctacaatgtc tctagattaa 300
acacagagga tttcccactc aggctggtgt cggctgctcc ctcccagaca tctgtgtacc 360
tttgcagaga ccttgcggcc gtgtcttccg acgctgacag tgtagata 408

<210> SEQ ID NO 452
<211> LENGTH: 411
<212> TYPE: DNA
<213> ORGANISM: Homo sapiens
<220> FEATURE:
<223> OTHER INFORMATION: TRBV6-9_BB_1

<400> SEQUENCE: 452
gttcgaagct ggcatgacac gaagacttgt acgccaccat gagcatcggg ctcctgtgct 60
gtgtggcctt ttctctcctg tgggcaggtc cagtgaatgc tggtgtcact cagaccccaa 120
aattccacat cctgaaaaca ggacagagca tgacactgca gtgtgcccag gatatgaacc 180
atggatactt gtcctggtat cgacaagacc caggcatggg gctgaggcgc attcattact 240
cagttgctgc tggtatcact gacaaaggag aagtccccga tggctacaat gtatccagat 300
caaacacaga ggatttcccg ctcaggctgg agtcagctgc tccctcccag acatctgtat 360
acttttgcag agaccttgcg gccgtgtctt ccgacgctga cagtgtagat a 411

<210> SEQ ID NO 453
<211> LENGTH: 414
<212> TYPE: DNA
<213> ORGANISM: Homo sapiens
<220> FEATURE:
<223> OTHER INFORMATION: TRBV7-2_BB_1

<400> SEQUENCE: 453
gttcgaagct ggcatgacac gaagacttgt acgccaccat gggcaccagg ctcctcttct 60
gggtggcctt ctgtctcctg ggggcagatc acacaggagc tggagtctcc cagtccccca 120
gtaacaaggt cacagagaag ggaaaggatg tagagctcag gtgtgatcca atttcaggtc 180
atactgccct ttactggtac cgacagagcc tggggcaggg cctggagttt ttaatttact 240
tccaaggcaa cagtgcacca gacaaatcag ggctgcccag tgatcgcttc tctgcagaga 300
ggactggggg atccgtctcc actctgacga tccagcgcac acagcaggag gactcggccg 360
tgtatctttg cagagacctt gcggccgtgt cttccgacgc tgacagtgta gata 414

<210> SEQ ID NO 454
<211> LENGTH: 414
<212> TYPE: DNA
<213> ORGANISM: Homo sapiens

<220> FEATURE:
<223> OTHER INFORMATION: TRBV7-3_BB_1

<400> SEQUENCE: 454
gttcgaagct ggcatgacac gaagacttgt acgccaccat gggcaccagg ctcctctgct 60
gggcagccct gtgcctcctg ggggcagatc acacaggtgc tggagtctcc cagaccccca 120
gtaacaaggt cacagagaag ggaaaatatg tagagctcag gtgtgatcca atttcaggtc 180
atactgccct ttactggtac cgacaaagcc tggggcaggg cccagagttt ctaatttact 240
tccaaggcac gggtgcggca gatgactcag ggctgcccaa cgatcggttc tttgcagtca 300
ggcctgaggg atccgtctct actctgaaga tccagcgcac agagcggggg gactcagccg 360
tgtatctttg cagagacctt gcggccgtgt cttccgacgc tgacagtgta gata 414

<210> SEQ ID NO 455
<211> LENGTH: 414
<212> TYPE: DNA
<213> ORGANISM: Homo sapiens
<220> FEATURE:
<223> OTHER INFORMATION: TRBV7-6_BB_1

<400> SEQUENCE: 455
gttcgaagct ggcatgacac gaagacttgt acgccaccat gggcaccagt ctcctatgct 60
gggtggtcct gggtttccta gggacagatc acacaggtgc tggagtctcc cagtctccca 120
ggtacaaagt cacaaagagg ggacaggatg tagctctcag gtgtgatcca atttcgggtc 180
atgtatccct ttattggtac cgacaggccc tggggcaggg cccagagttt ctgacttact 240
tcaattatga agcccaacaa gacaaatcag ggctgcccaa tgatcggttc tctgcagaga 300
ggcctgaggg atccatctcc actctgacga tccagcgcac agagcagcgg gactcggcca 360
tgtatcgttg cagagacctt gcggccgtgt cttccgacgc tgacagtgta gata 414

<210> SEQ ID NO 456
<211> LENGTH: 414
<212> TYPE: DNA
<213> ORGANISM: Homo sapiens
<220> FEATURE:
<223> OTHER INFORMATION: TRBV7-7_BB_1

<400> SEQUENCE: 456
gttcgaagct ggcatgacac gaagacttgt acgccaccat gggtaccagt ctcctatgct 60
gggtggtcct gggtttccta gggacagatc acacaggtgc tggagtctcc cagtctccca 120
ggtacaaagt cacaaagagg ggacaggatg taactctcag gtgtgatcca atttcgagtc 180
atgcaaccct ttattggtat caacaggccc tggggcaggg cccagagttt ctgacttact 240
tcaattatga agctcaacca gacaaatcag ggctgcccag tgatcggttc tctgcagaga 300
ggcctgaggg atccatctcc actctgacga ttcagcgcac agagcagcgg gactcagcca 360
tgtatcgttg cagagacctt gcggccgtgt cttccgacgc tgacagtgta gata 414

<210> SEQ ID NO 457
<211> LENGTH: 414
<212> TYPE: DNA
<213> ORGANISM: Homo sapiens
<220> FEATURE:
<223> OTHER INFORMATION: TRBV7-8_BB_1

<400> SEQUENCE: 457
gttcgaagct ggcatgacac gaagacttgt acgccaccat gggcaccagg ctcctctgct 60

```
gggtggtcct gggtttccta gggacagatc acacaggtgc tggagtctcc cagtccccta    120

ggtacaaagt cgcaaagaga ggacaggatg tagctctcag gtgtgatcca atttcgggtc    180

atgtatccct tttttggtac caacaggccc tggggcaggg gccagagttt ctgacttatt    240

tccagaatga agctcaacta gacaaatcgg ggctgcccag tgatcgcttc tttgcagaaa    300

ggcctgaggg atccgtctcc actctgaaga tccagcgcac acagcaggag gactccgccg    360

tgtatctttg cagagacctt gcggccgtgt cttccgacgc tgacagtgta gata          414
```

<210> SEQ ID NO 458
<211> LENGTH: 414
<212> TYPE: DNA
<213> ORGANISM: Homo sapiens
<220> FEATURE:
<223> OTHER INFORMATION: TRBV7-9_BB_1

<400> SEQUENCE: 458

```
gttcgaagct ggcatgacac gaagacttgt acgccaccat gggcaccagc ctcctctgct     60

ggatggccct gtgtctcctg gggGcagatc acgcagatac tggagtctcc cagaacccca    120

gacacaagat cacaaagagg ggacagaatg taactttcag gtgtgatcca atttctgaac    180

acaaccgcct ttattggtac cgacagaccc tggggcaggg cccagagttt ctgacttact    240

tccagaatga agctcaacta gaaaaatcaa ggctgctcag tgatcggttc tctgcagaga    300

ggcctaaggg atctttctcc accttggaga tccagcgcac agagcagggg gactcggcca    360

tgtatctttg cagagacctt gcggccgtgt cttccgacgc tgacagtgta gata          414
```

<210> SEQ ID NO 459
<211> LENGTH: 411
<212> TYPE: DNA
<213> ORGANISM: Homo sapiens
<220> FEATURE:
<223> OTHER INFORMATION: TRBV9_BB_1

<400> SEQUENCE: 459

```
gttcgaagct ggcatgacac gaagacttgt acgccaccat gggcttcagg ctcctctgct     60

gtgtggcctt ttgtctcctg ggagcaggcc cagtggattc tggagtcaca caaaccccaa    120

agcacctgat cacagcaact ggacagcgag tgacgctgag atgctcccct aggtctggtg    180

acctctctgt gtactggtac caacagagcc tggaccaggg cctccagttc ctcattcagt    240

attataatgg agaagagaga gcaaaaggaa acattcttga acgattctcc gcacaacagt    300

tccctgactt gcactctgaa ctaaacctga gctctctgga gctgggggac tcagctttgt    360

acttttgcag agaccttgcg gccgtgtctt ccgacgctga cagtgtagat a             411
```

<210> SEQ ID NO 460
<211> LENGTH: 411
<212> TYPE: DNA
<213> ORGANISM: Homo sapiens
<220> FEATURE:
<223> OTHER INFORMATION: TRBV10-1_BB_1

<400> SEQUENCE: 460

```
gttcgaagct ggcatgacac gaagacttgt acgccaccat gggcacgagg ctcttcttct     60

atgtggccct ttgtctgctg tgggcaggac acagggatgc tgaaatcacc cagagcccaa    120

gacacaagat cacagagaca ggaaggcagg tgaccttggc gtgtcaccag acttggaacc    180

acaacaatat gttctggtat cgacaagacc tgggacatgg gctgaggctg atccattact    240

catatggtgt tcaagacact aacaaaggag aagtctcaga tggctacagt gtctctagat    300
```

caaacacaga ggacctcccc ctcactctgg agtctgctgc ctcctcccag acatctgtat 360
acttttgcag agaccttgcg gccgtgtctt ccgacgctga cagtgtagat a 411

<210> SEQ ID NO 461
<211> LENGTH: 411
<212> TYPE: DNA
<213> ORGANISM: Homo sapiens
<220> FEATURE:
<223> OTHER INFORMATION: TRBV10-2_BB_1

<400> SEQUENCE: 461
gttcgaagct ggcatgacac gaagacttgt acgccaccat gggcaccagg ctcttcttct 60
atgtggccct ttgtctgctg tgggcaggac acagggatgc tggaatcacc cagagcccaa 120
gatacaagat cacagagaca ggaaggcagg tgaccttgat gtgtcaccag acttggagcc 180
acagctatat gttctggtat cgacaagacc tgggacatgg gctgaggctg atctattact 240
cagcagctgc tgatattaca gataaaggag aagtccccga tggctatgtt gtctccagat 300
ccaagacaga gaatttcccc ctcactctgg agtcagctac ccgctcccag acatctgtgt 360
acttttgcag agaccttgcg gccgtgtctt ccgacgctga cagtgtagat a 411

<210> SEQ ID NO 462
<211> LENGTH: 411
<212> TYPE: DNA
<213> ORGANISM: Homo sapiens
<220> FEATURE:
<223> OTHER INFORMATION: TRBV10-3_BB_1

<400> SEQUENCE: 462
gttcgaagct ggcatgacac gaagacttgt acgccaccat gggcacaagg ttgttcttct 60
atgtggccct ttgtctcctg tggacaggac acatggatgc tggaatcacc cagagcccaa 120
gacacaaggt cacagagaca ggaacaccag tgactctgag atgtcaccag actgagaacc 180
accgctatat gtactggtat cgacaagacc cggggcatgg gctgaggctg atccattact 240
catatggtgt taaagatact gacaaaggag aagtctcaga tggctatagt gtctctagat 300
caaagacaga ggatttcctc ctcactctgg agtccgctac cagctcccag acatctgtgt 360
acttttgcag agaccttgcg gccgtgtctt ccgacgctga cagtgtagat a 411

<210> SEQ ID NO 463
<211> LENGTH: 414
<212> TYPE: DNA
<213> ORGANISM: Homo sapiens
<220> FEATURE:
<223> OTHER INFORMATION: TRBV11-1_BB_1

<400> SEQUENCE: 463
gttcgaagct ggcatgacac gaagacttgt acgccaccat gagcaccagg cttctctgct 60
ggatggccct ctgtctcctg gggcagaac tctcagaagc tgaagttgcc cagtccccca 120
gatataagat tacagagaaa agccaggctg tggctttttg gtgtgatcct atttctggcc 180
atgctaccct ttactggtac cggcagatcc tgggacaggg cccggagctt ctggttcaat 240
ttcaggatga gagtgtagta gatgattcac agttgcctaa ggatcgattt tctgcagaga 300
ggctcaaagg agtagactcc actctcaaga tccagcctgc agagcttggg gactcggcca 360
tgtatctttg cagagacctt gcggccgtgt cttccgacgc tgacagtgta gata 414

<210> SEQ ID NO 464

<211> LENGTH: 414
<212> TYPE: DNA
<213> ORGANISM: Homo sapiens
<220> FEATURE:
<223> OTHER INFORMATION: TRBV11-2_BB_1

<400> SEQUENCE: 464
gttcgaagct ggcatgacac gaagacttgt acgccaccat gggcaccagg ctcctctgct 60
gggcggccct ctgtctcctg ggagcagaac tcacagaagc tggagttgcc cagtctccca 120
gatataagat tatagagaaa aggcagagtg tggctttttg gtgcaatcct atatctggcc 180
atgctaccct ttactggtac cagcagatcc tgggacaggg cccaaagctt ctgattcagt 240
ttcagaataa cggtgtagtg gatgattcac agttgcctaa ggatcgattt tctgcagaga 300
ggctcaaagg agtagactcc actctcaaga tccagcctgc aaagcttgag gactcggccg 360
tgtatctttg cagagacctt gcggccgtgt cttccgacgc tgacagtgta gata 414

<210> SEQ ID NO 465
<211> LENGTH: 414
<212> TYPE: DNA
<213> ORGANISM: Homo sapiens
<220> FEATURE:
<223> OTHER INFORMATION: TRBV11-3_BB_1

<400> SEQUENCE: 465
gttcgaagct ggcatgacac gaagacttgt acgccaccat gggtaccagg ctcctctgct 60
gggtggcctt ctgtctcctg gtggaagaac tcatagaagc tggagtggtt cagtctccca 120
gatataagat tatagagaaa aaacagcctg tggctttttg gtgcaatcct atttctggcc 180
acaataccct ttactggtac ctgcagaact tgggacaggg cccggagctt ctgattcgat 240
atgagaatga ggaagcagta gacgattcac agttgcctaa ggatcgattt tctgcagaga 300
ggctcaaagg agtagactcc actctcaaga tccagcctgc agagcttggg gactcggccg 360
tgtatctttg cagagacctt gcggccgtgt cttccgacgc tgacagtgta gata 414

<210> SEQ ID NO 466
<211> LENGTH: 414
<212> TYPE: DNA
<213> ORGANISM: Homo sapiens
<220> FEATURE:
<223> OTHER INFORMATION: TRBV12-3_BB_1

<400> SEQUENCE: 466
gttcgaagct ggcatgacac gaagacttgt acgccaccat ggactcctgg accttctgct 60
gtgtgtccct ttgcatcctg gtagcgaagc atacagatgc tggagttatc cagtcacccc 120
gccatgaggt gacagagatg ggacaagaag tgactctgag atgtaaacca atttcaggcc 180
acaactccct tttctggtac agacagacca tgatgcgggg actggagttg ctcatttact 240
ttaacaacaa cgttccgata gatgattcag ggatgcccga ggatcgattc tcagctaaga 300
tgcctaatgc atcattctcc actctgaaga tccagccctc agaacccagg gactcagctg 360
tgtacttttg cagagacctt gcggccgtgt cttccgacgc tgacagtgta gata 414

<210> SEQ ID NO 467
<211> LENGTH: 414
<212> TYPE: DNA
<213> ORGANISM: Homo sapiens
<220> FEATURE:
<223> OTHER INFORMATION: TRBV12-4_BB_1

<400> SEQUENCE: 467

```
gttcgaagct ggcatgacac gaagacttgt acgccaccat ggactcctgg accctctgct     60

gtgtgtccct ttgcatcctg gtagcaaagc acacagatgc tggagttatc cagtcacccc    120

ggcacgaggt gacagagatg ggacaagaag tgactctgag atgtaaacca atttcaggac    180

acgactacct tttctggtac agacagacca tgatgcgggg actggagttg ctcatttact    240

ttaacaacaa cgttccgata gatgattcag ggatgcccga ggatcgattc tcagctaaga    300

tgcctaatgc atcattctcc actctgaaga tccagccctc agaacccagg gactcagctg    360

tgtacttttg cagagacctt gcggccgtgt cttccgacgc tgacagtgta gata          414
```

<210> SEQ ID NO 468
<211> LENGTH: 414
<212> TYPE: DNA
<213> ORGANISM: Homo sapiens
<220> FEATURE:
<223> OTHER INFORMATION: TRBV12-5_BB_1

<400> SEQUENCE: 468

```
gttcgaagct ggcatgacac gaagacttgt acgccaccat ggccaccagg ctcctctgct     60

gtgtggttct ttgtctcctg ggagaagagc ttatagatgc tagagtcacc cagacaccaa    120

ggcacaaggt gacagagatg ggacaagaag taacaatgag atgtcagcca attttaggcc    180

acaatactgt tttctggtac agacagacca tgatgcaagg actggagttg ctggcttact    240

tccgcaaccg ggctcctcta gatgattcgg ggatgccgaa ggatcgattc tcagcagaga    300

tgcctgatgc aactttagcc actctgaaga tccagccctc agaacccagg gactcagctg    360

tgtacttttg cagagacctt gcggccgtgt cttccgacgc tgacagtgta gata          414
```

<210> SEQ ID NO 469
<211> LENGTH: 441
<212> TYPE: DNA
<213> ORGANISM: Homo sapiens
<220> FEATURE:
<223> OTHER INFORMATION: TRBV13_BB_1

<400> SEQUENCE: 469

```
gttcgaagct ggcatgacac gaagacttgt acgccaccat gcttagtcct gacctgcctg     60

actctgcctg gaacaccagg ctcctctgcc atgtcatgct ttgtctcctg ggagcagttt    120

cagtggctgc tggagtcatc cagtccccaa gacatctgat caaagaaaag agggaaacag    180

ccactctgaa atgctatcct atccctagac acgacactgt ctactggtac cagcagggtc    240

caggtcagga cccccagttc ctcatttcgt tttatgaaaa gatgcagagc gataaaggaa    300

gcatccctga tcgattctca gctcaacagt tcagtgacta tcattctgaa ctgaacatga    360

gctccttgga gctgggggac tcagccctgt acttttgcag agaccttgcg gccgtgtctt    420

ccgacgctga cagtgtagat a                                              441
```

<210> SEQ ID NO 470
<211> LENGTH: 414
<212> TYPE: DNA
<213> ORGANISM: Homo sapiens
<220> FEATURE:
<223> OTHER INFORMATION: TRBV14_BB_1

<400> SEQUENCE: 470

```
gttcgaagct ggcatgacac gaagacttgt acgccaccat ggtttccagg cttctcagtt     60

tagtgtccct ttgtctcctg ggagcaaagc acatagaagc tggagttact cagttcccca    120
```

-continued

```
gccacagcgt aatagagaag ggccagactg tgactctgag atgtgaccca atttctggac    180

atgataatct ttattggtat cgacgtgtta tgggaaaaga aataaaattt ctgttacatt    240

ttgtgaaaga gtctaaacag gatgagtccg gtatgcccaa caatcgattc ttagctgaaa    300

ggactggagg gacgtattct actctgaagg tgcagcctgc agaactggag gattctggag    360

tttacttttg cagagacctt gcggccgtgt cttccgacgc tgacagtgta gata          414


<210> SEQ ID NO 471
<211> LENGTH: 411
<212> TYPE: DNA
<213> ORGANISM: Homo sapiens
<220> FEATURE:
<223> OTHER INFORMATION: TRBV15_BB_1

<400> SEQUENCE: 471

gttcgaagct ggcatgacac gaagacttgt acgccaccat gggtcctggg cttctccact     60

ggatggccct ttgtctcctt ggaacaggtc atggggatgc catggtcatc cagaacccaa    120

gataccaggt tacccagttt ggaaagccag tgaccctgag ttgttctcag actttgaacc    180

ataacgtcat gtactggtac cagcagaagt caagtcaggc cccaaagctg ctgttccact    240

actatgacaa agattttaac aatgaagcag acacccctga taacttccaa tccaggaggc    300

cgaacacttc tttctgcttt cttgacatcc gctcaccagg cctgggggac acagccatgt    360

acctttgcag agaccttgcg gccgtgtctt ccgacgctga cagtgtagat a             411


<210> SEQ ID NO 472
<211> LENGTH: 414
<212> TYPE: DNA
<213> ORGANISM: Homo sapiens
<220> FEATURE:
<223> OTHER INFORMATION: TRBV16_BB_1

<400> SEQUENCE: 472

gttcgaagct ggcatgacac gaagacttgt acgccaccat gagcccaata ttcacctgca     60

tcacaatcct ttgtctgctg gctgcaggtt ctcctggtga agaagtcgcc cagactccaa    120

aacatcttgt cagaggggaa ggacagaaag caaaattata ttgtgcccca ataaaaggac    180

acagttatgt tttttggtac caacaggtcc tgaaaaacga gttcaagttc ttgatttcct    240

tccagaatga aaatgtcttt gatgaaacag gtatgcccaa ggaaagattt tcagctaagt    300

gcctcccaaa ttcaccctgt agccttgaga tccaggctac gaagcttgag gattcagcag    360

tgtacttttg cagagacctt gcggccgtgt cttccgacgc tgacagtgta gata          414


<210> SEQ ID NO 473
<211> LENGTH: 414
<212> TYPE: DNA
<213> ORGANISM: Homo sapiens
<220> FEATURE:
<223> OTHER INFORMATION: TRBV18_BB_1

<400> SEQUENCE: 473

gttcgaagct ggcatgacac gaagacttgt acgccaccat ggacaccaga gtactctgct     60

gtgcggtcat ctgccttctg gggggcaggac tctcaaatgc cggcgtcatg cagaacccaa    120

gacacctggt caggaggagg ggacaggagg caagactgag atgcagccca atgaaaggac    180

acagtcatgt ttactggtat cggcagctcc cagaggaagg tctgaaattc atggtttatc    240

tccagaaaga aaatatcata gatgagtcag gaatgccaaa ggaacgattt tctgctgaat    300

ttcccaaaga gggccccagc atcctgagga tccagcaggt agtgcgagga gattcggcag    360
```

```
cttacttttg cagagacctt gcggccgtgt cttccgacgc tgacagtgta gata         414


<210> SEQ ID NO 474
<211> LENGTH: 411
<212> TYPE: DNA
<213> ORGANISM: Homo sapiens
<220> FEATURE:
<223> OTHER INFORMATION: TRBV19_BB_1

<400> SEQUENCE: 474

gttcgaagct ggcatgacac gaagacttgt acgccaccat gagcaaccag gtgctctgct     60

gtgtggtcct ttgtttcctg ggagcaaaca ccgtggatgg tggaatcact cagtccccaa    120

agtacctgtt cagaaaggaa ggacagaatg tgaccctgag ttgtgaacag aatttgaacc    180

acgatgccat gtactggtac cgacaggacc cagggcaagg gctgagattg atctactact    240

cacagatagt aaatgacttt cagaaaggag atatagctga agggtacagc gtctctcggg    300

agaagaagga atcctttcct ctcactgtga catcggccca aaagaacccg acagctttct    360

atctttgcag agaccttgcg gccgtgtctt ccgacgctga cagtgtagat a             411


<210> SEQ ID NO 475
<211> LENGTH: 405
<212> TYPE: DNA
<213> ORGANISM: Homo sapiens
<220> FEATURE:
<223> OTHER INFORMATION: TRBV20-1_BB_1

<400> SEQUENCE: 475

gttcgaagct ggcatgacac gaagacttgt acgccaccat gctgctgctt ctgctgcttc     60

tggggccagg ctccgggctt ggtgctgtcg tctctcaaca tccgagctgg gttatctgta    120

agagtggaac ctctgtgaag atcgagtgcc gttccctgga ctttcaggcc acaactatgt    180

tttggtatcg tcagttcccg aaacagagtc tcatgctgat ggcaacttcc aatgagggct    240

ccaaggccac atacgagcaa ggcgtcgaga aggacaagtt tctcatcaac catgcaagcc    300

tgaccttgtc cactctgaca gtgaccagtg cccatcctga agatagcagc ttctacattt    360

gcagagacct tgcggccgtg tcttccgacg ctgacagtgt agata                    405


<210> SEQ ID NO 476
<211> LENGTH: 411
<212> TYPE: DNA
<213> ORGANISM: Homo sapiens
<220> FEATURE:
<223> OTHER INFORMATION: TRBV24-1_BB_1

<400> SEQUENCE: 476

gttcgaagct ggcatgacac gaagacttgt acgccaccat ggcctccctg ctcttcttct     60

gtggggcctt ttatctcctg ggaacagggt ccatggatgc tgatgttacc cagaccccaa    120

ggaataggat cacaaagaca ggaaagagga ttatgctgga atgttctcag actaagggtc    180

atgatagaat gtactggtat cgacaagacc caggactggg cctacggttg atctattact    240

cctttgatgt caaagatata aacaaaggag agatctctga tggatacagt gtctctcgac    300

aggcacaggc taaattctcc ctgtccctag agtctgccat ccccaaccag acagctcttt    360

acttttgcag agaccttgcg gccgtgtctt ccgacgctga cagtgtagat a             411


<210> SEQ ID NO 477
<211> LENGTH: 411
<212> TYPE: DNA
```

<213> ORGANISM: Homo sapiens
<220> FEATURE:
<223> OTHER INFORMATION: TRBV25-1_BB_1

<400> SEQUENCE: 477
gttcgaagct ggcatgacac gaagacttgt acgccaccat gactatcagg ctcctctgct 60
acatgggctt ttattttctg gggcaggcc tcatggaagc tgacatctac cagaccccaa 120
gataccttgt tatagggaca ggaaagaaga tcactctgga atgttctcaa accatgggcc 180
atgacaaaat gtactggtat caacaagatc caggaatgga actacacctc atccactatt 240
cctatggagt taattccaca gagaagggag atctttcctc tgagtcaaca gtctccagaa 300
taaggacgga gcattttccc ctgaccctgg agtctgccag gccctcacat acctctcagt 360
acctttgcag agaccttgcg gccgtgtctt ccgacgctga cagtgtagat a 411

<210> SEQ ID NO 478
<211> LENGTH: 411
<212> TYPE: DNA
<213> ORGANISM: Homo sapiens
<220> FEATURE:
<223> OTHER INFORMATION: TRBV27_BB_1

<400> SEQUENCE: 478
gttcgaagct ggcatgacac gaagacttgt acgccaccat gggcccccag ctccttggct 60
atgtggtcct ttgccttcta ggagcaggcc ccctggaagc ccaagtgacc cagaacccaa 120
gatacctcat cacagtgact ggaaagaagt taacagtgac ttgttctcag aatatgaacc 180
atgagtatat gtcctggtat cgacaagacc cagggctggg cttaaggcag atctactatt 240
caatgaatgt tgaggtgact gataagggag atgttcctga agggtacaaa gtctctcgaa 300
aagagaagag gaatttcccc ctgatcctgg agtcgcccag ccccaaccag acctctctgt 360
acttttgcag agaccttgcg gccgtgtctt ccgacgctga cagtgtagat a 411

<210> SEQ ID NO 479
<211> LENGTH: 411
<212> TYPE: DNA
<213> ORGANISM: Homo sapiens
<220> FEATURE:
<223> OTHER INFORMATION: TRBV28_BB_1

<400> SEQUENCE: 479
gttcgaagct ggcatgacac gaagacttgt acgccaccat gggaatcagg ctcctctgtc 60
gtgtggcctt ttgtttcctg gctgtaggcc tcgtagatgt gaaagtaacc cagagctcga 120
gatatctagt caaaaggacg ggagagaaag tttttctgga atgtgtccag gatatggacc 180
atgaaaatat gttctggtat cgacaagacc caggtctggg gctacggctg atctatttct 240
catatgatgt taaaatgaaa gaaaaaggag atattcctga ggggtacagt gtctctagag 300
agaagaagga gcgcttctcc ctgattctgg agtccgccag caccaaccag acatctatgt 360
acctttgcag agaccttgcg gccgtgtctt ccgacgctga cagtgtagat a 411

<210> SEQ ID NO 480
<211> LENGTH: 405
<212> TYPE: DNA
<213> ORGANISM: Homo sapiens
<220> FEATURE:
<223> OTHER INFORMATION: TRBV29-1_BB_1

<400> SEQUENCE: 480
gttcgaagct ggcatgacac gaagacttgt acgccaccat gctgagtcta ctgctccttc 60

```
tcctgggact aggctctgtg ttcagtgctg tcatctctca aaagccaagc agggatatct    120

gtcaacgtgg aacctccctg acgatccagt gtcaagtcga tagccaagtc accatgatgt    180

tctggtaccg tcagcaacct ggacagagcc tgacactgat cgcaactgca aatcagggct    240

ctgaggccac atatgagagt ggatttgtca ttgacaagtt tcccatcagc cgcccaaacc    300

taacattctc aactctgact gtgagcaaca tgagccctga agatagcagc atatatcttt    360

gcagagacct tgcggccgtg tcttccgacg ctgacagtgt agata                    405
```

<210> SEQ ID NO 481
<211> LENGTH: 405
<212> TYPE: DNA
<213> ORGANISM: Homo sapiens
<220> FEATURE:
<223> OTHER INFORMATION: TRBV30_BB_1

<400> SEQUENCE: 481

```
gttcgaagct ggcatgacac gaagacttgt acgccaccat gctctgctct ctccttgccc     60

ttctcctggg cactttcttt ggggtcagat ctcagactat tcatcaatgg ccagcgaccc    120

tggtgcagcc tgtgggcagc ccgctctctc tggagtgcac tgtggaggga acatcaaacc    180

ccaacctata ctggtaccga caggctgcag gcaggggcct ccagctgctc ttctactccg    240

ttggtattgg ccagatcagc tctgaggtgc cccagaatct ctcagcctcc agaccccagg    300

accggcagtt catcctgagt tctaagaagc tccttctcag tgactctggc ttctatcttt    360

gcagagacct tgcggccgtg tcttccgacg ctgacagtgt agata                    405
```

<210> SEQ ID NO 482
<211> LENGTH: 595
<212> TYPE: DNA
<213> ORGANISM: Homo sapiens
<220> FEATURE:
<223> OTHER INFORMATION: TRBC1 cloning fragment

<400> SEQUENCE: 482

```
cagcactcgt atgatcagag gaagactagg ccgcataggt ctcagtgttc ccacccgagg     60

tcgctgtgtt tgagccatca gaagcagaga tctcccacac ccaaaaggcc acactggtgt    120

gcctggccac aggcttcttc cccgaccacg tggagctgag ctggtgggtg aatgggaagg    180

aggtgcacag tggggtcagc acagacccgc agcccctcaa ggagcagccc gccctcaatg    240

actccagata ctgcctgagc agccgcctga gggtgtcggc caccttctgg cagaaccccc    300

gcaaccactt ccgctgtcaa gtccagttct acgggctctc ggagaatgac gagtggaccc    360

aggatagggc caaacccgtc acccagatcg tcagcgccga ggcctggggt agagcagact    420

gtggctttac ctcggtgtcc taccagcaag ggtcctgtc tgccaccatc ctctatgaga    480

tcctgctagg gaaggccacc ctgtatgctg tgctggtcag cgcccttgtg ttgatggcca    540

tggtcaagag aaaggatttc tgactaggtg tcttcgctac actgatccga tggtc         595
```

<210> SEQ ID NO 483
<211> LENGTH: 601
<212> TYPE: DNA
<213> ORGANISM: Homo sapiens
<220> FEATURE:
<223> OTHER INFORMATION: TRBC2 cloning fragment

<400> SEQUENCE: 483

```
cagcactcgt atgatcagag gaagactagg ccgcataggt ctcagtgttc ccacccgagg     60
```

```
tcgctgtgtt tgagccatca gaagcagaga tctcccacac ccaaaaggcc acactggtat    120

gcctggccac aggcttctac cccgaccacg tggagctgag ctggtgggtg aatgggaagg    180

aggtgcacag tggggtcagc acagacccgc agcccctcaa ggagcagccc gccctcaatg    240

actccagata ctgcctgagc agccgcctga gggtgtcggc caccttctgg cagaaccccc    300

gcaaccactt ccgctgtcaa gtccagttct acgggctctc ggagaatgac gagtggaccc    360

aggatagggc caaacccgtc acccagatcg tcagcgccga ggcctggggt agagcagact    420

gtggcttcac ctccgagtct taccagcaag ggtcctgtc tgccaccatc ctctatgaga    480

tcttgctagg gaaggccacc ttgtatgccg tgctggtcag tgccctcgtg ctgatggcca    540

tggtcaagag aaaggattcc agaggctagc taggtgtctt cgctacactg atccgatggt    600

c                                                                    601
```

<210> SEQ ID NO 484
<211> LENGTH: 891
<212> TYPE: DNA
<213> ORGANISM: Homo sapiens
<220> FEATURE:
<223> OTHER INFORMATION: V-C entry TRBV2_TRBC2

<400> SEQUENCE: 484

```
gccaccatgg atacctggct cgtatgctgg gcaattttta gtctcttgaa agcaggactc     60

acagaacctg aagtcaccca gactcccagc catcaggtca cacagatggg acaggaagtg    120

atcttgcgct gtgtccccat ctctaatcac ttatacttct attggtacag acaaatcttg    180

gggcagaaag tcgagtttct ggtttccttt tataataatg aaatctcaga gaagtctgaa    240

atattcgatg atcaattctc agttgaaagg cctgatggat caaatttcac tctgaagatc    300

cggtccacaa agctggagga ctcagccatg tacttttgca gagaccttgc ggccgcatag    360

gtctcagtgt tcccacccga ggtcgctgtg tttgagccat cagaagcaga gatctcccac    420

acccaaaagg ccacactggt atgcctggcc acaggcttct accccgacca cgtggagctg    480

agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttc acctccgagt cttaccagca aggggtcctg    780

tctgccacca tcctctatga gatcttgcta gggaaggcca ccttgtatgc cgtgctggtc    840

agtgccctcg tgctgatggc catggtcaag agaaaggatt ccagaggcta g             891
```

<210> SEQ ID NO 485
<211> LENGTH: 888
<212> TYPE: DNA
<213> ORGANISM: Homo sapiens
<220> FEATURE:
<223> OTHER INFORMATION: V-C entry TRBV3-1_TRBC2

<400> SEQUENCE: 485

```
gccaccatgg gctgcaggct cctctgctgt gtggtctttt gcctcctcca agcaggtccc     60

ttggacacag ctgtttccca gactccaaaa tacctggtca cacagatggg aaacgacaag    120

tccattaaat gtgaacaaaa tctgggccat gatactatgt attggtataa acaggactct    180

aagaaatttc tgaagataat gtttagctac aataataagg agctcattat aaatgaaaca    240

gttccaaatc gcttctcacc taaatctcca gacaaagctc acttaaatct tcacatcaat    300
```

```
tccctggagc ttggtgactc tgctgtgtat ttttgcagag accttgcggc cgcataggtc    360

tcagtgttcc cacccgaggt cgctgtgttt gagccatcag aagcagagat ctcccacacc    420

caaaaggcca cactggtatg cctggccaca ggcttctacc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggcttcacc tccgagtctt accagcaagg ggtcctgtct    780

gccaccatcc tctatgagat cttgctaggg aaggccacct tgtatgccgt gctggtcagt    840

gccctcgtgc tgatggccat ggtcaagaga aaggattcca gaggctag                 888
```

```
<210> SEQ ID NO 486
<211> LENGTH: 888
<212> TYPE: DNA
<213> ORGANISM: Homo sapiens
<220> FEATURE:
<223> OTHER INFORMATION: V-C entry TRBV4-1_TRBC2

<400> SEQUENCE: 486

gccaccatgg gctgcaggct gctctgctgt gcggttctct gtctcctggg agcagttccc     60

atagacactg aagttaccca gacaccaaaa cacctggtca tgggaatgac aaataagaag    120

tctttgaaat gtgaacaaca tatggggcac agggctatgt attggtacaa gcagaaagct    180

aagaagccac cggagctcat gtttgtctac agctatgaga aactctctat aaatgaaagt    240

gtgccaagtc gcttctcacc tgaatgcccc aacagctctc tcttaaacct tcacctacac    300

gccctgcagc cagaagattc agccctgtat ctttgcagag accttgcggc cgcataggtc    360

tcagtgttcc cacccgaggt cgctgtgttt gagccatcag aagcagagat ctcccacacc    420

caaaaggcca cactggtatg cctggccaca ggcttctacc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggcttcacc tccgagtctt accagcaagg ggtcctgtct    780

gccaccatcc tctatgagat cttgctaggg aaggccacct tgtatgccgt gctggtcagt    840

gccctcgtgc tgatggccat ggtcaagaga aaggattcca gaggctag                 888
```

```
<210> SEQ ID NO 487
<211> LENGTH: 888
<212> TYPE: DNA
<213> ORGANISM: Homo sapiens
<220> FEATURE:
<223> OTHER INFORMATION: V-C entry TRBV4-2_TRBC2

<400> SEQUENCE: 487

gccaccatgg gctgcaggct gctctgctgt gcggttctct gtctcctggg agcggtcccc     60

atggaaacgg gagttacgca gacaccaaga cacctggtca tgggaatgac aaataagaag    120

tctttgaaat gtgaacaaca tctggggcat aacgctatgt attggtacaa gcaaagtgct    180

aagaagccac tggagctcat gtttgtctac aactttaaag aacagactga aaacaacagt    240
```

gtgccaagtc gcttctcacc tgaatgcccc aacagctctc acttattcct tcacctacac 300
accctgcagc cagaagattc ggccctgtat ctttgcagag accttgcggc cgcataggtc 360
tcagtgttcc cacccgaggt cgctgtgttt gagccatcag aagcagagat ctcccacacc 420
caaaaggcca cactggtatg cctggccaca ggcttctacc ccgaccacgt ggagctgagc 480
tggtgggtga atgggaagga ggtgcacagt ggggtcagca cagacccgca gcccctcaag 540
gagcagcccg ccctcaatga ctccagatac tgcctgagca gccgcctgag ggtgtcggcc 600
accttctggc agaacccccg caaccacttc cgctgtcaag tccagttcta cgggctctcg 660
gagaatgacg agtggaccca ggatagggcc aaacccgtca cccagatcgt cagcgccgag 720
gcctggggta gagcagactg tggcttcacc tccgagtctt accagcaagg ggtcctgtct 780
gccaccatcc tctatgagat cttgctaggg aaggccacct tgtatgccgt gctggtcagt 840
gccctcgtgc tgatggccat ggtcaagaga aaggattcca gaggctag 888

<210> SEQ ID NO 488
<211> LENGTH: 888
<212> TYPE: DNA
<213> ORGANISM: Homo sapiens
<220> FEATURE:
<223> OTHER INFORMATION: V-C entry TRBV4-3_TRBC2

<400> SEQUENCE: 488
gccaccatgg gctgcaggct gctctgctgt gcggttctct gtctcctggg agcggtcccc 60
atggaaacgg gagttacgca gacaccaaga cacctggtca tgggaatgac aaataagaag 120
tctttgaaat gtgaacaaca tctgggtcat aacgctatgt attggtacaa gcaaagtgct 180
aagaagccac tggagctcat gtttgtctac agtcttgaag aacgggttga aaacaacagt 240
gtgccaagtc gcttctcacc tgaatgcccc aacagctctc acttattcct tcacctacac 300
accctgcagc cagaagattc ggccctgtat ctttgcagag accttgcggc cgcataggtc 360
tcagtgttcc cacccgaggt cgctgtgttt gagccatcag aagcagagat ctcccacacc 420
caaaaggcca cactggtatg cctggccaca ggcttctacc ccgaccacgt ggagctgagc 480
tggtgggtga atgggaagga ggtgcacagt ggggtcagca cagacccgca gcccctcaag 540
gagcagcccg ccctcaatga ctccagatac tgcctgagca gccgcctgag ggtgtcggcc 600
accttctggc agaacccccg caaccacttc cgctgtcaag tccagttcta cgggctctcg 660
gagaatgacg agtggaccca ggatagggcc aaacccgtca cccagatcgt cagcgccgag 720
gcctggggta gagcagactg tggcttcacc tccgagtctt accagcaagg ggtcctgtct 780
gccaccatcc tctatgagat cttgctaggg aaggccacct tgtatgccgt gctggtcagt 840
gccctcgtgc tgatggccat ggtcaagaga aaggattcca gaggctag 888

<210> SEQ ID NO 489
<211> LENGTH: 888
<212> TYPE: DNA
<213> ORGANISM: Homo sapiens
<220> FEATURE:
<223> OTHER INFORMATION: V-C entry TRBV5-1_TRBC2

<400> SEQUENCE: 489
gccaccatgg gctccaggct gctctgttgg gtgctgcttt gtctcctggg agcaggccca 60
gtaaaggctg gagtcactca aactccaaga tatctgatca aaacgagagg acagcaagtg 120
acactgagct gctcccctat ctctgggcat aggagtgtat cctggtacca acagacccca 180
ggacagggcc ttcagttcct ctttgaatac ttcagtgaga cacagagaaa caaaggaaac 240
ttccctggtc gattctcagg gcgccagttc tctaactctc gctctgagat gaatgtgagc 300
accttggagc tgggggactc ggccctttat ctttgcagag accttgcggc cgcataggtc 360
tcagtgttcc cacccgaggt cgctgtgttt gagccatcag aagcagagat ctcccacacc 420
caaaaggcca cactggtatg cctggccaca ggcttctacc ccgaccacgt ggagctgagc 480
tggtgggtga atgggaagga ggtgcacagt ggggtcagca cagacccgca gcccctcaag 540
gagcagcccg ccctcaatga ctccagatac tgcctgagca gccgcctgag ggtgtcggcc 600
accttctggc agaacccccg caaccacttc cgctgtcaag tccagttcta cgggctctcg 660
gagaatgacg agtggaccca ggatagggcc aaacccgtca cccagatcgt cagcgccgag 720
gcctggggta gagcagactg tggcttcacc tccgagtctt accagcaagg ggtcctgtct 780
gccaccatcc tctatgagat cttgctaggg aaggccacct tgtatgccgt gctggtcagt 840
gccctcgtgc tgatggccat ggtcaagaga aaggattcca gaggctag 888

<210> SEQ ID NO 490
<211> LENGTH: 888
<212> TYPE: DNA
<213> ORGANISM: Homo sapiens
<220> FEATURE:
<223> OTHER INFORMATION: V-C entry TRBV5-4_TRBC2

<400> SEQUENCE: 490
gccaccatgg gccctgggct cctctgctgg gtgctgcttt gtctcctggg agcaggctca 60
gtggagactg gagtcaccca aagtcccaca cacctgatca aaacgagagg acagcaagtg 120
actctgagat gctcttctca gtctgggcac aacactgtgt cctggtacca acaggccctg 180
ggtcaggggc cccagtttat ctttcagtat tatagggagg aagagaatgg cagaggaaac 240
ttccctccta gattctcagg actccagttc cctaattata gctctgagct gaatgtgaac 300
gccttggagc tggacgactc ggccctgtat ctttgcagag accttgcggc cgcataggtc 360
tcagtgttcc cacccgaggt cgctgtgttt gagccatcag aagcagagat ctcccacacc 420
caaaaggcca cactggtatg cctggccaca ggcttctacc ccgaccacgt ggagctgagc 480
tggtgggtga atgggaagga ggtgcacagt ggggtcagca cagacccgca gcccctcaag 540
gagcagcccg ccctcaatga ctccagatac tgcctgagca gccgcctgag ggtgtcggcc 600
accttctggc agaacccccg caaccacttc cgctgtcaag tccagttcta cgggctctcg 660
gagaatgacg agtggaccca ggatagggcc aaacccgtca cccagatcgt cagcgccgag 720
gcctggggta gagcagactg tggcttcacc tccgagtctt accagcaagg ggtcctgtct 780
gccaccatcc tctatgagat cttgctaggg aaggccacct tgtatgccgt gctggtcagt 840
gccctcgtgc tgatggccat ggtcaagaga aaggattcca gaggctag 888

<210> SEQ ID NO 491
<211> LENGTH: 888
<212> TYPE: DNA
<213> ORGANISM: Homo sapiens
<220> FEATURE:
<223> OTHER INFORMATION: V-C entry TRBV5-5_TRBC2

<400> SEQUENCE: 491
gccaccatgg gccctgggct cctctgctgg gtgctgcttt gtctcctggg agcaggccca 60
gtggacgctg gagtcaccca aagtcccaca cacctgatca aaacgagagg acagcaagtg 120
actctgagat gctctcctat ctctgggcac aagagtgtgt cctggtacca acaggtcctg 180

```
ggtcaggggc cccagtttat ctttcagtat tatgagaaag aagagagagg aagaggaaac    240

ttccctgatc gattctcagc tcgccagttc cctaactata gctctgagct gaatgtgaac    300

gccttgttgc tgggggactc ggccctgtat ctttgcagag accttgcggc cgcataggtc    360

tcagtgttcc cacccgaggt cgctgtgttt gagccatcag aagcagagat ctcccacacc    420

caaaaggcca cactggtatg cctggccaca ggcttctacc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggcttcacc tccgagtctt accagcaagg ggtcctgtct    780

gccaccatcc tctatgagat cttgctaggg aaggccacct tgtatgccgt gctggtcagt    840

gccctcgtgc tgatggccat ggtcaagaga aaggattcca gaggctag                 888
```

```
<210> SEQ ID NO 492
<211> LENGTH: 888
<212> TYPE: DNA
<213> ORGANISM: Homo sapiens
<220> FEATURE:
<223> OTHER INFORMATION: V-C entry TRBV5-6_TRBC2

<400> SEQUENCE: 492

gccaccatgg gccccgggct cctctgctgg gcactgcttt gtctcctggg agcaggctta     60

gtggacgctg gagtcaccca aagtcccaca cacctgatca aaacgagagg acagcaagtg    120

actctgagat gctctcctaa gtctgggcat gacactgtgt cctggtacca acaggccctg    180

ggtcaggggc cccagtttat ctttcagtat tatgaggagg aagagagaca gagaggcaac    240

ttccctgatc gattctcagg tcaccagttc cctaactata gctctgagct gaatgtgaac    300

gccttgttgc tgggggactc ggccctctat ctttgcagag accttgcggc cgcataggtc    360

tcagtgttcc cacccgaggt cgctgtgttt gagccatcag aagcagagat ctcccacacc    420

caaaaggcca cactggtatg cctggccaca ggcttctacc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggcttcacc tccgagtctt accagcaagg ggtcctgtct    780

gccaccatcc tctatgagat cttgctaggg aaggccacct tgtatgccgt gctggtcagt    840

gccctcgtgc tgatggccat ggtcaagaga aaggattcca gaggctag                 888
```

```
<210> SEQ ID NO 493
<211> LENGTH: 888
<212> TYPE: DNA
<213> ORGANISM: Homo sapiens
<220> FEATURE:
<223> OTHER INFORMATION: V-C entry TRBV5-7_TRBC2

<400> SEQUENCE: 493

gccaccatgg gccccgggct cctctgctgg gtgctgcttt gtcccctagg agaaggccca     60

gtggacgctg gagtcaccca aagtcccaca cacctgatca aaacgagagg acagcacgtg    120

actctgagat gctctcctat ctctgggcac accagtgtgt cctcgtacca acaggccctg    180
```

```
ggtcaggggc cccagtttat ctttcagtat tatgagaaag aagagagagg aagaggaaac    240

ttccctgatc aattctcagg tcaccagttc cctaactata gctctgagct gaatgtgaac    300

gccttgttgc taggggactc ggccctctat ctttgcagag accttgcggc cgcataggtc    360

tcagtgttcc cacccgaggt cgctgtgttt gagccatcag aagcagagat ctcccacacc    420

caaaaggcca cactggtatg cctggccaca ggcttctacc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggcttcacc tccgagtctt accagcaagg ggtcctgtct    780

gccaccatcc tctatgagat cttgctaggg aaggccacct tgtatgccgt gctggtcagt    840

gccctcgtgc tgatggccat ggtcaagaga aaggattcca gaggctag                 888
```

<210> SEQ ID NO 494
<211> LENGTH: 888
<212> TYPE: DNA
<213> ORGANISM: Homo sapiens
<220> FEATURE:
<223> OTHER INFORMATION: V-C entry TRBV5-8_TRBC2

<400> SEQUENCE: 494

```
gccaccatgg gacccaggct cctcttctgg gcactgcttt gtctcctcgg aacaggccca     60

gtggaggctg gagtcacaca aagtcccaca cacctgatca aaacgagagg acagcaagcg    120

actctgagat gctctcctat ctctgggcac accagtgtgt actggtacca acaggccctg    180

ggtctgggcc tccagttcct cctttggtat gacgagggtg aagagagaaa cagaggaaac    240

ttccctccta gattttcagg tcgccagttc cctaattata gctctgagct gaatgtgaac    300

gccttggagc tggaggactc ggccctgtat ctttgcagag accttgcggc cgcataggtc    360

tcagtgttcc cacccgaggt cgctgtgttt gagccatcag aagcagagat ctcccacacc    420

caaaaggcca cactggtatg cctggccaca ggcttctacc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggcttcacc tccgagtctt accagcaagg ggtcctgtct    780

gccaccatcc tctatgagat cttgctaggg aaggccacct tgtatgccgt gctggtcagt    840

gccctcgtgc tgatggccat ggtcaagaga aaggattcca gaggctag                 888
```

<210> SEQ ID NO 495
<211> LENGTH: 888
<212> TYPE: DNA
<213> ORGANISM: Homo sapiens
<220> FEATURE:
<223> OTHER INFORMATION: V-C entry TRBV6-1_TRBC2

<400> SEQUENCE: 495

```
gccaccatga gcatcgggct cctgtgctgt gtggcctttt ctctcctgtg ggcaagtcca     60

gtgaatgctg gtgtcactca gaccccaaaa ttccaggtcc tgaaaacagg acagagcatg    120
```

```
acactgcagt gtgcccagga tatgaaccat aactccatgt actggtatcg acaagaccca    180

ggcatgggac tgaggctgat ttattactca gcttctgagg gtaccactga caaaggagaa    240

gtccccaatg gctacaatgt ctccagatta aacaaacggg agttctcgct caggctggag    300

tcggctgctc cctcccagac atctgtgtac ttttgcagag accttgcggc cgcataggtc    360

tcagtgttcc cacccgaggt cgctgtgttt gagccatcag aagcagagat ctcccacacc    420

caaaaggcca cactggtatg cctggccaca ggcttctacc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggcttcacc tccgagtctt accagcaagg ggtcctgtct    780

gccaccatcc tctatgagat cttgctaggg aaggccacct tgtatgccgt gctggtcagt    840

gccctcgtgc tgatggccat ggtcaagaga aaggattcca gaggctag                 888
```

<210> SEQ ID NO 496
<211> LENGTH: 888
<212> TYPE: DNA
<213> ORGANISM: Homo sapiens
<220> FEATURE:
<223> OTHER INFORMATION: V-C entry TRBV6-3_TRBC2

<400> SEQUENCE: 496

```
gccaccatga gcctcgggct cctgtgctgt ggggtctttt ctctcctgtg ggcaggtcca     60

gtgaatgctg gtgtcactca gaccccaaaa ttccgggtcc tgaaaacagg acagagcatg    120

acactgctgt gtgcccagga tatgaaccat gaatacatgt actggtatcg acaagaccca    180

ggcatggggc tgaggctgat tcattactca gttggtgagg gtacaactgc caaaggagag    240

gtccctgatg gctacaatgt ctccagatta aaaaaacaga atttcctgct ggggttggag    300

tcggctgctc cctcccaaac atctgtgtac ttttgcagag accttgcggc cgcataggtc    360

tcagtgttcc cacccgaggt cgctgtgttt gagccatcag aagcagagat ctcccacacc    420

caaaaggcca cactggtatg cctggccaca ggcttctacc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggcttcacc tccgagtctt accagcaagg ggtcctgtct    780

gccaccatcc tctatgagat cttgctaggg aaggccacct tgtatgccgt gctggtcagt    840

gccctcgtgc tgatggccat ggtcaagaga aaggattcca gaggctag                 888
```

<210> SEQ ID NO 497
<211> LENGTH: 888
<212> TYPE: DNA
<213> ORGANISM: Homo sapiens
<220> FEATURE:
<223> OTHER INFORMATION: V-C entry TRBV6-4_TRBC2

<400> SEQUENCE: 497

```
gccaccatga gaatcaggct cctgtgctgt gtggcctttt ctctcctgtg ggcaggtcca     60

gtgattgctg ggatcaccca ggcaccaaca tctcagatcc tggcagcagg acggcgcatg    120
```

```
acactgagat gtacccagga tatgagacat aatgccatgt actggtatag acaagatcta    180

ggactggggc taaggctcat ccattattca aatactgcag gtaccactgg caaaggagaa    240

gtccctgatg gttatagtgt ctccagagca aacacagatg atttcccct cacgttggcg     300

tctgctgtac cctctcagac atctgtgtac ttttgcagag accttgcggc cgcataggtc    360

tcagtgttcc cacccgaggt cgctgtgttt gagccatcag aagcagagat ctcccacacc    420

caaaaggcca cactggtatg cctggccaca ggcttctacc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggcttcacc tccgagtctt accagcaagg ggtcctgtct    780

gccaccatcc tctatgagat cttgctaggg aaggccacct tgtatgccgt gctggtcagt    840

gccctcgtgc tgatggccat ggtcaagaga aaggattcca gaggctag                 888
```

<210> SEQ ID NO 498
<211> LENGTH: 888
<212> TYPE: DNA
<213> ORGANISM: Homo sapiens
<220> FEATURE:
<223> OTHER INFORMATION: V-C entry TRBV6-5_TRBC2

<400> SEQUENCE: 498

```
gccaccatga gcatcggcct cctgtgctgt gcagccttgt ctctcctgtg ggcaggtcca     60

gtgaatgctg gtgtcactca gaccccaaaa ttccaggtcc tgaaaacagg acagagcatg    120

acactgcagt gtgcccagga tatgaaccat gaatacatgt cctggtatcg acaagaccca    180

ggcatggggc tgaggctgat tcattactca gttggtgctg gtatcactga ccaaggagaa    240

gtccccaatg gctacaatgt ctccagatca accacagagg atttcccgct caggctgctg    300

tcggctgctc cctcccagac atctgtgtac ttttgcagag accttgcggc cgcataggtc    360

tcagtgttcc cacccgaggt cgctgtgttt gagccatcag aagcagagat ctcccacacc    420

caaaaggcca cactggtatg cctggccaca ggcttctacc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggcttcacc tccgagtctt accagcaagg ggtcctgtct    780

gccaccatcc tctatgagat cttgctaggg aaggccacct tgtatgccgt gctggtcagt    840

gccctcgtgc tgatggccat ggtcaagaga aaggattcca gaggctag                 888
```

<210> SEQ ID NO 499
<211> LENGTH: 888
<212> TYPE: DNA
<213> ORGANISM: Homo sapiens
<220> FEATURE:
<223> OTHER INFORMATION: V-C entry TRBV6-6_TRBC2

<400> SEQUENCE: 499

```
gccaccatga gcatcagcct cctgtgctgt gcagcctttc ctctcctgtg ggcaggtcca     60
```

```
gtgaatgctg gtgtcactca gaccccaaaa ttccgcatcc tgaagatagg acagagcatg    120

acactgcagt gtacccagga tatgaaccat aactacatgt actggtatcg acaagaccca    180

ggcatggggc tgaagctgat ttattattca gttggtgctg gtatcactga taaaggagaa    240

gtcccgaatg gctacaacgt ctccagatca accacagagg atttcccgct caggctggag    300

ttggctgctc cctcccagac atctgtgtac ttttgcagag accttgcggc cgcataggtc    360

tcagtgttcc cacccgaggt cgctgtgttt gagccatcag aagcagagat ctcccacacc    420

caaaaggcca cactggtatg cctggccaca ggcttctacc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggcttcacc tccgagtctt accagcaagg ggtcctgtct    780

gccaccatcc tctatgagat cttgctaggg aaggccacct tgtatgccgt gctggtcagt    840

gccctcgtgc tgatggccat ggtcaagaga aaggattcca gaggctag                 888
```

```
<210> SEQ ID NO 500
<211> LENGTH: 885
<212> TYPE: DNA
<213> ORGANISM: Homo sapiens
<220> FEATURE:
<223> OTHER INFORMATION: V-C entry TRBV6-8_TRBC2

<400> SEQUENCE: 500

gccaccatga gcctcgggct cctgtgctgt gcggcctttt ctctcctgtg ggcaggtccc     60

gtgaatgctg gtgtcactca gaccccaaaa ttccacatcc tgaaaacagg acagagcatg    120

acactgcagt gtgcccagga tatgaaccat ggatacatgt cctggtatcg acaagaccca    180

ggcatggggc tgagactgat ttactactca gctgctgctg gtactactga caaagaagtc    240

cccaatggct acaatgtctc tagattaaac acagaggatt tcccactcag gctggtgtcg    300

gctgctccct cccagacatc tgtgtacctt tgcagagacc ttgcggccgc ataggtctca    360

gtgttcccac ccgaggtcgc tgtgtttgag ccatcagaag cagagatctc ccacacccaa    420

aaggccacac tggtatgcct ggccacaggc ttctaccccg accacgtgga gctgagctgg    480

tgggtgaatg ggaaggaggt gcacagtggg gtcagcacag acccgcagcc cctcaaggag    540

cagcccgccc tcaatgactc cagatactgc ctgagcagcc gcctgagggt gtcggccacc    600

ttctggcaga acccccgcaa ccacttccgc tgtcaagtcc agttctacgg gctctcggag    660

aatgacgagt ggacccagga tagggccaaa cccgtcaccc agatcgtcag cgccgaggcc    720

tggggtagag cagactgtgg cttcacctcc gagtcttacc agcaaggggt cctgtctgcc    780

accatcctct atgagatctt gctagggaag gccaccttgt atgccgtgct ggtcagtgcc    840

ctcgtgctga tggccatggt caagagaaag gattccagag gctag                    885
```

```
<210> SEQ ID NO 501
<211> LENGTH: 888
<212> TYPE: DNA
<213> ORGANISM: Homo sapiens

<400> SEQUENCE: 501

gccaccatga gcatcgggct cctgtgctgt gtggcctttt ctctcctgtg ggcaggtcca     60

gtgaatgctg gtgtcactca gaccccaaaa ttccacatcc tgaaaacagg acagagcatg    120
```

```
acactgcagt gtgcccagga tatgaaccat ggatacttgt cctggtatcg acaagaccca    180

ggcatggggc tgaggcgcat tcattactca gttgctgctg gtatcactga caaaggagaa    240

gtccccgatg gctacaatgt atccagatca aacacagagg atttcccgct caggctggag    300

tcagctgctc cctcccagac atctgtatac ttttgcagag accttgcggc cgcataggtc    360

tcagtgttcc cacccgaggt cgctgtgttt gagccatcag aagcagagat ctcccacacc    420

caaaaggcca cactggtatg cctggccaca ggcttctacc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggcttcacc tccgagtctt accagcaagg ggtcctgtct    780

gccaccatcc tctatgagat cttgctaggg aaggccacct tgtatgccgt gctggtcagt    840

gccctcgtgc tgatggccat ggtcaagaga aaggattcca gaggctag                 888
```

<210> SEQ ID NO 502
<211> LENGTH: 891
<212> TYPE: DNA
<213> ORGANISM: Homo sapiens
<220> FEATURE:
<223> OTHER INFORMATION: V-C entry TRBV7-2_TRBC2

<400> SEQUENCE: 502

```
gccaccatgg gcaccaggct cctcttctgg gtggccttct gtctcctggg ggcagatcac     60

acaggagctg gagtctccca gtcccccagt aacaaggtca cagagaaggg aaaggatgta    120

gagctcaggt gtgatccaat ttcaggtcat actgcccttt actggtaccg acagagcctg    180

gggcagggcc tggagttttt aatttacttc caaggcaaca gtgcaccaga caaatcaggg    240

ctgcccagtg atcgcttctc tgcagagagg actgggggat ccgtctccac tctgacgatc    300

cagcgcacac agcaggagga ctcggccgtg tatctttgca gagaccttgc ggccgcatag    360

gtctcagtgt tcccacccga ggtcgctgtg tttgagccat cagaagcaga gatctcccac    420

acccaaaagg ccacactggt atgcctggcc acaggcttct accccgacca cgtggagctg    480

agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttc acctccgagt cttaccagca aggggtcctg    780

tctgccacca tcctctatga gatcttgcta gggaaggcca ccttgtatgc cgtgctggtc    840

agtgccctcg tgctgatggc catggtcaag agaaaggatt ccagaggcta g             891
```

<210> SEQ ID NO 503
<211> LENGTH: 891
<212> TYPE: DNA
<213> ORGANISM: Homo sapiens
<220> FEATURE:
<223> OTHER INFORMATION: V-C entry TRBV7-3_TRBC2

<400> SEQUENCE: 503

```
gccaccatgg gcaccaggct cctctgctgg gcagccctgt gcctcctggg ggcagatcac     60
```

```
acaggtgctg gagtctccca gacccccagt aacaaggtca cagagaaggg aaaatatgta    120

gagctcaggt gtgatccaat ttcaggtcat actgcccttt actggtaccg acaaagcctg    180

gggcagggcc cagagtttct aatttacttc caaggcacgg gtgcggcaga tgactcaggg    240

ctgcccaacg atcggttctt tgcagtcagg cctgagggat ccgtctctac tctgaagatc    300

cagcgcacag agcgggggga ctcagccgtg tatctttgca gagaccttgc ggccgcatag    360

gtctcagtgt tcccacccga ggtcgctgtg tttgagccat cagaagcaga gatctcccac    420

acccaaaagg ccacactggt atgcctggcc acaggcttct accccgacca cgtggagctg    480

agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttc acctccgagt cttaccagca aggggtcctg    780

tctgccacca tcctctatga gatcttgcta gggaaggcca ccttgtatgc cgtgctggtc    840

agtgccctcg tgctgatggc catggtcaag agaaaggatt ccagaggcta g             891
```

<210> SEQ ID NO 504
<211> LENGTH: 891
<212> TYPE: DNA
<213> ORGANISM: Homo sapiens
<220> FEATURE:
<223> OTHER INFORMATION: V-C entry TRBV7-6_TRBC2

<400> SEQUENCE: 504

```
gccaccatgg gcaccagtct cctatgctgg gtggtcctgg gtttcctagg gacagatcac     60

acaggtgctg gagtctccca gtctcccagg tacaaagtca caaagagggg acaggatgta    120

gctctcaggt gtgatccaat ttcgggtcat gtatcccttt attggtaccg acaggccctg    180

gggcagggcc cagagtttct gacttacttc aattatgaag cccaacaaga caaatcaggg    240

ctgcccaatg atcggttctc tgcagagagg cctgagggat ccatctccac tctgacgatc    300

cagcgcacag agcagcggga ctcggccatg tatcgttgca gagaccttgc ggccgcatag    360

gtctcagtgt tcccacccga ggtcgctgtg tttgagccat cagaagcaga gatctcccac    420

acccaaaagg ccacactggt atgcctggcc acaggcttct accccgacca cgtggagctg    480

agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttc acctccgagt cttaccagca aggggtcctg    780

tctgccacca tcctctatga gatcttgcta gggaaggcca ccttgtatgc cgtgctggtc    840

agtgccctcg tgctgatggc catggtcaag agaaaggatt ccagaggcta g             891
```

<210> SEQ ID NO 505
<211> LENGTH: 891
<212> TYPE: DNA
<213> ORGANISM: Homo sapiens
<220> FEATURE:
<223> OTHER INFORMATION: V-C entry TRBV7-7_TRBC2

<400> SEQUENCE: 505

```
gccaccatgg gtaccagtct cctatgctgg gtggtcctgg gtttcctagg gacagatcac     60
```

acaggtgctg gagtctccca gtctcccagg tacaaagtca caaagagggg acaggatgta 120
actctcaggt gtgatccaat ttcgagtcat gcaacccttt attggtatca acaggccctg 180
gggcagggcc cagagtttct gacttacttc aattatgaag ctcaaccaga caaatcaggg 240
ctgcccagtg atcggttctc tgcagagagg cctgagggat ccatctccac tctgacgatt 300
cagcgcacag agcagcggga ctcagccatg tatcgttgca gagaccttgc ggccgcatag 360
gtctcagtgt tcccacccga ggtcgctgtg tttgagccat cagaagcaga gatctcccac 420
acccaaaagg ccacactggt atgcctggcc acaggcttct accccgacca cgtggagctg 480
agctggtggg tgaatgggaa ggaggtgcac agtggggtca gcacagaccc gcagcccctc 540
aaggagcagc ccgccctcaa tgactccaga tactgcctga gcagccgcct gagggtgtcg 600
gccaccttct ggcagaaccc ccgcaaccac ttccgctgtc aagtccagtt ctacgggctc 660
tcggagaatg acgagtggac ccaggatagg gccaaacccg tcacccagat cgtcagcgcc 720
gaggcctggg gtagagcaga ctgtggcttc acctccgagt cttaccagca aggggtcctg 780
tctgccacca tcctctatga gatcttgcta gggaaggcca ccttgtatgc cgtgctggtc 840
agtgccctcg tgctgatggc catggtcaag agaaaggatt ccagaggcta g 891

<210> SEQ ID NO 506
<211> LENGTH: 891
<212> TYPE: DNA
<213> ORGANISM: Homo sapiens
<220> FEATURE:
<223> OTHER INFORMATION: V-C entry TRBV7-8_TRBC2

<400> SEQUENCE: 506
gccaccatgg gcaccaggct cctctgctgg gtggtcctgg gtttcctagg gacagatcac 60
acaggtgctg gagtctccca gtcccctagg tacaaagtcg caaagagagg acaggatgta 120
gctctcaggt gtgatccaat ttcgggtcat gtatcccttt tttggtacca acaggccctg 180
gggcaggggc cagagtttct gacttatttc cagaatgaag ctcaactaga caaatcgggg 240
ctgcccagtg atcgcttctt tgcagaaagg cctgagggat ccgtctccac tctgaagatc 300
cagcgcacac agcaggagga ctccgccgtg tatctttgca gagaccttgc ggccgcatag 360
gtctcagtgt tcccacccga ggtcgctgtg tttgagccat cagaagcaga gatctcccac 420
acccaaaagg ccacactggt atgcctggcc acaggcttct accccgacca cgtggagctg 480
agctggtggg tgaatgggaa ggaggtgcac agtggggtca gcacagaccc gcagcccctc 540
aaggagcagc ccgccctcaa tgactccaga tactgcctga gcagccgcct gagggtgtcg 600
gccaccttct ggcagaaccc ccgcaaccac ttccgctgtc aagtccagtt ctacgggctc 660
tcggagaatg acgagtggac ccaggatagg gccaaacccg tcacccagat cgtcagcgcc 720
gaggcctggg gtagagcaga ctgtggcttc acctccgagt cttaccagca aggggtcctg 780
tctgccacca tcctctatga gatcttgcta gggaaggcca ccttgtatgc cgtgctggtc 840
agtgccctcg tgctgatggc catggtcaag agaaaggatt ccagaggcta g 891

<210> SEQ ID NO 507
<211> LENGTH: 891
<212> TYPE: DNA
<213> ORGANISM: Homo sapiens
<220> FEATURE:
<223> OTHER INFORMATION: V-C entry TRBV7-9_TRBC2

<400> SEQUENCE: 507

```
gccaccatgg gcaccagcct cctctgctgg atggccctgt gtctcctggg ggcagatcac     60

gcagatactg gagtctccca gaaccccaga cacaagatca caaagagggg acagaatgta    120

actttcaggt gtgatccaat ttctgaacac aaccgccttt attggtaccg acagaccctg    180

gggcagggcc cagagtttct gacttacttc cagaatgaag ctcaactaga aaaatcaagg    240

ctgctcagtg atcggttctc tgcagagagg cctaagggat ctttctccac cttggagatc    300

cagcgcacag agcaggggga ctcggccatg tatctttgca gagaccttgc ggccgcatag    360

gtctcagtgt tcccacccga ggtcgctgtg tttgagccat cagaagcaga gatctcccac    420

acccaaaagg ccacactggt atgcctggcc acaggcttct accccgacca cgtggagctg    480

agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttc acctccgagt cttaccagca aggggtcctg    780

tctgccacca tcctctatga gatcttgcta gggaaggcca ccttgtatgc cgtgctggtc    840

agtgccctcg tgctgatggc catggtcaag agaaaggatt ccagaggcta g             891
```

<210> SEQ ID NO 508
<211> LENGTH: 888
<212> TYPE: DNA
<213> ORGANISM: Homo sapiens
<220> FEATURE:
<223> OTHER INFORMATION: V-C entry TRBV9_TRBC2

<400> SEQUENCE: 508

```
gccaccatgg gcttcaggct cctctgctgt gtggcctttt gtctcctggg agcaggccca     60

gtggattctg gagtcacaca aaccccaaag cacctgatca cagcaactgg acagcgagtg    120

acgctgagat gctcccctag gtctggtgac ctctctgtgt actggtacca acagagcctg    180

gaccagggcc tccagttcct cattcagtat tataatggag aagagagagc aaaaggaaac    240

attcttgaac gattctccgc acaacagttc cctgacttgc actctgaact aaacctgagc    300

tctctggagc tgggggactc agctttgtac ttttgcagag accttgcggc cgcataggtc    360

tcagtgttcc cacccgaggt cgctgtgttt gagccatcag aagcagagat ctcccacacc    420

caaaaggcca cactggtatg cctggccaca ggcttctacc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggcttcacc tccgagtctt accagcaagg ggtcctgtct    780

gccaccatcc tctatgagat cttgctaggg aaggccacct tgtatgccgt gctggtcagt    840

gccctcgtgc tgatggccat ggtcaagaga aaggattcca gaggctag                 888
```

<210> SEQ ID NO 509
<211> LENGTH: 888
<212> TYPE: DNA
<213> ORGANISM: Homo sapiens
<220> FEATURE:
<223> OTHER INFORMATION: V-C entry TRBV10-1_TRBC2

<400> SEQUENCE: 509

```
gccaccatgg gcacgaggct cttcttctat gtggcccttt gtctgctgtg ggcaggacac     60
agggatgctg aaatcaccca gagcccaaga cacaagatca cagagacagg aaggcaggtg    120
accttggcgt gtcaccagac ttggaaccac aacaatatgt tctggtatcg acaagacctg    180
ggacatgggc tgaggctgat ccattactca tatggtgttc aagacactaa caaaggagaa    240
gtctcagatg gctacagtgt ctctagatca aacacagagg acctcccct  cactctggag    300
tctgctgcct cctcccagac atctgtatac ttttgcagag accttgcggc cgcataggtc    360
tcagtgttcc cacccgaggt cgctgtgttt gagccatcag aagcagagat ctcccacacc    420
caaaaggcca cactggtatg cctggccaca ggcttctacc ccgaccacgt ggagctgagc    480
tggtgggtga atgggaagga ggtgcacagt ggggtcagca cagacccgca gcccctcaag    540
gagcagcccg ccctcaatga ctccagatac tgcctgagca gccgcctgag ggtgtcggcc    600
accttctggc agaacccccg caaccacttc cgctgtcaag tccagttcta cgggctctcg    660
gagaatgacg agtggaccca ggatagggcc aaacccgtca cccagatcgt cagcgccgag    720
gcctggggta gagcagactg tggcttcacc tccgagtctt accagcaagg ggtcctgtct    780
gccaccatcc tctatgagat cttgctaggg aaggccacct tgtatgccgt gctggtcagt    840
gccctcgtgc tgatggccat ggtcaagaga aaggattcca gaggctag                 888
```

<210> SEQ ID NO 510
<211> LENGTH: 888
<212> TYPE: DNA
<213> ORGANISM: Homo sapiens
<220> FEATURE:
<223> OTHER INFORMATION: V-C entry TRBV10-2_TRBC2

<400> SEQUENCE: 510

```
gccaccatgg gcaccaggct cttcttctat gtggcccttt gtctgctgtg ggcaggacac     60
agggatgctg gaatcaccca gagcccaaga tacaagatca cagagacagg aaggcaggtg    120
accttgatgt gtcaccagac ttggagccac agctatatgt tctggtatcg acaagacctg    180
ggacatgggc tgaggctgat ctattactca gcagctgctg atattacaga taaaggagaa    240
gtccccgatg gctatgttgt ctccagatcc aagacagaga atttcccct  cactctggag    300
tcagctaccc gctcccagac atctgtgtac ttttgcagag accttgcggc cgcataggtc    360
tcagtgttcc cacccgaggt cgctgtgttt gagccatcag aagcagagat ctcccacacc    420
caaaaggcca cactggtatg cctggccaca ggcttctacc ccgaccacgt ggagctgagc    480
tggtgggtga atgggaagga ggtgcacagt ggggtcagca cagacccgca gcccctcaag    540
gagcagcccg ccctcaatga ctccagatac tgcctgagca gccgcctgag ggtgtcggcc    600
accttctggc agaacccccg caaccacttc cgctgtcaag tccagttcta cgggctctcg    660
gagaatgacg agtggaccca ggatagggcc aaacccgtca cccagatcgt cagcgccgag    720
gcctggggta gagcagactg tggcttcacc tccgagtctt accagcaagg ggtcctgtct    780
gccaccatcc tctatgagat cttgctaggg aaggccacct tgtatgccgt gctggtcagt    840
gccctcgtgc tgatggccat ggtcaagaga aaggattcca gaggctag                 888
```

<210> SEQ ID NO 511
<211> LENGTH: 888
<212> TYPE: DNA
<213> ORGANISM: Homo sapiens
<220> FEATURE:
<223> OTHER INFORMATION: V-C entry TRBV10-3_TRBC2

<400> SEQUENCE: 511

```
gccaccatgg gcacaaggtt gttcttctat gtggcccttt gtctcctgtg gacaggacac     60

atggatgctg gaatcaccca gagcccaaga cacaaggtca cagagacagg aacaccagtg    120

actctgagat gtcaccagac tgagaaccac cgctatatgt actggtatcg acaagacccg    180

gggcatgggc tgaggctgat ccattactca tatggtgtta aagatactga caaaggagaa    240

gtctcagatg gctatagtgt ctctagatca aagacagagg atttcctcct cactctggag    300

tccgctacca gctcccagac atctgtgtac ttttgcagag accttgcggc cgcataggtc    360

tcagtgttcc cacccgaggt cgctgtgttt gagccatcag aagcagagat ctcccacacc    420

caaaaggcca cactggtatg cctggccaca ggcttctacc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggcttcacc tccgagtctt accagcaagg ggtcctgtct    780

gccaccatcc tctatgagat cttgctaggg aaggccacct tgtatgccgt gctggtcagt    840

gccctcgtgc tgatggccat ggtcaagaga aaggattcca gaggctag                 888
```

<210> SEQ ID NO 512
<211> LENGTH: 891
<212> TYPE: DNA
<213> ORGANISM: Homo sapiens
<220> FEATURE:
<223> OTHER INFORMATION: V-C entry TRBV11-1_TRBC2

<400> SEQUENCE: 512

```
gccaccatga gcaccaggct tctctgctgg atggccctct gtctcctggg ggcagaactc     60

tcagaagctg aagttgccca gtcccccaga tataagatta cagagaaaag ccaggctgtg    120

gctttttggt gtgatcctat ttctggccat gctacccttt actggtaccg gcagatcctg    180

ggacagggcc cggagcttct ggttcaattt caggatgaga gtgtagtaga tgattcacag    240

ttgcctaagg atcgattttc tgcagagagg ctcaaaggag tagactccac tctcaagatc    300

cagcctgcag agcttgggga ctcggccatg tatctttgca gagaccttgc ggccgcatag    360

gtctcagtgt tcccacccga ggtcgctgtg tttgagccat cagaagcaga gatctcccac    420

acccaaaagg ccacactggt atgcctggcc acaggcttct accccgacca cgtggagctg    480

agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttc acctccgagt cttaccagca aggggtcctg    780

tctgccacca tcctctatga gatcttgcta gggaaggcca ccttgtatgc cgtgctggtc    840

agtgccctcg tgctgatggc catggtcaag agaaaggatt ccagaggcta g             891
```

<210> SEQ ID NO 513
<211> LENGTH: 891
<212> TYPE: DNA
<213> ORGANISM: Homo sapiens
<220> FEATURE:
<223> OTHER INFORMATION: V-C entry TRBV11-2_TRBC2

<400> SEQUENCE: 513

```
gccaccatgg gcaccaggct cctctgctgg gcggccctct gtctcctggg agcagaactc     60
acagaagctg gagttgccca gtctcccaga tataagatta tagagaaaag gcagagtgtg    120
gctttttggt gcaatcctat atctggccat gctacccttt actggtacca gcagatcctg    180
ggacagggcc caaagcttct gattcagttt cagaataacg gtgtagtgga tgattcacag    240
ttgcctaagg atcgattttc tgcagagagg ctcaaaggag tagactccac tctcaagatc    300
cagcctgcaa agcttgagga ctcggccgtg tatctttgca gagaccttgc ggccgcatag    360
gtctcagtgt tcccacccga ggtcgctgtg tttgagccat cagaagcaga gatctcccac    420
acccaaaagg ccacactggt atgcctggcc acaggcttct accccgacca cgtggagctg    480
agctggtggg tgaatgggaa ggaggtgcac agtggggtca gcacagaccc gcagcccctc    540
aaggagcagc ccgccctcaa tgactccaga tactgcctga gcagccgcct gagggtgtcg    600
gccaccttct ggcagaaccc ccgcaaccac ttccgctgtc aagtccagtt ctacgggctc    660
tcggagaatg acgagtggac ccaggatagg gccaaacccg tcacccagat cgtcagcgcc    720
gaggcctggg gtagagcaga ctgtggcttc acctccgagt cttaccagca aggggtcctg    780
tctgccacca tcctctatga gatcttgcta gggaaggcca ccttgtatgc cgtgctggtc    840
agtgccctcg tgctgatggc catggtcaag agaaaggatt ccagaggcta g             891
```

<210> SEQ ID NO 514
<211> LENGTH: 891
<212> TYPE: DNA
<213> ORGANISM: Homo sapiens
<220> FEATURE:
<223> OTHER INFORMATION: V-C entry TRBV11-3_TRBC2

<400> SEQUENCE: 514

```
gccaccatgg gtaccaggct cctctgctgg gtggccttct gtctcctggt ggaagaactc     60
atagaagctg gagtggttca gtctcccaga tataagatta tagagaaaaa acagcctgtg    120
gctttttggt gcaatcctat ttctggccac aatacccttt actggtacct gcagaacttg    180
ggacagggcc cggagcttct gattcgatat gagaatgagg aagcagtaga cgattcacag    240
ttgcctaagg atcgattttc tgcagagagg ctcaaaggag tagactccac tctcaagatc    300
cagcctgcag agcttgggga ctcggccgtg tatctttgca gagaccttgc ggccgcatag    360
gtctcagtgt tcccacccga ggtcgctgtg tttgagccat cagaagcaga gatctcccac    420
acccaaaagg ccacactggt atgcctggcc acaggcttct accccgacca cgtggagctg    480
agctggtggg tgaatgggaa ggaggtgcac agtggggtca gcacagaccc gcagcccctc    540
aaggagcagc ccgccctcaa tgactccaga tactgcctga gcagccgcct gagggtgtcg    600
gccaccttct ggcagaaccc ccgcaaccac ttccgctgtc aagtccagtt ctacgggctc    660
tcggagaatg acgagtggac ccaggatagg gccaaacccg tcacccagat cgtcagcgcc    720
gaggcctggg gtagagcaga ctgtggcttc acctccgagt cttaccagca aggggtcctg    780
tctgccacca tcctctatga gatcttgcta gggaaggcca ccttgtatgc cgtgctggtc    840
agtgccctcg tgctgatggc catggtcaag agaaaggatt ccagaggcta g             891
```

<210> SEQ ID NO 515
<211> LENGTH: 891
<212> TYPE: DNA
<213> ORGANISM: Homo sapiens
<220> FEATURE:

<223> OTHER INFORMATION: V-C entry TRBV12-3_TRBC2

<400> SEQUENCE: 515

```
gccaccatgg actcctggac cttctgctgt gtgtcccttt gcatcctggt agcgaagcat     60
acagatgctg gagttatcca gtcaccccgc catgaggtga cagagatggg acaagaagtg    120
actctgagat gtaaaccaat ttcaggccac aactcccttt tctggtacag acagaccatg    180
atgcggggac tggagttgct catttacttt aacaacaacg ttccgataga tgattcaggg    240
atgcccgagg atcgattctc agctaagatg cctaatgcat cattctccac tctgaagatc    300
cagccctcag aacccaggga ctcagctgtg tacttttgca gagaccttgc ggccgcatag    360
gtctcagtgt tcccacccga ggtcgctgtg tttgagccat cagaagcaga gatctcccac    420
acccaaaagg ccacactggt atgcctggcc acaggcttct accccgacca cgtggagctg    480
agctggtggg tgaatgggaa ggaggtgcac agtggggtca gcacagaccc gcagcccctc    540
aaggagcagc ccgccctcaa tgactccaga tactgcctga gcagccgcct gagggtgtcg    600
gccaccttct ggcagaaccc ccgcaaccac ttccgctgtc aagtccagtt ctacgggctc    660
tcggagaatg acgagtggac ccaggatagg gccaaacccg tcacccagat cgtcagcgcc    720
gaggcctggg gtagagcaga ctgtggcttc acctccgagt cttaccagca aggggtcctg    780
tctgccacca tcctctatga gatcttgcta gggaaggcca ccttgtatgc cgtgctggtc    840
agtgccctcg tgctgatggc catggtcaag agaaaggatt ccagaggcta g             891
```

<210> SEQ ID NO 516
<211> LENGTH: 891
<212> TYPE: DNA
<213> ORGANISM: Homo sapiens
<220> FEATURE:
<223> OTHER INFORMATION: V-C entry TRBV12-4_TRBC2

<400> SEQUENCE: 516

```
gccaccatgg actcctggac cctctgctgt gtgtcccttt gcatcctggt agcaaagcac     60
acagatgctg gagttatcca gtcaccccgg cacgaggtga cagagatggg acaagaagtg    120
actctgagat gtaaaccaat ttcaggacac gactaccttt tctggtacag acagaccatg    180
atgcggggac tggagttgct catttacttt aacaacaacg ttccgataga tgattcaggg    240
atgcccgagg atcgattctc agctaagatg cctaatgcat cattctccac tctgaagatc    300
cagccctcag aacccaggga ctcagctgtg tacttttgca gagaccttgc ggccgcatag    360
gtctcagtgt tcccacccga ggtcgctgtg tttgagccat cagaagcaga gatctcccac    420
acccaaaagg ccacactggt atgcctggcc acaggcttct accccgacca cgtggagctg    480
agctggtggg tgaatgggaa ggaggtgcac agtggggtca gcacagaccc gcagcccctc    540
aaggagcagc ccgccctcaa tgactccaga tactgcctga gcagccgcct gagggtgtcg    600
gccaccttct ggcagaaccc ccgcaaccac ttccgctgtc aagtccagtt ctacgggctc    660
tcggagaatg acgagtggac ccaggatagg gccaaacccg tcacccagat cgtcagcgcc    720
gaggcctggg gtagagcaga ctgtggcttc acctccgagt cttaccagca aggggtcctg    780
tctgccacca tcctctatga gatcttgcta gggaaggcca ccttgtatgc cgtgctggtc    840
agtgccctcg tgctgatggc catggtcaag agaaaggatt ccagaggcta g             891
```

<210> SEQ ID NO 517
<211> LENGTH: 891
<212> TYPE: DNA
<213> ORGANISM: Homo sapiens
<220> FEATURE:
<223> OTHER INFORMATION: V-C entry TRBV12-5_TRBC2

<400> SEQUENCE: 517
gccaccatgg ccaccaggct cctctgctgt gtggttcttt gtctcctggg agaagagctt 60
atagatgcta gagtcaccca gacaccaagg cacaaggtga cagagatggg acaagaagta 120
acaatgagat gtcagccaat tttaggccac aatactgttt tctggtacag acagaccatg 180
atgcaaggac tggagttgct ggcttacttc cgcaaccggg ctcctctaga tgattcgggg 240
atgccgaagg atcgattctc agcagagatg cctgatgcaa ctttagccac tctgaagatc 300
cagccctcag aacccaggga ctcagctgtg tacttttgca gagaccttgc ggccgcatag 360
gtctcagtgt tcccacccga ggtcgctgtg tttgagccat cagaagcaga gatctcccac 420
acccaaaagg ccacactggt atgcctggcc acaggcttct accccgacca cgtggagctg 480
agctggtggg tgaatgggaa ggaggtgcac agtggggtca gcacagaccc gcagcccctc 540
aaggagcagc ccgccctcaa tgactccaga tactgcctga gcagccgcct gagggtgtcg 600
gccaccttct ggcagaaccc ccgcaaccac ttccgctgtc aagtccagtt ctacgggctc 660
tcggagaatg acgagtggac ccaggatagg gccaaacccg tcacccagat cgtcagcgcc 720
gaggcctggg gtagagcaga ctgtggcttc acctccgagt cttaccagca aggggtcctg 780
tctgccacca tcctctatga gatcttgcta gggaaggcca ccttgtatgc cgtgctggtc 840
agtgccctcg tgctgatggc catggtcaag agaaaggatt ccagaggcta g 891

<210> SEQ ID NO 518
<211> LENGTH: 918
<212> TYPE: DNA
<213> ORGANISM: Homo sapiens
<220> FEATURE:
<223> OTHER INFORMATION: V-C entry TRBV13_TRBC2

<400> SEQUENCE: 518
gccaccatgc ttagtcctga cctgcctgac tctgcctgga acaccaggct cctctgccat 60
gtcatgcttt gtctcctggg agcagtttca gtggctgctg gagtcatcca gtccccaaga 120
catctgatca aagaaaagag ggaaacagcc actctgaaat gctatcctat ccctagacac 180
gacactgtct actggtacca gcagggtcca ggtcaggacc cccagttcct catttcgttt 240
tatgaaaaga tgcagagcga taaaggaagc atccctgatc gattctcagc tcaacagttc 300
agtgactatc attctgaact gaacatgagc tccttggagc tgggggactc agccctgtac 360
ttttgcagag accttgcggc cgcataggtc tcagtgttcc cacccgaggt cgctgtgttt 420
gagccatcag aagcagagat ctcccacacc caaaaggcca cactggtatg cctggccaca 480
ggcttctacc ccgaccacgt ggagctgagc tggtgggtga atgggaagga ggtgcacagt 540
ggggtcagca cagacccgca gcccctcaag gagcagcccg ccctcaatga ctccagatac 600
tgcctgagca gccgcctgag ggtgtcggcc accttctggc agaacccccg caaccacttc 660
cgctgtcaag tccagttcta cgggctctcg gagaatgacg agtggaccca ggatagggcc 720
aaacccgtca cccagatcgt cagcgccgag gcctggggta gagcagactg tggcttcacc 780
tccgagtctt accagcaagg ggtcctgtct gccaccatcc tctatgagat cttgctaggg 840
aaggccacct tgtatgccgt gctggtcagt gccctcgtgc tgatggccat ggtcaagaga 900
aaggattcca gaggctag 918

<210> SEQ ID NO 519

```
<211> LENGTH: 891
<212> TYPE: DNA
<213> ORGANISM: Homo sapiens
<220> FEATURE:
<223> OTHER INFORMATION: V-C entry TRBV14_TRBC2

<400> SEQUENCE: 519

gccaccatgg tttccaggct tctcagttta gtgtcccttt gtctcctggg agcaaagcac     60

atagaagctg gagttactca gttccccagc cacagcgtaa tagagaaggg ccagactgtg    120

actctgagat gtgacccaat ttctggacat gataatcttt attggtatcg acgtgttatg    180

ggaaaagaaa taaaatttct gttacatttt gtgaaagagt ctaaacagga tgagtccggt    240

atgcccaaca atcgattctt agctgaaagg actggaggga cgtattctac tctgaaggtg    300

cagcctgcag aactggagga ttctggagtt tacttttgca gagaccttgc ggccgcatag    360

gtctcagtgt tcccacccga ggtcgctgtg tttgagccat cagaagcaga gatctcccac    420

acccaaaagg ccacactggt atgcctggcc acaggcttct accccgacca cgtggagctg    480

agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttc acctccgagt cttaccagca aggggtcctg    780

tctgccacca tcctctatga gatcttgcta gggaaggcca ccttgtatgc cgtgctggtc    840

agtgccctcg tgctgatggc catggtcaag agaaaggatt ccagaggcta g             891


<210> SEQ ID NO 520
<211> LENGTH: 888
<212> TYPE: DNA
<213> ORGANISM: Homo sapiens
<220> FEATURE:
<223> OTHER INFORMATION: V-C entry TRBV15_TRBC2

<400> SEQUENCE: 520

gccaccatgg gtcctgggct tctccactgg atggcccttt gtctccttgg aacaggtcat     60

ggggatgcca tggtcatcca gaacccaaga taccaggtta cccagtttgg aaagccagtg    120

accctgagtt gttctcagac tttgaaccat aacgtcatgt actggtacca gcagaagtca    180

agtcaggccc caaagctgct gttccactac tatgacaaag attttaacaa tgaagcagac    240

acccctgata acttccaatc caggaggccg aacacttctt tctgctttct tgacatccgc    300

tcaccaggcc tgggggacac agccatgtac ctttgcagag accttgcggc cgcataggtc    360

tcagtgttcc cacccgaggt cgctgtgttt gagccatcag aagcagagat ctcccacacc    420

caaaaggcca cactggtatg cctggccaca ggcttctacc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggcttcacc tccgagtctt accagcaagg ggtcctgtct    780

gccaccatcc tctatgagat cttgctaggg aaggccacct tgtatgccgt gctggtcagt    840

gccctcgtgc tgatggccat ggtcaagaga aaggattcca gaggctag                 888
```

<210> SEQ ID NO 521
<211> LENGTH: 891
<212> TYPE: DNA
<213> ORGANISM: Homo sapiens
<220> FEATURE:
<223> OTHER INFORMATION: V-C entry TRBV16_TRBC2

<400> SEQUENCE: 521

```
gccaccatga gcccaatatt cacctgcatc acaatccttt gtctgctggc tgcaggttct     60

cctggtgaag aagtcgccca gactccaaaa catcttgtca gaggggaagg acagaaagca    120

aaattatatt gtgccccaat aaaaggacac agttatgttt tttggtacca acaggtcctg    180

aaaaacgagt tcaagttctt gatttccttc cagaatgaaa atgtctttga tgaaacaggt    240

atgcccaagg aaagattttc agctaagtgc ctcccaaatt caccctgtag ccttgagatc    300

caggctacga agcttgagga ttcagcagtg tacttttgca gagaccttgc ggccgcatag    360

gtctcagtgt tcccacccga ggtcgctgtg tttgagccat cagaagcaga gatctcccac    420

acccaaaagg ccacactggt atgcctggcc acaggcttct accccgacca cgtggagctg    480

agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttc acctccgagt cttaccagca aggggtcctg    780

tctgccacca tcctctatga gatcttgcta gggaaggcca ccttgtatgc cgtgctggtc    840

agtgccctcg tgctgatggc catggtcaag agaaaggatt ccagaggcta g             891
```

<210> SEQ ID NO 522
<211> LENGTH: 891
<212> TYPE: DNA
<213> ORGANISM: Homo sapiens
<220> FEATURE:
<223> OTHER INFORMATION: V-C entry TRBV18_TRBC2

<400> SEQUENCE: 522

```
gccaccatgg acaccagagt actctgctgt gcggtcatct gccttctggg ggcaggactc     60

tcaaatgccg gcgtcatgca gaacccaaga cacctggtca ggaggagggg acaggaggca    120

agactgagat gcagcccaat gaaaggacac agtcatgttt actggtatcg gcagctccca    180

gaggaaggtc tgaaattcat ggtttatctc cagaaagaaa atatcataga tgagtcagga    240

atgccaaagg aacgattttc tgctgaattt cccaaagagg gccccagcat cctgaggatc    300

cagcaggtag tgcgaggaga ttcggcagct tacttttgca gagaccttgc ggccgcatag    360

gtctcagtgt tcccacccga ggtcgctgtg tttgagccat cagaagcaga gatctcccac    420

acccaaaagg ccacactggt atgcctggcc acaggcttct accccgacca cgtggagctg    480

agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttc acctccgagt cttaccagca aggggtcctg    780

tctgccacca tcctctatga gatcttgcta gggaaggcca ccttgtatgc cgtgctggtc    840

agtgccctcg tgctgatggc catggtcaag agaaaggatt ccagaggcta g             891
```

<210> SEQ ID NO 523
<211> LENGTH: 888
<212> TYPE: DNA
<213> ORGANISM: Homo sapiens
<220> FEATURE:
<223> OTHER INFORMATION: V-C entry TRBV19_TRBC2

<400> SEQUENCE: 523

```
gccaccatga gcaaccaggt gctctgctgt gtggtccttt gtttcctggg agcaaacacc     60
gtggatggtg gaatcactca gtccccaaag tacctgttca gaaaggaagg acagaatgtg    120
accctgagtt gtgaacagaa tttgaaccac gatgccatgt actggtaccg acaggaccca    180
gggcaagggc tgagattgat ctactactca cagatagtaa atgactttca gaaaggagat    240
atagctgaag ggtacagcgt ctctcgggag aagaaggaat cctttcctct cactgtgaca    300
tcggcccaaa agaacccgac agctttctat ctttgcagag accttgcggc cgcataggtc    360
tcagtgttcc cacccgaggt cgctgtgttt gagccatcag aagcagagat ctcccacacc    420
caaaaggcca cactggtatg cctggccaca ggcttctacc ccgaccacgt ggagctgagc    480
tggtgggtga atgggaagga ggtgcacagt ggggtcagca cagacccgca gcccctcaag    540
gagcagcccg ccctcaatga ctccagatac tgcctgagca gccgcctgag ggtgtcggcc    600
accttctggc agaacccccg caaccacttc cgctgtcaag tccagttcta cgggctctcg    660
gagaatgacg agtggaccca ggatagggcc aaacccgtca cccagatcgt cagcgccgag    720
gcctggggta gagcagactg tggcttcacc tccgagtctt accagcaagg ggtcctgtct    780
gccaccatcc tctatgagat cttgctaggg aaggccacct tgtatgccgt gctggtcagt    840
gccctcgtgc tgatggccat ggtcaagaga aaggattcca gaggctag                  888
```

<210> SEQ ID NO 524
<211> LENGTH: 882
<212> TYPE: DNA
<213> ORGANISM: Homo sapiens
<220> FEATURE:
<223> OTHER INFORMATION: V-C entry TRBV20-1_TRBC2

<400> SEQUENCE: 524

```
gccaccatgc tgctgcttct gctgcttctg ggccaggct ccgggcttgg tgctgtcgtc     60
tctcaacatc cgagctgggt tatctgtaag agtggaacct ctgtgaagat cgagtgccgt    120
tccctggact ttcaggccac aactatgttt tggtatcgtc agttcccgaa acagagtctc    180
atgctgatgg caacttccaa tgagggctcc aaggccacat acgagcaagg cgtcgagaag    240
gacaagtttc tcatcaacca tgcaagcctg accttgtcca ctctgacagt gaccagtgcc    300
catcctgaag atagcagctt ctacatttgc agagaccttg cggccgcata ggtctcagtg    360
ttcccacccg aggtcgctgt gtttgagcca tcagaagcag agatctccca cacccaaaag    420
gccacactgg tatgcctggc cacaggcttc taccccgacc acgtggagct gagctggtgg    480
gtgaatggga aggaggtgca cagtggggtc agcacagacc cgcagcccct caaggagcag    540
cccgccctca atgactccag atactgcctg agcagccgcc tgagggtgtc ggccaccttc    600
tggcagaacc cccgcaacca cttccgctgt caagtccagt tctacgggct ctcggagaat    660
gacgagtgga cccaggatag ggccaaaccc gtcacccaga tcgtcagcgc cgaggcctgg    720
ggtagagcag actgtggctt cacctccgag tcttaccagc aaggggtcct gtctgccacc    780
atcctctatg agatcttgct agggaaggcc accttgtatg ccgtgctggt cagtgccctc    840
gtgctgatgg ccatggtcaa gagaaaggat tccagaggct ag                        882
```

<210> SEQ ID NO 525
<211> LENGTH: 888
<212> TYPE: DNA
<213> ORGANISM: Homo sapiens
<220> FEATURE:
<223> OTHER INFORMATION: V-C entry TRBV24-1_TRBC2

<400> SEQUENCE: 525
gccaccatgg cctccctgct cttcttctgt ggggcctttt atctcctggg aacagggtcc 60
atggatgctg atgttaccca gaccccaagg aataggatca caaagacagg aaagaggatt 120
atgctggaat gttctcagac taagggtcat gatagaatgt actggtatcg acaagaccca 180
ggactgggcc tacggttgat ctattactcc tttgatgtca aagatataaa caaaggagag 240
atctctgatg gatacagtgt ctctcgacag gcacaggcta aattctccct gtccctagag 300
tctgccatcc ccaaccagac agctctttac ttttgcagag accttgcggc cgcataggtc 360
tcagtgttcc cacccgaggt cgctgtgttt gagccatcag aagcagagat ctcccacacc 420
caaaaggcca cactggtatg cctggccaca ggcttctacc ccgaccacgt ggagctgagc 480
tggtgggtga atgggaagga ggtgcacagt ggggtcagca cagacccgca gcccctcaag 540
gagcagcccg ccctcaatga ctccagatac tgcctgagca gccgcctgag ggtgtcggcc 600
accttctggc agaacccccg caaccacttc cgctgtcaag tccagttcta cgggctctcg 660
gagaatgacg agtggaccca ggatagggcc aaacccgtca cccagatcgt cagcgccgag 720
gcctggggta gagcagactg tggcttcacc tccgagtctt accagcaagg ggtcctgtct 780
gccaccatcc tctatgagat cttgctaggg aaggccacct tgtatgccgt gctggtcagt 840
gccctcgtgc tgatggccat ggtcaagaga aaggattcca gaggctag 888

<210> SEQ ID NO 526
<211> LENGTH: 888
<212> TYPE: DNA
<213> ORGANISM: Homo sapiens
<220> FEATURE:
<223> OTHER INFORMATION: V-C entry TRBV25-1_TRBC2

<400> SEQUENCE: 526
gccaccatga ctatcaggct cctctgctac atgggctttt attttctggg ggcaggcctc 60
atggaagctg acatctacca gaccccaaga taccttgtta tagggacagg aaagaagatc 120
actctggaat gttctcaaac catgggccat gacaaaatgt actggtatca acaagatcca 180
ggaatggaac tacacctcat ccactattcc tatggagtta attccacaga gaagggagat 240
ctttcctctg agtcaacagt ctccagaata aggacggagc attttcccct gaccctggag 300
tctgccaggc cctcacatac ctctcagtac ctttgcagag accttgcggc cgcataggtc 360
tcagtgttcc cacccgaggt cgctgtgttt gagccatcag aagcagagat ctcccacacc 420
caaaaggcca cactggtatg cctggccaca ggcttctacc ccgaccacgt ggagctgagc 480
tggtgggtga atgggaagga ggtgcacagt ggggtcagca cagacccgca gcccctcaag 540
gagcagcccg ccctcaatga ctccagatac tgcctgagca gccgcctgag ggtgtcggcc 600
accttctggc agaacccccg caaccacttc cgctgtcaag tccagttcta cgggctctcg 660
gagaatgacg agtggaccca ggatagggcc aaacccgtca cccagatcgt cagcgccgag 720
gcctggggta gagcagactg tggcttcacc tccgagtctt accagcaagg ggtcctgtct 780
gccaccatcc tctatgagat cttgctaggg aaggccacct tgtatgccgt gctggtcagt 840
gccctcgtgc tgatggccat ggtcaagaga aaggattcca gaggctag 888

<210> SEQ ID NO 527
<211> LENGTH: 888
<212> TYPE: DNA
<213> ORGANISM: Homo sapiens
<220> FEATURE:
<223> OTHER INFORMATION: V-C entry TRBV27_TRBC2

<400> SEQUENCE: 527
gccaccatgg gcccccagct ccttggctat gtggtccttt gccttctagg agcaggcccc 60
ctggaagccc aagtgaccca gaacccaaga tacctcatca cagtgactgg aaagaagtta 120
acagtgactt gttctcagaa tatgaaccat gagtatatgt cctggtatcg acaagaccca 180
gggctgggct taaggcagat ctactattca atgaatgttg aggtgactga taagggagat 240
gttcctgaag ggtacaaagt ctctcgaaaa gagaagagga atttcccccct gatcctggag 300 tcgcccagcc ccaaccagac ctctctgtac ttttgcagag accttgcggc cgcataggtc 360
tcagtgttcc cacccgaggt cgctgtgttt gagccatcag aagcagagat ctcccacacc 420
caaaaggcca cactggtatg cctggccaca ggcttctacc ccgaccacgt ggagctgagc 480
tggtgggtga atgggaagga ggtgcacagt ggggtcagca cagacccgca gcccctcaag 540
gagcagcccg ccctcaatga ctccagatac tgcctgagca gccgcctgag ggtgtcggcc 600
accttctggc agaacccccg caaccacttc cgctgtcaag tccagttcta cgggctctcg 660
gagaatgacg agtggaccca ggatagggcc aaacccgtca cccagatcgt cagcgccgag 720
gcctggggta gagcagactg tggcttcacc tccgagtctt accagcaagg ggtcctgtct 780
gccaccatcc tctatgagat cttgctaggg aaggccacct tgtatgccgt gctggtcagt 840
gccctcgtgc tgatggccat ggtcaagaga aaggattcca gaggctag 888

<210> SEQ ID NO 528
<211> LENGTH: 888
<212> TYPE: DNA
<213> ORGANISM: Homo sapiens
<220> FEATURE:
<223> OTHER INFORMATION: V-C entry TRBV28_TRBC2

<400> SEQUENCE: 528
gccaccatgg gaatcaggct cctctgtcgt gtggcctttt gtttcctggc tgtaggcctc 60
gtagatgtga aagtaaccca gagctcgaga tatctagtca aaaggacggg agagaaagtt 120
tttctggaat gtgtccagga tatggaccat gaaaatatgt tctggtatcg acaagaccca 180
ggtctggggc tacggctgat ctatttctca tatgatgtta aaatgaaaga aaaaggagat 240
attcctgagg ggtacagtgt ctctagagag aagaaggagc gcttctccct gattctggag 300
tccgccagca ccaaccagac atctatgtac ctttgcagag accttgcggc cgcataggtc 360
tcagtgttcc cacccgaggt cgctgtgttt gagccatcag aagcagagat ctcccacacc 420
caaaaggcca cactggtatg cctggccaca ggcttctacc ccgaccacgt ggagctgagc 480
tggtgggtga atgggaagga ggtgcacagt ggggtcagca cagacccgca gcccctcaag 540
gagcagcccg ccctcaatga ctccagatac tgcctgagca gccgcctgag ggtgtcggcc 600
accttctggc agaacccccg caaccacttc cgctgtcaag tccagttcta cgggctctcg 660
gagaatgacg agtggaccca ggatagggcc aaacccgtca cccagatcgt cagcgccgag 720
gcctggggta gagcagactg tggcttcacc tccgagtctt accagcaagg ggtcctgtct 780
gccaccatcc tctatgagat cttgctaggg aaggccacct tgtatgccgt gctggtcagt 840
gccctcgtgc tgatggccat ggtcaagaga aaggattcca gaggctag 888

<210> SEQ ID NO 529
<211> LENGTH: 882
<212> TYPE: DNA
<213> ORGANISM: Homo sapiens
<220> FEATURE:
<223> OTHER INFORMATION: V-C entry TRBV29-1_TRBC2

<400> SEQUENCE: 529
gccaccatgc tgagtctact gctccttctc ctgggactag gctctgtgtt cagtgctgtc 60
atctctcaaa agccaagcag ggatatctgt caacgtggaa cctccctgac gatccagtgt 120
caagtcgata gccaagtcac catgatgttc tggtaccgtc agcaacctgg acagagcctg 180
acactgatcg caactgcaaa tcagggctct gaggccacat atgagagtgg atttgtcatt 240
gacaagtttc ccatcagccg cccaaaccta acattctcaa ctctgactgt gagcaacatg 300
agccctgaag atagcagcat atatctttgc agagaccttg cggccgcata ggtctcagtg 360
ttcccacccg aggtcgctgt gtttgagcca tcagaagcag agatctccca cacccaaaag 420
gccacactgg tatgcctggc cacaggcttc taccccgacc acgtggagct gagctggtgg 480
gtgaatggga aggaggtgca cagtggggtc agcacagacc cgcagcccct caaggagcag 540
cccgccctca atgactccag atactgcctg agcagccgcc tgagggtgtc ggccaccttc 600
tggcagaacc cccgcaacca cttccgctgt caagtccagt tctacgggct ctcggagaat 660
gacgagtgga cccaggatag ggccaaaccc gtcacccaga tcgtcagcgc cgaggcctgg 720
ggtagagcag actgtggctt cacctccgag tcttaccagc aaggggtcct gtctgccacc 780
atcctctatg agatcttgct agggaaggcc accttgtatg ccgtgctggt cagtgccctc 840
gtgctgatgg ccatggtcaa gagaaaggat tccagaggct ag 882

<210> SEQ ID NO 530
<211> LENGTH: 882
<212> TYPE: DNA
<213> ORGANISM: Homo sapiens
<220> FEATURE:
<223> OTHER INFORMATION: V-C entry TRBV30_TRBC2

<400> SEQUENCE: 530
gccaccatgc tctgctctct ccttgccctt ctcctgggca ctttctttgg ggtcagatct 60
cagactattc atcaatggcc agcgaccctg gtgcagcctg tgggcagccc gctctctctg 120
gagtgcactg tggagggaac atcaaacccc aacctatact ggtaccgaca ggctgcaggc 180
aggggcctcc agctgctctt ctactccgtt ggtattggcc agatcagctc tgaggtgccc 240
cagaatctct cagcctccag accccaggac cggcagttca tcctgagttc taagaagctc 300
cttctcagtg actctggctt ctatctttgc agagaccttg cggccgcata ggtctcagtg 360
ttcccacccg aggtcgctgt gtttgagcca tcagaagcag agatctccca cacccaaaag 420
gccacactgg tatgcctggc cacaggcttc taccccgacc acgtggagct gagctggtgg 480
gtgaatggga aggaggtgca cagtggggtc agcacagacc cgcagcccct caaggagcag 540
cccgccctca atgactccag atactgcctg agcagccgcc tgagggtgtc ggccaccttc 600
tggcagaacc cccgcaacca cttccgctgt caagtccagt tctacgggct ctcggagaat 660
gacgagtgga cccaggatag ggccaaaccc gtcacccaga tcgtcagcgc cgaggcctgg 720
ggtagagcag actgtggctt cacctccgag tcttaccagc aaggggtcct gtctgccacc 780

```
atcctctatg agatcttgct agggaaggcc accttgtatg ccgtgctggt cagtgccctc    840

gtgctgatgg ccatggtcaa gagaaaggat tccagaggct ag                       882


<210> SEQ ID NO 531
<211> LENGTH: 885
<212> TYPE: DNA
<213> ORGANISM: Homo sapiens
<220> FEATURE:
<223> OTHER INFORMATION: V-C entry TRBV2_TRBC1

<400> SEQUENCE: 531

gccaccatgg atacctggct cgtatgctgg gcaatttta gtctcttgaa agcaggactc     60

acagaacctg aagtcaccca gactcccagc catcaggtca cacagatggg acaggaagtg    120

atcttgcgct gtgtccccat ctctaatcac ttatacttct attggtacag acaaatcttg    180

gggcagaaag tcgagtttct ggtttccttt tataataatg aaatctcaga gaagtctgaa    240

atattcgatg atcaattctc agttgaaagg cctgatggat caaatttcac tctgaagatc    300

cggtccacaa agctggagga ctcagccatg tacttttgca gagaccttgc ggccgcatag    360

gtctcagtgt tcccacccga ggtcgctgtg tttgagccat cagaagcaga gatctcccac    420

acccaaaagg ccacactggt gtgcctggcc acaggcttct tccccgacca cgtggagctg    480

agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttt acctcggtgt cctaccagca aggggtcctg    780

tctgccacca tcctctatga gatcctgcta gggaaggcca ccctgtatgc tgtgctggtc    840

agcgcccttg tgttgatggc catggtcaag agaaaggatt tctga                    885


<210> SEQ ID NO 532
<211> LENGTH: 882
<212> TYPE: DNA
<213> ORGANISM: Homo sapiens
<220> FEATURE:
<223> OTHER INFORMATION: V-C entry TRBV3-1_TRBC1

<400> SEQUENCE: 532

gccaccatgg gctgcaggct cctctgctgt gtggtctttt gcctcctcca agcaggtccc     60

ttggacacag ctgtttccca gactccaaaa tacctggtca cacagatggg aaacgacaag    120

tccattaaat gtgaacaaaa tctgggccat gatactatgt attggtataa acaggactct    180

aagaaatttc tgaagataat gtttagctac aataataagg agctcattat aaatgaaaca    240

gttccaaatc gcttctcacc taaatctcca gacaaagctc acttaaatct tcacatcaat    300

tccctggagc ttggtgactc tgctgtgtat ttttgcagag accttgcggc cgcataggtc    360

tcagtgttcc cacccgaggt cgctgtgttt gagccatcag aagcagagat ctcccacacc    420

caaaaggcca cactggtgtg cctggccaca ggcttcttcc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggctttacc tcggtgtcct accagcaagg ggtcctgtct    780
```

gccaccatcc tctatgagat cctgctaggg aaggccaccc tgtatgctgt gctggtcagc 840
gcccttgtgt tgatggccat ggtcaagaga aaggatttct ga 882

<210> SEQ ID NO 533
<211> LENGTH: 882
<212> TYPE: DNA
<213> ORGANISM: Homo sapiens
<220> FEATURE:
<223> OTHER INFORMATION: V-C entry TRBV4-1_TRBC1

<400> SEQUENCE: 533
gccaccatgg gctgcaggct gctctgctgt gcggttctct gtctcctggg agcagttccc 60
atagacactg aagttaccca gacaccaaaa cacctggtca tgggaatgac aaataagaag 120
tctttgaaat gtgaacaaca tatggggcac agggctatgt attggtacaa gcagaaagct 180
aagaagccac cggagctcat gtttgtctac agctatgaga aactctctat aaatgaaagt 240
gtgccaagtc gcttctcacc tgaatgcccc aacagctctc tcttaaacct tcacctacac 300
gccctgcagc cagaagattc agccctgtat ctttgcagag accttgcggc cgcataggtc 360
tcagtgttcc cacccgaggt cgctgtgttt gagccatcag aagcagagat ctcccacacc 420
caaaaggcca cactggtgtg cctggccaca ggcttcttcc ccgaccacgt ggagctgagc 480
tggtgggtga atgggaagga ggtgcacagt ggggtcagca cagacccgca gcccctcaag 540
gagcagcccg ccctcaatga ctccagatac tgcctgagca gccgcctgag ggtgtcggcc 600
accttctggc agaacccccg caaccacttc cgctgtcaag tccagttcta cgggctctcg 660
gagaatgacg agtggaccca ggatagggcc aaacccgtca cccagatcgt cagcgccgag 720
gcctggggta gagcagactg tggctttacc tcggtgtcct accagcaagg ggtcctgtct 780
gccaccatcc tctatgagat cctgctaggg aaggccaccc tgtatgctgt gctggtcagc 840
gcccttgtgt tgatggccat ggtcaagaga aaggatttct ga 882

<210> SEQ ID NO 534
<211> LENGTH: 882
<212> TYPE: DNA
<213> ORGANISM: Homo sapiens
<220> FEATURE:
<223> OTHER INFORMATION: V-C entry TRBV4-2_TRBC1

<400> SEQUENCE: 534
gccaccatgg gctgcaggct gctctgctgt gcggttctct gtctcctggg agcggtcccc 60
atggaaacgg gagttacgca gacaccaaga cacctggtca tgggaatgac aaataagaag 120
tctttgaaat gtgaacaaca tctggggcat aacgctatgt attggtacaa gcaaagtgct 180
aagaagccac tggagctcat gtttgtctac aactttaaag aacagactga aaacaacagt 240
gtgccaagtc gcttctcacc tgaatgcccc aacagctctc acttattcct tcacctacac 300
accctgcagc cagaagattc ggccctgtat ctttgcagag accttgcggc cgcataggtc 360
tcagtgttcc cacccgaggt cgctgtgttt gagccatcag aagcagagat ctcccacacc 420
caaaaggcca cactggtgtg cctggccaca ggcttcttcc ccgaccacgt ggagctgagc 480
tggtgggtga atgggaagga ggtgcacagt ggggtcagca cagacccgca gcccctcaag 540
gagcagcccg ccctcaatga ctccagatac tgcctgagca gccgcctgag ggtgtcggcc 600
accttctggc agaacccccg caaccacttc cgctgtcaag tccagttcta cgggctctcg 660
gagaatgacg agtggaccca ggatagggcc aaacccgtca cccagatcgt cagcgccgag 720
gcctggggta gagcagactg tggctttacc tcggtgtcct accagcaagg ggtcctgtct 780
gccaccatcc tctatgagat cctgctaggg aaggccaccc tgtatgctgt gctggtcagc 840
gcccttgtgt tgatggccat ggtcaagaga aaggatttct ga 882

<210> SEQ ID NO 535
<211> LENGTH: 882
<212> TYPE: DNA
<213> ORGANISM: Homo sapiens
<220> FEATURE:
<223> OTHER INFORMATION: V-C entry TRBV4-3_TRBC1

<400> SEQUENCE: 535
gccaccatgg gctgcaggct gctctgctgt gcggttctct gtctcctggg agcggtcccc 60
atggaaacgg gagttacgca gacaccaaga cacctggtca tgggaatgac aaataagaag 120
tctttgaaat gtgaacaaca tctgggtcat aacgctatgt attggtacaa gcaaagtgct 180
aagaagccac tggagctcat gtttgtctac agtcttgaag aacgggttga aaacaacagt 240
gtgccaagtc gcttctcacc tgaatgcccc aacagctctc acttattcct tcacctacac 300
accctgcagc cagaagattc ggccctgtat ctttgcagag accttgcggc cgcataggtc 360
tcagtgttcc cacccgaggt cgctgtgttt gagccatcag aagcagagat ctcccacacc 420
caaaaggcca cactggtgtg cctggccaca ggcttcttcc ccgaccacgt ggagctgagc 480
tggtgggtga atgggaagga ggtgcacagt ggggtcagca cagacccgca gcccctcaag 540
gagcagcccg ccctcaatga ctccagatac tgcctgagca gccgcctgag ggtgtcggcc 600
accttctggc agaacccccg caaccacttc cgctgtcaag tccagttcta cgggctctcg 660
gagaatgacg agtggaccca ggatagggcc aaacccgtca cccagatcgt cagcgccgag 720
gcctggggta gagcagactg tggctttacc tcggtgtcct accagcaagg ggtcctgtct 780
gccaccatcc tctatgagat cctgctaggg aaggccaccc tgtatgctgt gctggtcagc 840
gcccttgtgt tgatggccat ggtcaagaga aaggatttct ga 882

<210> SEQ ID NO 536
<211> LENGTH: 882
<212> TYPE: DNA
<213> ORGANISM: Homo sapiens
<220> FEATURE:
<223> OTHER INFORMATION: V-C entry TRBV5-1_TRBC1

<400> SEQUENCE: 536
gccaccatgg gctccaggct gctctgttgg gtgctgcttt gtctcctggg agcaggccca 60
gtaaaggctg gagtcactca aactccaaga tatctgatca aaacgagagg acagcaagtg 120
acactgagct gctcccctat ctctgggcat aggagtgtat cctggtacca acagacccca 180
ggacagggcc ttcagttcct ctttgaatac ttcagtgaga cacagagaaa caaaggaaac 240
ttccctggtc gattctcagg gcgccagttc tctaactctc gctctgagat gaatgtgagc 300
accttggagc tgggggactc ggccctttat ctttgcagag accttgcggc cgcataggtc 360
tcagtgttcc cacccgaggt cgctgtgttt gagccatcag aagcagagat ctcccacacc 420
caaaaggcca cactggtgtg cctggccaca ggcttcttcc ccgaccacgt ggagctgagc 480
tggtgggtga atgggaagga ggtgcacagt ggggtcagca cagacccgca gcccctcaag 540
gagcagcccg ccctcaatga ctccagatac tgcctgagca gccgcctgag ggtgtcggcc 600
accttctggc agaacccccg caaccacttc cgctgtcaag tccagttcta cgggctctcg 660
gagaatgacg agtggaccca ggatagggcc aaacccgtca cccagatcgt cagcgccgag 720

```
gcctggggta gagcagactg tggctttacc tcggtgtcct accagcaagg ggtcctgtct    780

gccaccatcc tctatgagat cctgctaggg aaggccaccc tgtatgctgt gctggtcagc    840

gcccttgtgt tgatggccat ggtcaagaga aaggatttct ga                       882


<210> SEQ ID NO 537
<211> LENGTH: 882
<212> TYPE: DNA
<213> ORGANISM: Homo sapiens
<220> FEATURE:
<223> OTHER INFORMATION: V-C entry TRBV5-4_TRBC1

<400> SEQUENCE: 537

gccaccatgg gccctgggct cctctgctgg gtgctgcttt gtctcctggg agcaggctca     60

gtggagactg gagtcaccca aagtcccaca cacctgatca aaacgagagg acagcaagtg    120

actctgagat gctcttctca gtctgggcac aacactgtgt cctggtacca acaggccctg    180

ggtcaggggc cccagtttat ctttcagtat tatagggagg aagagaatgg cagaggaaac    240

ttccctccta gattctcagg actccagttc cctaattata gctctgagct gaatgtgaac    300

gccttggagc tggacgactc ggccctgtat ctttgcagag accttgcggc cgcataggtc    360

tcagtgttcc cacccgaggt cgctgtgttt gagccatcag aagcagagat ctcccacacc    420

caaaaggcca cactggtgtg cctggccaca ggcttcttcc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggctttacc tcggtgtcct accagcaagg ggtcctgtct    780

gccaccatcc tctatgagat cctgctaggg aaggccaccc tgtatgctgt gctggtcagc    840

gcccttgtgt tgatggccat ggtcaagaga aaggatttct ga                       882


<210> SEQ ID NO 538
<211> LENGTH: 882
<212> TYPE: DNA
<213> ORGANISM: Homo sapiens
<220> FEATURE:
<223> OTHER INFORMATION: V-C entry TRBV5-5_TRBC1

<400> SEQUENCE: 538

gccaccatgg gccctgggct cctctgctgg gtgctgcttt gtctcctggg agcaggccca     60

gtggacgctg gagtcaccca aagtcccaca cacctgatca aaacgagagg acagcaagtg    120

actctgagat gctctcctat ctctgggcac aagagtgtgt cctggtacca acaggtcctg    180

ggtcaggggc cccagtttat ctttcagtat tatgagaaag aagagagagg aagaggaaac    240

ttccctgatc gattctcagc tcgccagttc cctaactata gctctgagct gaatgtgaac    300

gccttgttgc tgggggactc ggccctgtat ctttgcagag accttgcggc cgcataggtc    360

tcagtgttcc cacccgaggt cgctgtgttt gagccatcag aagcagagat ctcccacacc    420

caaaaggcca cactggtgtg cctggccaca ggcttcttcc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660
```

```
gagaatgacg agtggaccca ggatagggcc aaacccgtca cccagatcgt cagcgccgag    720

gcctggggta gagcagactg tggctttacc tcggtgtcct accagcaagg ggtcctgtct    780

gccaccatcc tctatgagat cctgctaggg aaggccaccc tgtatgctgt gctggtcagc    840

gcccttgtgt tgatggccat ggtcaagaga aaggatttct ga                       882
```

<210> SEQ ID NO 539
<211> LENGTH: 882
<212> TYPE: DNA
<213> ORGANISM: Homo sapiens
<220> FEATURE:
<223> OTHER INFORMATION: V-C entry TRBV5-6_TRBC1

<400> SEQUENCE: 539

```
gccaccatgg gccccgggct cctctgctgg gcactgcttt gtctcctggg agcaggctta     60

gtggacgctg gagtcaccca aagtcccaca cacctgatca aaacgagagg acagcaagtg    120

actctgagat gctctcctaa gtctgggcat gacactgtgt cctggtacca acaggccctg    180

ggtcaggggc cccagtttat ctttcagtat tatgaggagg aagagagaca gagaggcaac    240

ttccctgatc gattctcagg tcaccagttc cctaactata gctctgagct gaatgtgaac    300

gccttgttgc tgggggactc ggccctctat ctttgcagag accttgcggc cgcataggtc    360

tcagtgttcc cacccgaggt cgctgtgttt gagccatcag aagcagagat ctcccacacc    420

caaaaggcca cactggtgtg cctggccaca ggcttcttcc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggctttacc tcggtgtcct accagcaagg ggtcctgtct    780

gccaccatcc tctatgagat cctgctaggg aaggccaccc tgtatgctgt gctggtcagc    840

gcccttgtgt tgatggccat ggtcaagaga aaggatttct ga                       882
```

<210> SEQ ID NO 540
<211> LENGTH: 882
<212> TYPE: DNA
<213> ORGANISM: Homo sapiens
<220> FEATURE:
<223> OTHER INFORMATION: V-C entry TRBV5-7_TRBC1

<400> SEQUENCE: 540

```
gccaccatgg gccccgggct cctctgctgg gtgctgcttt gtcccctagg agaaggccca     60

gtggacgctg gagtcaccca aagtcccaca cacctgatca aaacgagagg acagcacgtg    120

actctgagat gctctcctat ctctgggcac accagtgtgt cctcgtacca acaggccctg    180

ggtcaggggc cccagtttat ctttcagtat tatgagaaag aagagagagg aagaggaaac    240

ttccctgatc aattctcagg tcaccagttc cctaactata gctctgagct gaatgtgaac    300

gccttgttgc taggggactc ggccctctat ctttgcagag accttgcggc cgcataggtc    360

tcagtgttcc cacccgaggt cgctgtgttt gagccatcag aagcagagat ctcccacacc    420

caaaaggcca cactggtgtg cctggccaca ggcttcttcc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660
```

gagaatgacg agtggaccca ggatagggcc aaacccgtca cccagatcgt cagcgccgag 720
gcctggggta gagcagactg tggctttacc tcggtgtcct accagcaagg ggtcctgtct 780
gccaccatcc tctatgagat cctgctaggg aaggccaccc tgtatgctgt gctggtcagc 840
gcccttgtgt tgatggccat ggtcaagaga aaggatttct ga 882

<210> SEQ ID NO 541
<211> LENGTH: 882
<212> TYPE: DNA
<213> ORGANISM: Homo sapiens
<220> FEATURE:
<223> OTHER INFORMATION: V-C entry TRBV5-8_TRBC1

<400> SEQUENCE: 541
gccaccatgg gacccaggct cctcttctgg gcactgcttt gtctcctcgg aacaggccca 60
gtggaggctg gagtcacaca aagtcccaca cacctgatca aaacgagagg acagcaagcg 120
actctgagat gctctcctat ctctgggcac accagtgtgt actggtacca acaggccctg 180
ggtctgggcc tccagttcct cctttggtat gacgagggtg aagagagaaa cagaggaaac 240
ttccctccta gattttcagg tcgccagttc cctaattata gctctgagct gaatgtgaac 300
gccttggagc tggaggactc ggccctgtat ctttgcagag accttgcggc cgcataggtc 360
tcagtgttcc cacccgaggt cgctgtgttt gagccatcag aagcagagat ctcccacacc 420
caaaaggcca cactggtgtg cctggccaca ggcttcttcc ccgaccacgt ggagctgagc 480
tggtgggtga atgggaagga ggtgcacagt ggggtcagca cagacccgca gcccctcaag 540
gagcagcccg ccctcaatga ctccagatac tgcctgagca gccgcctgag ggtgtcggcc 600
accttctggc agaacccccg caaccacttc cgctgtcaag tccagttcta cgggctctcg 660
gagaatgacg agtggaccca ggatagggcc aaacccgtca cccagatcgt cagcgccgag 720
gcctggggta gagcagactg tggctttacc tcggtgtcct accagcaagg ggtcctgtct 780
gccaccatcc tctatgagat cctgctaggg aaggccaccc tgtatgctgt gctggtcagc 840
gcccttgtgt tgatggccat ggtcaagaga aaggatttct ga 882

<210> SEQ ID NO 542
<211> LENGTH: 882
<212> TYPE: DNA
<213> ORGANISM: Homo sapiens
<220> FEATURE:
<223> OTHER INFORMATION: V-C entry TRBV6-1_TRBC1

<400> SEQUENCE: 542
gccaccatga gcatcgggct cctgtgctgt gtggcctttt ctctcctgtg ggcaagtcca 60
gtgaatgctg gtgtcactca gaccccaaaa ttccaggtcc tgaaaacagg acagagcatg 120
acactgcagt gtgcccagga tatgaaccat aactccatgt actggtatcg acaagaccca 180
ggcatgggac tgaggctgat ttattactca gcttctgagg gtaccactga caaaggagaa 240
gtccccaatg gctacaatgt ctccagatta aacaaacggg agttctcgct caggctggag 300
tcggctgctc cctcccagac atctgtgtac ttttgcagag accttgcggc cgcataggtc 360
tcagtgttcc cacccgaggt cgctgtgttt gagccatcag aagcagagat ctcccacacc 420
caaaaggcca cactggtgtg cctggccaca ggcttcttcc ccgaccacgt ggagctgagc 480
tggtgggtga atgggaagga ggtgcacagt ggggtcagca cagacccgca gcccctcaag 540
gagcagcccg ccctcaatga ctccagatac tgcctgagca gccgcctgag ggtgtcggcc 600
accttctggc agaacccccg caaccacttc cgctgtcaag tccagttcta cgggctctcg 660
gagaatgacg agtggaccca ggatagggcc aaacccgtca cccagatcgt cagcgccgag 720
gcctggggta gagcagactg tggctttacc tcggtgtcct accagcaagg ggtcctgtct 780
gccaccatcc tctatgagat cctgctaggg aaggccaccc tgtatgctgt gctggtcagc 840
gcccttgtgt tgatggccat ggtcaagaga aaggatttct ga 882

<210> SEQ ID NO 543
<211> LENGTH: 882
<212> TYPE: DNA
<213> ORGANISM: Homo sapiens
<220> FEATURE:
<223> OTHER INFORMATION: V-C entry TRBV6-3_TRBC1

<400> SEQUENCE: 543
gccaccatga gcctcgggct cctgtgctgt ggggtctttt ctctcctgtg ggcaggtcca 60
gtgaatgctg gtgtcactca gaccccaaaa ttccgggtcc tgaaaacagg acagagcatg 120
acactgctgt gtgcccagga tatgaaccat gaatacatgt actggtatcg acaagaccca 180
ggcatggggc tgaggctgat tcattactca gttggtgagg gtacaactgc caaaggagag 240
gtccctgatg gctacaatgt ctccagatta aaaaaacaga atttcctgct ggggttggag 300
tcggctgctc cctcccaaac atctgtgtac ttttgcagag accttgcggc cgcataggtc 360
tcagtgttcc cacccgaggt cgctgtgttt gagccatcag aagcagagat ctcccacacc 420
caaaaggcca cactggtgtg cctggccaca ggcttcttcc ccgaccacgt ggagctgagc 480
tggtgggtga atgggaagga ggtgcacagt ggggtcagca cagacccgca gcccctcaag 540
gagcagcccg ccctcaatga ctccagatac tgcctgagca gccgcctgag ggtgtcggcc 600
accttctggc agaacccccg caaccacttc cgctgtcaag tccagttcta cgggctctcg 660
gagaatgacg agtggaccca ggatagggcc aaacccgtca cccagatcgt cagcgccgag 720
gcctggggta gagcagactg tggctttacc tcggtgtcct accagcaagg ggtcctgtct 780
gccaccatcc tctatgagat cctgctaggg aaggccaccc tgtatgctgt gctggtcagc 840
gcccttgtgt tgatggccat ggtcaagaga aaggatttct ga 882

<210> SEQ ID NO 544
<211> LENGTH: 882
<212> TYPE: DNA
<213> ORGANISM: Homo sapiens
<220> FEATURE:
<223> OTHER INFORMATION: V-C entry TRBV6-4_TRBC1

<400> SEQUENCE: 544
gccaccatga gaatcaggct cctgtgctgt gtggcctttt ctctcctgtg ggcaggtcca 60
gtgattgctg ggatcaccca ggcaccaaca tctcagatcc tggcagcagg acggcgcatg 120
acactgagat gtacccagga tatgagacat aatgccatgt actggtatag acaagatcta 180
ggactggggc taaggctcat ccattattca aatactgcag gtaccactgg caaaggagaa 240
gtccctgatg gttatagtgt ctccagagca aacacagatg atttcccct cacgttggcg 300 tctgctgtac cctctcagac atctgtgtac ttttgcagag accttgcggc cgcataggtc 360
tcagtgttcc cacccgaggt cgctgtgttt gagccatcag aagcagagat ctcccacacc 420
caaaaggcca cactggtgtg cctggccaca ggcttcttcc ccgaccacgt ggagctgagc 480
tggtgggtga atgggaagga ggtgcacagt ggggtcagca cagacccgca gcccctcaag 540
gagcagcccg ccctcaatga ctccagatac tgcctgagca gccgcctgag ggtgtcggcc 600

```
accttctggc agaaccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggctttacc tcggtgtcct accagcaagg ggtcctgtct    780

gccaccatcc tctatgagat cctgctaggg aaggccaccc tgtatgctgt gctggtcagc    840

gcccttgtgt tgatggccat ggtcaagaga aaggatttct ga                       882
```

<210> SEQ ID NO 545
<211> LENGTH: 882
<212> TYPE: DNA
<213> ORGANISM: Homo sapiens
<220> FEATURE:
<223> OTHER INFORMATION: V-C entry TRBV6-5_TRBC1

<400> SEQUENCE: 545

```
gccaccatga gcatcggcct cctgtgctgt gcagccttgt ctctcctgtg ggcaggtcca     60

gtgaatgctg gtgtcactca gaccccaaaa ttccaggtcc tgaaaacagg acagagcatg    120

acactgcagt gtgcccagga tatgaaccat gaatacatgt cctggtatcg acaagaccca    180

ggcatggggc tgaggctgat tcattactca gttggtgctg gtatcactga ccaaggagaa    240

gtccccaatg gctacaatgt ctccagatca accacagagg atttcccgct caggctgctg    300

tcggctgctc cctcccagac atctgtgtac ttttgcagag accttgcggc cgcataggtc    360

tcagtgttcc cacccgaggt cgctgtgttt gagccatcag aagcagagat ctcccacacc    420

caaaaggcca cactggtgtg cctggccaca ggcttcttcc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaaccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggctttacc tcggtgtcct accagcaagg ggtcctgtct    780

gccaccatcc tctatgagat cctgctaggg aaggccaccc tgtatgctgt gctggtcagc    840

gcccttgtgt tgatggccat ggtcaagaga aaggatttct ga                       882
```

<210> SEQ ID NO 546
<211> LENGTH: 882
<212> TYPE: DNA
<213> ORGANISM: Homo sapiens
<220> FEATURE:
<223> OTHER INFORMATION: V-C entry TRBV6-6_TRBC1

<400> SEQUENCE: 546

```
gccaccatga gcatcagcct cctgtgctgt gcagcctttc ctctcctgtg ggcaggtcca     60

gtgaatgctg gtgtcactca gaccccaaaa ttccgcatcc tgaagatagg acagagcatg    120

acactgcagt gtacccagga tatgaaccat aactacatgt actggtatcg acaagaccca    180

ggcatggggc tgaagctgat ttattattca gttggtgctg gtatcactga taaaggagaa    240

gtcccgaatg gctacaacgt ctccagatca accacagagg atttcccgct caggctggag    300

ttggctgctc cctcccagac atctgtgtac ttttgcagag accttgcggc cgcataggtc    360

tcagtgttcc cacccgaggt cgctgtgttt gagccatcag aagcagagat ctcccacacc    420

caaaaggcca cactggtgtg cctggccaca ggcttcttcc ccgaccacgt ggagctgagc    480

tggtgggtga atgggaagga ggtgcacagt ggggtcagca cagacccgca gcccctcaag    540
```

gagcagcccg ccctcaatga ctccagatac tgcctgagca gccgcctgag ggtgtcggcc 600
accttctggc agaacccccg caaccacttc cgctgtcaag tccagttcta cgggctctcg 660
gagaatgacg agtggaccca ggatagggcc aaacccgtca cccagatcgt cagcgccgag 720
gcctggggta gagcagactg tggctttacc tcggtgtcct accagcaagg ggtcctgtct 780
gccaccatcc tctatgagat cctgctaggg aaggccaccc tgtatgctgt gctggtcagc 840
gcccttgtgt tgatggccat ggtcaagaga aaggatttct ga 882

<210> SEQ ID NO 547
<211> LENGTH: 879
<212> TYPE: DNA
<213> ORGANISM: Homo sapiens
<220> FEATURE:
<223> OTHER INFORMATION: V-C entry TRBV6-8_TRBC1

<400> SEQUENCE: 547
gccaccatga gcctcgggct cctgtgctgt gcggcctttt ctctcctgtg ggcaggtccc 60
gtgaatgctg gtgtcactca gaccccaaaa ttccacatcc tgaaaacagg acagagcatg 120
acactgcagt gtgcccagga tatgaaccat ggatacatgt cctggtatcg acaagaccca 180
ggcatggggc tgagactgat ttactactca gctgctgctg gtactactga caaagaagtc 240
cccaatggct acaatgtctc tagattaaac acagaggatt tcccactcag gctggtgtcg 300
gctgctccct cccagacatc tgtgtacctt tgcagagacc ttgcggccgc ataggtctca 360
gtgttcccac ccgaggtcgc tgtgtttgag ccatcagaag cagagatctc ccacacccaa 420
aaggccacac tggtgtgcct ggccacaggc ttcttccccg accacgtgga gctgagctgg 480
tgggtgaatg ggaaggaggt gcacagtggg gtcagcacag acccgcagcc cctcaaggag 540
cagcccgccc tcaatgactc cagatactgc ctgagcagcc gcctgagggt gtcggccacc 600
ttctggcaga acccccgcaa ccacttccgc tgtcaagtcc agttctacgg gctctcggag 660
aatgacgagt ggacccagga tagggccaaa cccgtcaccc agatcgtcag cgccgaggcc 720
tggggtagag cagactgtgg ctttacctcg gtgtcctacc agcaaggggt cctgtctgcc 780
accatcctct atgagatcct gctagggaag gccaccctgt atgctgtgct ggtcagcgcc 840
cttgtgttga tggccatggt caagagaaag gatttctga 879

<210> SEQ ID NO 548
<211> LENGTH: 882
<212> TYPE: DNA
<213> ORGANISM: Homo sapiens
<220> FEATURE:
<223> OTHER INFORMATION: V-C entry TRBV6-9_TRBC1

<400> SEQUENCE: 548
gccaccatga gcatcgggct cctgtgctgt gtggcctttt ctctcctgtg ggcaggtcca 60
gtgaatgctg gtgtcactca gaccccaaaa ttccacatcc tgaaaacagg acagagcatg 120
acactgcagt gtgcccagga tatgaaccat ggatacttgt cctggtatcg acaagaccca 180
ggcatggggc tgaggcgcat tcattactca gttgctgctg gtatcactga caaaggagaa 240
gtccccgatg gctacaatgt atccagatca aacacagagg atttcccgct caggctggag 300
tcagctgctc cctcccagac atctgtatac ttttgcagag accttgcggc cgcataggtc 360
tcagtgttcc cacccgaggt cgctgtgttt gagccatcag aagcagagat ctcccacacc 420
caaaaggcca cactggtgtg cctggccaca ggcttcttcc ccgaccacgt ggagctgagc 480
tggtgggtga atgggaagga ggtgcacagt ggggtcagca cagacccgca gcccctcaag 540

```
gagcagcccg ccctcaatga ctccagatac tgcctgagca gccgcctgag ggtgtcggcc    600
accttctggc agaacccccg caaccacttc cgctgtcaag tccagttcta cgggctctcg    660
gagaatgacg agtggaccca ggatagggcc aaacccgtca cccagatcgt cagcgccgag    720
gcctggggta gagcagactg tggctttacc tcggtgtcct accagcaagg ggtcctgtct    780
gccaccatcc tctatgagat cctgctaggg aaggccaccc tgtatgctgt gctggtcagc    840
gcccttgtgt tgatggccat ggtcaagaga aaggatttct ga                        882
```

<210> SEQ ID NO 549
<211> LENGTH: 885
<212> TYPE: DNA
<213> ORGANISM: Homo sapiens
<220> FEATURE:
<223> OTHER INFORMATION: V-C entry TRBV7-2_TRBC1

<400> SEQUENCE: 549

```
gccaccatgg gcaccaggct cctcttctgg gtggccttct gtctcctggg ggcagatcac     60
acaggagctg gagtctccca gtcccccagt aacaaggtca cagagaaggg aaaggatgta    120
gagctcaggt gtgatccaat ttcaggtcat actgcccttt actggtaccg acagagcctg    180
gggcagggcc tggagttttt aatttacttc caaggcaaca gtgcaccaga caaatcaggg    240
ctgcccagtg atcgcttctc tgcagagagg actgggggat ccgtctccac tctgacgatc    300
cagcgcacac agcaggagga ctcggccgtg tatctttgca gagaccttgc ggccgcatag    360
gtctcagtgt tcccacccga ggtcgctgtg tttgagccat cagaagcaga gatctcccac    420
acccaaaagg ccacactggt gtgcctggcc acaggcttct tccccgacca cgtggagctg    480
agctggtggg tgaatgggaa ggaggtgcac agtggggtca gcacagaccc gcagcccctc    540
aaggagcagc ccgccctcaa tgactccaga tactgcctga gcagccgcct gagggtgtcg    600
gccaccttct ggcagaaccc ccgcaaccac ttccgctgtc aagtccagtt ctacgggctc    660
tcggagaatg acgagtggac ccaggatagg gccaaacccg tcacccagat cgtcagcgcc    720
gaggcctggg gtagagcaga ctgtggcttt acctcggtgt cctaccagca aggggtcctg    780
tctgccacca tcctctatga gatcctgcta gggaaggcca ccctgtatgc tgtgctggtc    840
agcgcccttg tgttgatggc catggtcaag agaaaggatt tctga                     885
```

<210> SEQ ID NO 550
<211> LENGTH: 885
<212> TYPE: DNA
<213> ORGANISM: Homo sapiens
<220> FEATURE:
<223> OTHER INFORMATION: V-C entry TRBV7-3_TRBC1

<400> SEQUENCE: 550

```
gccaccatgg gcaccaggct cctctgctgg gcagccctgt gcctcctggg ggcagatcac     60
acaggtgctg gagtctccca gacccccagt aacaaggtca cagagaaggg aaaatatgta    120
gagctcaggt gtgatccaat ttcaggtcat actgcccttt actggtaccg acaaagcctg    180
gggcagggcc cagagtttct aatttacttc caaggcacgg gtgcggcaga tgactcaggg    240
ctgcccaacg atcggttctt tgcagtcagg cctgagggat ccgtctctac tctgaagatc    300
cagcgcacag agcgggggga ctcagccgtg tatctttgca gagaccttgc ggccgcatag    360
gtctcagtgt tcccacccga ggtcgctgtg tttgagccat cagaagcaga gatctcccac    420
acccaaaagg ccacactggt gtgcctggcc acaggcttct tccccgacca cgtggagctg    480
```

```
agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttt acctcggtgt cctaccagca aggggtcctg    780

tctgccacca tcctctatga gatcctgcta gggaaggcca ccctgtatgc tgtgctggtc    840

agcgcccttg tgttgatggc catggtcaag agaaaggatt tctga                    885
```

```
<210> SEQ ID NO 551
<211> LENGTH: 885
<212> TYPE: DNA
<213> ORGANISM: Homo sapiens
<220> FEATURE:
<223> OTHER INFORMATION: V-C entry TRBV7-6_TRBC1

<400> SEQUENCE: 551

gccaccatgg gcaccagtct cctatgctgg gtggtcctgg gtttcctagg gacagatcac     60

acaggtgctg gagtctccca gtctcccagg tacaaagtca caaagagggg acaggatgta    120

gctctcaggt gtgatccaat ttcgggtcat gtatcccttt attggtaccg acaggccctg    180

gggcagggcc cagagtttct gacttacttc aattatgaag cccaacaaga caaatcaggg    240

ctgcccaatg atcggttctc tgcagagagg cctgagggat ccatctccac tctgacgatc    300

cagcgcacag agcagcggga ctcggccatg tatcgttgca gagaccttgc ggccgcatag    360

gtctcagtgt tcccacccga ggtcgctgtg tttgagccat cagaagcaga gatctcccac    420

acccaaaagg ccacactggt gtgcctggcc acaggcttct tccccgacca cgtggagctg    480

agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttt acctcggtgt cctaccagca aggggtcctg    780

tctgccacca tcctctatga gatcctgcta gggaaggcca ccctgtatgc tgtgctggtc    840

agcgcccttg tgttgatggc catggtcaag agaaaggatt tctga                    885
```

```
<210> SEQ ID NO 552
<211> LENGTH: 885
<212> TYPE: DNA
<213> ORGANISM: Homo sapiens
<220> FEATURE:
<223> OTHER INFORMATION: V-C entry TRBV7-7_TRBC1

<400> SEQUENCE: 552

gccaccatgg gtaccagtct cctatgctgg gtggtcctgg gtttcctagg gacagatcac     60

acaggtgctg gagtctccca gtctcccagg tacaaagtca caaagagggg acaggatgta    120

actctcaggt gtgatccaat ttcgagtcat gcaacccttt attggtatca acaggccctg    180

gggcagggcc cagagtttct gacttacttc aattatgaag ctcaaccaga caaatcaggg    240

ctgcccagtg atcggttctc tgcagagagg cctgagggat ccatctccac tctgacgatt    300

cagcgcacag agcagcggga ctcagccatg tatcgttgca gagaccttgc ggccgcatag    360

gtctcagtgt tcccacccga ggtcgctgtg tttgagccat cagaagcaga gatctcccac    420

acccaaaagg ccacactggt gtgcctggcc acaggcttct tccccgacca cgtggagctg    480
```

agctggtggg tgaatgggaa ggaggtgcac agtggggtca gcacagaccc gcagcccctc 540
aaggagcagc ccgccctcaa tgactccaga tactgcctga gcagccgcct gagggtgtcg 600
gccaccttct ggcagaaccc ccgcaaccac ttccgctgtc aagtccagtt ctacgggctc 660
tcggagaatg acgagtggac ccaggatagg gccaaacccg tcacccagat cgtcagcgcc 720
gaggcctggg gtagagcaga ctgtggcttt acctcggtgt cctaccagca aggggtcctg 780
tctgccacca tcctctatga gatcctgcta gggaaggcca ccctgtatgc tgtgctggtc 840
agcgcccttg tgttgatggc catggtcaag agaaaggatt tctga 885

<210> SEQ ID NO 553
<211> LENGTH: 885
<212> TYPE: DNA
<213> ORGANISM: Homo sapiens
<220> FEATURE:
<223> OTHER INFORMATION: V-C entry TRBV7-8_TRBC1

<400> SEQUENCE: 553
gccaccatgg gcaccaggct cctctgctgg gtggtcctgg gtttcctagg gacagatcac 60
acaggtgctg gagtctccca gtcccctagg tacaaagtcg caaagagagg acaggatgta 120
gctctcaggt gtgatccaat ttcgggtcat gtatcccttt tttggtacca acaggccctg 180
gggcaggggc cagagtttct gacttatttc cagaatgaag ctcaactaga caaatcgggg 240
ctgcccagtg atcgcttctt tgcagaaagg cctgagggat ccgtctccac tctgaagatc 300
cagcgcacac agcaggagga ctccgccgtg tatctttgca gagaccttgc ggccgcatag 360
gtctcagtgt tcccacccga ggtcgctgtg tttgagccat cagaagcaga gatctcccac 420
acccaaaagg ccacactggt gtgcctggcc acaggcttct tccccgacca cgtggagctg 480
agctggtggg tgaatgggaa ggaggtgcac agtggggtca gcacagaccc gcagcccctc 540
aaggagcagc ccgccctcaa tgactccaga tactgcctga gcagccgcct gagggtgtcg 600
gccaccttct ggcagaaccc ccgcaaccac ttccgctgtc aagtccagtt ctacgggctc 660
tcggagaatg acgagtggac ccaggatagg gccaaacccg tcacccagat cgtcagcgcc 720
gaggcctggg gtagagcaga ctgtggcttt acctcggtgt cctaccagca aggggtcctg 780
tctgccacca tcctctatga gatcctgcta gggaaggcca ccctgtatgc tgtgctggtc 840
agcgcccttg tgttgatggc catggtcaag agaaaggatt tctga 885

<210> SEQ ID NO 554
<211> LENGTH: 885
<212> TYPE: DNA
<213> ORGANISM: Homo sapiens
<220> FEATURE:
<223> OTHER INFORMATION: V-C entry TRBV7-9_TRBC1

<400> SEQUENCE: 554
gccaccatgg gcaccagcct cctctgctgg atggccctgt gtctcctggg ggcagatcac 60
gcagatactg gagtctccca gaaccccaga cacaagatca caaagagggg acagaatgta 120
actttcaggt gtgatccaat ttctgaacac aaccgccttt attggtaccg acagaccctg 180
gggcagggcc cagagtttct gacttacttc cagaatgaag ctcaactaga aaaatcaagg 240
ctgctcagtg atcggttctc tgcagagagg cctaagggat ctttctccac cttggagatc 300
cagcgcacag agcaggggga ctcggccatg tatctttgca gagaccttgc ggccgcatag 360
gtctcagtgt tcccacccga ggtcgctgtg tttgagccat cagaagcaga gatctcccac 420

```
acccaaaagg ccacactggt gtgcctggcc acaggcttct tccccgacca cgtggagctg    480
agctggtggg tgaatgggaa ggaggtgcac agtggggtca gcacagaccc gcagcccctc    540
aaggagcagc ccgccctcaa tgactccaga tactgcctga gcagccgcct gagggtgtcg    600
gccaccttct ggcagaaccc ccgcaaccac ttccgctgtc aagtccagtt ctacgggctc    660
tcggagaatg acgagtggac ccaggatagg gccaaacccg tcacccagat cgtcagcgcc    720
gaggcctggg gtagagcaga ctgtggcttt acctcggtgt cctaccagca aggggtcctg    780
tctgccacca tcctctatga gatcctgcta gggaaggcca ccctgtatgc tgtgctggtc    840
agcgcccttg tgttgatggc catggtcaag agaaaggatt tctga                    885
```

<210> SEQ ID NO 555
<211> LENGTH: 882
<212> TYPE: DNA
<213> ORGANISM: Homo sapiens
<220> FEATURE:
<223> OTHER INFORMATION: V-C entry TRBV9_TRBC1

<400> SEQUENCE: 555

```
gccaccatgg gcttcaggct cctctgctgt gtggcctttt gtctcctggg agcaggccca     60
gtggattctg gagtcacaca aaccccaaag cacctgatca cagcaactgg acagcgagtg    120
acgctgagat gctcccctag gtctggtgac ctctctgtgt actggtacca acagagcctg    180
gaccagggcc tccagttcct cattcagtat tataatggag aagagagagc aaaaggaaac    240
attcttgaac gattctccgc acaacagttc cctgacttgc actctgaact aaacctgagc    300
tctctggagc tgggggactc agctttgtac ttttgcagag accttgcggc cgcataggtc    360
tcagtgttcc cacccgaggt cgctgtgttt gagccatcag aagcagagat ctcccacacc    420
caaaaggcca cactggtgtg cctggccaca ggcttcttcc ccgaccacgt ggagctgagc    480
tggtgggtga atgggaagga ggtgcacagt ggggtcagca cagacccgca gcccctcaag    540
gagcagcccg ccctcaatga ctccagatac tgcctgagca gccgcctgag ggtgtcggcc    600
accttctggc agaacccccg caaccacttc cgctgtcaag tccagttcta cgggctctcg    660
gagaatgacg agtggaccca ggatagggcc aaacccgtca cccagatcgt cagcgccgag    720
gcctggggta gagcagactg tggctttacc tcggtgtcct accagcaagg ggtcctgtct    780
gccaccatcc tctatgagat cctgctaggg aaggccaccc tgtatgctgt gctggtcagc    840
gcccttgtgt tgatggccat ggtcaagaga aaggatttct ga                       882
```

<210> SEQ ID NO 556
<211> LENGTH: 882
<212> TYPE: DNA
<213> ORGANISM: Homo sapiens
<220> FEATURE:
<223> OTHER INFORMATION: V-C entry TRBV10-1_TRBC1

<400> SEQUENCE: 556

```
gccaccatgg gcacgaggct cttcttctat gtggcccttt gtctgctgtg ggcaggacac     60
agggatgctg aaatcaccca gagcccaaga cacaagatca cagagacagg aaggcaggtg    120
accttggcgt gtcaccagac ttggaaccac aacaatatgt tctggtatcg acaagacctg    180
ggacatgggc tgaggctgat ccattactca tatggtgttc aagacactaa caaaggagaa    240
gtctcagatg gctacagtgt ctctagatca aacacagagg acctcccccct cactctggag    300
tctgctgcct cctcccagac atctgtatac ttttgcagag accttgcggc cgcataggtc    360
tcagtgttcc cacccgaggt cgctgtgttt gagccatcag aagcagagat ctcccacacc    420
```

```
caaaaggcca cactggtgtg cctggccaca ggcttcttcc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggctttacc tcggtgtcct accagcaagg ggtcctgtct    780

gccaccatcc tctatgagat cctgctaggg aaggccaccc tgtatgctgt gctggtcagc    840

gcccttgtgt tgatggccat ggtcaagaga aaggatttct ga                        882
```

<210> SEQ ID NO 557
<211> LENGTH: 882
<212> TYPE: DNA
<213> ORGANISM: Homo sapiens
<220> FEATURE:
<223> OTHER INFORMATION: V-C entry TRBV10-2_TRBC1

<400> SEQUENCE: 557

```
gccaccatgg gcaccaggct cttcttctat gtggcccttt gtctgctgtg ggcaggacac     60

agggatgctg gaatcaccca gagcccaaga tacaagatca cagagacagg aaggcaggtg    120

accttgatgt gtcaccagac ttggagccac agctatatgt tctggtatcg acaagacctg    180

ggacatgggc tgaggctgat ctattactca gcagctgctg atattacaga taaaggagaa    240

gtccccgatg gctatgttgt ctccagatcc aagacagaga atttccccct cactctggag    300

tcagctaccc gctcccagac atctgtgtac ttttgcagag accttgcggc cgcataggtc    360

tcagtgttcc cacccgaggt cgctgtgttt gagccatcag aagcagagat ctcccacacc    420

caaaaggcca cactggtgtg cctggccaca ggcttcttcc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggctttacc tcggtgtcct accagcaagg ggtcctgtct    780

gccaccatcc tctatgagat cctgctaggg aaggccaccc tgtatgctgt gctggtcagc    840

gcccttgtgt tgatggccat ggtcaagaga aaggatttct ga                        882
```

<210> SEQ ID NO 558
<211> LENGTH: 882
<212> TYPE: DNA
<213> ORGANISM: Homo sapiens
<220> FEATURE:
<223> OTHER INFORMATION: V-C entry TRBV10-3_TRBC1

<400> SEQUENCE: 558

```
gccaccatgg gcacaaggtt gttcttctat gtggcccttt gtctcctgtg gacaggacac     60

atggatgctg gaatcaccca gagcccaaga cacaaggtca cagagacagg aacaccagtg    120

actctgagat gtcaccagac tgagaaccac cgctatatgt actggtatcg acaagacccg    180

gggcatgggc tgaggctgat ccattactca tatggtgtta aagatactga caaaggagaa    240

gtctcagatg gctatagtgt ctctagatca aagacagagg atttcctcct cactctggag    300

tccgctacca gctcccagac atctgtgtac ttttgcagag accttgcggc cgcataggtc    360
```

```
tcagtgttcc cacccgaggt cgctgtgttt gagccatcag aagcagagat ctcccacacc    420

caaaaggcca cactggtgtg cctggccaca ggcttcttcc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggctttacc tcggtgtcct accagcaagg ggtcctgtct    780

gccaccatcc tctatgagat cctgctaggg aaggccaccc tgtatgctgt gctggtcagc    840

gcccttgtgt tgatggccat ggtcaagaga aaggatttct ga                       882
```

<210> SEQ ID NO 559
<211> LENGTH: 885
<212> TYPE: DNA
<213> ORGANISM: Homo sapiens
<220> FEATURE:
<223> OTHER INFORMATION: V-C entry TRBV11-1_TRBC1

<400> SEQUENCE: 559

```
gccaccatga gcaccaggct tctctgctgg atggccctct gtctcctggg ggcagaactc     60

tcagaagctg aagttgccca gtcccccaga tataagatta cagagaaaag ccaggctgtg    120

gctttttggt gtgatcctat ttctggccat gctacccttt actggtaccg gcagatcctg    180

ggacagggcc cggagcttct ggttcaattt caggatgaga gtgtagtaga tgattcacag    240

ttgcctaagg atcgattttc tgcagagagg ctcaaaggag tagactccac tctcaagatc    300

cagcctgcag agcttgggga ctcggccatg tatctttgca gagaccttgc ggccgcatag    360

gtctcagtgt tcccacccga ggtcgctgtg tttgagccat cagaagcaga gatctcccac    420

acccaaaagg ccacactggt gtgcctggcc acaggcttct tccccgacca cgtggagctg    480

agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttt acctcggtgt cctaccagca aggggtcctg    780

tctgccacca tcctctatga gatcctgcta gggaaggcca ccctgtatgc tgtgctggtc    840

agcgcccttg tgttgatggc catggtcaag agaaaggatt tctga                    885
```

<210> SEQ ID NO 560
<211> LENGTH: 885
<212> TYPE: DNA
<213> ORGANISM: Homo sapiens
<220> FEATURE:
<223> OTHER INFORMATION: V-C entry TRBV11-2_TRBC1

<400> SEQUENCE: 560

```
gccaccatgg gcaccaggct cctctgctgg gcggccctct gtctcctggg agcagaactc     60

acagaagctg gagttgccca gtctcccaga tataagatta tagagaaaag gcagagtgtg    120

gctttttggt gcaatcctat atctggccat gctacccttt actggtacca gcagatcctg    180

ggacagggcc caaagcttct gattcagttt cagaataacg gtgtagtgga tgattcacag    240

ttgcctaagg atcgattttc tgcagagagg ctcaaaggag tagactccac tctcaagatc    300

cagcctgcaa agcttgagga ctcggccgtg tatctttgca gagaccttgc ggccgcatag    360
```

```
gtctcagtgt tcccacccga ggtcgctgtg tttgagccat cagaagcaga gatctcccac    420

acccaaaagg ccacactggt gtgcctggcc acaggcttct tccccgacca cgtggagctg    480

agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttt acctcggtgt cctaccagca aggggtcctg    780

tctgccacca tcctctatga gatcctgcta gggaaggcca ccctgtatgc tgtgctggtc    840

agcgcccttg tgttgatggc catggtcaag agaaaggatt tctga                    885
```

<210> SEQ ID NO 561
<211> LENGTH: 885
<212> TYPE: DNA
<213> ORGANISM: Homo sapiens
<220> FEATURE:
<223> OTHER INFORMATION: V-C entry TRBV11-3_TRBC1

<400> SEQUENCE: 561

```
gccaccatgg gtaccaggct cctctgctgg gtggccttct gtctcctggt ggaagaactc     60

atagaagctg gagtggttca gtctcccaga tataagatta tagagaaaaa acagcctgtg    120

gctttttggt gcaatcctat ttctggccac aatacccttt actggtacct gcagaacttg    180

ggacagggcc cggagcttct gattcgatat gagaatgagg aagcagtaga cgattcacag    240

ttgcctaagg atcgattttc tgcagagagg ctcaaaggag tagactccac tctcaagatc    300

cagcctgcag agcttgggga ctcggccgtg tatctttgca gagaccttgc ggccgcatag    360

gtctcagtgt tcccacccga ggtcgctgtg tttgagccat cagaagcaga gatctcccac    420

acccaaaagg ccacactggt gtgcctggcc acaggcttct tccccgacca cgtggagctg    480

agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttt acctcggtgt cctaccagca aggggtcctg    780

tctgccacca tcctctatga gatcctgcta gggaaggcca ccctgtatgc tgtgctggtc    840

agcgcccttg tgttgatggc catggtcaag agaaaggatt tctga                    885
```

<210> SEQ ID NO 562
<211> LENGTH: 885
<212> TYPE: DNA
<213> ORGANISM: Homo sapiens
<220> FEATURE:
<223> OTHER INFORMATION: V-C entry TRBV12-3_TRBC1

<400> SEQUENCE: 562

```
gccaccatgg actcctggac cttctgctgt gtgtcccttt gcatcctggt agcgaagcat     60

acagatgctg gagttatcca gtcaccccgc catgaggtga cagagatggg acaagaagtg    120

actctgagat gtaaaccaat ttcaggccac aactcccttt tctggtacag acagaccatg    180

atgcggggac tggagttgct catttacttt aacaacaacg ttccgataga tgattcaggg    240

atgcccgagg atcgattctc agctaagatg cctaatgcat cattctccac tctgaagatc    300
```

```
cagccctcag aacccaggga ctcagctgtg tacttttgca gagaccttgc ggccgcatag    360

gtctcagtgt tcccacccga ggtcgctgtg tttgagccat cagaagcaga gatctcccac    420

acccaaaagg ccacactggt gtgcctggcc acaggcttct tccccgacca cgtggagctg    480

agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttt acctcggtgt cctaccagca aggggtcctg    780

tctgccacca tcctctatga gatcctgcta gggaaggcca ccctgtatgc tgtgctggtc    840

agcgcccttg tgttgatggc catggtcaag agaaaggatt tctga                    885
```

<210> SEQ ID NO 563
<211> LENGTH: 885
<212> TYPE: DNA
<213> ORGANISM: Homo sapiens
<220> FEATURE:
<223> OTHER INFORMATION: V-C entry TRBV12-4_TRBC1

<400> SEQUENCE: 563

```
gccaccatgg actcctggac cctctgctgt gtgtcccttt gcatcctggt agcaaagcac     60

acagatgctg gagttatcca gtcaccccgg cacgaggtga cagagatggg acaagaagtg    120

actctgagat gtaaaccaat ttcaggacac gactaccttt tctggtacag acagaccatg    180

atgcggggac tggagttgct catttacttt aacaacaacg ttccgataga tgattcaggg    240

atgcccgagg atcgattctc agctaagatg cctaatgcat cattctccac tctgaagatc    300

cagccctcag aacccaggga ctcagctgtg tacttttgca gagaccttgc ggccgcatag    360

gtctcagtgt tcccacccga ggtcgctgtg tttgagccat cagaagcaga gatctcccac    420

acccaaaagg ccacactggt gtgcctggcc acaggcttct tccccgacca cgtggagctg    480

agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttt acctcggtgt cctaccagca aggggtcctg    780

tctgccacca tcctctatga gatcctgcta gggaaggcca ccctgtatgc tgtgctggtc    840

agcgcccttg tgttgatggc catggtcaag agaaaggatt tctga                    885
```

<210> SEQ ID NO 564
<211> LENGTH: 885
<212> TYPE: DNA
<213> ORGANISM: Homo sapiens
<220> FEATURE:
<223> OTHER INFORMATION: V-C entry TRBV12-5_TRBC1

<400> SEQUENCE: 564

```
gccaccatgg ccaccaggct cctctgctgt gtggttcttt gtctcctggg agaagagctt     60

atagatgcta gagtcaccca gacaccaagg cacaaggtga cagagatggg acaagaagta    120

acaatgagat gtcagccaat tttaggccac aatactgttt tctggtacag acagaccatg    180

atgcaaggac tggagttgct ggcttacttc cgcaaccggg ctcctctaga tgattcgggg    240

atgccgaagg atcgattctc agcagagatg cctgatgcaa ctttagccac tctgaagatc    300
```

```
cagccctcag aacccaggga ctcagctgtg tacttttgca gagaccttgc ggccgcatag    360

gtctcagtgt tcccacccga ggtcgctgtg tttgagccat cagaagcaga gatctcccac    420

acccaaaagg ccacactggt gtgcctggcc acaggcttct tccccgacca cgtggagctg    480

agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttt acctcggtgt cctaccagca aggggtcctg    780

tctgccacca tcctctatga gatcctgcta gggaaggcca ccctgtatgc tgtgctggtc    840

agcgcccttg tgttgatggc catggtcaag agaaaggatt tctga                   885
```

<210> SEQ ID NO 565
<211> LENGTH: 912
<212> TYPE: DNA
<213> ORGANISM: Homo sapiens
<220> FEATURE:
<223> OTHER INFORMATION: V-C entry TRBV13_TRBC1

<400> SEQUENCE: 565

```
gccaccatgc ttagtcctga cctgcctgac tctgcctgga acaccaggct cctctgccat     60

gtcatgcttt gtctcctggg agcagtttca gtggctgctg gagtcatcca gtccccaaga    120

catctgatca aagaaaagag ggaaacagcc actctgaaat gctatcctat ccctagacac    180

gacactgtct actggtacca gcagggtcca ggtcaggacc cccagttcct catttcgttt    240

tatgaaaaga tgcagagcga taaaggaagc atccctgatc gattctcagc tcaacagttc    300

agtgactatc attctgaact gaacatgagc tccttggagc tgggggactc agccctgtac    360

ttttgcagag accttgcggc cgcataggtc tcagtgttcc cacccgaggt cgctgtgttt    420

gagccatcag aagcagagat ctcccacacc caaaaggcca cactggtgtg cctggccaca    480

ggcttcttcc ccgaccacgt ggagctgagc tggtgggtga atgggaagga ggtgcacagt    540

ggggtcagca cagacccgca gcccctcaag gagcagcccg ccctcaatga ctccagatac    600

tgcctgagca gccgcctgag ggtgtcggcc accttctggc agaacccccg caaccacttc    660

cgctgtcaag tccagttcta cgggctctcg gagaatgacg agtggaccca ggatagggcc    720

aaacccgtca cccagatcgt cagcgccgag gcctggggta gagcagactg tggctttacc    780

tcggtgtcct accagcaagg ggtcctgtct gccaccatcc tctatgagat cctgctaggg    840

aaggccaccc tgtatgctgt gctggtcagc gcccttgtgt tgatggccat ggtcaagaga    900

aaggatttct ga                                                       912
```

<210> SEQ ID NO 566
<211> LENGTH: 885
<212> TYPE: DNA
<213> ORGANISM: Homo sapiens
<220> FEATURE:
<223> OTHER INFORMATION: V-C entry TRBV14_TRBC1

<400> SEQUENCE: 566

```
gccaccatgg tttccaggct tctcagttta gtgtcccttt gtctcctggg agcaaagcac     60

atagaagctg gagttactca gttccccagc cacagcgtaa tagagaaggg ccagactgtg    120

actctgagat gtgacccaat ttctggacat gataatcttt attggtatcg acgtgttatg    180
```

```
ggaaaagaaa taaaatttct gttacatttt gtgaaagagt ctaaacagga tgagtccggt    240

atgcccaaca atcgattctt agctgaaagg actggaggga cgtattctac tctgaaggtg    300

cagcctgcag aactggagga ttctggagtt tacttttgca gagaccttgc ggccgcatag    360

gtctcagtgt tcccacccga ggtcgctgtg tttgagccat cagaagcaga gatctcccac    420

acccaaaagg ccacactggt gtgcctggcc acaggcttct tccccgacca cgtggagctg    480

agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttt acctcggtgt cctaccagca aggggtcctg    780

tctgccacca tcctctatga gatcctgcta gggaaggcca ccctgtatgc tgtgctggtc    840

agcgcccttg tgttgatggc catggtcaag agaaaggatt tctga                    885
```

<210> SEQ ID NO 567
<211> LENGTH: 882
<212> TYPE: DNA
<213> ORGANISM: Homo sapiens
<220> FEATURE:
<223> OTHER INFORMATION: V-C entry TRBV15_TRBC1

<400> SEQUENCE: 567

```
gccaccatgg gtcctgggct tctccactgg atggcccttt gtctccttgg aacaggtcat     60

ggggatgcca tggtcatcca gaacccaaga taccaggtta cccagtttgg aaagccagtg    120

accctgagtt gttctcagac tttgaaccat aacgtcatgt actggtacca gcagaagtca    180

agtcaggccc caaagctgct gttccactac tatgacaaag attttaacaa tgaagcagac    240

acccctgata acttccaatc caggaggccg aacacttctt tctgctttct tgacatccgc    300

tcaccaggcc tgggggacac agccatgtac ctttgcagag accttgcggc cgcataggtc    360

tcagtgttcc cacccgaggt cgctgtgttt gagccatcag aagcagagat ctcccacacc    420

caaaaggcca cactggtgtg cctggccaca ggcttcttcc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggctttacc tcggtgtcct accagcaagg ggtcctgtct    780

gccaccatcc tctatgagat cctgctaggg aaggccaccc tgtatgctgt gctggtcagc    840

gcccttgtgt tgatggccat ggtcaagaga aaggatttct ga                       882
```

<210> SEQ ID NO 568
<211> LENGTH: 885
<212> TYPE: DNA
<213> ORGANISM: Homo sapiens
<220> FEATURE:
<223> OTHER INFORMATION: V-C entry TRBV16_TRBC1

<400> SEQUENCE: 568

```
gccaccatga gcccaatatt cacctgcatc acaatccttt gtctgctggc tgcaggttct     60

cctggtgaag aagtcgccca gactccaaaa catcttgtca gaggggaagg acagaaagca    120

aaattatatt gtgccccaat aaaaggacac agttatgttt tttggtacca acaggtcctg    180
```

```
aaaaacgagt tcaagttctt gatttccttc cagaatgaaa atgtctttga tgaaacaggt    240

atgcccaagg aaagattttc agctaagtgc ctcccaaatt caccctgtag ccttgagatc    300

caggctacga agcttgagga ttcagcagtg tacttttgca gagaccttgc ggccgcatag    360

gtctcagtgt tcccacccga ggtcgctgtg tttgagccat cagaagcaga gatctcccac    420

acccaaaagg ccacactggt gtgcctggcc acaggcttct tccccgacca cgtggagctg    480

agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttt acctcggtgt cctaccagca aggggtcctg    780

tctgccacca tcctctatga gatcctgcta gggaaggcca ccctgtatgc tgtgctggtc    840

agcgcccttg tgttgatggc catggtcaag agaaaggatt tctga                    885
```

<210> SEQ ID NO 569
<211> LENGTH: 885
<212> TYPE: DNA
<213> ORGANISM: Homo sapiens
<220> FEATURE:
<223> OTHER INFORMATION: V-C entry TRBV18_TRBC1

<400> SEQUENCE: 569

```
gccaccatgg acaccagagt actctgctgt gcggtcatct gccttctggg ggcaggactc     60

tcaaatgccg gcgtcatgca gaacccaaga cacctggtca ggaggagggg acaggaggca    120

agactgagat gcagcccaat gaaaggacac agtcatgttt actggtatcg gcagctccca    180

gaggaaggtc tgaaattcat ggtttatctc cagaaagaaa atatcataga tgagtcagga    240

atgccaaagg aacgattttc tgctgaattt cccaaagagg gccccagcat cctgaggatc    300

cagcaggtag tgcgaggaga ttcggcagct tacttttgca gagaccttgc ggccgcatag    360

gtctcagtgt tcccacccga ggtcgctgtg tttgagccat cagaagcaga gatctcccac    420

acccaaaagg ccacactggt gtgcctggcc acaggcttct tccccgacca cgtggagctg    480

agctggtggg tgaatgggaa ggaggtgcac agtggggtca gcacagaccc gcagcccctc    540

aaggagcagc ccgccctcaa tgactccaga tactgcctga gcagccgcct gagggtgtcg    600

gccaccttct ggcagaaccc ccgcaaccac ttccgctgtc aagtccagtt ctacgggctc    660

tcggagaatg acgagtggac ccaggatagg gccaaacccg tcacccagat cgtcagcgcc    720

gaggcctggg gtagagcaga ctgtggcttt acctcggtgt cctaccagca aggggtcctg    780

tctgccacca tcctctatga gatcctgcta gggaaggcca ccctgtatgc tgtgctggtc    840

agcgcccttg tgttgatggc catggtcaag agaaaggatt tctga                    885
```

<210> SEQ ID NO 570
<211> LENGTH: 882
<212> TYPE: DNA
<213> ORGANISM: Homo sapiens
<220> FEATURE:
<223> OTHER INFORMATION: V-C entry TRBV19_TRBC1

<400> SEQUENCE: 570

```
gccaccatga gcaaccaggt gctctgctgt gtggtccttt gtttcctggg agcaaacacc     60

gtggatggtg gaatcactca gtccccaaag tacctgttca gaaaggaagg acagaatgtg    120
```

```
accctgagtt gtgaacagaa tttgaaccac gatgccatgt actggtaccg acaggaccca    180
gggcaagggc tgagattgat ctactactca cagatagtaa atgactttca gaaaggagat    240
atagctgaag ggtacagcgt ctctcgggag aagaaggaat cctttcctct cactgtgaca    300
tcggcccaaa agaacccgac agctttctat ctttgcagag accttgcggc cgcataggtc    360
tcagtgttcc cacccgaggt cgctgtgttt gagccatcag aagcagagat ctcccacacc    420
caaaaggcca cactggtgtg cctggccaca ggcttcttcc ccgaccacgt ggagctgagc    480
tggtgggtga atgggaagga ggtgcacagt ggggtcagca cagacccgca gcccctcaag    540
gagcagcccg ccctcaatga ctccagatac tgcctgagca gccgcctgag ggtgtcggcc    600
accttctggc agaacccccg caaccacttc cgctgtcaag tccagttcta cgggctctcg    660
gagaatgacg agtggaccca ggatagggcc aaacccgtca cccagatcgt cagcgccgag    720
gcctggggta gagcagactg tggctttacc tcggtgtcct accagcaagg ggtcctgtct    780
gccaccatcc tctatgagat cctgctaggg aaggccaccc tgtatgctgt gctggtcagc    840
gcccttgtgt tgatggccat ggtcaagaga aaggatttct ga                       882
```

<210> SEQ ID NO 571
<211> LENGTH: 876
<212> TYPE: DNA
<213> ORGANISM: Homo sapiens
<220> FEATURE:
<223> OTHER INFORMATION: V-C entry TRBV20-1_TRBC1

<400> SEQUENCE: 571

```
gccaccatgc tgctgcttct gctgcttctg ggccaggct ccgggcttgg tgctgtcgtc      60
tctcaacatc cgagctgggt tatctgtaag agtggaacct ctgtgaagat cgagtgccgt    120
tccctggact ttcaggccac aactatgttt tggtatcgtc agttcccgaa acagagtctc    180
atgctgatgg caacttccaa tgagggctcc aaggccacat acgagcaagg cgtcgagaag    240
gacaagtttc tcatcaacca tgcaagcctg accttgtcca ctctgacagt gaccagtgcc    300
catcctgaag atagcagctt ctacatttgc agagaccttg cggccgcata ggtctcagtg    360
ttcccacccg aggtcgctgt gtttgagcca tcagaagcag agatctccca cacccaaaag    420
gccacactgg tgtgcctggc cacaggcttc ttccccgacc acgtggagct gagctggtgg    480
gtgaatggga aggaggtgca cagtggggtc agcacagacc cgcagcccct caaggagcag    540
cccgccctca atgactccag atactgcctg agcagccgcc tgagggtgtc ggccaccttc    600
tggcagaacc cccgcaacca cttccgctgt caagtccagt tctacgggct ctcggagaat    660
gacgagtgga cccaggatag ggccaaaccc gtcacccaga tcgtcagcgc cgaggcctgg    720
ggtagagcag actgtggctt tacctcggtg tcctaccagc aaggggtcct gtctgccacc    780
atcctctatg agatcctgct agggaaggcc accctgtatg ctgtgctggt cagcgccctt    840
gtgttgatgg ccatggtcaa gagaaaggat ttctga                              876
```

<210> SEQ ID NO 572
<211> LENGTH: 882
<212> TYPE: DNA
<213> ORGANISM: Homo sapiens
<220> FEATURE:
<223> OTHER INFORMATION: V-C entry TRBV24-1_TRBC1

<400> SEQUENCE: 572

```
gccaccatgg cctccctgct cttcttctgt ggggcctttt atctcctggg aacagggtcc     60
atggatgctg atgttaccca gaccccaagg aataggatca caaagacagg aaagaggatt    120
```

```
atgctggaat gttctcagac taagggtcat gatagaatgt actggtatcg acaagaccca    180

ggactgggcc tacggttgat ctattactcc tttgatgtca aagatataaa caaaggagag    240

atctctgatg gatacagtgt ctctcgacag gcacaggcta aattctccct gtccctagag    300

tctgccatcc ccaaccagac agctctttac ttttgcagag accttgcggc cgcataggtc    360

tcagtgttcc cacccgaggt cgctgtgttt gagccatcag aagcagagat ctcccacacc    420

caaaaggcca cactggtgtg cctggccaca ggcttcttcc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggctttacc tcggtgtcct accagcaagg ggtcctgtct    780

gccaccatcc tctatgagat cctgctaggg aaggccaccc tgtatgctgt gctggtcagc    840

gcccttgtgt tgatggccat ggtcaagaga aaggatttct ga                        882
```

```
<210> SEQ ID NO 573
<211> LENGTH: 882
<212> TYPE: DNA
<213> ORGANISM: Homo sapiens
<220> FEATURE:
<223> OTHER INFORMATION: V-C entry TRBV25-1_TRBC1

<400> SEQUENCE: 573

gccaccatga ctatcaggct cctctgctac atgggctttt attttctggg ggcaggcctc     60

atggaagctg acatctacca gaccccaaga taccttgtta tagggacagg aaagaagatc    120

actctggaat gttctcaaac catgggccat gacaaaatgt actggtatca acaagatcca    180

ggaatggaac tacacctcat ccactattcc tatggagtta attccacaga gaagggagat    240

ctttcctctg agtcaacagt ctccagaata aggacggagc attttcccct gaccctggag    300

tctgccaggc cctcacatac ctctcagtac ctttgcagag accttgcggc cgcataggtc    360

tcagtgttcc cacccgaggt cgctgtgttt gagccatcag aagcagagat ctcccacacc    420

caaaaggcca cactggtgtg cctggccaca ggcttcttcc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggctttacc tcggtgtcct accagcaagg ggtcctgtct    780

gccaccatcc tctatgagat cctgctaggg aaggccaccc tgtatgctgt gctggtcagc    840

gcccttgtgt tgatggccat ggtcaagaga aaggatttct ga                        882
```

```
<210> SEQ ID NO 574
<211> LENGTH: 882
<212> TYPE: DNA
<213> ORGANISM: Homo sapiens
<220> FEATURE:
<223> OTHER INFORMATION: V-C entry TRBV27_TRBC1

<400> SEQUENCE: 574

gccaccatgg gcccccagct ccttggctat gtggtccttt gccttctagg agcaggcccc     60
```

```
ctggaagccc aagtgaccca gaacccaaga tacctcatca cagtgactgg aaagaagtta    120

acagtgactt gttctcagaa tatgaaccat gagtatatgt cctggtatcg acaagaccca    180

gggctgggct taaggcagat ctactattca atgaatgttg aggtgactga taagggagat    240

gttcctgaag ggtacaaagt ctctcgaaaa gagaagagga atttcccccct gatcctggag   300

tcgcccagcc ccaaccagac ctctctgtac ttttgcagag accttgcggc cgcataggtc    360

tcagtgttcc cacccgaggt cgctgtgttt gagccatcag aagcagagat ctcccacacc    420

caaaaggcca cactggtgtg cctggccaca ggcttcttcc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggctttacc tcggtgtcct accagcaagg ggtcctgtct    780

gccaccatcc tctatgagat cctgctaggg aaggccaccc tgtatgctgt gctggtcagc    840

gcccttgtgt tgatggccat ggtcaagaga aaggatttct ga                       882
```

<210> SEQ ID NO 575
<211> LENGTH: 882
<212> TYPE: DNA
<213> ORGANISM: Homo sapiens
<220> FEATURE:
<223> OTHER INFORMATION: V-C entry TRBV28_TRBC1

<400> SEQUENCE: 575

```
gccaccatgg gaatcaggct cctctgtcgt gtggcctttt gtttcctggc tgtaggcctc     60

gtagatgtga aagtaaccca gagctcgaga tatctagtca aaaggacggg agagaaagtt    120

tttctggaat gtgtccagga tatggaccat gaaaatatgt tctggtatcg acaagaccca    180

ggtctggggc tacggctgat ctatttctca tatgatgtta aaatgaaaga aaaaggagat    240

attcctgagg ggtacagtgt ctctagagag aagaaggagc gcttctccct gattctggag    300

tccgccagca ccaaccagac atctatgtac ctttgcagag accttgcggc cgcataggtc    360

tcagtgttcc cacccgaggt cgctgtgttt gagccatcag aagcagagat ctcccacacc    420

caaaaggcca cactggtgtg cctggccaca ggcttcttcc ccgaccacgt ggagctgagc    480

tggtgggtga atgggaagga ggtgcacagt ggggtcagca cagacccgca gcccctcaag    540

gagcagcccg ccctcaatga ctccagatac tgcctgagca gccgcctgag ggtgtcggcc    600

accttctggc agaacccccg caaccacttc cgctgtcaag tccagttcta cgggctctcg    660

gagaatgacg agtggaccca ggatagggcc aaacccgtca cccagatcgt cagcgccgag    720

gcctggggta gagcagactg tggctttacc tcggtgtcct accagcaagg ggtcctgtct    780

gccaccatcc tctatgagat cctgctaggg aaggccaccc tgtatgctgt gctggtcagc    840

gcccttgtgt tgatggccat ggtcaagaga aaggatttct ga                       882
```

<210> SEQ ID NO 576
<211> LENGTH: 876
<212> TYPE: DNA
<213> ORGANISM: Homo sapiens
<220> FEATURE:
<223> OTHER INFORMATION: V-C entry TRBV29-1_TRBC1

<400> SEQUENCE: 576

```
gccaccatgc tgagtctact gctccttctc ctgggactag gctctgtgtt cagtgctgtc     60
```

```
atctctcaaa agccaagcag ggatatctgt caacgtggaa cctccctgac gatccagtgt    120

caagtcgata gccaagtcac catgatgttc tggtaccgtc agcaacctgg acagagcctg    180

acactgatcg caactgcaaa tcagggctct gaggccacat atgagagtgg atttgtcatt    240

gacaagtttc ccatcagccg cccaaaccta acattctcaa ctctgactgt gagcaacatg    300

agccctgaag atagcagcat atatctttgc agagaccttg cggccgcata ggtctcagtg    360

ttcccacccg aggtcgctgt gtttgagcca tcagaagcag agatctccca cacccaaaag    420

gccacactgg tgtgcctggc cacaggcttc ttccccgacc acgtggagct gagctggtgg    480

gtgaatggga aggaggtgca cagtggggtc agcacagacc cgcagcccct caaggagcag    540

cccgccctca atgactccag atactgcctg agcagccgcc tgagggtgtc ggccaccttc    600

tggcagaacc cccgcaacca cttccgctgt caagtccagt tctacgggct ctcggagaat    660

gacgagtgga cccaggatag ggccaaaccc gtcacccaga tcgtcagcgc cgaggcctgg    720

ggtagagcag actgtggctt tacctcggtg tcctaccagc aaggggtcct gtctgccacc    780

atcctctatg agatcctgct agggaaggcc accctgtatg ctgtgctggt cagcgccctt    840

gtgttgatgg ccatggtcaa gagaaaggat ttctga                              876
```

```
<210> SEQ ID NO 577
<211> LENGTH: 876
<212> TYPE: DNA
<213> ORGANISM: Homo sapiens
<220> FEATURE:
<223> OTHER INFORMATION: V-C entry TRBV30_TRBC1

<400> SEQUENCE: 577

gccaccatgc tctgctctct ccttgccctt ctcctgggca ctttctttgg ggtcagatct     60

cagactattc atcaatggcc agcgaccctg gtgcagcctg tgggcagccc gctctctctg    120

gagtgcactg tggagggaac atcaaacccc aacctatact ggtaccgaca ggctgcaggc    180

aggggcctcc agctgctctt ctactccgtt ggtattggcc agatcagctc tgaggtgccc    240

cagaatctct cagcctccag accccaggac cggcagttca tcctgagttc taagaagctc    300

cttctcagtg actctggctt ctatctttgc agagaccttg cggccgcata ggtctcagtg    360

ttcccacccg aggtcgctgt gtttgagcca tcagaagcag agatctccca cacccaaaag    420

gccacactgg tgtgcctggc cacaggcttc ttccccgacc acgtggagct gagctggtgg    480

gtgaatggga aggaggtgca cagtggggtc agcacagacc cgcagcccct caaggagcag    540

cccgccctca atgactccag atactgcctg agcagccgcc tgagggtgtc ggccaccttc    600

tggcagaacc cccgcaacca cttccgctgt caagtccagt tctacgggct ctcggagaat    660

gacgagtgga cccaggatag ggccaaaccc gtcacccaga tcgtcagcgc cgaggcctgg    720

ggtagagcag actgtggctt tacctcggtg tcctaccagc aaggggtcct gtctgccacc    780

atcctctatg agatcctgct agggaaggcc accctgtatg ctgtgctggt cagcgccctt    840

gtgttgatgg ccatggtcaa gagaaaggat ttctga                              876

<210> SEQ ID NO 578
<211> LENGTH: 64
<212> TYPE: DNA
<213> ORGANISM: Artificial Sequence
<220> FEATURE:
<223> OTHER INFORMATION: TRBJ-C1_receiving_F1

<400> SEQUENCE: 578
```

aattcggtct cgaagtcttc tgcggccgct gaagacacag gacctgaaca aggtgttgag 60
accc 64

<210> SEQ ID NO 579
<211> LENGTH: 64
<212> TYPE: DNA
<213> ORGANISM: Artificial Sequence
<220> FEATURE:
<223> OTHER INFORMATION: TRBJ-C2_receiving_F1

<400> SEQUENCE: 579
aattcggtct cgaagtcttc tgcggccgct gaagacacag gacctgaaaa acgtgttgag 60
accc 64

<210> SEQ ID NO 580
<211> LENGTH: 64
<212> TYPE: DNA
<213> ORGANISM: Artificial Sequence
<220> FEATURE:
<223> OTHER INFORMATION: TRBJ-C1_receiving_R1

<400> SEQUENCE: 580
tcgagggtct caacaccttg ttcaggtcct gtgtcttcag cggccgcaga agacttcgag 60
accg 64

<210> SEQ ID NO 581
<211> LENGTH: 64
<212> TYPE: DNA
<213> ORGANISM: Artificial Sequence
<220> FEATURE:
<223> OTHER INFORMATION: TRBJ-C2_receiving_R1

<400> SEQUENCE: 581
tcgagggtct caacacgttt ttcaggtcct gtgtcttcag cggccgcaga agacttcgag 60
accg 64

<210> SEQ ID NO 582
<211> LENGTH: 2366
<212> TYPE: DNA
<213> ORGANISM: Artificial Sequence
<220> FEATURE:
<223> OTHER INFORMATION: TRB J_C1 receiving cassette vector

<400> SEQUENCE: 582
gccagggttt tcccagtcac gacgttgtaa aacgacggcc agtgagcgcg acgtaatacg 60
actcactata gggcgaattg gcggaaggcc gtcaaggccg catgaattcg gtctcgaagt 120
cttctgcggc cgctgaagac acaggacctg aacaaggtgt tgagaccctc gagctgggcc 180
tcatgggcct tccgctcact gcccgctttc cagtcgggaa acctgtcgtg ccagctgcat 240
taacatggtc atagctgttt ccttgcgtat tgggcgctct ccgcttcctc gctcactgac 300
tcgctgcgct cggtcgttcg ggtaaagcct ggggtgccta atgagcaaaa ggccagcaaa 360
aggccaggaa ccgtaaaaag gccgcgttgc tggcgttttt ccataggctc cgcccccctg 420
acgagcatca caaaaatcga cgctcaagtc agaggtggcg aaacccgaca ggactataaa 480
gataccaggc gtttccccct ggaagctccc tcgtgcgctc tcctgttccg accctgccgc 540
ttaccggata cctgtccgcc tttctccctt cgggaagcgt ggcgctttct catagctcac 600
gctgtaggta tctcagttcg gtgtaggtcg ttcgctccaa gctgggctgt gtgcacgaac 660
cccccgttca gcccgaccgc tgcgccttat ccggtaacta tcgtcttgag tccaacccgg 720

```
taagacacga cttatcgcca ctggcagcag ccactggtaa caggattagc agagcgaggt    780

atgtaggcgg tgctacagag ttcttgaagt ggtggcctaa ctacggctac actagaagaa    840

cagtatttgg tatctgcgct ctgctgaagc cagttacctt cggaaaaaga gttggtagct    900

cttgatccgg caaacaaacc accgctggta gcggtggttt ttttgtttgc aagcagcaga    960

ttacgcgcag aaaaaaagga tctcaagaag atcctttgat cttttctacg gggtctgacg   1020

ctcagtggaa cgaaaactca cgttaaggga ttttggtcat gagattatca aaaaggatct   1080

tcacctagat ccttttaaat taaaaatgaa gttttaaatc aatctaaagt atatatgagt   1140

aaacttggtc tgacagttag aaaaattcgt ccagcatcag atgaaattgc agtttgttca   1200

tgtccgggtt atcaatacca tatttctgga acagacgttt ctgcaggctc gggctaaatt   1260

cacccagaca attccacaga attgccagat cctgataacg atctgcaata ccaacacgac   1320

caacatcaat gcagccaatc agtttaccct catcaaaaat caggttatcc aggctaaaat   1380

caccatgggt aacaacgcta tccggactaa acggcagcag tttatgcatt tctttccaaa   1440

cctgttcaac aggccaacca ttacgttcat catcaaaatc gcttgcatca accagaccat   1500

tattcatacg gctctgtgcc tgtgccagac gaaaaacacg atcgctatta aacggacaat   1560

tacaaaccgg aatgctatgc agacgacgca gaaaaactgc cagtgcatca acaatatttt   1620

cgcctgaatc cggatattct tccagaacct gaaatgcggt tttacccgga attgcggtgg   1680

tcagcagcca tgcatcatcc ggtgtacgaa taaaatgttt aatggtcggc agcggcataa   1740

attcggtcag ccaattcaga cgaaccattt catcggtcac atcatttgca acgctacctt   1800

taccatgttt cagaaacagt tccggtgcat ccggtttacc atacagacga taaatggttg   1860

caccgctctg accaacatta tcacgtgccc atttatagcc atacagatct gcatccatat   1920

tgctattcag acgcggacgg ctacagctgg tttcacgctg aatatggctc atactcttcc   1980

tttttcaata ttattgaagc atttatcagg gttattgtct catgagcgga tacatatttg   2040

aatgtattta gaaaaataaa caaatagggg ttccgcgcac atttccccga aaagtgccac   2100

ctaaattgta agcgttaata ttttgttaaa attcgcgtta aatttttgtt aaatcagctc   2160

atttttttaac caataggccg aaatcggcaa aatcccttat aaatcaaaag aatagaccga   2220

gatagggttg agtggccgct acagggcgct cccattcgcc attcaggctg cgcaactgtt   2280

gggaagggcg tttcggtgcg ggcctcttcg ctattacgcc agctggcgaa agggggatgt   2340

gctgcaaggc gattaagttg ggtaac                                        2366
```

```
<210> SEQ ID NO 583
<211> LENGTH: 2366
<212> TYPE: DNA
<213> ORGANISM: Artificial Sequence
<220> FEATURE:
<223> OTHER INFORMATION: TRB J_C2 receiving cassette vector

<400> SEQUENCE: 583
```

```
gccagggttt tcccagtcac gacgttgtaa aacgacggcc agtgagcgcg acgtaatacg     60

actcactata gggcgaattg gcggaaggcc gtcaaggccg catgaattcg gtctcgaagt    120

cttctgcggc cgctgaagac acaggacctg aaaaacgtgt tgagaccctc gagctgggcc    180

tcatgggcct tccgctcact gcccgctttc cagtcgggaa acctgtcgtg ccagctgcat    240

taacatggtc atagctgttt ccttgcgtat tgggcgctct ccgcttcctc gctcactgac    300

tcgctgcgct cggtcgttcg ggtaaagcct ggggtgccta atgagcaaaa ggccagcaaa    360
```

```
aggccaggaa ccgtaaaaag gccgcgttgc tggcgttttt ccataggctc cgcccccctg    420

acgagcatca caaaaatcga cgctcaagtc agaggtggcg aaacccgaca ggactataaa    480

gataccaggc gtttccccct ggaagctccc tcgtgcgctc tcctgttccg accctgccgc    540

ttaccggata cctgtccgcc tttctccctt cgggaagcgt ggcgctttct catagctcac    600

gctgtaggta tctcagttcg gtgtaggtcg ttcgctccaa gctgggctgt gtgcacgaac    660

cccccgttca gcccgaccgc tgcgccttat ccggtaacta tcgtcttgag tccaacccgg    720

taagacacga cttatcgcca ctggcagcag ccactggtaa caggattagc agagcgaggt    780

atgtaggcgg tgctacagag ttcttgaagt ggtggcctaa ctacggctac actagaagaa    840

cagtatttgg tatctgcgct ctgctgaagc cagttacctt cggaaaaaga gttggtagct    900

cttgatccgg caaacaaacc accgctggta gcggtggttt ttttgtttgc aagcagcaga    960

ttacgcgcag aaaaaaagga tctcaagaag atcctttgat cttttctacg gggtctgacg   1020

ctcagtggaa cgaaaactca cgttaaggga ttttggtcat gagattatca aaaaggatct   1080

tcacctagat ccttttaaat taaaaatgaa gttttaaatc aatctaaagt atatatgagt   1140

aaacttggtc tgacagttag aaaaattcgt ccagcatcag atgaaattgc agtttgttca   1200

tgtccgggtt atcaatacca tatttctgga acagacgttt ctgcaggctc gggctaaatt   1260

cacccagaca attccacaga attgccagat cctgataacg atctgcaata ccaacacgac   1320

caacatcaat gcagccaatc agtttaccct catcaaaaat caggttatcc aggctaaaat   1380

caccatgggt aacaacgcta tccggactaa acggcagcag tttatgcatt tctttccaaa   1440

cctgttcaac aggccaacca ttacgttcat catcaaaatc gcttgcatca accagaccat   1500

tattcatacg gctctgtgcc tgtgccagac gaaaaacacg atcgctatta aacggacaat   1560

tacaaaccgg aatgctatgc agacgacgca gaaaaactgc cagtgcatca acaatatttt   1620

cgcctgaatc cggatattct tccagaacct gaaatgcggt tttacccgga attgcggtgg   1680

tcagcagcca tgcatcatcc ggtgtacgaa taaaatgttt aatggtcggc agcggcataa   1740

attcggtcag ccaattcaga cgaaccattt catcggtcac atcatttgca acgctacctt   1800

taccatgttt cagaaacagt tccggtgcat ccggtttacc atacagacga taaatggttg   1860

caccgctctg accaacatta tcacgtgccc atttatagcc atacagatct gcatccatat   1920

tgctattcag acgcggacgg ctacagctgg tttcacgctg aatatggctc atactcttcc   1980

tttttcaata ttattgaagc atttatcagg gttattgtct catgagcgga tacatatttg   2040

aatgtattta gaaaaataaa caaatagggg ttccgcgcac atttccccga aaagtgccac   2100

ctaaattgta agcgttaata ttttgttaaa attcgcgtta aatttttgtt aaatcagctc   2160

atttttaac caataggccg aaatcggcaa aatcccttat aaatcaaaag aatagaccga    2220

gatagggttg agtggccgct acagggcgct cccattcgcc attcaggctg cgcaactgtt   2280

gggaagggcg tttcggtgcg ggcctcttcg ctattacgcc agctggcgaa agggggatgt   2340

gctgcaaggc gattaagttg ggtaac                                        2366
```

```
<210> SEQ ID NO 584
<211> LENGTH: 35
<212> TYPE: DNA
<213> ORGANISM: Homo sapiens
<220> FEATURE:
<223> OTHER INFORMATION: TRBJ1-1*01_BB-S_F1

<400> SEQUENCE: 584

ctcgtttgga caaggcacca gactcacagt tgtag                                35
```

<210> SEQ ID NO 585
<211> LENGTH: 35
<212> TYPE: DNA
<213> ORGANISM: Homo sapiens
<220> FEATURE:
<223> OTHER INFORMATION: TRBJ1-2*01_BB-S_F1

<400> SEQUENCE: 585
ctcgtttggt tcggggacca ggttaaccgt tgtag 35

<210> SEQ ID NO 586
<211> LENGTH: 35
<212> TYPE: DNA
<213> ORGANISM: Homo sapiens
<220> FEATURE:
<223> OTHER INFORMATION: TRBJ1-3*01_BB-S_F1

<400> SEQUENCE: 586
ctcgtttgga gagggaagtt ggctcactgt tgtag 35

<210> SEQ ID NO 587
<211> LENGTH: 35
<212> TYPE: DNA
<213> ORGANISM: Homo sapiens
<220> FEATURE:
<223> OTHER INFORMATION: TRBJ1-4*01_BB-S_F1

<400> SEQUENCE: 587
ctcgtttggc agtggaaccc agctctctgt cttgg 35

<210> SEQ ID NO 588
<211> LENGTH: 35
<212> TYPE: DNA
<213> ORGANISM: Homo sapiens
<220> FEATURE:
<223> OTHER INFORMATION: TRBJ1-5*01_BB-S_F1

<400> SEQUENCE: 588
ctcgtttggt gatgggactc gactctccat cctag 35

<210> SEQ ID NO 589
<211> LENGTH: 35
<212> TYPE: DNA
<213> ORGANISM: Homo sapiens
<220> FEATURE:
<223> OTHER INFORMATION: TRBJ1-6*01_BB-S_F1

<400> SEQUENCE: 589
ctcgtttggg aacgggacca ggctcactgt gacag 35

<210> SEQ ID NO 590
<211> LENGTH: 35
<212> TYPE: DNA
<213> ORGANISM: Homo sapiens
<220> FEATURE:
<223> OTHER INFORMATION: TRBJ2-1*01_BB-S_F1

<400> SEQUENCE: 590
ctcgtttggg ccagggacac ggctcaccgt gctag 35

<210> SEQ ID NO 591
<211> LENGTH: 35
<212> TYPE: DNA
<213> ORGANISM: Homo sapiens
<220> FEATURE:

<223> OTHER INFORMATION: TRBJ2-2*01_BB-S_F1

<400> SEQUENCE: 591
ctcgtttgga gaaggctcta ggctgaccgt actgg 35

<210> SEQ ID NO 592
<211> LENGTH: 35
<212> TYPE: DNA
<213> ORGANISM: Homo sapiens
<220> FEATURE:
<223> OTHER INFORMATION: TRBJ2-3*01_BB-S_F1

<400> SEQUENCE: 592
ctcgtttggc ccaggcaccc ggctgacagt gctcg 35

<210> SEQ ID NO 593
<211> LENGTH: 35
<212> TYPE: DNA
<213> ORGANISM: Homo sapiens
<220> FEATURE:
<223> OTHER INFORMATION: TRBJ2-4*01_BB-S_F1

<400> SEQUENCE: 593
ctcgtttggc gccgggaccc ggctctcagt gctgg 35

<210> SEQ ID NO 594
<211> LENGTH: 35
<212> TYPE: DNA
<213> ORGANISM: Homo sapiens
<220> FEATURE:
<223> OTHER INFORMATION: TRBJ2-5*01_BB-S_F1

<400> SEQUENCE: 594
ctcgtttggg ccaggcacgc ggctcctggt gctcg 35

<210> SEQ ID NO 595
<211> LENGTH: 35
<212> TYPE: DNA
<213> ORGANISM: Homo sapiens
<220> FEATURE:
<223> OTHER INFORMATION: TRBJ2-6*01_BB-S_F1

<400> SEQUENCE: 595
ctcgtttggg gccggcagca ggctgaccgt gctgg 35

<210> SEQ ID NO 596
<211> LENGTH: 35
<212> TYPE: DNA
<213> ORGANISM: Homo sapiens
<220> FEATURE:
<223> OTHER INFORMATION: TRBJ2-7*01_BB-S_F1

<400> SEQUENCE: 596
ctcgtttggg ccgggcacca ggctcacggt cacag 35

<210> SEQ ID NO 597
<211> LENGTH: 35
<212> TYPE: DNA
<213> ORGANISM: Homo sapiens
<220> FEATURE:
<223> OTHER INFORMATION: TRBJ1-1*01_BB-S_R1

<400> SEQUENCE: 597
tcctctacaa ctgtgagtct ggtgccttgt ccaaa 35

<210> SEQ ID NO 598
<211> LENGTH: 35
<212> TYPE: DNA
<213> ORGANISM: Homo sapiens
<220> FEATURE:
<223> OTHER INFORMATION: TRBJ1-2*01_BB-S_R1

<400> SEQUENCE: 598
tcctctacaa cggttaacct ggtccccgaa ccaaa 35

<210> SEQ ID NO 599
<211> LENGTH: 35
<212> TYPE: DNA
<213> ORGANISM: Homo sapiens
<220> FEATURE:
<223> OTHER INFORMATION: TRBJ1-3*01_BB-S_R1

<400> SEQUENCE: 599
tcctctacaa cagtgagcca acttccctct ccaaa 35

<210> SEQ ID NO 600
<211> LENGTH: 35
<212> TYPE: DNA
<213> ORGANISM: Homo sapiens
<220> FEATURE:
<223> OTHER INFORMATION: TRBJ1-4*01_BB-S_R1

<400> SEQUENCE: 600
tcctccaaga cagagagctg ggttccactg ccaaa 35

<210> SEQ ID NO 601
<211> LENGTH: 35
<212> TYPE: DNA
<213> ORGANISM: Homo sapiens
<220> FEATURE:
<223> OTHER INFORMATION: TRBJ1-5*01_BB-S_R1

<400> SEQUENCE: 601
tcctctagga tggagagtcg agtcccatca ccaaa 35

<210> SEQ ID NO 602
<211> LENGTH: 35
<212> TYPE: DNA
<213> ORGANISM: Homo sapiens
<220> FEATURE:
<223> OTHER INFORMATION: TRBJ1-6*01_BB-S_R1

<400> SEQUENCE: 602
tcctctgtca cagtgagcct ggtcccgttc ccaaa 35

<210> SEQ ID NO 603
<211> LENGTH: 35
<212> TYPE: DNA
<213> ORGANISM: Homo sapiens
<220> FEATURE:
<223> OTHER INFORMATION: TRBJ2-1*01_BB-S_R1

<400> SEQUENCE: 603
tcctctagca cggtgagccg tgtccctggc ccaaa 35

<210> SEQ ID NO 604
<211> LENGTH: 35
<212> TYPE: DNA
<213> ORGANISM: Homo sapiens
<220> FEATURE:
<223> OTHER INFORMATION: TRBJ2-2*01_BB-S_R1

<400> SEQUENCE: 604
tcctccagta cggtcagcct agagccttct ccaaa 35

<210> SEQ ID NO 605
<211> LENGTH: 35
<212> TYPE: DNA
<213> ORGANISM: Homo sapiens
<220> FEATURE:
<223> OTHER INFORMATION: TRBJ2-3*01_BB-S_R1

<400> SEQUENCE: 605
tcctcgagca ctgtcagccg ggtgcctggg ccaaa 35

<210> SEQ ID NO 606
<211> LENGTH: 35
<212> TYPE: DNA
<213> ORGANISM: Homo sapiens
<220> FEATURE:
<223> OTHER INFORMATION: TRBJ2-4*01_BB-S_R1

<400> SEQUENCE: 606
tcctccagca ctgagagccg ggtcccggcg ccaaa 35

<210> SEQ ID NO 607
<211> LENGTH: 35
<212> TYPE: DNA
<213> ORGANISM: Homo sapiens
<220> FEATURE:
<223> OTHER INFORMATION: TRBJ2-5*01_BB-S_R1

<400> SEQUENCE: 607
tcctcgagca ccaggagccg cgtgcctggc ccaaa 35

<210> SEQ ID NO 608
<211> LENGTH: 35
<212> TYPE: DNA
<213> ORGANISM: Homo sapiens
<220> FEATURE:
<223> OTHER INFORMATION: TRBJ2-6*01_BB-S_R1

<400> SEQUENCE: 608
tcctccagca cggtcagcct gctgccggcc ccaaa 35

<210> SEQ ID NO 609
<211> LENGTH: 35
<212> TYPE: DNA
<213> ORGANISM: Homo sapiens
<220> FEATURE:
<223> OTHER INFORMATION: TRBJ2-7*01_BB-S_R1

<400> SEQUENCE: 609
tcctctgtga ccgtgagcct ggtgcccggc ccaaa 35

<210> SEQ ID NO 610
<211> LENGTH: 44
<212> TYPE: DNA
<213> ORGANISM: Homo sapiens
<220> FEATURE:
<223> OTHER INFORMATION: TRBJ1-1*01_BB-L_F1

<400> SEQUENCE: 610
ctcggaagct ttctttggac aaggcaccag actcacagtt gtag 44

<210> SEQ ID NO 611
<211> LENGTH: 44

<212> TYPE: DNA
<213> ORGANISM: Homo sapiens
<220> FEATURE:
<223> OTHER INFORMATION: TRBJ1-2*01_BB-L_F1

<400> SEQUENCE: 611
ctcgggctac acctttggtt cggggaccag gttaaccgtt gtag 44

<210> SEQ ID NO 612
<211> LENGTH: 44
<212> TYPE: DNA
<213> ORGANISM: Homo sapiens
<220> FEATURE:
<223> OTHER INFORMATION: TRBJ1-3*01_BB-L_F1

<400> SEQUENCE: 612
ctcgaccata tattttggag agggaagttg gctcactgtt gtag 44

<210> SEQ ID NO 613
<211> LENGTH: 47
<212> TYPE: DNA
<213> ORGANISM: Homo sapiens
<220> FEATURE:
<223> OTHER INFORMATION: TRBJ1-4*01_BB-L_F1

<400> SEQUENCE: 613
ctcggaaaag ctgttctttg gcagtggaac ccagctctct gtcttgg 47

<210> SEQ ID NO 614
<211> LENGTH: 44
<212> TYPE: DNA
<213> ORGANISM: Homo sapiens
<220> FEATURE:
<223> OTHER INFORMATION: TRBJ1-5*01_BB-L_F1

<400> SEQUENCE: 614
ctcgccccag catttggtg atgggactcg actctccatc ctag 44

<210> SEQ ID NO 615
<211> LENGTH: 47
<212> TYPE: DNA
<213> ORGANISM: Homo sapiens
<220> FEATURE:
<223> OTHER INFORMATION: TRBJ1-6*01_BB-L_F1

<400> SEQUENCE: 615
ctcgtcaccc ctccactttg ggaacgggac caggctcact gtgacag 47

<210> SEQ ID NO 616
<211> LENGTH: 44
<212> TYPE: DNA
<213> ORGANISM: Homo sapiens
<220> FEATURE:
<223> OTHER INFORMATION: TRB J Long segment part

<400> SEQUENCE: 616
ctcggagcag ttctttgggc cagggacacg gctcaccgtg ctag 44

<210> SEQ ID NO 617
<211> LENGTH: 47
<212> TYPE: DNA
<213> ORGANISM: Homo sapiens
<220> FEATURE:
<223> OTHER INFORMATION: TRB J Long segment part

<400> SEQUENCE: 617
ctcgggggag ctgttctttg gagaaggctc taggctgacc gtactgg 47

<210> SEQ ID NO 618
<211> LENGTH: 44
<212> TYPE: DNA
<213> ORGANISM: Homo sapiens
<220> FEATURE:
<223> OTHER INFORMATION: TRB J Long segment part

<400> SEQUENCE: 618
ctcgacgcag tattttggcc caggcacccg gctgacagtg ctcg 44

<210> SEQ ID NO 619
<211> LENGTH: 44
<212> TYPE: DNA
<213> ORGANISM: Homo sapiens
<220> FEATURE:
<223> OTHER INFORMATION: TRB J Long segment part

<400> SEQUENCE: 619
ctcgattcag tactttggcg ccgggacccg gctctcagtg ctgg 44

<210> SEQ ID NO 620
<211> LENGTH: 44
<212> TYPE: DNA
<213> ORGANISM: Homo sapiens
<220> FEATURE:
<223> OTHER INFORMATION: TRB J Long segment part

<400> SEQUENCE: 620
ctcgacccag tactttgggc caggcacgcg gctcctggtg ctcg 44

<210> SEQ ID NO 621
<211> LENGTH: 47
<212> TYPE: DNA
<213> ORGANISM: Homo sapiens
<220> FEATURE:
<223> OTHER INFORMATION: TRB J Long segment part

<400> SEQUENCE: 621
ctcgaacgtc ctgacttttg gggccggcag caggctgacc gtgctgg 47

<210> SEQ ID NO 622
<211> LENGTH: 41
<212> TYPE: DNA
<213> ORGANISM: Homo sapiens
<220> FEATURE:
<223> OTHER INFORMATION: TRB J Long segment part

<400> SEQUENCE: 622
ctcgcagtac tttgggccgg gcaccaggct cacggtcaca g 41

<210> SEQ ID NO 623
<211> LENGTH: 44
<212> TYPE: DNA
<213> ORGANISM: Homo sapiens
<220> FEATURE:
<223> OTHER INFORMATION: TRBJ1-1*01_BB-L_R1

<400> SEQUENCE: 623
tcctctacaa ctgtgagtct ggtgccttgt ccaaagaaag cttc 44

<210> SEQ ID NO 624
<211> LENGTH: 44
<212> TYPE: DNA
<213> ORGANISM: Homo sapiens

<220> FEATURE:
<223> OTHER INFORMATION: TRBJ1-2*01_BB-L_R1

<400> SEQUENCE: 624
tcctctacaa cggttaacct ggtccccgaa ccaaaggtgt agcc 44

<210> SEQ ID NO 625
<211> LENGTH: 44
<212> TYPE: DNA
<213> ORGANISM: Homo sapiens
<220> FEATURE:
<223> OTHER INFORMATION: TRBJ1-3*01_BB-L_R1

<400> SEQUENCE: 625
tcctctacaa cagtgagcca acttccctct ccaaaatata tggt 44

<210> SEQ ID NO 626
<211> LENGTH: 47
<212> TYPE: DNA
<213> ORGANISM: Homo sapiens
<220> FEATURE:
<223> OTHER INFORMATION: TRBJ1-4*01_BB-L_R1

<400> SEQUENCE: 626
tcctccaaga cagagagctg ggttccactg ccaaagaaca gcttttc 47

<210> SEQ ID NO 627
<211> LENGTH: 44
<212> TYPE: DNA
<213> ORGANISM: Homo sapiens
<220> FEATURE:
<223> OTHER INFORMATION: TRBJ1-5*01_BB-L_R1

<400> SEQUENCE: 627
tcctctagga tggagagtcg agtcccatca ccaaaatgct gggg 44

<210> SEQ ID NO 628
<211> LENGTH: 47
<212> TYPE: DNA
<213> ORGANISM: Homo sapiens
<220> FEATURE:
<223> OTHER INFORMATION: TRBJ1-6*01_BB-L_R1

<400> SEQUENCE: 628
tcctctgtca cagtgagcct ggtcccgttc ccaaagtgga ggggtga 47

<210> SEQ ID NO 629
<211> LENGTH: 44
<212> TYPE: DNA
<213> ORGANISM: Homo sapiens
<220> FEATURE:
<223> OTHER INFORMATION: TRBJ2-1*01_BB-L_R1

<400> SEQUENCE: 629
tcctctagca cggtgagccg tgtccctggc ccaaagaact gctc 44

<210> SEQ ID NO 630
<211> LENGTH: 47
<212> TYPE: DNA
<213> ORGANISM: Homo sapiens
<220> FEATURE:
<223> OTHER INFORMATION: TRBJ2-2*01_BB-L_R1

<400> SEQUENCE: 630
tcctccagta cggtcagcct agagccttct ccaaagaaca gctcccc 47

<210> SEQ ID NO 631
<211> LENGTH: 44
<212> TYPE: DNA
<213> ORGANISM: Homo sapiens
<220> FEATURE:
<223> OTHER INFORMATION: TRBJ2-3*01_BB-L_R1

<400> SEQUENCE: 631
tcctcgagca ctgtcagccg ggtgcctggg ccaaaatact gcgt 44

<210> SEQ ID NO 632
<211> LENGTH: 44
<212> TYPE: DNA
<213> ORGANISM: Homo sapiens
<220> FEATURE:
<223> OTHER INFORMATION: TRBJ2-4*01_BB-L_R1

<400> SEQUENCE: 632
tcctccagca ctgagagccg ggtcccggcg ccaaagtact gaat 44

<210> SEQ ID NO 633
<211> LENGTH: 44
<212> TYPE: DNA
<213> ORGANISM: Homo sapiens
<220> FEATURE:
<223> OTHER INFORMATION: TRBJ2-5*01_BB-L_R1

<400> SEQUENCE: 633
tcctcgagca ccaggagccg cgtgcctggc ccaaagtact gggt 44

<210> SEQ ID NO 634
<211> LENGTH: 47
<212> TYPE: DNA
<213> ORGANISM: Homo sapiens
<220> FEATURE:
<223> OTHER INFORMATION: TRBJ2-6*01_BB-L_R1

<400> SEQUENCE: 634
tcctccagca cggtcagcct gctgccggcc ccaaaagtca ggacgtt 47

<210> SEQ ID NO 635
<211> LENGTH: 41
<212> TYPE: DNA
<213> ORGANISM: Homo sapiens
<220> FEATURE:
<223> OTHER INFORMATION: TRBJ2-7*01_BB-L_R1

<400> SEQUENCE: 635
tcctctgtga ccgtgagcct ggtgcccggc ccaaagtact g 41

<210> SEQ ID NO 636
<211> LENGTH: 63
<212> TYPE: DNA
<213> ORGANISM: Homo sapiens
<220> FEATURE:
<223> OTHER INFORMATION: J Donor_Short_C1_TRBJ1-1

<400> SEQUENCE: 636
ggtctcgttt ggacaaggca ccagactcac agttgtagag gacctgaaca aggtgttgag 60
acc 63

<210> SEQ ID NO 637
<211> LENGTH: 63
<212> TYPE: DNA
<213> ORGANISM: Homo sapiens
<220> FEATURE:
<223> OTHER INFORMATION: J Donor_Short_C1_TRBJ1-2

<400> SEQUENCE: 637
ggtctcgttt ggttcgggga ccaggttaac cgttgtagag gacctgaaca aggtgttgag 60
acc 63

<210> SEQ ID NO 638
<211> LENGTH: 63
<212> TYPE: DNA
<213> ORGANISM: Homo sapiens
<220> FEATURE:
<223> OTHER INFORMATION: J Donor_Short_C1_TRBJ1-3

<400> SEQUENCE: 638
ggtctcgttt ggagagggaa gttggctcac tgttgtagag gacctgaaca aggtgttgag 60
acc 63

<210> SEQ ID NO 639
<211> LENGTH: 63
<212> TYPE: DNA
<213> ORGANISM: Homo sapiens
<220> FEATURE:
<223> OTHER INFORMATION: J Donor_Short_C1_TRBJ1-4

<400> SEQUENCE: 639
ggtctcgttt ggcagtggaa cccagctctc tgtcttggag gacctgaaca aggtgttgag 60
acc 63

<210> SEQ ID NO 640
<211> LENGTH: 63
<212> TYPE: DNA
<213> ORGANISM: Homo sapiens
<220> FEATURE:
<223> OTHER INFORMATION: J Donor_Short_C1_TRBJ1-5

<400> SEQUENCE: 640
ggtctcgttt ggtgatggga ctcgactctc catcctagag gacctgaaca aggtgttgag 60
acc 63

<210> SEQ ID NO 641
<211> LENGTH: 63
<212> TYPE: DNA
<213> ORGANISM: Homo sapiens
<220> FEATURE:
<223> OTHER INFORMATION: J Donor_Short_C1_TRBJ1-6

<400> SEQUENCE: 641
ggtctcgttt gggaacggga ccaggctcac tgtgacagag gacctgaaca aggtgttgag 60
acc 63

<210> SEQ ID NO 642
<211> LENGTH: 63
<212> TYPE: DNA
<213> ORGANISM: Homo sapiens
<220> FEATURE:
<223> OTHER INFORMATION: J Donor_Short_C1_TRBJ2-1

<400> SEQUENCE: 642
ggtctcgttt gggccaggga cacggctcac cgtgctagag gacctgaaca aggtgttgag 60
acc 63

<210> SEQ ID NO 643
<211> LENGTH: 63
<212> TYPE: DNA
<213> ORGANISM: Homo sapiens
<220> FEATURE:
<223> OTHER INFORMATION: J Donor_Short_C1_TRBJ2-2

<400> SEQUENCE: 643
ggtctcgttt ggagaaggct ctaggctgac cgtactggag gacctgaaca aggtgttgag 60
acc 63

<210> SEQ ID NO 644
<211> LENGTH: 63
<212> TYPE: DNA
<213> ORGANISM: Homo sapiens
<220> FEATURE:
<223> OTHER INFORMATION: J Donor_Short_C1_TRBJ2-3

<400> SEQUENCE: 644
ggtctcgttt ggcccaggca cccggctgac agtgctcgag gacctgaaca aggtgttgag 60
acc 63

<210> SEQ ID NO 645
<211> LENGTH: 63
<212> TYPE: DNA
<213> ORGANISM: Homo sapiens
<220> FEATURE:
<223> OTHER INFORMATION: J Donor_Short_C1_TRBJ2-4

<400> SEQUENCE: 645
ggtctcgttt ggcgccggga cccggctctc agtgctggag gacctgaaca aggtgttgag 60
acc 63

<210> SEQ ID NO 646
<211> LENGTH: 63
<212> TYPE: DNA
<213> ORGANISM: Homo sapiens
<220> FEATURE:
<223> OTHER INFORMATION: J Donor_Short_C1_TRBJ2-5

<400> SEQUENCE: 646
ggtctcgttt gggccaggca cgcggctcct ggtgctcgag gacctgaaca aggtgttgag 60
acc 63

<210> SEQ ID NO 647
<211> LENGTH: 63
<212> TYPE: DNA
<213> ORGANISM: Homo sapiens
<220> FEATURE:
<223> OTHER INFORMATION: J Donor_Short_C1_TRBJ2-6

<400> SEQUENCE: 647
ggtctcgttt ggggccggca gcaggctgac cgtgctggag gacctgaaca aggtgttgag 60
acc 63

<210> SEQ ID NO 648
<211> LENGTH: 63
<212> TYPE: DNA
<213> ORGANISM: Homo sapiens
<220> FEATURE:
<223> OTHER INFORMATION: J Donor_Short_C1_TRBJ2-7

<400> SEQUENCE: 648
ggtctcgttt gggccgggca ccaggctcac ggtcacagag gacctgaaca aggtgttgag 60
acc 63

<210> SEQ ID NO 649
<211> LENGTH: 63
<212> TYPE: DNA
<213> ORGANISM: Homo sapiens
<220> FEATURE:
<223> OTHER INFORMATION: J Donor_Short_C2_TRBJ1-1

<400> SEQUENCE: 649
ggtctcgttt ggacaaggca ccagactcac agttgtagag gacctgaaaa acgtgttgag 60
acc 63

<210> SEQ ID NO 650
<211> LENGTH: 63
<212> TYPE: DNA
<213> ORGANISM: Homo sapiens
<220> FEATURE:
<223> OTHER INFORMATION: J Donor_Short_C2_TRBJ1-2

<400> SEQUENCE: 650
ggtctcgttt ggttcgggga ccaggttaac cgttgtagag gacctgaaaa acgtgttgag 60
acc 63

<210> SEQ ID NO 651
<211> LENGTH: 63
<212> TYPE: DNA
<213> ORGANISM: Homo sapiens
<220> FEATURE:
<223> OTHER INFORMATION: J Donor_Short_C2_TRBJ1-3

<400> SEQUENCE: 651
ggtctcgttt ggagagggaa gttggctcac tgttgtagag gacctgaaaa acgtgttgag 60
acc 63

<210> SEQ ID NO 652
<211> LENGTH: 63
<212> TYPE: DNA
<213> ORGANISM: Homo sapiens
<220> FEATURE:
<223> OTHER INFORMATION: J Donor_Short_C2_TRBJ1-4

<400> SEQUENCE: 652
ggtctcgttt ggcagtggaa cccagctctc tgtcttggag gacctgaaaa acgtgttgag 60
acc 63

<210> SEQ ID NO 653
<211> LENGTH: 63
<212> TYPE: DNA
<213> ORGANISM: Homo sapiens
<220> FEATURE:
<223> OTHER INFORMATION: J Donor_Short_C2_TRBJ1-5

<400> SEQUENCE: 653
ggtctcgttt ggtgatggga ctcgactctc catcctagag gacctgaaaa acgtgttgag 60
acc 63

<210> SEQ ID NO 654
<211> LENGTH: 63
<212> TYPE: DNA

<213> ORGANISM: Homo sapiens
<220> FEATURE:
<223> OTHER INFORMATION: J Donor_Short_C2_TRBJ1-6

<400> SEQUENCE: 654
ggtctcgttt gggaacggga ccaggctcac tgtgacagag gacctgaaaa acgtgttgag 60
acc 63

<210> SEQ ID NO 655
<211> LENGTH: 63
<212> TYPE: DNA
<213> ORGANISM: Homo sapiens
<220> FEATURE:
<223> OTHER INFORMATION: J Donor_Short_C2_TRBJ2-1

<400> SEQUENCE: 655
ggtctcgttt gggccaggga cacggctcac cgtgctagag gacctgaaaa acgtgttgag 60
acc 63

<210> SEQ ID NO 656
<211> LENGTH: 63
<212> TYPE: DNA
<213> ORGANISM: Homo sapiens
<220> FEATURE:
<223> OTHER INFORMATION: J Donor_Short_C2_TRBJ2-2

<400> SEQUENCE: 656
ggtctcgttt ggagaaggct ctaggctgac cgtactggag gacctgaaaa acgtgttgag 60
acc 63

<210> SEQ ID NO 657
<211> LENGTH: 63
<212> TYPE: DNA
<213> ORGANISM: Homo sapiens
<220> FEATURE:
<223> OTHER INFORMATION: J Donor_Short_C2_TRBJ2-3

<400> SEQUENCE: 657
ggtctcgttt ggcccaggca cccggctgac agtgctcgag gacctgaaaa acgtgttgag 60
acc 63

<210> SEQ ID NO 658
<211> LENGTH: 63
<212> TYPE: DNA
<213> ORGANISM: Homo sapiens
<220> FEATURE:
<223> OTHER INFORMATION: J Donor_Short_C2_TRBJ2-4

<400> SEQUENCE: 658
ggtctcgttt ggcgccggga cccggctctc agtgctggag gacctgaaaa acgtgttgag 60
acc 63

<210> SEQ ID NO 659
<211> LENGTH: 63
<212> TYPE: DNA
<213> ORGANISM: Homo sapiens
<220> FEATURE:
<223> OTHER INFORMATION: J Donor_Short_C2_TRBJ2-5

<400> SEQUENCE: 659
ggtctcgttt gggccaggca cgcggctcct ggtgctcgag gacctgaaaa acgtgttgag 60
acc 63

<210> SEQ ID NO 660
<211> LENGTH: 63
<212> TYPE: DNA
<213> ORGANISM: Homo sapiens
<220> FEATURE:
<223> OTHER INFORMATION: TRB C2 J Short donor vector

<400> SEQUENCE: 660
ggtctcgttt ggggccggca gcaggctgac cgtgctggag gacctgaaaa acgtgttgag 60
acc 63

<210> SEQ ID NO 661
<211> LENGTH: 63
<212> TYPE: DNA
<213> ORGANISM: Homo sapiens
<220> FEATURE:
<223> OTHER INFORMATION: J Donor_Short_C2_TRBJ2-7

<400> SEQUENCE: 661
ggtctcgttt gggccgggca ccaggctcac ggtcacagag gacctgaaaa acgtgttgag 60
acc 63

<210> SEQ ID NO 662
<211> LENGTH: 72
<212> TYPE: DNA
<213> ORGANISM: Homo sapiens
<220> FEATURE:
<223> OTHER INFORMATION: J Donor_Long_C1_TRBJ1-1

<400> SEQUENCE: 662
ggtctcggaa gctttctttg gacaaggcac cagactcaca gttgtagagg acctgaacaa 60
ggtgttgaga cc 72

<210> SEQ ID NO 663
<211> LENGTH: 72
<212> TYPE: DNA
<213> ORGANISM: Homo sapiens
<220> FEATURE:
<223> OTHER INFORMATION: J Donor_Long_C1_TRBJ1-2

<400> SEQUENCE: 663
ggtctcgggc tacacctttg gttcggggac caggttaacc gttgtagagg acctgaacaa 60
ggtgttgaga cc 72

<210> SEQ ID NO 664
<211> LENGTH: 72
<212> TYPE: DNA
<213> ORGANISM: Homo sapiens
<220> FEATURE:
<223> OTHER INFORMATION: J Donor_Long_C1_TRBJ1-3

<400> SEQUENCE: 664
ggtctcgacc atatattttg gagagggaag ttggctcact gttgtagagg acctgaacaa 60
ggtgttgaga cc 72

<210> SEQ ID NO 665
<211> LENGTH: 75
<212> TYPE: DNA
<213> ORGANISM: Homo sapiens
<220> FEATURE:
<223> OTHER INFORMATION: J Donor_Long_C1_TRBJ1-4

<400> SEQUENCE: 665
ggtctcggaa aagctgttct ttggcagtgg aacccagctc tctgtcttgg aggacctgaa 60
caaggtgttg agacc 75

<210> SEQ ID NO 666
<211> LENGTH: 72
<212> TYPE: DNA
<213> ORGANISM: Homo sapiens
<220> FEATURE:
<223> OTHER INFORMATION: J Donor_Long_C1_TRBJ1-5

<400> SEQUENCE: 666
ggtctcgccc cagcattttg gtgatgggac tcgactctcc atcctagagg acctgaacaa 60
ggtgttgaga cc 72

<210> SEQ ID NO 667
<211> LENGTH: 75
<212> TYPE: DNA
<213> ORGANISM: Homo sapiens
<220> FEATURE:
<223> OTHER INFORMATION: J Donor_Long_C1_TRBJ1-6

<400> SEQUENCE: 667
ggtctcgtca cccctccact ttgggaacgg gaccaggctc actgtgacag aggacctgaa 60
caaggtgttg agacc 75

<210> SEQ ID NO 668
<211> LENGTH: 72
<212> TYPE: DNA
<213> ORGANISM: Homo sapiens
<220> FEATURE:
<223> OTHER INFORMATION: J Donor_Long_C1_TRBJ2-1

<400> SEQUENCE: 668
ggtctcggag cagttctttg ggccagggac acggctcacc gtgctagagg acctgaacaa 60
ggtgttgaga cc 72

<210> SEQ ID NO 669
<211> LENGTH: 75
<212> TYPE: DNA
<213> ORGANISM: Homo sapiens
<220> FEATURE:
<223> OTHER INFORMATION: J Donor_Long_C1_TRBJ2-2

<400> SEQUENCE: 669
ggtctcgggg gagctgttct ttggagaagg ctctaggctg accgtactgg aggacctgaa 60
caaggtgttg agacc 75

<210> SEQ ID NO 670
<211> LENGTH: 72
<212> TYPE: DNA
<213> ORGANISM: Homo sapiens
<220> FEATURE:
<223> OTHER INFORMATION: J Donor_Long_C1_TRBJ2-3

<400> SEQUENCE: 670
ggtctcgacg cagtattttg gcccaggcac ccggctgaca gtgctcgagg acctgaacaa 60
ggtgttgaga cc 72

<210> SEQ ID NO 671
<211> LENGTH: 72

<212> TYPE: DNA
<213> ORGANISM: Homo sapiens
<220> FEATURE:
<223> OTHER INFORMATION: J Donor_Long_C1_TRBJ2-4

<400> SEQUENCE: 671
ggtctcgatt cagtactttg gcgccgggac ccggctctca gtgctggagg acctgaacaa 60
ggtgttgaga cc 72

<210> SEQ ID NO 672
<211> LENGTH: 72
<212> TYPE: DNA
<213> ORGANISM: Homo sapiens
<220> FEATURE:
<223> OTHER INFORMATION: J Donor_Long_C1_TRBJ2-5

<400> SEQUENCE: 672
ggtctcgacc cagtactttg ggccaggcac gcggctcctg gtgctcgagg acctgaacaa 60
ggtgttgaga cc 72

<210> SEQ ID NO 673
<211> LENGTH: 75
<212> TYPE: DNA
<213> ORGANISM: Homo sapiens
<220> FEATURE:
<223> OTHER INFORMATION: J Donor_Long_C1_TRBJ2-6

<400> SEQUENCE: 673
ggtctcgaac gtcctgactt ttggggccgg cagcaggctg accgtgctgg aggacctgaa 60
caaggtgttg agacc 75

<210> SEQ ID NO 674
<211> LENGTH: 69
<212> TYPE: DNA
<213> ORGANISM: Homo sapiens
<220> FEATURE:
<223> OTHER INFORMATION: J Donor_Long_C1_TRBJ2-7

<400> SEQUENCE: 674
ggtctcgcag tactttgggc cgggcaccag gctcacggtc acagaggacc tgaacaaggt 60
gttgagacc 69

<210> SEQ ID NO 675
<211> LENGTH: 72
<212> TYPE: DNA
<213> ORGANISM: Homo sapiens
<220> FEATURE:
<223> OTHER INFORMATION: J Donor_Long_C2_TRBJ1-1

<400> SEQUENCE: 675
ggtctcggaa gctttctttg gacaaggcac cagactcaca gttgtagagg acctgaaaaa 60
cgtgttgaga cc 72

<210> SEQ ID NO 676
<211> LENGTH: 72
<212> TYPE: DNA
<213> ORGANISM: Homo sapiens
<220> FEATURE:
<223> OTHER INFORMATION: J Donor_Long_C2_TRBJ1-2

<400> SEQUENCE: 676
ggtctcgggc tacacctttg gttcggggac caggttaacc gttgtagagg acctgaaaaa 60
cgtgttgaga cc 72

<210> SEQ ID NO 677
<211> LENGTH: 72
<212> TYPE: DNA
<213> ORGANISM: Homo sapiens
<220> FEATURE:
<223> OTHER INFORMATION: J Donor_Long_C2_TRBJ1-3

<400> SEQUENCE: 677
ggtctcgacc atatattttg gagagggaag ttggctcact gttgtagagg acctgaaaaa 60
cgtgttgaga cc 72

<210> SEQ ID NO 678
<211> LENGTH: 75
<212> TYPE: DNA
<213> ORGANISM: Homo sapiens
<220> FEATURE:
<223> OTHER INFORMATION: J Donor_Long_C2_TRBJ1-4

<400> SEQUENCE: 678
ggtctcggaa aagctgttct ttggcagtgg aacccagctc tctgtcttgg aggacctgaa 60
aaacgtgttg agacc 75

<210> SEQ ID NO 679
<211> LENGTH: 72
<212> TYPE: DNA
<213> ORGANISM: Homo sapiens
<220> FEATURE:
<223> OTHER INFORMATION: J Donor_Long_C2_TRBJ1-5

<400> SEQUENCE: 679
ggtctcgccc cagcattttg gtgatgggac tcgactctcc atcctagagg acctgaaaaa 60
cgtgttgaga cc 72

<210> SEQ ID NO 680
<211> LENGTH: 75
<212> TYPE: DNA
<213> ORGANISM: Homo sapiens
<220> FEATURE:
<223> OTHER INFORMATION: J Donor_Long_C2_TRBJ1-6

<400> SEQUENCE: 680
ggtctcgtca cccctccact ttgggaacgg gaccaggctc actgtgacag aggacctgaa 60
aaacgtgttg agacc 75

<210> SEQ ID NO 681
<211> LENGTH: 72
<212> TYPE: DNA
<213> ORGANISM: Homo sapiens
<220> FEATURE:
<223> OTHER INFORMATION: J Donor_Long_C2_TRBJ2-1

<400> SEQUENCE: 681
ggtctcggag cagttctttg ggccagggac acggctcacc gtgctagagg acctgaaaaa 60
cgtgttgaga cc 72

<210> SEQ ID NO 682
<211> LENGTH: 75
<212> TYPE: DNA
<213> ORGANISM: Homo sapiens
<220> FEATURE:
<223> OTHER INFORMATION: J Donor_Long_C2_TRBJ2-2

<400> SEQUENCE: 682
ggtctcgggg gagctgttct ttggagaagg ctctaggctg accgtactgg aggacctgaa 60
aaacgtgttg agacc 75

<210> SEQ ID NO 683
<211> LENGTH: 72
<212> TYPE: DNA
<213> ORGANISM: Homo sapiens
<220> FEATURE:
<223> OTHER INFORMATION: J Donor_Long_C2_TRBJ2-3

<400> SEQUENCE: 683
ggtctcgacg cagtattttg gcccaggcac ccggctgaca gtgctcgagg acctgaaaaa 60
cgtgttgaga cc 72

<210> SEQ ID NO 684
<211> LENGTH: 72
<212> TYPE: DNA
<213> ORGANISM: Homo sapiens
<220> FEATURE:
<223> OTHER INFORMATION: J Donor_Long_C2_TRBJ2-4

<400> SEQUENCE: 684
ggtctcgatt cagtactttg gcgccgggac ccggctctca gtgctggagg acctgaaaaa 60
cgtgttgaga cc 72

<210> SEQ ID NO 685
<211> LENGTH: 72
<212> TYPE: DNA
<213> ORGANISM: Homo sapiens
<220> FEATURE:
<223> OTHER INFORMATION: J Donor_Long_C2_TRBJ2-5

<400> SEQUENCE: 685
ggtctcgacc cagtactttg ggccaggcac gcggctcctg gtgctcgagg acctgaaaaa 60
cgtgttgaga cc 72

<210> SEQ ID NO 686
<211> LENGTH: 75
<212> TYPE: DNA
<213> ORGANISM: Homo sapiens
<220> FEATURE:
<223> OTHER INFORMATION: J Donor_Long_C2_TRBJ2-6

<400> SEQUENCE: 686
ggtctcgaac gtcctgactt ttggggccgg cagcaggctg accgtgctgg aggacctgaa 60
aaacgtgttg agacc 75

<210> SEQ ID NO 687
<211> LENGTH: 69
<212> TYPE: DNA
<213> ORGANISM: Homo sapiens
<220> FEATURE:
<223> OTHER INFORMATION: J Donor_Long_C2_TRBJ2-7

<400> SEQUENCE: 687
ggtctcgcag tactttgggc cgggcaccag gctcacggtc acagaggacc tgaaaaacgt 60
gttgagacc 69

<210> SEQ ID NO 688

<211> LENGTH: 2471
<212> TYPE: DNA
<213> ORGANISM: Artificial Sequence
<220> FEATURE:
<223> OTHER INFORMATION: V-C entry backbone F14/F15

<400> SEQUENCE: 688

```
tctagacgaa gttcctattc cgaagttcct attcttatag gagtatagga acttcctcga     60
gctgggcctc atgggccttc cgctcactgc ccgctttcca gtcgggaaac ctgtcgtgcc    120
agctgcatta acatggtcat agctgtttcc ttgcgtattg ggcgctctcc gcttcctcgc    180
tcactgactc gctgcgctcg gtcgttcggg taaagcctgg ggtgcctaat gagcaaaagg    240
ccagcaaaag gccaggaacc gtaaaaaggc cgcgttgctg gcgtttttcc ataggctccg    300
ccccctgac gagcatcaca aaaatcgacg ctcaagtcag aggtggcgaa acccgacagg     360
actataaaga taccaggcgt ttccccctgg aagctccctc gtgcgctctc ctgttccgac    420
cctgccgctt accggatacc tgtccgcctt tctcccttcg ggaagcgtgg cgctttctca    480
tagctcacgc tgtaggtatc tcagttcggt gtaggtcgtt cgctccaagc tgggctgtgt    540
gcacgaaccc cccgttcagc ccgaccgctg cgccttatcc ggtaactatc gtcttgagtc    600
caacccggta agacacgact tatcgccact ggcagcagcc actggtaaca ggattagcag    660
agcgaggtat gtaggcggtg ctacagagtt cttgaagtgg tggcctaact acggctacac    720
tagaagaaca gtatttggta tctgcgctct gctgaagcca gttaccttcg gaaaaagagt    780
tggtagctct tgatccggca aacaaaccac cgctggtagc ggtggttttt ttgtttgcaa    840
gcagcagatt acgcgcagaa aaaaaggatc tcaagaagat cctttgatct tttctacggg    900
gtctgacgct cagtggaacg aaaactcacg ttaagggatt ttggtcatga gattatcaaa    960
aaggatcttc acctagatcc ttttaaatta aaaatgaagt tttaaatcaa tctaaagtat   1020
atatgagtaa acttggtctg acagttacca atgcttaatc agtgaggcac ctatctcagc   1080
gatctgtcta tttcgttcat ccatagttgc ctgactcccc gtcgtgtaga taactacgat   1140
acgggagggc ttaccatctg gccccagtgc tgcaatgata ccgcgagaac cacgctcacc   1200
ggctccagat ttatcagcaa taaaccagcc agccggaagg gccgagcgca gaagtggtcc   1260
tgcaacttta tccgcctcca tccagtctat taattgttgc cgggaagcta gagtaagtag   1320
ttcgccagtt aatagtttgc gcaacgttgt tgccattgct acaggcatcg tggtgtcacg   1380
ctcgtcgttt ggtatggctt cattcagctc cggttcccaa cgatcaaggc gagttacatg   1440
atcccccatg ttgtgcaaaa aagcggttag ctccttcggt cctccgatcg ttgtcagaag   1500
taagttggcc gcagtgttat cactcatggt tatggcagca ctgcataatt ctcttactgt   1560
catgccatcc gtaagatgct tttctgtgac tggtgagtac tcaaccaagt cattctgaga   1620
atagtgtatg cggcgaccga gttgctcttg cccggcgtca atacgggata ataccgcgcc   1680
acatagcaga actttaaaag tgctcatcat tggaaaacgt tcttcggggc gaaaactctc   1740
aaggatctta ccgctgttga gatccagttc gatgtaaccc actcgtgcac ccaactgatc   1800
ttcagcatct tttactttca ccagcgtttc tgggtgagca aaaacaggaa ggcaaaatgc   1860
cgcaaaaaag ggaataaggg cgacacggaa atgttgaata ctcatactct tcctttttca   1920
atattattga agcatttatc agggttattg tctcatgagc ggatacatat ttgaatgtat   1980
ttagaaaaat aaacaaatag gggttccgcg cacatttccc cgaaaagtgc cacctaaatt   2040
gtaagcgtta atattttgtt aaaattcgcg ttaaattttt gttaaatcag ctcatttttt   2100
aaccaatagg ccgaaatcgg caaaatccct tataaatcaa aagaatagac cgagataggg   2160
```

ttgagtggcc gctacagggc gctcccattc gccattcagg ctgcgcaact gttgggaagg 2220
gcgtttcggt gcgggcctct tcgctattac gccagctggc gaaaggggga tgtgctgcaa 2280
ggcgattaag ttgggtaacg ccagggtttt cccagtcacg acgttgtaaa acgacggcca 2340
gtgagcgcga cgtaatacga ctcactatag ggcgaattgg cggaaggccg tcaaggccgc 2400
atgaattcgc taccgggaag ttcctattcc gaagttccta ttctatcaga agtataggaa 2460
cttcaggtac c 2471

<210> SEQ ID NO 689
<211> LENGTH: 2471
<212> TYPE: DNA
<213> ORGANISM: Artificial Sequence
<220> FEATURE:
<223> OTHER INFORMATION: V-C entry backbone FRT/F3

<400> SEQUENCE: 689
tctagacgaa gttcctattc cgaagttcct attcttcaaa tagtatagga acttcctcga 60
gctgggcctc atgggccttc cgctcactgc ccgctttcca gtcgggaaac ctgtcgtgcc 120
agctgcatta acatggtcat agctgtttcc ttgcgtattg ggcgctctcc gcttcctcgc 180
tcactgactc gctgcgctcg gtcgttcggg taaagcctgg ggtgcctaat gagcaaaagg 240
ccagcaaaag gccaggaacc gtaaaaaggc cgcgttgctg gcgtttttcc ataggctccg 300
cccccctgac gagcatcaca aaaatcgacg ctcaagtcag aggtggcgaa acccgacagg 360
actataaaga taccaggcgt ttccccctgg aagctccctc gtgcgctctc ctgttccgac 420
cctgccgctt accggatacc tgtccgcctt tctcccttcg ggaagcgtgg cgctttctca 480
tagctcacgc tgtaggtatc tcagttcggt gtaggtcgtt cgctccaagc tgggctgtgt 540
gcacgaaccc cccgttcagc ccgaccgctg cgccttatcc ggtaactatc gtcttgagtc 600
caacccggta agacacgact tatcgccact ggcagcagcc actggtaaca ggattagcag 660
agcgaggtat gtaggcggtg ctacagagtt cttgaagtgg tggcctaact acggctacac 720
tagaagaaca gtatttggta tctgcgctct gctgaagcca gttaccttcg gaaaaagagt 780
tggtagctct tgatccggca aacaaaccac cgctggtagc ggtggttttt ttgtttgcaa 840
gcagcagatt acgcgcagaa aaaaaggatc tcaagaagat cctttgatct tttctacggg 900
gtctgacgct cagtggaacg aaaactcacg ttaagggatt ttggtcatga gattatcaaa 960
aaggatcttc acctagatcc ttttaaatta aaaatgaagt tttaaatcaa tctaaagtat 1020
atatgagtaa acttggtctg acagttacca atgcttaatc agtgaggcac ctatctcagc 1080
gatctgtcta tttcgttcat ccatagttgc ctgactcccc gtcgtgtaga taactacgat 1140
acgggagggc ttaccatctg gccccagtgc tgcaatgata ccgcgagaac cacgctcacc 1200
ggctccagat ttatcagcaa taaaccagcc agccggaagg gccgagcgca gaagtggtcc 1260
tgcaacttta tccgcctcca tccagtctat taattgttgc cgggaagcta gagtaagtag 1320
ttcgccagtt aatagtttgc gcaacgttgt tgccattgct acaggcatcg tggtgtcacg 1380
ctcgtcgttt ggtatggctt cattcagctc cggttcccaa cgatcaaggc gagttacatg 1440
atcccccatg ttgtgcaaaa aagcggttag ctccttcggt cctccgatcg ttgtcagaag 1500
taagttggcc gcagtgttat cactcatggt tatggcagca ctgcataatt ctcttactgt 1560
catgccatcc gtaagatgct tttctgtgac tggtgagtac tcaaccaagt cattctgaga 1620
atagtgtatg cggcgaccga gttgctcttg cccggcgtca atacgggata ataccgcgcc 1680
acatagcaga actttaaaag tgctcatcat tggaaaacgt tcttcggggc gaaaactctc 1740
aaggatctta ccgctgttga gatccagttc gatgtaaccc actcgtgcac ccaactgatc 1800
ttcagcatct tttactttca ccagcgtttc tgggtgagca aaaacaggaa ggcaaaatgc 1860
cgcaaaaaag ggaataaggg cgacacggaa atgttgaata ctcatactct tcctttttca 1920
atattattga agcatttatc agggttattg tctcatgagc ggatacatat ttgaatgtat 1980
ttagaaaaat aaacaaatag gggttccgcg cacatttccc cgaaaagtgc cacctaaatt 2040
gtaagcgtta atattttgtt aaaattcgcg ttaaattttt gttaaatcag ctcatttttt 2100
aaccaatagg ccgaaatcgg caaaatccct tataaatcaa aagaatagac cgagataggg 2160
ttgagtggcc gctacagggc gctcccattc gccattcagg ctgcgcaact gttgggaagg 2220
gcgtttcggt gcgggcctct tcgctattac gccagctggc gaaaggggga tgtgctgcaa 2280
ggcgattaag ttgggtaacg ccagggtttt cccagtcacg acgttgtaaa acgacggcca 2340
gtgagcgcga cgtaatacga ctcactatag ggcgaattgg cggaaggccg tcaaggccgc 2400
atgaattcgc taccgggaag ttcctattcc gaagttccta ttctctagaa agtataggaa 2460
cttcaggtac c 2471

<210> SEQ ID NO 690

<400> SEQUENCE: 690

000

<210> SEQ ID NO 691

<400> SEQUENCE: 691

000

<210> SEQ ID NO 692

<400> SEQUENCE: 692

000

<210> SEQ ID NO 693

<400> SEQUENCE: 693

000

<210> SEQ ID NO 694

<400> SEQUENCE: 694

000

<210> SEQ ID NO 695

<400> SEQUENCE: 695

000

<210> SEQ ID NO 696

<400> SEQUENCE: 696

000

<210> SEQ ID NO 697

<400> SEQUENCE: 697

000

<210> SEQ ID NO 698

<400> SEQUENCE: 698

000

<210> SEQ ID NO 699

<400> SEQUENCE: 699

000

<210> SEQ ID NO 700

<400> SEQUENCE: 700

000

<210> SEQ ID NO 701
<211> LENGTH: 816
<212> TYPE: DNA
<213> ORGANISM: Homo sapiens
<220> FEATURE:
<223> OTHER INFORMATION: JG9 TRA FL

<400> SEQUENCE: 701

```
atgctccttg aacatttatt aataatcttg tggatgcagc tgacatgggt cagtggtcaa     60

cagctgaatc agagtcctca atctatgttt atccaggaag gagaagatgt ctccatgaac    120

tgcacttctt caagcatatt taacacctgg ctatggtaca agcaggaccc tggggaaggt    180

cctgtcctct tgatagcctt atataaggct ggtgaattga cctcaaatgg aagactgact    240

gctcagtttg gtataaccag aaaggacagc ttcctgaata tctcagcatc catacccagt    300

gatgtaggca tctacttctg tgctggaccc atgaaaacct cctacgacaa ggtgatattt    360

gggccaggga caagcttatc agtcattcca aatatccaga accctgaccc tgccgtgtac    420

cagctgagag actctaaatc cagtgacaag tctgtctgcc tattcaccga ttttgattct    480

caaacaaatg tgtcacaaag taaggattct gatgtgtata tcacagacaa aactgtgcta    540

gacatgaggt ctatggactt caagagcaac agtgctgtgg cctggagcaa caaatctgac    600

tttgcatgtg caaacgcctt caacaacagc attattccag aagacacctt cttccccagc    660

ccagaaagtt cctgtgatgt caagctggtc gagaaaagct ttgaaacaga tacgaaccta    720

aactttcaaa acctgtcagt gattgggttc cgaatcctcc tcctgaaagt ggccgggttt    780

aatctgctca tgacgctgcg gctgtggtcc agctga                              816
```

<210> SEQ ID NO 702
<211> LENGTH: 927
<212> TYPE: DNA
<213> ORGANISM: Homo sapiens
<220> FEATURE:
<223> OTHER INFORMATION: JG9 TRB FL

<400> SEQUENCE: 702

```
atggactcct ggaccttctg ctgtgtgtcc ctttgcatcc tggtagcaaa gcacacagat     60

gctggagtta tccagtcacc ccggcacgag gtgacagaga tgggacaaga agtgactctg    120

agatgtaaac caatttcagg acacgactac cttttctggt acagacagac catgatgcgg    180
```

ggactggagt tgctcattta ctttaacaac aacgttccga tagatgattc agggatgccc 240
gaggatcgat tctcagctaa gatgcctaat gcatcattct ccactctgaa gatccagccc 300
tcagaaccca gggactcagc tgtgtacttc tgtgccagca gttcggcaaa ctatggctac 360
accttcggtt cggggaccag gttaaccgtt gtagaggacc tgaacaaggt gttcccaccc 420
gaggtcgctg tgtttgagcc atcagaagca gagatctccc acacccaaaa ggccacactg 480
gtgtgcctgg ccacaggctt cttccctgac cacgtggagc tgagctggtg ggtgaatggg 540
aaggaggtgc acagtggggt cagcacggac ccgcagcccc tcaaggagca gcccgccctc 600
aatgactcca gatactgcct gagcagccgc ctgagggtct cggccacctt ctggcagaac 660
ccccgcaacc acttccgctg tcaagtccag ttctacgggc tctcggagaa tgacgagtgg 720
acccaggata gggccaaacc cgtcacccag atcgtcagcg ccgaggcctg gggtagagca 780
gactgtggct ttacctcggt gtcctaccag caaggggtcc tgtctgccac catcctctat 840
gagatcctgc tagggaaggc caccctgtat gctgtgctgg tcagcgccct tgtgttgatg 900
gccatggtca agagaaagga tttctga 927

<210> SEQ ID NO 703
<211> LENGTH: 40
<212> TYPE: DNA
<213> ORGANISM: Homo sapiens
<220> FEATURE:
<223> OTHER INFORMATION: JG9 TRA odeCDR3 F

<400> SEQUENCE: 703
ctgcgctgga cccatgaaaa cctcctacga caaggtgata 40

<210> SEQ ID NO 704
<211> LENGTH: 40
<212> TYPE: DNA
<213> ORGANISM: Homo sapiens
<220> FEATURE:
<223> OTHER INFORMATION: JG9 TRA odeCDR3 R

<400> SEQUENCE: 704
caaatatcac cttgtcgtag gaggttttca tgggtccagc 40

<210> SEQ ID NO 705
<211> LENGTH: 34
<212> TYPE: DNA
<213> ORGANISM: Homo sapiens
<220> FEATURE:
<223> OTHER INFORMATION: JG9 TRB odeCDR3 F

<400> SEQUENCE: 705
ttgcgccagc agttccgcaa actatggcta cacc 34

<210> SEQ ID NO 706
<211> LENGTH: 34
<212> TYPE: DNA
<213> ORGANISM: Homo sapiens
<220> FEATURE:
<223> OTHER INFORMATION: JG9 TRB odeCDR3 R

<400> SEQUENCE: 706
caaaggtgta gccatagttt gcggaactgc tggc 34

<210> SEQ ID NO 707

<400> SEQUENCE: 707

000

<210> SEQ ID NO 708

<400> SEQUENCE: 708

000

<210> SEQ ID NO 709

<400> SEQUENCE: 709

000

<210> SEQ ID NO 710

<400> SEQUENCE: 710

000

<210> SEQ ID NO 711

<400> SEQUENCE: 711

000

<210> SEQ ID NO 712

<400> SEQUENCE: 712

000

<210> SEQ ID NO 713

<400> SEQUENCE: 713

000

<210> SEQ ID NO 714

<400> SEQUENCE: 714

000

<210> SEQ ID NO 715

<400> SEQUENCE: 715

000

<210> SEQ ID NO 716

<400> SEQUENCE: 716

000

<210> SEQ ID NO 717

<400> SEQUENCE: 717

000

<210> SEQ ID NO 718

<400> SEQUENCE: 718

000

<210> SEQ ID NO 719

<400> SEQUENCE: 719

000

<210> SEQ ID NO 720

<400> SEQUENCE: 720

000

<210> SEQ ID NO 721

<400> SEQUENCE: 721

000

<210> SEQ ID NO 722

<400> SEQUENCE: 722

000

<210> SEQ ID NO 723

<400> SEQUENCE: 723

000

<210> SEQ ID NO 724

<400> SEQUENCE: 724

000

<210> SEQ ID NO 725

<400> SEQUENCE: 725

000

<210> SEQ ID NO 726

<400> SEQUENCE: 726

000

<210> SEQ ID NO 727

<400> SEQUENCE: 727

000

<210> SEQ ID NO 728

<400> SEQUENCE: 728

000

<210> SEQ ID NO 729

<400> SEQUENCE: 729

000

<210> SEQ ID NO 730

<400> SEQUENCE: 730

000

<210> SEQ ID NO 731

<400> SEQUENCE: 731

000

<210> SEQ ID NO 732

<400> SEQUENCE: 732

000

<210> SEQ ID NO 733

<400> SEQUENCE: 733

000

<210> SEQ ID NO 734

<400> SEQUENCE: 734

000

<210> SEQ ID NO 735

<400> SEQUENCE: 735

000

<210> SEQ ID NO 736

<400> SEQUENCE: 736

000

<210> SEQ ID NO 737

<400> SEQUENCE: 737

000

<210> SEQ ID NO 738

<400> SEQUENCE: 738

000

<210> SEQ ID NO 739

<400> SEQUENCE: 739

000

<210> SEQ ID NO 740

<400> SEQUENCE: 740

000

<210> SEQ ID NO 741

<400> SEQUENCE: 741

000

<210> SEQ ID NO 742

<400> SEQUENCE: 742

000

<210> SEQ ID NO 743
<211> LENGTH: 40
<212> TYPE: DNA
<213> ORGANISM: Artificial Sequence
<220> FEATURE:
<223> OTHER INFORMATION: Forward TRA odeCDR3 - 3 positions degenerate
<220> FEATURE:
<221> NAME/KEY: misc_feature
<222> LOCATION: 15
<223> OTHER INFORMATION: /note="n = a, t, c or g"
<220> FEATURE:
<221> NAME/KEY: misc_feature
<222> LOCATION: 20
<223> OTHER INFORMATION: /note="n = a, t, c or g"
<220> FEATURE:
<221> NAME/KEY: misc_feature
<222> LOCATION: 26
<223> OTHER INFORMATION: /note="n = a, t, c or g"

<400> SEQUENCE: 743
ctgcgctgga cccangaaan cctccnacga caaggtgata 40

<210> SEQ ID NO 744
<211> LENGTH: 40
<212> TYPE: DNA
<213> ORGANISM: Artificial Sequence
<220> FEATURE:
<223> OTHER INFORMATION: Reverse TRA odeCDR3 - 3 positions degenerate
<220> FEATURE:
<221> NAME/KEY: misc_feature
<222> LOCATION: 19
<223> OTHER INFORMATION: /note="n = a, t, c or g"
<220> FEATURE:
<221> NAME/KEY: misc_feature
<222> LOCATION: 25
<223> OTHER INFORMATION: /note="n = a, t, c or g"
<220> FEATURE:
<221> NAME/KEY: misc_feature
<222> LOCATION: 30
<223> OTHER INFORMATION: /note="n = a, t, c or g"

<400> SEQUENCE: 744
caaatatcac cttgtcgtng gaggntttcn tgggtccagc 40

<210> SEQ ID NO 745
<211> LENGTH: 6071
<212> TYPE: DNA
<213> ORGANISM: Artificial Sequence
<220> FEATURE:
<223> OTHER INFORMATION: pcDNA3.1_GFP vector V1.A.4

<400> SEQUENCE: 745
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300

```
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgccaccat ggaatccgat gagtctggcc tgcccgccat    960
ggaaatcgag tgcagaatca ccggcaccct gaacggcgtg gaatttgagc tcgtgggcgg   1020
aggcgagggc acacctgaac agggcagaat gaccaacaag atgaagtcca ccaagggggc   1080
cctgaccttc agcccctacc tgctgtctca cgtgatgggc tacggcttct accacttcgg   1140
cacctacccc agcggctacg agaacccttt cctgcacgcc atcaacaacg gcggctacac   1200
caacacccgg atcgagaagt acgaggacgg cggcgtgctg cacgtgtcct tcagctacag   1260
atacgaggcc ggcagagtga tcggcgactt caaagtgatg ggcaccggat tccccgagga   1320
cagcgtgatc ttcaccgaca agatcatccg gtccaacgcc accgtggaac atctgcaccc   1380
catgggcgac aacgacctgg acggcagctt caccagaacc ttctccctgc gggatggcgg   1440
ctactacagc agcgtggtgg acagccacat gcacttcaag agcgccatcc accccagcat   1500
cctccagaac ggcggaccca tgttcgcctt cagacgggtg gaagaggacc acagcaacac   1560
cgagctgggc atcgtggaat accagcacgc cttcaagacc cccgatgccg atgccggcga   1620
ggaatgagtc gagtctagag ggcccgttta aacccgctga tcagcctcga ctgtgccttc   1680
tagttgccag ccatctgttg tttgcccctc ccccgtgcct tccttgaccc tggaaggtgc   1740
cactcccact gtcctttcct aataaaatga ggaaattgca tcgcattgtc tgagtaggtg   1800
tcattctatt ctggggggtg gggtggggca ggacagcaag ggggaggatt gggaagacaa   1860
tagcaggcat gctggggatg cggtgggctc tatggcttct gaggcggaaa gaaccagctg   1920
gggctctagg gggtatcccc acgcgccctg tagcggcgca ttaagcgcgg cgggtgtggt   1980
ggttacgcgc agcgtgaccg ctacacttgc cagcgcccta gcgcccgctc ctttcgcttt   2040
cttcccttcc tttctcgcca cgttcgccgg ctttccccgt caagctctaa atcgggggct   2100
ccctttaggg ttccgattta gtgctttacg gcacctcgac cccaaaaaac ttgattaggg   2160
tgatggttca cgtagtgggc catcgccctg atagacggtt tttcgccctt tgacgttgga   2220
gtccacgttc tttaatagtg gactcttgtt ccaaactgga acaacactca accctatctc   2280
ggtctattct tttgatttat aagggatttt gccgatttcg gcctattggt taaaaaatga   2340
gctgatttaa caaaaattta acgcgaatta attctgtgga atgtgtgtca gttagggtgt   2400
ggaaagtccc caggctcccc agcaggcaga agtatgcaaa gcatgcatct caattagtca   2460
gcaaccaggt gtggaaagtc cccaggctcc ccagcaggca gaagtatgca aagcatgcat   2520
ctcaattagt cagcaaccat agtcccgccc ctaactccgc ccatcccgcc cctaactccg   2580
cccagttccg cccattctcc gccccatggc tgactaattt tttttattta tgcagaggcc   2640
gaggccgcct ctgcctctga gctattccag aagtagtgag gaggcttttt tggaggccta   2700
```

```
ggcttttgca aaaagctccc gggagcttgt atatccattt tcggatctga tcaagagaca   2760

ggatgaggat cgtttcgcat gattgaacaa gatggattgc acgcaggttc tccggccgct   2820

tgggtggaga ggctattcgg ctatgactgg gcacaacaga caatcggctg ctctgatgcc   2880

gccgtgttcc ggctgtcagc gcaggggcgc ccggttcttt ttgtcaagac cgacctgtcc   2940

ggtgccctga atgaactgca ggacgaggca gcgcggctat cgtggctggc cacgacgggc   3000

gttccttgcg cagctgtgct cgacgttgtc actgaagcgg gaagggactg gctgctattg   3060

ggcgaagtgc cggggcagga tctcctgtca tctcaccttg ctcctgccga gaaagtatcc   3120

atcatggctg atgcaatgcg gcggctgcat acgcttgatc cggctacctg cccattcgac   3180

caccaagcga aacatcgcat cgagcgagca cgtactcgga tggaagccgg tcttgtcgat   3240

caggatgatc tggacgaaga gcatcagggg ctcgcgccag ccgaactgtt cgccaggctc   3300

aaggcgcgca tgcccgacgg cgaggatctc gtcgtgaccc atggcgatgc ctgcttgccg   3360

aatatcatgg tggaaaatgg ccgcttttct ggattcatcg actgtggccg gctgggtgtg   3420

gcggaccgct atcaggacat agcgttggct acccgtgata ttgctgaaga gcttggcggc   3480

gaatgggctg accgcttcct cgtgctttac ggtatcgccg ctcccgattc gcagcgcatc   3540

gccttctatc gccttcttga cgagttcttc tgagcgggac tctggggttc gaaatgaccg   3600

accaagcgac gcccaacctg ccatcacgag atttcgattc caccgccgcc ttctatgaaa   3660

ggttgggctt cggaatcgtt ttccgggacg ccggctggat gatcctccag cgcggggatc   3720

tcatgctgga gttcttcgcc caccccaact tgtttattgc agcttataat ggttacaaat   3780

aaagcaatag catcacaaat ttcacaaata aagcattttt ttcactgcat tctagttgtg   3840

gtttgtccaa actcatcaat gtatcttatc atgtctgtat accgtcgacc tctagctaga   3900

gcttggcgta atcatggtca tagctgtttc ctgtgtgaaa ttgttatccg ctcacaattc   3960

cacacaacat acgagccgga agcataaagt gtaaagcctg gggtgcctaa tgagtgagct   4020

aactcacatt aattgcgttg cgctcactgc ccgctttcca gtcgggaaac ctgtcgtgcc   4080

agctgcatta atgaatcggc caacgcgcgg ggagaggcgg tttgcgtatt gggcgctctt   4140

ccgcttcctc gctcactgac tcgctgcgct cggtcgttcg gctgcggcga gcggtatcag   4200

ctcactcaaa ggcggtaata cggttatcca cagaatcagg ggataacgca ggaaagaaca   4260

tgtgagcaaa aggccagcaa aaggccagga accgtaaaaa ggccgcgttg ctggcgtttt   4320

tccataggct ccgcccccct gacgagcatc acaaaaatcg acgctcaagt cagaggtggc   4380

gaaacccgac aggactataa agataccagg cgtttccccc tggaagctcc ctcgtgcgct   4440

ctcctgttcc gaccctgccg cttaccggat acctgtccgc ctttctccct tcgggaagcg   4500

tggcgctttc tcatagctca cgctgtaggt atctcagttc ggtgtaggtc gttcgctcca   4560

agctgggctg tgtgcacgaa ccccccgttc agcccgaccg ctgcgcctta tccggtaact   4620

atcgtcttga gtccaacccg gtaagacacg acttatcgcc actggcagca gccactggta   4680

acaggattag cagagcgagg tatgtaggcg gtgctacaga gttcttgaag tggtggccta   4740

actacggcta cactagaaga acagtatttg gtatctgcgc tctgctgaag ccagttacct   4800

tcggaaaaag agttggtagc tcttgatccg gcaaacaaac caccgctggt agcggttttt   4860

ttgtttgcaa gcagcagatt acgcgcagaa aaaaaggatc tcaagaagat cctttgatct   4920

tttctacggg gtctgacgct cagtggaacg aaaactcacg ttaagggatt ttggtcatga   4980

gattatcaaa aaggatcttc acctagatcc ttttaaatta aaaatgaagt tttaaatcaa   5040
```

```
tctaaagtat atatgagtaa acttggtctg acagttacca atgcttaatc agtgaggcac   5100
ctatctcagc gatctgtcta tttcgttcat ccatagttgc ctgactcccc gtcgtgtaga   5160
taactacgat acgggagggc ttaccatctg gccccagtgc tgcaatgata ccgcgagacc   5220
cacgctcacc ggctccagat ttatcagcaa taaaccagcc agccggaagg gccgagcgca   5280
gaagtggtcc tgcaacttta tccgcctcca tccagtctat taattgttgc cgggaagcta   5340
gagtaagtag ttcgccagtt aatagtttgc gcaacgttgt tgccattgct acaggcatcg   5400
tggtgtcacg ctcgtcgttt ggtatggctt cattcagctc cggttcccaa cgatcaaggc   5460
gagttacatg atcccccatg ttgtgcaaaa aagcggttag ctccttcggt cctccgatcg   5520
ttgtcagaag taagttggcc gcagtgttat cactcatggt tatggcagca ctgcataatt   5580
ctcttactgt catgccatcc gtaagatgct tttctgtgac tggtgagtac tcaaccaagt   5640
cattctgaga atagtgtatg cggcgaccga gttgctcttg cccggcgtca atacgggata   5700
ataccgcgcc acatagcaga actttaaaag tgctcatcat tggaaaacgt tcttcggggc   5760
gaaaactctc aaggatctta ccgctgttga gatccagttc gatgtaaccc actcgtgcac   5820
ccaactgatc ttcagcatct tttactttca ccagcgtttc tgggtgagca aaaacaggaa   5880
ggcaaaatgc cgcaaaaaag ggaataaggg cgacacggaa atgttgaata ctcatactct   5940
tcctttttca atattattga agcatttatc agggttattg tctcatgagc ggatacatat   6000
ttgaatgtat ttagaaaaat aaacaaatag gggttccgcg cacatttccc cgaaaagtgc   6060
cacctgacgt c                                                        6071
```

<210> SEQ ID NO 746
<211> LENGTH: 6068
<212> TYPE: DNA
<213> ORGANISM: Artificial Sequence
<220> FEATURE:
<223> OTHER INFORMATION: pcDNA3.1_RFP vector V1.A.6

<400> SEQUENCE: 746

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgccaccat gagcgagctg atcaaagaaa acatgcacat    960
gaagctgtac atggaaggca ccgtgaacaa ccaccacttc aagtgcacca gcgagggcga   1020
```

```
gggcaagcct tacgagggca cccagaccat gaagatcaag gtggtggaag gcggccctct   1080
gcccttcgcc tttgatatcc tggccaccag ctttatgtac ggcagcaagg ccttcatcaa   1140
ccacacccag ggcatccccg atttcttcaa gcagagcttc cccgagggct tcacctggga   1200
gcggatcacc acatacgagg acggcggagt gctgaccgcc acccaggata ccagcttcca   1260
gaacggctgc atcatctaca acgtgaagat taacggcgtg aacttcccca gcaacggccc   1320
cgtgatgcag aagaaaacca gaggctggga ggccaacacc gagatgctgt accctgccga   1380
tggcggcctg agaggccatt ctcagatggc cctgaaactc gtgggcggag gctacctgca   1440
ctgctccttc aagaccacct acagaagcaa gaagcccgcc aagaacctga agatgcccgg   1500
cttccacttc gtggaccacc ggctggaacg gatcaaagag gccgacaaag aaacctacgt   1560
ggaacagcac gagatggccg tggccaagta ctgcgacctg cctagcaagc tgggccacag   1620
atgagtcgag tctagagggc ccgtttaaac ccgctgatca gcctcgactg tgccttctag   1680
ttgccagcca tctgttgttt gcccctcccc cgtgccttcc ttgaccctgg aaggtgccac   1740
tcccactgtc ctttcctaat aaaatgagga aattgcatcg cattgtctga gtaggtgtca   1800
ttctattctg gggggtgggg tggggcagga cagcaagggg gaggattggg aagacaatag   1860
caggcatgct ggggatgcgg tgggctctat ggcttctgag gcggaaagaa ccagctgggg   1920
ctctaggggg tatccccacg cgccctgtag cggcgcatta agcgcggcgg gtgtggtggt   1980
tacgcgcagc gtgaccgcta cacttgccag cgccctagcg cccgctcctt tcgctttctt   2040
cccttccttt ctcgccacgt tcgccggctt tccccgtcaa gctctaaatc gggggctccc   2100
tttagggttc cgatttagtg ctttacggca cctcgacccc aaaaaacttg attagggtga   2160
tggttcacgt agtgggccat cgccctgata gacggttttt cgccctttga cgttggagtc   2220
cacgttcttt aatagtggac tcttgttcca aactggaaca acactcaacc ctatctcggt   2280
ctattctttt gatttataag ggattttgcc gatttcggcc tattggttaa aaaatgagct   2340
gatttaacaa aaatttaacg cgaattaatt ctgtggaatg tgtgtcagtt agggtgtgga   2400
aagtccccag gctccccagc aggcagaagt atgcaaagca tgcatctcaa ttagtcagca   2460
accaggtgtg gaaagtcccc aggctcccca gcaggcagaa gtatgcaaag catgcatctc   2520
aattagtcag caaccatagt cccgccccta actccgccca tcccgcccct aactccgccc   2580
agttccgccc attctccgcc ccatggctga ctaatttttt ttatttatgc agaggccgag   2640
gccgcctctg cctctgagct attccagaag tagtgaggag gcttttttgg aggcctaggc   2700
ttttgcaaaa agctcccggg agcttgtata tccattttcg gatctgatca agagacagga   2760
tgaggatcgt ttcgcatgat tgaacaagat ggattgcacg caggttctcc ggccgcttgg   2820
gtggagaggc tattcggcta tgactgggca caacagacaa tcggctgctc tgatgccgcc   2880
gtgttccggc tgtcagcgca ggggcgcccg gttctttttg tcaagaccga cctgtccggt   2940
gccctgaatg aactgcagga cgaggcagcg cggctatcgt ggctggccac gacgggcgtt   3000
ccttgcgcag ctgtgctcga cgttgtcact gaagcgggaa gggactggct gctattgggc   3060
gaagtgccgg ggcaggatct cctgtcatct caccttgctc ctgccgagaa agtatccatc   3120
atggctgatg caatgcggcg gctgcatacg cttgatccgg ctacctgccc attcgaccac   3180
caagcgaaac atcgcatcga gcgagcacgt actcggatgg aagccggtct tgtcgatcag   3240
gatgatctgg acgaagagca tcaggggctc gcgccagccg aactgttcgc caggctcaag   3300
gcgcgcatgc ccgacggcga ggatctcgtc gtgacccatg gcgatgcctg cttgccgaat   3360
```

```
atcatggtgg aaaatggccg cttttctgga ttcatcgact gtggccggct gggtgtggcg   3420
gaccgctatc aggacatagc gttggctacc cgtgatattg ctgaagagct tggcggcgaa   3480
tgggctgacc gcttcctcgt gctttacggt atcgccgctc ccgattcgca gcgcatcgcc   3540
ttctatcgcc ttcttgacga gttcttctga gcgggactct ggggttcgaa atgaccgacc   3600
aagcgacgcc caacctgcca tcacgagatt tcgattccac cgccgccttc tatgaaaggt   3660
tgggcttcgg aatcgttttc cgggacgccg gctggatgat cctccagcgc ggggatctca   3720
tgctggagtt cttcgcccac cccaacttgt ttattgcagc ttataatggt tacaaataaa   3780
gcaatagcat cacaaatttc acaaataaag catttttttc actgcattct agttgtggtt   3840
tgtccaaact catcaatgta tcttatcatg tctgtatacc gtcgacctct agctagagct   3900
tggcgtaatc atggtcatag ctgtttcctg tgtgaaattg ttatccgctc acaattccac   3960
acaacatacg agccggaagc ataaagtgta aagcctgggg tgcctaatga gtgagctaac   4020
tcacattaat tgcgttgcgc tcactgcccg ctttccagtc gggaaacctg tcgtgccagc   4080
tgcattaatg aatcggccaa cgcgcgggga gaggcggttt gcgtattggg cgctcttccg   4140
cttcctcgct cactgactcg ctgcgctcgg tcgttcggct gcggcgagcg gtatcagctc   4200
actcaaaggc ggtaatacgg ttatccacag aatcagggga taacgcagga aagaacatgt   4260
gagcaaaagg ccagcaaaag gccaggaacc gtaaaaaggc cgcgttgctg gcgtttttcc   4320
ataggctccg cccccctgac gagcatcaca aaaatcgacg ctcaagtcag aggtggcgaa   4380
acccgacagg actataaaga taccaggcgt ttccccctgg aagctccctc gtgcgctctc   4440
ctgttccgac cctgccgctt accggatacc tgtccgcctt tctcccttcg ggaagcgtgg   4500
cgctttctca tagctcacgc tgtaggtatc tcagttcggt gtaggtcgtt cgctccaagc   4560
tgggctgtgt gcacgaaccc cccgttcagc ccgaccgctg cgccttatcc ggtaactatc   4620
gtcttgagtc caacccggta agacacgact tatcgccact ggcagcagcc actggtaaca   4680
ggattagcag agcgaggtat gtaggcggtg ctacagagtt cttgaagtgg tggcctaact   4740
acggctacac tagaagaaca gtatttggta tctgcgctct gctgaagcca gttaccttcg   4800
gaaaaagagt tggtagctct tgatccggca aacaaaccac cgctggtagc ggtttttttg   4860
tttgcaagca gcagattacg cgcagaaaaa aaggatctca agaagatcct ttgatctttt   4920
ctacggggtc tgacgctcag tggaacgaaa actcacgtta agggattttg gtcatgagat   4980
tatcaaaaag gatcttcacc tagatccttt taaattaaaa atgaagtttt aaatcaatct   5040
aaagtatata tgagtaaact tggtctgaca gttaccaatg cttaatcagt gaggcaccta   5100
tctcagcgat ctgtctattt cgttcatcca tagttgcctg actccccgtc gtgtagataa   5160
ctacgatacg ggagggctta ccatctggcc ccagtgctgc aatgataccg cgagacccac   5220
gctcaccggc tccagattta tcagcaataa accagccagc cggaagggcc gagcgcagaa   5280
gtggtcctgc aactttatcc gcctccatcc agtctattaa ttgttgccgg gaagctagag   5340
taagtagttc gccagttaat agtttgcgca acgttgttgc cattgctaca ggcatcgtgg   5400
tgtcacgctc gtcgtttggt atggcttcat tcagctccgg ttcccaacga tcaaggcgag   5460
ttacatgatc ccccatgttg tgcaaaaaag cggttagctc cttcggtcct ccgatcgttg   5520
tcagaagtaa gttggccgca gtgttatcac tcatggttat ggcagcactg cataattctc   5580
ttactgtcat gccatccgta agatgctttt ctgtgactgg tgagtactca accaagtcat   5640
tctgagaata gtgtatgcgg cgaccgagtt gctcttgccc ggcgtcaata cgggataata   5700
ccgcgccaca tagcagaact ttaaaagtgc tcatcattgg aaaacgttct tcggggcgaa   5760
```

```
aactctcaag gatcttaccg ctgttgagat ccagttcgat gtaacccact cgtgcaccca   5820

actgatcttc agcatctttt actttcacca gcgtttctgg gtgagcaaaa acaggaaggc   5880

aaaatgccgc aaaaaaggga ataagggcga cacggaaatg ttgaatactc atactcttcc   5940

tttttcaata ttattgaagc atttatcagg gttattgtct catgagcgga tacatatttg   6000

aatgtattta gaaaaataaa caaatagggg ttccgcgcac atttccccga aaagtgccac   6060

ctgacgtc                                                            6068
```

<210> SEQ ID NO 747
<211> LENGTH: 6071
<212> TYPE: DNA
<213> ORGANISM: Artificial Sequence
<220> FEATURE:
<223> OTHER INFORMATION: pMA-SV40pA vector V1.C.2

<400> SEQUENCE: 747

```
gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtttaaactt aagcttggta ccgccaccat ggaatccgat gagtctggcc tgcccgccat    960

ggaaatcgag tgcagaatca ccggcaccct gaacggcgtg gaatttgagc tcgtgggcgg   1020

aggcgagggc acacctgaac agggcagaat gaccaacaag atgaagtcca ccaagggggc   1080

cctgaccttc agcccctacc tgctgtctca cgtgatgggc tacggcttct accacttcgg   1140

cacctacccc agcggctacg agaacccttt cctgcacgcc atcaacaacg gcggctacac   1200

caacacccgg atcgagaagt acgaggacgg cggcgtgctg cacgtgtcct tcagctacag   1260

atacgaggcc ggcagagtga tcggcgactt caaagtgatg ggcaccggat tccccgagga   1320

cagcgtgatc ttcaccgaca agatcatccg gtccaacgcc accgtggaac atctgcaccc   1380

catgggcgac aacgacctgg acggcagctt caccagaacc ttctccctgc gggatggcgg   1440

ctactacagc agcgtggtgg acagccacat gcacttcaag agcgccatcc accccagcat   1500

cctccagaac ggcggaccca tgttcgcctt cagacgggtg gaagaggacc acagcaacac   1560

cgagctgggc atcgtggaat accagcacgc cttcaagacc cccgatgccg atgccggcga   1620

ggaatgagtc gagtctagag ggcccgttta aacccgctga tcagcctcga ctgtgccttc   1680
```

```
tagttgccag ccatctgttg tttgcccctc ccccgtgcct tccttgaccc tggaaggtgc   1740
cactcccact gtcctttcct aataaaatga ggaaattgca tcgcattgtc tgagtaggtg   1800
tcattctatt ctggggggtg gggtggggca ggacagcaag ggggaggatt gggaagacaa   1860
tagcaggcat gctggggatg cggtgggctc tatggcttct gaggcggaaa gaaccagctg   1920
gggctctagg gggtatcccc acgcgccctg tagcggcgca ttaagcgcgg cgggtgtggt   1980
ggttacgcgc agcgtgaccg ctacacttgc cagcgcccta gcgcccgctc ctttcgcttt   2040
cttcccttcc tttctcgcca cgttcgccgg ctttccccgt caagctctaa atcgggggct   2100
ccctttaggg ttccgattta gtgctttacg gcacctcgac cccaaaaaac ttgattaggg   2160
tgatggttca cgtagtgggc catcgccctg atagacggtt tttcgccctt tgacgttgga   2220
gtccacgttc tttaatagtg gactcttgtt ccaaactgga acaacactca accctatctc   2280
ggtctattct tttgatttat aagggatttt gccgatttcg gcctattggt taaaaaatga   2340
gctgatttaa caaaaattta acgcgaatta attctgtgga atgtgtgtca gttagggtgt   2400
ggaaagtccc caggctcccc agcaggcaga agtatgcaaa gcatgcatct caattagtca   2460
gcaaccaggt gtggaaagtc cccaggctcc ccagcaggca gaagtatgca aagcatgcat   2520
ctcaattagt cagcaaccat agtcccgccc ctaactccgc ccatcccgcc cctaactccg   2580
cccagttccg cccattctcc gccccatggc tgactaattt tttttattta tgcagaggcc   2640
gaggccgcct ctgcctctga gctattccag aagtagtgag gaggcttttt tggaggccta   2700
ggcttttgca aaaagctccc gggagcttgt atatccattt tcggatctga tcaagagaca   2760
ggatgaggat cgtttcgcat gattgaacaa gatggattgc acgcaggttc tccggccgct   2820
tgggtggaga ggctattcgg ctatgactgg gcacaacaga caatcggctg ctctgatgcc   2880
gccgtgttcc ggctgtcagc gcaggggcgc ccggttcttt ttgtcaagac cgacctgtcc   2940
ggtgccctga atgaactgca ggacgaggca gcgcggctat cgtggctggc cacgacgggc   3000
gttccttgcg cagctgtgct cgacgttgtc actgaagcgg gaagggactg gctgctattg   3060
ggcgaagtgc cggggcagga tctcctgtca tctcaccttg ctcctgccga gaaagtatcc   3120
atcatggctg atgcaatgcg gcggctgcat acgcttgatc cggctacctg cccattcgac   3180
caccaagcga aacatcgcat cgagcgagca cgtactcgga tggaagccgg tcttgtcgat   3240
caggatgatc tggacgaaga gcatcagggg ctcgcgccag ccgaactgtt cgccaggctc   3300
aaggcgcgca tgcccgacgg cgaggatctc gtcgtgaccc atggcgatgc ctgcttgccg   3360
aatatcatgg tggaaaatgg ccgcttttct ggattcatcg actgtggccg gctgggtgtg   3420
gcggaccgct atcaggacat agcgttggct acccgtgata ttgctgaaga gcttggcggc   3480
gaatgggctg accgcttcct cgtgctttac ggtatcgccg ctcccgattc gcagcgcatc   3540
gccttctatc gccttcttga cgagttcttc tgagcgggac tctggggttc gaaatgaccg   3600
accaagcgac gcccaacctg ccatcacgag atttcgattc caccgccgcc ttctatgaaa   3660
ggttgggctt cggaatcgtt ttccgggacg ccggctggat gatcctccag cgcggggatc   3720
tcatgctgga gttcttcgcc caccccaact tgtttattgc agcttataat ggttacaaat   3780
aaagcaatag catcacaaat ttcacaaata aagcattttt ttcactgcat tctagttgtg   3840
gtttgtccaa actcatcaat gtatcttatc atgtctgtat accgtcgacc tctagctaga   3900
gcttggcgta atcatggtca tagctgtttc ctgtgtgaaa ttgttatccg ctcacaattc   3960
cacacaacat acgagccgga agcataaagt gtaaagcctg gggtgcctaa tgagtgagct   4020
aactcacatt aattgcgttg cgctcactgc ccgctttcca gtcgggaaac ctgtcgtgcc   4080
```

```
agctgcatta atgaatcggc caacgcgcgg ggagaggcgg tttgcgtatt gggcgctctt   4140

ccgcttcctc gctcactgac tcgctgcgct cggtcgttcg gctgcggcga gcggtatcag   4200

ctcactcaaa ggcggtaata cggttatcca cagaatcagg ggataacgca ggaaagaaca   4260

tgtgagcaaa aggccagcaa aaggccagga accgtaaaaa ggccgcgttg ctggcgtttt   4320

tccataggct ccgcccccct gacgagcatc acaaaaatcg acgctcaagt cagaggtggc   4380

gaaacccgac aggactataa agataccagg cgtttccccc tggaagctcc ctcgtgcgct   4440

ctcctgttcc gaccctgccg cttaccggat acctgtccgc ctttctccct tcgggaagcg   4500

tggcgctttc tcatagctca cgctgtaggt atctcagttc ggtgtaggtc gttcgctcca   4560

agctgggctg tgtgcacgaa ccccccgttc agcccgaccg ctgcgcctta tccggtaact   4620

atcgtcttga gtccaacccg gtaagacacg acttatcgcc actggcagca gccactggta   4680

acaggattag cagagcgagg tatgtaggcg gtgctacaga gttcttgaag tggtggccta   4740

actacggcta cactagaaga acagtatttg gtatctgcgc tctgctgaag ccagttacct   4800

tcggaaaaag agttggtagc tcttgatccg gcaaacaaac caccgctggt agcggttttt   4860

ttgtttgcaa gcagcagatt acgcgcagaa aaaaaggatc tcaagaagat cctttgatct   4920

tttctacggg gtctgacgct cagtggaacg aaaactcacg ttaagggatt ttggtcatga   4980

gattatcaaa aaggatcttc acctagatcc ttttaaatta aaaatgaagt tttaaatcaa   5040

tctaaagtat atatgagtaa acttggtctg acagttacca atgcttaatc agtgaggcac   5100

ctatctcagc gatctgtcta tttcgttcat ccatagttgc ctgactcccc gtcgtgtaga   5160

taactacgat acgggagggc ttaccatctg gccccagtgc tgcaatgata ccgcgagacc   5220

cacgctcacc ggctccagat ttatcagcaa taaaccagcc agccggaagg gccgagcgca   5280

gaagtggtcc tgcaacttta tccgcctcca tccagtctat taattgttgc cgggaagcta   5340

gagtaagtag ttcgccagtt aatagtttgc gcaacgttgt tgccattgct acaggcatcg   5400

tggtgtcacg ctcgtcgttt ggtatggctt cattcagctc cggttcccaa cgatcaaggc   5460

gagttacatg atcccccatg ttgtgcaaaa aagcggttag ctccttcggt cctccgatcg   5520

ttgtcagaag taagttggcc gcagtgttat cactcatggt tatggcagca ctgcataatt   5580

ctcttactgt catgccatcc gtaagatgct tttctgtgac tggtgagtac tcaaccaagt   5640

cattctgaga atagtgtatg cggcgaccga gttgctcttg cccggcgtca atacgggata   5700

ataccgcgcc acatagcaga actttaaaag tgctcatcat tggaaaacgt tcttcggggc   5760

gaaaactctc aaggatctta ccgctgttga gatccagttc gatgtaaccc actcgtgcac   5820

ccaactgatc ttcagcatct tttactttca ccagcgtttc tgggtgagca aaaacaggaa   5880

ggcaaaatgc cgcaaaaaag ggaataaggg cgacacggaa atgttgaata ctcatactct   5940

tcctttttca atattattga agcatttatc agggttattg tctcatgagc ggatacatat   6000

ttgaatgtat ttagaaaaat aaacaaatag gggttccgcg cacatttccc cgaaaagtgc   6060

cacctgacgt c                                                         6071
```

<210> SEQ ID NO 748
<211> LENGTH: 6275
<212> TYPE: DNA
<213> ORGANISM: Artificial Sequence
<220> FEATURE:
<223> OTHER INFORMATION: pMA-CS-JG9-TCRbeta vector V3.C.5

<400> SEQUENCE: 748

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccaccatg gactcctgga ccttctgctg    960
tgtgtccctt tgcatcctgg tagcaaagca cacagatgct ggagttatcc agtcaccccg   1020
gcacgaggtg acagagatgg gacaagaagt gactctgaga tgtaaaccaa tttcaggaca   1080
cgactacctt ttctggtaca gacagaccat gatgcgggga ctggagttgc tcatttactt   1140
taacaacaac gttccgatag atgattcagg gatgcccgag gatcgattct cagctaagat   1200
gcctaatgca tcattctcca ctctgaagat ccagccctca gaacccaggg actcagctgt   1260
gtacttctgt gccagcagtt cggcaaacta tggctacacc ttcggttcgg ggaccaggtt   1320
aaccgttgta gaggacctga acaaggtgtt cccacccgag gtcgctgtgt ttgagccatc   1380
agaagcagag atctcccaca cccaaaaggc cacactggtg tgcctggcca caggcttctt   1440
ccctgaccac gtggagctga gctggtgggt gaatgggaag gaggtgcaca gtggggtcag   1500
cacggacccg cagcccctca aggagcagcc cgccctcaat gactccagat actgcctgag   1560
cagccgcctg agggtctcgg ccaccttctg gcagaacccc cgcaaccact tccgctgtca   1620
agtccagttc tacgggctct cggagaatga cgagtggacc caggataggg ccaaacccgt   1680
cacccagatc gtcagcgccg aggcctgggg tagagcagac tgtggcttta cctcggtgtc   1740
ctaccagcaa ggggtcctgt ctgccaccat cctctatgag atcctgctag ggaaggccac   1800
cctgtatgct gtgctggtca gcgcccttgt gttgatggcc atggtcaaga gaaaggattt   1860
ctgattctag acgactgtgc cttctagttg ccagccatct gttgtttgcc cctcccccgt   1920
gccttccttg accctggaag gtgccactcc cactgtcctt tcctaataaa atgaggaaat   1980
tgcatcgcat tgtctgagta ggtgtcattc tattctgggg ggtggggtgg ggcaggacag   2040
caagggggag gattgggaag acaatagcag gcatgctggg gatgcggtgg gctctatggc   2100
ttctgaggcg gaaagaacca gctggggctc taggggggtat ccccacgcgc cctgtagcgg  2160
cgcattaagc gcggcgggtg tggtggttac gcgcagcgtg accgctacac ttgccagcgc   2220
cctagcgccc gctcctttcg ctttcttccc ttcctttctc gccacgttcg ccggctttcc   2280
ccgtcaagct ctaaatcggg ggctcccttt agggttccga tttagtgctt tacggcacct   2340
cgaccccaaa aaacttgatt agggtgatgg ttcacgtagt gggccatcgc cctgatagac   2400
```

```
ggtttttcgc cctttgacgt tggagtccac gttctttaat agtggactct tgttccaaac   2460
tggaacaaca ctcaacccta tctcggtcta ttcttttgat ttataaggga ttttgccgat   2520
ttcggcctat tggttaaaaa atgagctgat ttaacaaaaa tttaacgcga attaattctg   2580
tggaatgtgt gtcagttagg gtgtggaaag tccccaggct ccccagcagg cagaagtatg   2640
caaagcatgc atctcaatta gtcagcaacc aggtgtggaa agtccccagg ctccccagca   2700
ggcagaagta tgcaaagcat gcatctcaat tagtcagcaa ccatagtccc gcccctaact   2760
ccgcccatcc cgcccctaac tccgcccagt tccgcccatt ctccgcccca tggctgacta   2820
atttttttta tttatgcaga ggccgaggcc gcctctgcct ctgagctatt ccagaagtag   2880
tgaggaggct tttttggagg cctaggcttt tgcaaaaagc tcccgggagc ttgtatatcc   2940
attttcggat ctgatcaaga gacaggatga ggatcgtttc gcatgattga acaagatgga   3000
ttgcacgcag gttctccggc cgcttgggtg gagaggctat tcggctatga ctgggcacaa   3060
cagacaatcg gctgctctga tgccgccgtg ttccggctgt cagcgcaggg gcgcccggtt   3120
ctttttgtca agaccgacct gtccggtgcc ctgaatgaac tgcaggacga ggcagcgcgg   3180
ctatcgtggc tggccacgac gggcgttcct tgcgcagctg tgctcgacgt tgtcactgaa   3240
gcgggaaggg actggctgct attgggcgaa gtgccggggc aggatctcct gtcatctcac   3300
cttgctcctg ccgagaaagt atccatcatg gctgatgcaa tgcggcggct gcatacgctt   3360
gatccggcta cctgcccatt cgaccaccaa gcgaaacatc gcatcgagcg agcacgtact   3420
cggatggaag ccggtcttgt cgatcaggat gatctggacg aagagcatca ggggctcgcg   3480
ccagccgaac tgttcgccag gctcaaggcg cgcatgcccg acggcgagga tctcgtcgtg   3540
acccatggcg atgcctgctt gccgaatatc atggtggaaa atggccgctt ttctggattc   3600
atcgactgtg gccggctggg tgtggcggac cgctatcagg acatagcgtt ggctacccgt   3660
gatattgctg aagagcttgg cggcgaatgg gctgaccgct tcctcgtgct ttacggtatc   3720
gccgctcccg attcgcagcg catcgccttc tatcgccttc ttgacgagtt cttctgagcg   3780
ggactctggg gttcgaaatg accgaccaag cgacgcccaa cctgccatca cgagatttcg   3840
attccaccgc cgccttctat gaaaggttgg gcttcggaat cgttttccgg gacgccggct   3900
ggatgatcct ccagcgcggg gatctcatgc tggagttctt cgcccacccc aacttgttta   3960
ttgcagctta taatggttac aaataaagca atagcatcac aaatttcaca aataaagcat   4020
ttttttcact gcattctagt tgtggtttgt ccaaactcat caatgtatct tatcatgtct   4080
gtataccgtc gacctctagc tagagcttgg cgtaatcatg gtcatagctg tttcctgtgt   4140
gaaattgtta tccgctcaca attccacaca acatacgagc cggaagcata aagtgtaaag   4200
cctggggtgc ctaatgagtg agctaactca cattaattgc gttgcgctca ctgcccgctt   4260
tccagtcggg aaacctgtcg tgccagctgc attaatgaat cggccaacgc gcggggagag   4320
gcggtttgcg tattgggcgc tcttccgctt cctcgctcac tgactcgctg cgctcggtcg   4380
ttcggctgcg gcgagcggta tcagctcact caaaggcggt aatacggtta tccacagaat   4440
caggggataa cgcaggaaag aacatgtgag caaaaggcca gcaaaaggcc aggaaccgta   4500
aaaaggccgc gttgctggcg tttttccata ggctccgccc ccctgacgag catcacaaaa   4560
atcgacgctc aagtcagagg tggcgaaacc cgacaggact ataaagatac caggcgtttc   4620
cccctggaag ctccctcgtg cgctctcctg ttccgaccct gccgcttacc ggatacctgt   4680
ccgcctttct cccttcggga agcgtggcgc tttctcatag ctcacgctgt aggtatctca   4740
```

```
gttcggtgta ggtcgttcgc tccaagctgg gctgtgtgca cgaacccccc gttcagcccg   4800
accgctgcgc cttatccggt aactatcgtc ttgagtccaa cccggtaaga cacgacttat   4860
cgccactggc agcagccact ggtaacagga ttagcagagc gaggtatgta ggcggtgcta   4920
cagagttctt gaagtggtgg cctaactacg gctacactag aagaacagta tttggtatct   4980
gcgctctgct gaagccagtt accttcggaa aaagagttgg tagctcttga tccggcaaac   5040
aaaccaccgc tggtagcggt ttttttgttt gcaagcagca gattacgcgc agaaaaaaag   5100
gatctcaaga agatcctttg atcttttcta cggggtctga cgctcagtgg aacgaaaact   5160
cacgttaagg gattttggtc atgagattat caaaaaggat cttcacctag atccttttaa   5220
attaaaaatg aagttttaaa tcaatctaaa gtatatatga gtaaacttgg tctgacagtt   5280
accaatgctt aatcagtgag gcacctatct cagcgatctg tctatttcgt tcatccatag   5340
ttgcctgact ccccgtcgtg tagataacta cgatacggga gggcttacca tctggcccca   5400
gtgctgcaat gataccgcga gacccacgct caccggctcc agatttatca gcaataaacc   5460
agccagccgg aagggccgag cgcagaagtg gtcctgcaac tttatccgcc tccatccagt   5520
ctattaattg ttgccgggaa gctagagtaa gtagttcgcc agttaatagt ttgcgcaacg   5580
ttgttgccat tgctacaggc atcgtggtgt cacgctcgtc gtttggtatg gcttcattca   5640
gctccggttc ccaacgatca aggcgagtta catgatcccc catgttgtgc aaaaaagcgg   5700
ttagctcctt cggtcctccg atcgttgtca gaagtaagtt ggccgcagtg ttatcactca   5760
tggttatggc agcactgcat aattctctta ctgtcatgcc atccgtaaga tgcttttctg   5820
tgactggtga gtactcaacc aagtcattct gagaatagtg tatgcggcga ccgagttgct   5880
cttgcccggc gtcaatacgg gataataccg cgccacatag cagaacttta aaagtgctca   5940
tcattggaaa acgttcttcg gggcgaaaac tctcaaggat cttaccgctg ttgagatcca   6000
gttcgatgta acccactcgt gcacccaact gatcttcagc atcttttact ttcaccagcg   6060
tttctgggtg agcaaaaaca ggaaggcaaa atgccgcaaa aaagggaata agggcgacac   6120
ggaaatgttg aatactcata ctcttccttt ttcaatatta ttgaagcatt tatcagggtt   6180
attgtctcat gagcggatac atatttgaat gtatttagaa aaataaacaa ataggggttc   6240
cgcgcacatt tccccgaaaa gtgccacctg acgtc                              6275
```

```
<210> SEQ ID NO 749
<211> LENGTH: 3182
<212> TYPE: DNA
<213> ORGANISM: Artificial Sequence
<220> FEATURE:
<223> OTHER INFORMATION: pMA-F14-GFP-F15 vector V4.H9

<400> SEQUENCE: 749
```

```
ctaaattgta agcgttaata ttttgttaaa attcgcgtta aatttttgtt aaatcagctc     60
atttttaac caataggccg aaatcggcaa aatcccttat aaatcaaaag aatagaccga     120
gatagggttg agtggccgct acagggcgct cccattcgcc attcaggctg cgcaactgtt    180
gggaagggcg tttcggtgcg ggcctcttcg ctattacgcc agctggcgaa agggggatgt    240
gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggccgcatg aattcgctac cgggaagttc ctattccgaa gttcctattc tatcagaagt    420
ataggaactt caggtaccgc caccatggaa tccgatgagt ctggcctgcc cgccatggaa    480
atcgagtgca gaatcaccgg caccctgaac ggcgtggaat ttgagctcgt gggcggaggc    540
```

```
gagggcacac ctgaacaggg cagaatgacc aacaagatga agtccaccaa gggggccctg    600

accttcagcc cctacctgct gtctcacgtg atgggctacg gcttctacca cttcggcacc    660

taccccagcg gctacgagaa ccctttcctg cacgccatca acaacggcgg ctacaccaac    720

acccggatcg agaagtacga ggacggcggc gtgctgcacg tgtccttcag ctacagatac    780

gaggccggca gagtgatcgg cgacttcaaa gtgatgggca ccggattccc cgaggacagc    840

gtgatcttca ccgacaagat catccggtcc aacgccaccg tggaacatct gcaccccatg    900

ggcgacaacg acctggacgg cagcttcacc agaaccttct ccctgcggga tggcggctac    960

tacagcagcg tggtggacag ccacatgcac ttcaagagcg ccatccaccc cagcatcctc   1020

cagaacggcg gacccatgtt cgccttcaga cgggtggaag aggaccacag caacaccgag   1080

ctgggcatcg tggaatacca gcacgccttc aagacccccg atgccgatgc cggcgaggaa   1140

tgagtcgagt ctagacgaag ttcctattcc gaagttccta ttcttatagg agtataggaa   1200

cttcctcgag ctgggcctca tgggccttcc gctcactgcc cgctttccag tcgggaaacc   1260

tgtcgtgcca gctgcattaa catggtcata gctgtttcct tgcgtattgg gcgctctccg   1320

cttcctcgct cactgactcg ctgcgctcgg tcgttcgggt aaagcctggg gtgcctaatg   1380

agcaaaaggc cagcaaaagg ccaggaaccg taaaaaggcc gcgttgctgg cgtttttcca   1440

taggctccgc ccccctgacg agcatcacaa aaatcgacgc tcaagtcaga ggtggcgaaa   1500

cccgacagga ctataaagat accaggcgtt tccccctgga agctccctcg tgcgctctcc   1560

tgttccgacc ctgccgctta ccggatacct gtccgccttt ctcccttcgg gaagcgtggc   1620

gctttctcat agctcacgct gtaggtatct cagttcggtg taggtcgttc gctccaagct   1680

gggctgtgtg cacgaacccc ccgttcagcc cgaccgctgc gccttatccg gtaactatcg   1740

tcttgagtcc aacccggtaa gacacgactt atcgccactg gcagcagcca ctggtaacag   1800

gattagcaga gcgaggtatg taggcggtgc tacagagttc ttgaagtggt ggcctaacta   1860

cggctacact agaagaacag tatttggtat ctgcgctctg ctgaagccag ttaccttcgg   1920

aaaaagagtt ggtagctctt gatccggcaa acaaaccacc gctggtagcg gtggtttttt   1980

tgtttgcaag cagcagatta cgcgcagaaa aaaaggatct caagaagatc ctttgatctt   2040

ttctacgggg tctgacgctc agtggaacga aaactcacgt taagggattt tggtcatgag   2100

attatcaaaa aggatcttca cctagatcct tttaaattaa aaatgaagtt ttaaatcaat   2160

ctaaagtata tatgagtaaa cttggtctga cagttaccaa tgcttaatca gtgaggcacc   2220

tatctcagcg atctgtctat ttcgttcatc catagttgcc tgactccccg tcgtgtagat   2280

aactacgata cgggagggct taccatctgg ccccagtgct gcaatgatac cgcgagaacc   2340

acgctcaccg gctccagatt tatcagcaat aaaccagcca gccggaaggg ccgagcgcag   2400

aagtggtcct gcaactttat ccgcctccat ccagtctatt aattgttgcc gggaagctag   2460

agtaagtagt tcgccagtta atagtttgcg caacgttgtt gccattgcta caggcatcgt   2520

ggtgtcacgc tcgtcgtttg gtatggcttc attcagctcc ggttcccaac gatcaaggcg   2580

agttacatga tcccccatgt tgtgcaaaaa agcggttagc tccttcggtc ctccgatcgt   2640

tgtcagaagt aagttggccg cagtgttatc actcatggtt atggcagcac tgcataattc   2700

tcttactgtc atgccatccg taagatgctt ttctgtgact ggtgagtact caaccaagtc   2760

attctgagaa tagtgtatgc ggcgaccgag ttgctcttgc ccggcgtcaa tacgggataa   2820

taccgcgcca catagcagaa ctttaaaagt gctcatcatt ggaaaacgtt cttcggggcg   2880
```

```
aaaactctca aggatcttac cgctgttgag atccagttcg atgtaaccca ctcgtgcacc   2940
caactgatct tcagcatctt ttactttcac cagcgtttct gggtgagcaa aaacaggaag   3000
gcaaaatgcc gcaaaaaagg gaataagggc gacacggaaa tgttgaatac tcatactctt   3060
cctttttcaa tattattgaa gcatttatca gggttattgt ctcatgagcg gatacatatt   3120
tgaatgtatt tagaaaaata aacaaatagg ggttccgcgc acatttcccc gaaaagtgcc   3180
ac                                                                  3182
```

<210> SEQ ID NO 750
<211> LENGTH: 3291
<212> TYPE: DNA
<213> ORGANISM: Artificial Sequence
<220> FEATURE:
<223> OTHER INFORMATION: pMA-F14-TCR-JG9-alpha-F15 vector V7.A.3

<400> SEQUENCE: 750

```
acgaagttcc tattccgaag ttcctattct tataggagta taggaacttc ctcgagctgg     60
gcctcatggg ccttccgctc actgcccgct ttccagtcgg gaaacctgtc gtgccagctg    120
cattaacatg gtcatagctg tttccttgcg tattgggcgc tctccgcttc ctcgctcact    180
gactcgctgc gctcggtcgt tcgggtaaag cctggggtgc ctaatgagca aaaggccagc    240
aaaaggccag gaaccgtaaa aaggccgcgt tgctggcgtt tttccatagg ctccgccccc    300
ctgacgagca tcacaaaaat cgacgctcaa gtcagaggtg gcgaaacccg acaggactat    360
aaagatacca ggcgtttccc cctggaagct ccctcgtgcg ctctcctgtt ccgaccctgc    420
cgcttaccgg atacctgtcc gcctttctcc cttcgggaag cgtggcgctt tctcatagct    480
cacgctgtag gtatctcagt tcggtgtagg tcgttcgctc caagctgggc tgtgtgcacg    540
aaccccccgt tcagcccgac cgctgcgcct tatccggtaa ctatcgtctt gagtccaacc    600
cggtaagaca cgacttatcg ccactggcag cagccactgg taacaggatt agcagagcga    660
ggtatgtagg cggtgctaca gagttcttga agtggtggcc taactacggc tacactagaa    720
gaacagtatt tggtatctgc gctctgctga agccagttac cttcggaaaa agagttggta    780
gctcttgatc cggcaaacaa accaccgctg gtagcggtgg tttttttgtt tgcaagcagc    840
agattacgcg cagaaaaaaa ggatctcaag aagatccttt gatcttttct acggggtctg    900
acgctcagtg gaacgaaaac tcacgttaag ggattttggt catgagatta tcaaaaagga    960
tcttcaccta gatcctttta aattaaaaat gaagttttaa atcaatctaa agtatatatg   1020
agtaaacttg gtctgacagt taccaatgct taatcagtga ggcacctatc tcagcgatct   1080
gtctatttcg ttcatccata gttgcctgac tccccgtcgt gtagataact acgatacggg   1140
agggcttacc atctggcccc agtgctgcaa tgataccgcg agaaccacgc tcaccggctc   1200
cagatttatc agcaataaac cagccagccg gaagggccga gcgcagaagt ggtcctgcaa   1260
ctttatccgc ctccatccag tctattaatt gttgccggga agctagagta agtagttcgc   1320
cagttaatag tttgcgcaac gttgttgcca ttgctacagg catcgtggtg tcacgctcgt   1380
cgtttggtat ggcttcattc agctccggtt cccaacgatc aaggcgagtt acatgatccc   1440
ccatgttgtg caaaaaagcg gttagctcct tcggtcctcc gatcgttgtc agaagtaagt   1500
tggccgcagt gttatcactc atggttatgg cagcactgca taattctctt actgtcatgc   1560
catccgtaag atgcttttct gtgactggtg agtactcaac caagtcattc tgagaatagt   1620
gtatgcggcg accgagttgc tcttgcccgg cgtcaatacg ggataatacc gcgccacata   1680
gcagaacttt aaaagtgctc atcattggaa aacgttcttc ggggcgaaaa ctctcaagga   1740
```

```
tcttaccgct gttgagatcc agttcgatgt aacccactcg tgcacccaac tgatcttcag   1800

catcttttac tttcaccagc gtttctgggt gagcaaaaac aggaaggcaa aatgccgcaa   1860

aaaagggaat aagggcgaca cggaaatgtt gaatactcat actcttcctt tttcaatatt   1920

attgaagcat ttatcagggt tattgtctca tgagcggata catatttgaa tgtatttaga   1980

aaaataaaca aataggggtt ccgcgcacat ttccccgaaa agtgccacct aaattgtaag   2040

cgttaatatt ttgttaaaat tcgcgttaaa tttttgttaa atcagctcat tttttaacca   2100

ataggccgaa atcggcaaaa tcccttataa atcaaaagaa tagaccgaga tagggttgag   2160

tggccgctac agggcgctcc cattcgccat tcaggctgcg caactgttgg gaagggcgtt   2220

tcggtgcggg cctcttcgct attacgccag ctggcgaaag ggggatgtgc tgcaaggcga   2280

ttaagttggg taacgccagg gttttcccag tcacgacgtt gtaaaacgac ggccagtgag   2340

cgcgacgtaa tacgactcac tatagggcga attggcggaa ggccgtcaag gccgcatgaa   2400

ttcgctaccg ggaagttcct attccgaagt tcctattcta tcagaagtat aggaacttca   2460

ggtacgccac catgctcctt gaacatttat taataatctt gtggatgcag ctgacatggg   2520

tcagtggtca acagctgaat cagagtcctc aatctatgtt tatccaggaa ggagaagatg   2580

tctccatgaa ctgcacttct tcaagcatat ttaacacctg gctatggtac aagcaggaac   2640

ctggggaagg tcctgtcctc ttgatagcct tatataaggc tggtgaattg acctcaaatg   2700

gaaggctgac tgctcagttt ggtataacca gaaaggacag cttcctgaat atctcagcat   2760

ccatacctag tgatgtaggc atctacttct gcgctggacc catgaaaacc tcctacgaca   2820

aggtgatatt tgggccaggg acaagcttat cagtcattcc aaatatccag aaccctgacc   2880

ctgccgtgta ccagctgaga gactctaaat ccagtgacaa gtctgtctgc ctattcaccg   2940

attttgattc tcaaacaaat gtgtcacaaa gtaaggattc tgatgtgtat atcacagaca   3000

aaactgtgct agacatgagg tctatggact tcaagagcaa cagtgctgtg gcctggagca   3060

acaaatctga ctttgcatgt gcaaacgcct tcaacaacag cattattcca gaggacacct   3120

tcttccccag cccagaaagt tcctgtgatg tcaagctggt cgagaaaagc tttgaaacag   3180

atacgaacct aaactttcaa aacctgtcag tgattgggtt ccgaatcctc ctcctgaaag   3240

tggccgggtt taatctgctc atgacgctgc ggctgtggtc cagctgacta g            3291
```

```
<210> SEQ ID NO 751
<211> LENGTH: 3408
<212> TYPE: DNA
<213> ORGANISM: Artificial Sequence
<220> FEATURE:
<223> OTHER INFORMATION: pMA-FRT-TCR-JG9-beta-F3 vector V7.A.4

<400> SEQUENCE: 751

ctaaattgta agcgttaata ttttgttaaa attcgcgtta aatttttgtt aaatcagctc     60

atttttaac caataggccg aaatcggcaa aatcccttat aaatcaaaag aatagaccga    120

gatagggttg agtggccgct acagggcgct cccattcgcc attcaggctg cgcaactgtt    180

gggaagggcg tttcggtgcg ggcctcttcg ctattacgcc agctggcgaa agggggatgt    240

gctgcaaggc gattaagttg ggtaacgcca gggttttccc agtcacgacg ttgtaaaacg    300

acggccagtg agcgcgacgt aatacgactc actatagggc gaattggcgg aaggccgtca    360

aggccgcatg aattcgctac cgggaagttc ctattccgaa gttcctattc tctagaaagt    420

ataggaactt caggtacgcc accatggact cctggaccct ctgctgtgtg tccctttgca    480
```

```
tcctggtagc aaagcacaca gatgctggag ttatccagtc accccggcac gaggtgacag    540
agatgggaca agaagtgact ctgagatgta aaccaatttc aggacacgac taccttttct    600
ggtacagaca gaccatgatg cggggactgg agttgctcat ttactttaac aacaacgttc    660
cgatagatga ttcagggatg cccgaggatc gattctcagc taagatgcct aatgcatcat    720
tctccactct gaagatccag ccctcagaac ccagggactc agctgtgtac ttttgcgcca    780
gcagttccgc aaactatggc tacacctttg gttcggggac caggttaacc gttgtagagg    840
acctgaacaa ggtgttccca cccgaggtcg ctgtgtttga gccatcagaa gcagagatct    900
cccacaccca aaaggccaca ctggtatgcc tggccacagg cttctacccc gaccacgtgg    960
agctgagctg gtgggtgaat gggaaggagg tgcacagtgg ggtcagcaca gacccgcagc   1020
ccctcaagga gcagcccgcc ctcaatgact ccagatactg cctgagcagc cgcctgaggg   1080
tgtcggccac cttctggcag aacccccgca accacttccg ctgtcaagtc cagttctacg   1140
ggctctcgga gaatgacgag tggacccagg atagggccaa acccgtcacc cagatcgtca   1200
gcgccgaggc ctggggtaga gcagactgtg gcttcacctc cgagtcttac cagcaagggg   1260
tcctgtctgc caccatcctc tatgagatct tgctagggaa ggccaccttg tatgccgtgc   1320
tggtcagtgc cctcgtgctg atggccatgg tcaagagaaa ggattccaga ggctagctag   1380
acgaagttcc tattccgaag ttcctattct tcaaatagta taggaacttc ctcgagctgg   1440
gcctcatggg ccttccgctc actgcccgct ttccagtcgg gaaacctgtc gtgccagctg   1500
cattaacatg gtcatagctg tttccttgcg tattgggcgc tctccgcttc ctcgctcact   1560
gactcgctgc gctcggtcgt tcgggtaaag cctggggtgc ctaatgagca aaaggccagc   1620
aaaaggccag gaaccgtaaa aaggccgcgt tgctggcgtt tttccatagg ctccgccccc   1680
ctgacgagca tcacaaaaat cgacgctcaa gtcagaggtg gcgaaacccg acaggactat   1740
aaagatacca ggcgtttccc cctggaagct ccctcgtgcg ctctcctgtt ccgaccctgc   1800
cgcttaccgg atacctgtcc gcctttctcc cttcgggaag cgtggcgctt tctcatagct   1860
cacgctgtag gtatctcagt tcggtgtagg tcgttcgctc caagctgggc tgtgtgcacg   1920
aaccccccgt tcagcccgac cgctgcgcct tatccggtaa ctatcgtctt gagtccaacc   1980
cggtaagaca cgacttatcg ccactggcag cagccactgg taacaggatt agcagagcga   2040
ggtatgtagg cggtgctaca gagttcttga agtggtggcc taactacggc tacactagaa   2100
gaacagtatt tggtatctgc gctctgctga agccagttac cttcggaaaa agagttggta   2160
gctcttgatc cggcaaacaa accaccgctg gtagcggtgg tttttttgtt tgcaagcagc   2220
agattacgcg cagaaaaaaa ggatctcaag aagatccttt gatcttttct acggggtctg   2280
acgctcagtg gaacgaaaac tcacgttaag ggattttggt catgagatta tcaaaaagga   2340
tcttcaccta gatcctttta aattaaaaat gaagttttaa atcaatctaa agtatatatg   2400
agtaaacttg gtctgacagt taccaatgct taatcagtga ggcacctatc tcagcgatct   2460
gtctatttcg ttcatccata gttgcctgac tccccgtcgt gtagataact acgatacggg   2520
agggcttacc atctggcccc agtgctgcaa tgataccgcg agaaccacgc tcaccggctc   2580
cagatttatc agcaataaac cagccagccg gaagggccga gcgcagaagt ggtcctgcaa   2640
ctttatccgc ctccatccag tctattaatt gttgccggga agctagagta agtagttcgc   2700
cagttaatag tttgcgcaac gttgttgcca ttgctacagg catcgtggtg tcacgctcgt   2760
cgtttggtat ggcttcattc agctccggtt cccaacgatc aaggcgagtt acatgatccc   2820
ccatgttgtg caaaaaagcg gttagctcct tcggtcctcc gatcgttgtc agaagtaagt   2880
```

```
tggccgcagt gttatcactc atggttatgg cagcactgca taattctctt actgtcatgc   2940

catccgtaag atgcttttct gtgactggtg agtactcaac caagtcattc tgagaatagt   3000

gtatgcggcg accgagttgc tcttgcccgg cgtcaatacg ggataatacc gcgccacata   3060

gcagaacttt aaaagtgctc atcattggaa aacgttcttc ggggcgaaaa ctctcaagga   3120

tcttaccgct gttgagatcc agttcgatgt aacccactcg tgcacccaac tgatcttcag   3180

catcttttac tttcaccagc gtttctgggt gagcaaaaac aggaaggcaa aatgccgcaa   3240

aaaagggaat aagggcgaca cggaaatgtt gaatactcat actcttcctt tttcaatatt   3300

attgaagcat ttatcagggt tattgtctca tgagcggata catatttgaa tgtatttaga   3360

aaaataaaca aataggggtt ccgcgcacat ttccccgaaa agtgccac                 3408
```

<210> SEQ ID NO 752
<211> LENGTH: 3291
<212> TYPE: DNA
<213> ORGANISM: Artificial Sequence
<220> FEATURE:
<223> OTHER INFORMATION: F14-TCRaF15 CDR3degen.64mix vector V8.F.8
<220> FEATURE:
<221> NAME/KEY: variation
<222> LOCATION: 2803
<223> OTHER INFORMATION: /replace="n"= "a", "g", "c", or "t"
<220> FEATURE:
<221> NAME/KEY: variation
<222> LOCATION: 2808
<223> OTHER INFORMATION: /replace="n"= "a", "g", "c", or "t"
<220> FEATURE:
<221> NAME/KEY: variation
<222> LOCATION: 2814
<223> OTHER INFORMATION: /replace="n"= "a", "g", "c", or "t"

<400> SEQUENCE: 752

```
acgaagttcc tattccgaag ttcctattct tataggagta taggaacttc ctcgagctgg     60

gcctcatggg ccttccgctc actgcccgct ttccagtcgg gaaacctgtc gtgccagctg    120

cattaacatg gtcatagctg tttccttgcg tattgggcgc tctccgcttc ctcgctcact    180

gactcgctgc gctcggtcgt tcgggtaaag cctggggtgc ctaatgagca aaaggccagc    240

aaaaggccag gaaccgtaaa aaggccgcgt tgctggcgtt tttccatagg ctccgccccc    300

ctgacgagca tcacaaaaat cgacgctcaa gtcagaggtg gcgaaacccg acaggactat    360

aaagatacca ggcgtttccc cctggaagct ccctcgtgcg ctctcctgtt ccgaccctgc    420

cgcttaccgg atacctgtcc gcctttctcc cttcgggaag cgtggcgctt tctcatagct    480

cacgctgtag gtatctcagt tcggtgtagg tcgttcgctc caagctgggc tgtgtgcacg    540

aaccccccgt tcagcccgac cgctgcgcct tatccggtaa ctatcgtctt gagtccaacc    600

cggtaagaca cgacttatcg ccactggcag cagccactgg taacaggatt agcagagcga    660

ggtatgtagg cggtgctaca gagttcttga agtggtggcc taactacggc tacactagaa    720

gaacagtatt tggtatctgc gctctgctga agccagttac cttcggaaaa agagttggta    780

gctcttgatc cggcaaacaa accaccgctg gtagcggtgg tttttttgtt tgcaagcagc    840

agattacgcg cagaaaaaaa ggatctcaag aagatccttt gatcttttct acggggtctg    900

acgctcagtg gaacgaaaac tcacgttaag ggattttggt catgagatta tcaaaaagga    960

tcttcaccta gatcctttta aattaaaaat gaagttttaa atcaatctaa agtatatatg   1020

agtaaacttg gtctgacagt taccaatgct taatcagtga ggcacctatc tcagcgatct   1080

gtctatttcg ttcatccata gttgcctgac tccccgtcgt gtagataact acgatacggg   1140
```

-continued

```
agggcttacc atctggcccc agtgctgcaa tgataccgcg agaaccacgc tcaccggctc   1200
cagatttatc agcaataaac cagccagccg gaagggccga gcgcagaagt ggtcctgcaa   1260
ctttatccgc ctccatccag tctattaatt gttgccggga agctagagta agtagttcgc   1320
cagttaatag tttgcgcaac gttgttgcca ttgctacagg catcgtggtg tcacgctcgt   1380
cgtttggtat ggcttcattc agctccggtt cccaacgatc aaggcgagtt acatgatccc   1440
ccatgttgtg caaaaaagcg gttagctcct tcggtcctcc gatcgttgtc agaagtaagt   1500
tggccgcagt gttatcactc atggttatgg cagcactgca taattctctt actgtcatgc   1560
catccgtaag atgcttttct gtgactggtg agtactcaac caagtcattc tgagaatagt   1620
gtatgcggcg accgagttgc tcttgcccgg cgtcaatacg ggataatacc gcgccacata   1680
gcagaacttt aaaagtgctc atcattggaa aacgttcttc ggggcgaaaa ctctcaagga   1740
tcttaccgct gttgagatcc agttcgatgt aacccactcg tgcacccaac tgatcttcag   1800
catcttttac tttcaccagc gtttctgggt gagcaaaaac aggaaggcaa aatgccgcaa   1860
aaaagggaat aagggcgaca cggaaatgtt gaatactcat actcttcctt tttcaatatt   1920
attgaagcat ttatcagggt tattgtctca tgagcggata catatttgaa tgtatttaga   1980
aaaataaaca aataggggtt ccgcgcacat ttccccgaaa agtgccacct aaattgtaag   2040
cgttaatatt ttgttaaaat tcgcgttaaa tttttgttaa atcagctcat tttttaacca   2100
ataggccgaa atcggcaaaa tcccttataa atcaaaagaa tagaccgaga tagggttgag   2160
tggccgctac agggcgctcc cattcgccat tcaggctgcg caactgttgg gaagggcgtt   2220
tcggtgcggg cctcttcgct attacgccag ctggcgaaag gggatgtgc tgcaaggcga   2280
ttaagttggg taacgccagg gttttcccag tcacgacgtt gtaaaacgac ggccagtgag   2340
cgcgacgtaa tacgactcac tatagggcga attggcggaa ggccgtcaag gccgcatgaa   2400
ttcgctaccg ggaagttcct attccgaagt tcctattcta tcagaagtat aggaacttca   2460
ggtacgccac catgctcctt gaacatttat taataatctt gtggatgcag ctgacatggg   2520
tcagtggtca acagctgaat cagagtcctc aatctatgtt tatccaggaa ggagaagatg   2580
tctccatgaa ctgcacttct tcaagcatat ttaacacctg gctatggtac aagcaggaac   2640
ctggggaagg tcctgtcctc ttgatagcct tatataaggc tggtgaattg acctcaaatg   2700
gaaggctgac tgctcagttt ggtataacca gaaaggacag cttcctgaat atctcagcat   2760
ccatacctag tgatgtaggc atctacttct gcgctggacc cangaaancc tccnacgaca   2820
aggtgatatt tgggccaggg acaagcttat cagtcattcc aaatatccag aaccctgacc   2880
ctgccgtgta ccagctgaga gactctaaat ccagtgacaa gtctgtctgc ctattcaccg   2940
attttgattc tcaaacaaat gtgtcacaaa gtaaggattc tgatgtgtat atcacagaca   3000
aaactgtgct agacatgagg tctatggact tcaagagcaa cagtgctgtg gcctggagca   3060
acaaatctga ctttgcatgt gcaaacgcct tcaacaacag cattattcca gaggacacct   3120
tcttccccag cccagaaagt tcctgtgatg tcaagctggt cgagaaaagc tttgaaacag   3180
atacgaacct aaactttcaa aacctgtcag tgattgggtt ccgaatcctc ctcctgaaag   3240
tggccgggtt taatctgctc atgacgctgc ggctgtggtc cagctgacta g            3291
```

<210> SEQ ID NO 753
<211> LENGTH: 4542
<212> TYPE: DNA
<213> ORGANISM: Artificial Sequence
<220> FEATURE:
<223> OTHER INFORMATION: CMVpro-Flp-sv40pA-V2 vector V4.I.8

<400> SEQUENCE: 753

```
ctaaattgta agcgttaata ttttgttaaa attcgcgtta aatttttgtt aaatcagctc     60
atttttaac caataggccg aaatcggcaa aatcccttat aaatcaaaag aatagaccga    120
gatagggttg agtggccgct acagggcgct cccattcgcc attcaggctg cgcaactgtt    180
gggaagggcg tttcggtgcg ggcctcttcg ctattacgcc agctggcgaa agggggatgt    240
gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggccgcatg aattcgctac cggtatagta atcaattacg gggtcattag ttcatagccc    420
atatatggag ttccgcgtta cataacttac ggtaaatggc ccgcctggct gaccgcccaa    480
cgacccccgc ccattgacgt caataatgac gtatgttccc atagtaacgc caatagggac    540
tttccattga cgtcaatggg tggagtattt acggtaaact gcccacttgg cagtacatca    600
agtgtatcat atgccaagta cgccccctat tgacgtcaat gacggtaaat ggcccgcctg    660
gcattatgcc cagtacatga ccttatggga ctttcctact tggcagtaca tctacgtatt    720
agtcatcgct attaccatgg tgatgcggtt ttggcagtac atcaatgggc gtggatagcg    780
gtttgactca cggggatttc caagtctcca ccccattgac gtcaatggga gtttgttttg    840
gcaccaaaat caacgggact ttccaaaatg tcgtaacaac tccgccccat tgacgcaaat    900
gggcggtagg cgtgtacggt gggaggtcta tataagcaga gctggtttag tgaaccgtca    960
gatcaggtac catggccccc aagaaaaagc ggaaagtggg catccacggc gtgccagctg   1020
caggcggctc tatgagccag ttcgacatcc tgtgcaagac ccccacctaag gtgctcgtgc   1080
ggcagttcgt ggaaagattc gagaggccta gcggcgagaa gatcgcctct tgtgctgccg   1140
agctgaccta cctgtgctgg atgatcaccc acaacggcac cgccatcaag cgggccacct   1200
tcatgagcta caataccatc atcagcaaca gcctgagctt cgacatcgtg aacaagagcc   1260
tgcagttcaa gtacaagacc cagaaggcca ccatcctgga agccagcctg aagaaactga   1320
tccccgcctg ggagtttacc atcatcccat acaatggcca gaaacatcag agcgacatta   1380
ccgatatcgt gtccagcctc cagctgcagt tcgagagtag cgaagaagcc gacaagggca   1440
acagccacag caagaagatg ctgaaggccc tgctgagcga gggcgagagc atctgggaga   1500
tcacagagaa gatcctgaac agcttcgagt acaccagccg gttcaccaag accaagaccc   1560
tgtaccagtt cctgttcctg gccaccttta tcaactgcgg ccggttctcc gacatcaaga   1620
acgtggaccc caagagcttc aagctggtgc agaacaagta cctgggcgtg atcattcagt   1680
gcctcgtgac cgagacaaag accagcgtgt cccggcacat ctactttttc agcgccagag   1740
gccggatcga ccccctggtg tacctggacg agttcctgag aaacagcgag cccgtgctga   1800
agagagtgaa ccggaccggc aacagcagct ccaacaagca ggaataccag ctgctgaagg   1860
acaacctcgt gcggtcctac aacaaggccc tgaagaaaaa cgccccctac cccatcttcg   1920
ccattaagaa cggccccaag tcccacatcg gccggcacct gatgaccagc tttctgagca   1980
tgaagggcct gacagagctg accaacgtcg tgggcaattg gagcgacaag agggcctctg   2040
ccgtggccag aaccacctac acccaccaga tcacagccat ccccgaccac tacttcgccc   2100
tggtgtctcg gtactacgcc tacgacccca tcagcaaaga gatgatcgcc ctgaaggacg   2160
agacaaaccc catcgaggaa tggcagcaca tcgagcagct gaagggcagc gccgagggca   2220
gcatcagata ccctgcctgg aacggcatca tctcccagga agtgctggac tacctgagca   2280
```

-continued

```
gctacatcaa ccggcggatc tgatctagac ctgatcataa tcaagccata tcacatctgt   2340
agaggtttac ttgctttaaa aaacctccac acctccccct gaacctgaaa cataaaatga   2400
atgcaattgt tgttgttaac ttgtttattg cagcttataa tggttacaaa taaagcaata   2460
gcatcacaaa tttcacaaat aaagcatttt tttcactgca ttctagttgt ggtttgtcca   2520
aactcatcaa tgtatcttat catgtctgga tctgcggatc caatctcgag ctgggcctca   2580
tgggccttcc gctcactgcc cgctttccag tcgggaaacc tgtcgtgcca gctgcattaa   2640
catggtcata gctgtttcct tgcgtattgg gcgctctccg cttcctcgct cactgactcg   2700
ctgcgctcgg tcgttcgggt aaagcctggg gtgcctaatg agcaaaaggc cagcaaaagg   2760
ccaggaaccg taaaaaggcc gcgttgctgg cgtttttcca taggctccgc ccccctgacg   2820
agcatcacaa aaatcgacgc tcaagtcaga ggtggcgaaa cccgacagga ctataaagat   2880
accaggcgtt tccccctgga agctccctcg tgcgctctcc tgttccgacc ctgccgctta   2940
ccggatacct gtccgccttt ctcccttcgg gaagcgtggc gctttctcat agctcacgct   3000
gtaggtatct cagttcggtg taggtcgttc gctccaagct gggctgtgtg cacgaacccc   3060
ccgttcagcc cgaccgctgc gccttatccg gtaactatcg tcttgagtcc aacccggtaa   3120
gacacgactt atcgccactg gcagcagcca ctggtaacag gattagcaga gcgaggtatg   3180
taggcggtgc tacagagttc ttgaagtggt ggcctaacta cggctacact agaagaacag   3240
tatttggtat ctgcgctctg ctgaagccag ttaccttcgg aaaaagagtt ggtagctctt   3300
gatccggcaa acaaaccacc gctggtagcg gtggtttttt tgtttgcaag cagcagatta   3360
cgcgcagaaa aaaaggatct caagaagatc ctttgatctt ttctacgggg tctgacgctc   3420
agtggaacga aaactcacgt taagggattt tggtcatgag attatcaaaa aggatcttca   3480
cctagatcct tttaaattaa aaatgaagtt ttaaatcaat ctaaagtata tatgagtaaa   3540
cttggtctga cagttaccaa tgcttaatca gtgaggcacc tatctcagcg atctgtctat   3600
ttcgttcatc catagttgcc tgactccccg tcgtgtagat aactacgata cgggagggct   3660
taccatctgg ccccagtgct gcaatgatac cgcgagaacc acgctcaccg gctccagatt   3720
tatcagcaat aaaccagcca gccggaaggg ccgagcgcag aagtggtcct gcaactttat   3780
ccgcctccat ccagtctatt aattgttgcc gggaagctag agtaagtagt tcgccagtta   3840
atagtttgcg caacgttgtt gccattgcta caggcatcgt ggtgtcacgc tcgtcgtttg   3900
gtatggcttc attcagctcc ggttcccaac gatcaaggcg agttacatga tcccccatgt   3960
tgtgcaaaaa agcggttagc tccttcggtc ctccgatcgt tgtcagaagt aagttggccg   4020
cagtgttatc actcatggtt atggcagcac tgcataattc tcttactgtc atgccatccg   4080
taagatgctt ttctgtgact ggtgagtact caaccaagtc attctgagaa tagtgtatgc   4140
ggcgaccgag ttgctcttgc ccggcgtcaa tacgggataa taccgcgcca catagcagaa   4200
ctttaaaagt gctcatcatt ggaaaacgtt cttcggggcg aaaactctca aggatcttac   4260
cgctgttgag atccagttcg atgtaaccca ctcgtgcacc caactgatct tcagcatctt   4320
ttactttcac cagcgtttct gggtgagcaa aaacaggaag gcaaaatgcc gcaaaaaagg   4380
gaataagggc gacacggaaa tgttgaatac tcatactctt cctttttcaa tattattgaa   4440
gcatttatca gggttattgt ctcatgagcg gatacatatt tgaatgtatt tagaaaaata   4500
aacaaatagg ggttccgcgc acatttcccc gaaaagtgcc ac                      4542
```

<210> SEQ ID NO 754
<211> LENGTH: 4030

<212> TYPE: DNA
<213> ORGANISM: Artificial Sequence
<220> FEATURE:
<223> OTHER INFORMATION: JG9-TRA CDR3 64 variants vectors backbone
VP.7751.RC1-A1 to H8

<400> SEQUENCE: 754

```
cggggtctga cgctcagtgg aacgaaaact cacgttaagg gattttggtc atgagattat     60

caaaaaggat cttcacctag atccttttaa attaaaaatg aagttttaaa tcaatctaaa    120

gtatatatga gtaaacttgg tctgacagtt accaatgctt aatcagtgag gcacctatct    180

cagcgatctg tctatttcgt tcatccatag ttgcctgact ccccgtcgtg tagataacta    240

cgatacggga gggcttacca tctggcccca gtgctgcaat gataccgcga gaaccacgct    300

caccggctcc agatttatca gcaataaacc agccagccgg aagggccgag cgcagaagtg    360

gtcctgcaac tttatccgcc tccatccagt ctattaattg ttgccgggaa gctagagtaa    420

gtagttcgcc agttaatagt ttgcgcaacg ttgttgccat tgctacaggc atcgtggtgt    480

cacgctcgtc gtttggtatg gcttcattca gctccggttc ccaacgatca aggcgagtta    540

catgatcccc catgttgtgc aaaaaagcgg ttagctcctt cggtcctccg atcgttgtca    600

gaagtaagtt ggccgcagtg ttatcactca tggttatggc agcactgcat aattctctta    660

ctgtcatgcc atccgtaaga tgcttttctg tgactggtga gtactcaacc aagtcattct    720

gagaatagtg tatgcggcga ccgagttgct cttgcccggc gtcaatacgg gataataccg    780

cgccacatag cagaacttta aaagtgctca tcattggaaa acgttcttcg gggcgaaaac    840

tctcaaggat cttaccgctg ttgagatcca gttcgatgta acccactcgt gcacccaact    900

gatcttcagc atcttttact ttcaccagcg tttctgggtg agcaaaaaca ggaaggcaaa    960

atgccgcaaa aaagggaata agggcgacac ggaaatgttg aatactcata ctcttccttt   1020

ttcaatatta ttgaagcatt tatcagggtt attgtctcat gagcggatac atatttgaat   1080

gtatttagaa aaataaacaa ataggggttc cgcgcacatt tccccgaaaa gtgccaccta   1140

aattgtaagc gttaatattt tgttaaaatt cgcgttaaat ttttgttaaa tcagctcatt   1200

ttttaaccaa taggccgaaa tcggcaaaat cccttataaa tcaaaagaat agaccgagat   1260

agggttgagt ggccgctaca gggcgctccc attcgccatt caggctgcgc aactgttggg   1320

aagggcgttt cggtgcgggc ctcttcgcta ttacgccagc tggcgaaagg gggatgtgct   1380

gcaaggcgat taagttgggt aacgccaggg ttttcccagt cacgacgttg taaaacgacg   1440

gccagtgagc gcgacgtaat acgactcact atagggcgaa ttggcggaag gccgtcaagg   1500

ccgcatgaat tcgctaccgg tatagtaatc aattacgggg tcattagttc atagcccata   1560

tatggagttc cgcgttacat aacttacggt aaatggcccg cctggctgac cgcccaacga   1620

cccccgccca ttgacgtcaa taatgacgta tgttcccata gtaacgccaa tagggacttt   1680

ccattgacgt caatgggtgg agtatttacg gtaaactgcc cacttggcag tacatcaagt   1740

gtatcatatg ccaagtacgc cccctattga cgtcaatgac ggtaaatggc ccgcctggca   1800

ttatgcccag tacatgacct tatgggactt tcctacttgg cagtacatct acgtattagt   1860

catcgctatt accatggtga tgcggttttg gcagtacatc aatgggcgtg gatagcggtt   1920

tgactcacgg ggatttccaa gtctccaccc cattgacgtc aatgggagtt tgttttggca   1980

ccaaaatcaa cgggactttc caaaatgtcg taacaactcc gccccattga cgcaaatggg   2040

cggtaggcgt gtacggtggg aggtctatat aagcagagct ggtttagtga accgtcagat   2100

caggtacgcc accatgctcc ttgaacattt attaataatc ttgtggatgc agctgacatg   2160
```

```
ggtcagtggt caacagctga atcagagtcc tcaatctatg tttatccagg aaggagaaga   2220
tgtctccatg aactgcactt cttcaagcat atttaacacc tggctatggt acaagcagga   2280
acctggggaa ggtcctgtcc tcttgatagc cttatataag gctggtgaat tgacctcaaa   2340
tggaaggctg actgctcagt ttggtataac cagaaaggac agcttcctga atatctcagc   2400
atccatacct agtgatgtag gcatctactt ctgcgctgga cccatgaaaa cctcctacga   2460
caaggtgata tttgggccag ggacaagctt atcagtcatt ccaaatatcc agaaccctga   2520
ccctgccgtg taccagctga gagactctaa atccagtgac aagtctgtct gcctattcac   2580
cgattttgat tctcaaacaa atgtgtcaca aagtaaggat tctgatgtgt atatcacaga   2640
caaaactgtg ctagacatga ggtctatgga cttcaagagc aacagtgctg tggcctggag   2700
caacaaatct gactttgcat gtgcaaacgc cttcaacaac agcattattc cagaggacac   2760
cttcttcccc agcccagaaa gttcctgtga tgtcaagctg gtcgagaaaa gctttgaaac   2820
agatacgaac ctaaactttc aaaacctgtc agtgattggg ttccgaatcc tcctcctgaa   2880
agtggccggg tttaatctgc tcatgacgct gcggctgtgg tccagctgac tagacctgat   2940
cataatcaag ccatatcaca tctgtagagg tttacttgct ttaaaaaacc tccacacctc   3000
cccctgaacc tgaaacataa aatgaatgca attgttgttg ttaacttgtt tattgcagct   3060
tataatggtt acaaataaag caatagcatc acaaatttca caaataaagc atttttttca   3120
ctgcattcta gttgtggttt gtccaaactc atcaatgtat cttatcatgt ctggatctgc   3180
ggatccaatc tcgagctggg cctcatgggc cttccgctca ctgcccgctt tccagtcggg   3240
aaacctgtcg tgccagctgc attaacatgg tcatagctgt ttccttgcgt attgggcgct   3300
ctccgcttcc tcgctcactg actcgctgcg ctcggtcgtt cgggtaaagc ctggggtgcc   3360
taatgagcaa aaggccagca aaaggccagg aaccgtaaaa aggccgcgtt gctggcgttt   3420
ttccataggc tccgcccccc tgacgagcat cacaaaaatc gacgctcaag tcagaggtgg   3480
cgaaacccga caggactata aagataccag gcgtttcccc ctggaagctc cctcgtgcgc   3540
tctcctgttc cgaccctgcc gcttaccgga tacctgtccg cctttctccc ttcgggaagc   3600
gtggcgcttt ctcatagctc acgctgtagg tatctcagtt cggtgtaggt cgttcgctcc   3660
aagctgggct gtgtgcacga accccccgtt cagcccgacc gctgcgcctt atccggtaac   3720
tatcgtcttg agtccaaccc ggtaagacac gacttatcgc cactggcagc agccactggt   3780
aacaggatta gcagagcgag gtatgtaggc ggtgctacag agttcttgaa gtggtggcct   3840
aactacggct acactagaag aacagtattt ggtatctgcg ctctgctgaa gccagttacc   3900
ttcggaaaaa gagttggtag ctcttgatcc ggcaaacaaa ccaccgctgg tagcggtggt   3960
tttttgtttg caagcagcag attacgcgca gaaaaaaagg atctcaagaa gatcctttga   4020
atcttttcta                                                          4030
```

<210> SEQ ID NO 755
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant VP.7751.RC1_A1

<400> SEQUENCE: 755

```
tgcgctggac ccaagaaaac ctccaacgac aaggtgatat tt                        42
```

<210> SEQ ID NO 756
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_A2

<400> SEQUENCE: 756
tgcgctggac ccaagaaaac ctcccacgac aaggtgatat tt 42

<210> SEQ ID NO 757
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_A3

<400> SEQUENCE: 757
tgcgctggac ccaagaaaac ctccgacgac aaggtgatat tt 42

<210> SEQ ID NO 758
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_A4

<400> SEQUENCE: 758
tgcgctggac ccaagaaaac ctcctacgac aaggtgatat tt 42

<210> SEQ ID NO 759
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_A5

<400> SEQUENCE: 759
tgcgctggac ccaagaaacc ctccaacgac aaggtgatat tt 42

<210> SEQ ID NO 760
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_A6

<400> SEQUENCE: 760
tgcgctggac ccaagaaacc ctcccacgac aaggtgatat tt 42

<210> SEQ ID NO 761
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_A7

<400> SEQUENCE: 761
tgcgctggac ccaagaaacc ctccgacgac aaggtgatat tt 42

<210> SEQ ID NO 762

<211> LENGTH: 42
<212> TYPE: DNA
<213> ORGANISM: Artificial Sequence
<220> FEATURE:
<223> OTHER INFORMATION: CDR3 sequence of a JG9-TRA 64 variant VP.7751.RC1_A8

<400> SEQUENCE: 762
tgcgctggac ccaagaaacc ctcctacgac aaggtgatat tt 42

<210> SEQ ID NO 763
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant VP.7751.RC1_B1

<400> SEQUENCE: 763
tgcgctggac ccaagaaagc ctccaacgac aaggtgatat tt 42

<210> SEQ ID NO 764
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant VP.7751.RC1_B2

<400> SEQUENCE: 764
tgcgctggac ccaagaaagc ctcccacgac aaggtgatat tt 42

<210> SEQ ID NO 765
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant VP.7751.RC1_B3

<400> SEQUENCE: 765
tgcgctggac ccaagaaagc ctccgacgac aaggtgatat tt 42

<210> SEQ ID NO 766
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant VP.7751.RC1_B4

<400> SEQUENCE: 766
tgcgctggac ccaagaaagc ctcctacgac aaggtgatat tt 42

<210> SEQ ID NO 767
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant VP.7751.RC1_B5

<400> SEQUENCE: 767
tgcgctggac ccaagaaatc ctccaacgac aaggtgatat tt 42

<210> SEQ ID NO 768
<211> LENGTH: 42

<212> TYPE: DNA
<213> ORGANISM: Artificial Sequence
<220> FEATURE:
<223> OTHER INFORMATION: CDR3 sequence of a JG9-TRA 64 variant
VP.7751.RC1_B6

<400> SEQUENCE: 768
tgcgctggac ccaagaaatc ctcccacgac aaggtgatat tt 42

<210> SEQ ID NO 769
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_B7

<400> SEQUENCE: 769
tgcgctggac ccaagaaatc ctccgacgac aaggtgatat tt 42

<210> SEQ ID NO 770
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_B8

<400> SEQUENCE: 770
tgcgctggac ccaagaaatc ctcctacgac aaggtgatat tt 42

<210> SEQ ID NO 771
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_C1

<400> SEQUENCE: 771
tgcgctggac ccacgaaaac ctccaacgac aaggtgatat tt 42

<210> SEQ ID NO 772
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_C2

<400> SEQUENCE: 772
tgcgctggac ccacgaaaac ctcccacgac aaggtgatat tt 42

<210> SEQ ID NO 773
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_C3

<400> SEQUENCE: 773
tgcgctggac ccacgaaaac ctccgacgac aaggtgatat tt 42

<210> SEQ ID NO 774
<211> LENGTH: 42
<212> TYPE: DNA

<213> ORGANISM: Artificial Sequence
<220> FEATURE:
<223> OTHER INFORMATION: CDR3 sequence of a JG9-TRA 64 variant
VP.7751.RC1_C4

<400> SEQUENCE: 774
tgcgctggac ccacgaaaac ctcctacgac aaggtgatat tt 42

<210> SEQ ID NO 775
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_C5

<400> SEQUENCE: 775
tgcgctggac ccacgaaacc ctccaacgac aaggtgatat tt 42

<210> SEQ ID NO 776
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_C6

<400> SEQUENCE: 776
tgcgctggac ccacgaaacc ctcccacgac aaggtgatat tt 42

<210> SEQ ID NO 777
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_C7

<400> SEQUENCE: 777
tgcgctggac ccacgaaacc ctcctacgac aaggtgatat tt 42

<210> SEQ ID NO 778
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_D1

<400> SEQUENCE: 778
tgcgctggac ccacgaaagc ctccaacgac aaggtgatat tt 42

<210> SEQ ID NO 779
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_D2

<400> SEQUENCE: 779
tgcgctggac ccacgaaagc ctcccacgac aaggtgatat tt 42

<210> SEQ ID NO 780
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_D3

<400> SEQUENCE: 780
tgcgctggac ccacgaaagc ctccgacgac aaggtgatat tt 42

<210> SEQ ID NO 781
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_D4

<400> SEQUENCE: 781
tgcgctggac ccacgaaagc ctcctacgac aaggtgatat tt 42

<210> SEQ ID NO 782
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_D5

<400> SEQUENCE: 782
tgcgctggac ccacgaaatc ctccaacgac aaggtgatat tt 42

<210> SEQ ID NO 783
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_D6

<400> SEQUENCE: 783
tgcgctggac ccacgaaatc ctcccacgac aaggtgatat tt 42

<210> SEQ ID NO 784
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_D7

<400> SEQUENCE: 784
tgcgctggac ccacgaaatc ctccgacgac aaggtgatat tt 42

<210> SEQ ID NO 785
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_D8

<400> SEQUENCE: 785
tgcgctggac ccacgaaatc ctcctacgac aaggtgatat tt 42

<210> SEQ ID NO 786
<211> LENGTH: 42
<212> TYPE: DNA
<213> ORGANISM: Artificial Sequence
<220> FEATURE:

<223> OTHER INFORMATION: CDR3 sequence of a JG9-TRA 64 variant
      VP.7751.RC1_E1

<400> SEQUENCE: 786
tgcgctggac ccaggaaaac ctccaacgac aaggtgatat tt 42

<210> SEQ ID NO 787
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
      VP.7751.RC1_E2

<400> SEQUENCE: 787
tgcgctggac ccaggaaaac ctcccacgac aaggtgatat tt 42

<210> SEQ ID NO 788
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
      VP.7751.RC1_E3

<400> SEQUENCE: 788
tgcgctggac ccaggaaaac ctccgacgac aaggtgatat tt 42

<210> SEQ ID NO 789
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
      VP.7751.RC1_E4

<400> SEQUENCE: 789
tgcgctggac ccaggaaaac ctcctacgac aaggtgatat tt 42

<210> SEQ ID NO 790
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
      VP.7751.RC1_E5

<400> SEQUENCE: 790
tgcgctggac ccaggaaacc ctccaacgac aaggtgatat tt 42

<210> SEQ ID NO 791
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
      VP.7751.RC1_E6

<400> SEQUENCE: 791
tgcgctggac ccaggaaacc ctcccacgac aaggtgatat tt 42

<210> SEQ ID NO 792
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant

VP.7751.RC1_E7

<400> SEQUENCE: 792
tgcgctggac ccaggaaacc ctccgacgac aaggtgatat tt 42

<210> SEQ ID NO 793
<211> LENGTH: 42
<212> TYPE: PRT
<213> ORGANISM: Artificial Sequence
<220> FEATURE:
<223> OTHER INFORMATION: CDR3 sequence of a JG9-TRA 64 variant
VP.7751.RC1_E8

<400> SEQUENCE: 793

Thr Gly Cys Gly Cys Thr Gly Gly Ala Cys Cys Cys Ala Gly Gly Ala
1 5 10 15

Ala Ala Cys Cys Cys Thr Cys Cys Thr Ala Cys Gly Ala Cys Ala Ala
20 25 30

Gly Gly Thr Gly Ala Thr Ala Thr Thr Thr
35 40

<210> SEQ ID NO 794
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_F1

<400> SEQUENCE: 794
tgcgctggac ccaggaaagc ctccaacgac aaggtgatat tt 42

<210> SEQ ID NO 795
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_F2

<400> SEQUENCE: 795
tgcgctggac ccaggaaagc ctcccacgac aaggtgatat tt 42

<210> SEQ ID NO 796
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_F3

<400> SEQUENCE: 796
tgcgctggac ccaggaaagc ctccgacgac aaggtgatat tt 42

<210> SEQ ID NO 797
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_F4

<400> SEQUENCE: 797
tgcgctggac ccaggaaagc ctcctacgac aaggtgatat tt 42

<210> SEQ ID NO 798
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_F5

<400> SEQUENCE: 798
tgcgctggac ccaggaaatc ctccaacgac aaggtgatat tt 42

<210> SEQ ID NO 799
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_F6

<400> SEQUENCE: 799
tgcgctggac ccaggaaatc ctcccacgac aaggtgatat tt 42

<210> SEQ ID NO 800
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_F7

<400> SEQUENCE: 800
tgcgctggac ccaggaaatc ctccgacgac aaggtgatat tt 42

<210> SEQ ID NO 801
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_F8

<400> SEQUENCE: 801
tgcgctggac ccaggaaatc ctcctacgac aaggtgatat tt 42

<210> SEQ ID NO 802
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_G1

<400> SEQUENCE: 802
tgcgctggac ccatgaaaac ctccaacgac aaggtgatat tt 42

<210> SEQ ID NO 803
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_G2

<400> SEQUENCE: 803
tgcgctggac ccatgaaaac ctcccacgac aaggtgatat tt 42

<210> SEQ ID NO 804

<211> LENGTH: 42
<212> TYPE: DNA
<213> ORGANISM: Artificial Sequence
<220> FEATURE:
<223> OTHER INFORMATION: CDR3 sequence of a JG9-TRA 64 variant VP.7751.RC1_G3

<400> SEQUENCE: 804
tgcgctggac ccatgaaaac ctccgacgac aaggtgatat tt 42

<210> SEQ ID NO 805
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant VP.7751.RC1_G4

<400> SEQUENCE: 805
tgcgctggac ccatgaaaac ctcctacgac aaggtgatat tt 42

<210> SEQ ID NO 806
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant VP.7751.RC1_G5

<400> SEQUENCE: 806
tgcgctggac ccatgaaacc ctccaacgac aaggtgatat tt 42

<210> SEQ ID NO 807
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant VP.7751.RC1_G6

<400> SEQUENCE: 807
tgcgctggac ccatgaaacc ctcccacgac aaggtgatat tt 42

<210> SEQ ID NO 808
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant VP.7751.RC1_G7

<400> SEQUENCE: 808
tgcgctggac ccatgaaacc ctccgacgac aaggtgatat tt 42

<210> SEQ ID NO 809
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant VP.7751.RC1_G8

<400> SEQUENCE: 809
tgcgctggac ccatgaaacc ctcctacgac aaggtgatat tt 42

<210> SEQ ID NO 810
<211> LENGTH: 42

<212> TYPE: DNA
<213> ORGANISM: Artificial Sequence
<220> FEATURE:
<223> OTHER INFORMATION: CDR3 sequence of a JG9-TRA 64 variant VP.7751.RC1_H1

<400> SEQUENCE: 810
tgcgctggac ccatgaaagc ctccaacgac aaggtgatat tt 42

<210> SEQ ID NO 811
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant VP.7751.RC1_H2

<400> SEQUENCE: 811
tgcgctggac ccatgaaagc ctcccacgac aaggtgatat tt 42

<210> SEQ ID NO 812
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant VP.7751.RC1_H3

<400> SEQUENCE: 812
tgcgctggac ccatgaaagc ctccgacgac aaggtgatat tt 42

<210> SEQ ID NO 813
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant VP.7751.RC1_H4

<400> SEQUENCE: 813
tgcgctggac ccatgaaagc ctcctacgac aaggtgatat tt 42

<210> SEQ ID NO 814
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant VP.7751.RC1_H5

<400> SEQUENCE: 814
tgcgctggac ccatgaaatc ctccaacgac aaggtgatat tt 42

<210> SEQ ID NO 815
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant VP.7751.RC1_H6

<400> SEQUENCE: 815
tgcgctggac ccatgaaatc ctcccacgac aaggtgatat tt 42

<210> SEQ ID NO 816
<211> LENGTH: 42
<212> TYPE: DNA

<213> ORGANISM: Artificial Sequence
<220> FEATURE:
<223> OTHER INFORMATION: CDR3 sequence of a JG9-TRA 64 variant
VP.7751.RC1_H7

<400> SEQUENCE: 816
tgcgctggac ccatgaaatc ctccgacgac aaggtgatat tt 42

<210> SEQ ID NO 817
<211> LENGTH: 42
<212> TYPE: DNA
<213> ORGANISM: Artificial Sequence
<220> FEATURE:
<223> OTHER INFORMATION: CDR3 sequence of a JG9-TRA 64 variant
VP.7751.RC1_H8

<400> SEQUENCE: 817
tgcgctggac ccatgaaatc ctcctacgac aaggtgatat tt 42

<210> SEQ ID NO 818
<211> LENGTH: 19
<212> TYPE: DNA
<213> ORGANISM: Artificial Sequence
<220> FEATURE:
<223> OTHER INFORMATION: TRAC-GT-F1

<400> SEQUENCE: 818
atgtgcaaac gccttcaac 19

<210> SEQ ID NO 819
<211> LENGTH: 20
<212> TYPE: DNA
<213> ORGANISM: Artificial Sequence
<220> FEATURE:
<223> OTHER INFORMATION: TRAC-GT-R1

<400> SEQUENCE: 819
ttcggaaccc aatcactgac 20

<210> SEQ ID NO 820
<211> LENGTH: 26
<212> TYPE: DNA
<213> ORGANISM: Artificial Sequence
<220> FEATURE:
<223> OTHER INFORMATION: TRAC-probe-FAM

<400> SEQUENCE: 820
tttctcgacc agcttgacat cacagg 26

<210> SEQ ID NO 821
<211> LENGTH: 21
<212> TYPE: DNA
<213> ORGANISM: Artificial Sequence
<220> FEATURE:
<223> OTHER INFORMATION: TRBC2-GT-F1

<400> SEQUENCE: 821
gctgtcaagt ccagttctac g 21

<210> SEQ ID NO 822
<211> LENGTH: 20
<212> TYPE: DNA
<213> ORGANISM: Artificial Sequence
<220> FEATURE:
<223> OTHER INFORMATION: TRBC2-GT-R1

<400> SEQUENCE: 822

```
cttgctggta agactcggag                                                   20


<210> SEQ ID NO 823
<211> LENGTH: 23
<212> TYPE: DNA
<213> ORGANISM: Artificial Sequence
<220> FEATURE:
<223> OTHER INFORMATION: TRBC2-probe-FAM

<400> SEQUENCE: 823

caaacccgtc acccagatcg tca                                               23


<210> SEQ ID NO 824
<211> LENGTH: 23
<212> TYPE: DNA
<213> ORGANISM: Artificial Sequence
<220> FEATURE:
<223> OTHER INFORMATION: TRAC-TCRA-ex1-F1

<400> SEQUENCE: 824

ctgatcctct tgtcccacag ata                                               23


<210> SEQ ID NO 825
<211> LENGTH: 26
<212> TYPE: DNA
<213> ORGANISM: Artificial Sequence
<220> FEATURE:
<223> OTHER INFORMATION: TRAC-TCRA-ex1-F1

<400> SEQUENCE: 825

gacttgtcac tggatttaga gtctct                                            26


<210> SEQ ID NO 826
<211> LENGTH: 22
<212> TYPE: DNA
<213> ORGANISM: Artificial Sequence
<220> FEATURE:
<223> OTHER INFORMATION: TRAC-probe(HEX)

<400> SEQUENCE: 826

atccagaacc ctgaccctgc cg                                                22
```

The invention claimed is:

1. A two-part device, wherein a first part is a multicomponent T cell receptor (TCR) open reading frame (ORF) reconstitution and engineering system (TORES), and a second part is a multicomponent engineered TCR-presenting cell system (eTPCS), wherein:

(I) the TORES comprises three separate components:

(a) a vector carrying variable and constant (V-C) T-cell receptor (TCR) gene segments, designated as V-C entry vector component 1A;

(b) a vector carrying joining (J) TCR gene segments, designated as J donor vector component 1B; and (c) a complementarity-determining region 3 (CDR3) vector designated as component 1C, comprising an oligonucleotide duplex encoding CDR3 (odeCDR3), wherein, when recombined, components 1A, 1B, and 1C provide a genetic integration vector, designated as genetic integration vector component 2C or 2E, each encoding an analyte TCR ORF of alpha, beta, delta, or gamma selected from:

(a) a native TCR chain;

(b) a sequence-diversified TCR chain; and (c) a synthetic TCR chain;

(II) the eTPCS comprises three separate components:

(a) an eTPC component designated as eTPC component 2A, wherein eTPC component 2A lacks endogenous expression of TCR chains alpha, beta, delta and gamma, and expresses cluster of differentiation 3 (CD3) proteins which are conditionally presented on the surface of the cell only when the cell expresses a complementary pair of TCR chains, and (b) a genomic receiver sites component, designated as components 2B and 2D, each for integration of a single ORF encoding one analyte TCR chain of alpha, beta, delta or gamma, wherein the genomic receiver site components 2B and 2D are each selected from:

(a) a synthetic construct designed for recombinase mediated cassette exchange (RMCE); and (b) a synthetic construct designed for site directed homologous recombination; and (c) genetic integration vector component 2C or 2E; and wherein the genetic integration vector components 2C and 2E each recombine with the genomic receiver site components 2B and 2D, respectively.

2. The two-part device of claim 1, wherein the eTPCS provides one or more analyte eTPC in which one or more TORES-derived analyte TCR chains are presented, and the one or more analyte eTPC is selected from (a) an eTPC expressing a TCR pair (eTPC-t);

(b) an eTPC expressing one TCR chain (eTPC-x); and (c) one or more libraries of (a) or (b).

3. The two-part device of claim 2, wherein a pair of analyte TCR chains are expressed as TCR surface proteins (TCRsp) in complex with CD3 by an analyte eTPC.

4. The two-part device of claim 1, wherein the V-C entry vector component 1A comprises:

(a) an origin of replication, (b) a first positive selection marker, (c) one or more 5' genetic elements, (d) a Kozak Sequence, (e) a TCR variable gene segment, (f) a first Type IIS sequence, for site specific recognition and cleavage by a Type IIS restriction enzyme, (g) a negative selection marker, (h) a second Type IIS sequence, (i) a TCR constant gene segment, and (j) one or more 3' genetic elements.

5. The two-part device of claim 4, wherein the J donor vector component 1B comprises:

(a) an origin of replication, (b) a second positive selection marker, (c) a third Type IIS sequence, (d) a TCR Joining gene segment, (e) a C part, corresponding to a small 5' portion of a constant gene segment, and (f) a fourth Type IIS sequence.

6. The two-part device of claim 5, wherein the first positive selection marker of component 1A and the second positive selection marker of component 1B are different and are selected from an antibiotic resistance gene and an auxotroph complementing gene.

7. The two-part device claim 5, wherein the CDR3 vector component 1C comprises:

(a) a first single-stranded overhang sequence complementary to the first Type IIS restriction enzyme recognition and cleavage site in the V-C entry vector component 1A, (b) a double-stranded segment encoding a TCR CDR3 region and devoid of the negative selection element present in V-C entry vector component 1A, and devoid of the Type IIS restriction sequences present in V-C entry vector component 1A and J donor vector component 1B, and (c) a second single-stranded overhang sequence complementary to the third Type IIS restriction enzyme recognition and cleavage site in the J donor vector component 1B;

or the CDR3 vector component 1C comprises (d) a single double-stranded DNA molecule encoding a TCR CDR3 flanked by Type IIS restriction enzyme sites such that when cleaved generates a product comprising V-C, CDR3, and J (V-CDR3-J-C TCR ORF).

8. The two-part device of claim 4, wherein the 5' genetic element of the V-C entry vector component 1A further comprises one or more elements selected from:

(a) a gene cis/acting element, (b) a heterospecific recognition site for recombinase enzymes, (c) a 5' homologous recombination arm for a genomic site of interest, (d) a mRNA splice acceptor site, (e) an internal ribosomal entry site, and (f) an epigenetic insulator sequence, wherein the 5' genetic element must contain at least element (b) or element (c).

9. The two-part device of claim 8, wherein the negative selection marker in the V-C entry vector component 1A is selected from one or more of the following:

(a) a restriction enzyme recognition site not contained elsewhere in the first component or within the TCR joining gene segment, (b) a gene encoding a conditional bactericidal agent, and (c) a reporter element.

10. The two-part device of claim 4, wherein the 3' genetic element of the V-C entry vector component 1A further comprises one or more elements selected from:

(a) a terminator element, (b) a heterospecific recognition site for recombinase enzymes, (c) a 3' homologous recombination arm for a genomic site of interest, (d) a mRNA splice donor site, (e) an internal ribosomal entry site, and (f) an epigenetic insulator sequence wherein the 3' genetic element must contain at least element (b) or element (c).

11. The two-part device of claim 1, wherein the eTPC component 2A is a cell that lacks endogenous surface expression of at least one family of analyte antigen-presenting complexes (aAPX) or analyte antigenic molecule (aAM).

12. The two-part device of claim 11, wherein the family of aAPX is selected from any of the following:

(a) human leukocyte antigen (HLA) class I;

(b) HLA class II; and (c) non-HLA antigen-presenting complex.

13. The two-part device of claim 12, wherein the genomic receiver site components 2B and 2D each comprise at least one of the following genetic elements:

(a) heterospecific recombinase sites;

(b) homologous arms;

(c) a eukaryotic promoter;

(d) a eukaryotic conditional regulatory element;

(e) a eukaryotic terminator;

(f) a selection marker;

(g) a splice acceptor site;

(h) a splice donor site;

(i) a non-protein coding gene;

(j) an insulator;

(k) a mobile genetic element;

(l) a meganuclease recognition site;

(m) an internal ribosome entry site (IRES);

(n) a viral self-cleaving peptide element; and (o) a Kozak consensus sequence.

14. The two-part device of claim 12, wherein the genomic receiver site components 2B and 2D are for RMCE integration of a single ORF and each comprises:

(a) a eukaryotic promoter;

(b) a pair of heterospecific recombinase sites that recombine with those of the genetic integration vector component 2C or 2E;

(c) a Kozak consensus sequence;
(d) a selection marker; and
(e) a eukaryotic terminator.

15. The two-part device of claim 12, wherein the two-part device comprises the genetic integration vector components 2C and 2E that are each for RMCE integration of a single ORF and each comprises the following genetic elements contributed by the V-C entry vector component 1A:
(a) a pair of heterospecific recombinase sites that recombine with those of the genomic receiver site components 2B or 2D;
(b) a Kozak consensus sequence; and
(c) a TCR ORF reconstituted by operation of the TORES.

16. The two-part device of claim 12, wherein the two-part device comprises the genetic integration vector components 2C and 2E and the TORES provides a single analyte TCR chain pair.

17. The two-part device of claim 16, wherein the analyte TCR chain pair encoding sequences are from:
(a) paired sequencing of TCR chain ORF sequence(s) from primary T-cells and reconstitution in the part 1 TORES;
(b) unpaired sequencing of TCR chain ORF sequence(s) from primary T-cells and reconstitution in part 1 TORES; or
(c) synthetic TCR chain ORF sequence(s) generated by operation of the TORES.

18. The two-part device of claim 16, wherein the genetic integration vector components 2C and 2E are combined with the eTPC component 2A to integrate two complementary analyte TCR chains encoded in the genetic integration vector components 2C and 2E into the genomic receiver site components 2B and 2D, thereby obtaining a cell that expresses an analyte TCRsp on its surface.

19. The two-part device of claim 16, wherein the genetic integration vector component 2C is combined with the eTPC component 2A to integrate one analyte TCR chain encoded in the genetic integration vector component 2C into the genomic receiver site component 2B, thereby obtaining a cell, designated eTPC-x, expresses a single TCR chain.

20. The two-part device of claim 19, wherein the genetic integration vector component 2E is combined with the eTPC-x to integrate one analyte TCR chain encoded in the genetic integration vector component 2E that is complementary to the TCR chain expressed in the eTPC-x into the genomic receiver site component 2D of the eTPC-x, thereby obtaining a cell that expresses a TCRsp on its surface.

21. The two-part device of claim 12, wherein the two-part device comprises the genetic integration vector components 2C and 2E and the TORES provides a library of analyte TCR chain pairs encoded by the genetic integration vector components 2C and 2E.

22. The two-part device of claim 11, wherein the aAM is selected from:
(a) a polypeptide or complex of polypeptides translated from the analyte antigenic molecule ORF(s);
(b) a peptide from a polypeptide translated from the analyte antigenic molecule ORF(s);
(c) a peptide from the component A proteome;
(d) a polypeptide from the component A proteome; or
(e) a metabolite from the component A metabolome.

23. The two-part device of claim 11, wherein the eTPC component 2A expresses cluster of differentiation 4 (CD4) or cluster of differentiation 8 (CD8).

24. The two-part device of claim 11, wherein the eTPC component 2A expresses TCR co-receptors.

25. The two-part device of claim 11, wherein the eTPC component 2A expresses cluster of differentiation 28 (CD28) or cluster of differentiation 45 (CD45).

26. The two-part device of claim 11, wherein the two-part device comprises the genetic integration vector components 2C and 2E wherein each comprises at least one of the following genetic elements:
(a) heterospecific recombinase sites;
(b) homologous arms;
(c) a eukaryotic promoter;
(d) a eukaryotic conditional regulatory element;
(e) a eukaryotic terminator;
(f) a selection marker;
(g) a selection marker of integration;
(h) a splice acceptor site;
(i) a splice donor site;
(j) a non-protein coding gene;
(k) an insulator;
(l) a mobile genetic element;
(m) a meganuclease recognition site;
(n) an internal ribosome entry site (IRES);
(o) a viral self-cleaving peptide element;
(p) an antibiotic resistance cassette;
(q) a bacterial origin of replication;
(r) a yeast origin of replication;
(s) a cloning site; and
(t) a Kozak consensus sequence.

27. The two-part device of claim 1, wherein: the eTPC component 2A:
(a) lacks endogenous expression of TCR chains alpha, beta, delta and gamma,
(b) expresses CD3 proteins which are conditionally presented on the surface of the cell only when the cell expresses a complementary pair of TCR chains, and
(c) contains the genomic receiver site component 2B for integration of a single ORF encoding at least one analyte TCR chain of alpha, beta, delta or gamma, or two ORFs encoding pair of analyte TCR chains, and the genetic integration vector component 2C recombines with the genomic receiver site component 2B, and wherein the genetic integration vector component 2C encodes:
(i) a single ORF encoding at least one analyte TCR chain of alpha, beta, delta and/or gamma; or
(ii) two ORFs encoding a pair of analyte TCR chains.

28. The two-part device of claim 27, wherein the single ORF (i) or two ORFs (ii) of the genetic integration vector component 2C encodes a selection marker of integration, such that the analyte TCR chains can be expressed as a TCR surface protein (TCRsp) in complex with the CD3 on the surface of the eTPC component 2A.

29. The two-part device of claim 1, wherein the eTPC component 2A further contains a synthetic genomic TCR-stimulation response element, designated as component 2F and selected from:
(a) a single component synthetic construct containing at least one native promoter or at least one synthetic promoter and at least one reporter; and
(b) a multi-component synthetic construct designed with at least one native promoter or at least one synthetic promoter and at least one reporter, and wherein activation of (a) or (b) is dependent on at least one signal transduction pathway selected from a synthetic pathway, a native pathway or a combination thereof.

30. The two-part device of claim 1, wherein the genomic receiver site components 2B and 2D are synthetic constructs designed for recombinase mediated cassette exchange (RMCE).

31. The two-part device of claim 1, wherein the two-part device generates at least one cell, designated an analyte eTPC-t, that expresses a TCRsp on its surface.

32. The two-part device of claim 1, wherein genetic integration vector components 2C and 2E each encodes a selection marker of integration, such that the analyte TCR chains can be expressed as TCR surface protein (TCRsp) in complex with the CD3 on the surface of the eTPC component 2A.

* * * * *